US012358967B2

(12) United States Patent
Zhou et al.

(10) Patent No.: US 12,358,967 B2
(45) Date of Patent: *Jul. 15, 2025

(54) METHODS OF OBTAINING TUMOR-SPECIFIC T CELL RECEPTORS

(71) Applicants: SYZ Cell Therapy Co., Guangdong (CN); HRYZ Biotech Co., Guangdong (CN)

(72) Inventors: Xiangjun Zhou, Shenzhen (CN); Yanyan Han, Shenzhen (CN); Xihe Chen, Shenzhen (CN)

(73) Assignees: HRYZ (SHANGHAI) BIOTECH CO., Shanghai (CN); HRYZ (GUANGZHOU) BIOTECH CO., Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/843,916

(22) Filed: Jun. 17, 2022

(65) Prior Publication Data

US 2022/0402999 A1 Dec. 22, 2022

Related U.S. Application Data

(62) Division of application No. 17/047,059, filed as application No. PCT/CN2019/082408 on Apr. 12, 2019, now Pat. No. 11,390,659.

(51) Int. Cl.

| | |
|---|---|
| ***A61K 35/17*** | (2025.01) |
| ***A61K 40/11*** | (2025.01) |
| ***A61K 40/19*** | (2025.01) |
| ***A61K 40/24*** | (2025.01) |
| ***A61K 40/32*** | (2025.01) |
| ***A61K 40/42*** | (2025.01) |
| ***A61K 40/46*** | (2025.01) |
| ***A61P 35/00*** | (2006.01) |
| ***C07K 14/725*** | (2006.01) |
| ***C12N 5/078*** | (2010.01) |
| ***C12N 5/0783*** | (2010.01) |
| ***C12N 5/0784*** | (2010.01) |
| ***C12N 5/22*** | (2006.01) |
| ***C12P 21/02*** | (2006.01) |
| *A61K 38/00* | (2006.01) |

(52) U.S. Cl.

CPC .......... *C07K 14/7051* (2013.01); *A61K 40/11* (2025.01); *A61K 40/19* (2025.01); *A61K 40/24* (2025.01); *A61K 40/32* (2025.01); *A61K 40/4201* (2025.01); *A61K 40/4205* (2025.01); *A61K 40/4208* (2025.01); *A61K 40/4232* (2025.01); *A61K 40/4239* (2025.01); *A61K 40/424* (2025.01); *A61K 40/4241* (2025.01); *A61K 40/4243* (2025.01); *A61K 40/4246* (2025.01); *A61K 40/4266* (2025.01); *A61K 40/4268* (2025.01); *A61K 40/4269* (2025.01); *A61K 40/46* (2025.01); *A61P 35/00* (2018.01); *C12N 5/0636* (2013.01); *C12N 5/0639* (2013.01); *C12P 21/02* (2013.01); *A61K 38/00* (2013.01); *C12N 2502/1114* (2013.01); *C12N 2502/1121* (2013.01)

(58) Field of Classification Search

None

See application file for complete search history.

(56) References Cited

U.S. PATENT DOCUMENTS

| | | | |
|---|---|---|---|
| 5,399,346 | A | 3/1995 | Anderson |
| 5,580,859 | A | 12/1996 | Felgner |
| 5,589,466 | A | 12/1996 | Felgner |
| 6,326,193 | B1 | 12/2001 | Liu |
| 7,999,092 | B2 | 8/2011 | Han |
| 10,538,573 | B2 | 1/2020 | Maurer et al. |
| 10,967,054 | B2 | 4/2021 | Xiangjun et al. |
| 10,987,412 | B2 | 4/2021 | Schneck et al. |
| 11,219,675 | B2 | 1/2022 | Zhou et al. |
| 11,219,676 | B2 | 1/2022 | Zhou et al. |
| 11,229,689 | B2 | 1/2022 | Zhou et al. |
| 11,390,659 | B2 | 7/2022 | Zhou |
| 11,471,519 | B2 | 10/2022 | Zhou et al. |
| 2018/0078624 | A1 | 3/2018 | Zhou |
| 2019/0321478 | A1 | 10/2019 | Alten et al. |
| 2021/0113676 | A1 | 4/2021 | Zhou et al. |
| 2021/0154285 | A1 | 5/2021 | Zhou et al. |
| 2021/0198341 | A1 | 7/2021 | Zhou et al. |

(Continued)

FOREIGN PATENT DOCUMENTS

| | | | |
|---|---|---|---|
| CN | 104593325 | A | 5/2015 |
| CN | 105452448 | A | 3/2016 |

(Continued)

OTHER PUBLICATIONS

Magalhaes et al, (2019) Facing the future: challenges and opportunities in adoptive T cell therapy in cancer, Expert Opinion on Biological Therapy, 19:8, 811-827.*
Liu et al, TCR-T Immunotherapy: The Challenges and Solutions. Front. Oncol, 2022, pp. 1-14.*
Yu et al, T cell immunotherapy for cervical cancer: challenges and opportunities. Front. Immunol., 2023, pp. 1-12.*

(Continued)

*Primary Examiner* — Maria Marvich
(74) *Attorney, Agent, or Firm* — MORRISON & FOERSTER LLP

(57) ABSTRACT

Provided methods of obtaining a plurality of T cell receptors specifically recognizing a target tumor antigen peptide from an individual that has clinically benefitted from an immunotherapy, such as Multiple Antigen Specific Cell Therapy. Also provided tumor-specific TCRs, engineered immune cells expressing the TCRs and methods of treating a disease using the engineered immune cells.

20 Claims, 92 Drawing Sheets

Specification includes a Sequence Listing.

(56) References Cited

U.S. PATENT DOCUMENTS

| | | | |
|---|---|---|---|
| 2021/0268083 | A1 | 9/2021 | Zhou et al. |
| 2022/0125904 | A1 | 4/2022 | Zhou et al. |
| 2022/0211829 | A1 | 7/2022 | Zhou et al. |
| 2022/0403000 | A1 | 12/2022 | Zhou et al. |
| 2023/0023834 | A1 | 1/2023 | Zhou et al. |
| 2023/0212253 | A1 | 7/2023 | Zhou et al. |
| 2024/0052010 | A1 | 2/2024 | Zhou |

FOREIGN PATENT DOCUMENTS

| | | | |
|---|---|---|---|
| CN | 106645677 | A | 5/2017 |
| CN | 107002038 | A | 8/2017 |
| CN | 107530392 | A | 1/2018 |
| CN | 107735492 | A | 2/2018 |
| CN | 108884136 | A | 11/2018 |
| EP | 2215220 | B1 | 1/2018 |
| WO | 2001029058 | A1 | 4/2001 |
| WO | 200196584 | A2 | 12/2001 |
| WO | 2002000730 | A2 | 1/2002 |
| WO | 2006127150 | A2 | 11/2006 |
| WO | 2011139371 | A1 | 11/2011 |
| WO | 2012038055 | A1 | 3/2012 |
| WO | 2015009604 | A1 | 1/2015 |
| WO | 2015009606 | A1 | 1/2015 |
| WO | 2016145578 | A1 | 9/2016 |
| WO | 2016146035 | A1 | 9/2016 |
| WO | 2016154625 | A1 | 9/2016 |
| WO | 2017211371 | A2 | 12/2017 |
| WO | 2019183924 | A1 | 10/2019 |
| WO | 2019185041 | A1 | 10/2019 |
| WO | 2019196087 | A1 | 10/2019 |
| WO | 2019196088 | A1 | 10/2019 |
| WO | 2019196923 | A1 | 10/2019 |
| WO | 2019196924 | A1 | 10/2019 |

OTHER PUBLICATIONS

Bernal, M. et al. (Sep. 2012, e-pub. Jul. 26, 2012). “Implication Of The α2-microglobulin Gene In The Generation Of Tumor Escape Phenotypes” Cancer Immunol. Immunother 61(9):1359-1371.

Buonaguro, L. et al. (Jan. 2011, e-pub. Nov. 3, 2010). “Translating Tumor Antigens into Cancer Vaccines,” Clinical And Vaccine Immunology 18(1):23-34.

Cadhila, B. et al. (2017). “Enabling T Cell Recruitment to Tumours as a Strategy for Improving Adoptive T Cell Therapy,” European Oncology & Haematology 13(1):66-73.

Datta, R. et al. (Nov. 1992). “Ionizing Radiation Activates Transcription of the EGR1 Gene Via CArG Elements,” Proc. Natl. Acad. Sci. USA 89(1):10149-10153.

Davis, M.M. et al. (Apr. 1998). “Ligand Recognition By αβ T Cell Receptors,” Annu Rev Immunol 16:(15):523-544.

Davis, M.M. et al. (Aug. 4, 1988). “T-Cell Antigen Receptor Genes and T-Cell Recognition,” Nature 334:395-402.

Durgeau, A. et al. (Jan. 22, 2018). “Recent Advances in Targeting CD8 T-Cell Immunity for More Effective Cancer Immunotherapy,” Front. Immunol. 22:1-14.

Edgar, R.C. (2004, e-pub. Mar. 19, 2004). “Muscle: Multiple Sequence Alignment With High Accuracy And High Throughput,” Nucleic Acids Research 32(5):1792-1797.

Edgar, R.C. (Aug. 19, 2004). “Muscle: A Multiple Sequence Alignment Method With Reduced Time And Space Complexity,” BMC Bioinformatics 5(113):1-19.

GenBank Accession No. AGU90416.1 (Sep. 8, 2013). “E7 [Human Papilloniavirus Type 18],” 1 page.

GenBank Accession No. AMN10004.1 (Mar. 7, 2016). “E7 Protein, Partial [Human Papilloniavirus Type 18],” 1 page.

GenBank Accession No. EDM09270.1 (Jul. 26, 2016). “Regulator Of G-Protein Signaling 5, Isoform CRA_B [Rattus Norvegicus],” 2 pages.

GenBank Accession No. EGW06162.1 (Mar. 14, 2015). “Regulator Of G-Protein Signaling 5 [Cricetulus Griseus],” 2 pages.

Gingrich, J.R. et al. (1998). “Inducible Gene Expression in the Nervous System of Transgenic Mice,” Annual Rev. Neurosci. 21:377-405.

Hollingsworth. R.E. et al. (2019, e-pub. Feb. 8, 2019). “Turning the Corner On Therapeutic Cancer Vaccines,” Vaccines 4(7):1-10.

Kim, J.H. et al. (Apr. 2011). “High Cleavage Efficiency of a 2A Peptide Derived from Porcine Teschovirus-1 in Human Cell Lines, Zebrafish and Mice,” PLOS One 6(4):e18556, 8 pages.

Larche, M. (2008). “Determining MHC Restriction of T-Cell Responses,” No. 6 in Methods Mol. Med., Jones, M.G et al. eds., Humana Press, Totowa, New Jersey, USA, 138:57-72, 27 pages.

Lefranc, M.-P. (1999). “The IMGT Unique Numbering For Immunoglobulins, T-Cell Receptors, and Ig-Like Domains,” The Immunologist 7(4):132-136.

Liang, X. et al. (Jul. 1, 2018). “Abstract 2554: Clone Tumor-Specific Tors From A Cell-Based Immunotherapy-Benefit Cervical Cancer Patient,” Cancer Res 78(Supplement 13):4 pages (Abstract Only).

Lichtenegger, F. S. et al. (Feb. 27, 2018). Targeting LAG-3 and IPD-1 to Enhance T Cell Activation by Antigen-Presenting Cells Frontiers in Immunology 9:1-12.

Lu, Y.-C. et al. (Oct. 10, 2017). “Treatment Of Patients With Metastatic Cancer Using A Major Histocompatibility Complex Class II-Restricted T-Cell Receptor Targeting The Cancer Germline Antigen MAGE-A3.” Journal of Clinical Oncology 35(29):3322-3329, 13 pages.

Mader, S. et al. (Jun. 1993). “A Steroid-Inducible Promoter for the Controlled Overexpression of Cloned Genes in Eukaryotic Cells.” Proc. Natl. Acad. Sci. USA 90:5603-5607.

Manome, Y. et al. (Oct. 1993). “Coinduction of c-jun Gene Expression and Internucleosomal DNA Fragmentation by Ionizing Radiation,” Biochemistry 32(40):10607-10613.

Morrow, M.P. et al. (2016, e-pub. Nov. 20, 2016). “Augmentation Of Cellular And Humeral Immune Responses To HPV16 And HPV18 E6 And E7 Antigens By VGX-3100”, Molecular Therapy—Oncolytics 3:16025, 11 pages.

Nagarsheth, N.B. et al. (2021) “TCR-Engineered T Cells Targeting E7 For Patients With Metastatic HPV-Associated Epithelial Cancers,” Nature medicine 27(3):419-425.

Shukla, S.A. et al. (Nov. 2015; e-published on Sep. 15, 2015). “Comprehensive Analysis of Cancer-Associated Somatic Mutations in Class I HLA Genes,” Nature Biotechnology 33(11):1152-1158.

Spencer, D. M. et al. (Nov. 12, 1993). “Controlling Signal Transduction with Synthetic Ligands,” Science 262(5136):1019-1024.

Ui-Tel, K. et al. (2000). “Sensitive Assay of RNA Interference in *Drosophila* and Chinese Hamster Cultured Cells Using Firefly Luciferase Gene As Target,” FEBS Letters 479:79-82.

Mgneron, N. et al. (Jul. 15, 2013). “Database of T Cell-Defined Human Tumor Antigens: the 2013 Update,” Cancer Immunity 13:15, pp. 1-6.

Yang, X. et al. (2009; e-published on Dec. 19, 2008). “An Introduction to Epitope Prediction Methods and Software” Rev. Med. Virol. 19(2):77-96.

Zhang, L. et al. (Mar. 31, 2018). Progress in T Cell Receptor-Gene Engineered T Cell Immunotherapy for Solid Tumors, Tumor 38:256-263.

* cited by examiner

| Ag | TCR | Clonotypes T1 | T2 | T3 | shared X 2 | shared X 3 |
|---|---|---|---|---|---|---|
| CEA | TCRα | 405 | 415 | 575 | 77 | 6 |
| | TCRβ | 392 | 247 | 714 | 62 | 18 |
| RGS5 | TCRα | 253 | 157 | 584 | 39 | 6 |
| | TCRβ | 268 | 344 | 690 | 47 | 10 |
| HPV 18E7 | TCRα | 144 | 239 | 514 | 20 | 3 |
| | TCRβ | 171 | 304 | 561 | 24 | 3 |

FIG. 12

TCR construct composition (SEQ ID NO: 95)

Other options:

T2A: GSGEGRGSLLTCGDVEENPGP (SEQ ID NO: 195)
E2A: GSGQCTNYALLKLAGDVESNPGP (SEQ ID NO: 196)
F2A: GSGVKQTLNFDLLKLAGDVESNPGP (SEQ ID NO: 197)

m: murinized
J: joining region
V: variable region
C: constant region
CDR1/2/3: complementarity determining region 1/2/3
α: alpha chain
β: beta chain

| Antigen | Epitope | HLA restriction | TCR ID | TCR clone | TCRβ Vβ | TCRβ Jβ | TCRβ Cβ | linker | TCRα Vα | TCRα Jα | TCRα Cα | SEQ ID (amino acid) | SEQ ID (nucleic acid) |
|---|---|---|---|---|---|---|---|---|---|---|---|---|---|
| RGS5 | Positions 16-30 AKEIKIKLGILLQKP (SEQ ID NO: 82) | HLA-DPA1*02:02/DPB1*05:01 | 09B03 | 6 | TRBV30*01 | TRBJ2-2*01 | Cβ2 | P2A | TRAV16*01 | TRAJ23*01 | Cα | 143 | 144 |
| | | | 09B03-L | | TRBV30*01 | TRBJ2-2*01 | mCβ1 | P2A | TRAV16*01 | TRAJ23*01 | mCα | 145 | 146 |
| | | | P09E06 | 2 | TRBV11-2*01 | TRBJ1-1*01 | Cβ1 | P2A | TRAV26-1*01 | TRAJ43*01 | Cα | 147 | 148 |
| | | | P09E06-L | | TRBV11-2*01 | TRBJ1-1*01 | mCβ1 | P2A | TRAV26-1*01 | TRAJ43*01 | mCα | 149 | 150 |
| | | HLA-DRA/DRB1*09:01 and HLA-DRA/DRB4*01:03 | 09D01 | 3 | TRBV20-1*05 | TRBJ2-3*01 | Cβ2 | P2A | TRAV12-1*01 | TRAJ12*01 | Cα | 151 | 152 |
| | | | 09D01-L | | TRBV20-1*05 | TRBJ2-3*01 | mCβ1 | P2A | TRAV12-1*01 | TRAJ12*01 | mCα | 153 | 154 |
| | | | 09D01N | | TRBV20-1*05# | TRBJ2-3*01 | Cβ2 | P2A | TRAV12-1*01 | TRAJ12*01 | Cα | 155 | 156 |
| | | | 09D01N-L | | TRBV20-1*05# | TRBJ2-3*01 | mCβ1 | P2A | TRAV12-1*01 | TRAJ12*01 | mCα | 157 | 158 |
| | | | 09H05 | 4 | TRBV20-1*05 | TRBJ2-5*01 | Cβ2 | P2A | TRAV12-1*01 | TRAJ12*01 | Cα | 159 | 160 |
| | | | 09H05-L | | TRBV20-1*05 | TRBJ2-5*01 | mCβ1 | P2A | TRAV12-1*01 | TRAJ12*01 | mCα | 161 | 162 |
| | | | 09H05N | | TRBV20-1*05# | TRBJ2-5*01 | Cβ2 | P2A | TRAV12-1*01 | TRAJ12*01 | Cα | 163 | 164 |
| | | | 09H05N-L | | TRBV20-1*05# | TRBJ2-5*01 | mCβ1 | P2A | TRAV12-1*01 | TRAJ12*01 | mCα | 165 | 166 |
| | Positions 1-30 MCKGLAALPHSCLERAKEIKIKLGILLQKP (SEQ ID NO: 83) | HLA-DRA/DRB1*09:01 and HLA-DRA/DRB4*01:03 | 09E01 | 5 | TRBV6-5*01 | TRBJ1-5*01 | Cβ1 | P2A | TRAV25*01 | TRAJ49*01 | Cα | 167 | 168 |
| | | | 09E01-L | | TRBV6-5*01 | TRBJ1-5*01 | mCβ1 | P2A | TRAV25*01 | TRAJ49*01 | mCα | 169 | 170 |

FIG. 25A

| Antigen | Epitope | HLA restriction | TCR ID | TCR clone | TCRβ | | | linker | TCRa | | | SEQ ID (amino acid) | SEQ ID (nucleic acid) |
|---|---|---|---|---|---|---|---|---|---|---|---|---|---|
| | | | | | Vβ | Jβ | Cβ | | Vα | Jα | Cα | | |
| HPV18-E7 | Positions 80-94 ADDLR AFQQL FLNTL (SEQ ID NO: 84) | HLA-DRA/DRB1*09:01 | 33A02 | 5 | TRBV20-1*01 | TRBJ2-1*01 | Cβ2 | P2A | TRAV8-3*02 | TRAJ54*01 | Cα | 171 | 172 |
| | | | 33A02-L | | TRBV20-1*01 | TRBJ2-1*01 | mCβ1 | P2A | TRAV8-3*02 | TRAJ54*01 | mCα | 173 | 174 |
| | | | 33A02N | | TRBV20-1*01 | TRBJ2-1*01 | Cβ2 | P2A | TRAV8-3*02 | TRAJ54*01 | Cα | 175 | 176 |
| | | | 33A02N-L | | TRBV20-1*01 | TRBJ2-1*01 | mCβ1 | P2A | TRAV8-3*02 | TRAJ54*01 | mCα | 177 | 178 |
| | Positions 84-102 RAFQQ LFLNTL SFVCP WCA (SEQ ID NO: 85) | HLA-DRA/DRB1*09:01 | P09B08 | 1 | TRBV19*01 | TRBJ2-1*01 | Cβ2 | P2A | TRAV12-3*01 | TRAJ38*01 | Cα | 179 | 180 |
| | | | P09B08-L | | TRBV19*01 | TRBJ2-1*01 | mCβ1 | P2A | TRAV12-3*01 | TRAJ38*01 | mCα | 181 | 182 |
| | | HLA-DRA/DRB1*09:01 and HLA-DRA/DRB4*01:03 | 10F04 | 3 | TRBV19*01 | TRBJ1-4*01 | Cβ1 | P2A | TRAV12-3*01 | TRAJ41*01 | Cα | 183 | 184 |
| | | | 10F04-L | | TRBV19*01 | TRBJ1-4*01 | mCβ1 | P2A | TRAV12-3*01 | TRAJ41*01 | mCα | 185 | 186 |
| | | HLA-II | 09B12 | 4 | TRBV9*01 | TRBJ2-7*01 | Cβ2 | P2A | TRAV9-2*01 | TRAJ53*01 | Cα | 187 | 188 |
| | | | 09B12-L | | TRBV9*01 | TRBJ2-7*01 | mCβ1 | P2A | TRAV9-2*01 | TRAJ53*01 | mCα | 189 | 190 |
| | Positions 76-105 VESSA DDLRA FQQLFL NTLSFV CPWCA SQQ (SEQ ID NO: 86) | HLA-DPA1*02:02/DPB1*05:01 and HLA-DPA1*01:03/DPB1*02:01 and HLA-DPA1*01:03/DPB1*05:01 | 33D05 | 6 | TRBV7-9*01 | TRBJ2-5*01 | Cβ2 | P2A | TRAV8-2*01 | TRAJ3*01 | Cα | 191 | 192 |
| | | | 33D05-L | | TRBV7-9*01 | TRBJ2-5*01 | mCβ1 | P2A | TRAV8-2*01 | TRAJ3*01 | mCα | 193 | 194 |

FIG. 25B

TCR-T
- TCR expression
  - FACS: TRBV30[a]
  - FACS: mTCRβ[b]
- Peptide recognition
  - FACS: CD3/IFN-γ/TNF-α
  - ELISA: IFN-γ

[a]: anti-human TCR Vβ chain
[b]: anti-mouse TCR β chain .

Conclusion:

1. The expression and function of 09B03 were enhanced by TCR murinization.
2. 09B03 and 09B03-L specifically recognized the 30aa peptide of RGS5 (1-30).

HLA restriction

| Donor | Autologous | 7 | 8 | 1 | 6 | 5 | 9 |
|---|---|---|---|---|---|---|---|
| DPA1*01:03 DPB1*02:01 | + | + | + | — | — | + | + |
| DPA1*02:02 DPB1*02:01 | + | + | + | — | — | — | — |
| DPA1*02:02 DPB1*05:01 | + | — | — | + | + | — | — |
| DPA1*01:03 DPB1*05:01 | + | — | — | — | — | — | — |

Conclusion: 09B03-L recognizes $RGS5_{16-30}$ presented by HLA-DPA1*02:02/DPB1*05:01.

TCR-T
- TCR expression
  - FACS: TRBV11-2[a]
  - FACS: mTCRβ[b]
- Peptide recognition
  - FACS: CD3/IFN-γ/TNF-α
  - ELISA: IFN-γ

[a]: anti-human TCR Vβ chain
[b]: anti-mouse TCR β chain .

Conclusion:

1. The expression and function of P09E06 enhanced by TCR munnization.
2. P09E06 and P09E06-L specifically recognized the 30aa peptide of RGS5 (1-30).

Conclusion: P09E06-L recognizes the epitope AKEIKIKLGILLQKP (RGS5:16-30).

Conclusion: P09E06-L is restricted to HLA-DP.

Conclusion: P09E06-L recognizes $RGS5_{16\text{-}30}$ presented by HLA-DPA1*02:02/DPB1*05:01.

TCR-T
- TCR expression
  - FACS: TRBV9[a]
  - FACS: mTCRβ[b]
- Peptide recognition
  - FACS: CD3/IFN-γ/TNF-α
  - ELISA: IFN-γ

[a]: anti-human TCR Vβ chain

[b]: anti-mouse TCR β chain .

Conclusion:

1. The expression and function of 09B12 were enhanced by TCR murinization.
2. 09B12 and 09B12-L specifically recognized the 30aa peptide of HPV18E7 (76-105).

Conclusion: 09B12-L recognizes the epitope RAFQQLFLNTLSFVCPWCA (HPV18E7:84-102).

HLA restriction by HLA blocking assay
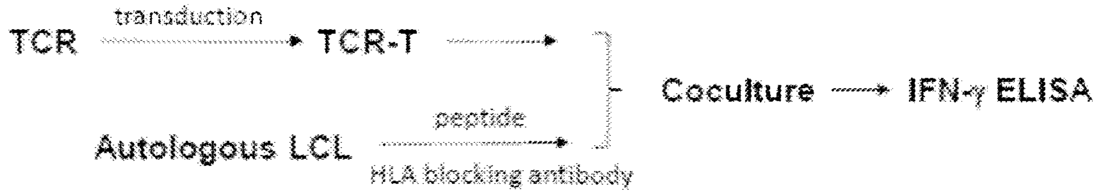
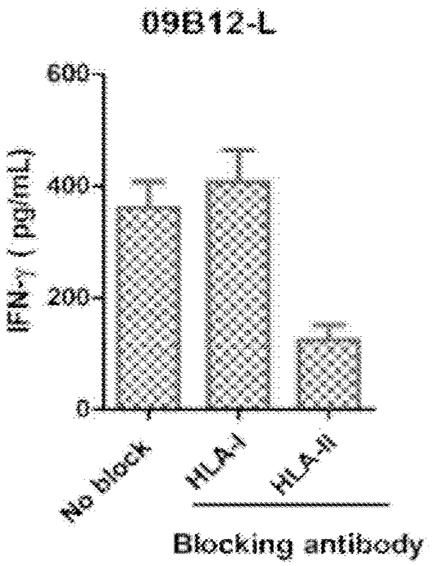
Conclusion: 09B12-L is restricted to HLA-II.
FIG. 28C

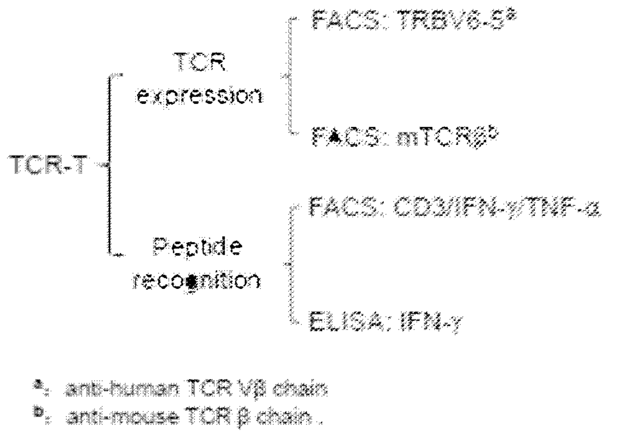
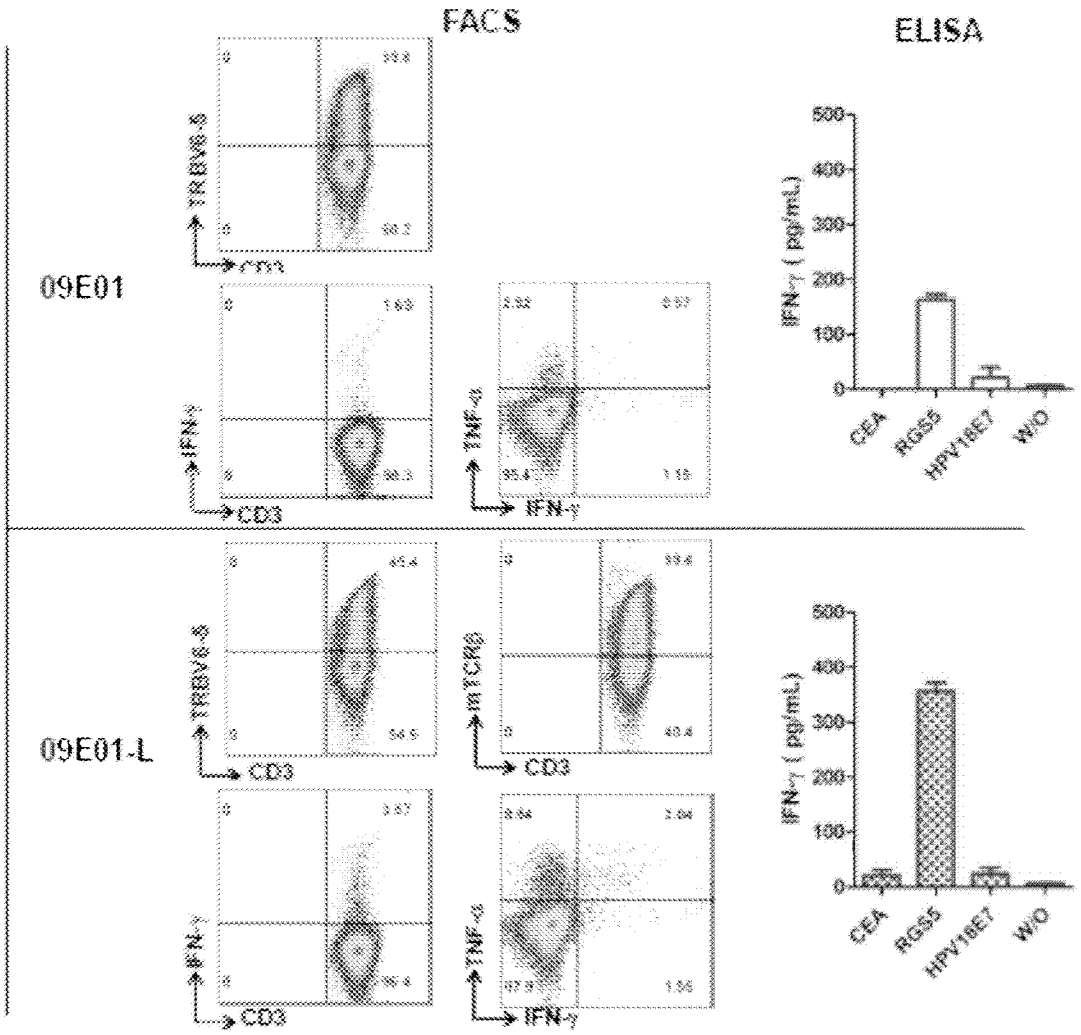
Conclusion:
1. The expression and function of 09E01 were enhanced by TCR murinization.
2. 09E01 and 09E01-L specifically recognized the 30aa peptide of RGS5 (1-30).
FIG. 29A HLA restriction
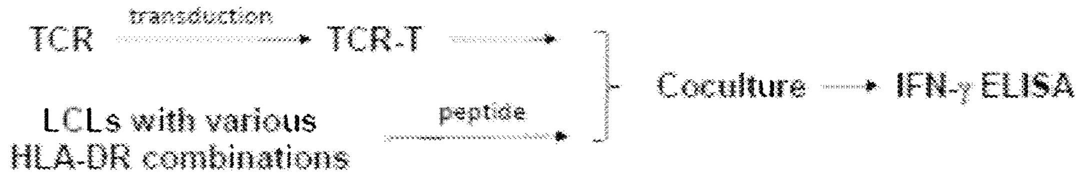
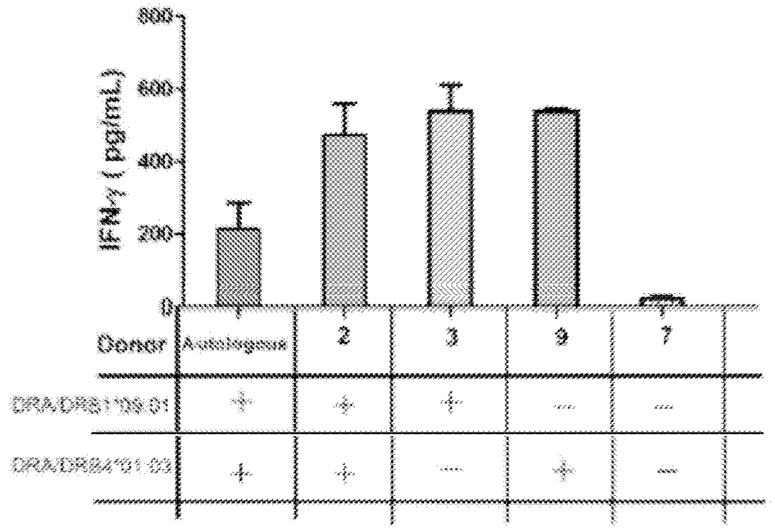
Conclusion: 09E01-L recognizes $RGS5_{1-30}$ presented by DRA/DRB1*09:01 and DRA/DRB4*01:03.
FIG. 29C TCR-T
- TCR expression
  - FACS: TRBV19[a]
  - FACS: mTCRβ[b]
- Peptide recognition
  - FACS: CD3/IFN-γ/TNF-α
  - ELISA: IFN-γ a: anti-human TCR Vβ chain
b: anti-mouse TCR β chain

Conclusion:

1. The expression and function of 10F04 were enhanced by TCR murinization.
2. 10F04 and 10F04-L specifically recognized the 30aa peptide of HPV18E7 (76-105).

Conclusion: 10F04-L recognizes the epitope RAFQQLFLNTLSFVCPWCA (HPV18E7:84-102).

HLA restriction by HLA blocking assay

Conclusion: 10F04-L is restricted to HLA-DR.

HLA restriction

Conclusion: 10F04-L recognizes HPV18E7$_{84-102}$ presented by DRA/DRB1*09:01 and DRA/DRB4*01:03.

HLA restriction

Conclusion: 33D05-L recognizes HPV18E7$_{76-105}$ presented by HLA-DPA1*02:02/DPB1*05:01 and HLA-DPA1*01:03/DPB1*02:01 and HLA-DPA1*01:03/DPB1*05:01.

TCR-T
- TCR expression
  - FACS: TRBV19[a]
  - FACS: mTCRβ[b]
- Peptide recognition
  - FACS: CD3/IFN-γ/TNF-α
  - ELISA: IFN-γ

[a]: anti-human TCR Vβ chain

[b]: anti-mouse TCR β chain.

Conclusion:

1. The expression and function of P09B08 were enhanced by TCR murinization.
2. P09B08 and P09B08-L specifically recognized the 30aa peptide of HPV18E7 (76-105).

Conclusion: P09B08-L recognizes the epitope RAFQQLFLNTLSFVCPWCA (HPV18E7:84-102).

Conclusion: P09B08-L is restricted to HLA-DR.

HLA restriction

Conclusion: P09B08-L recognizes HPV18E7$_{84-102}$ presented by DRA/DRB1*09:01.

Conclusion: 09H05-L recognizes the epitope AKEIKIKLGILLQKP (RGS5:16-30).

HLA restriction

Conclusion: 09H05-L recognizes $RGS5_{16\text{-}30}$ presented by DRA/DRB1*09:01 and DRA/DRB4*01:03.

HLA restriction

Conclusion: 09H05N-L recognizes $RGS5_{16\text{-}30}$ presented by DRA/DRB1*09:01 and DRA/DRB4*01:03.

Conclusion: 09D01-L recognizes the epitope AKEIKIKLGILLQKP (RGS5:16-30).

Conclusion: 09D01-L recognizes $RGS5_{16-30}$ presented by DRA/DRB1*09:01 and DRA/DRB4*01:03.

HLA restriction

Conclusion: 09D01N-L recognizes $RGS5_{16-30}$ presented by DRA/DRB1*09:01 and DRA/DRB4*01:03.

TCR-T
- TCR expression
  - FACS: TRBV20-1[a]
  - FACS: mTCRβ[b]
- Peptide recognition
  - FACS: CD3/IFN-γ/TNF-α
  - ELISA: IFN-γ a: anti-human TCR Vβ chain
b: anti-mouse TCR β chain .

Conclusion:

1. The expression and function of 33A02N were enhanced by TCR murinization.

2. 33A02N and 33A02N-L specifically recognized the 30aa peptide of HPV18E7 (76-105).

Conclusion: 33A02-L recognizes the epitope ADDLRAFQQLFLNTL (HPV18E7:80-94).

Conclusion: 33A02-L and 33A02N-L are restricted to HLA-DR.

HLA restriction

Conclusion: 33A02-L recognizes HPV18E7$_{80-94}$ presented by DRA/DRB1*09:01 .

DC-Sti : Pool

SEQUENCE LISTING

```
<160> NUMBER OF SEQ ID NOS: 293

<210> SEQ ID NO 1
<211> LENGTH: 90
<212> TYPE: PRT
<213> ORGANISM: Artificial Sequence
<220> FEATURE:
<223> OTHER INFORMATION: Synthetic Construct

<400> SEQUENCE: 1

Tyr Gly Pro Asp Thr Pro Ile Ile Ser Pro Pro Asp Ser Ser Tyr Leu
1               5                   10                  15

Ser Gly Ala Asn Leu Asn Leu Ser Cys His Ser Ala Ser Asn Pro Ser
            20                  25                  30

Pro Gln Tyr Ser Trp Arg Ile Asn Gly Ile Pro Gln Gln His Thr Gln
        35                  40                  45

Val Leu Phe Ile Ala Lys Ile Gln Pro Asn Asn Asn Gly Thr Tyr Ala
    50                  55                  60

Cys Phe Val Ser Asn Leu Ala Thr Gly Arg Asn Asn Ser Ile Val Lys
65                  70                  75                  80
```

```
Ser Ile Thr Val Ser Ala Ser Gly Thr Ser
                85                  90


<210> SEQ ID NO 2
<211> LENGTH: 50
<212> TYPE: PRT
<213> ORGANISM: Artificial Sequence
<220> FEATURE:
<223> OTHER INFORMATION: Synthetic Construct

<400> SEQUENCE: 2

Met Cys Lys Gly Leu Ala Ala Leu Pro His Ser Cys Leu Glu Arg Ala
1               5                   10                  15

Lys Glu Ile Lys Ile Lys Leu Gly Ile Leu Leu Gln Lys Pro Asp Ser
            20                  25                  30

Val Gly Asp Leu Val Ile Pro Tyr Asn Glu Lys Pro Glu Lys Pro Ala
        35                  40                  45

Lys Thr
    50


<210> SEQ ID NO 3
<211> LENGTH: 105
<212> TYPE: PRT
<213> ORGANISM: Artificial Sequence
<220> FEATURE:
<223> OTHER INFORMATION: Synthetic Construct

<400> SEQUENCE: 3

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Lys Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105


<210> SEQ ID NO 4
<211> LENGTH: 12
<212> TYPE: PRT
<213> ORGANISM: Artificial Sequence
<220> FEATURE:
<223> OTHER INFORMATION: Synthetic Construct

<400> SEQUENCE: 4

Cys Ile Gly Pro Phe Gly Asn Glu Lys Leu Thr Phe
1               5                   10


<210> SEQ ID NO 5
<211> LENGTH: 267
<212> TYPE: PRT
<213> ORGANISM: Artificial Sequence
<220> FEATURE:
<223> OTHER INFORMATION: Synthetic Construct

<400> SEQUENCE: 5
```

-continued

```
Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Gly Pro Phe Gly Asn Glu
            100                 105                 110

Lys Leu Thr Phe Gly Thr Gly Thr Arg Leu Thr Ile Ile Pro Asn Ile
        115                 120                 125

Gln Asn Pro Asp Pro Ala Val Tyr Gln Leu Arg Asp Ser Lys Ser Ser
    130                 135                 140

Asp Lys Ser Val Cys Leu Phe Thr Asp Phe Asp Ser Gln Thr Asn Val
145                 150                 155                 160

Ser Gln Ser Lys Asp Ser Asp Val Tyr Ile Thr Asp Lys Thr Val Leu
                165                 170                 175

Asp Met Arg Ser Met Asp Phe Lys Ser Asn Ser Ala Val Ala Trp Ser
            180                 185                 190

Asn Lys Ser Asp Phe Ala Cys Ala Asn Ala Phe Asn Asn Ser Ile Ile
        195                 200                 205

Pro Glu Asp Thr Phe Phe Pro Ser Pro Glu Ser Ser Cys Asp Val Lys
    210                 215                 220

Leu Val Glu Lys Ser Phe Glu Thr Asp Thr Asn Leu Asn Phe Gln Asn
225                 230                 235                 240

Leu Ser Val Ile Gly Phe Arg Ile Leu Leu Leu Lys Val Ala Gly Phe
                245                 250                 255

Asn Leu Leu Met Thr Leu Arg Leu Trp Ser Ser
            260                 265
```

<210> SEQ ID NO 6
<211> LENGTH: 801
<212> TYPE: DNA
<213> ORGANISM: Artificial Sequence
<220> FEATURE:
<223> OTHER INFORMATION: Synthetic Construct

<400> SEQUENCE: 6

```
atgaggctgg tggcaagagt aactgtgttt ctgacctttg gaactataat tgatgctaag     60

accacccagc ccccctccat ggattgcgct gaaggaagag ctgcaaacct gccttgtaat    120

cactctacca tcagtggaaa tgagtatgtg tattggtatc gacagattca ctcccagggg    180

ccacagtata tcattcatgg tctaaaaaac aatgaaacca atgaaatggc ctctctgatc    240

atcacagaag acagaaagtc cagcaccttg atcctgcccc acgctacgct gagagacact    300

gctgtgtact attgcatcgg cccctttgga aatgagaaat taacctttgg gactggaaca    360

agactcacca tcatacccaa tatccagaac cctgaccctg ccgtgtacca gctgagagac    420

tctaaatcca gtgacaagtc tgtctgccta ttcaccgatt ttgattctca aacaaatgtg    480

tcacaaagta aggattctga tgtgtatatc acagacaaaa ctgtgctaga catgaggtct    540
```

-continued

```
atggacttca agagcaacag tgctgtggcc tggagcaaca aatctgactt tgcatgtgca    600

aacgccttca acaacagcat tattccagaa gacaccttct tccccagccc agaaagttcc    660

tgtgatgtca agctggtcga gaaaagcttt gaaacagata cgaacctaaa ctttcaaaac    720

ctgtcagtga ttgggttccg aatcctcctc ctgaaagtgg ccgggtttaa tctgctcatg    780

acgctgcggc tgtggtccag c                                              801
```

<210> SEQ ID NO 7
<211> LENGTH: 14
<212> TYPE: PRT
<213> ORGANISM: Artificial Sequence
<220> FEATURE:
<223> OTHER INFORMATION: Synthetic Construct

<400> SEQUENCE: 7

```
Cys Ala Ser Ser Leu Asp Arg Thr Val Tyr Gly Tyr Thr Phe
1               5                   10
```

<210> SEQ ID NO 8
<211> LENGTH: 310
<212> TYPE: PRT
<213> ORGANISM: Artificial Sequence
<220> FEATURE:
<223> OTHER INFORMATION: Synthetic Construct

<400> SEQUENCE: 8

```
Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
            20                  25                  30

Arg Arg Gly Gln Glu Ala Arg Leu Arg Cys Ser Pro Met Lys Gly His
        35                  40                  45

Ser His Val Tyr Trp Tyr Arg Gln Leu Pro Glu Glu Gly Leu Lys Phe
    50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
            100                 105                 110

Ser Ser Leu Asp Arg Thr Val Tyr Gly Tyr Thr Phe Gly Ser Gly Thr
        115                 120                 125

Arg Leu Thr Val Val Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
```

-continued

```
            245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310


<210> SEQ ID NO 9
<211> LENGTH: 930
<212> TYPE: DNA
<213> ORGANISM: Artificial Sequence
<220> FEATURE:
<223> OTHER INFORMATION: Synthetic Construct

<400> SEQUENCE: 9

atggacacca gagtactctg ctgtgcggtc atctgtcttc tgggggcagg tctctcaaat      60

gccggcgtca tgcagaaccc aagacacctg gtcaggagga ggggacagga ggcaagactg     120

agatgcagcc caatgaaagg acacagtcat gtttactggt atcggcagct cccagaggaa     180

ggtctgaaat tcatggttta tctccagaaa gaaaatatca tagatgagtc aggaatgcca     240

aaggaacgat tttctgctga atttcccaaa gagggcccca gcatcctgag gatccagcag     300

gtagtgcgag gagattcggc agcttatttc tgtgccagct cactggacag gaccgtctat     360

ggctacacct tcggttcggg gaccaggtta accgttgtag aggacctgaa caaggtgttc     420

ccacccgagg tcgctgtgtt tgagccatca gaagcagaga tctcccacac ccaaaaggcc     480

acactggtgt gcctggccac aggcttcttc cccgaccacg tggagctgag ctggtgggtg     540

aatgggaagg aggtgcacag tggggtcagc acggacccgc agcccctcaa ggagcagccc     600

gccctcaatg actccagata ctgcctgagc agccgcctga gggtctcggc caccttctgg     660

cagaaccccc gcaaccactt ccgctgtcaa gtccagttct acgggctctc ggagaatgac     720

gagtggaccc aggatagggc caaacccgtc acccagatcg tcagcgccga ggcctggggt     780

agagcagact gtggctttac ctcggtgtcc taccagcaag ggtcctgtc tgccaccatc      840

ctctatgaga tcctgctagg gaaggccacc ctgtatgctg tgctggtcag cgcccttgtg     900

ttgatggcca tggtcaagag aaaggatttc                                      930


<210> SEQ ID NO 10
<211> LENGTH: 14
<212> TYPE: PRT
<213> ORGANISM: Artificial Sequence
<220> FEATURE:
<223> OTHER INFORMATION: Synthetic Construct

<400> SEQUENCE: 10

Cys Ala Leu Ser Gly Gly Ala Asn Ala Gly Lys Ser Thr Phe
1               5                   10


<210> SEQ ID NO 11
<211> LENGTH: 270
<212> TYPE: PRT
<213> ORGANISM: Artificial Sequence
<220> FEATURE:
<223> OTHER INFORMATION: Synthetic Construct

<400> SEQUENCE: 11
```

-continued

```
Met Lys Pro Thr Leu Ile Ser Val Leu Val Ile Ile Phe Ile Leu Arg
1               5                   10                  15

Gly Thr Arg Ala Gln Arg Val Thr Gln Pro Glu Lys Leu Leu Ser Val
            20                  25                  30

Phe Lys Gly Ala Pro Val Glu Leu Lys Cys Asn Tyr Ser Tyr Ser Gly
        35                  40                  45

Ser Pro Glu Leu Phe Trp Tyr Val Gln Tyr Ser Arg Gln Arg Leu Gln
    50                  55                  60

Leu Leu Leu Arg His Ile Ser Arg Glu Ser Ile Lys Gly Phe Thr Ala
65                  70                  75                  80

Asp Leu Asn Lys Gly Glu Thr Ser Phe His Leu Lys Lys Pro Phe Ala
                85                  90                  95

Gln Glu Glu Asp Ser Ala Met Tyr Tyr Cys Ala Leu Ser Gly Gly Ala
            100                 105                 110

Asn Ala Gly Lys Ser Thr Phe Gly Asp Gly Thr Thr Leu Thr Val Lys
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 12
<211> LENGTH: 810
<212> TYPE: DNA
<213> ORGANISM: Artificial Sequence
<220> FEATURE:
<223> OTHER INFORMATION: Synthetic Construct

<400> SEQUENCE: 12

```
atgaagccca ccctcatctc agtgcttgtg ataatattta tactcagagg aacaagagcc      60

cagagagtga ctcagcccga gaagctcctc tctgtcttta aaggggcccc agtggagctg     120

aagtgcaact attcctattc tgggagtcct gaactcttct ggtatgtcca gtactccaga     180

caacgcctcc agttactctt gagacacatc tctagagaga gcatcaaagg cttcactgct     240

gaccttaaca aaggcgagac atctttccac ctgaagaaac catttgctca agaggaagac     300

tcagccatgt attactgtgc tctaagtggc ggagccaatg caggcaaatc aacctttggg     360

gatgggacta cgctcactgt gaagccaaat atccagaacc ctgaccctgc cgtgtaccag     420

ctgagagact ctaaatccag tgacaagtct gtctgcctat tcaccgattt tgattctcaa     480

acaaatgtgt cacaaagtaa ggattctgat gtgtatatca cagacaaaac tgtgctagac     540
```

```
atgaggtcta tggacttcaa gagcaacagt gctgtggcct ggagcaacaa atctgacttt    600

gcatgtgcaa acgccttcaa caacagcatt attccagaag acaccttctt ccccagccca    660

gaaagttcct gtgatgtcaa gctggtcgag aaaagctttg aaacagatac gaacctaaac    720

tttcaaaacc tgtcagtgat tgggttccga atcctcctcc tgaaagtggc cgggtttaat    780

ctgctcatga cgctgcggct gtggtccagc                                      810


<210> SEQ ID NO 13
<211> LENGTH: 12
<212> TYPE: PRT
<213> ORGANISM: Artificial Sequence
<220> FEATURE:
<223> OTHER INFORMATION: Synthetic Construct

<400> SEQUENCE: 13

Cys Ala Ser Ser Glu Leu Gly Asn Thr Ile Tyr Phe
1               5                   10


<210> SEQ ID NO 14
<211> LENGTH: 308
<212> TYPE: PRT
<213> ORGANISM: Artificial Sequence
<220> FEATURE:
<223> OTHER INFORMATION: Synthetic Construct

<400> SEQUENCE: 14

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Leu Gly Asn Thr Ile Tyr Phe Gly Glu Gly Ser Trp Leu
        115                 120                 125

Thr Val Val Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
```

-continued

```
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305


<210> SEQ ID NO 15
<211> LENGTH: 924
<212> TYPE: DNA
<213> ORGANISM: Artificial Sequence
<220> FEATURE:
<223> OTHER INFORMATION: Synthetic Construct

<400> SEQUENCE: 15

atggatacct ggctcgtatg ctgggcaatt tttagtctct tgaaagcagg actcacagaa      60

cctgaagtca cccagactcc cagccatcag gtcacacaga tgggacagga agtgatcttg     120

cgctgtgtcc ccatctctaa tcacttatac ttctattggt acagacaaat cttggggcag     180

aaagtcgagt ttctggtttc cttttataat aatgaaatct cagagaagtc tgaaatattc     240

gatgatcaat tctcagttga aaggcctgat ggatcaaatt tcactctgaa gatccggtcc     300

acaaagctgg aggactcagc catgtacttc tgtgccagca gtgaactagg aaacaccata     360

tattttggag agggaagttg gctcactgtt gtagaggacc tgaacaaggt gttcccaccc     420

gaggtcgctg tgtttgagcc atcagaagca gagatctccc acacccaaaa ggccacactg     480

gtgtgcctgg ccacaggctt cttccccgac cacgtggagc tgagctggtg ggtgaatggg     540

aaggaggtgc acagtggggt cagcacggac ccgcagcccc tcaaggagca gcccgccctc     600

aatgactcca gatactgcct gagcagccgc ctgagggtct cggccacctt ctggcagaac     660

ccccgcaacc acttccgctg tcaagtccag ttctacgggc tctcggagaa tgacgagtgg     720

acccaggata gggccaaacc cgtcacccag atcgtcagcg ccgaggcctg gggtagagca     780

gactgtggct ttacctcggt gtcctaccag caaggggtcc tgtctgccac catcctctat     840

gagatcctgc tagggaaggc caccctgtat gctgtgctgg tcagcgccct tgtgttgatg     900

gccatggtca agagaaagga tttc                                           924


<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Cys Ala Ala His Ala Asp Tyr Lys Leu Ser Phe
1               5                   10


<210> SEQ ID NO 17
<211> LENGTH: 279
<212> TYPE: PRT
<213> ORGANISM: Artificial Sequence
<220> FEATURE:
<223> OTHER INFORMATION: Synthetic Construct

<400> SEQUENCE: 17
```

-continued

```
Met Asp Lys Ile Leu Gly Ala Ser Phe Leu Val Leu Trp Leu Gln Leu
1               5                   10                  15

Cys Trp Val Ser Gly Gln Gln Lys Glu Lys Ser Asp Gln Gln Gln Val
            20                  25                  30

Lys Gln Ser Pro Gln Ser Leu Ile Val Gln Lys Gly Gly Ile Ser Ile
        35                  40                  45

Ile Asn Cys Ala Tyr Glu Asn Thr Ala Phe Asp Tyr Phe Pro Trp Tyr
    50                  55                  60

Gln Gln Phe Pro Gly Lys Gly Pro Ala Leu Leu Ile Ala Ile Arg Pro
65                  70                  75                  80

Asp Val Ser Glu Lys Lys Glu Gly Arg Phe Thr Ile Ser Phe Asn Lys
                85                  90                  95

Ser Ala Lys Gln Phe Ser Leu His Ile Met Asp Ser Gln Pro Gly Asp
            100                 105                 110

Ser Ala Thr Tyr Phe Cys Ala Ala His Ala Asp Tyr Lys Leu Ser Phe
        115                 120                 125

Gly Ala Gly Thr Thr Val Thr Val Arg Ala Asn Ile Gln Asn Pro Asp
    130                 135                 140

Pro Ala Val Tyr Gln Leu Arg Asp Ser Lys Ser Ser Asp Lys Ser Val
145                 150                 155                 160

Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Arg Ser
            180                 185                 190

Met Asp Phe Lys Ser Asn Ser Ala Val Ala Trp Ser Asn Lys Ser Asp
        195                 200                 205

Phe Ala Cys Ala Asn Ala Phe Asn Asn Ser Ile Ile Pro Glu Asp Thr
    210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
            260                 265                 270

Thr Leu Arg Leu Trp Ser Ser
        275


<210> SEQ ID NO 18
<211> LENGTH: 837
<212> TYPE: DNA
<213> ORGANISM: Artificial Sequence
<220> FEATURE:
<223> OTHER INFORMATION: Synthetic Construct

<400> SEQUENCE: 18

atggacaaga tcttaggagc atcattttta gttctgtggc ttcaactatg ctgggtgagt      60

ggccaacaga aggagaaaag tgaccagcag caggtgaaac aaagtcctca atctttgata     120

gtccagaaag gagggatttc aattataaac tgtgcttatg agaacactgc gtttgactac     180

tttccatggt accaacaatt ccctgggaaa ggccctgcat tattgatagc catacgtcca     240

gatgtgagtg aaaagaaaga aggaagattc acaatctcct tcaataaaag tgccaagcag     300

ttctcattgc atatcatgga ttcccagcct ggagactcag ccacctactt ctgtgcagca     360

cacgccgact acaagctcag ctttggagcc ggaaccacag taactgtaag agcaaatatc     420

cagaaccctg accctgccgt gtaccagctg agagactcta aatccagtga caagtctgtc     480
```

```
tgcctattca ccgattttga ttctcaaaca aatgtgtcac aaagtaagga ttctgatgtg    540

tatatcacag acaaaactgt gctagacatg aggtctatgg acttcaagag caacagtgct    600

gtggcctgga gcaacaaatc tgactttgca tgtgcaaacg ccttcaacaa cagcattatt    660

ccagaagaca ccttcttccc cagcccagaa agttcctgtg atgtcaagct ggtcgagaaa    720

agctttgaaa cagatacgaa cctaaacttt caaaacctgt cagtgattgg gttccgaatc    780

ctcctcctga aagtggccgg gtttaatctg ctcatgacgc tgcggctgtg gtccagc       837
```

```
<210> SEQ ID NO 19
<211> LENGTH: 15
<212> TYPE: PRT
<213> ORGANISM: Artificial Sequence
<220> FEATURE:
<223> OTHER INFORMATION: Synthetic Construct

<400> SEQUENCE: 19

Cys Ala Ser Ser Leu Asp Arg Ala Thr Asn Glu Lys Leu Phe Phe
1               5                   10                  15


<210> SEQ ID NO 20
<211> LENGTH: 311
<212> TYPE: PRT
<213> ORGANISM: Artificial Sequence
<220> FEATURE:
<223> OTHER INFORMATION: Synthetic Construct

<400> SEQUENCE: 20

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
            20                  25                  30

Arg Arg Gly Gln Glu Ala Arg Leu Arg Cys Ser Pro Met Lys Gly His
        35                  40                  45

Ser His Val Tyr Trp Tyr Arg Gln Leu Pro Glu Glu Gly Leu Lys Phe
    50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
            100                 105                 110

Ser Ser Leu Asp Arg Ala Thr Asn Glu Lys Leu Phe Phe Gly Ser Gly
        115                 120                 125

Thr Gln Leu Ser Val Leu Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
```

```
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Phe
305                 310
```

<210> SEQ ID NO 21
<211> LENGTH: 933
<212> TYPE: DNA
<213> ORGANISM: Artificial Sequence
<220> FEATURE:
<223> OTHER INFORMATION: Synthetic Construct

<400> SEQUENCE: 21

```
atggacacca gagtactctg ctgtgcggtc atctgtcttc tgggggcagg tctctcaaat      60

gccggcgtca tgcagaaccc aagacacctg gtcaggagga ggggacagga ggcaagactg     120

agatgcagcc caatgaaagg acacagtcat gtttactggt atcggcagct cccagaggaa     180

ggtctgaaat tcatggttta tctccagaaa gaaaatatca tagatgagtc aggaatgcca     240

aaggaacgat ttctgctga atttcccaaa gagggcccca gcatcctgag gatccagcag      300

gtagtgcgag gagattcggc agcttatttc tgtgccagct ctcttgacag ggcgacaaat     360

gaaaaactgt tttttggcag tggaacccag ctctctgtct tggaggacct gaacaaggtg     420

ttcccacccg aggtcgctgt gtttgagcca tcagaagcag agatctccca cacccaaaag     480

gccacactgg tgtgcctggc cacaggcttc ttccccgacc acgtggagct gagctggtgg     540

gtgaatggga aggaggtgca cagtggggtc agcacggacc cgcagcccct caaggagcag     600

cccgccctca atgactccag atactgcctg agcagccgcc tgagggtctc ggccaccttc     660

tggcagaacc cccgcaacca cttccgctgt caagtccagt tctacgggct ctcggagaat     720

gacgagtgga cccaggatag ggccaaaccc gtcacccaga tcgtcagcgc cgaggcctgg     780

ggtagagcag actgtggctt tacctcggtg tcctaccagc aaggggtcct gtctgccacc     840

atcctctatg agatcctgct agggaaggcc accctgtatg ctgtgctggt cagcgccctt     900

gtgttgatgg ccatggtcaa gagaaaggat ttc                                  933
```

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

```
Cys Ala Leu Asn Asn Asp Tyr Lys Leu Ser Phe
1               5                   10
```

<210> SEQ ID NO 23
<211> LENGTH: 273
<212> TYPE: PRT
<213> ORGANISM: Artificial Sequence
<220> FEATURE:
<223> OTHER INFORMATION: Synthetic Construct -continued

<400> SEQUENCE: 23

Met Ala Cys Pro Gly Phe Leu Trp Ala Leu Val Ile Ser Thr Cys Leu
1 5 10 15

Glu Phe Ser Met Ala Gln Thr Val Thr Gln Ser Gln Pro Glu Met Ser
20 25 30

Val Gln Glu Ala Glu Thr Val Thr Leu Ser Cys Thr Tyr Asp Thr Ser
35 40 45

Glu Ser Asp Tyr Tyr Leu Phe Trp Tyr Lys Gln Pro Pro Ser Arg Gln
50 55 60

Met Ile Leu Val Ile Arg Gln Glu Ala Tyr Lys Gln Gln Asn Ala Thr
65 70 75 80

Glu Asn Arg Phe Ser Val Asn Phe Gln Lys Ala Ala Lys Ser Phe Ser
85 90 95

Leu Lys Ile Ser Asp Ser Gln Leu Gly Asp Ala Ala Met Tyr Phe Cys
100 105 110

Ala Leu Asn Asn Asp Tyr Lys Leu Ser Phe Gly Ala Gly Thr Thr Val
115 120 125

Thr Val Arg Ala Asn Ile Gln Asn Pro Asp Pro Ala Val Tyr Gln Leu
130 135 140

Arg Asp Ser Lys Ser Ser Asp Lys Ser Val Cys Leu Phe Thr Asp Phe
145 150 155 160

Asp Ser Gln Thr Asn Val Ser Gln Ser Lys Asp Ser Asp Val Tyr Ile
165 170 175

Thr Asp Lys Thr Val Leu Asp Met Arg Ser Met Asp Phe Lys Ser Asn
180 185 190

Ser Ala Val Ala Trp Ser Asn Lys Ser Asp Phe Ala Cys Ala Asn Ala
195 200 205

Phe Asn Asn Ser Ile Ile Pro Glu Asp Thr Phe Phe Pro Ser Pro Glu
210 215 220

Ser Ser Cys Asp Val Lys Leu Val Glu Lys Ser Phe Glu Thr Asp Thr
225 230 235 240

Asn Leu Asn Phe Gln Asn Leu Ser Val Ile Gly Phe Arg Ile Leu Leu
245 250 255

Leu Lys Val Ala Gly Phe Asn Leu Leu Met Thr Leu Arg Leu Trp Ser
260 265 270

Ser

<210> SEQ ID NO 24
<211> LENGTH: 819
<212> TYPE: DNA
<213> ORGANISM: Artificial Sequence
<220> FEATURE:
<223> OTHER INFORMATION: Synthetic Construct

<400> SEQUENCE: 24
atggcatgcc ctggcttcct gtgggcactt gtgatctcca cctgtcttga atttagcatg 60
gctcagacag tcactcagtc tcaaccagag atgtctgtgc aggaggcaga gaccgtgacc 120
ctgagctgca catatgacac cagtgagagt gattattatt tattctggta caagcagcct 180
cccagcaggc agatgattct cgttattcgc caagaagctt ataagcaaca gaatgcaaca 240
gagaatcgtt tctctgtgaa cttccagaaa gcagccaaat ccttcagtct caagatctca 300
gactcacagc tgggggatgc cgcgatgtat ttctgtgccc ttaataacga ctacaagctc 360
agctttggag ccggaaccac agtaactgta agagcaaata tccagaaccc tgaccctgcc 420

-continued gtgtaccagc tgagagactc taaatccagt gacaagtctg tctgcctatt caccgatttt 480
gattctcaaa caaatgtgtc acaaagtaag gattctgatg tgtatatcac agacaaaact 540
gtgctagaca tgaggtctat ggacttcaag agcaacagtg ctgtggcctg gagcaacaaa 600
tctgactttg catgtgcaaa cgccttcaac aacagcatta ttccagaaga caccttcttc 660
cccagcccag aaagttcctg tgatgtcaag ctggtcgaga aaagctttga aacagatacg 720
aacctaaact ttcaaaacct gtcagtgatt gggttccgaa tcctcctcct gaaagtggcc 780
gggtttaatc tgctcatgac gctgcggctg tggtccagc 819

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

Cys Ala Ser Ser Asp Lys Gly Phe Asp Glu Gln Phe Phe
1 5 10

<210> SEQ ID NO 26
<211> LENGTH: 310
<212> TYPE: PRT
<213> ORGANISM: Artificial Sequence
<220> FEATURE:
<223> OTHER INFORMATION: Synthetic Construct

<400> SEQUENCE: 26

Met Ser Asn Gln Val Leu Cys Cys Val Val Leu Cys Phe Leu Gly Ala
1 5 10 15

Asn Thr Val Asp Gly Gly Ile Thr Gln Ser Pro Lys Tyr Leu Phe Arg
20 25 30

Lys Glu Gly Gln Asn Val Thr Leu Ser Cys Glu Gln Asn Leu Asn His
35 40 45

Asp Ala Met Tyr Trp Tyr Arg Gln Asp Pro Gly Gln Gly Leu Arg Leu
50 55 60

Ile Tyr Tyr Ser Gln Ile Val Asn Asp Phe Gln Lys Gly Asp Ile Ala
65 70 75 80

Glu Gly Tyr Ser Val Ser Arg Glu Lys Lys Glu Ser Phe Pro Leu Thr
85 90 95

Val Thr Ser Ala Gln Lys Asn Pro Thr Ala Phe Tyr Leu Cys Ala Ser
100 105 110

Ser Asp Lys Gly Phe Asp Glu Gln Phe Phe Gly Pro Gly Thr Arg Leu
115 120 125

Thr Val Leu Glu Asp Leu Lys Asn Val Phe Pro Pro Glu Val Ala Val
130 135 140

Phe Glu Pro Ser Glu Ala Glu Ile Ser His Thr Gln Lys Ala Thr Leu
145 150 155 160

Val Cys Leu Ala Thr Gly Phe Tyr Pro Asp His Val Glu Leu Ser Trp
165 170 175

Trp Val Asn Gly Lys Glu Val His Ser Gly Val Ser Thr Asp Pro Gln
180 185 190

Pro Leu Lys Glu Gln Pro Ala Leu Asn Asp Ser Arg Tyr Cys Leu Ser
195 200 205

Ser Arg Leu Arg Val Ser Ala Thr Phe Trp Gln Asn Pro Arg Asn His
210 215 220

```
Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310


<210> SEQ ID NO 27
<211> LENGTH: 930
<212> TYPE: DNA
<213> ORGANISM: Artificial Sequence
<220> FEATURE:
<223> OTHER INFORMATION: Synthetic Construct

<400> SEQUENCE: 27

atgagcaacc aggtgctctg ctgtgtggtc ctttgtttcc tgggagcaaa caccgtggat      60

ggtggaatca ctcagtcccc aaagtacctg ttcagaaagg aaggacagaa tgtgaccctg     120

agttgtgaac agaatttgaa ccacgatgcc atgtactggt accgacagga cccagggcaa     180

gggctgagat tgatctacta ctcacagata gtaaatgact ttcagaaagg agatatagct     240

gaagggtaca gcgtctctcg ggagaagaag gaatcctttc ctctcactgt gacatcggcc     300

caaaagaacc cgacagcttt ctatctctgt gccagtagtg ataaggggtt tgatgagcag     360

ttcttcgggc cagggacacg gctcaccgtg ctagaggacc tgaaaaacgt gttcccaccc     420

gaggtcgctg tgtttgagcc atcagaagca gagatctccc acacccaaaa ggccacactg     480

gtgtgcctgg ccacaggctt ctaccccgac cacgtggagc tgagctggtg ggtgaatggg     540

aaggaggtgc acagtggggt cagcacagac ccgcagcccc tcaaggagca gcccgccctc     600

aatgactcca gatactgcct gagcagccgc ctgagggtct cggccacctt ctggcagaac     660

ccccgcaacc acttccgctg tcaagtccag ttctacgggc tctcggagaa tgacgagtgg     720

acccaggata gggccaaacc tgtcacccag atcgtcagcg ccgaggcctg ggtagagca     780

gactgtggct tcacctccga gtcttaccag caaggggtcc tgtctgccac catcctctat     840

gagatcttgc tagggaaggc caccttgtat gccgtgctgg tcagtgccct cgtgctgatg     900

gccatggtca agagaaagga ttccagaggc                                     930


<210> SEQ ID NO 28
<211> LENGTH: 14
<212> TYPE: PRT
<213> ORGANISM: Artificial Sequence
<220> FEATURE:
<223> OTHER INFORMATION: Synthetic Construct

<400> SEQUENCE: 28

Cys Ile Val Arg Ala Trp Tyr Asn Asn Asn Asp Met Arg Phe
1               5                   10


<210> SEQ ID NO 29
<211> LENGTH: 269
<212> TYPE: PRT
<213> ORGANISM: Artificial Sequence
```

<220> FEATURE:
<223> OTHER INFORMATION: Synthetic Construct

<400> SEQUENCE: 29

Met Arg Leu Val Ala Arg Val Thr Val Phe Leu Thr Phe Gly Thr Ile
1 5 10 15

Ile Asp Ala Lys Thr Thr Gln Pro Pro Ser Met Asp Cys Ala Glu Gly
20 25 30

Arg Ala Ala Asn Leu Pro Cys Asn His Ser Thr Ile Ser Gly Asn Glu
35 40 45

Tyr Val Tyr Trp Tyr Arg Gln Ile His Ser Gln Gly Pro Gln Tyr Ile
50 55 60

Ile His Gly Leu Lys Asn Asn Glu Thr Asn Glu Met Ala Ser Leu Ile
65 70 75 80

Ile Thr Glu Asp Arg Lys Ser Ser Thr Leu Ile Leu Pro His Ala Thr
85 90 95

Leu Arg Asp Thr Ala Val Tyr Tyr Cys Ile Val Arg Ala Trp Tyr Asn
100 105 110

Asn Asn Asp Met Arg Phe Gly Ala Gly Thr Arg Leu Thr Val Lys Pro
115 120 125

Asn Ile Gln Asn Pro Asp Pro Ala Val Tyr Gln Leu Arg Asp Ser Lys
130 135 140

Ser Ser Asp Lys Ser Val Cys Leu Phe Thr Asp Phe Asp Ser Gln Thr
145 150 155 160

Asn Val Ser Gln Ser Lys Asp Ser Asp Val Tyr Ile Thr Asp Lys Thr
165 170 175

Val Leu Asp Met Arg Ser Met Asp Phe Lys Ser Asn Ser Ala Val Ala
180 185 190

Trp Ser Asn Lys Ser Asp Phe Ala Cys Ala Asn Ala Phe Asn Asn Ser
195 200 205

Ile Ile Pro Glu Asp Thr Phe Phe Pro Ser Pro Glu Ser Ser Cys Asp
210 215 220

Val Lys Leu Val Glu Lys Ser Phe Glu Thr Asp Thr Asn Leu Asn Phe
225 230 235 240

Gln Asn Leu Ser Val Ile Gly Phe Arg Ile Leu Leu Leu Lys Val Ala
245 250 255

Gly Phe Asn Leu Leu Met Thr Leu Arg Leu Trp Ser Ser
260 265

<210> SEQ ID NO 30
<211> LENGTH: 807
<212> TYPE: DNA
<213> ORGANISM: Artificial Sequence
<220> FEATURE:
<223> OTHER INFORMATION: Synthetic Construct

<400> SEQUENCE: 30
atgaggctgg tggcaagagt aactgtgttt ctgacctttg gaactataat tgatgctaag 60
accacccagc ccccctccat ggattgcgct gaaggaagag ctgcaaacct gccttgtaat 120
cactctacca tcagtggaaa tgagtatgtg tattggtatc gacagattca ctcccagggg 180
ccacagtata tcattcatgg tctaaaaaac aatgaaacca atgaaatggc ctctctgatc 240
atcacagaag acagaaagtc cagcaccttg atcctgcccc acgctacgct gagagacact 300
gctgtgtact attgcatcgt cagagcttgg tacaataaca atgacatgcg ctttggagca 360
gggaccagac tgacagtaaa accaaatatc cagaaccctg accctgccgt gtaccagctg 420

```
agagactcta aatccagtga caagtctgtc tgcctattca ccgattttga ttctcaaaca    480

aatgtgtcac aaagtaagga ttctgatgtg tatatcacag acaaaactgt gctagacatg    540

aggtctatgg acttcaagag caacagtgct gtggcctgga gcaacaaatc tgactttgca    600

tgtgcaaacg ccttcaacaa cagcattatt ccagaagaca ccttcttccc cagcccagaa    660

agttcctgtg atgtcaagct ggtcgagaaa agctttgaaa cagatacgaa cctaaacttt    720

caaaacctgt cagtgattgg gttccgaatc ctcctcctga aagtggccgg gtttaatctg    780

ctcatgacgc tgcggctgtg gtccagc                                        807


<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Cys Ala Ser Arg Asp Thr Glu Ala Phe Phe
1               5                   10


<210> SEQ ID NO 32
<211> LENGTH: 306
<212> TYPE: PRT
<213> ORGANISM: Artificial Sequence
<220> FEATURE:
<223> OTHER INFORMATION: Synthetic Construct

<400> SEQUENCE: 32

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Arg Asp Thr Glu Ala Phe Phe Gly Gln Gly Thr Arg Leu Thr Val
        115                 120                 125

Val Glu Asp Leu Asn Lys Val Phe Pro Pro Glu Val Ala Val Phe Glu
    130                 135                 140

Pro Ser Glu Ala Glu Ile Ser His Thr Gln Lys Ala Thr Leu Val Cys
145                 150                 155                 160

Leu Ala Thr Gly Phe Phe Pro Asp His Val Glu Leu Ser Trp Trp Val
                165                 170                 175

Asn Gly Lys Glu Val His Ser Gly Val Ser Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
    210                 215                 220
```

```
Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Val Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Ala Leu Val Leu Met Ala Met Val Lys Arg Lys
    290                 295                 300

Asp Phe
305
```

<210> SEQ ID NO 33
<211> LENGTH: 918
<212> TYPE: DNA
<213> ORGANISM: Artificial Sequence
<220> FEATURE:
<223> OTHER INFORMATION: Synthetic Construct

<400> SEQUENCE: 33

```
atgggcacca ggctcctctg ctgggcggcc ctctgtctcc tgggagcaga actcacagaa     60

gctggagttg cccagtctcc cagatataag attatagaga aaaggcagag tgtggctttt    120

tggtgcaatc ctatatctgg ccatgctacc ctttactggt accagcagat cctgggacag    180

ggcccaaagc ttctgattca gtttcagaat aacggtgtag tggatgattc acagttgcct    240

aaggatcgat tttctgcaga gaggctcaaa ggagtagact ccactctcaa gatccagcct    300

gcaaagcttg aggactcggc cgtgtatctc tgtgccagca gggacactga agctttcttt    360

ggacaaggca ccagactcac agttgtagag gacctgaaca aggtgttccc acccgaggtc    420

gctgtgtttg agccatcaga agcagagatc tcccacaccc aaaaggccac actggtgtgc    480

ctggccacag gcttcttccc cgaccacgtg gagctgagct ggtgggtgaa tgggaaggag    540

gtgcacagtg ggtcagcac ggacccgcag cccctcaagg agcagcccgc cctcaatgac    600

tccagatact gcctgagcag ccgcctgagg gtctcggcca ccttctggca gaaccccccgc   660

aaccacttcc gctgtcaagt ccagttctac gggctctcgg agaatgacga gtggacccag    720

gatagggcca aacccgtcac ccagatcgtc agcgccgagg cctggggtag agcagactgt    780

ggctttacct cggtgtccta ccagcaaggg gtcctgtctg ccaccatcct ctatgagatc    840

ctgctaggga aggccaccct gtatgctgtg ctggtcagcg cccttgtgtt gatggccatg    900

gtcaagagaa aggatttc                                                  918
```

<210> SEQ ID NO 34
<211> LENGTH: 14
<212> TYPE: PRT
<213> ORGANISM: Artificial Sequence
<220> FEATURE:
<223> OTHER INFORMATION: Synthetic Construct

<400> SEQUENCE: 34

```
Cys Val Val Asn Met Arg Asp Ser Ser Tyr Lys Leu Ile Phe
1               5                   10
```

<210> SEQ ID NO 35
<211> LENGTH: 273
<212> TYPE: PRT
<213> ORGANISM: Artificial Sequence
<220> FEATURE:
<223> OTHER INFORMATION: Synthetic Construct

<400> SEQUENCE: 35

Met Ile Ser Leu Arg Val Leu Leu Val Ile Leu Trp Leu Gln Leu Ser
1 5 10 15

Trp Val Trp Ser Gln Arg Lys Glu Val Glu Gln Asp Pro Gly Pro Phe
20 25 30

Asn Val Pro Glu Gly Ala Thr Val Ala Phe Asn Cys Thr Tyr Ser Asn
35 40 45

Ser Ala Ser Gln Ser Phe Phe Trp Tyr Arg Gln Asp Cys Arg Lys Glu
50 55 60

Pro Lys Leu Leu Met Ser Val Tyr Ser Ser Gly Asn Glu Asp Gly Arg
65 70 75 80

Phe Thr Ala Gln Leu Asn Arg Ala Ser Gln Tyr Ile Ser Leu Leu Ile
85 90 95

Arg Asp Ser Lys Leu Ser Asp Ser Ala Thr Tyr Leu Cys Val Val Asn
100 105 110

Met Arg Asp Ser Ser Tyr Lys Leu Ile Phe Gly Ser Gly Thr Arg Leu
115 120 125

Leu Val Arg Pro Asp Ile Gln Asn Pro Asp Pro Ala Val Tyr Gln Leu
130 135 140

Arg Asp Ser Lys Ser Ser Asp Lys Ser Val Cys Leu Phe Thr Asp Phe
145 150 155 160

Asp Ser Gln Thr Asn Val Ser Gln Ser Lys Asp Ser Asp Val Tyr Ile
165 170 175

Thr Asp Lys Thr Val Leu Asp Met Arg Ser Met Asp Phe Lys Ser Asn
180 185 190

Ser Ala Val Ala Trp Ser Asn Lys Ser Asp Phe Ala Cys Ala Asn Ala
195 200 205

Phe Asn Asn Ser Ile Ile Pro Glu Asp Thr Phe Phe Pro Ser Pro Glu
210 215 220

Ser Ser Cys Asp Val Lys Leu Val Glu Lys Ser Phe Glu Thr Asp Thr
225 230 235 240

Asn Leu Asn Phe Gln Asn Leu Ser Val Ile Gly Phe Arg Ile Leu Leu
245 250 255

Leu Lys Val Ala Gly Phe Asn Leu Leu Met Thr Leu Arg Leu Trp Ser
260 265 270

Ser

<210> SEQ ID NO 36
<211> LENGTH: 819
<212> TYPE: DNA
<213> ORGANISM: Artificial Sequence
<220> FEATURE:
<223> OTHER INFORMATION: Synthetic Construct

<400> SEQUENCE: 36
atgatatcct tgagagtttt actggtgatc ctgtggcttc agttaagctg ggtttggagc 60
caacggaagg aggtggagca ggatcctgga cccttcaatg ttccagaggg agccactgtc 120
gctttcaact gtacttacag caacagtgct tctcagtctt tcttctggta cagacaggat 180
tgcaggaaag aacctaagtt gctgatgtcc gtatactcca gtggtaatga agatggaagg 240
tttacagcac agctcaatag agccagccag tatatttccc tgctcatcag agactccaag 300
ctcagtgatt cagccaccta cctctgtgtg gtgaacatga gggatagcag ctataaattg 360

```
atcttcggga gtgggaccag actgctggtc aggcctgata tccagaaccc tgaccctgcc    420

gtgtaccagc tgagagactc taaatccagt gacaagtctg tctgcctatt caccgatttt    480

gattctcaaa caaatgtgtc acaaagtaag gattctgatg tgtatatcac agacaaaact    540

gtgctagaca tgaggtctat ggacttcaag agcaacagtg ctgtggcctg gagcaacaaa    600

tctgactttg catgtgcaaa cgccttcaac aacagcatta ttccagaaga caccttcttc    660

cccagcccag aaagttcctg tgatgtcaag ctggtcgaga aaagctttga aacagatacg    720

aacctaaact ttcaaaacct gtcagtgatt gggttccgaa tcctcctcct gaaagtggcc    780

gggtttaatc tgctcatgac gctgcggctg tggtccagc                           819
```

```
<210> SEQ ID NO 37
<211> LENGTH: 13
<212> TYPE: PRT
<213> ORGANISM: Artificial Sequence
<220> FEATURE:
<223> OTHER INFORMATION: Synthetic Construct

<400> SEQUENCE: 37

Cys Ser Ala His Glu Arg Ile Thr Asp Thr Gln Tyr Phe
1               5                   10


<210> SEQ ID NO 38
<211> LENGTH: 309
<212> TYPE: PRT
<213> ORGANISM: Artificial Sequence
<220> FEATURE:
<223> OTHER INFORMATION: Synthetic Construct

<400> SEQUENCE: 38

Met Leu Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Lys Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala His
            100                 105                 110

Glu Arg Ile Thr Asp Thr Gln Tyr Phe Gly Pro Gly Thr Arg Leu Thr
        115                 120                 125

Val Leu Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205
```

-continued

```
Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly
305


<210> SEQ ID NO 39
<211> LENGTH: 927
<212> TYPE: DNA
<213> ORGANISM: Artificial Sequence
<220> FEATURE:
<223> OTHER INFORMATION: Synthetic Construct

<400> SEQUENCE: 39

atgctgctgc ttctgctgct tctggggcca gcaggctccg ggcttggtgc tgtcgtctct      60

caacatccga gcagggttat ctgtaagagt ggaacctctg tgaagatcga gtgccgttcc     120

ctggactttc aggccacaac tatgttttgg tatcgtcagt tcccgaaaaa gagtctcatg     180

ctgatggcaa cttccaatga gggctccaag gccacatacg agcaaggcgt cgagaaggac     240

aagtttctca tcaaccatgc aagcctgacc ttgtccactc tgacagtgac cagtgcccat     300

cctgaagaca gcagcttcta catctgcagt gcccatgagc ggatcacaga tacgcagtat     360

tttggcccag gcacccggct gacagtgctc gaggacctga aaaacgtgtt cccacccgag     420

gtcgctgtgt ttgagccatc agaagcagag atctcccaca cccaaaaggc cacactggtg     480

tgcctggcca caggcttcta ccccgaccac gtggagctga gctggtgggt gaatgggaag     540

gaggtgcaca gtggggtcag cacagacccg cagcccctca aggagcagcc cgccctcaat     600

gactccagat actgcctgag cagccgcctg agggtctcgg ccaccttctg gcagaacccc     660

cgcaaccact tccgctgtca agtccagttc tacgggctct cggagaatga cgagtggacc     720

caggataggg ccaaacctgt cacccagatc gtcagcgccg aggcctgggg tagagcagac     780

tgtggcttca cctccgagtc ttaccagcaa ggggtcctgt ctgccaccat cctctatgag     840

atcttgctag ggaaggccac cttgtatgcc gtgctggtca gtgccctcgt gctgatggcc     900

atggtcaaga gaaaggattc cagaggc                                         927


<210> SEQ ID NO 40
<211> LENGTH: 14
<212> TYPE: PRT
<213> ORGANISM: Artificial Sequence
<220> FEATURE:
<223> OTHER INFORMATION: Synthetic Construct

<400> SEQUENCE: 40

Cys Val Val Asn Met Lys Asp Ser Ser Tyr Lys Leu Ile Phe
1               5                   10


<210> SEQ ID NO 41
<211> LENGTH: 273
```

<212> TYPE: PRT
<213> ORGANISM: Artificial Sequence
<220> FEATURE:
<223> OTHER INFORMATION: Synthetic Construct

<400> SEQUENCE: 41

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Met Lys Asp Ser Ser Tyr Lys Leu Ile Phe Gly Ser Gly Thr Arg Leu
        115                 120                 125

Leu Val Arg Pro Asp Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 42
<211> LENGTH: 819
<212> TYPE: DNA
<213> ORGANISM: Artificial Sequence
<220> FEATURE:
<223> OTHER INFORMATION: Synthetic Construct

<400> SEQUENCE: 42
atgatatcct tgagagtttt actggtgatc ctgtggcttc agttaagctg ggtttggagc 60
caacggaagg aggtggagca ggatcctgga cccttcaatg ttccagaggg agccactgtc 120
gctttcaact gtacttacag caacagtgct tctcagtctt tcttctggta cagacaggat 180
tgcaggaaag aacctaagtt gctgatgtcc gtatactcca gtggtaatga agatggaagg 240
tttacagcac agctcaatag agccagccag tatatttccc tgctcatcag agactccaag 300

-continued

```
ctcagtgatt cagccaccta cctctgtgtg gtgaacatga aggatagcag ctataaattg    360

atcttcggga gtgggaccag actgctggtc aggcctgata tccagaaccc tgaccctgcc    420

gtgtaccagc tgagagactc taaatccagt gacaagtctg tctgcctatt caccgatttt    480

gattctcaaa caaatgtgtc acaaagtaag gattctgatg tgtatatcac agacaaaact    540

gtgctagaca tgaggtctat ggacttcaag agcaacagtg ctgtggcctg gagcaacaaa    600

tctgactttg catgtgcaaa cgccttcaac aacagcatta ttccagaaga caccttcttc    660

cccagcccag aaagttcctg tgatgtcaag ctggtcgaga aaagctttga aacagatacg    720

aacctaaact ttcaaaacct gtcagtgatt gggttccgaa tcctcctcct gaaagtggcc    780

gggtttaatc tgctcatgac gctgcggctg tggtccagc                           819
```

<210> SEQ ID NO 43
<211> LENGTH: 15
<212> TYPE: PRT
<213> ORGANISM: Artificial Sequence
<220> FEATURE:
<223> OTHER INFORMATION: Synthetic Construct

<400> SEQUENCE: 43

```
Cys Ser Ala Leu Glu Gly Thr Ser Gly Lys Glu Thr Gln Tyr Phe
1               5                   10                  15
```

<210> SEQ ID NO 44
<211> LENGTH: 311
<212> TYPE: PRT
<213> ORGANISM: Artificial Sequence
<220> FEATURE:
<223> OTHER INFORMATION: Synthetic Construct

<400> SEQUENCE: 44

```
Met Leu Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Lys Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Leu
            100                 105                 110

Glu Gly Thr Ser Gly Lys Glu Thr Gln Tyr Phe Gly Pro Gly Thr Arg
        115                 120                 125

Leu Leu Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
```

-continued

```
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310


<210> SEQ ID NO 45
<211> LENGTH: 933
<212> TYPE: DNA
<213> ORGANISM: Artificial Sequence
<220> FEATURE:
<223> OTHER INFORMATION: Synthetic Construct

<400> SEQUENCE: 45

atgctgctgc ttctgctgct tctggggcca gcaggctccg ggcttggtgc tgtcgtctct      60

caacatccga gcagggttat ctgtaagagt ggaacctctg tgaagatcga gtgccgttcc     120

ctggactttc aggccacaac tatgttttgg tatcgtcagt tcccgaaaaa gagtctcatg     180

ctgatggcaa cttccaatga gggctccaag gccacatacg agcaaggcgt cgagaaggac     240

aagtttctca tcaaccatgc aagcctgacc ttgtccactc tgacagtgac cagtgcccat     300

cctgaagaca gcagcttcta catctgcagt gctttagagg ggactagcgg gaaagagacc     360

cagtacttcg ggccaggcac gcggctcctg gtgctcgagg acctgaaaaa cgtgttccca     420

cccgaggtcg ctgtgtttga gccatcagaa gcagagatct cccacaccca aaaggccaca     480

ctggtgtgcc tggccacagg cttctacccc gaccacgtgg agctgagctg gtgggtgaat     540

gggaaggagg tgcacagtgg ggtcagcaca gacccgcagc ccctcaagga gcagcccgcc     600

ctcaatgact ccagatactg cctgagcagc cgcctgaggg tctcggccac cttctggcag     660

aacccccgca accacttccg ctgtcaagtc cagttctacg ggctctcgga gaatgacgag     720

tggacccagg atagggccaa acctgtcacc cagatcgtca gcgccgaggc ctggggtaga     780

gcagactgtg gcttcacctc cgagtcttac cagcaagggg tcctgtctgc caccatcctc     840

tatgagatct tgctagggaa ggccaccttg tatgccgtgc tggtcagtgc cctcgtgctg     900

atggccatgg tcaagagaaa ggattccaga ggc                                  933


<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Cys Ala Gly Pro Gly Asn Gln Phe Tyr Phe
1               5                   10
```

<210> SEQ ID NO 47
<211> LENGTH: 267
<212> TYPE: PRT
<213> ORGANISM: Artificial Sequence
<220> FEATURE:
<223> OTHER INFORMATION: Synthetic Construct

<400> SEQUENCE: 47

```
Met Leu Leu Ile Thr Ser Met Leu Val Leu Trp Met Gln Leu Ser Gln
1               5                   10                  15

Val Asn Gly Gln Gln Val Met Gln Ile Pro Gln Tyr Gln His Val Gln
            20                  25                  30

Glu Gly Glu Asp Phe Thr Thr Tyr Cys Asn Ser Ser Thr Thr Leu Ser
        35                  40                  45

Asn Ile Gln Trp Tyr Lys Gln Arg Pro Gly Gly His Pro Val Phe Leu
    50                  55                  60

Ile Gln Leu Val Lys Ser Gly Glu Val Lys Lys Gln Lys Arg Leu Thr
65                  70                  75                  80

Phe Gln Phe Gly Glu Ala Lys Lys Asn Ser Ser Leu His Ile Thr Ala
                85                  90                  95

Thr Gln Thr Thr Asp Val Gly Thr Tyr Phe Cys Ala Gly Pro Gly Asn
            100                 105                 110

Gln Phe Tyr Phe Gly Thr Gly Thr Ser Leu Thr Val Ile Pro Asn Ile
        115                 120                 125

Gln Asn Pro Asp Pro Ala Val Tyr Gln Leu Arg Asp Ser Lys Ser Ser
    130                 135                 140

Asp Lys Ser Val Cys Leu Phe Thr Asp Phe Asp Ser Gln Thr Asn Val
145                 150                 155                 160

Ser Gln Ser Lys Asp Ser Asp Val Tyr Ile Thr Asp Lys Thr Val Leu
                165                 170                 175

Asp Met Arg Ser Met Asp Phe Lys Ser Asn Ser Ala Val Ala Trp Ser
            180                 185                 190

Asn Lys Ser Asp Phe Ala Cys Ala Asn Ala Phe Asn Asn Ser Ile Ile
        195                 200                 205

Pro Glu Asp Thr Phe Phe Pro Ser Pro Glu Ser Ser Cys Asp Val Lys
    210                 215                 220

Leu Val Glu Lys Ser Phe Glu Thr Asp Thr Asn Leu Asn Phe Gln Asn
225                 230                 235                 240

Leu Ser Val Ile Gly Phe Arg Ile Leu Leu Leu Lys Val Ala Gly Phe
                245                 250                 255

Asn Leu Leu Met Thr Leu Arg Leu Trp Ser Ser
            260                 265
```

<210> SEQ ID NO 48
<211> LENGTH: 801
<212> TYPE: DNA
<213> ORGANISM: Artificial Sequence
<220> FEATURE:
<223> OTHER INFORMATION: Synthetic Construct

<400> SEQUENCE: 48

```
atgctactca tcacatcaat gttggtctta tggatgcaat tgtcacaggt gaatggacaa     60

caggtaatgc aaattcctca gtaccagcat gtacaagaag gagaggactt caccacgtac    120

tgcaattcct caactacttt aagcaatata cagtggtata agcaaaggcc tggtggacat    180

cccgtttttt tgatacagtt agtgaagagt ggagaagtga agaagcagaa aagactgaca    240

tttcagtttg gagaagcaaa aaagaacagc tccctgcaca tcacagccac ccagactaca    300
```

```
gatgtaggaa cctacttctg tgcagggccc ggtaaccagt tctattttgg gacagggaca    360

agtttgacgg tcattccaaa tatccagaac cctgaccctg ccgtgtacca gctgagagac    420

tctaaatcca gtgacaagtc tgtctgccta ttcaccgatt ttgattctca aacaaatgtg    480

tcacaaagta aggattctga tgtgtatatc acagacaaaa ctgtgctaga catgaggtct    540

atggacttca agagcaacag tgctgtggcc tggagcaaca aatctgactt tgcatgtgca    600

aacgccttca acaacagcat tattccagaa gacaccttct tccccagccc agaaagttcc    660

tgtgatgtca agctggtcga gaaaagcttt gaaacagata cgaacctaaa ctttcaaaac    720

ctgtcagtga ttgggttccg aatcctcctc ctgaaagtgg ccgggtttaa tctgctcatg    780

acgctgcggc tgtggtccag c                                               801


<210> SEQ ID NO 49
<211> LENGTH: 14
<212> TYPE: PRT
<213> ORGANISM: Artificial Sequence
<220> FEATURE:
<223> OTHER INFORMATION: Synthetic Construct

<400> SEQUENCE: 49

Cys Ala Ser Ser Ser Trp Asp Arg Asp Gln Pro Gln His Phe
1               5                   10


<210> SEQ ID NO 50
<211> LENGTH: 309
<212> TYPE: PRT
<213> ORGANISM: Artificial Sequence
<220> FEATURE:
<223> OTHER INFORMATION: Synthetic Construct

<400> SEQUENCE: 50

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Ser Trp Asp Arg Asp Gln Pro Gln His Phe Gly Asp Gly Thr Arg
        115                 120                 125

Leu Ser Ile Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
```

```
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305


<210> SEQ ID NO 51
<211> LENGTH: 927
<212> TYPE: DNA
<213> ORGANISM: Artificial Sequence
<220> FEATURE:
<223> OTHER INFORMATION: Synthetic Construct

<400> SEQUENCE: 51

atgagcatcg gcctcctgtg ctgtgcagcc ttgtctctcc tgtgggcagg tccagtgaat     60

gctggtgtca ctcagacccc aaaattccag gtcctgaaga caggacagag catgacactg    120

cagtgtgccc aggatatgaa ccatgaatac atgtcctggt atcgacaaga cccaggcatg    180

gggctgaggc tgattcatta ctcagttggt gctggtatca ctgaccaagg agaagtcccc    240

aatggctaca atgtctccag atcaaccaca gaggatttcc cgctcaggct gctgtcggct    300

gctccctccc agacatctgt gtacttctgt gccagcagtt catgggacag ggatcagccc    360

cagcattttg gtgatgggac tcgactctcc atcctagagg acctgaacaa ggtgttccca    420

cccgaggtcg ctgtgtttga gccatcagaa gcagagatct cccacaccca aaaggccaca    480

ctggtgtgcc tggccacagg cttcttcccc gaccacgtgg agctgagctg gtgggtgaat    540

gggaaggagg tgcacagtgg ggtcagcacg gacccgcagc ccctcaagga gcagcccgcc    600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acccgtcacc cagatcgtca gcgccgaggc ctggggtaga    780

gcagactgtg gctttacctc ggtgtcctac cagcaagggg tcctgtctgc caccatcctc    840

tatgagatcc tgctagggaa ggccaccctg tatgctgtgc tggtcagcgc ccttgtgttg    900

atggccatgg tcaagagaaa ggatttc                                        927


<210> SEQ ID NO 52
<211> LENGTH: 16
<212> TYPE: PRT
<213> ORGANISM: Artificial Sequence
<220> FEATURE:
<223> OTHER INFORMATION: Synthetic Construct

<400> SEQUENCE: 52

Cys Ala Leu Ser Ala Leu Pro Tyr Asn Gln Gly Gly Lys Leu Ile Phe
1               5                   10                  15
```

-continued

<210> SEQ ID NO 53
<211> LENGTH: 272
<212> TYPE: PRT
<213> ORGANISM: Artificial Sequence
<220> FEATURE:
<223> OTHER INFORMATION: Synthetic Construct

<400> SEQUENCE: 53

Met Lys Pro Thr Leu Ile Ser Val Leu Val Ile Ile Phe Ile Leu Arg
1 5 10 15

Gly Thr Arg Ala Gln Arg Val Thr Gln Pro Glu Lys Leu Leu Ser Val
20 25 30

Phe Lys Gly Ala Pro Val Glu Leu Lys Cys Asn Tyr Ser Tyr Ser Gly
35 40 45

Ser Pro Glu Leu Phe Trp Tyr Val Gln Tyr Ser Arg Gln Arg Leu Gln
50 55 60

Leu Leu Leu Arg His Ile Ser Arg Glu Ser Ile Lys Gly Phe Thr Ala
65 70 75 80

Asp Leu Asn Lys Gly Glu Thr Ser Phe His Leu Lys Lys Pro Phe Ala
85 90 95

Gln Glu Glu Asp Ser Ala Met Tyr Tyr Cys Ala Leu Ser Ala Leu Pro
100 105 110

Tyr Asn Gln Gly Gly Lys Leu Ile Phe Gly Gln Gly Thr Glu Leu Ser
115 120 125

Val Lys Pro Asn Ile Gln Asn Pro Asp Pro Ala Val Tyr Gln Leu Arg
130 135 140

Asp Ser Lys Ser Ser Asp Lys Ser Val Cys Leu Phe Thr Asp Phe Asp
145 150 155 160

Ser Gln Thr Asn Val Ser Gln Ser Lys Asp Ser Asp Val Tyr Ile Thr
165 170 175

Asp Lys Thr Val Leu Asp Met Arg Ser Met Asp Phe Lys Ser Asn Ser
180 185 190

Ala Val Ala Trp Ser Asn Lys Ser Asp Phe Ala Cys Ala Asn Ala Phe
195 200 205

Asn Asn Ser Ile Ile Pro Glu Asp Thr Phe Phe Pro Ser Pro Glu Ser
210 215 220

Ser Cys Asp Val Lys Leu Val Glu Lys Ser Phe Glu Thr Asp Thr Asn
225 230 235 240

Leu Asn Phe Gln Asn Leu Ser Val Ile Gly Phe Arg Ile Leu Leu Leu
245 250 255

Lys Val Ala Gly Phe Asn Leu Leu Met Thr Leu Arg Leu Trp Ser Ser
260 265 270

<210> SEQ ID NO 54
<211> LENGTH: 816
<212> TYPE: DNA
<213> ORGANISM: Artificial Sequence
<220> FEATURE:
<223> OTHER INFORMATION: Synthetic Construct

<400> SEQUENCE: 54
atgaagccca ccctcatctc agtgcttgtg ataatattta tactcagagg aacaagagcc 60
cagagagtga ctcagcccga gaagctcctc tctgtcttta aaggggcccc agtggagctg 120
aagtgcaact attcctattc tgggagtcct gaactcttct ggtatgtcca gtactccaga 180
caacgcctcc agttactctt gagacacatc tctagagaga gcatcaaagg cttcactgct 240
gaccttaaca aaggcgagac atctttccac ctgaagaaac catttgctca agaggaagac 300

```
tcagccatgt attactgtgc tctaagtgcc ctcccctata accagggagg aaagcttatc    360

ttcggacagg gaacggagtt atctgtgaaa cccaatatcc agaaccctga ccctgccgtg    420

taccagctga gagactctaa atccagtgac aagtctgtct gcctattcac cgattttgat    480

tctcaaacaa atgtgtcaca aagtaaggat tctgatgtgt atatcacaga caaaactgtg    540

ctagacatga ggtctatgga cttcaagagc aacagtgctg tggcctggag caacaaatct    600

gactttgcat gtgcaaacgc cttcaacaac agcattattc cagaagacac cttcttcccc    660

agcccagaaa gttcctgtga tgtcaagctg gtcgagaaaa gctttgaaac agatacgaac    720

ctaaactttc aaaacctgtc agtgattggg ttccgaatcc tcctcctgaa agtggccggg    780

tttaatctgc tcatgacgct gcggctgtgg tccagc                               816
```

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

```
Cys Ala Trp Ala Arg Ser Arg Glu Leu Phe Phe
1               5                   10
```

<210> SEQ ID NO 56
<211> LENGTH: 306
<212> TYPE: PRT
<213> ORGANISM: Artificial Sequence
<220> FEATURE:
<223> OTHER INFORMATION: Synthetic Construct

<400> SEQUENCE: 56

```
Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
            20                  25                  30

Gly Ser Pro Leu Ser Leu Glu Cys Thr Val Glu Gly Thr Ser Asn Pro
        35                  40                  45

Asn Leu Tyr Trp Tyr Arg Gln Ala Ala Gly Arg Gly Leu Gln Leu Leu
    50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ala Arg
            100                 105                 110

Ser Arg Glu Leu Phe Phe Gly Glu Gly Ser Arg Leu Thr Val Leu Glu
        115                 120                 125

Asp Leu Lys Asn Val Phe Pro Pro Glu Val Ala Val Phe Glu Pro Ser
    130                 135                 140

Glu Ala Glu Ile Ser His Thr Gln Lys Ala Thr Leu Val Cys Leu Ala
145                 150                 155                 160

Thr Gly Phe Tyr Pro Asp His Val Glu Leu Ser Trp Trp Val Asn Gly
                165                 170                 175

Lys Glu Val His Ser Gly Val Ser Thr Asp Pro Gln Pro Leu Lys Glu
            180                 185                 190

Gln Pro Ala Leu Asn Asp Ser Arg Tyr Cys Leu Ser Ser Arg Leu Arg
```

```
        195                 200                 205

Val Ser Ala Thr Phe Trp Gln Asn Pro Arg Asn His Phe Arg Cys Gln
    210                 215                 220

Val Gln Phe Tyr Gly Leu Ser Glu Asn Asp Glu Trp Thr Gln Asp Arg
225                 230                 235                 240

Ala Lys Pro Val Thr Gln Ile Val Ser Ala Glu Ala Trp Gly Arg Ala
                245                 250                 255

Asp Cys Gly Phe Thr Ser Glu Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Ala Leu Val Leu Met Ala Met Val Lys Arg Lys Asp Ser
    290                 295                 300

Arg Gly
305


<210> SEQ ID NO 57
<211> LENGTH: 918
<212> TYPE: DNA
<213> ORGANISM: Artificial Sequence
<220> FEATURE:
<223> OTHER INFORMATION: Synthetic Construct

<400> SEQUENCE: 57

atgctctgct ctctccttgc ccttctcctg ggcactttct ttggggtcag atctcagact      60

attcatcaat ggccagcgac cctggtgcag cctgtgggca gcccgctctc tctggagtgc     120

actgtggagg gaacatcaaa ccccaaccta tactggtacc gacaggctgc aggcaggggc     180

ctccagctgc tcttctactc cgttggtatt ggccagatca gctctgaggt gccccagaat     240

ctctcagcct ccagacccca ggaccggcag ttcatcctga gttctaagaa gctccttctc     300

agtgactctg gcttctatct ctgtgcctgg gcgaggagca gggagctgtt ttttggagaa     360

ggctctaggc tgaccgtact ggaggacctg aaaaacgtgt tcccacccga ggtcgctgtg     420

tttgagccat cagaagcaga gatctcccac acccaaaagg ccacactggt gtgcctggcc     480

acaggcttct accccgacca cgtggagctg agctggtggg tgaatgggaa ggaggtgcac     540

agtggggtca gcacagaccc gcagcccctc aaggagcagc ccgccctcaa tgactccaga     600

tactgcctga gcagccgcct gagggtctcg gccaccttct ggcagaaccc ccgcaaccac     660

ttccgctgtc aagtccagtt ctacgggctc tcggagaatg acgagtggac ccaggatagg     720

gccaaacctg tcacccagat cgtcagcgcc gaggcctggg gtagagcaga ctgtggcttc     780

acctccgagt cttaccagca aggggtcctg tctgccacca tcctctatga gatcttgcta     840

gggaaggcca ccttgtatgc cgtgctggtc agtgccctcg tgctgatggc catggtcaag     900

agaaaggatt ccagaggc                                                   918


<210> SEQ ID NO 58
<211> LENGTH: 13
<212> TYPE: PRT
<213> ORGANISM: Artificial Sequence
<220> FEATURE:
<223> OTHER INFORMATION: Synthetic Construct

<400> SEQUENCE: 58

Cys Ala Phe Tyr Ala Gly Asn Asn Arg Lys Leu Ile Trp
1               5                   10
```

<210> SEQ ID NO 59
<211> LENGTH: 274
<212> TYPE: PRT
<213> ORGANISM: Artificial Sequence
<220> FEATURE:
<223> OTHER INFORMATION: Synthetic Construct

<400> SEQUENCE: 59

Met Met Lys Ser Leu Arg Val Leu Leu Val Ile Leu Trp Leu Gln Leu
1 5 10 15

Ser Trp Val Trp Ser Gln Gln Lys Glu Val Glu Gln Asp Pro Gly Pro
20 25 30

Leu Ser Val Pro Glu Gly Ala Ile Val Ser Leu Asn Cys Thr Tyr Ser
35 40 45

Asn Ser Ala Phe Gln Tyr Phe Met Trp Tyr Arg Gln Tyr Ser Arg Lys
50 55 60

Gly Pro Glu Leu Leu Met Tyr Thr Tyr Ser Ser Gly Asn Lys Glu Asp
65 70 75 80

Gly Arg Phe Thr Ala Gln Val Asp Lys Ser Ser Lys Tyr Ile Ser Leu
85 90 95

Phe Ile Arg Asp Ser Gln Pro Ser Asp Ser Ala Thr Tyr Leu Cys Ala
100 105 110

Phe Tyr Ala Gly Asn Asn Arg Lys Leu Ile Trp Gly Leu Gly Thr Ser
115 120 125

Leu Ala Val Asn Pro Asn Ile Gln Asn Pro Asp Pro Ala Val Tyr Gln
130 135 140

Leu Arg Asp Ser Lys Ser Ser Asp Lys Ser Val Cys Leu Phe Thr Asp
145 150 155 160

Phe Asp Ser Gln Thr Asn Val Ser Gln Ser Lys Asp Ser Asp Val Tyr
165 170 175

Ile Thr Asp Lys Thr Val Leu Asp Met Arg Ser Met Asp Phe Lys Ser
180 185 190

Asn Ser Ala Val Ala Trp Ser Asn Lys Ser Asp Phe Ala Cys Ala Asn
195 200 205

Ala Phe Asn Asn Ser Ile Ile Pro Glu Asp Thr Phe Phe Pro Ser Pro
210 215 220

Glu Ser Ser Cys Asp Val Lys Leu Val Glu Lys Ser Phe Glu Thr Asp
225 230 235 240

Thr Asn Leu Asn Phe Gln Asn Leu Ser Val Ile Gly Phe Arg Ile Leu
245 250 255

Leu Leu Lys Val Ala Gly Phe Asn Leu Leu Met Thr Leu Arg Leu Trp
260 265 270

Ser Ser

<210> SEQ ID NO 60
<211> LENGTH: 822
<212> TYPE: DNA
<213> ORGANISM: Artificial Sequence
<220> FEATURE:
<223> OTHER INFORMATION: Synthetic Construct

<400> SEQUENCE: 60
atgatgaaat ccttgagagt tttactggtg atcctgtggc ttcagttaag ctgggtttgg 60
agccaacaga aggaggtgga gcaggatcct ggaccactca gtgttccaga gggagccatt 120
gtttctctca actgcactta cagcaacagt gcttttcaat acttcatgtg gtacagacag 180
tattccagaa aaggccctga gttgctgatg tacacatact ccagtggtaa caaagaagat 240

```
ggaaggttta cagcacaggt cgataaatcc agcaagtata tctccttgtt catcagagac    300

tcacagccca gtgattcagc cacctacctc tgtgcattct atgctggcaa caaccgtaag    360

ctgatttggg gattgggaac aagcctggca gtaaatccga atatccagaa ccctgaccct    420

gccgtgtacc agctgagaga ctctaaatcc agtgacaagt ctgtctgcct attcaccgat    480

tttgattctc aaacaaatgt gtcacaaagt aaggattctg atgtgtatat cacagacaaa    540

actgtgctag acatgaggtc tatggacttc aagagcaaca gtgctgtggc ctggagcaac    600

aaatctgact ttgcatgtgc aaacgccttc aacaacagca ttattccaga agacaccttc    660

ttccccagcc cagaaagttc ctgtgatgtc aagctggtcg agaaaagctt tgaaacagat    720

acgaacctaa actttcaaaa cctgtcagtg attgggttcc gaatcctcct cctgaaagtg    780

gccgggttta atctgctcat gacgctgcgg ctgtggtcca gc                       822
```

<210> SEQ ID NO 61
<211> LENGTH: 15
<212> TYPE: PRT
<213> ORGANISM: Artificial Sequence
<220> FEATURE:
<223> OTHER INFORMATION: Synthetic Construct

<400> SEQUENCE: 61

```
Cys Ala Ser Ser Ile Asp Pro Ala Thr Ser His Glu Gln Phe Phe
1               5                   10                  15
```

<210> SEQ ID NO 62
<211> LENGTH: 312
<212> TYPE: PRT
<213> ORGANISM: Artificial Sequence
<220> FEATURE:
<223> OTHER INFORMATION: Synthetic Construct

<400> SEQUENCE: 62

```
Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Asp Pro Ala Thr Ser His Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190
```

Pro Gln Pro Leu Lys Glu Gln Pro Ala Leu Asn Asp Ser Arg Tyr Cys
195 200 205

Leu Ser Ser Arg Leu Arg Val Ser Ala Thr Phe Trp Gln Asn Pro Arg
210 215 220

Asn His Phe Arg Cys Gln Val Gln Phe Tyr Gly Leu Ser Glu Asn Asp
225 230 235 240

Glu Trp Thr Gln Asp Arg Ala Lys Pro Val Thr Gln Ile Val Ser Ala
245 250 255

Glu Ala Trp Gly Arg Ala Asp Cys Gly Phe Thr Ser Glu Ser Tyr Gln
260 265 270

Gln Gly Val Leu Ser Ala Thr Ile Leu Tyr Glu Ile Leu Leu Gly Lys
275 280 285

Ala Thr Leu Tyr Ala Val Leu Val Ser Ala Leu Val Leu Met Ala Met
290 295 300

Val Lys Arg Lys Asp Ser Arg Gly
305 310

<210> SEQ ID NO 63
<211> LENGTH: 936
<212> TYPE: DNA
<213> ORGANISM: Artificial Sequence
<220> FEATURE:
<223> OTHER INFORMATION: Synthetic Construct

<400> SEQUENCE: 63
atgagcaacc aggtgctctg ctgtgtggtc ctttgtttcc tgggagcaaa caccgtggat 60
ggtggaatca ctcagtcccc aaagtacctg ttcagaaagg aaggacagaa tgtgaccctg 120
agttgtgaac agaatttgaa ccacgatgcc atgtactggt accgacagga cccagggcaa 180
gggctgagat tgatctacta ctcacagata gtaaatgact ttcagaaagg agatatagct 240
gaagggtaca gcgtctctcg ggagaagaag gaatcctttc ctctcactgt gacatcggcc 300
caaaagaacc cgacagcttt ctatctctgt gccagtagta tagatccggc gactagtcat 360
gagcagttct tcgggccagg gacacggctc accgtgctag aggacctgaa aaacgtgttc 420
ccacccgagg tcgctgtgtt tgagccatca gaagcagaga tctcccacac ccaaaaggcc 480
acactggtgt gcctggccac aggcttctac cccgaccacg tggagctgag ctggtgggtg 540
aatgggaagg aggtgcacag tggggtcagc acagacccgc agcccctcaa ggagcagccc 600
gccctcaatg actccagata ctgcctgagc agccgcctga gggtctcggc caccttctgg 660
cagaaccccc gcaaccactt ccgctgtcaa gtccagttct acgggctctc ggagaatgac 720
gagtggaccc aggatagggc caaacctgtc acccagatcg tcagcgccga ggcctggggt 780
agagcagact gtggcttcac ctccgagtct taccagcaag ggtcctgtc tgccaccatc 840 ctctatgaga tcttgctagg gaaggccacc ttgtatgccg tgctggtcag tgccctcgtg 900
ctgatggcca tggtcaagag aaaggattcc agaggc 936

<210> SEQ ID NO 64
<211> LENGTH: 12
<212> TYPE: PRT
<213> ORGANISM: Artificial Sequence
<220> FEATURE:
<223> OTHER INFORMATION: Synthetic Construct

<400> SEQUENCE: 64

Cys Ala Leu Ser Gly Arg Arg Asp Asp Met Arg Phe
1 5 10

<210> SEQ ID NO 65
<211> LENGTH: 268
<212> TYPE: PRT
<213> ORGANISM: Artificial Sequence
<220> FEATURE:
<223> OTHER INFORMATION: Synthetic Construct

<400> SEQUENCE: 65

```
Met Lys Pro Thr Leu Ile Ser Val Leu Val Ile Ile Phe Ile Leu Arg
1               5                   10                  15

Gly Thr Arg Ala Gln Arg Val Thr Gln Pro Glu Lys Leu Leu Ser Val
            20                  25                  30

Phe Lys Gly Ala Pro Val Glu Leu Lys Cys Asn Tyr Ser Tyr Ser Gly
        35                  40                  45

Ser Pro Glu Leu Phe Trp Tyr Val Gln Tyr Ser Arg Gln Arg Leu Gln
    50                  55                  60

Leu Leu Leu Arg His Ile Ser Arg Glu Ser Ile Lys Gly Phe Thr Ala
65                  70                  75                  80

Asp Leu Asn Lys Gly Glu Thr Ser Phe His Leu Lys Lys Pro Phe Ala
                85                  90                  95

Gln Glu Glu Asp Ser Ala Met Tyr Tyr Cys Ala Leu Ser Gly Arg Arg
            100                 105                 110

Asp Asp Met Arg Phe Gly Ala Gly Thr Arg Leu Thr Val Lys Pro Asn
        115                 120                 125

Ile Gln Asn Pro Asp Pro Ala Val Tyr Gln Leu Arg Asp Ser Lys Ser
    130                 135                 140

Ser Asp Lys Ser Val Cys Leu Phe Thr Asp Phe Asp Ser Gln Thr Asn
145                 150                 155                 160

Val Ser Gln Ser Lys Asp Ser Asp Val Tyr Ile Thr Asp Lys Thr Val
                165                 170                 175

Leu Asp Met Arg Ser Met Asp Phe Lys Ser Asn Ser Ala Val Ala Trp
            180                 185                 190

Ser Asn Lys Ser Asp Phe Ala Cys Ala Asn Ala Phe Asn Asn Ser Ile
        195                 200                 205

Ile Pro Glu Asp Thr Phe Phe Pro Ser Pro Glu Ser Ser Cys Asp Val
    210                 215                 220

Lys Leu Val Glu Lys Ser Phe Glu Thr Asp Thr Asn Leu Asn Phe Gln
225                 230                 235                 240

Asn Leu Ser Val Ile Gly Phe Arg Ile Leu Leu Leu Lys Val Ala Gly
                245                 250                 255

Phe Asn Leu Leu Met Thr Leu Arg Leu Trp Ser Ser
            260                 265
```

<210> SEQ ID NO 66
<211> LENGTH: 804
<212> TYPE: DNA
<213> ORGANISM: Artificial Sequence
<220> FEATURE:
<223> OTHER INFORMATION: Synthetic Construct

<400> SEQUENCE: 66

```
atgaagccca ccctcatctc agtgcttgtg ataatattta tactcagagg aacaagagcc     60

cagagagtga ctcagcccga gaagctcctc tctgtcttta aaggggcccc agtggagctg    120

aagtgcaact attcctattc tgggagtcct gaactcttct ggtatgtcca gtactccaga    180

caacgcctcc agttactctt gagacacatc tctagagaga gcatcaaagg cttcactgct    240
```

```
gaccttaaca aaggcgagac atctttccac ctgaagaaac catttgctca agaggaagac    300

tcagccatgt attactgtgc tctaagtggc cgtcgggatg acatgcgctt tggagcaggg    360

accagactga cagtaaaacc aaatatccag aaccctgacc ctgccgtgta ccagctgaga    420

gactctaaat ccagtgacaa gtctgtctgc ctattcaccg attttgattc tcaaacaaat    480

gtgtcacaaa gtaaggattc tgatgtgtat atcacagaca aaactgtgct agacatgagg    540

tctatggact tcaagagcaa cagtgctgtg gcctggagca acaaatctga ctttgcatgt    600

gcaaacgcct tcaacaacag cattattcca gaagacacct tcttccccag cccagaaagt    660

tcctgtgatg tcaagctggt cgagaaaagc tttgaaacag atacgaacct aaactttcaa    720

aacctgtcag tgattgggtt ccgaatcctc ctcctgaaag tggccgggtt taatctgctc    780

atgacgctgc ggctgtggtc cagc                                           804


<210> SEQ ID NO 67
<211> LENGTH: 12
<212> TYPE: PRT
<213> ORGANISM: Artificial Sequence
<220> FEATURE:
<223> OTHER INFORMATION: Synthetic Construct

<400> SEQUENCE: 67

Cys Ala Ser Ser Phe Arg Gly Asp Glu Gln Phe Phe
1               5                   10


<210> SEQ ID NO 68
<211> LENGTH: 310
<212> TYPE: PRT
<213> ORGANISM: Artificial Sequence
<220> FEATURE:
<223> OTHER INFORMATION: Synthetic Construct

<400> SEQUENCE: 68

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Phe Arg Gly Asp Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190
```

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 69
<211> LENGTH: 930
<212> TYPE: DNA
<213> ORGANISM: Artificial Sequence
<220> FEATURE:
<223> OTHER INFORMATION: Synthetic Construct

<400> SEQUENCE: 69
atgggcacca gcctcctctg ctggatggcc ctgtgtctcc tgggggcaga tcacgcagat 60
actggagtct cccagaaccc cagacacaag atcacaaaga ggggacagaa tgtaactttc 120
aggtgtgatc caatttctga acacaaccgc ctttattggt accgacagac cctggggcag 180
ggcccagagt ttctgactta cttccagaat gaagctcaac tagaaaaatc aaggctgctc 240
agtgatcggt tctctgcaga gaggcctaag ggatctttct ccaccttgga gatccagcgc 300
acagagcagg gggactcggc catgtatctc tgtgccagca gcttcagggg agacgagcag 360
ttcttcgggc cagggacacg gctcaccgtg ctagaggacc tgaaaaacgt gttcccaccc 420
gaggtcgctg tgtttgagcc atcagaagca gagatctccc acacccaaaa ggccacactg 480
gtgtgcctgg ccacaggctt ctaccccgac cacgtggagc tgagctggtg ggtgaatggg 540
aaggaggtgc acagtggggt cagcacagac ccgcagcccc tcaaggagca gcccgccctc 600
aatgactcca gatactgcct gagcagccgc ctgagggtct cggccacctt ctggcagaac 660
ccccgcaacc acttccgctg tcaagtccag ttctacgggc tctcggagaa tgacgagtgg 720
acccaggata gggccaaacc tgtcacccag atcgtcagcg ccgaggcctg ggtagagca 780 gactgtggct tcacctccga gtcttaccag caaggggtcc tgtctgccac catcctctat 840
gagatcttgc tagggaaggc caccttgtat gccgtgctgg tcagtgccct cgtgctgatg 900
gccatggtca agagaaagga ttccagaggc 930

<210> SEQ ID NO 70
<211> LENGTH: 13
<212> TYPE: PRT
<213> ORGANISM: Artificial Sequence
<220> FEATURE:
<223> OTHER INFORMATION: Synthetic Construct

<400> SEQUENCE: 70

Cys Ala Met Ser Pro Arg Ser Gly Tyr Ala Leu Asn Phe
1               5                   10

<210> SEQ ID NO 71
<211> LENGTH: 274
<212> TYPE: PRT
<213> ORGANISM: Artificial Sequence
<220> FEATURE:
<223> OTHER INFORMATION: Synthetic Construct

<400> SEQUENCE: 71

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Pro Arg Ser Gly Tyr Ala Leu Asn Phe Gly Lys Gly Thr Ser
        115                 120                 125

Leu Leu Val Thr Pro His Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 72
<211> LENGTH: 822
<212> TYPE: DNA
<213> ORGANISM: Artificial Sequence
<220> FEATURE:
<223> OTHER INFORMATION: Synthetic Construct

<400> SEQUENCE: 72

```
atgatgaaat ccttgagagt tttactggtg atcctgtggc ttcagttaag ctgggtttgg     60

agccaacaga aggaggtgga gcaggatcct ggaccactca gtgttccaga gggagccatt    120

gtttctctca actgcactta cagcaacagt gcttttcaat acttcatgtg gtacagacag    180
```

```
tattccagaa aaggccctga gttgctgatg tacacatact ccagtggtaa caaagaagat    240

ggaaggttta cagcacaggt cgataaatcc agcaagtata tctccttgtt catcagagac    300

tcacagccca gtgattcagc cacctacctc tgtgcaatga gccctcggag cgggtatgca    360

ctcaacttcg gcaaaggcac ctcgctgttg gtcacacccc atatccagaa ccctgaccct    420

gccgtgtacc agctgagaga ctctaaatcc agtgacaagt ctgtctgcct attcaccgat    480

tttgattctc aaacaaatgt gtcacaaagt aaggattctg atgtgtatat cacagacaaa    540

actgtgctag acatgaggtc tatggacttc aagagcaaca gtgctgtggc ctggagcaac    600

aaatctgact ttgcatgtgc aaacgccttc aacaacagca ttattccaga agacaccttc    660

ttccccagcc cagaaagttc ctgtgatgtc aagctggtcg agaaaagctt tgaaacagat    720

acgaacctaa actttcaaaa cctgtcagtg attgggttcc gaatcctcct cctgaaagtg    780

gccgggttta atctgctcat gacgctgcgg ctgtggtcca gc                       822
```

```
<210> SEQ ID NO 73
<211> LENGTH: 15
<212> TYPE: PRT
<213> ORGANISM: Artificial Sequence
<220> FEATURE:
<223> OTHER INFORMATION: Synthetic Construct

<400> SEQUENCE: 73

Cys Ala Ser Ser Met Asp Ala Ala Leu Gly Glu Lys Leu Phe Phe
1               5                   10                  15


<210> SEQ ID NO 74
<211> LENGTH: 310
<212> TYPE: PRT
<213> ORGANISM: Artificial Sequence
<220> FEATURE:
<223> OTHER INFORMATION: Synthetic Construct

<400> SEQUENCE: 74

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Met Asp Ala Ala Leu Gly Glu Lys Leu Phe Phe Gly Ser Gly Thr
        115                 120                 125

Gln Leu Ser Val Leu Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175
```

-continued

```
Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310
```

<210> SEQ ID NO 75
<211> LENGTH: 930
<212> TYPE: DNA
<213> ORGANISM: Artificial Sequence
<220> FEATURE:
<223> OTHER INFORMATION: Synthetic Construct

<400> SEQUENCE: 75

```
atgagcaacc aggtgctctg ctgtgtggtc ctttgtttcc tgggagcaaa caccgtggat      60

ggtggaatca ctcagtcccc aaagtacctg ttcagaaagg aaggacagaa tgtgaccctg     120

agttgtgaac agaatttgaa ccacgatgcc atgtactggt accgacagga cccagggcaa     180

gggctgagat tgatctacta ctcacagata gtaaatgact ttcagaaagg agatatagct     240

gaagggtaca gcgtctctcg ggagaagaag gaatcctttc ctctcactgt gacatcggcc     300

caaaagaacc cgacagcttt ctatctctgt gccagtagta tggacgccgc cttgggtgaa     360

aaactgtttt ttggcagtgg aacccagctc tctgtcttgg aggacctgaa caaggtgttc     420

ccacccgagg tcgctgtgtt tgagccatca gaagcagaga tctcccacac ccaaaaggcc     480

acactggtgt gcctggccac aggcttcttc cccgaccacg tggagctgag ctggtgggtg     540

aatgggaagg aggtgcacag tggggtcagc acggacccgc agcccctcaa ggagcagccc     600

gccctcaatg actccagata ctgcctgagc agccgcctga gggtctcggc caccttctgg     660

cagaaccccc gcaaccactt ccgctgtcaa gtccagttct acgggctctc ggagaatgac     720

gagtggaccc aggatagggc caaacccgtc acccagatcg tcagcgccga ggcctggggt     780

agagcagact gtggctttac ctcggtgtcc taccagcaag ggtcctgtc tgccaccatc      840

ctctatgaga tcctgctagg gaaggccacc ctgtatgctg tgctggtcag cgcccttgtg     900

ttgatggcca tggtcaagag aaaggatttc                                      930
```

<210> SEQ ID NO 76
<211> LENGTH: 14
<212> TYPE: PRT
<213> ORGANISM: Artificial Sequence
<220> FEATURE:
<223> OTHER INFORMATION: Synthetic Construct

<400> SEQUENCE: 76

-continued

Cys Ala Leu Arg Ser Gly Gly Ser Asn Tyr Lys Leu Thr Phe
1 5 10

<210> SEQ ID NO 77
<211> LENGTH: 273
<212> TYPE: PRT
<213> ORGANISM: Artificial Sequence
<220> FEATURE:
<223> OTHER INFORMATION: Synthetic Construct

<400> SEQUENCE: 77

Met Asn Tyr Ser Pro Gly Leu Val Ser Leu Ile Leu Leu Leu Leu Gly
1 5 10 15

Arg Thr Arg Gly Asn Ser Val Thr Gln Met Glu Gly Pro Val Thr Leu
20 25 30

Ser Glu Glu Ala Phe Leu Thr Ile Asn Cys Thr Tyr Thr Ala Thr Gly
35 40 45

Tyr Pro Ser Leu Phe Trp Tyr Val Gln Tyr Pro Gly Glu Gly Leu Gln
50 55 60

Leu Leu Leu Lys Ala Thr Lys Ala Asp Asp Lys Gly Ser Asn Lys Gly
65 70 75 80

Phe Glu Ala Thr Tyr Arg Lys Glu Thr Thr Ser Phe His Leu Glu Lys
85 90 95

Gly Ser Val Gln Val Ser Asp Ser Ala Val Tyr Phe Cys Ala Leu Arg
100 105 110

Ser Gly Gly Ser Asn Tyr Lys Leu Thr Phe Gly Lys Gly Thr Leu Leu
115 120 125

Thr Val Asn Pro Asn Ile Gln Asn Pro Asp Pro Ala Val Tyr Gln Leu
130 135 140

Arg Asp Ser Lys Ser Ser Asp Lys Ser Val Cys Leu Phe Thr Asp Phe
145 150 155 160

Asp Ser Gln Thr Asn Val Ser Gln Ser Lys Asp Ser Asp Val Tyr Ile
165 170 175

Thr Asp Lys Thr Val Leu Asp Met Arg Ser Met Asp Phe Lys Ser Asn
180 185 190

Ser Ala Val Ala Trp Ser Asn Lys Ser Asp Phe Ala Cys Ala Asn Ala
195 200 205

Phe Asn Asn Ser Ile Ile Pro Glu Asp Thr Phe Phe Pro Ser Pro Glu
210 215 220

Ser Ser Cys Asp Val Lys Leu Val Glu Lys Ser Phe Glu Thr Asp Thr
225 230 235 240

Asn Leu Asn Phe Gln Asn Leu Ser Val Ile Gly Phe Arg Ile Leu Leu
245 250 255

Leu Lys Val Ala Gly Phe Asn Leu Leu Met Thr Leu Arg Leu Trp Ser
260 265 270

Ser

<210> SEQ ID NO 78
<211> LENGTH: 819
<212> TYPE: DNA
<213> ORGANISM: Artificial Sequence
<220> FEATURE:
<223> OTHER INFORMATION: Synthetic Construct

<400> SEQUENCE: 78
atgaactatt ctccaggctt agtatctctg atactcttac tgcttggaag aacccgtgga 60
aattcagtga cccagatgga agggccagtg actctctcag aagaggcctt cctgactata 120
aactgcacgt acacagccac aggataccct tcccttttct ggtatgtcca atatcctgga 180
gaaggtctac agctcctcct gaaagccacg aaggctgatg acaagggaag caacaaaggt 240
tttgaagcca cataccgtaa agaaaccact tctttccact tggagaaagg ctcagttcaa 300
gtgtcagact cagcggtgta cttctgtgct ctgaggagtg gaggtagcaa ctataaactg 360
acatttggaa aaggaactct cttaaccgtg aatccaaata tccagaaccc tgaccctgcc 420
gtgtaccagc tgagagactc taaatccagt gacaagtctg tctgcctatt caccgatttt 480
gattctcaaa caaatgtgtc acaaagtaag gattctgatg tgtatatcac agacaaaact 540
gtgctagaca tgaggtctat ggacttcaag agcaacagtg ctgtggcctg gagcaacaaa 600
tctgactttg catgtgcaaa cgccttcaac aacagcatta ttccagaaga caccttcttc 660
cccagcccag aaagttcctg tgatgtcaag ctggtcgaga aaagctttga aacagatacg 720
aacctaaact ttcaaaacct gtcagtgatt gggttccgaa tcctcctcct gaaagtggcc 780
gggtttaatc tgctcatgac gctgcggctg tggtccagc 819

<210> SEQ ID NO 79
<211> LENGTH: 14
<212> TYPE: PRT
<213> ORGANISM: Artificial Sequence
<220> FEATURE:
<223> OTHER INFORMATION: Synthetic Construct

<400> SEQUENCE: 79

Cys Ala Ser Ser Val Glu Trp Gly Thr Tyr Glu Gln Tyr Phe
1 5 10

<210> SEQ ID NO 80
<211> LENGTH: 311
<212> TYPE: PRT
<213> ORGANISM: Artificial Sequence
<220> FEATURE:
<223> OTHER INFORMATION: Synthetic Construct

<400> SEQUENCE: 80

Met Gly Phe Arg Leu Leu Cys Cys Val Ala Phe Cys Leu Leu Gly Ala
1 5 10 15

Gly Pro Val Asp Ser Gly Val Thr Gln Thr Pro Lys His Leu Ile Thr
20 25 30

Ala Thr Gly Gln Arg Val Thr Leu Arg Cys Ser Pro Arg Ser Gly Asp
35 40 45

Leu Ser Val Tyr Trp Tyr Gln Gln Ser Leu Asp Gln Gly Leu Gln Phe
50 55 60

Leu Ile Gln Tyr Tyr Asn Gly Glu Glu Arg Ala Lys Gly Asn Ile Leu
65 70 75 80

Glu Arg Phe Ser Ala Gln Gln Phe Pro Asp Leu His Ser Glu Leu Asn
85 90 95

Leu Ser Ser Leu Glu Leu Gly Asp Ser Ala Leu Tyr Phe Cys Ala Ser
100 105 110

Ser Val Glu Trp Gly Thr Tyr Glu Gln Tyr Phe Gly Pro Gly Thr Arg
115 120 125

Leu Thr Val Thr Glu Asp Leu Lys Asn Val Phe Pro Pro Glu Val Ala
130 135 140

Val Phe Glu Pro Ser Glu Ala Glu Ile Ser His Thr Gln Lys Ala Thr
145 150 155 160

Leu Val Cys Leu Ala Thr Gly Phe Tyr Pro Asp His Val Glu Leu Ser

-continued

```
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310
```

<210> SEQ ID NO 81
<211> LENGTH: 933
<212> TYPE: DNA
<213> ORGANISM: Artificial Sequence
<220> FEATURE:
<223> OTHER INFORMATION: Synthetic Construct

<400> SEQUENCE: 81

```
atgggcttca ggctcctctg ctgtgtggcc ttttgtctcc tgggagcagg cccagtggat      60

tctggagtca cacaaacccc aaagcacctg atcacagcaa ctggacagcg agtgacgctg     120

agatgctccc ctaggtctgg agacctctct gtgtactggt accaacagag cctggaccag     180

ggcctccagt tcctcattca gtattataat ggagaagaga gagcaaaagg aaacattctt     240

gaacgattct ccgcacaaca gttccctgac ttgcactctg aactaaacct gagctctctg     300

gagctggggg actcagcttt gtatttctgt gccagcagcg tagaatgggg tacctacgag     360

cagtacttcg ggccgggcac caggctcacg gtcacagagg acctgaaaaa cgtgttccca     420

cccgaggtcg ctgtgtttga gccatcagaa gcagagatct cccacaccca aaaggccaca     480

ctggtgtgcc tggccacagg cttctacccc gaccacgtgg agctgagctg gtgggtgaat     540

gggaaggagg tgcacagtgg ggtcagcaca gacccgcagc ccctcaagga gcagcccgcc     600

ctcaatgact ccagatactg cctgagcagc cgcctgaggg tctcggccac cttctggcag     660

aacccccgca accacttccg ctgtcaagtc cagttctacg ggctctcgga gaatgacgag     720

tggacccagg atagggccaa acctgtcacc cagatcgtca gcgccgaggc ctggggtaga     780

gcagactgtg gcttcacctc cgagtcttac cagcaagggg tcctgtctgc caccatcctc     840

tatgagatct tgctagggaa ggccaccttg tatgccgtgc tggtcagtgc cctcgtgctg     900

atggccatgg tcaagagaaa ggattccaga ggc                                  933
```

<210> SEQ ID NO 82
<211> LENGTH: 15
<212> TYPE: PRT
<213> ORGANISM: Artificial Sequence
<220> FEATURE:
<223> OTHER INFORMATION: Synthetic Construct

<400> SEQUENCE: 82

Ala Lys Glu Ile Lys Ile Lys Leu Gly Ile Leu Leu Gln Lys Pro
1 5 10 15

<210> SEQ ID NO 83
<211> LENGTH: 30
<212> TYPE: PRT
<213> ORGANISM: Artificial Sequence
<220> FEATURE:
<223> OTHER INFORMATION: Synthetic Construct

<400> SEQUENCE: 83

Met Cys Lys Gly Leu Ala Ala Leu Pro His Ser Cys Leu Glu Arg Ala
1 5 10 15

Lys Glu Ile Lys Ile Lys Leu Gly Ile Leu Leu Gln Lys Pro
20 25 30

<210> SEQ ID NO 84
<211> LENGTH: 15
<212> TYPE: PRT
<213> ORGANISM: Artificial Sequence
<220> FEATURE:
<223> OTHER INFORMATION: Synthetic Construct

<400> SEQUENCE: 84

Ala Asp Asp Leu Arg Ala Phe Gln Gln Leu Phe Leu Asn Thr Leu
1 5 10 15

<210> SEQ ID NO 85
<211> LENGTH: 19
<212> TYPE: PRT
<213> ORGANISM: Artificial Sequence
<220> FEATURE:
<223> OTHER INFORMATION: Synthetic Construct

<400> SEQUENCE: 85

Arg Ala Phe Gln Gln Leu Phe Leu Asn Thr Leu Ser Phe Val Cys Pro
1 5 10 15

Trp Cys Ala

<210> SEQ ID NO 86
<211> LENGTH: 30
<212> TYPE: PRT
<213> ORGANISM: Artificial Sequence
<220> FEATURE:
<223> OTHER INFORMATION: Synthetic Construct

<400> SEQUENCE: 86

Val Glu Ser Ser Ala Asp Asp Leu Arg Ala Phe Gln Gln Leu Phe Leu
1 5 10 15

Asn Thr Leu Ser Phe Val Cys Pro Trp Cys Ala Ser Gln Gln
20 25 30

<210> SEQ ID NO 87
<211> LENGTH: 12
<212> TYPE: PRT
<213> ORGANISM: Artificial Sequence
<220> FEATURE:
<223> OTHER INFORMATION: Synthetic Construct

<400> SEQUENCE: 87

Cys Ala Val Tyr Gln Gly Ala Gln Lys Leu Val Phe
1 5 10

<210> SEQ ID NO 88
<211> LENGTH: 272
<212> TYPE: PRT
<213> ORGANISM: Artificial Sequence
<220> FEATURE:
<223> OTHER INFORMATION: Synthetic Construct

<400> SEQUENCE: 88

```
Met Leu Leu Glu Leu Ile Pro Leu Leu Gly Ile His Phe Val Leu Arg
1               5                   10                  15

Thr Ala Arg Ala Gln Ser Val Thr Gln Pro Asp Ile His Ile Thr Val
            20                  25                  30

Ser Glu Gly Ala Ser Leu Glu Leu Arg Cys Asn Tyr Ser Tyr Gly Ala
        35                  40                  45

Thr Pro Tyr Leu Phe Trp Tyr Val Gln Ser Pro Gly Gln Gly Leu Gln
    50                  55                  60

Leu Leu Leu Lys Tyr Phe Ser Gly Asp Thr Leu Val Gln Gly Ile Lys
65                  70                  75                  80

Gly Phe Glu Ala Glu Phe Lys Arg Ser Gln Ser Ser Phe Asn Leu Arg
                85                  90                  95

Lys Pro Ser Val His Trp Ser Asp Ala Ala Glu Tyr Phe Cys Ala Val
            100                 105                 110

Tyr Gln Gly Ala Gln Lys Leu Val Phe Gly Gln Gly Thr Arg Leu Thr
        115                 120                 125

Ile Asn Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270
```

<210> SEQ ID NO 89
<211> LENGTH: 816
<212> TYPE: DNA
<213> ORGANISM: Artificial Sequence
<220> FEATURE:
<223> OTHER INFORMATION: Synthetic Construct

<400> SEQUENCE: 89

```
atgctcctgg agcttatccc actgctgggg atacattttg tcctgagaac tgccagagcc      60

cagtcagtga cccagcctga catccacatc actgtctctg aaggagcctc actggagttg     120

agatgtaact attcctatgg ggcaacacct tatctcttct ggtatgtcca gtcccccggc     180

caaggcctcc agctgctcct gaagtacttt tcaggagaca ctctggttca aggcattaaa     240

ggctttgagg ctgaatttaa gaggagtcaa tcttccttca acctgaggaa accctctgtg     300
```

```
cattggagtg atgctgctga gtacttctgt gctgtgtatc agggagccca gaagctggta    360

tttggccaag gaaccaggct gactatcaac ccaaatatcc agaaccctga ccctgccgtg    420

taccagctga gagactctaa atccagtgac aagtctgtct gcctattcac cgattttgat    480

tctcaaacaa atgtgtcaca aagtaaggat tctgatgtgt atatcacaga caaaactgtg    540

ctagacatga ggtctatgga cttcaagagc aacagtgctg tggcctggag caacaaatct    600

gactttgcat gtgcaaacgc cttcaacaac agcattattc cagaagacac cttcttcccc    660

agcccagaaa gttcctgtga tgtcaagctg gtcgagaaaa gctttgaaac agatacgaac    720

ctaaactttc aaaacctgtc agtgattggg ttccgaatcc tcctcctgaa agtggccggg    780

tttaatctgc tcatgacgct gcggctgtgg tccagc                              816
```

<210> SEQ ID NO 90
<211> LENGTH: 15
<212> TYPE: PRT
<213> ORGANISM: Artificial Sequence
<220> FEATURE:
<223> OTHER INFORMATION: Synthetic Construct

<400> SEQUENCE: 90

```
Cys Ser Ala Pro Trp Leu Ala Gly Leu Tyr Asn Glu Gln Phe Phe
1               5                   10                  15
```

<210> SEQ ID NO 91
<211> LENGTH: 310
<212> TYPE: PRT
<213> ORGANISM: Artificial Sequence
<220> FEATURE:
<223> OTHER INFORMATION: Synthetic Construct

<400> SEQUENCE: 91

```
Met Leu Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Pro Trp
            100                 105                 110

Leu Ala Gly Leu Tyr Asn Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
```

```
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310
```

<210> SEQ ID NO 92
<211> LENGTH: 930
<212> TYPE: DNA
<213> ORGANISM: Artificial Sequence
<220> FEATURE:
<223> OTHER INFORMATION: Synthetic Construct

<400> SEQUENCE: 92

```
atgctgctgc ttctgctgct tctggggcca ggctccgggc ttggtgctgt cgtctctcaa      60

catccgagct gggttatctg taagagtgga acctctgtga agatcgagtg ccgttccctg     120

gactttcagg ccacaactat gttttggtat cgtcagttcc cgaaacagag tctcatgctg     180

atggcaactt ccaatgaggg ctccaaggcc acatacgagc aaggcgtcga gaaggacaag     240

tttctcatca accatgcaag cctgaccttg tccactctga cagtgaccag tgcccatcct     300

gaagacagca gcttctacat ctgcagtgct ccgtggctag cggggttgta caatgagcag     360

ttcttcgggc cagggacacg gctcaccgtg ctagaggacc tgaaaaacgt gttcccaccc     420

gaggtcgctg tgtttgagcc atcagaagca gagatctccc acacccaaaa ggccacactg     480

gtgtgcctgg ccacaggctt ctaccccgac cacgtggagc tgagctggtg ggtgaatggg     540

aaggaggtgc acagtggggt cagcacagac ccgcagcccc tcaaggagca gcccgccctc     600

aatgactcca gatactgcct gagcagccgc ctgagggtct cggccacctt ctggcagaac     660

ccccgcaacc acttccgctg tcaagtccag ttctacgggc tctcggagaa tgacgagtgg     720

acccaggata gggccaaacc tgtcacccag atcgtcagcg ccgaggcctg ggtagagca      780

gactgtggct tcacctccga gtcttaccag caaggggtcc tgtctgccac catcctctat     840

gagatcttgc tagggaaggc caccttgtat gccgtgctgg tcagtgccct cgtgctgatg     900

gccatggtca agagaaagga ttccagaggc                                      930
```

<210> SEQ ID NO 93
<211> LENGTH: 16
<212> TYPE: PRT
<213> ORGANISM: Artificial Sequence
<220> FEATURE:
<223> OTHER INFORMATION: Synthetic Construct

<400> SEQUENCE: 93

```
Cys Val Val Ser Ala Ile Gly Tyr Ser Ser Ala Ser Lys Ile Ile Phe
1               5                   10                  15
```

<210> SEQ ID NO 94
<211> LENGTH: 276
<212> TYPE: PRT
<213> ORGANISM: Artificial Sequence
<220> FEATURE:
<223> OTHER INFORMATION: Synthetic Construct

<400> SEQUENCE: 94

Met Leu Leu Leu Leu Val Pro Val Leu Glu Val Ile Phe Thr Leu Gly
1 5 10 15

Gly Thr Arg Ala Gln Ser Val Thr Gln Leu Asp Ser His Val Ser Val
20 25 30

Ser Glu Gly Thr Pro Val Leu Leu Arg Cys Asn Tyr Ser Ser Ser Tyr
35 40 45

Ser Pro Ser Leu Phe Trp Tyr Val Gln His Pro Asn Lys Gly Leu Gln
50 55 60

Leu Leu Leu Lys Tyr Thr Ser Ala Ala Thr Leu Val Lys Gly Ile Asn
65 70 75 80

Gly Phe Glu Ala Glu Phe Lys Lys Ser Glu Thr Ser Phe His Leu Thr
85 90 95

Lys Pro Ser Ala His Met Ser Asp Ala Ala Glu Tyr Phe Cys Val Val
100 105 110

Ser Ala Ile Gly Tyr Ser Ser Ala Ser Lys Ile Ile Phe Gly Ser Gly
115 120 125

Thr Arg Leu Ser Ile Arg Pro Asn Ile Gln Asn Pro Asp Pro Ala Val
130 135 140

Tyr Gln Leu Arg Asp Ser Lys Ser Ser Asp Lys Ser Val Cys Leu Phe
145 150 155 160

Thr Asp Phe Asp Ser Gln Thr Asn Val Ser Gln Ser Lys Asp Ser Asp
165 170 175

Val Tyr Ile Thr Asp Lys Thr Val Leu Asp Met Arg Ser Met Asp Phe
180 185 190

Lys Ser Asn Ser Ala Val Ala Trp Ser Asn Lys Ser Asp Phe Ala Cys
195 200 205

Ala Asn Ala Phe Asn Asn Ser Ile Ile Pro Glu Asp Thr Phe Phe Pro
210 215 220

Ser Pro Glu Ser Ser Cys Asp Val Lys Leu Val Glu Lys Ser Phe Glu
225 230 235 240

Thr Asp Thr Asn Leu Asn Phe Gln Asn Leu Ser Val Ile Gly Phe Arg
245 250 255

Ile Leu Leu Leu Lys Val Ala Gly Phe Asn Leu Leu Met Thr Leu Arg
260 265 270

Leu Trp Ser Ser
275

<210> SEQ ID NO 95
<211> LENGTH: 828
<212> TYPE: DNA
<213> ORGANISM: Artificial Sequence
<220> FEATURE:
<223> OTHER INFORMATION: Synthetic Construct

<400> SEQUENCE: 95
atgctcctgc tgctcgtccc agtgctcgag gtgattttta ctctgggagg aaccagagcc 60
cagtcggtga cccagcttga cagccacgtc tctgtctctg aaggaacccc ggtgctgctg 120
aggtgcaact actcatcttc ttattcacca tctctcttct ggtatgtgca acaccccaac 180

-continued

```
aaaggactcc agcttctcct gaagtacaca tcagcggcca ccctggttaa aggcatcaac    240

ggttttgagg ctgaatttaa gaagagtgaa acctccttcc acctgacgaa accctcagcc    300

catatgagcg acgcggctga gtacttctgt gttgtgagtg ccattgggta cagcagtgct    360

tccaagataa tctttggatc agggaccaga ctcagcatcc ggccaaatat ccagaaccct    420

gaccctgccg tgtaccagct gagagactct aaatccagtg acaagtctgt ctgcctattc    480

accgattttg attctcaaac aaatgtgtca caaagtaagg attctgatgt gtatatcaca    540

gacaaaactg tgctagacat gaggtctatg gacttcaaga gcaacagtgc tgtggcctgg    600

agcaacaaat ctgactttgc atgtgcaaac gccttcaaca acagcattat tccagaagac    660

accttcttcc ccagcccaga aagttcctgt gatgtcaagc tggtcgagaa aagctttgaa    720

acagatacga acctaaactt tcaaaacctg tcagtgattg ggttccgaat cctcctcctg    780

aaagtggccg ggtttaatct gctcatgacg ctgcggctgt ggtccagc                 828
```

<210> SEQ ID NO 96
<211> LENGTH: 16
<212> TYPE: PRT
<213> ORGANISM: Artificial Sequence
<220> FEATURE:
<223> OTHER INFORMATION: Synthetic Construct

<400> SEQUENCE: 96

```
Cys Ala Ser Ser Leu Val Ala Gly Gly Pro Ala Glu Thr Gln Tyr Phe
1               5                   10                  15
```

<210> SEQ ID NO 97
<211> LENGTH: 314
<212> TYPE: PRT
<213> ORGANISM: Artificial Sequence
<220> FEATURE:
<223> OTHER INFORMATION: Synthetic Construct

<400> SEQUENCE: 97

```
Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Ala Gly Gly Pro Ala Glu Thr Gln Tyr Phe Gly Pro
        115                 120                 125

Gly Thr Arg Leu Leu Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
```

-continued 180 185 190

Thr Asp Pro Gln Pro Leu Lys Glu Gln Pro Ala Leu Asn Asp Ser Arg
195 200 205

Tyr Cys Leu Ser Ser Arg Leu Arg Val Ser Ala Thr Phe Trp Gln Asn
210 215 220

Pro Arg Asn His Phe Arg Cys Gln Val Gln Phe Tyr Gly Leu Ser Glu
225 230 235 240

Asn Asp Glu Trp Thr Gln Asp Arg Ala Lys Pro Val Thr Gln Ile Val
245 250 255

Ser Ala Glu Ala Trp Gly Arg Ala Asp Cys Gly Phe Thr Ser Glu Ser
260 265 270

Tyr Gln Gln Gly Val Leu Ser Ala Thr Ile Leu Tyr Glu Ile Leu Leu
275 280 285

Gly Lys Ala Thr Leu Tyr Ala Val Leu Val Ser Ala Leu Val Leu Met
290 295 300

Ala Met Val Lys Arg Lys Asp Ser Arg Gly
305 310

<210> SEQ ID NO 98
<211> LENGTH: 942
<212> TYPE: DNA
<213> ORGANISM: Artificial Sequence
<220> FEATURE:
<223> OTHER INFORMATION: Synthetic Construct

<400> SEQUENCE: 98
atgggcacca gcctcctctg ctggatggcc ctgtgtctcc tgggggcaga tcacgcagat 60
actggagtct cccagaaccc cagacacaag atcacaaaga ggggacagaa tgtaactttc 120
aggtgtgatc caatttctga acacaaccgc ctttattggt accgacagac cctggggcag 180
ggcccagagt ttctgactta cttccagaat gaagctcaac tagaaaaatc aaggctgctc 240
agtgatcggt tctctgcaga gaggcctaag ggatctttct ccaccttgga gatccagcgc 300
acagagcagg gggactcggc catgtatctc tgtgccagca gcttagttgc gggagggccc 360
gcagagaccc agtacttcgg gccaggcacg cggctcctgg tgctcgagga cctgaaaaac 420
gtgttcccac ccgaggtcgc tgtgtttgag ccatcagaag cagagatctc ccacacccaa 480
aaggccacac tggtgtgcct ggccacaggc ttctaccccg accacgtgga gctgagctgg 540
tgggtgaatg ggaaggaggt gcacagtggg gtcagcacag acccgcagcc cctcaaggag 600
cagcccgccc tcaatgactc cagatactgc ctgagcagcc gcctgagggt ctcggccacc 660
ttctggcaga acccccgcaa ccacttccgc tgtcaagtcc agttctacgg gctctcggag 720
aatgacgagt ggacccagga tagggccaaa cctgtcaccc agatcgtcag cgccgaggcc 780
tggggtagag cagactgtgg cttcacctcc gagtcttacc agcaaggggt cctgtctgcc 840
accatcctct atgagatctt gctagggaag gccaccttgt atgccgtgct ggtcagtgcc 900
ctcgtgctga tggccatggt caagagaaag gattccagag gc 942

<210> SEQ ID NO 99
<211> LENGTH: 22
<212> TYPE: PRT
<213> ORGANISM: Artificial Sequence
<220> FEATURE:
<223> OTHER INFORMATION: Synthetic Construct

<400> SEQUENCE: 99

Gly Ser Gly Ala Thr Asn Phe Ser Leu Leu Lys Gln Ala Gly Asp Val

-continued

```
1               5                   10                  15

Glu Glu Asn Pro Gly Pro
            20


<210> SEQ ID NO 100
<211> LENGTH: 66
<212> TYPE: DNA
<213> ORGANISM: Artificial Sequence
<220> FEATURE:
<223> OTHER INFORMATION: Synthetic Construct

<400> SEQUENCE: 100

ggaagcggcg ccacgaactt ctctctgtta aagcaagcag gagacgtgga agaaaacccc     60

ggtccc                                                                66


<210> SEQ ID NO 101
<211> LENGTH: 19
<212> TYPE: PRT
<213> ORGANISM: Artificial Sequence
<220> FEATURE:
<223> OTHER INFORMATION: Synthetic Construct

<400> SEQUENCE: 101

Met Glu Ala Val Val Thr Thr Leu Pro Arg Glu Gly Gly Val Arg Pro
1               5                   10                  15

Ser Arg Lys


<210> SEQ ID NO 102
<211> LENGTH: 57
<212> TYPE: DNA
<213> ORGANISM: Artificial Sequence
<220> FEATURE:
<223> OTHER INFORMATION: Synthetic Construct

<400> SEQUENCE: 102

atggaggcag tggtcacaac tctccccaga gaaggtggtg tgaggccatc acggaag        57


<210> SEQ ID NO 103
<211> LENGTH: 269
<212> TYPE: PRT
<213> ORGANISM: Artificial Sequence
<220> FEATURE:
<223> OTHER INFORMATION: Synthetic Construct

<400> SEQUENCE: 103

Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Ala Trp Tyr Asn
            100                 105                 110

Asn Asn Asp Met Arg Phe Gly Ala Gly Thr Arg Leu Thr Val Lys Pro
        115                 120                 125
```

```
Asn Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 104
<211> LENGTH: 795
<212> TYPE: DNA
<213> ORGANISM: Artificial Sequence
<220> FEATURE:
<223> OTHER INFORMATION: Synthetic Construct

<400> SEQUENCE: 104

```
atgaggctgg tggcaagagt aactgtgttt ctgacctttg gaactataat tgatgctaag      60

accacccagc ccccctccat ggattgcgct gaaggaagag ctgcaaacct gccttgtaat     120

cactctacca tcagtggaaa tgagtatgtg tattggtatc gacagattca ctcccagggg     180

ccacagtata tcattcatgg tctaaaaaac aatgaaacca atgaaatggc ctctctgatc     240

atcacagaag acagaaagtc cagcaccttg atcctgcccc acgctacgct gagagacact     300

gctgtgtact attgcatcgt cagagcttgg tacaataaca atgacatgcg ctttggagca     360

gggaccagac tgacagtaaa accaaatatc cagaacccag aacctgctgt gtaccagtta     420

aaagatcctc ggtctcagga cagcaccctc tgcctgttca ccgactttga ctcccaaatc     480

aatgtgccga aaaccatgga atctggaacg ttcatcactg acaaaactgt gctggacatg     540

aaagctatgg attccaagag caatggggcc attgcctgga gcaaccagac aagcttcacc     600

tgccaagata tcttcaaaga gaccaacgcc acctacccca gttcagacgt tccctgtgat     660

gccacgttga ctgagaaaag ctttgaaaca gatatgaacc taaactttca aaacctgctg     720

gttatggttc tccgaatcct cctgctgaaa gtagccggat ttaacctgct catgacgctg     780

aggctgtggt ccagt                                                      795
```

<210> SEQ ID NO 105
<211> LENGTH: 302
<212> TYPE: PRT
<213> ORGANISM: Artificial Sequence
<220> FEATURE:
<223> OTHER INFORMATION: Synthetic Construct

<400> SEQUENCE: 105

```
Met Gly Thr Arg Leu Leu Cys Trp Ala Ala Leu Cys Leu Leu Gly Ala
1               5                   10                  15
```

-continued

Glu Leu Thr Glu Ala Gly Val Ala Gln Ser Pro Arg Tyr Lys Ile Ile
20 25 30

Glu Lys Arg Gln Ser Val Ala Phe Trp Cys Asn Pro Ile Ser Gly His
35 40 45

Ala Thr Leu Tyr Trp Tyr Gln Gln Ile Leu Gly Gln Gly Pro Lys Leu
50 55 60

Leu Ile Gln Phe Gln Asn Asn Gly Val Val Asp Asp Ser Gln Leu Pro
65 70 75 80

Lys Asp Arg Phe Ser Ala Glu Arg Leu Lys Gly Val Asp Ser Thr Leu
85 90 95

Lys Ile Gln Pro Ala Lys Leu Glu Asp Ser Ala Val Tyr Leu Cys Ala
100 105 110

Ser Arg Asp Thr Glu Ala Phe Phe Gly Gln Gly Thr Arg Leu Thr Val
115 120 125

Val Glu Asp Leu Arg Asn Val Thr Pro Pro Lys Val Ser Leu Phe Glu
130 135 140

Pro Ser Lys Ala Glu Ile Ala Asn Lys Gln Lys Ala Thr Leu Val Cys
145 150 155 160

Leu Ala Arg Gly Phe Phe Pro Asp His Val Glu Leu Ser Trp Trp Val
165 170 175

Asn Gly Lys Glu Val His Ser Gly Val Ser Thr Asp Pro Gln Ala Tyr
180 185 190

Lys Glu Ser Asn Tyr Ser Tyr Cys Leu Ser Ser Arg Leu Arg Val Ser
195 200 205

Ala Thr Phe Trp His Asn Pro Arg Asn His Phe Arg Cys Gln Val Gln
210 215 220

Phe His Gly Leu Ser Glu Glu Asp Lys Trp Pro Glu Gly Ser Pro Lys
225 230 235 240

Pro Val Thr Gln Asn Ile Ser Ala Glu Ala Trp Gly Arg Ala Asp Cys
245 250 255

Gly Ile Thr Ser Ala Ser Tyr Gln Gln Gly Val Leu Ser Ala Thr Ile
260 265 270

Leu Tyr Glu Ile Leu Leu Gly Lys Ala Thr Leu Tyr Ala Val Leu Val
275 280 285

Ser Thr Leu Val Val Met Ala Met Val Lys Arg Lys Asn Ser
290 295 300

<210> SEQ ID NO 106
<211> LENGTH: 906
<212> TYPE: DNA
<213> ORGANISM: Artificial Sequence
<220> FEATURE:
<223> OTHER INFORMATION: Synthetic Construct

<400> SEQUENCE: 106
atgggcacca ggctcctctg ctgggcggcc ctctgtctcc tgggagcaga actcacagaa 60
gctggagttg cccagtctcc cagatataag attatagaga aaaggcagag tgtggctttt 120
tggtgcaatc ctatatctgg ccatgctacc ctttactggt accagcagat cctgggacag 180
ggcccaaagc ttctgattca gtttcagaat aacggtgtag tggatgattc acagttgcct 240
aaggatcgat tttctgcaga gaggctcaaa ggagtagact ccactctcaa gatccagcct 300
gcaaagcttg aggactcggc cgtgtatctc tgtgccagca gggacactga agctttcttt 360
ggacaaggca ccagactcac agttgtagag gatctgagaa atgtgactcc acccaaggtc 420
tccttgtttg agccatcaaa agcagagatt gcaaacaaac aaaaggctac cctcgtgtgc 480

-continued

```
ttggccaggg gcttcttccc tgaccacgtg gagctgagct ggtgggtgaa tggcaaggag    540

gtccacagtg ggtcagcac ggaccctcag gcctacaagg agagcaatta tagctactgc    600

ctgagcagcc gcctgagggt ctctgctacc ttctggcaca atcctcgcaa ccacttccgc    660

tgccaagtgc agttccatgg gctttcagag gaggacaagt ggccagaggg ctcacccaaa    720

cctgtcacac agaacatcag tgcagaggcc tggggccgag cagactgtgg gattacctca    780

gcatcctatc aacaaggggt cttgtctgcc accatcctct atgagatcct gctagggaaa    840

gccaccctgt atgctgtgct tgtcagtaca ctggtggtga tggctatggt caaaagaaaa    900

aattca                                                               906


<210> SEQ ID NO 107
<211> LENGTH: 269
<212> TYPE: PRT
<213> ORGANISM: Artificial Sequence
<220> FEATURE:
<223> OTHER INFORMATION: Synthetic Construct

<400> SEQUENCE: 107

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Met Arg Asp Ser Ser Tyr Lys Leu Ile Phe Gly Ser Gly Thr Arg Leu
        115                 120                 125

Leu Val Arg Pro Asp Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Leu Val Met Val Leu Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 108
<211> LENGTH: 807
<212> TYPE: DNA
<213> ORGANISM: Artificial Sequence
<220> FEATURE:
<223> OTHER INFORMATION: Synthetic Construct

<400> SEQUENCE: 108
atgatatcct tgagagtttt actggtgatc ctgtggcttc agttaagctg ggtttggagc 60
caacggaagg aggtggagca ggatcctgga cccttcaatg ttccagaggg agccactgtc 120
gctttcaact gtacttacag caacagtgct tctcagtctt tcttctggta cagacaggat 180
tgcaggaaag aacctaagtt gctgatgtcc gtatactcca gtggtaatga agatggaagg 240
tttacagcac agctcaatag agccagccag tatatttccc tgctcatcag agactccaag 300
ctcagtgatt cagccaccta cctctgtgtg gtgaacatga gggatagcag ctataaattg 360
atcttcggga gtgggaccag actgctggtc aggcctgata tccagaaccc agaacctgct 420
gtgtaccagt taaaagatcc tcggtctcag gacagcaccc tctgcctgtt caccgacttt 480
gactcccaaa tcaatgtgcc gaaaaccatg gaatctggaa cgttcatcac tgacaaaact 540
gtgctggaca tgaaagctat ggattccaag agcaatgggg ccattgcctg gagcaaccag 600
acaagcttca cctgccaaga tatcttcaaa gagaccaacg ccacctaccc cagttcagac 660
gttccctgtg atgccacgtt gactgagaaa agctttgaaa cagatatgaa cctaaacttt 720
caaaacctgc tggttatggt tctccgaatc ctcctgctga aagtagccgg atttaacctg 780
ctcatgacgc tgaggctgtg gtccagt 807

<210> SEQ ID NO 109
<211> LENGTH: 303
<212> TYPE: PRT
<213> ORGANISM: Artificial Sequence
<220> FEATURE:
<223> OTHER INFORMATION: Synthetic Construct

<400> SEQUENCE: 109

Met Leu Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Lys Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala His
            100                 105                 110

Glu Arg Ile Thr Asp Thr Gln Tyr Phe Gly Pro Gly Thr Arg Leu Thr
        115                 120                 125

Val Leu Glu Asp Leu Arg Asn Val Thr Pro Pro Lys Val Ser Leu Phe
    130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
180 185 190

Tyr Lys Glu Ser Asn Tyr Ser Tyr Cys Leu Ser Ser Arg Leu Arg Val
195 200 205

Ser Ala Thr Phe Trp His Asn Pro Arg Asn His Phe Arg Cys Gln Val
210 215 220

Gln Phe His Gly Leu Ser Glu Glu Asp Lys Trp Pro Glu Gly Ser Pro
225 230 235 240

Lys Pro Val Thr Gln Asn Ile Ser Ala Glu Ala Trp Gly Arg Ala Asp
245 250 255

Cys Gly Ile Thr Ser Ala Ser Tyr Gln Gln Gly Val Leu Ser Ala Thr
260 265 270

Ile Leu Tyr Glu Ile Leu Leu Gly Lys Ala Thr Leu Tyr Ala Val Leu
275 280 285

Val Ser Thr Leu Val Val Met Ala Met Val Lys Arg Lys Asn Ser
290 295 300

<210> SEQ ID NO 110
<211> LENGTH: 909
<212> TYPE: DNA
<213> ORGANISM: Artificial Sequence
<220> FEATURE:
<223> OTHER INFORMATION: Synthetic Construct

<400> SEQUENCE: 110
atgctgctgc ttctgctgct tctggggcca gcaggctccg ggcttggtgc tgtcgtctct 60
caacatccga gcagggttat ctgtaagagt ggaacctctg tgaagatcga gtgccgttcc 120
ctggactttc aggccacaac tatgttttgg tatcgtcagt tcccgaaaaa gagtctcatg 180
ctgatggcaa cttccaatga gggctccaag gccacatacg agcaaggcgt cgagaaggac 240
aagtttctca tcaaccatgc aagcctgacc ttgtccactc tgacagtgac cagtgcccat 300
cctgaagaca gcagcttcta catctgcagt gcccatgagc ggatcacaga tacgcagtat 360
tttggcccag gcacccggct gacagtgctc gaggatctga gaaatgtgac tccacccaag 420
gtctccttgt ttgagccatc aaaagcagag attgcaaaca aacaaaaggc taccctcgtg 480
tgcttggcca ggggcttctt ccctgaccac gtggagctga gctggtgggt gaatggcaag 540
gaggtccaca gtggggtcag cacggaccct caggcctaca aggagagcaa ttatagctac 600
tgcctgagca gccgcctgag ggtctctgct accttctggc acaatcctcg caaccacttc 660
cgctgccaag tgcagttcca tgggctttca gaggaggaca agtggccaga gggctcaccc 720
aaacctgtca cacagaacat cagtgcagag gcctggggcc gagcagactg tgggattacc 780
tcagcatcct atcaacaagg ggtcttgtct gccaccatcc tctatgagat cctgctaggg 840
aaagccaccc tgtatgctgt gcttgtcagt acactggtgg tgatggctat ggtcaaaaga 900
aaaaattca 909

<210> SEQ ID NO 111
<211> LENGTH: 269
<212> TYPE: PRT
<213> ORGANISM: Artificial Sequence
<220> FEATURE:
<223> OTHER INFORMATION: Synthetic Construct

<400> SEQUENCE: 111

Met Ile Ser Leu Arg Val Leu Leu Val Ile Leu Trp Leu Gln Leu Ser
1 5 10 15

```
Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Met Lys Asp Ser Ser Tyr Lys Leu Ile Phe Gly Ser Gly Thr Arg Leu
        115                 120                 125

Leu Val Arg Pro Asp Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Leu Val Met Val Leu Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 112
<211> LENGTH: 807
<212> TYPE: DNA
<213> ORGANISM: Artificial Sequence
<220> FEATURE:
<223> OTHER INFORMATION: Synthetic Construct

<400> SEQUENCE: 112

```
atgatatcct tgagagtttt actggtgatc ctgtggcttc agttaagctg ggtttggagc     60

caacggaagg aggtggagca ggatcctgga cccttcaatg ttccagaggg agccactgtc    120

gctttcaact gtacttacag caacagtgct tctcagtctt tcttctggta cagacaggat    180

tgcaggaaag aacctaagtt gctgatgtcc gtatactcca gtggtaatga agatggaagg    240

tttacagcac agctcaatag agccagccag tatatttccc tgctcatcag agactccaag    300

ctcagtgatt cagccaccta cctctgtgtg gtgaacatga aggatagcag ctataaattg    360

atcttcggga gtgggaccag actgctggtc aggcctgata tccagaaccc agaacctgct    420

gtgtaccagt taaaagatcc tcggtctcag gacagcaccc tctgcctgtt caccgacttt    480

gactcccaaa tcaatgtgcc gaaaaccatg gaatctggaa cgttcatcac tgacaaaact    540

gtgctggaca tgaaagctat ggattccaag agcaatgggg ccattgcctg gagcaaccag    600
```

```
acaagcttca cctgccaaga tatcttcaaa gagaccaacg ccacctaccc cagttcagac    660

gttccctgtg atgccacgtt gactgagaaa agctttgaaa cagatatgaa cctaaacttt    720

caaaacctgc tggttatggt tctccgaatc ctcctgctga aagtagccgg atttaacctg    780

ctcatgacgc tgaggctgtg gtccagt                                        807
```

<210> SEQ ID NO 113
<211> LENGTH: 305
<212> TYPE: PRT
<213> ORGANISM: Artificial Sequence
<220> FEATURE:
<223> OTHER INFORMATION: Synthetic Construct

<400> SEQUENCE: 113

```
Met Leu Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Lys Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Leu
            100                 105                 110

Glu Gly Thr Ser Gly Lys Glu Thr Gln Tyr Phe Gly Pro Gly Thr Arg
        115                 120                 125

Leu Leu Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305
```

<210> SEQ ID NO 114
<211> LENGTH: 915
<212> TYPE: DNA
<213> ORGANISM: Artificial Sequence
<220> FEATURE:
<223> OTHER INFORMATION: Synthetic Construct

<400> SEQUENCE: 114
atgctgctgc ttctgctgct tctggggcca gcaggctccg ggcttggtgc tgtcgtctct 60
caacatccga gcagggttat ctgtaagagt ggaacctctg tgaagatcga gtgccgttcc 120
ctggactttc aggccacaac tatgttttgg tatcgtcagt tcccgaaaaa gagtctcatg 180
ctgatggcaa cttccaatga gggctccaag gccacatacg agcaaggcgt cgagaaggac 240
aagtttctca tcaaccatgc aagcctgacc ttgtccactc tgacagtgac cagtgcccat 300
cctgaagaca gcagcttcta catctgcagt gctttagagg ggactagcgg gaaagagacc 360
cagtacttcg ggccaggcac gcggctcctg gtgctcgagg atctgagaaa tgtgactcca 420
cccaaggtct ccttgtttga gccatcaaaa gcagagattg caaacaaaca aaaggctacc 480
ctcgtgtgct tggccagggg cttcttccct gaccacgtgg agctgagctg gtgggtgaat 540
ggcaaggagg tccacagtgg ggtcagcacg gaccctcagg cctacaagga gagcaattat 600
agctactgcc tgagcagccg cctgagggtc tctgctacct tctggcacaa tcctcgcaac 660
cacttccgct gccaagtgca gttccatggg ctttcagagg aggacaagtg gccagagggc 720
tcacccaaac ctgtcacaca gaacatcagt gcagaggcct ggggccgagc agactgtggg 780
attacctcag catcctatca acaaggggtc ttgtctgcca ccatcctcta tgagatcctg 840
ctagggaaag ccaccctgta tgctgtgctt gtcagtacac tggtggtgat ggctatggtc 900
aaaagaaaaa attca 915

<210> SEQ ID NO 115
<211> LENGTH: 263
<212> TYPE: PRT
<213> ORGANISM: Artificial Sequence
<220> FEATURE:
<223> OTHER INFORMATION: Synthetic Construct

<400> SEQUENCE: 115

Met Leu Leu Ile Thr Ser Met Leu Val Leu Trp Met Gln Leu Ser Gln
1 5 10 15

Val Asn Gly Gln Gln Val Met Gln Ile Pro Gln Tyr Gln His Val Gln
20 25 30

Glu Gly Glu Asp Phe Thr Thr Tyr Cys Asn Ser Ser Thr Thr Leu Ser
35 40 45

Asn Ile Gln Trp Tyr Lys Gln Arg Pro Gly Gly His Pro Val Phe Leu
50 55 60

Ile Gln Leu Val Lys Ser Gly Glu Val Lys Lys Gln Lys Arg Leu Thr
65 70 75 80

Phe Gln Phe Gly Glu Ala Lys Lys Asn Ser Ser Leu His Ile Thr Ala
85 90 95

Thr Gln Thr Thr Asp Val Gly Thr Tyr Phe Cys Ala Gly Pro Gly Asn
100 105 110

Gln Phe Tyr Phe Gly Thr Gly Thr Ser Leu Thr Val Ile Pro Asn Ile
115 120 125

Gln Asn Pro Glu Pro Ala Val Tyr Gln Leu Lys Asp Pro Arg Ser Gln
130 135 140

Asp Ser Thr Leu Cys Leu Phe Thr Asp Phe Asp Ser Gln Ile Asn Val

-continued

```
145                 150                 155                 160

Pro Lys Thr Met Glu Ser Gly Thr Phe Ile Thr Asp Lys Thr Val Leu
                165                 170                 175

Asp Met Lys Ala Met Asp Ser Lys Ser Asn Gly Ala Ile Ala Trp Ser
            180                 185                 190

Asn Gln Thr Ser Phe Thr Cys Gln Asp Ile Phe Lys Glu Thr Asn Ala
        195                 200                 205

Thr Tyr Pro Ser Ser Asp Val Pro Cys Asp Ala Thr Leu Thr Glu Lys
    210                 215                 220

Ser Phe Glu Thr Asp Met Asn Leu Asn Phe Gln Asn Leu Leu Val Met
225                 230                 235                 240

Val Leu Arg Ile Leu Leu Leu Lys Val Ala Gly Phe Asn Leu Leu Met
                245                 250                 255

Thr Leu Arg Leu Trp Ser Ser
            260


<210> SEQ ID NO 116
<211> LENGTH: 789
<212> TYPE: DNA
<213> ORGANISM: Artificial Sequence
<220> FEATURE:
<223> OTHER INFORMATION: Synthetic Construct

<400> SEQUENCE: 116

atgctactca tcacatcaat gttggtctta tggatgcaat tgtcacaggt gaatggacaa      60

caggtaatgc aaattcctca gtaccagcat gtacaagaag gagaggactt caccacgtac     120

tgcaattcct caactacttt aagcaatata cagtggtata agcaaaggcc tggtggacat     180

cccgtttttt tgatacagtt agtgaagagt ggagaagtga agaagcagaa aagactgaca     240

tttcagtttg gagaagcaaa aaagaacagc tccctgcaca tcacagccac ccagactaca     300

gatgtaggaa cctacttctg tgcagggccc ggtaaccagt tctattttgg gacagggaca     360

agtttgacgg tcattccaaa tatccagaac ccagaacctg ctgtgtacca gttaaaagat     420

cctcggtctc aggacagcac cctctgcctg ttcaccgact ttgactccca aatcaatgtg     480

ccgaaaacca tggaatctgg aacgttcatc actgacaaaa ctgtgctgga catgaaagct     540

atggattcca agagcaatgg ggccattgcc tggagcaacc agacaagctt cacctgccaa     600

gatatcttca aagagaccaa cgccacctac cccagttcag acgttccctg tgatgccacg     660

ttgactgaga aaagctttga aacagatatg aacctaaact ttcaaaacct gctggttatg     720

gttctccgaa tcctcctgct gaaagtagcc ggatttaacc tgctcatgac gctgaggctg     780

tggtccagt                                                             789


<210> SEQ ID NO 117
<211> LENGTH: 305
<212> TYPE: PRT
<213> ORGANISM: Artificial Sequence
<220> FEATURE:
<223> OTHER INFORMATION: Synthetic Construct

<400> SEQUENCE: 117

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45
```

```
Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Ser Trp Asp Arg Asp Gln Pro Gln His Phe Gly Asp Gly Thr Arg
        115                 120                 125

Leu Ser Ile Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305
```

<210> SEQ ID NO 118
<211> LENGTH: 915
<212> TYPE: DNA
<213> ORGANISM: Artificial Sequence
<220> FEATURE:
<223> OTHER INFORMATION: Synthetic Construct

<400> SEQUENCE: 118

```
atgagcatcg gcctcctgtg ctgtgcagcc ttgtctctcc tgtgggcagg tccagtgaat     60

gctggtgtca ctcagacccc aaaattccag gtcctgaaga caggacagag catgacactg    120

cagtgtgccc aggatatgaa ccatgaatac atgtcctggt atcgacaaga cccaggcatg    180

gggctgaggc tgattcatta ctcagttggt gctggtatca ctgaccaagg agaagtcccc    240

aatggctaca atgtctccag atcaaccaca gaggatttcc cgctcaggct gctgtcggct    300

gctccctccc agacatctgt gtacttctgt gccagcagtt catgggacag ggatcagccc    360

cagcattttg gtgatgggac tcgactctcc atcctagagg atctgagaaa tgtgactcca    420

cccaaggtct ccttgtttga gccatcaaaa gcagagattg caaacaaaca aaaggctacc    480

ctcgtgtgct tggccagggg cttcttccct gaccacgtgg agctgagctg gtgggtgaat    540
```

```
ggcaaggagg tccacagtgg ggtcagcacg gaccctcagg cctacaagga gagcaattat    600

agctactgcc tgagcagccg cctgagggtc tctgctacct tctggcacaa tcctcgcaac    660

cacttccgct gccaagtgca gttccatggg ctttcagagg aggacaagtg gccagagggc    720

tcacccaaac ctgtcacaca gaacatcagt gcagaggcct ggggccgagc agactgtggg    780

attacctcag catcctatca acaaggggtc ttgtctgcca ccatcctcta tgagatcctg    840

ctagggaaag ccaccctgta tgctgtgctt gtcagtacac tggtggtgat ggctatggtc    900

aaaagaaaaa attca                                                      915
```

<210> SEQ ID NO 119
<211> LENGTH: 268
<212> TYPE: PRT
<213> ORGANISM: Artificial Sequence
<220> FEATURE:
<223> OTHER INFORMATION: Synthetic Construct

<400> SEQUENCE: 119

```
Met Lys Pro Thr Leu Ile Ser Val Leu Val Ile Ile Phe Ile Leu Arg
1               5                   10                  15

Gly Thr Arg Ala Gln Arg Val Thr Gln Pro Glu Lys Leu Leu Ser Val
            20                  25                  30

Phe Lys Gly Ala Pro Val Glu Leu Lys Cys Asn Tyr Ser Tyr Ser Gly
        35                  40                  45

Ser Pro Glu Leu Phe Trp Tyr Val Gln Tyr Ser Arg Gln Arg Leu Gln
    50                  55                  60

Leu Leu Leu Arg His Ile Ser Arg Glu Ser Ile Lys Gly Phe Thr Ala
65                  70                  75                  80

Asp Leu Asn Lys Gly Glu Thr Ser Phe His Leu Lys Lys Pro Phe Ala
                85                  90                  95

Gln Glu Glu Asp Ser Ala Met Tyr Tyr Cys Ala Leu Ser Ala Leu Pro
            100                 105                 110

Tyr Asn Gln Gly Gly Lys Leu Ile Phe Gly Gln Gly Thr Glu Leu Ser
        115                 120                 125

Val Lys Pro Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Leu Val Met Val Leu Arg Ile Leu Leu Leu Lys Val Ala Gly
                245                 250                 255

Phe Asn Leu Leu Met Thr Leu Arg Leu Trp Ser Ser
            260                 265
```

<210> SEQ ID NO 120
<211> LENGTH: 804

<212> TYPE: DNA
<213> ORGANISM: Artificial Sequence
<220> FEATURE:
<223> OTHER INFORMATION: Synthetic Construct

<400> SEQUENCE: 120
atgaagccca ccctcatctc agtgcttgtg ataatattta tactcagagg aacaagagcc 60
cagagagtga ctcagcccga gaagctcctc tctgtcttta aggggcccc agtggagctg 120 aagtgcaact attcctattc tgggagtcct gaactcttct ggtatgtcca gtactccaga 180
caacgcctcc agttactctt gagacacatc tctagagaga gcatcaaagg cttcactgct 240
gaccttaaca aaggcgagac atctttccac ctgaagaaac catttgctca agaggaagac 300
tcagccatgt attactgtgc tctaagtgcc ctcccctata accagggagg aaagcttatc 360
ttcggacagg gaacggagtt atctgtgaaa cccaatatcc agaacccaga acctgctgtg 420
taccagttaa aagatcctcg gtctcaggac agcaccctct gcctgttcac cgactttgac 480
tcccaaatca atgtgccgaa aaccatggaa tctggaacgt tcatcactga caaaactgtg 540
ctggacatga aagctatgga ttccaagagc aatggggcca ttgcctggag caaccagaca 600
agcttcacct gccaagatat cttcaaagag accaacgcca cctaccccag ttcagacgtt 660
ccctgtgatg ccacgttgac tgagaaaagc tttgaaacag atatgaacct aaactttcaa 720
aacctgctgg ttatggttct ccgaatcctc ctgctgaaag tagccggatt taacctgctc 780
atgacgctga ggctgtggtc cagt 804

<210> SEQ ID NO 121
<211> LENGTH: 300
<212> TYPE: PRT
<213> ORGANISM: Artificial Sequence
<220> FEATURE:
<223> OTHER INFORMATION: Synthetic Construct

<400> SEQUENCE: 121

Met Leu Cys Ser Leu Leu Ala Leu Leu Leu Gly Thr Phe Phe Gly Val
1 5 10 15

Arg Ser Gln Thr Ile His Gln Trp Pro Ala Thr Leu Val Gln Pro Val
20 25 30

Gly Ser Pro Leu Ser Leu Glu Cys Thr Val Glu Gly Thr Ser Asn Pro
35 40 45

Asn Leu Tyr Trp Tyr Arg Gln Ala Ala Gly Arg Gly Leu Gln Leu Leu
50 55 60

Phe Tyr Ser Val Gly Ile Gly Gln Ile Ser Ser Glu Val Pro Gln Asn
65 70 75 80

Leu Ser Ala Ser Arg Pro Gln Asp Arg Gln Phe Ile Leu Ser Ser Lys
85 90 95

Lys Leu Leu Leu Ser Asp Ser Gly Phe Tyr Leu Cys Ala Trp Ala Arg
100 105 110

Ser Arg Glu Leu Phe Phe Gly Glu Gly Ser Arg Leu Thr Val Leu Glu
115 120 125

Asp Leu Arg Asn Val Thr Pro Pro Lys Val Ser Leu Phe Glu Pro Ser
130 135 140

Lys Ala Glu Ile Ala Asn Lys Gln Lys Ala Thr Leu Val Cys Leu Ala
145 150 155 160

Arg Gly Phe Phe Pro Asp His Val Glu Leu Ser Trp Trp Val Asn Gly
165 170 175

Lys Glu Val His Ser Gly Val Ser Thr Asp Pro Gln Ala Tyr Lys Glu

```
            180                 185                 190

Ser Asn Tyr Ser Tyr Cys Leu Ser Ser Arg Leu Arg Val Ser Ala Thr
        195                 200                 205

Phe Trp His Asn Pro Arg Asn His Phe Arg Cys Gln Val Gln Phe His
    210                 215                 220

Gly Leu Ser Glu Glu Asp Lys Trp Pro Glu Gly Ser Pro Lys Pro Val
225                 230                 235                 240

Thr Gln Asn Ile Ser Ala Glu Ala Trp Gly Arg Ala Asp Cys Gly Ile
                245                 250                 255

Thr Ser Ala Ser Tyr Gln Gln Gly Val Leu Ser Ala Thr Ile Leu Tyr
            260                 265                 270

Glu Ile Leu Leu Gly Lys Ala Thr Leu Tyr Ala Val Leu Val Ser Thr
        275                 280                 285

Leu Val Val Met Ala Met Val Lys Arg Lys Asn Ser
    290                 295                 300


<210> SEQ ID NO 122
<211> LENGTH: 900
<212> TYPE: DNA
<213> ORGANISM: Artificial Sequence
<220> FEATURE:
<223> OTHER INFORMATION: Synthetic Construct

<400> SEQUENCE: 122

atgctctgct ctctccttgc ccttctcctg ggcactttct ttggggtcag atctcagact      60

attcatcaat ggccagcgac cctggtgcag cctgtgggca gcccgctctc tctggagtgc     120

actgtggagg gaacatcaaa ccccaaccta tactggtacc gacaggctgc aggcaggggc     180

ctccagctgc tcttctactc cgttggtatt ggccagatca gctctgaggt gccccagaat     240

ctctcagcct ccagacccca ggaccggcag ttcatcctga gttctaagaa gctccttctc     300

agtgactctg gcttctatct ctgtgcctgg gcgaggagca gggagctgtt ttttggagaa     360

ggctctaggc tgaccgtact ggaggatctg agaaatgtga ctccacccaa ggtctccttg     420

tttgagccat caaaagcaga gattgcaaac aaacaaaagg ctaccctcgt gtgcttggcc     480

aggggcttct tccctgacca cgtggagctg agctggtggg tgaatggcaa ggaggtccac     540

agtggggtca gcacggaccc tcaggcctac aaggagagca attatagcta ctgcctgagc     600

agccgcctga gggtctctgc taccttctgg cacaatcctc gcaaccactt ccgctgccaa     660

gtgcagttcc atgggctttc agaggaggac aagtggccag agggctcacc caaacctgtc     720

acacagaaca tcagtgcaga ggcctggggc cgagcagact gtgggattac ctcagcatcc     780

tatcaacaag ggtcttgtc tgccaccatc ctctatgaga tcctgctagg gaaagccacc     840

ctgtatgctg tgcttgtcag tacactggtg gtgatggcta tggtcaaaag aaaaaattca     900


<210> SEQ ID NO 123
<211> LENGTH: 270
<212> TYPE: PRT
<213> ORGANISM: Artificial Sequence
<220> FEATURE:
<223> OTHER INFORMATION: Synthetic Construct

<400> SEQUENCE: 123

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30
```

-continued

```
Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Phe Tyr Ala Gly Asn Asn Arg Lys Leu Ile Trp Gly Leu Gly Thr Ser
        115                 120                 125

Leu Ala Val Asn Pro Asn Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Leu Val Met Val Leu Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 124
<211> LENGTH: 810
<212> TYPE: DNA
<213> ORGANISM: Artificial Sequence
<220> FEATURE:
<223> OTHER INFORMATION: Synthetic Construct

<400> SEQUENCE: 124

```
atgatgaaat ccttgagagt tttactggtg atcctgtggc ttcagttaag ctgggtttgg     60

agccaacaga aggaggtgga gcaggatcct ggaccactca gtgttccaga gggagccatt    120

gtttctctca actgcactta cagcaacagt gcttttcaat acttcatgtg gtacagacag    180

tattccagaa aaggccctga gttgctgatg tacacatact ccagtggtaa caaagaagat    240

ggaaggttta cagcacaggt cgataaatcc agcaagtata tctccttgtt catcagagac    300

tcacagccca gtgattcagc cacctacctc tgtgcattct atgctggcaa caaccgtaag    360

ctgatttggg gattgggaac aagcctggca gtaaatccga atatccagaa cccagaacct    420

gctgtgtacc agttaaaaga tcctcggtct caggacagca ccctctgcct gttcaccgac    480

tttgactccc aaatcaatgt gccgaaaacc atggaatctg gaacgttcat cactgacaaa    540

actgtgctgg acatgaaagc tatggattcc aagagcaatg gggccattgc ctggagcaac    600

cagacaagct tcacctgcca agatatcttc aaagagacca acgccaccta ccccagttca    660

gacgttccct gtgatgccac gttgactgag aaaagctttg aaacagatat gaacctaaac    720
```

-continued tttcaaaacc tgctggttat ggttctccga atcctcctgc tgaaagtagc cggatttaac 780
ctgctcatga cgctgaggct gtggtccagt 810

<210> SEQ ID NO 125
<211> LENGTH: 306
<212> TYPE: PRT
<213> ORGANISM: Artificial Sequence
<220> FEATURE:
<223> OTHER INFORMATION: Synthetic Construct

<400> SEQUENCE: 125

Met Ser Asn Gln Val Leu Cys Cys Val Val Leu Cys Phe Leu Gly Ala
1 5 10 15

Asn Thr Val Asp Gly Gly Ile Thr Gln Ser Pro Lys Tyr Leu Phe Arg
20 25 30

Lys Glu Gly Gln Asn Val Thr Leu Ser Cys Glu Gln Asn Leu Asn His
35 40 45

Asp Ala Met Tyr Trp Tyr Arg Gln Asp Pro Gly Gln Gly Leu Arg Leu
50 55 60

Ile Tyr Tyr Ser Gln Ile Val Asn Asp Phe Gln Lys Gly Asp Ile Ala
65 70 75 80

Glu Gly Tyr Ser Val Ser Arg Glu Lys Lys Glu Ser Phe Pro Leu Thr
85 90 95

Val Thr Ser Ala Gln Lys Asn Pro Thr Ala Phe Tyr Leu Cys Ala Ser
100 105 110

Ser Ile Asp Pro Ala Thr Ser His Glu Gln Phe Phe Gly Pro Gly Thr
115 120 125

Arg Leu Thr Val Leu Glu Asp Leu Arg Asn Val Thr Pro Pro Lys Val
130 135 140

Ser Leu Phe Glu Pro Ser Lys Ala Glu Ile Ala Asn Lys Gln Lys Ala
145 150 155 160

Thr Leu Val Cys Leu Ala Arg Gly Phe Phe Pro Asp His Val Glu Leu
165 170 175

Ser Trp Trp Val Asn Gly Lys Glu Val His Ser Gly Val Ser Thr Asp
180 185 190

Pro Gln Ala Tyr Lys Glu Ser Asn Tyr Ser Tyr Cys Leu Ser Ser Arg
195 200 205

Leu Arg Val Ser Ala Thr Phe Trp His Asn Pro Arg Asn His Phe Arg
210 215 220

Cys Gln Val Gln Phe His Gly Leu Ser Glu Glu Asp Lys Trp Pro Glu
225 230 235 240

Gly Ser Pro Lys Pro Val Thr Gln Asn Ile Ser Ala Glu Ala Trp Gly
245 250 255

Arg Ala Asp Cys Gly Ile Thr Ser Ala Ser Tyr Gln Gln Gly Val Leu
260 265 270

Ser Ala Thr Ile Leu Tyr Glu Ile Leu Leu Gly Lys Ala Thr Leu Tyr
275 280 285

Ala Val Leu Val Ser Thr Leu Val Val Met Ala Met Val Lys Arg Lys
290 295 300

Asn Ser
305

<210> SEQ ID NO 126
<211> LENGTH: 918
<212> TYPE: DNA
<213> ORGANISM: Artificial Sequence
<220> FEATURE:
<223> OTHER INFORMATION: Synthetic Construct

<400> SEQUENCE: 126
atgagcaacc aggtgctctg ctgtgtggtc ctttgtttcc tgggagcaaa caccgtggat 60
ggtggaatca ctcagtcccc aaagtacctg ttcagaaagg aaggacagaa tgtgaccctg 120
agttgtgaac agaatttgaa ccacgatgcc atgtactggt accgacagga cccagggcaa 180
gggctgagat tgatctacta ctcacagata gtaaatgact ttcagaaagg agatatagct 240
gaagggtaca gcgtctctcg ggagaagaag gaatcctttc ctctcactgt gacatcggcc 300
caaaagaacc cgacagcttt ctatctctgt gccagtagta tagatccggc gactagtcat 360
gagcagttct tcgggccagg gacacggctc accgtgctag aggatctgag aaatgtgact 420
ccacccaagg tctccttgtt tgagccatca aaagcagaga ttgcaaacaa acaaaaggct 480
accctcgtgt gcttggccag gggcttcttc cctgaccacg tggagctgag ctggtgggtg 540
aatggcaagg aggtccacag tggggtcagc acggaccctc aggcctacaa ggagagcaat 600
tatagctact gcctgagcag ccgcctgagg gtctctgcta ccttctggca caatcctcgc 660
aaccacttcc gctgccaagt gcagttccat gggctttcag aggaggacaa gtggccagag 720
ggctcaccca aacctgtcac acagaacatc agtgcagagg cctggggccg agcagactgt 780
gggattacct cagcatccta tcaacaaggg gtcttgtctg ccaccatcct ctatgagatc 840
ctgctaggga aagccaccct gtatgctgtg cttgtcagta cactggtggt gatggctatg 900
gtcaaaagaa aaaattca 918

<210> SEQ ID NO 127
<211> LENGTH: 270
<212> TYPE: PRT
<213> ORGANISM: Artificial Sequence
<220> FEATURE:
<223> OTHER INFORMATION: Synthetic Construct

<400> SEQUENCE: 127

Met Met Lys Ser Leu Arg Val Leu Leu Val Ile Leu Trp Leu Gln Leu
1 5 10 15

Ser Trp Val Trp Ser Gln Gln Lys Glu Val Glu Gln Asp Pro Gly Pro
20 25 30

Leu Ser Val Pro Glu Gly Ala Ile Val Ser Leu Asn Cys Thr Tyr Ser
35 40 45

Asn Ser Ala Phe Gln Tyr Phe Met Trp Tyr Arg Gln Tyr Ser Arg Lys
50 55 60

Gly Pro Glu Leu Leu Met Tyr Thr Tyr Ser Ser Gly Asn Lys Glu Asp
65 70 75 80

Gly Arg Phe Thr Ala Gln Val Asp Lys Ser Ser Lys Tyr Ile Ser Leu
85 90 95

Phe Ile Arg Asp Ser Gln Pro Ser Asp Ser Ala Thr Tyr Leu Cys Ala
100 105 110

Met Ser Pro Arg Ser Gly Tyr Ala Leu Asn Phe Gly Lys Gly Thr Ser
115 120 125

Leu Leu Val Thr Pro His Ile Gln Asn Pro Glu Pro Ala Val Tyr Gln
130 135 140

Leu Lys Asp Pro Arg Ser Gln Asp Ser Thr Leu Cys Leu Phe Thr Asp
145 150 155 160

Phe Asp Ser Gln Ile Asn Val Pro Lys Thr Met Glu Ser Gly Thr Phe
165 170 175

```
Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Leu Val Met Val Leu Arg Ile Leu Leu Leu Lys Val
                245                 250                 255

Ala Gly Phe Asn Leu Leu Met Thr Leu Arg Leu Trp Ser Ser
            260                 265                 270


<210> SEQ ID NO 128
<211> LENGTH: 810
<212> TYPE: DNA
<213> ORGANISM: Artificial Sequence
<220> FEATURE:
<223> OTHER INFORMATION: Synthetic Construct

<400> SEQUENCE: 128

atgatgaaat ccttgagagt tttactggtg atcctgtggc ttcagttaag ctgggtttgg      60

agccaacaga aggaggtgga gcaggatcct ggaccactca gtgttccaga gggagccatt     120

gtttctctca actgcactta cagcaacagt gcttttcaat acttcatgtg gtacagacag     180

tattccagaa aaggccctga gttgctgatg tacacatact ccagtggtaa caaagaagat     240

ggaaggttta cagcacaggt cgataaatcc agcaagtata tctccttgtt catcagagac     300

tcacagccca gtgattcagc cacctacctc tgtgcaatga gccctcggag cgggtatgca     360

ctcaacttcg gcaaaggcac ctcgctgttg gtcacacccc atatccagaa cccagaacct     420

gctgtgtacc agttaaaaga tcctcggtct caggacagca ccctctgcct gttcaccgac     480

tttgactccc aaatcaatgt gccgaaaacc atggaatctg gaacgttcat cactgacaaa     540

actgtgctgg acatgaaagc tatggattcc aagagcaatg gggccattgc ctggagcaac     600

cagacaagct tcacctgcca agatatcttc aaagagacca acgccaccta ccccagttca     660

gacgttccct gtgatgccac gttgactgag aaaagctttg aaacagatat gaacctaaac     720

tttcaaaacc tgctggttat ggttctccga atcctcctgc tgaaagtagc cggatttaac     780

ctgctcatga cgctgaggct gtggtccagt                                      810


<210> SEQ ID NO 129
<211> LENGTH: 306
<212> TYPE: PRT
<213> ORGANISM: Artificial Sequence
<220> FEATURE:
<223> OTHER INFORMATION: Synthetic Construct

<400> SEQUENCE: 129

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60
```

-continued

```
Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Met Asp Ala Ala Leu Gly Glu Lys Leu Phe Phe Gly Ser Gly Thr
        115                 120                 125

Gln Leu Ser Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser
305


<210> SEQ ID NO 130
<211> LENGTH: 918
<212> TYPE: DNA
<213> ORGANISM: Artificial Sequence
<220> FEATURE:
<223> OTHER INFORMATION: Synthetic Construct

<400> SEQUENCE: 130

atgagcaacc aggtgctctg ctgtgtggtc ctttgtttcc tgggagcaaa caccgtggat      60

ggtggaatca ctcagtcccc aaagtacctg ttcagaaagg aaggacagaa tgtgaccctg     120

agttgtgaac agaatttgaa ccacgatgcc atgtactggt accgacagga cccagggcaa     180

gggctgagat tgatctacta ctcacagata gtaaatgact ttcagaaagg agatatagct     240

gaagggtaca gcgtctctcg ggagaagaag gaatcctttc ctctcactgt gacatcggcc     300

caaaagaacc cgacagcttt ctatctctgt gccagtagta tggacgccgc cttgggtgaa     360

aaactgtttt ttggcagtgg aacccagctc tctgtcttgg aggatctgag aaatgtgact     420

ccacccaagg tctccttgtt tgagccatca aaagcagaga ttgcaaacaa acaaaaggct     480

accctcgtgt gcttggccag gggcttcttc cctgaccacg tggagctgag ctggtgggtg     540

aatggcaagg aggtccacag tggggtcagc acggaccctc aggcctacaa ggagagcaat     600

tatagctact gcctgagcag ccgcctgagg gtctctgcta ccttctggca caatcctcgc     660
```

aaccacttcc gctgccaagt gcagttccat gggctttcag aggaggacaa gtggccagag 720
ggctcaccca aacctgtcac acagaacatc agtgcagagg cctggggccg agcagactgt 780
gggattacct cagcatccta tcaacaaggg gtcttgtctg ccaccatcct ctatgagatc 840
ctgctaggga aagccaccct gtatgctgtg cttgtcagta cactggtggt gatggctatg 900
gtcaaaagaa aaaattca 918

<210> SEQ ID NO 131
<211> LENGTH: 269
<212> TYPE: PRT
<213> ORGANISM: Artificial Sequence
<220> FEATURE:
<223> OTHER INFORMATION: Synthetic Construct

<400> SEQUENCE: 131

Met Asn Tyr Ser Pro Gly Leu Val Ser Leu Ile Leu Leu Leu Leu Gly
1 5 10 15

Arg Thr Arg Gly Asn Ser Val Thr Gln Met Glu Gly Pro Val Thr Leu
20 25 30

Ser Glu Glu Ala Phe Leu Thr Ile Asn Cys Thr Tyr Thr Ala Thr Gly
35 40 45

Tyr Pro Ser Leu Phe Trp Tyr Val Gln Tyr Pro Gly Glu Gly Leu Gln
50 55 60

Leu Leu Leu Lys Ala Thr Lys Ala Asp Asp Lys Gly Ser Asn Lys Gly
65 70 75 80

Phe Glu Ala Thr Tyr Arg Lys Glu Thr Thr Ser Phe His Leu Glu Lys
85 90 95

Gly Ser Val Gln Val Ser Asp Ser Ala Val Tyr Phe Cys Ala Leu Arg
100 105 110

Ser Gly Gly Ser Asn Tyr Lys Leu Thr Phe Gly Lys Gly Thr Leu Leu
115 120 125

Thr Val Asn Pro Asn Ile Gln Asn Pro Glu Pro Ala Val Tyr Gln Leu
130 135 140

Lys Asp Pro Arg Ser Gln Asp Ser Thr Leu Cys Leu Phe Thr Asp Phe
145 150 155 160

Asp Ser Gln Ile Asn Val Pro Lys Thr Met Glu Ser Gly Thr Phe Ile
165 170 175

Thr Asp Lys Thr Val Leu Asp Met Lys Ala Met Asp Ser Lys Ser Asn
180 185 190

Gly Ala Ile Ala Trp Ser Asn Gln Thr Ser Phe Thr Cys Gln Asp Ile
195 200 205

Phe Lys Glu Thr Asn Ala Thr Tyr Pro Ser Ser Asp Val Pro Cys Asp
210 215 220

Ala Thr Leu Thr Glu Lys Ser Phe Glu Thr Asp Met Asn Leu Asn Phe
225 230 235 240

Gln Asn Leu Leu Val Met Val Leu Arg Ile Leu Leu Leu Lys Val Ala
245 250 255

Gly Phe Asn Leu Leu Met Thr Leu Arg Leu Trp Ser Ser
260 265

<210> SEQ ID NO 132
<211> LENGTH: 807
<212> TYPE: DNA
<213> ORGANISM: Artificial Sequence
<220> FEATURE:
<223> OTHER INFORMATION: Synthetic Construct

<400> SEQUENCE: 132
atgaactatt ctccaggctt agtatctctg atactcttac tgcttggaag aacccgtgga 60
aattcagtga cccagatgga agggccagtg actctctcag aagaggcctt cctgactata 120
aactgcacgt acacagccac aggataccct tccctttttct ggtatgtcca atatcctgga 180
gaaggtctac agctcctcct gaaagccacg aaggctgatg acaagggaag caacaaaggt 240
tttgaagcca cataccgtaa agaaaccact tctttccact tggagaaagg ctcagttcaa 300
gtgtcagact cagcggtgta cttctgtgct ctgaggagtg gaggtagcaa ctataaactg 360
acatttggaa aaggaactct cttaaccgtg aatccaaata tccagaaccc agaacctgct 420
gtgtaccagt taaaagatcc tcggtctcag gacagcaccc tctgcctgtt caccgacttt 480
gactcccaaa tcaatgtgcc gaaaaccatg gaatctggaa cgttcatcac tgacaaaact 540
gtgctggaca tgaaagctat ggattccaag agcaatgggg ccattgcctg gagcaaccag 600
acaagcttca cctgccaaga tatcttcaaa gagaccaacg ccacctaccc cagttcagac 660
gttccctgtg atgccacgtt gactgagaaa agctttgaaa cagatatgaa cctaaacttt 720
caaaacctgc tggttatggt tctccgaatc ctcctgctga aagtagccgg atttaacctg 780
ctcatgacgc tgaggctgtg gtccagt 807

<210> SEQ ID NO 133
<211> LENGTH: 305
<212> TYPE: PRT
<213> ORGANISM: Artificial Sequence
<220> FEATURE:
<223> OTHER INFORMATION: Synthetic Construct

<400> SEQUENCE: 133

Met Gly Phe Arg Leu Leu Cys Cys Val Ala Phe Cys Leu Leu Gly Ala
1 5 10 15

Gly Pro Val Asp Ser Gly Val Thr Gln Thr Pro Lys His Leu Ile Thr
20 25 30

Ala Thr Gly Gln Arg Val Thr Leu Arg Cys Ser Pro Arg Ser Gly Asp
35 40 45

Leu Ser Val Tyr Trp Tyr Gln Gln Ser Leu Asp Gln Gly Leu Gln Phe
50 55 60

Leu Ile Gln Tyr Tyr Asn Gly Glu Glu Arg Ala Lys Gly Asn Ile Leu
65 70 75 80

Glu Arg Phe Ser Ala Gln Gln Phe Pro Asp Leu His Ser Glu Leu Asn
85 90 95

Leu Ser Ser Leu Glu Leu Gly Asp Ser Ala Leu Tyr Phe Cys Ala Ser
100 105 110

Ser Val Glu Trp Gly Thr Tyr Glu Gln Tyr Phe Gly Pro Gly Thr Arg
115 120 125

Leu Thr Val Thr Glu Asp Leu Arg Asn Val Thr Pro Pro Lys Val Ser
130 135 140

Leu Phe Glu Pro Ser Lys Ala Glu Ile Ala Asn Lys Gln Lys Ala Thr
145 150 155 160

Leu Val Cys Leu Ala Arg Gly Phe Phe Pro Asp His Val Glu Leu Ser
165 170 175

Trp Trp Val Asn Gly Lys Glu Val His Ser Gly Val Ser Thr Asp Pro
180 185 190

Gln Ala Tyr Lys Glu Ser Asn Tyr Ser Tyr Cys Leu Ser Ser Arg Leu
195 200 205

```
Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305
```

<210> SEQ ID NO 134
<211> LENGTH: 915
<212> TYPE: DNA
<213> ORGANISM: Artificial Sequence
<220> FEATURE:
<223> OTHER INFORMATION: Synthetic Construct

<400> SEQUENCE: 134

```
atgggcttca ggctcctctg ctgtgtggcc ttttgtctcc tgggagcagg cccagtggat     60

tctggagtca cacaaacccc aaagcacctg atcacagcaa ctggacagcg agtgacgctg    120

agatgctccc ctaggtctgg agacctctct gtgtactggt accaacagag cctggaccag    180

ggcctccagt tcctcattca gtattataat ggagaagaga gagcaaaagg aaacattctt    240

gaacgattct ccgcacaaca gttccctgac ttgcactctg aactaaacct gagctctctg    300

gagctggggg actcagcttt gtatttctgt gccagcagcg tagaatgggg tacctacgag    360

cagtacttcg ggccgggcac caggctcacg gtcacagagg atctgagaaa tgtgactcca    420

cccaaggtct ccttgtttga gccatcaaaa gcagagattg caaacaaaca aaaggctacc    480

ctcgtgtgct tggccagggg cttcttccct gaccacgtgg agctgagctg gtgggtgaat    540

ggcaaggagg tccacagtgg ggtcagcacg gaccctcagg cctacaagga gagcaattat    600

agctactgcc tgagcagccg cctgagggtc tctgctacct tctggcacaa tcctcgcaac    660

cacttccgct gccaagtgca gttccatggg ctttcagagg aggacaagtg gccagagggc    720

tcacccaaac ctgtcacaca gaacatcagt gcagaggcct ggggccgagc agactgtggg    780

attacctcag catcctatca acaaggggtc ttgtctgcca ccatcctcta tgagatcctg    840

ctagggaaag ccaccctgta tgctgtgctt gtcagtacac tggtggtgat ggctatggtc    900

aaaagaaaaa attca                                                     915
```

<210> SEQ ID NO 135
<211> LENGTH: 268
<212> TYPE: PRT
<213> ORGANISM: Artificial Sequence
<220> FEATURE:
<223> OTHER INFORMATION: Synthetic Construct

<400> SEQUENCE: 135

```
Met Leu Leu Glu Leu Ile Pro Leu Leu Gly Ile His Phe Val Leu Arg
1               5                   10                  15

Thr Ala Arg Ala Gln Ser Val Thr Gln Pro Asp Ile His Ile Thr Val
            20                  25                  30
```

```
Ser Glu Gly Ala Ser Leu Glu Leu Arg Cys Asn Tyr Ser Tyr Gly Ala
        35                  40                  45

Thr Pro Tyr Leu Phe Trp Tyr Val Gln Ser Pro Gly Gln Gly Leu Gln
    50                  55                  60

Leu Leu Leu Lys Tyr Phe Ser Gly Asp Thr Leu Val Gln Gly Ile Lys
65                  70                  75                  80

Gly Phe Glu Ala Glu Phe Lys Arg Ser Gln Ser Ser Phe Asn Leu Arg
                85                  90                  95

Lys Pro Ser Val His Trp Ser Asp Ala Ala Glu Tyr Phe Cys Ala Val
            100                 105                 110

Tyr Gln Gly Ala Gln Lys Leu Val Phe Gly Gln Gly Thr Arg Leu Thr
        115                 120                 125

Ile Asn Pro Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Leu Val Met Val Leu Arg Ile Leu Leu Leu Lys Val Ala Gly
                245                 250                 255

Phe Asn Leu Leu Met Thr Leu Arg Leu Trp Ser Ser
            260                 265
```

<210> SEQ ID NO 136
<211> LENGTH: 804
<212> TYPE: DNA
<213> ORGANISM: Artificial Sequence
<220> FEATURE:
<223> OTHER INFORMATION: Synthetic Construct

<400> SEQUENCE: 136

```
atgctcctgg agcttatccc actgctgggg atacattttg tcctgagaac tgccagagcc     60

cagtcagtga cccagcctga catccacatc actgtctctg aaggagcctc actggagttg    120

agatgtaact attcctatgg ggcaacacct tatctcttct ggtatgtcca gtcccccggc    180

caaggcctcc agctgctcct gaagtacttt tcaggagaca ctctggttca aggcattaaa    240

ggctttgagg ctgaatttaa gaggagtcaa tcttccttca acctgaggaa accctctgtg    300

cattggagtg atgctgctga gtacttctgt gctgtgtatc agggagccca gaagctggta    360

tttggccaag gaaccaggct gactatcaac ccaaatatcc agaacccaga acctgctgtg    420

taccagttaa aagatcctcg gtctcaggac agcaccctct gcctgttcac cgactttgac    480

tcccaaatca atgtgccgaa aaccatggaa tctggaacgt tcatcactga caaaactgtg    540

ctggacatga aagctatgga ttccaagagc aatggggcca ttgcctggag caaccagaca    600

agcttcacct gccaagatat cttcaaagag accaacgcca cctaccccag ttcagacgtt    660

ccctgtgatg ccacgttgac tgagaaaagc tttgaaacag atatgaacct aaactttcaa    720
```

aacctgctgg ttatggttct ccgaatcctc ctgctgaaag tagccggatt taacctgctc 780
atgacgctga ggctgtggtc cagt 804

<210> SEQ ID NO 137
<211> LENGTH: 304
<212> TYPE: PRT
<213> ORGANISM: Artificial Sequence
<220> FEATURE:
<223> OTHER INFORMATION: Synthetic Construct

<400> SEQUENCE: 137

Met Leu Leu Leu Leu Leu Leu Leu Gly Pro Gly Ser Gly Leu Gly Ala
1 5 10 15

Val Val Ser Gln His Pro Ser Trp Val Ile Cys Lys Ser Gly Thr Ser
20 25 30

Val Lys Ile Glu Cys Arg Ser Leu Asp Phe Gln Ala Thr Thr Met Phe
35 40 45

Trp Tyr Arg Gln Phe Pro Lys Gln Ser Leu Met Leu Met Ala Thr Ser
50 55 60

Asn Glu Gly Ser Lys Ala Thr Tyr Glu Gln Gly Val Glu Lys Asp Lys
65 70 75 80

Phe Leu Ile Asn His Ala Ser Leu Thr Leu Ser Thr Leu Thr Val Thr
85 90 95

Ser Ala His Pro Glu Asp Ser Ser Phe Tyr Ile Cys Ser Ala Pro Trp
100 105 110

Leu Ala Gly Leu Tyr Asn Glu Gln Phe Phe Gly Pro Gly Thr Arg Leu
115 120 125

Thr Val Leu Glu Asp Leu Arg Asn Val Thr Pro Pro Lys Val Ser Leu
130 135 140

Phe Glu Pro Ser Lys Ala Glu Ile Ala Asn Lys Gln Lys Ala Thr Leu
145 150 155 160

Val Cys Leu Ala Arg Gly Phe Phe Pro Asp His Val Glu Leu Ser Trp
165 170 175

Trp Val Asn Gly Lys Glu Val His Ser Gly Val Ser Thr Asp Pro Gln
180 185 190

Ala Tyr Lys Glu Ser Asn Tyr Ser Tyr Cys Leu Ser Ser Arg Leu Arg
195 200 205

Val Ser Ala Thr Phe Trp His Asn Pro Arg Asn His Phe Arg Cys Gln
210 215 220

Val Gln Phe His Gly Leu Ser Glu Glu Asp Lys Trp Pro Glu Gly Ser
225 230 235 240

Pro Lys Pro Val Thr Gln Asn Ile Ser Ala Glu Ala Trp Gly Arg Ala
245 250 255

Asp Cys Gly Ile Thr Ser Ala Ser Tyr Gln Gln Gly Val Leu Ser Ala
260 265 270

Thr Ile Leu Tyr Glu Ile Leu Leu Gly Lys Ala Thr Leu Tyr Ala Val
275 280 285

Leu Val Ser Thr Leu Val Val Met Ala Met Val Lys Arg Lys Asn Ser
290 295 300

<210> SEQ ID NO 138
<211> LENGTH: 912
<212> TYPE: DNA
<213> ORGANISM: Artificial Sequence
<220> FEATURE:
<223> OTHER INFORMATION: Synthetic Construct

<400> SEQUENCE: 138
atgctgctgc ttctgctgct tctggggcca ggctccgggc ttggtgctgt cgtctctcaa 60
catccgagct gggttatctg taagagtgga acctctgtga agatcgagtg ccgttccctg 120
gactttcagg ccacaactat gttttggtat cgtcagttcc cgaaacagag tctcatgctg 180
atggcaactt ccaatgaggg ctccaaggcc acatacgagc aaggcgtcga gaaggacaag 240
tttctcatca accatgcaag cctgaccttg tccactctga cagtgaccag tgcccatcct 300
gaagacagca gcttctacat ctgcagtgct ccgtggctag cggggttgta caatgagcag 360
ttcttcgggc cagggacacg gctcaccgtg ctagaggatc tgagaaatgt gactccaccc 420
aaggtctcct tgtttgagcc atcaaaagca gagattgcaa acaaacaaaa ggctaccctc 480
gtgtgcttgg ccaggggctt cttccctgac cacgtggagc tgagctggtg ggtgaatggc 540
aaggaggtcc acagtggggt cagcacggac cctcaggcct acaaggagag caattatagc 600
tactgcctga gcagccgcct gagggtctct gctaccttct ggcacaatcc tcgcaaccac 660
ttccgctgcc aagtgcagtt ccatgggctt tcagaggagg acaagtggcc agagggctca 720
cccaaacctg tcacacagaa catcagtgca gaggcctggg gccgagcaga ctgtgggatt 780
acctcagcat cctatcaaca aggggtcttg tctgccacca tcctctatga gatcctgcta 840
gggaaagcca ccctgtatgc tgtgcttgtc agtacactgg tggtgatggc tatggtcaaa 900
agaaaaaatt ca 912

<210> SEQ ID NO 139
<211> LENGTH: 272
<212> TYPE: PRT
<213> ORGANISM: Artificial Sequence
<220> FEATURE:
<223> OTHER INFORMATION: Synthetic Construct

<400> SEQUENCE: 139

Met Leu Leu Leu Leu Val Pro Val Leu Glu Val Ile Phe Thr Leu Gly
1 5 10 15

Gly Thr Arg Ala Gln Ser Val Thr Gln Leu Asp Ser His Val Ser Val
20 25 30

Ser Glu Gly Thr Pro Val Leu Leu Arg Cys Asn Tyr Ser Ser Ser Tyr
35 40 45

Ser Pro Ser Leu Phe Trp Tyr Val Gln His Pro Asn Lys Gly Leu Gln
50 55 60

Leu Leu Leu Lys Tyr Thr Ser Ala Ala Thr Leu Val Lys Gly Ile Asn
65 70 75 80

Gly Phe Glu Ala Glu Phe Lys Lys Ser Glu Thr Ser Phe His Leu Thr
85 90 95

Lys Pro Ser Ala His Met Ser Asp Ala Ala Glu Tyr Phe Cys Val Val
100 105 110

Ser Ala Ile Gly Tyr Ser Ser Ala Ser Lys Ile Ile Phe Gly Ser Gly
115 120 125

Thr Arg Leu Ser Ile Arg Pro Asn Ile Gln Asn Pro Glu Pro Ala Val
130 135 140

Tyr Gln Leu Lys Asp Pro Arg Ser Gln Asp Ser Thr Leu Cys Leu Phe
145 150 155 160

Thr Asp Phe Asp Ser Gln Ile Asn Val Pro Lys Thr Met Glu Ser Gly
165 170 175

Thr Phe Ile Thr Asp Lys Thr Val Leu Asp Met Lys Ala Met Asp Ser

```
            180                 185                 190

Lys Ser Asn Gly Ala Ile Ala Trp Ser Asn Gln Thr Ser Phe Thr Cys
        195                 200                 205

Gln Asp Ile Phe Lys Glu Thr Asn Ala Thr Tyr Pro Ser Ser Asp Val
    210                 215                 220

Pro Cys Asp Ala Thr Leu Thr Glu Lys Ser Phe Glu Thr Asp Met Asn
225                 230                 235                 240

Leu Asn Phe Gln Asn Leu Leu Val Met Val Leu Arg Ile Leu Leu Leu
                245                 250                 255

Lys Val Ala Gly Phe Asn Leu Leu Met Thr Leu Arg Leu Trp Ser Ser
            260                 265                 270


<210> SEQ ID NO 140
<211> LENGTH: 816
<212> TYPE: DNA
<213> ORGANISM: Artificial Sequence
<220> FEATURE:
<223> OTHER INFORMATION: Synthetic Construct

<400> SEQUENCE: 140

atgctcctgc tgctcgtccc agtgctcgag gtgattttta ctctgggagg aaccagagcc      60

cagtcggtga cccagcttga cagccacgtc tctgtctctg aaggaacccc ggtgctgctg     120

aggtgcaact actcatcttc ttattcacca tctctcttct ggtatgtgca acaccccaac     180

aaaggactcc agcttctcct gaagtacaca tcagcggcca ccctggttaa aggcatcaac     240

ggttttgagg ctgaatttaa gaagagtgaa acctccttcc acctgacgaa accctcagcc     300

catatgagcg acgcggctga gtacttctgt gttgtgagtg ccattgggta cagcagtgct     360

tccaagataa tctttggatc agggaccaga ctcagcatcc ggccaaatat ccagaaccca     420

gaacctgctg tgtaccagtt aaaagatcct cggtctcagg acagcaccct ctgcctgttc     480

accgactttg actcccaaat caatgtgccg aaaaccatgg aatctggaac gttcatcact     540

gacaaaactg tgctggacat gaaagctatg gattccaaga gcaatggggc cattgcctgg     600

agcaaccaga caagcttcac ctgccaagat atcttcaaag agaccaacgc cacctacccc     660

agttcagacg ttccctgtga tgccacgttg actgagaaaa gctttgaaac agatatgaac     720

ctaaactttc aaaacctgct ggttatggtt ctccgaatcc tcctgctgaa agtagccgga     780

tttaacctgc tcatgacgct gaggctgtgg tccagt                               816


<210> SEQ ID NO 141
<211> LENGTH: 308
<212> TYPE: PRT
<213> ORGANISM: Artificial Sequence
<220> FEATURE:
<223> OTHER INFORMATION: Synthetic Construct

<400> SEQUENCE: 141

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80
```

```
Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Ala Gly Gly Pro Ala Glu Thr Gln Tyr Phe Gly Pro
        115                 120                 125

Gly Thr Arg Leu Leu Val Leu Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
    290                 295                 300

Arg Lys Asn Ser
305
```

<210> SEQ ID NO 142
<211> LENGTH: 924
<212> TYPE: DNA
<213> ORGANISM: Artificial Sequence
<220> FEATURE:
<223> OTHER INFORMATION: Synthetic Construct

<400> SEQUENCE: 142

```
atgggcacca gcctcctctg ctggatggcc ctgtgtctcc tgggggcaga tcacgcagat     60

actggagtct cccagaaccc cagacacaag atcacaaaga ggggacagaa tgtaactttc    120

aggtgtgatc caatttctga acacaaccgc ctttattggt accgacagac cctggggcag    180

ggcccagagt ttctgactta cttccagaat gaagctcaac tagaaaaatc aaggctgctc    240

agtgatcggt tctctgcaga gaggcctaag ggatctttct ccaccttgga gatccagcgc    300

acagagcagg gggactcggc catgtatctc tgtgccagca gcttagttgc gggagggccc    360

gcagagaccc agtacttcgg gccaggcacg cggctcctgg tgctcgagga tctgagaaat    420

gtgactccac ccaaggtctc cttgtttgag ccatcaaaag cagagattgc aaacaaacaa    480

aaggctaccc tcgtgtgctt ggccaggggc ttcttccctg accacgtgga gctgagctgg    540

tgggtgaatg gcaaggaggt ccacagtggg gtcagcacgg accctcaggc ctacaaggag    600

agcaattata gctactgcct gagcagccgc ctgagggtct ctgctacctt ctggcacaat    660

cctcgcaacc acttccgctg ccaagtgcag ttccatgggc tttcagagga ggacaagtgg    720
```

ccagagggct cacccaaacc tgtcacacag aacatcagtg cagaggcctg gggccgagca 780
gactgtggga ttacctcagc atcctatcaa caaggggtct tgtctgccac catcctctat 840
gagatcctgc tagggaaagc caccctgtat gctgtgcttg tcagtacact ggtggtgatg 900
gctatggtca aaagaaaaaa ttca 924

<210> SEQ ID NO 143
<211> LENGTH: 600
<212> TYPE: PRT
<213> ORGANISM: Artificial Sequence
<220> FEATURE:
<223> OTHER INFORMATION: Synthetic Construct

<400> SEQUENCE: 143

Met Leu Cys Ser Leu Leu Ala Leu Leu Leu Gly Thr Phe Phe Gly Val
1 5 10 15

Arg Ser Gln Thr Ile His Gln Trp Pro Ala Thr Leu Val Gln Pro Val
20 25 30

Gly Ser Pro Leu Ser Leu Glu Cys Thr Val Glu Gly Thr Ser Asn Pro
35 40 45

Asn Leu Tyr Trp Tyr Arg Gln Ala Ala Gly Arg Gly Leu Gln Leu Leu
50 55 60

Phe Tyr Ser Val Gly Ile Gly Gln Ile Ser Ser Glu Val Pro Gln Asn
65 70 75 80

Leu Ser Ala Ser Arg Pro Gln Asp Arg Gln Phe Ile Leu Ser Ser Lys
85 90 95

Lys Leu Leu Leu Ser Asp Ser Gly Phe Tyr Leu Cys Ala Trp Ala Arg
100 105 110

Ser Arg Glu Leu Phe Phe Gly Glu Gly Ser Arg Leu Thr Val Leu Glu
115 120 125

Asp Leu Lys Asn Val Phe Pro Pro Glu Val Ala Val Phe Glu Pro Ser
130 135 140

Glu Ala Glu Ile Ser His Thr Gln Lys Ala Thr Leu Val Cys Leu Ala
145 150 155 160

Thr Gly Phe Tyr Pro Asp His Val Glu Leu Ser Trp Trp Val Asn Gly
165 170 175

Lys Glu Val His Ser Gly Val Ser Thr Asp Pro Gln Pro Leu Lys Glu
180 185 190

Gln Pro Ala Leu Asn Asp Ser Arg Tyr Cys Leu Ser Ser Arg Leu Arg
195 200 205

Val Ser Ala Thr Phe Trp Gln Asn Pro Arg Asn His Phe Arg Cys Gln
210 215 220

Val Gln Phe Tyr Gly Leu Ser Glu Asn Asp Glu Trp Thr Gln Asp Arg
225 230 235 240

Ala Lys Pro Val Thr Gln Ile Val Ser Ala Glu Ala Trp Gly Arg Ala
245 250 255

Asp Cys Gly Phe Thr Ser Glu Ser Tyr Gln Gln Gly Val Leu Ser Ala
260 265 270

Thr Ile Leu Tyr Glu Ile Leu Leu Gly Lys Ala Thr Leu Tyr Ala Val
275 280 285

Leu Val Ser Ala Leu Val Leu Met Ala Met Val Lys Arg Lys Asp Ser
290 295 300

Arg Gly Gly Ser Gly Ala Thr Asn Phe Ser Leu Leu Lys Gln Ala Gly
305 310 315 320

-continued

```
Asp Val Glu Glu Asn Pro Gly Pro Met Lys Pro Thr Leu Ile Ser Val
                325                 330                 335

Leu Val Ile Ile Phe Ile Leu Arg Gly Thr Arg Ala Gln Arg Val Thr
            340                 345                 350

Gln Pro Glu Lys Leu Leu Ser Val Phe Lys Gly Ala Pro Val Glu Leu
        355                 360                 365

Lys Cys Asn Tyr Ser Tyr Ser Gly Ser Pro Glu Leu Phe Trp Tyr Val
    370                 375                 380

Gln Tyr Ser Arg Gln Arg Leu Gln Leu Leu Leu Arg His Ile Ser Arg
385                 390                 395                 400

Glu Ser Ile Lys Gly Phe Thr Ala Asp Leu Asn Lys Gly Glu Thr Ser
                405                 410                 415

Phe His Leu Lys Lys Pro Phe Ala Gln Glu Glu Asp Ser Ala Met Tyr
            420                 425                 430

Tyr Cys Ala Leu Ser Ala Leu Pro Tyr Asn Gln Gly Gly Lys Leu Ile
        435                 440                 445

Phe Gly Gln Gly Thr Glu Leu Ser Val Lys Pro Asn Ile Gln Asn Pro
    450                 455                 460

Asp Pro Ala Val Tyr Gln Leu Arg Asp Ser Lys Ser Ser Asp Lys Ser
465                 470                 475                 480

Val Cys Leu Phe Thr Asp Phe Asp Ser Gln Thr Asn Val Ser Gln Ser
                485                 490                 495

Lys Asp Ser Asp Val Tyr Ile Thr Asp Lys Thr Val Leu Asp Met Arg
            500                 505                 510

Ser Met Asp Phe Lys Ser Asn Ser Ala Val Ala Trp Ser Asn Lys Ser
        515                 520                 525

Asp Phe Ala Cys Ala Asn Ala Phe Asn Asn Ser Ile Ile Pro Glu Asp
    530                 535                 540

Thr Phe Phe Pro Ser Pro Glu Ser Ser Cys Asp Val Lys Leu Val Glu
545                 550                 555                 560

Lys Ser Phe Glu Thr Asp Thr Asn Leu Asn Phe Gln Asn Leu Ser Val
                565                 570                 575

Ile Gly Phe Arg Ile Leu Leu Leu Lys Val Ala Gly Phe Asn Leu Leu
            580                 585                 590

Met Thr Leu Arg Leu Trp Ser Ser
        595                 600
```

<210> SEQ ID NO 144
<211> LENGTH: 1803
<212> TYPE: DNA
<213> ORGANISM: Artificial Sequence
<220> FEATURE:
<223> OTHER INFORMATION: Synthetic Construct

<400> SEQUENCE: 144

```
atgctctgct ctctccttgc ccttctcctg ggcactttct ttggggtcag atctcagact      60

attcatcaat ggccagcgac cctggtgcag cctgtgggca gccccgctctc tctggagtgc    120

actgtggagg gaacatcaaa ccccaaccta tactggtacc gacaggctgc aggcaggggc    180

ctccagctgc tcttctactc cgttggtatt ggccagatca gctctgaggt gccccagaat    240

ctctcagcct ccagacccca ggaccggcag ttcatcctga gttctaagaa gctccttctc    300

agtgactctg gcttctatct ctgtgcctgg gcgaggagca gggagctgtt ttttggagaa    360

ggctctaggc tgaccgtact ggaggacctg aaaaacgtgt tcccacccga ggtcgctgtg    420

tttgagccat cagaagcaga gatctcccac acccaaaagg ccacactggt gtgcctggcc    480
```

```
acaggcttct accccgacca cgtggagctg agctggtggg tgaatgggaa ggaggtgcac    540

agtggggtca gcacagaccc gcagcccctc aaggagcagc ccgccctcaa tgactccaga    600

tactgcctga gcagccgcct gagggtctcg gccaccttct ggcagaaccc ccgcaaccac    660

ttccgctgtc aagtccagtt ctacgggctc tcggagaatg acgagtggac ccaggatagg    720

gccaaacctg tcacccagat cgtcagcgcc gaggcctggg gtagagcaga ctgtggcttc    780

acctccgagt cttaccagca aggggtcctg tctgccacca tcctctatga gatcttgcta    840

gggaaggcca ccttgtatgc cgtgctggtc agtgccctcg tgctgatggc catggtcaag    900

agaaaggatt ccagaggcgg aagcggcgcc acgaacttct ctctgttaaa gcaagcagga    960

gacgtggaag aaaaccccgg tcccatgaag cccaccctca tctcagtgct tgtgataata   1020

tttatactca gaggaacaag agcccagaga gtgactcagc ccgagaagct cctctctgtc   1080

tttaaagggg ccccagtgga gctgaagtgc aactattcct attctgggag tcctgaactc   1140

ttctggtatg tccagtactc cagacaacgc ctccagttac tcttgagaca catctctaga   1200

gagagcatca aaggcttcac tgctgacctt aacaaaggcg agacatcttt ccacctgaag   1260

aaaccatttg ctcaagagga agactcagcc atgtattact gtgctctaag tgccctcccc   1320

tataaccagg gaggaaagct tatcttcgga cagggaacgg agttatctgt gaaacccaat   1380

atccagaacc ctgaccctgc cgtgtaccag ctgagagact ctaaatccag tgacaagtct   1440

gtctgcctat tcaccgattt tgattctcaa acaaatgtgt cacaaagtaa ggattctgat   1500

gtgtatatca cagacaaaac tgtgctagac atgaggtcta tggacttcaa gagcaacagt   1560

gctgtggcct ggagcaacaa atctgacttt gcatgtgcaa acgccttcaa caacagcatt   1620

attccagaag acaccttctt ccccagccca gaaagttcct gtgatgtcaa gctggtcgag   1680

aaaagctttg aaacagatac gaacctaaac tttcaaaacc tgtcagtgat tgggttccga   1740

atcctcctcc tgaaagtggc cgggtttaat ctgctcatga cgctgcggct gtggtccagc   1800

tga                                                                 1803
```

<210> SEQ ID NO 145
<211> LENGTH: 590
<212> TYPE: PRT
<213> ORGANISM: Artificial Sequence
<220> FEATURE:
<223> OTHER INFORMATION: Synthetic Construct

<400> SEQUENCE: 145

```
Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
            20                  25                  30

Gly Ser Pro Leu Ser Leu Glu Cys Thr Val Glu Gly Thr Ser Asn Pro
        35                  40                  45

Asn Leu Tyr Trp Tyr Arg Gln Ala Ala Gly Arg Gly Leu Gln Leu Leu
    50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ala Arg
            100                 105                 110

Ser Arg Glu Leu Phe Phe Gly Glu Gly Ser Arg Leu Thr Val Leu Glu
```

```
        115                 120                 125

Asp Leu Arg Asn Val Thr Pro Pro Lys Val Ser Leu Phe Glu Pro Ser
    130                 135                 140

Lys Ala Glu Ile Ala Asn Lys Gln Lys Ala Thr Leu Val Cys Leu Ala
145                 150                 155                 160

Arg Gly Phe Phe Pro Asp His Val Glu Leu Ser Trp Trp Val Asn Gly
                165                 170                 175

Lys Glu Val His Ser Gly Val Ser Thr Asp Pro Gln Ala Tyr Lys Glu
            180                 185                 190

Ser Asn Tyr Ser Tyr Cys Leu Ser Ser Arg Leu Arg Val Ser Ala Thr
        195                 200                 205

Phe Trp His Asn Pro Arg Asn His Phe Arg Cys Gln Val Gln Phe His
    210                 215                 220

Gly Leu Ser Glu Glu Asp Lys Trp Pro Glu Gly Ser Pro Lys Pro Val
225                 230                 235                 240

Thr Gln Asn Ile Ser Ala Glu Ala Trp Gly Arg Ala Asp Cys Gly Ile
                245                 250                 255

Thr Ser Ala Ser Tyr Gln Gln Gly Val Leu Ser Ala Thr Ile Leu Tyr
            260                 265                 270

Glu Ile Leu Leu Gly Lys Ala Thr Leu Tyr Ala Val Leu Val Ser Thr
        275                 280                 285

Leu Val Val Met Ala Met Val Lys Arg Lys Asn Ser Gly Ser Gly Ala
    290                 295                 300

Thr Asn Phe Ser Leu Leu Lys Gln Ala Gly Asp Val Glu Glu Asn Pro
305                 310                 315                 320

Gly Pro Met Lys Pro Thr Leu Ile Ser Val Leu Val Ile Ile Phe Ile
                325                 330                 335

Leu Arg Gly Thr Arg Ala Gln Arg Val Thr Gln Pro Glu Lys Leu Leu
            340                 345                 350

Ser Val Phe Lys Gly Ala Pro Val Glu Leu Lys Cys Asn Tyr Ser Tyr
        355                 360                 365

Ser Gly Ser Pro Glu Leu Phe Trp Tyr Val Gln Tyr Ser Arg Gln Arg
    370                 375                 380

Leu Gln Leu Leu Leu Arg His Ile Ser Arg Glu Ser Ile Lys Gly Phe
385                 390                 395                 400

Thr Ala Asp Leu Asn Lys Gly Glu Thr Ser Phe His Leu Lys Lys Pro
                405                 410                 415

Phe Ala Gln Glu Glu Asp Ser Ala Met Tyr Tyr Cys Ala Leu Ser Ala
            420                 425                 430

Leu Pro Tyr Asn Gln Gly Gly Lys Leu Ile Phe Gly Gln Gly Thr Glu
        435                 440                 445

Leu Ser Val Lys Pro Asn Ile Gln Asn Pro Glu Pro Ala Val Tyr Gln
    450                 455                 460

Leu Lys Asp Pro Arg Ser Gln Asp Ser Thr Leu Cys Leu Phe Thr Asp
465                 470                 475                 480

Phe Asp Ser Gln Ile Asn Val Pro Lys Thr Met Glu Ser Gly Thr Phe
                485                 490                 495

Ile Thr Asp Lys Thr Val Leu Asp Met Lys Ala Met Asp Ser Lys Ser
            500                 505                 510

Asn Gly Ala Ile Ala Trp Ser Asn Gln Thr Ser Phe Thr Cys Gln Asp
        515                 520                 525

Ile Phe Lys Glu Thr Asn Ala Thr Tyr Pro Ser Ser Asp Val Pro Cys
    530                 535                 540
```

```
Asp Ala Thr Leu Thr Glu Lys Ser Phe Glu Thr Asp Met Asn Leu Asn
545                 550                 555                 560

Phe Gln Asn Leu Leu Val Met Val Leu Arg Ile Leu Leu Leu Lys Val
                565                 570                 575

Ala Gly Phe Asn Leu Leu Met Thr Leu Arg Leu Trp Ser Ser
            580                 585                 590


<210> SEQ ID NO 146
<211> LENGTH: 1773
<212> TYPE: DNA
<213> ORGANISM: Artificial Sequence
<220> FEATURE:
<223> OTHER INFORMATION: Synthetic Construct

<400> SEQUENCE: 146

atgctctgct ctctccttgc ccttctcctg ggcactttct ttggggtcag atctcagact      60

attcatcaat ggccagcgac cctggtgcag cctgtgggca gcccgctctc tctggagtgc     120

actgtggagg gaacatcaaa ccccaaccta tactggtacc gacaggctgc aggcaggggc     180

ctccagctgc tcttctactc cgttggtatt ggccagatca gctctgaggt gccccagaat     240

ctctcagcct ccagacccca ggaccggcag ttcatcctga gttctaagaa gctccttctc     300

agtgactctg gcttctatct ctgtgcctgg gcgaggagca gggagctgtt ttttggagaa     360

ggctctaggc tgaccgtact ggaggatctg agaaatgtga ctccacccaa ggtctccttg     420

tttgagccat caaaagcaga gattgcaaac aaacaaaagg ctaccctcgt gtgcttggcc     480

aggggcttct tccctgacca cgtggagctg agctggtggg tgaatggcaa ggaggtccac     540

agtggggtca gcacggaccc tcaggcctac aaggagagca attatagcta ctgcctgagc     600

agccgcctga gggtctctgc taccttctgg cacaatcctc gcaaccactt ccgctgccaa     660

gtgcagttcc atgggctttc agaggaggac aagtggccag agggctcacc caaacctgtc     720

acacagaaca tcagtgcaga ggcctggggc cgagcagact gtgggattac ctcagcatcc     780

tatcaacaag ggtcttgtc tgccaccatc ctctatgaga tcctgctagg gaaagccacc     840

ctgtatgctg tgcttgtcag tacactggtg gtgatggcta tggtcaaaag aaaaaattca     900

ggaagcggcg ccacgaactt ctctctgtta aagcaagcag gagacgtgga agaaaacccc     960

ggtcccatga agcccaccct catctcagtg cttgtgataa tatttatact cagaggaaca    1020

agagcccaga gagtgactca gcccgagaag ctcctctctg tctttaaagg ggccccagtg    1080

gagctgaagt gcaactattc ctattctggg agtcctgaac tcttctggta tgtccagtac    1140

tccagacaac gcctccagtt actcttgaga cacatctcta gagagagcat caaaggcttc    1200

actgctgacc ttaacaaagg cgagacatct ttccacctga agaaaccatt tgctcaagag    1260

gaagactcag ccatgtatta ctgtgctcta agtgccctcc cctataacca gggaggaaag    1320

cttatcttcg gacagggaac ggagttatct gtgaaaccca atatccagaa cccagaacct    1380

gctgtgtacc agttaaaaga tcctcggtct caggacagca ccctctgcct gttcaccgac    1440

tttgactccc aaatcaatgt gccgaaaacc atggaatctg gaacgttcat cactgacaaa    1500

actgtgctgg acatgaaagc tatggattcc aagagcaatg gggccattgc ctggagcaac    1560

cagacaagct tcacctgcca agatatcttc aaagagacca acgccaccta ccccagttca    1620

gacgttccct gtgatgccac gttgactgag aaaagctttg aaacagatat gaacctaaac    1680

tttcaaaacc tgctggttat ggttctccga atcctcctgc tgaaagtagc cggatttaac    1740

ctgctcatga cgctgaggct gtggtccagt tga                                 1773
```

<210> SEQ ID NO 147
<211> LENGTH: 597
<212> TYPE: PRT
<213> ORGANISM: Artificial Sequence
<220> FEATURE:
<223> OTHER INFORMATION: Synthetic Construct

<400> SEQUENCE: 147

Met Gly Thr Arg Leu Leu Cys Trp Ala Ala Leu Cys Leu Leu Gly Ala
1 5 10 15

Glu Leu Thr Glu Ala Gly Val Ala Gln Ser Pro Arg Tyr Lys Ile Ile
20 25 30

Glu Lys Arg Gln Ser Val Ala Phe Trp Cys Asn Pro Ile Ser Gly His
35 40 45

Ala Thr Leu Tyr Trp Tyr Gln Gln Ile Leu Gly Gln Gly Pro Lys Leu
50 55 60

Leu Ile Gln Phe Gln Asn Asn Gly Val Val Asp Asp Ser Gln Leu Pro
65 70 75 80

Lys Asp Arg Phe Ser Ala Glu Arg Leu Lys Gly Val Asp Ser Thr Leu
85 90 95

Lys Ile Gln Pro Ala Lys Leu Glu Asp Ser Ala Val Tyr Leu Cys Ala
100 105 110

Ser Arg Asp Thr Glu Ala Phe Phe Gly Gln Gly Thr Arg Leu Thr Val
115 120 125

Val Glu Asp Leu Asn Lys Val Phe Pro Pro Glu Val Ala Val Phe Glu
130 135 140

Pro Ser Glu Ala Glu Ile Ser His Thr Gln Lys Ala Thr Leu Val Cys
145 150 155 160

Leu Ala Thr Gly Phe Phe Pro Asp His Val Glu Leu Ser Trp Trp Val
165 170 175

Asn Gly Lys Glu Val His Ser Gly Val Ser Thr Asp Pro Gln Pro Leu
180 185 190

Lys Glu Gln Pro Ala Leu Asn Asp Ser Arg Tyr Cys Leu Ser Ser Arg
195 200 205

Leu Arg Val Ser Ala Thr Phe Trp Gln Asn Pro Arg Asn His Phe Arg
210 215 220

Cys Gln Val Gln Phe Tyr Gly Leu Ser Glu Asn Asp Glu Trp Thr Gln
225 230 235 240

Asp Arg Ala Lys Pro Val Thr Gln Ile Val Ser Ala Glu Ala Trp Gly
245 250 255

Arg Ala Asp Cys Gly Phe Thr Ser Val Ser Tyr Gln Gln Gly Val Leu
260 265 270

Ser Ala Thr Ile Leu Tyr Glu Ile Leu Leu Gly Lys Ala Thr Leu Tyr
275 280 285

Ala Val Leu Val Ser Ala Leu Val Leu Met Ala Met Val Lys Arg Lys
290 295 300

Asp Phe Gly Ser Gly Ala Thr Asn Phe Ser Leu Leu Lys Gln Ala Gly
305 310 315 320

Asp Val Glu Glu Asn Pro Gly Pro Met Arg Leu Val Ala Arg Val Thr
325 330 335

Val Phe Leu Thr Phe Gly Thr Ile Ile Asp Ala Lys Thr Thr Gln Pro
340 345 350

Pro Ser Met Asp Cys Ala Glu Gly Arg Ala Ala Asn Leu Pro Cys Asn
355 360 365

His Ser Thr Ile Ser Gly Asn Glu Tyr Val Tyr Trp Tyr Arg Gln Ile
370 375 380

His Ser Gln Gly Pro Gln Tyr Ile Ile His Gly Leu Lys Asn Asn Glu
385 390 395 400

Thr Asn Glu Met Ala Ser Leu Ile Ile Thr Glu Asp Arg Lys Ser Ser
405 410 415

Thr Leu Ile Leu Pro His Ala Thr Leu Arg Asp Thr Ala Val Tyr Tyr
420 425 430

Cys Ile Val Arg Ala Trp Tyr Asn Asn Asn Asp Met Arg Phe Gly Ala
435 440 445

Gly Thr Arg Leu Thr Val Lys Pro Asn Ile Gln Asn Pro Asp Pro Ala
450 455 460

Val Tyr Gln Leu Arg Asp Ser Lys Ser Ser Asp Lys Ser Val Cys Leu
465 470 475 480

Phe Thr Asp Phe Asp Ser Gln Thr Asn Val Ser Gln Ser Lys Asp Ser
485 490 495

Asp Val Tyr Ile Thr Asp Lys Thr Val Leu Asp Met Arg Ser Met Asp
500 505 510

Phe Lys Ser Asn Ser Ala Val Ala Trp Ser Asn Lys Ser Asp Phe Ala
515 520 525

Cys Ala Asn Ala Phe Asn Asn Ser Ile Ile Pro Glu Asp Thr Phe Phe
530 535 540

Pro Ser Pro Glu Ser Ser Cys Asp Val Lys Leu Val Glu Lys Ser Phe
545 550 555 560

Glu Thr Asp Thr Asn Leu Asn Phe Gln Asn Leu Ser Val Ile Gly Phe
565 570 575

Arg Ile Leu Leu Leu Lys Val Ala Gly Phe Asn Leu Leu Met Thr Leu
580 585 590

Arg Leu Trp Ser Ser
595

<210> SEQ ID NO 148
<211> LENGTH: 1794
<212> TYPE: DNA
<213> ORGANISM: Artificial Sequence
<220> FEATURE:
<223> OTHER INFORMATION: Synthetic Construct

<400> SEQUENCE: 148
atgggcacca ggctcctctg ctgggcggcc ctctgtctcc tgggagcaga actcacagaa 60
gctggagttg cccagtctcc cagatataag attatagaga aaaggcagag tgtggctttt 120
tggtgcaatc ctatatctgg ccatgctacc ctttactggt accagcagat cctgggacag 180
ggcccaaagc ttctgattca gtttcagaat aacggtgtag tggatgattc acagttgcct 240
aaggatcgat tttctgcaga gaggctcaaa ggagtagact ccactctcaa gatccagcct 300
gcaaagcttg aggactcggc cgtgtatctc tgtgccagca gggacactga agctttcttt 360
ggacaaggca ccagactcac agttgtagag gacctgaaca aggtgttccc acccgaggtc 420
gctgtgtttg agccatcaga agcagagatc tcccacaccc aaaaggccac actggtgtgc 480
ctggccacag gcttcttccc cgaccacgtg gagctgagct ggtgggtgaa tgggaaggag 540
gtgcacagtg ggtcagcac ggacccgcag cccctcaagg agcagcccgc cctcaatgac 600
tccagatact gcctgagcag ccgcctgagg gtctcggcca ccttctggca gaacccccgc 660
aaccacttcc gctgtcaagt ccagttctac gggctctcgg agaatgacga gtggacccag 720

```
gatagggcca aacccgtcac ccagatcgtc agcgccgagg cctggggtag agcagactgt    780

ggctttacct cggtgtccta ccagcaaggg gtcctgtctg ccaccatcct ctatgagatc    840

ctgctaggga aggccaccct gtatgctgtg ctggtcagcg cccttgtgtt gatggccatg    900

gtcaagagaa aggatttcgg aagcggcgcc acgaacttct ctctgttaaa gcaagcagga    960

gacgtggaag aaaaccccgg tcccatgagg ctggtggcaa gagtaactgt gtttctgacc   1020

tttggaacta taattgatgc taagaccacc cagcccccct ccatggattg cgctgaagga   1080

agagctgcaa acctgccttg taatcactct accatcagtg gaaatgagta tgtgtattgg   1140

tatcgacaga ttcactccca ggggccacag tatatcattc atggtctaaa aaacaatgaa   1200

accaatgaaa tggcctctct gatcatcaca gaagacagaa agtccagcac cttgatcctg   1260

ccccacgcta cgctgagaga cactgctgtg tactattgca tcgtcagagc ttggtacaat   1320

aacaatgaca tgcgctttgg agcagggacc agactgacag taaaaccaaa tatccagaac   1380

cctgaccctg ccgtgtacca gctgagagac tctaaatcca gtgacaagtc tgtctgccta   1440

ttcaccgatt ttgattctca aacaaatgtg tcacaaagta aggattctga tgtgtatatc   1500

acagacaaaa ctgtgctaga catgaggtct atggacttca agagcaacag tgctgtggcc   1560

tggagcaaca aatctgactt tgcatgtgca aacgccttca acaacagcat tattccagaa   1620

gacaccttct tccccagccc agaaagttcc tgtgatgtca agctggtcga gaaaagcttt   1680

gaaacagata cgaacctaaa ctttcaaaac ctgtcagtga ttgggttccg aatcctcctc   1740

ctgaaagtgg ccgggtttaa tctgctcatg acgctgcggc tgtggtccag ctga         1794
```

<210> SEQ ID NO 149
<211> LENGTH: 589
<212> TYPE: PRT
<213> ORGANISM: Artificial Sequence
<220> FEATURE:
<223> OTHER INFORMATION: Synthetic Construct

<400> SEQUENCE: 149

```
Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Arg Asp Thr Glu Ala Phe Phe Gly Gln Gly Thr Arg Leu Thr Val
        115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175
```

-continued

```
Asn Gly Lys Glu Val His Ser Gly Val Ser Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Met Arg Leu Val Ala Arg Val Thr Val Phe Leu Thr
                325                 330                 335

Phe Gly Thr Ile Ile Asp Ala Lys Thr Thr Gln Pro Pro Ser Met Asp
            340                 345                 350

Cys Ala Glu Gly Arg Ala Ala Asn Leu Pro Cys Asn His Ser Thr Ile
        355                 360                 365

Ser Gly Asn Glu Tyr Val Tyr Trp Tyr Arg Gln Ile His Ser Gln Gly
    370                 375                 380

Pro Gln Tyr Ile Ile His Gly Leu Lys Asn Asn Glu Thr Asn Glu Met
385                 390                 395                 400

Ala Ser Leu Ile Ile Thr Glu Asp Arg Lys Ser Ser Thr Leu Ile Leu
                405                 410                 415

Pro His Ala Thr Leu Arg Asp Thr Ala Val Tyr Tyr Cys Ile Val Arg
            420                 425                 430

Ala Trp Tyr Asn Asn Asn Asp Met Arg Phe Gly Ala Gly Thr Arg Leu
        435                 440                 445

Thr Val Lys Pro Asn Ile Gln Asn Pro Glu Pro Ala Val Tyr Gln Leu
    450                 455                 460

Lys Asp Pro Arg Ser Gln Asp Ser Thr Leu Cys Leu Phe Thr Asp Phe
465                 470                 475                 480

Asp Ser Gln Ile Asn Val Pro Lys Thr Met Glu Ser Gly Thr Phe Ile
                485                 490                 495

Thr Asp Lys Thr Val Leu Asp Met Lys Ala Met Asp Ser Lys Ser Asn
            500                 505                 510

Gly Ala Ile Ala Trp Ser Asn Gln Thr Ser Phe Thr Cys Gln Asp Ile
        515                 520                 525

Phe Lys Glu Thr Asn Ala Thr Tyr Pro Ser Ser Asp Val Pro Cys Asp
    530                 535                 540

Ala Thr Leu Thr Glu Lys Ser Phe Glu Thr Asp Met Asn Leu Asn Phe
545                 550                 555                 560

Gln Asn Leu Leu Val Met Val Leu Arg Ile Leu Leu Leu Lys Val Ala
                565                 570                 575

Gly Phe Asn Leu Leu Met Thr Leu Arg Leu Trp Ser Ser
            580                 585
```

<210> SEQ ID NO 150
<211> LENGTH: 1770
<212> TYPE: DNA
<213> ORGANISM: Artificial Sequence
<220> FEATURE:
<223> OTHER INFORMATION: Synthetic Construct

<400> SEQUENCE: 150
atgggcacca ggctcctctg ctgggcggcc ctctgtctcc tgggagcaga actcacagaa 60
gctggagttg cccagtctcc cagatataag attatagaga aaaggcagag tgtggctttt 120
tggtgcaatc ctatatctgg ccatgctacc ctttactggt accagcagat cctgggacag 180
ggcccaaagc ttctgattca gtttcagaat aacggtgtag tggatgattc acagttgcct 240
aaggatcgat tttctgcaga gaggctcaaa ggagtagact ccactctcaa gatccagcct 300
gcaaagcttg aggactcggc cgtgtatctc tgtgccagca gggacactga agctttcttt 360
ggacaaggca ccagactcac agttgtagag gatctgagaa atgtgactcc acccaaggtc 420
tccttgtttg agccatcaaa agcagagatt gcaaacaaac aaaaggctac cctcgtgtgc 480
ttggccaggg gcttcttccc tgaccacgtg gagctgagct ggtgggtgaa tggcaaggag 540
gtccacagtg ggtcagcac ggaccctcag gcctacaagg agagcaatta tagctactgc 600
ctgagcagcc gcctgagggt ctctgctacc ttctggcaca atcctcgcaa ccacttccgc 660
tgccaagtgc agttccatgg gctttcagag gaggacaagt ggccagaggg ctcacccaaa 720
cctgtcacac agaacatcag tgcagaggcc tggggccgag cagactgtgg gattacctca 780
gcatcctatc aacaaggggt cttgtctgcc accatcctct atgagatcct gctagggaaa 840
gccaccctgt atgctgtgct tgtcagtaca ctggtggtga tggctatggt caaaagaaaa 900
aattcaggaa gcggcgccac gaacttctct ctgttaaagc aagcaggaga cgtggaagaa 960
aaccccggtc ccatgaggct ggtggcaaga gtaactgtgt ttctgacctt tggaactata 1020
attgatgcta agaccaccca gcccccctcc atggattgcg ctgaaggaag agctgcaaac 1080
ctgccttgta atcactctac catcagtgga aatgagtatg tgtattggta tcgacagatt 1140
cactcccagg ggccacagta tatcattcat ggtctaaaaa acaatgaaac caatgaaatg 1200
gcctctctga tcatcacaga agacagaaag tccagcacct tgatcctgcc ccacgctacg 1260
ctgagagaca ctgctgtgta ctattgcatc gtcagagctt ggtacaataa caatgacatg 1320
cgctttggag cagggaccag actgacagta aaaccaaata tccagaaccc agaacctgct 1380
gtgtaccagt taaaagatcc tcggtctcag gacagcaccc tctgcctgtt caccgacttt 1440
gactcccaaa tcaatgtgcc gaaaaccatg gaatctggaa cgttcatcac tgacaaaact 1500
gtgctggaca tgaaagctat ggattccaag agcaatgggg ccattgcctg gagcaaccag 1560
acaagcttca cctgccaaga tatcttcaaa gagaccaacg ccacctaccc cagttcagac 1620
gttccctgtg atgccacgtt gactgagaaa agctttgaaa cagatatgaa cctaaacttt 1680
caaaacctgc tggttatggt tctccgaatc ctcctgctga aagtagccgg atttaacctg 1740
ctcatgacgc tgaggctgtg gtccagttga 1770

<210> SEQ ID NO 151
<211> LENGTH: 604
<212> TYPE: PRT
<213> ORGANISM: Artificial Sequence
<220> FEATURE:
<223> OTHER INFORMATION: Synthetic Construct

<400> SEQUENCE: 151

-continued

```
Met Leu Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Lys Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala His
            100                 105                 110

Glu Arg Ile Thr Asp Thr Gln Tyr Phe Gly Pro Gly Thr Arg Leu Thr
        115                 120                 125

Val Leu Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly Gly Ser Gly Ala Thr Asn Phe Ser Leu Leu Lys
305                 310                 315                 320

Gln Ala Gly Asp Val Glu Glu Asn Pro Gly Pro Met Ile Ser Leu Arg
                325                 330                 335

Val Leu Leu Val Ile Leu Trp Leu Gln Leu Ser Trp Val Trp Ser Gln
            340                 345                 350

Arg Lys Glu Val Glu Gln Asp Pro Gly Pro Phe Asn Val Pro Glu Gly
        355                 360                 365

Ala Thr Val Ala Phe Asn Cys Thr Tyr Ser Asn Ser Ala Ser Gln Ser
    370                 375                 380

Phe Phe Trp Tyr Arg Gln Asp Cys Arg Lys Glu Pro Lys Leu Leu Met
385                 390                 395                 400

Ser Val Tyr Ser Ser Gly Asn Glu Asp Gly Arg Phe Thr Ala Gln Leu
                405                 410                 415
```

-continued

```
Asn Arg Ala Ser Gln Tyr Ile Ser Leu Leu Ile Arg Asp Ser Lys Leu
            420                 425                 430

Ser Asp Ser Ala Thr Tyr Leu Cys Val Val Asn Met Arg Asp Ser Ser
        435                 440                 445

Tyr Lys Leu Ile Phe Gly Ser Gly Thr Arg Leu Leu Val Arg Pro Asp
    450                 455                 460

Ile Gln Asn Pro Asp Pro Ala Val Tyr Gln Leu Arg Asp Ser Lys Ser
465                 470                 475                 480

Ser Asp Lys Ser Val Cys Leu Phe Thr Asp Phe Asp Ser Gln Thr Asn
                485                 490                 495

Val Ser Gln Ser Lys Asp Ser Asp Val Tyr Ile Thr Asp Lys Thr Val
            500                 505                 510

Leu Asp Met Arg Ser Met Asp Phe Lys Ser Asn Ser Ala Val Ala Trp
        515                 520                 525

Ser Asn Lys Ser Asp Phe Ala Cys Ala Asn Ala Phe Asn Asn Ser Ile
    530                 535                 540

Ile Pro Glu Asp Thr Phe Phe Pro Ser Pro Glu Ser Ser Cys Asp Val
545                 550                 555                 560

Lys Leu Val Glu Lys Ser Phe Glu Thr Asp Thr Asn Leu Asn Phe Gln
                565                 570                 575

Asn Leu Ser Val Ile Gly Phe Arg Ile Leu Leu Leu Lys Val Ala Gly
            580                 585                 590

Phe Asn Leu Leu Met Thr Leu Arg Leu Trp Ser Ser
        595                 600
```

<210> SEQ ID NO 152
<211> LENGTH: 1815
<212> TYPE: DNA
<213> ORGANISM: Artificial Sequence
<220> FEATURE:
<223> OTHER INFORMATION: Synthetic Construct

<400> SEQUENCE: 152

```
atgctgctgc ttctgctgct tctggggcca gcaggctccg ggcttggtgc tgtcgtctct      60

caacatccga gcagggttat ctgtaagagt ggaacctctg tgaagatcga gtgccgttcc     120

ctggactttc aggccacaac tatgttttgg tatcgtcagt tcccgaaaaa gagtctcatg     180

ctgatggcaa cttccaatga gggctccaag gccacatacg agcaaggcgt cgagaaggac     240

aagtttctca tcaaccatgc aagcctgacc ttgtccactc tgacagtgac cagtgcccat     300

cctgaagaca gcagcttcta catctgcagt gcccatgagc ggatcacaga tacgcagtat     360

tttggcccag gcacccggct gacagtgctc gaggacctga aaaacgtgtt cccacccgag     420

gtcgctgtgt ttgagccatc agaagcagag atctcccaca cccaaaaggc cacactggtg     480

tgcctggcca caggcttcta ccccgaccac gtggagctga gctggtgggt gaatgggaag     540

gaggtgcaca gtggggtcag cacagacccg cagcccctca aggagcagcc cgccctcaat     600

gactccagat actgcctgag cagccgcctg agggtctcgg ccaccttctg gcagaacccc     660

cgcaaccact tccgctgtca agtccagttc tacgggctct cggagaatga cgagtggacc     720

caggataggg ccaaacctgt cacccagatc gtcagcgccg aggcctgggg tagagcagac     780

tgtggcttca cctccgagtc ttaccagcaa ggggtcctgt ctgccaccat cctctatgag     840

atcttgctag ggaaggccac cttgtatgcc gtgctggtca gtgccctcgt gctgatggcc     900

atggtcaaga gaaaggattc cagaggcgga agcggcgcca cgaacttctc tctgttaaag     960

caagcaggag acgtggaaga aaaccccggt cccatgatat ccttgagagt tttactggtg    1020
```

```
atcctgtggc ttcagttaag ctgggtttgg agccaacgga aggaggtgga gcaggatcct   1080

ggacccttca atgttccaga gggagccact gtcgctttca actgtactta cagcaacagt   1140

gcttctcagt ctttcttctg gtacagacag gattgcagga aagaacctaa gttgctgatg   1200

tccgtatact ccagtggtaa tgaagatgga aggtttacag cacagctcaa tagagccagc   1260

cagtatattt ccctgctcat cagagactcc aagctcagtg attcagccac ctacctctgt   1320

gtggtgaaca tgagggatag cagctataaa ttgatcttcg ggagtgggac cagactgctg   1380

gtcaggcctg atatccagaa ccctgaccct gccgtgtacc agctgagaga ctctaaatcc   1440

agtgacaagt ctgtctgcct attcaccgat tttgattctc aaacaaatgt gtcacaaagt   1500

aaggattctg atgtgtatat cacagacaaa actgtgctag acatgaggtc tatggacttc   1560

aagagcaaca gtgctgtggc ctggagcaac aaatctgact ttgcatgtgc aaacgccttc   1620

aacaacagca ttattccaga agacaccttc ttccccagcc cagaaagttc ctgtgatgtc   1680

aagctggtcg agaaaagctt tgaaacagat acgaacctaa actttcaaaa cctgtcagtg   1740

attgggttcc gaatcctcct cctgaaagtg gccgggttta atctgctcat gacgctgcgg   1800

ctgtggtcca gctga                                                    1815
```

```
<210> SEQ ID NO 153
<211> LENGTH: 594
<212> TYPE: PRT
<213> ORGANISM: Artificial Sequence
<220> FEATURE:
<223> OTHER INFORMATION: Synthetic Construct

<400> SEQUENCE: 153

Met Leu Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Lys Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala His
            100                 105                 110

Glu Arg Ile Thr Asp Thr Gln Tyr Phe Gly Pro Gly Thr Arg Leu Thr
        115                 120                 125

Val Leu Glu Asp Leu Arg Asn Val Thr Pro Pro Lys Val Ser Leu Phe
    130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
            180                 185                 190

Tyr Lys Glu Ser Asn Tyr Ser Tyr Cys Leu Ser Ser Arg Leu Arg Val
        195                 200                 205

Ser Ala Thr Phe Trp His Asn Pro Arg Asn His Phe Arg Cys Gln Val
```

```
    210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr Gln Gln Gly Val Leu Ser Ala Thr
            260                 265                 270

Ile Leu Tyr Glu Ile Leu Leu Gly Lys Ala Thr Leu Tyr Ala Val Leu
        275                 280                 285

Val Ser Thr Leu Val Val Met Ala Met Val Lys Arg Lys Asn Ser Gly
    290                 295                 300

Ser Gly Ala Thr Asn Phe Ser Leu Leu Lys Gln Ala Gly Asp Val Glu
305                 310                 315                 320

Glu Asn Pro Gly Pro Met Ile Ser Leu Arg Val Leu Leu Val Ile Leu
                325                 330                 335

Trp Leu Gln Leu Ser Trp Val Trp Ser Gln Arg Lys Glu Val Glu Gln
            340                 345                 350

Asp Pro Gly Pro Phe Asn Val Pro Glu Gly Ala Thr Val Ala Phe Asn
        355                 360                 365

Cys Thr Tyr Ser Asn Ser Ala Ser Gln Ser Phe Phe Trp Tyr Arg Gln
    370                 375                 380

Asp Cys Arg Lys Glu Pro Lys Leu Leu Met Ser Val Tyr Ser Ser Gly
385                 390                 395                 400

Asn Glu Asp Gly Arg Phe Thr Ala Gln Leu Asn Arg Ala Ser Gln Tyr
                405                 410                 415

Ile Ser Leu Leu Ile Arg Asp Ser Lys Leu Ser Asp Ser Ala Thr Tyr
            420                 425                 430

Leu Cys Val Val Asn Met Arg Asp Ser Ser Tyr Lys Leu Ile Phe Gly
        435                 440                 445

Ser Gly Thr Arg Leu Leu Val Arg Pro Asp Ile Gln Asn Pro Glu Pro
    450                 455                 460

Ala Val Tyr Gln Leu Lys Asp Pro Arg Ser Gln Asp Ser Thr Leu Cys
465                 470                 475                 480

Leu Phe Thr Asp Phe Asp Ser Gln Ile Asn Val Pro Lys Thr Met Glu
                485                 490                 495

Ser Gly Thr Phe Ile Thr Asp Lys Thr Val Leu Asp Met Lys Ala Met
            500                 505                 510

Asp Ser Lys Ser Asn Gly Ala Ile Ala Trp Ser Asn Gln Thr Ser Phe
        515                 520                 525

Thr Cys Gln Asp Ile Phe Lys Glu Thr Asn Ala Thr Tyr Pro Ser Ser
    530                 535                 540

Asp Val Pro Cys Asp Ala Thr Leu Thr Glu Lys Ser Phe Glu Thr Asp
545                 550                 555                 560

Met Asn Leu Asn Phe Gln Asn Leu Leu Val Met Val Leu Arg Ile Leu
                565                 570                 575

Leu Leu Lys Val Ala Gly Phe Asn Leu Leu Met Thr Leu Arg Leu Trp
            580                 585                 590

Ser Ser
```

<210> SEQ ID NO 154
<211> LENGTH: 1785
<212> TYPE: DNA
<213> ORGANISM: Artificial Sequence
<220> FEATURE:

<223> OTHER INFORMATION: Synthetic Construct

<400> SEQUENCE: 154
atgctgctgc ttctgctgct tctggggcca gcaggctccg ggcttggtgc tgtcgtctct 60
caacatccga gcagggttat ctgtaagagt ggaacctctg tgaagatcga gtgccgttcc 120
ctggactttc aggccacaac tatgttttgg tatcgtcagt tcccgaaaaa gagtctcatg 180
ctgatggcaa cttccaatga gggctccaag gccacatacg agcaaggcgt cgagaaggac 240
aagtttctca tcaaccatgc aagcctgacc ttgtccactc tgacagtgac cagtgcccat 300
cctgaagaca gcagcttcta catctgcagt gcccatgagc ggatcacaga tacgcagtat 360
tttggcccag gcacccggct gacagtgctc gaggatctga gaaatgtgac tccacccaag 420
gtctccttgt ttgagccatc aaaagcagag attgcaaaca aacaaaaggc taccctcgtg 480
tgcttggcca ggggcttctt ccctgaccac gtggagctga gctggtgggt gaatggcaag 540
gaggtccaca gtggggtcag cacggaccct caggcctaca aggagagcaa ttatagctac 600
tgcctgagca gccgcctgag ggtctctgct accttctggc acaatcctcg caaccacttc 660
cgctgccaag tgcagttcca tgggctttca gaggaggaca agtggccaga gggctcaccc 720
aaacctgtca cacagaacat cagtgcagag gcctggggcc gagcagactg tgggattacc 780
tcagcatcct atcaacaagg ggtcttgtct gccaccatcc tctatgagat cctgctaggg 840
aaagccaccc tgtatgctgt gcttgtcagt acactggtgg tgatggctat ggtcaaaaga 900
aaaaattcag gaagcggcgc cacgaacttc tctctgttaa agcaagcagg agacgtggaa 960
gaaaaccccg gtcccatgat atccttgaga gttttactgg tgatcctgtg gcttcagtta 1020
agctgggttt ggagccaacg gaaggaggtg gagcaggatc ctggaccctt caatgttcca 1080
gagggagcca ctgtcgcttt caactgtact tacagcaaca gtgcttctca gtctttcttc 1140
tggtacagac aggattgcag gaaagaacct aagttgctga tgtccgtata ctccagtggt 1200
aatgaagatg gaaggtttac agcacagctc aatagagcca gccagtatat ttccctgctc 1260
atcagagact ccaagctcag tgattcagcc acctacctct gtgtggtgaa catgagggat 1320
agcagctata aattgatctt cgggagtggg accagactgc tggtcaggcc tgatatccag 1380
aacccagaac ctgctgtgta ccagttaaaa gatcctcggt ctcaggacag caccctctgc 1440
ctgttcaccg actttgactc ccaaatcaat gtgccgaaaa ccatggaatc tggaacgttc 1500
atcactgaca aaactgtgct ggacatgaaa gctatggatt ccaagagcaa tggggccatt 1560
gcctggagca accagacaag cttcacctgc caagatatct tcaaagagac caacgccacc 1620
taccccagtt cagacgttcc ctgtgatgcc acgttgactg agaaaagctt tgaaacagat 1680
atgaacctaa actttcaaaa cctgctggtt atggttctcc gaatcctcct gctgaaagta 1740
gccggattta acctgctcat gacgctgagg ctgtggtcca gttga 1785

<210> SEQ ID NO 155
<211> LENGTH: 622
<212> TYPE: PRT
<213> ORGANISM: Artificial Sequence
<220> FEATURE:
<223> OTHER INFORMATION: Synthetic Construct

<400> SEQUENCE: 155

Met Glu Ala Val Val Thr Thr Leu Pro Arg Glu Gly Gly Val Arg Pro
1 5 10 15

Ser Arg Lys Met Leu Leu Leu Leu Leu Leu Leu Gly Pro Gly Ser Gly
20 25 30

-continued

```
Leu Gly Ala Val Val Ser Gln His Pro Ser Arg Val Ile Cys Lys Ser
        35                  40                  45

Gly Thr Ser Val Lys Ile Glu Cys Arg Ser Leu Asp Phe Gln Ala Thr
    50                  55                  60

Thr Met Phe Trp Tyr Arg Gln Phe Pro Lys Lys Ser Leu Met Leu Met
65                  70                  75                  80

Ala Thr Ser Asn Glu Gly Ser Lys Ala Thr Tyr Glu Gln Gly Val Glu
                85                  90                  95

Lys Asp Lys Phe Leu Ile Asn His Ala Ser Leu Thr Leu Ser Thr Leu
            100                 105                 110

Thr Val Thr Ser Ala His Pro Glu Asp Ser Ser Phe Tyr Ile Cys Ser
        115                 120                 125

Ala His Glu Arg Ile Thr Asp Thr Gln Tyr Phe Gly Pro Gly Thr Arg
    130                 135                 140

Leu Thr Val Leu Glu Asp Leu Lys Asn Val Phe Pro Pro Glu Val Ala
145                 150                 155                 160

Val Phe Glu Pro Ser Glu Ala Glu Ile Ser His Thr Gln Lys Ala Thr
                165                 170                 175

Leu Val Cys Leu Ala Thr Gly Phe Tyr Pro Asp His Val Glu Leu Ser
            180                 185                 190

Trp Trp Val Asn Gly Lys Glu Val His Ser Gly Val Ser Thr Asp Pro
        195                 200                 205

Gln Pro Leu Lys Glu Gln Pro Ala Leu Asn Asp Ser Arg Tyr Cys Leu
    210                 215                 220

Ser Ser Arg Leu Arg Val Ser Ala Thr Phe Trp Gln Asn Pro Arg Asn
225                 230                 235                 240

His Phe Arg Cys Gln Val Gln Phe Tyr Gly Leu Ser Glu Asn Asp Glu
                245                 250                 255

Trp Thr Gln Asp Arg Ala Lys Pro Val Thr Gln Ile Val Ser Ala Glu
            260                 265                 270

Ala Trp Gly Arg Ala Asp Cys Gly Phe Thr Ser Glu Ser Tyr Gln Gln
        275                 280                 285

Gly Val Leu Ser Ala Thr Ile Leu Tyr Glu Ile Leu Leu Gly Lys Ala
    290                 295                 300

Thr Leu Tyr Ala Val Leu Val Ser Ala Leu Val Leu Met Ala Met Val
305                 310                 315                 320

Lys Arg Lys Asp Ser Arg Gly Gly Ser Gly Ala Thr Asn Phe Ser Leu
                325                 330                 335

Leu Lys Gln Ala Gly Asp Val Glu Glu Asn Pro Gly Pro Met Ile Ser
            340                 345                 350

Leu Arg Val Leu Leu Val Ile Leu Trp Leu Gln Leu Ser Trp Val Trp
        355                 360                 365

Ser Gln Arg Lys Glu Val Glu Gln Asp Pro Gly Pro Phe Asn Val Pro
    370                 375                 380

Glu Gly Ala Thr Val Ala Phe Asn Cys Thr Tyr Ser Asn Ser Ala Ser
385                 390                 395                 400

Gln Ser Phe Phe Trp Tyr Arg Gln Asp Cys Arg Lys Glu Pro Lys Leu
                405                 410                 415

Leu Met Ser Val Tyr Ser Ser Gly Asn Glu Asp Gly Arg Phe Thr Ala
            420                 425                 430

Gln Leu Asn Arg Ala Ser Gln Tyr Ile Ser Leu Leu Ile Arg Asp Ser
        435                 440                 445
```

-continued

```
Lys Leu Ser Asp Ser Ala Thr Tyr Leu Cys Val Val Asn Met Arg Asp
    450                 455                 460

Ser Ser Tyr Lys Leu Ile Phe Gly Ser Gly Thr Arg Leu Leu Val Arg
465                 470                 475                 480

Pro Asp Ile Gln Asn Pro Asp Pro Ala Val Tyr Gln Leu Arg Asp Ser
                485                 490                 495

Lys Ser Ser Asp Lys Ser Val Cys Leu Phe Thr Asp Phe Asp Ser Gln
            500                 505                 510

Thr Asn Val Ser Gln Ser Lys Asp Ser Asp Val Tyr Ile Thr Asp Lys
        515                 520                 525

Thr Val Leu Asp Met Arg Ser Met Asp Phe Lys Ser Asn Ser Ala Val
    530                 535                 540

Ala Trp Ser Asn Lys Ser Asp Phe Ala Cys Ala Asn Ala Phe Asn Asn
545                 550                 555                 560

Ser Ile Ile Pro Glu Asp Thr Phe Phe Pro Ser Pro Glu Ser Ser Cys
                565                 570                 575

Asp Val Lys Leu Val Glu Lys Ser Phe Glu Thr Asp Thr Asn Leu Asn
            580                 585                 590

Phe Gln Asn Leu Ser Val Ile Gly Phe Arg Ile Leu Leu Leu Lys Val
        595                 600                 605

Ala Gly Phe Asn Leu Leu Met Thr Leu Arg Leu Trp Ser Ser
    610                 615                 620
```

<210> SEQ ID NO 156
<211> LENGTH: 1869
<212> TYPE: DNA
<213> ORGANISM: Artificial Sequence
<220> FEATURE:
<223> OTHER INFORMATION: Synthetic Construct

<400> SEQUENCE: 156

```
atggaggcag tggtcacaac tctccccaga gaaggtggtg tgaggccatc acggaagatg     60

ctgctgcttc tgctgcttct ggggccaggc tccgggcttg gtgctgtcgt ctctcaacat    120

ccgagcaggg ttatctgtaa gagtggaacc tctgtgaaga tcgagtgccg ttccctggac    180

tttcaggcca caactatgtt ttggtatcgt cagttcccga aaaagagtct catgctgatg    240

gcaacttcca atgagggctc caaggccaca tacgagcaag gcgtcgagaa ggacaagttt    300

ctcatcaacc atgcaagcct gaccttgtcc actctgacag tgaccagtgc ccatcctgaa    360

gacagcagct tctacatctg cagtgcccat gagcggatca cagatacgca gtattttggc    420

ccaggcaccc ggctgacagt gctcgaggac ctgaaaaacg tgttccccac cgaggtcgct    480

gtgtttgagc catcagaagc agagatctcc cacacccaaa aggccacact ggtgtgcctg    540

gccacaggct tctaccccga ccacgtggag ctgagctggt gggtgaatgg gaaggaggtg    600

cacagtgggg tcagcacaga cccgcagccc ctcaaggagc agcccgccct caatgactcc    660

agatactgcc tgagcagccg cctgagggtc tcggccacct tctggcagaa cccccgcaac    720

cacttccgct gtcaagtcca gttctacggg ctctcggaga atgacgagtg gacccaggat    780

agggccaaac ctgtcaccca gatcgtcagc gccgaggcct ggggtagagc agactgtggc    840

ttcacctccg agtcttacca gcaaggggtc ctgtctgcca ccatcctcta tgagatcttg    900

ctagggaagg ccaccttgta tgccgtgctg gtcagtgccc tcgtgctgat ggccatggtc    960

aagagaaagg attccagagg cggaagcggc gccacgaact tctctctgtt aaagcaagca   1020

ggagacgtgg aagaaaaccc cggtcccatg atatccttga gagttttact ggtgatcctg   1080
```

-continued

```
tggcttcagt taagctgggt ttggagccaa cggaaggagg tggagcagga tcctggaccc   1140

ttcaatgttc cagagggagc cactgtcgct ttcaactgta cttacagcaa cagtgcttct   1200

cagtctttct tctggtacag acaggattgc aggaaagaac ctaagttgct gatgtccgta   1260

tactccagtg gtaatgaaga tggaaggttt acagcacagc tcaatagagc cagccagtat   1320

atttccctgc tcatcagaga ctccaagctc agtgattcag ccacctacct ctgtgtggtg   1380

aacatgaggg atagcagcta taaattgatc ttcgggagtg ggaccagact gctggtcagg   1440

cctgatatcc agaaccctga ccctgccgtg taccagctga gagactctaa atccagtgac   1500

aagtctgtct gcctattcac cgattttgat tctcaaacaa atgtgtcaca aagtaaggat   1560

tctgatgtgt atatcacaga caaaactgtg ctagacatga ggtctatgga cttcaagagc   1620

aacagtgctg tggcctggag caacaaatct gactttgcat gtgcaaacgc cttcaacaac   1680

agcattattc cagaagacac cttcttcccc agcccagaaa gttcctgtga tgtcaagctg   1740

gtcgagaaaa gctttgaaac agatacgaac ctaaactttc aaaacctgtc agtgattggg   1800

ttccgaatcc tcctcctgaa agtggccggg tttaatctgc tcatgacgct gcggctgtgg   1860

tccagctga                                                            1869
```

<210> SEQ ID NO 157
<211> LENGTH: 612
<212> TYPE: PRT
<213> ORGANISM: Artificial Sequence
<220> FEATURE:
<223> OTHER INFORMATION: Synthetic Construct

<400> SEQUENCE: 157

```
Met Glu Ala Val Val Thr Thr Leu Pro Arg Glu Gly Gly Val Arg Pro
1               5                   10                  15

Ser Arg Lys Met Leu Leu Leu Leu Leu Leu Leu Gly Pro Gly Ser Gly
            20                  25                  30

Leu Gly Ala Val Val Ser Gln His Pro Ser Arg Val Ile Cys Lys Ser
        35                  40                  45

Gly Thr Ser Val Lys Ile Glu Cys Arg Ser Leu Asp Phe Gln Ala Thr
    50                  55                  60

Thr Met Phe Trp Tyr Arg Gln Phe Pro Lys Lys Ser Leu Met Leu Met
65                  70                  75                  80

Ala Thr Ser Asn Glu Gly Ser Lys Ala Thr Tyr Glu Gln Gly Val Glu
                85                  90                  95

Lys Asp Lys Phe Leu Ile Asn His Ala Ser Leu Thr Leu Ser Thr Leu
            100                 105                 110

Thr Val Thr Ser Ala His Pro Glu Asp Ser Ser Phe Tyr Ile Cys Ser
        115                 120                 125

Ala His Glu Arg Ile Thr Asp Thr Gln Tyr Phe Gly Pro Gly Thr Arg
    130                 135                 140

Leu Thr Val Leu Glu Asp Leu Arg Asn Val Thr Pro Pro Lys Val Ser
145                 150                 155                 160

Leu Phe Glu Pro Ser Lys Ala Glu Ile Ala Asn Lys Gln Lys Ala Thr
                165                 170                 175

Leu Val Cys Leu Ala Arg Gly Phe Phe Pro Asp His Val Glu Leu Ser
            180                 185                 190

Trp Trp Val Asn Gly Lys Glu Val His Ser Gly Val Ser Thr Asp Pro
        195                 200                 205

Gln Ala Tyr Lys Glu Ser Asn Tyr Ser Tyr Cys Leu Ser Ser Arg Leu
    210                 215                 220
```

```
Arg Val Ser Ala Thr Phe Trp His Asn Pro Arg Asn His Phe Arg Cys
225                 230                 235                 240

Gln Val Gln Phe His Gly Leu Ser Glu Glu Asp Lys Trp Pro Glu Gly
                245                 250                 255

Ser Pro Lys Pro Val Thr Gln Asn Ile Ser Ala Glu Ala Trp Gly Arg
            260                 265                 270

Ala Asp Cys Gly Ile Thr Ser Ala Ser Tyr Gln Gln Gly Val Leu Ser
        275                 280                 285

Ala Thr Ile Leu Tyr Glu Ile Leu Leu Gly Lys Ala Thr Leu Tyr Ala
    290                 295                 300

Val Leu Val Ser Thr Leu Val Val Met Ala Met Val Lys Arg Lys Asn
305                 310                 315                 320

Ser Gly Ser Gly Ala Thr Asn Phe Ser Leu Leu Lys Gln Ala Gly Asp
                325                 330                 335

Val Glu Glu Asn Pro Gly Pro Met Ile Ser Leu Arg Val Leu Leu Val
            340                 345                 350

Ile Leu Trp Leu Gln Leu Ser Trp Val Trp Ser Gln Arg Lys Glu Val
        355                 360                 365

Glu Gln Asp Pro Gly Pro Phe Asn Val Pro Glu Gly Ala Thr Val Ala
    370                 375                 380

Phe Asn Cys Thr Tyr Ser Asn Ser Ala Ser Gln Ser Phe Phe Trp Tyr
385                 390                 395                 400

Arg Gln Asp Cys Arg Lys Glu Pro Lys Leu Leu Met Ser Val Tyr Ser
                405                 410                 415

Ser Gly Asn Glu Asp Gly Arg Phe Thr Ala Gln Leu Asn Arg Ala Ser
            420                 425                 430

Gln Tyr Ile Ser Leu Leu Ile Arg Asp Ser Lys Leu Ser Asp Ser Ala
        435                 440                 445

Thr Tyr Leu Cys Val Val Asn Met Arg Asp Ser Ser Tyr Lys Leu Ile
    450                 455                 460

Phe Gly Ser Gly Thr Arg Leu Leu Val Arg Pro Asp Ile Gln Asn Pro
465                 470                 475                 480

Glu Pro Ala Val Tyr Gln Leu Lys Asp Pro Arg Ser Gln Asp Ser Thr
                485                 490                 495

Leu Cys Leu Phe Thr Asp Phe Asp Ser Gln Ile Asn Val Pro Lys Thr
            500                 505                 510

Met Glu Ser Gly Thr Phe Ile Thr Asp Lys Thr Val Leu Asp Met Lys
        515                 520                 525

Ala Met Asp Ser Lys Ser Asn Gly Ala Ile Ala Trp Ser Asn Gln Thr
    530                 535                 540

Ser Phe Thr Cys Gln Asp Ile Phe Lys Glu Thr Asn Ala Thr Tyr Pro
545                 550                 555                 560

Ser Ser Asp Val Pro Cys Asp Ala Thr Leu Thr Glu Lys Ser Phe Glu
                565                 570                 575

Thr Asp Met Asn Leu Asn Phe Gln Asn Leu Leu Val Met Val Leu Arg
            580                 585                 590

Ile Leu Leu Leu Lys Val Ala Gly Phe Asn Leu Leu Met Thr Leu Arg
        595                 600                 605

Leu Trp Ser Ser
    610
```

<210> SEQ ID NO 158
<211> LENGTH: 1839

<212> TYPE: DNA
<213> ORGANISM: Artificial Sequence
<220> FEATURE:
<223> OTHER INFORMATION: Synthetic Construct

<400> SEQUENCE: 158
atggaggcag tggtcacaac tctccccaga gaaggtggtg tgaggccatc acggaagatg 60
ctgctgcttc tgctgcttct ggggccaggc tccgggcttg gtgctgtcgt ctctcaacat 120
ccgagcaggg ttatctgtaa gagtggaacc tctgtgaaga tcgagtgccg ttccctggac 180
tttcaggcca caactatgtt ttggtatcgt cagttcccga aaaagagtct catgctgatg 240
gcaacttcca atgagggctc caaggccaca tacgagcaag gcgtcgagaa ggacaagttt 300
ctcatcaacc atgcaagcct gaccttgtcc actctgacag tgaccagtgc ccatcctgaa 360
gacagcagct tctacatctg cagtgcccat gagcggatca cagatacgca gtattttggc 420
ccaggcaccc ggctgacagt gctcgaggat ctgagaaatg tgactccacc caaggtctcc 480
ttgtttgagc catcaaaagc agagattgca aacaaacaaa aggctaccct cgtgtgcttg 540
gccaggggct tcttccctga ccacgtggag ctgagctggt gggtgaatgg caaggaggtc 600
cacagtgggg tcagcacgga ccctcaggcc tacaaggaga gcaattatag ctactgcctg 660
agcagccgcc tgagggtctc tgctaccttc tggcacaatc ctcgcaacca cttccgctgc 720
caagtgcagt tccatgggct ttcagaggag gacaagtggc cagagggctc acccaaacct 780
gtcacacaga acatcagtgc agaggcctgg ggccgagcag actgtgggat tacctcagca 840
tcctatcaac aaggggtctt gtctgccacc atcctctatg agatcctgct agggaaagcc 900
accctgtatg ctgtgcttgt cagtacactg gtggtgatgg ctatggtcaa aagaaaaaat 960
tcaggaagcg gcgccacgaa cttctctctg ttaaagcaag caggagacgt ggaagaaaac 1020
cccggtccca tgatatcctt gagagtttta ctggtgatcc tgtggcttca gttaagctgg 1080
gtttggagcc aacggaagga ggtggagcag gatcctggac ccttcaatgt tccagaggga 1140
gccactgtcg ctttcaactg tacttacagc aacagtgctt ctcagtcttt cttctggtac 1200
agacaggatt gcaggaaaga acctaagttg ctgatgtccg tatactccag tggtaatgaa 1260
gatggaaggt ttacagcaca gctcaataga gccagccagt atatttccct gctcatcaga 1320
gactccaagc tcagtgattc agccacctac ctctgtgtgg tgaacatgag ggatagcagc 1380
tataaattga tcttcgggag tgggaccaga ctgctggtca ggcctgatat ccagaaccca 1440
gaacctgctg tgtaccagtt aaaagatcct cggtctcagg acagcaccct ctgcctgttc 1500
accgactttg actcccaaat caatgtgccg aaaaccatgg aatctggaac gttcatcact 1560
gacaaaactg tgctggacat gaaagctatg gattccaaga gcaatggggc cattgcctgg 1620
agcaaccaga caagcttcac ctgccaagat atcttcaaag agaccaacgc cacctacccc 1680
agttcagacg ttccctgtga tgccacgttg actgagaaaa gctttgaaac agatatgaac 1740
ctaaactttc aaaacctgct ggttatggtt ctccgaatcc tcctgctgaa agtagccgga 1800
tttaacctgc tcatgacgct gaggctgtgg tccagttga 1839

<210> SEQ ID NO 159
<211> LENGTH: 606
<212> TYPE: PRT
<213> ORGANISM: Artificial Sequence
<220> FEATURE:
<223> OTHER INFORMATION: Synthetic Construct

<400> SEQUENCE: 159

-continued

```
Met Leu Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Lys Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Leu
            100                 105                 110

Glu Gly Thr Ser Gly Lys Glu Thr Gln Tyr Phe Gly Pro Gly Thr Arg
        115                 120                 125

Leu Leu Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Ile Ser
                325                 330                 335

Leu Arg Val Leu Leu Val Ile Leu Trp Leu Gln Leu Ser Trp Val Trp
            340                 345                 350

Ser Gln Arg Lys Glu Val Glu Gln Asp Pro Gly Pro Phe Asn Val Pro
        355                 360                 365

Glu Gly Ala Thr Val Ala Phe Asn Cys Thr Tyr Ser Asn Ser Ala Ser
    370                 375                 380

Gln Ser Phe Phe Trp Tyr Arg Gln Asp Cys Arg Lys Glu Pro Lys Leu
385                 390                 395                 400

Leu Met Ser Val Tyr Ser Ser Gly Asn Glu Asp Gly Arg Phe Thr Ala
                405                 410                 415

Gln Leu Asn Arg Ala Ser Gln Tyr Ile Ser Leu Leu Ile Arg Asp Ser
```

-continued

```
            420                 425                 430

Lys Leu Ser Asp Ser Ala Thr Tyr Leu Cys Val Val Asn Met Lys Asp
        435                 440                 445

Ser Ser Tyr Lys Leu Ile Phe Gly Ser Gly Thr Arg Leu Leu Val Arg
    450                 455                 460

Pro Asp Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
        515                 520                 525

Ala Trp Ser Asn Lys Ser Asp Phe Ala Cys Ala Asn Ala Phe Asn Asn
    530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser
        595                 600                 605
```

<210> SEQ ID NO 160
<211> LENGTH: 1821
<212> TYPE: DNA
<213> ORGANISM: Artificial Sequence
<220> FEATURE:
<223> OTHER INFORMATION: Synthetic Construct

<400> SEQUENCE: 160

```
atgctgctgc ttctgctgct tctggggcca gcaggctccg ggcttggtgc tgtcgtctct      60

caacatccga gcagggttat ctgtaagagt ggaacctctg tgaagatcga gtgccgttcc     120

ctggactttc aggccacaac tatgttttgg tatcgtcagt tcccgaaaaa gagtctcatg     180

ctgatggcaa cttccaatga gggctccaag gccacatacg agcaaggcgt cgagaaggac     240

aagtttctca tcaaccatgc aagcctgacc ttgtccactc tgacagtgac cagtgcccat     300

cctgaagaca gcagcttcta catctgcagt gctttagagg ggactagcgg gaaagagacc     360

cagtacttcg ggccaggcac gcggctcctg gtgctcgagg acctgaaaaa cgtgttccca     420

cccgaggtcg ctgtgtttga gccatcagaa gcagagatct cccacaccca aaaggccaca     480

ctggtgtgcc tggccacagg cttctacccc gaccacgtgg agctgagctg gtgggtgaat     540

gggaaggagg tgcacagtgg ggtcagcaca gacccgcagc ccctcaagga gcagcccgcc     600

ctcaatgact ccagatactg cctgagcagc cgcctgaggg tctcggccac cttctggcag     660

aacccccgca accacttccg ctgtcaagtc cagttctacg ggctctcgga gaatgacgag     720

tggacccagg atagggccaa acctgtcacc cagatcgtca gcgccgaggc ctggggtaga     780

gcagactgtg gcttcacctc cgagtcttac cagcaagggg tcctgtctgc caccatcctc     840

tatgagatct tgctagggaa ggccaccttg tatgccgtgc tggtcagtgc cctcgtgctg     900

atggccatgg tcaagagaaa ggattccaga ggcggaagcg gcgccacgaa cttctctctg     960

ttaaagcaag caggagacgt ggaagaaaac cccggtccca tgatatcctt gagagtttta    1020
```

-continued

```
ctggtgatcc tgtggcttca gttaagctgg gtttggagcc aacggaagga ggtggagcag   1080

gatcctggac ccttcaatgt tccagaggga gccactgtcg ctttcaactg tacttacagc   1140

aacagtgctt ctcagtcttt cttctggtac agacaggatt gcaggaaaga acctaagttg   1200

ctgatgtccg tatactccag tggtaatgaa gatggaaggt ttacagcaca gctcaataga   1260

gccagccagt atatttccct gctcatcaga gactccaagc tcagtgattc agccacctac   1320

ctctgtgtgg tgaacatgaa ggatagcagc tataaattga tcttcgggag tgggaccaga   1380

ctgctggtca ggcctgatat ccagaaccct gaccctgccg tgtaccagct gagagactct   1440

aaatccagtg acaagtctgt ctgcctattc accgattttg attctcaaac aaatgtgtca   1500

caaagtaagg attctgatgt gtatatcaca gacaaaactg tgctagacat gaggtctatg   1560

gacttcaaga gcaacagtgc tgtggcctgg agcaacaaat ctgactttgc atgtgcaaac   1620

gccttcaaca acagcattat tccagaagac accttcttcc ccagcccaga aagttcctgt   1680

gatgtcaagc tggtcgagaa aagctttgaa acagatacga acctaaactt tcaaaacctg   1740

tcagtgattg ggttccgaat cctcctcctg aaagtggccg ggtttaatct gctcatgacg   1800

ctgcggctgt ggtccagctg a                                             1821
```

<210> SEQ ID NO 161
<211> LENGTH: 596
<212> TYPE: PRT
<213> ORGANISM: Artificial Sequence
<220> FEATURE:
<223> OTHER INFORMATION: Synthetic Construct

<400> SEQUENCE: 161

```
Met Leu Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Lys Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Leu
            100                 105                 110

Glu Gly Thr Ser Gly Lys Glu Thr Gln Tyr Phe Gly Pro Gly Thr Arg
        115                 120                 125

Leu Leu Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220
```

```
Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser Gly Ser Gly Ala Thr Asn Phe Ser Leu Leu Lys Gln Ala Gly Asp
305                 310                 315                 320

Val Glu Glu Asn Pro Gly Pro Met Ile Ser Leu Arg Val Leu Leu Val
                325                 330                 335

Ile Leu Trp Leu Gln Leu Ser Trp Val Trp Ser Gln Arg Lys Glu Val
            340                 345                 350

Glu Gln Asp Pro Gly Pro Phe Asn Val Pro Glu Gly Ala Thr Val Ala
        355                 360                 365

Phe Asn Cys Thr Tyr Ser Asn Ser Ala Ser Gln Ser Phe Phe Trp Tyr
    370                 375                 380

Arg Gln Asp Cys Arg Lys Glu Pro Lys Leu Leu Met Ser Val Tyr Ser
385                 390                 395                 400

Ser Gly Asn Glu Asp Gly Arg Phe Thr Ala Gln Leu Asn Arg Ala Ser
                405                 410                 415

Gln Tyr Ile Ser Leu Leu Ile Arg Asp Ser Lys Leu Ser Asp Ser Ala
            420                 425                 430

Thr Tyr Leu Cys Val Val Asn Met Lys Asp Ser Ser Tyr Lys Leu Ile
        435                 440                 445

Phe Gly Ser Gly Thr Arg Leu Leu Val Arg Pro Asp Ile Gln Asn Pro
    450                 455                 460

Glu Pro Ala Val Tyr Gln Leu Lys Asp Pro Arg Ser Gln Asp Ser Thr
465                 470                 475                 480

Leu Cys Leu Phe Thr Asp Phe Asp Ser Gln Ile Asn Val Pro Lys Thr
                485                 490                 495

Met Glu Ser Gly Thr Phe Ile Thr Asp Lys Thr Val Leu Asp Met Lys
            500                 505                 510

Ala Met Asp Ser Lys Ser Asn Gly Ala Ile Ala Trp Ser Asn Gln Thr
        515                 520                 525

Ser Phe Thr Cys Gln Asp Ile Phe Lys Glu Thr Asn Ala Thr Tyr Pro
    530                 535                 540

Ser Ser Asp Val Pro Cys Asp Ala Thr Leu Thr Glu Lys Ser Phe Glu
545                 550                 555                 560

Thr Asp Met Asn Leu Asn Phe Gln Asn Leu Leu Val Met Val Leu Arg
                565                 570                 575

Ile Leu Leu Leu Lys Val Ala Gly Phe Asn Leu Leu Met Thr Leu Arg
            580                 585                 590

Leu Trp Ser Ser
        595
```

<210> SEQ ID NO 162
<211> LENGTH: 1791
<212> TYPE: DNA
<213> ORGANISM: Artificial Sequence
<220> FEATURE:

<223> OTHER INFORMATION: Synthetic Construct

<400> SEQUENCE: 162
atgctgctgc ttctgctgct tctggggcca gcaggctccg ggcttggtgc tgtcgtctct 60
caacatccga gcagggttat ctgtaagagt ggaacctctg tgaagatcga gtgccgttcc 120
ctggactttc aggccacaac tatgttttgg tatcgtcagt tcccgaaaaa gagtctcatg 180
ctgatggcaa cttccaatga gggctccaag gccacatacg agcaaggcgt cgagaaggac 240
aagtttctca tcaaccatgc aagcctgacc ttgtccactc tgacagtgac cagtgcccat 300
cctgaagaca gcagcttcta catctgcagt gctttagagg ggactagcgg gaaagagacc 360
cagtacttcg ggccaggcac gcggctcctg gtgctcgagg atctgagaaa tgtgactcca 420
cccaaggtct ccttgtttga gccatcaaaa gcagagattg caaacaaaca aaaggctacc 480
ctcgtgtgct tggccagggg cttcttccct gaccacgtgg agctgagctg gtgggtgaat 540
ggcaaggagg tccacagtgg ggtcagcacg gaccctcagg cctacaagga gagcaattat 600
agctactgcc tgagcagccg cctgagggtc tctgctacct tctggcacaa tcctcgcaac 660
cacttccgct gccaagtgca gttccatggg ctttcagagg aggacaagtg gccagagggc 720
tcacccaaac ctgtcacaca gaacatcagt gcagaggcct ggggccgagc agactgtggg 780
attacctcag catcctatca acaaggggtc ttgtctgcca ccatcctcta tgagatcctg 840
ctagggaaag ccaccctgta tgctgtgctt gtcagtacac tggtggtgat ggctatggtc 900
aaaagaaaaa attcaggaag cggcgccacg aacttctctc tgttaaagca agcaggagac 960
gtggaagaaa accccggtcc catgatatcc ttgagagttt tactggtgat cctgtggctt 1020
cagttaagct gggtttggag ccaacggaag gaggtggagc aggatcctgg acccttcaat 1080
gttccagagg gagccactgt cgctttcaac tgtacttaca gcaacagtgc ttctcagtct 1140
ttcttctggt acagacagga ttgcaggaaa gaacctaagt tgctgatgtc cgtatactcc 1200
agtggtaatg aagatggaag gtttacagca cagctcaata gagccagcca gtatatttcc 1260
ctgctcatca gagactccaa gctcagtgat tcagccacct acctctgtgt ggtgaacatg 1320
aaggatagca gctataaatt gatcttcggg agtgggacca gactgctggt caggcctgat 1380
atccagaacc cagaacctgc tgtgtaccag ttaaaagatc ctcggtctca ggacagcacc 1440
ctctgcctgt tcaccgactt tgactcccaa atcaatgtgc cgaaaaccat ggaatctgga 1500
acgttcatca ctgacaaaac tgtgctggac atgaaagcta tggattccaa gagcaatggg 1560
gccattgcct ggagcaacca gacaagcttc acctgccaag atatcttcaa agagaccaac 1620
gccacctacc ccagttcaga cgttccctgt gatgccacgt tgactgagaa aagctttgaa 1680
acagatatga acctaaactt tcaaaacctg ctggttatgg ttctccgaat cctcctgctg 1740
aaagtagccg gatttaacct gctcatgacg ctgaggctgt ggtccagttg a 1791

<210> SEQ ID NO 163
<211> LENGTH: 624
<212> TYPE: PRT
<213> ORGANISM: Artificial Sequence
<220> FEATURE:
<223> OTHER INFORMATION: Synthetic Construct

<400> SEQUENCE: 163

Met Glu Ala Val Val Thr Thr Leu Pro Arg Glu Gly Gly Val Arg Pro
1 5 10 15

Ser Arg Lys Met Leu Leu Leu Leu Leu Leu Leu Gly Pro Gly Ser Gly
20 25 30

```
Leu Gly Ala Val Val Ser Gln His Pro Ser Arg Val Ile Cys Lys Ser
        35                  40                  45

Gly Thr Ser Val Lys Ile Glu Cys Arg Ser Leu Asp Phe Gln Ala Thr
    50                  55                  60

Thr Met Phe Trp Tyr Arg Gln Phe Pro Lys Lys Ser Leu Met Leu Met
65                  70                  75                  80

Ala Thr Ser Asn Glu Gly Ser Lys Ala Thr Tyr Glu Gln Gly Val Glu
                85                  90                  95

Lys Asp Lys Phe Leu Ile Asn His Ala Ser Leu Thr Leu Ser Thr Leu
            100                 105                 110

Thr Val Thr Ser Ala His Pro Glu Asp Ser Ser Phe Tyr Ile Cys Ser
        115                 120                 125

Ala Leu Glu Gly Thr Ser Gly Lys Glu Thr Gln Tyr Phe Gly Pro Gly
    130                 135                 140

Thr Arg Leu Leu Val Leu Glu Asp Leu Lys Asn Val Phe Pro Pro Glu
145                 150                 155                 160

Val Ala Val Phe Glu Pro Ser Glu Ala Glu Ile Ser His Thr Gln Lys
                165                 170                 175

Ala Thr Leu Val Cys Leu Ala Thr Gly Phe Tyr Pro Asp His Val Glu
            180                 185                 190

Leu Ser Trp Trp Val Asn Gly Lys Glu Val His Ser Gly Val Ser Thr
        195                 200                 205

Asp Pro Gln Pro Leu Lys Glu Gln Pro Ala Leu Asn Asp Ser Arg Tyr
    210                 215                 220

Cys Leu Ser Ser Arg Leu Arg Val Ser Ala Thr Phe Trp Gln Asn Pro
225                 230                 235                 240

Arg Asn His Phe Arg Cys Gln Val Gln Phe Tyr Gly Leu Ser Glu Asn
                245                 250                 255

Asp Glu Trp Thr Gln Asp Arg Ala Lys Pro Val Thr Gln Ile Val Ser
            260                 265                 270

Ala Glu Ala Trp Gly Arg Ala Asp Cys Gly Phe Thr Ser Glu Ser Tyr
        275                 280                 285

Gln Gln Gly Val Leu Ser Ala Thr Ile Leu Tyr Glu Ile Leu Leu Gly
    290                 295                 300

Lys Ala Thr Leu Tyr Ala Val Leu Val Ser Ala Leu Val Leu Met Ala
305                 310                 315                 320

Met Val Lys Arg Lys Asp Ser Arg Gly Gly Ser Gly Ala Thr Asn Phe
                325                 330                 335

Ser Leu Leu Lys Gln Ala Gly Asp Val Glu Glu Asn Pro Gly Pro Met
            340                 345                 350

Ile Ser Leu Arg Val Leu Leu Val Ile Leu Trp Leu Gln Leu Ser Trp
        355                 360                 365

Val Trp Ser Gln Arg Lys Glu Val Glu Gln Asp Pro Gly Pro Phe Asn
    370                 375                 380

Val Pro Glu Gly Ala Thr Val Ala Phe Asn Cys Thr Tyr Ser Asn Ser
385                 390                 395                 400

Ala Ser Gln Ser Phe Phe Trp Tyr Arg Gln Asp Cys Arg Lys Glu Pro
                405                 410                 415

Lys Leu Leu Met Ser Val Tyr Ser Ser Gly Asn Glu Asp Gly Arg Phe
            420                 425                 430

Thr Ala Gln Leu Asn Arg Ala Ser Gln Tyr Ile Ser Leu Leu Ile Arg
        435                 440                 445
```

```
Asp Ser Lys Leu Ser Asp Ser Ala Thr Tyr Leu Cys Val Val Asn Met
    450                 455                 460

Lys Asp Ser Ser Tyr Lys Leu Ile Phe Gly Ser Gly Thr Arg Leu Leu
465                 470                 475                 480

Val Arg Pro Asp Ile Gln Asn Pro Asp Pro Ala Val Tyr Gln Leu Arg
                485                 490                 495

Asp Ser Lys Ser Ser Asp Lys Ser Val Cys Leu Phe Thr Asp Phe Asp
            500                 505                 510

Ser Gln Thr Asn Val Ser Gln Ser Lys Asp Ser Asp Val Tyr Ile Thr
        515                 520                 525

Asp Lys Thr Val Leu Asp Met Arg Ser Met Asp Phe Lys Ser Asn Ser
    530                 535                 540

Ala Val Ala Trp Ser Asn Lys Ser Asp Phe Ala Cys Ala Asn Ala Phe
545                 550                 555                 560

Asn Asn Ser Ile Ile Pro Glu Asp Thr Phe Phe Pro Ser Pro Glu Ser
                565                 570                 575

Ser Cys Asp Val Lys Leu Val Glu Lys Ser Phe Glu Thr Asp Thr Asn
            580                 585                 590

Leu Asn Phe Gln Asn Leu Ser Val Ile Gly Phe Arg Ile Leu Leu Leu
        595                 600                 605

Lys Val Ala Gly Phe Asn Leu Leu Met Thr Leu Arg Leu Trp Ser Ser
    610                 615                 620
```

<210> SEQ ID NO 164
<211> LENGTH: 1875
<212> TYPE: DNA
<213> ORGANISM: Artificial Sequence
<220> FEATURE:
<223> OTHER INFORMATION: Synthetic Construct

<400> SEQUENCE: 164

```
atggaggcag tggtcacaac tctccccaga gaaggtggtg tgaggccatc acggaagatg     60

ctgctgcttc tgctgcttct ggggccaggc tccgggcttg gtgctgtcgt ctctcaacat    120

ccgagcaggg ttatctgtaa gagtggaacc tctgtgaaga tcgagtgccg ttccctggac    180

tttcaggcca caactatgtt ttggtatcgt cagttcccga aaaagagtct catgctgatg    240

gcaacttcca atgagggctc caaggccaca tacgagcaag gcgtcgagaa ggacaagttt    300

ctcatcaacc atgcaagcct gaccttgtcc actctgacag tgaccagtgc ccatcctgaa    360

gacagcagct tctacatctg cagtgcttta gaggggacta gcgggaaaga gacccagtac    420

ttcgggccag gcacgcggct cctggtgctc gaggacctga aaaacgtgtt cccacccgag    480

gtcgctgtgt ttgagccatc agaagcagag atctcccaca cccaaaaggc cacactggtg    540

tgcctggcca caggcttcta ccccgaccac gtggagctga gctggtgggt gaatgggaag    600

gaggtgcaca gtggggtcag cacagacccg cagcccctca aggagcagcc cgccctcaat    660

gactccagat actgcctgag cagccgcctg agggtctcgg ccaccttctg gcagaacccc    720

cgcaaccact tccgctgtca agtccagttc tacgggctct cggagaatga cgagtggacc    780

caggataggg ccaaacctgt cacccagatc gtcagcgccg aggcctgggg tagagcagac    840

tgtggcttca cctccgagtc ttaccagcaa ggggtcctgt ctgccaccat cctctatgag    900

atcttgctag ggaaggccac cttgtatgcc gtgctggtca gtgccctcgt gctgatggcc    960

atggtcaaga gaaaggattc cagaggcgga agcggcgcca cgaacttctc tctgttaaag   1020

caagcaggag acgtggaaga aaaccccggt cccatgatat ccttgagagt tttactggtg   1080
```

```
atcctgtggc ttcagttaag ctgggtttgg agccaacgga aggaggtgga gcaggatcct   1140

ggacccttca atgttccaga gggagccact gtcgctttca actgtactta cagcaacagt   1200

gcttctcagt ctttcttctg gtacagacag gattgcagga aagaacctaa gttgctgatg   1260

tccgtatact ccagtggtaa tgaagatgga aggtttacag cacagctcaa tagagccagc   1320

cagtatattt ccctgctcat cagagactcc aagctcagtg attcagccac ctacctctgt   1380

gtggtgaaca tgaaggatag cagctataaa ttgatcttcg ggagtgggac cagactgctg   1440

gtcaggcctg atatccagaa ccctgaccct gccgtgtacc agctgagaga ctctaaatcc   1500

agtgacaagt ctgtctgcct attcaccgat tttgattctc aaacaaatgt gtcacaaagt   1560

aaggattctg atgtgtatat cacagacaaa actgtgctag acatgaggtc tatggacttc   1620

aagagcaaca gtgctgtggc ctggagcaac aaatctgact ttgcatgtgc aaacgccttc   1680

aacaacagca ttattccaga agacaccttc ttccccagcc cagaaagttc ctgtgatgtc   1740

aagctggtcg agaaaagctt tgaaacagat acgaacctaa actttcaaaa cctgtcagtg   1800

attgggttcc gaatcctcct cctgaaagtg gccgggttta atctgctcat gacgctgcgg   1860

ctgtggtcca gctga                                                    1875
```

```
<210> SEQ ID NO 165
<211> LENGTH: 614
<212> TYPE: PRT
<213> ORGANISM: Artificial Sequence
<220> FEATURE:
<223> OTHER INFORMATION: Synthetic Construct

<400> SEQUENCE: 165

Met Glu Ala Val Val Thr Thr Leu Pro Arg Glu Gly Gly Val Arg Pro
1               5                   10                  15

Ser Arg Lys Met Leu Leu Leu Leu Leu Leu Leu Gly Pro Gly Ser Gly
            20                  25                  30

Leu Gly Ala Val Val Ser Gln His Pro Ser Arg Val Ile Cys Lys Ser
        35                  40                  45

Gly Thr Ser Val Lys Ile Glu Cys Arg Ser Leu Asp Phe Gln Ala Thr
    50                  55                  60

Thr Met Phe Trp Tyr Arg Gln Phe Pro Lys Lys Ser Leu Met Leu Met
65                  70                  75                  80

Ala Thr Ser Asn Glu Gly Ser Lys Ala Thr Tyr Glu Gln Gly Val Glu
                85                  90                  95

Lys Asp Lys Phe Leu Ile Asn His Ala Ser Leu Thr Leu Ser Thr Leu
            100                 105                 110

Thr Val Thr Ser Ala His Pro Glu Asp Ser Ser Phe Tyr Ile Cys Ser
        115                 120                 125

Ala Leu Glu Gly Thr Ser Gly Lys Glu Thr Gln Tyr Phe Gly Pro Gly
    130                 135                 140

Thr Arg Leu Leu Val Leu Glu Asp Leu Arg Asn Val Thr Pro Pro Lys
145                 150                 155                 160

Val Ser Leu Phe Glu Pro Ser Lys Ala Glu Ile Ala Asn Lys Gln Lys
                165                 170                 175

Ala Thr Leu Val Cys Leu Ala Arg Gly Phe Phe Pro Asp His Val Glu
            180                 185                 190

Leu Ser Trp Trp Val Asn Gly Lys Glu Val His Ser Gly Val Ser Thr
        195                 200                 205

Asp Pro Gln Ala Tyr Lys Glu Ser Asn Tyr Ser Tyr Cys Leu Ser Ser
    210                 215                 220
```

```
Arg Leu Arg Val Ser Ala Thr Phe Trp His Asn Pro Arg Asn His Phe
225                 230                 235                 240

Arg Cys Gln Val Gln Phe His Gly Leu Ser Glu Glu Asp Lys Trp Pro
                245                 250                 255

Glu Gly Ser Pro Lys Pro Val Thr Gln Asn Ile Ser Ala Glu Ala Trp
            260                 265                 270

Gly Arg Ala Asp Cys Gly Ile Thr Ser Ala Ser Tyr Gln Gln Gly Val
        275                 280                 285

Leu Ser Ala Thr Ile Leu Tyr Glu Ile Leu Leu Gly Lys Ala Thr Leu
    290                 295                 300

Tyr Ala Val Leu Val Ser Thr Leu Val Val Met Ala Met Val Lys Arg
305                 310                 315                 320

Lys Asn Ser Gly Ser Gly Ala Thr Asn Phe Ser Leu Leu Lys Gln Ala
                325                 330                 335

Gly Asp Val Glu Glu Asn Pro Gly Pro Met Ile Ser Leu Arg Val Leu
            340                 345                 350

Leu Val Ile Leu Trp Leu Gln Leu Ser Trp Val Trp Ser Gln Arg Lys
        355                 360                 365

Glu Val Glu Gln Asp Pro Gly Pro Phe Asn Val Pro Glu Gly Ala Thr
    370                 375                 380

Val Ala Phe Asn Cys Thr Tyr Ser Asn Ser Ala Ser Gln Ser Phe Phe
385                 390                 395                 400

Trp Tyr Arg Gln Asp Cys Arg Lys Glu Pro Lys Leu Leu Met Ser Val
                405                 410                 415

Tyr Ser Ser Gly Asn Glu Asp Gly Arg Phe Thr Ala Gln Leu Asn Arg
            420                 425                 430

Ala Ser Gln Tyr Ile Ser Leu Leu Ile Arg Asp Ser Lys Leu Ser Asp
        435                 440                 445

Ser Ala Thr Tyr Leu Cys Val Val Asn Met Lys Asp Ser Ser Tyr Lys
    450                 455                 460

Leu Ile Phe Gly Ser Gly Thr Arg Leu Leu Val Arg Pro Asp Ile Gln
465                 470                 475                 480

Asn Pro Glu Pro Ala Val Tyr Gln Leu Lys Asp Pro Arg Ser Gln Asp
                485                 490                 495

Ser Thr Leu Cys Leu Phe Thr Asp Phe Asp Ser Gln Ile Asn Val Pro
            500                 505                 510

Lys Thr Met Glu Ser Gly Thr Phe Ile Thr Asp Lys Thr Val Leu Asp
        515                 520                 525

Met Lys Ala Met Asp Ser Lys Ser Asn Gly Ala Ile Ala Trp Ser Asn
    530                 535                 540

Gln Thr Ser Phe Thr Cys Gln Asp Ile Phe Lys Glu Thr Asn Ala Thr
545                 550                 555                 560

Tyr Pro Ser Ser Asp Val Pro Cys Asp Ala Thr Leu Thr Glu Lys Ser
                565                 570                 575

Phe Glu Thr Asp Met Asn Leu Asn Phe Gln Asn Leu Leu Val Met Val
            580                 585                 590

Leu Arg Ile Leu Leu Leu Lys Val Ala Gly Phe Asn Leu Leu Met Thr
        595                 600                 605

Leu Arg Leu Trp Ser Ser
    610
```

<210> SEQ ID NO 166
<211> LENGTH: 1845

<212> TYPE: DNA
<213> ORGANISM: Artificial Sequence
<220> FEATURE:
<223> OTHER INFORMATION: Synthetic Construct

<400> SEQUENCE: 166
atggaggcag tggtcacaac tctccccaga gaaggtggtg tgaggccatc acggaagatg 60
ctgctgcttc tgctgcttct ggggccaggc tccgggcttg gtgctgtcgt ctctcaacat 120
ccgagcaggg ttatctgtaa gagtggaacc tctgtgaaga tcgagtgccg ttccctggac 180
tttcaggcca caactatgtt ttggtatcgt cagttcccga aaaagagtct catgctgatg 240
gcaacttcca atgagggctc caaggccaca tacgagcaag gcgtcgagaa ggacaagttt 300
ctcatcaacc atgcaagcct gaccttgtcc actctgacag tgaccagtgc ccatcctgaa 360
gacagcagct tctacatctg cagtgcttta gaggggacta gcgggaaaga gacccagtac 420
ttcgggccag gcacgcggct cctggtgctc gaggatctga gaaatgtgac tccacccaag 480
gtctccttgt ttgagccatc aaaagcagag attgcaaaca aacaaaaggc taccctcgtg 540
tgcttggcca ggggcttctt ccctgaccac gtggagctga gctggtgggt gaatggcaag 600
gaggtccaca gtggggtcag cacggaccct caggcctaca aggagagcaa ttatagctac 660
tgcctgagca gccgcctgag ggtctctgct accttctggc acaatcctcg caaccacttc 720
cgctgccaag tgcagttcca tgggctttca gaggaggaca agtggccaga gggctcaccc 780
aaacctgtca cacagaacat cagtgcagag gcctggggcc gagcagactg tgggattacc 840
tcagcatcct atcaacaagg ggtcttgtct gccaccatcc tctatgagat cctgctaggg 900
aaagccaccc tgtatgctgt gcttgtcagt acactggtgg tgatggctat ggtcaaaaga 960
aaaaattcag gaagcggcgc cacgaacttc tctctgttaa agcaagcagg agacgtggaa 1020
gaaaaccccg gtcccatgat atccttgaga gttttactgg tgatcctgtg gcttcagtta 1080
agctgggttt ggagccaacg gaaggaggtg gagcaggatc ctggaccctt caatgttcca 1140
gagggagcca ctgtcgcttt caactgtact tacagcaaca gtgcttctca gtctttcttc 1200
tggtacagac aggattgcag gaaagaacct aagttgctga tgtccgtata ctccagtggt 1260
aatgaagatg gaaggtttac agcacagctc aatagagcca gccagtatat ttccctgctc 1320
atcagagact ccaagctcag tgattcagcc acctacctct gtgtggtgaa catgaaggat 1380
agcagctata aattgatctt cgggagtggg accagactgc tggtcaggcc tgatatccag 1440
aacccagaac ctgctgtgta ccagttaaaa gatcctcggt ctcaggacag caccctctgc 1500
ctgttcaccg actttgactc ccaaatcaat gtgccgaaaa ccatggaatc tggaacgttc 1560
atcactgaca aaactgtgct ggacatgaaa gctatggatt ccaagagcaa tggggccatt 1620
gcctggagca accagacaag cttcacctgc caagatatct tcaaagagac caacgccacc 1680
taccccagtt cagacgttcc ctgtgatgcc acgttgactg agaaaagctt tgaaacagat 1740
atgaacctaa actttcaaaa cctgctggtt atggttctcc gaatcctcct gctgaaagta 1800
gccggattta acctgctcat gacgctgagg ctgtggtcca gttga 1845

<210> SEQ ID NO 167
<211> LENGTH: 598
<212> TYPE: PRT
<213> ORGANISM: Artificial Sequence
<220> FEATURE:
<223> OTHER INFORMATION: Synthetic Construct

<400> SEQUENCE: 167

-continued

```
Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Ser Trp Asp Arg Asp Gln Pro Gln His Phe Gly Asp Gly Thr Arg
        115                 120                 125

Leu Ser Ile Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Leu Leu Ile Thr
                325                 330                 335

Ser Met Leu Val Leu Trp Met Gln Leu Ser Gln Val Asn Gly Gln Gln
            340                 345                 350

Val Met Gln Ile Pro Gln Tyr Gln His Val Gln Glu Gly Glu Asp Phe
        355                 360                 365

Thr Thr Tyr Cys Asn Ser Ser Thr Thr Leu Ser Asn Ile Gln Trp Tyr
    370                 375                 380

Lys Gln Arg Pro Gly Gly His Pro Val Phe Leu Ile Gln Leu Val Lys
385                 390                 395                 400

Ser Gly Glu Val Lys Lys Gln Lys Arg Leu Thr Phe Gln Phe Gly Glu
                405                 410                 415

Ala Lys Lys Asn Ser Ser Leu His Ile Thr Ala Thr Gln Thr Thr Asp
```

```
            420                 425                 430

Val Gly Thr Tyr Phe Cys Ala Gly Pro Gly Asn Gln Phe Tyr Phe Gly
        435                 440                 445

Thr Gly Thr Ser Leu Thr Val Ile Pro Asn Ile Gln Asn Pro Asp Pro
    450                 455                 460

Ala Val Tyr Gln Leu Arg Asp Ser Lys Ser Ser Asp Lys Ser Val Cys
465                 470                 475                 480

Leu Phe Thr Asp Phe Asp Ser Gln Thr Asn Val Ser Gln Ser Lys Asp
                485                 490                 495

Ser Asp Val Tyr Ile Thr Asp Lys Thr Val Leu Asp Met Arg Ser Met
            500                 505                 510

Asp Phe Lys Ser Asn Ser Ala Val Ala Trp Ser Asn Lys Ser Asp Phe
        515                 520                 525

Ala Cys Ala Asn Ala Phe Asn Asn Ser Ile Ile Pro Glu Asp Thr Phe
    530                 535                 540

Phe Pro Ser Pro Glu Ser Ser Cys Asp Val Lys Leu Val Glu Lys Ser
545                 550                 555                 560

Phe Glu Thr Asp Thr Asn Leu Asn Phe Gln Asn Leu Ser Val Ile Gly
                565                 570                 575

Phe Arg Ile Leu Leu Leu Lys Val Ala Gly Phe Asn Leu Leu Met Thr
            580                 585                 590

Leu Arg Leu Trp Ser Ser
        595


<210> SEQ ID NO 168
<211> LENGTH: 1797
<212> TYPE: DNA
<213> ORGANISM: Artificial Sequence
<220> FEATURE:
<223> OTHER INFORMATION: Synthetic Construct

<400> SEQUENCE: 168

atgagcatcg gcctcctgtg ctgtgcagcc ttgtctctcc tgtgggcagg tccagtgaat     60

gctggtgtca ctcagacccc aaaattccag gtcctgaaga caggacagag catgacactg    120

cagtgtgccc aggatatgaa ccatgaatac atgtcctggt atcgacaaga cccaggcatg    180

gggctgaggc tgattcatta ctcagttggt gctggtatca ctgaccaagg agaagtcccc    240

aatggctaca atgtctccag atcaaccaca gaggatttcc cgctcaggct gctgtcggct    300

gctccctccc agacatctgt gtacttctgt gccagcagtt catgggacag ggatcagccc    360

cagcattttg gtgatgggac tcgactctcc atcctagagg acctgaacaa ggtgttccca    420

cccgaggtcg ctgtgtttga gccatcagaa gcagagatct cccacaccca aaaggccaca    480

ctggtgtgcc tggccacagg cttcttcccc gaccacgtgg agctgagctg gtgggtgaat    540

gggaaggagg tgcacagtgg ggtcagcacg gacccgcagc ccctcaagga gcagcccgcc    600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acccgtcacc cagatcgtca gcgccgaggc ctggggtaga    780

gcagactgtg gctttacctc ggtgtcctac cagcaagggg tcctgtctgc caccatcctc    840

tatgagatcc tgctagggaa ggccaccctg tatgctgtgc tggtcagcgc ccttgtgttg    900

atggccatgg tcaagagaaa ggatttcgga agcggcgcca cgaacttctc tctgttaaag    960

caagcaggag acgtggaaga aaaccccggt cccatgctac tcatcacatc aatgttggtc   1020
```

```
ttatggatgc aattgtcaca ggtgaatgga caacaggtaa tgcaaattcc tcagtaccag   1080

catgtacaag aaggagagga cttcaccacg tactgcaatt cctcaactac tttaagcaat   1140

atacagtggt ataagcaaag gcctggtgga catcccgttt ttttgataca gttagtgaag   1200

agtggagaag tgaagaagca gaaaagactg acatttcagt ttggagaagc aaaaaagaac   1260

agctccctgc acatcacagc cacccagact acagatgtag gaacctactt ctgtgcaggg   1320

cccggtaacc agttctattt tgggacaggg acaagtttga cggtcattcc aaatatccag   1380

aaccctgacc ctgccgtgta ccagctgaga gactctaaat ccagtgacaa gtctgtctgc   1440

ctattcaccg attttgattc tcaaacaaat gtgtcacaaa gtaaggattc tgatgtgtat   1500

atcacagaca aaactgtgct agacatgagg tctatggact tcaagagcaa cagtgctgtg   1560

gcctggagca acaaatctga ctttgcatgt gcaaacgcct tcaacaacag cattattcca   1620

gaagacacct tcttccccag cccagaaagt tcctgtgatg tcaagctggt cgagaaaagc   1680

tttgaaacag atacgaacct aaactttcaa aacctgtcag tgattgggtt ccgaatcctc   1740

ctcctgaaag tggccgggtt taatctgctc atgacgctgc ggctgtggtc cagctga      1797
```

```
<210> SEQ ID NO 169
<211> LENGTH: 590
<212> TYPE: PRT
<213> ORGANISM: Artificial Sequence
<220> FEATURE:
<223> OTHER INFORMATION: Synthetic Construct

<400> SEQUENCE: 169

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Ser Trp Asp Arg Asp Gln Pro Gln His Phe Gly Asp Gly Thr Arg
        115                 120                 125

Leu Ser Ile Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
```

```
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser Gly Ser Gly Ala Thr Asn Phe Ser Leu Leu Lys Gln Ala Gly Asp
305                 310                 315                 320

Val Glu Glu Asn Pro Gly Pro Met Leu Leu Ile Thr Ser Met Leu Val
                325                 330                 335

Leu Trp Met Gln Leu Ser Gln Val Asn Gly Gln Gln Val Met Gln Ile
            340                 345                 350

Pro Gln Tyr Gln His Val Gln Glu Gly Glu Asp Phe Thr Thr Tyr Cys
        355                 360                 365

Asn Ser Ser Thr Thr Leu Ser Asn Ile Gln Trp Tyr Lys Gln Arg Pro
    370                 375                 380

Gly Gly His Pro Val Phe Leu Ile Gln Leu Val Lys Ser Gly Glu Val
385                 390                 395                 400

Lys Lys Gln Lys Arg Leu Thr Phe Gln Phe Gly Glu Ala Lys Lys Asn
                405                 410                 415

Ser Ser Leu His Ile Thr Ala Thr Gln Thr Thr Asp Val Gly Thr Tyr
            420                 425                 430

Phe Cys Ala Gly Pro Gly Asn Gln Phe Tyr Phe Gly Thr Gly Thr Ser
        435                 440                 445

Leu Thr Val Ile Pro Asn Ile Gln Asn Pro Glu Pro Ala Val Tyr Gln
    450                 455                 460

Leu Lys Asp Pro Arg Ser Gln Asp Ser Thr Leu Cys Leu Phe Thr Asp
465                 470                 475                 480

Phe Asp Ser Gln Ile Asn Val Pro Lys Thr Met Glu Ser Gly Thr Phe
                485                 490                 495

Ile Thr Asp Lys Thr Val Leu Asp Met Lys Ala Met Asp Ser Lys Ser
            500                 505                 510

Asn Gly Ala Ile Ala Trp Ser Asn Gln Thr Ser Phe Thr Cys Gln Asp
        515                 520                 525

Ile Phe Lys Glu Thr Asn Ala Thr Tyr Pro Ser Ser Asp Val Pro Cys
    530                 535                 540

Asp Ala Thr Leu Thr Glu Lys Ser Phe Glu Thr Asp Met Asn Leu Asn
545                 550                 555                 560

Phe Gln Asn Leu Leu Val Met Val Leu Arg Ile Leu Leu Leu Lys Val
                565                 570                 575

Ala Gly Phe Asn Leu Leu Met Thr Leu Arg Leu Trp Ser Ser
            580                 585                 590


<210> SEQ ID NO 170
<211> LENGTH: 1773
<212> TYPE: DNA
<213> ORGANISM: Artificial Sequence
<220> FEATURE:
<223> OTHER INFORMATION: Synthetic Construct

<400> SEQUENCE: 170

atgagcatcg gcctcctgtg ctgtgcagcc ttgtctctcc tgtgggcagg tccagtgaat      60
```

```
gctggtgtca ctcagacccc aaaattccag gtcctgaaga caggacagag catgacactg    120

cagtgtgccc aggatatgaa ccatgaatac atgtcctggt atcgacaaga cccaggcatg    180

gggctgaggc tgattcatta ctcagttggt gctggtatca ctgaccaagg agaagtcccc    240

aatggctaca atgtctccag atcaaccaca gaggatttcc cgctcaggct gctgtcggct    300

gctccctccc agacatctgt gtacttctgt gccagcagtt catgggacag ggatcagccc    360

cagcattttg gtgatgggac tcgactctcc atcctagagg atctgagaaa tgtgactcca    420

cccaaggtct ccttgtttga gccatcaaaa gcagagattg caaacaaaca aaaggctacc    480

ctcgtgtgct tggccagggg cttcttccct gaccacgtgg agctgagctg gtgggtgaat    540

ggcaaggagg tccacagtgg ggtcagcacg gaccctcagg cctacaagga gagcaattat    600

agctactgcc tgagcagccg cctgagggtc tctgctacct tctggcacaa tcctcgcaac    660

cacttccgct gccaagtgca gttccatggg ctttcagagg aggacaagtg gccagagggc    720

tcacccaaac ctgtcacaca gaacatcagt gcagaggcct ggggccgagc agactgtggg    780

attacctcag catcctatca acaaggggtc ttgtctgcca ccatcctcta tgagatcctg    840

ctagggaaag ccaccctgta tgctgtgctt gtcagtacac tggtggtgat ggctatggtc    900

aaaagaaaaa attcaggaag cggcgccacg aacttctctc tgttaaagca agcaggagac    960

gtggaagaaa accccggtcc catgctactc atcacatcaa tgttggtctt atggatgcaa   1020

ttgtcacagg tgaatggaca acaggtaatg caaattcctc agtaccagca tgtacaagaa   1080

ggagaggact tcaccacgta ctgcaattcc tcaactactt taagcaatat acagtggtat   1140

aagcaaaggc ctggtggaca tcccgttttt ttgatacagt tagtgaagag tggagaagtg   1200

aagaagcaga aaagactgac atttcagttt ggagaagcaa aaaagaacag ctccctgcac   1260

atcacagcca cccagactac agatgtagga acctacttct gtgcagggcc cggtaaccag   1320

ttctattttg ggacagggac aagtttgacg gtcattccaa atatccagaa cccagaacct   1380

gctgtgtacc agttaaaaga tcctcggtct caggacagca ccctctgcct gttcaccgac   1440

tttgactccc aaatcaatgt gccgaaaacc atggaatctg gaacgttcat cactgacaaa   1500

actgtgctgg acatgaaagc tatggattcc aagagcaatg gggccattgc ctggagcaac   1560

cagacaagct tcacctgcca agatatcttc aaagagacca acgccaccta ccccagttca   1620

gacgttccct gtgatgccac gttgactgag aaaagctttg aaacagatat gaacctaaac   1680

tttcaaaacc tgctggttat ggttctccga atcctcctgc tgaaagtagc cggatttaac   1740

ctgctcatga cgctgaggct gtggtccagt tga                                1773
```

<210> SEQ ID NO 171
<211> LENGTH: 604
<212> TYPE: PRT
<213> ORGANISM: Artificial Sequence
<220> FEATURE:
<223> OTHER INFORMATION: Synthetic Construct

<400> SEQUENCE: 171

```
Met Leu Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
```

```
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Pro Trp
            100                 105                 110

Leu Ala Gly Leu Tyr Asn Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly Gly Ser Gly Ala Thr Asn Phe Ser Leu Leu
305                 310                 315                 320

Lys Gln Ala Gly Asp Val Glu Glu Asn Pro Gly Pro Met Leu Leu Glu
                325                 330                 335

Leu Ile Pro Leu Leu Gly Ile His Phe Val Leu Arg Thr Ala Arg Ala
            340                 345                 350

Gln Ser Val Thr Gln Pro Asp Ile His Ile Thr Val Ser Glu Gly Ala
        355                 360                 365

Ser Leu Glu Leu Arg Cys Asn Tyr Ser Tyr Gly Ala Thr Pro Tyr Leu
    370                 375                 380

Phe Trp Tyr Val Gln Ser Pro Gly Gln Gly Leu Gln Leu Leu Leu Lys
385                 390                 395                 400

Tyr Phe Ser Gly Asp Thr Leu Val Gln Gly Ile Lys Gly Phe Glu Ala
                405                 410                 415

Glu Phe Lys Arg Ser Gln Ser Ser Phe Asn Leu Arg Lys Pro Ser Val
            420                 425                 430

His Trp Ser Asp Ala Ala Glu Tyr Phe Cys Ala Val Tyr Gln Gly Ala
        435                 440                 445

Gln Lys Leu Val Phe Gly Gln Gly Thr Arg Leu Thr Ile Asn Pro Asn
    450                 455                 460

Ile Gln Asn Pro Asp Pro Ala Val Tyr Gln Leu Arg Asp Ser Lys Ser
465                 470                 475                 480
```

Ser Asp Lys Ser Val Cys Leu Phe Thr Asp Phe Asp Ser Gln Thr Asn
485 490 495

Val Ser Gln Ser Lys Asp Ser Asp Val Tyr Ile Thr Asp Lys Thr Val
500 505 510

Leu Asp Met Arg Ser Met Asp Phe Lys Ser Asn Ser Ala Val Ala Trp
515 520 525

Ser Asn Lys Ser Asp Phe Ala Cys Ala Asn Ala Phe Asn Asn Ser Ile
530 535 540

Ile Pro Glu Asp Thr Phe Phe Pro Ser Pro Glu Ser Ser Cys Asp Val
545 550 555 560

Lys Leu Val Glu Lys Ser Phe Glu Thr Asp Thr Asn Leu Asn Phe Gln
565 570 575

Asn Leu Ser Val Ile Gly Phe Arg Ile Leu Leu Leu Lys Val Ala Gly
580 585 590

Phe Asn Leu Leu Met Thr Leu Arg Leu Trp Ser Ser
595 600

<210> SEQ ID NO 172
<211> LENGTH: 1815
<212> TYPE: DNA
<213> ORGANISM: Artificial Sequence
<220> FEATURE:
<223> OTHER INFORMATION: Synthetic Construct

<400> SEQUENCE: 172
atgctgctgc ttctgctgct tctggggcca ggctccgggc ttggtgctgt cgtctctcaa 60
catccgagct gggttatctg taagagtgga acctctgtga agatcgagtg ccgttccctg 120
gactttcagg ccacaactat gttttggtat cgtcagttcc cgaaacagag tctcatgctg 180
atggcaactt ccaatgaggg ctccaaggcc acatacgagc aaggcgtcga gaaggacaag 240
tttctcatca accatgcaag cctgaccttg tccactctga cagtgaccag tgcccatcct 300
gaagacagca gcttctacat ctgcagtgct ccgtggctag cggggttgta caatgagcag 360
ttcttcgggc cagggacacg gctcaccgtg ctagaggacc tgaaaaacgt gttcccaccc 420
gaggtcgctg tgtttgagcc atcagaagca gagatctccc acacccaaaa ggccacactg 480
gtgtgcctgg ccacaggctt ctaccccgac cacgtggagc tgagctggtg ggtgaatggg 540
aaggaggtgc acagtggggt cagcacagac ccgcagcccc tcaaggagca gcccgccctc 600
aatgactcca gatactgcct gagcagccgc ctgagggtct cggccacctt ctggcagaac 660
ccccgcaacc acttccgctg tcaagtccag ttctacgggc tctcggagaa tgacgagtgg 720
acccaggata gggccaaacc tgtcacccag atcgtcagcg ccgaggcctg gggtagagca 780
gactgtggct tcacctccga gtcttaccag caaggggtcc tgtctgccac catcctctat 840
gagatcttgc tagggaaggc caccttgtat gccgtgctgg tcagtgccct cgtgctgatg 900
gccatggtca agagaaagga ttccagaggc ggaagcggcg ccacgaactt ctctctgtta 960
aagcaagcag gagacgtgga agaaaacccc ggtcccatgc tcctggagct tatcccactg 1020
ctggggatac attttgtcct gagaactgcc agagcccagt cagtgaccca gcctgacatc 1080
cacatcactg tctctgaagg agcctcactg gagttgagat gtaactattc ctatggggca 1140
acaccttatc tcttctggta tgtccagtcc cccggccaag gcctccagct gctcctgaag 1200
tacttttcag gagacactct ggttcaaggc attaaaggct ttgaggctga atttaagagg 1260
agtcaatctt ccttcaacct gaggaaaccc tctgtgcatt ggagtgatgc tgctgagtac 1320

```
ttctgtgctg tgtatcaggg agcccagaag ctggtatttg gccaaggaac caggctgact   1380

atcaacccaa atatccagaa ccctgaccct gccgtgtacc agctgagaga ctctaaatcc   1440

agtgacaagt ctgtctgcct attcaccgat tttgattctc aaacaaatgt gtcacaaagt   1500

aaggattctg atgtgtatat cacagacaaa actgtgctag acatgaggtc tatggacttc   1560

aagagcaaca gtgctgtggc ctggagcaac aaatctgact ttgcatgtgc aaacgccttc   1620

aacaacagca ttattccaga agacaccttc ttccccagcc cagaaagttc ctgtgatgtc   1680

aagctggtcg agaaaagctt tgaaacagat acgaacctaa actttcaaaa cctgtcagtg   1740

attgggttcc gaatcctcct cctgaaagtg gccgggttta atctgctcat gacgctgcgg   1800

ctgtggtcca gctga                                                    1815
```

<210> SEQ ID NO 173
<211> LENGTH: 594
<212> TYPE: PRT
<213> ORGANISM: Artificial Sequence
<220> FEATURE:
<223> OTHER INFORMATION: Synthetic Construct

<400> SEQUENCE: 173

```
Met Leu Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Pro Trp
            100                 105                 110

Leu Ala Gly Leu Tyr Asn Glu Gln Phe Phe Gly Pro Gly Thr Arg Leu
        115                 120                 125

Thr Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270
```

-continued

```
Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300

Gly Ser Gly Ala Thr Asn Phe Ser Leu Leu Lys Gln Ala Gly Asp Val
305                 310                 315                 320

Glu Glu Asn Pro Gly Pro Met Leu Leu Glu Leu Ile Pro Leu Leu Gly
                325                 330                 335

Ile His Phe Val Leu Arg Thr Ala Arg Ala Gln Ser Val Thr Gln Pro
            340                 345                 350

Asp Ile His Ile Thr Val Ser Glu Gly Ala Ser Leu Glu Leu Arg Cys
        355                 360                 365

Asn Tyr Ser Tyr Gly Ala Thr Pro Tyr Leu Phe Trp Tyr Val Gln Ser
    370                 375                 380

Pro Gly Gln Gly Leu Gln Leu Leu Leu Lys Tyr Phe Ser Gly Asp Thr
385                 390                 395                 400

Leu Val Gln Gly Ile Lys Gly Phe Glu Ala Glu Phe Lys Arg Ser Gln
                405                 410                 415

Ser Ser Phe Asn Leu Arg Lys Pro Ser Val His Trp Ser Asp Ala Ala
            420                 425                 430

Glu Tyr Phe Cys Ala Val Tyr Gln Gly Ala Gln Lys Leu Val Phe Gly
        435                 440                 445

Gln Gly Thr Arg Leu Thr Ile Asn Pro Asn Ile Gln Asn Pro Glu Pro
    450                 455                 460

Ala Val Tyr Gln Leu Lys Asp Pro Arg Ser Gln Asp Ser Thr Leu Cys
465                 470                 475                 480

Leu Phe Thr Asp Phe Asp Ser Gln Ile Asn Val Pro Lys Thr Met Glu
                485                 490                 495

Ser Gly Thr Phe Ile Thr Asp Lys Thr Val Leu Asp Met Lys Ala Met
            500                 505                 510

Asp Ser Lys Ser Asn Gly Ala Ile Ala Trp Ser Asn Gln Thr Ser Phe
        515                 520                 525

Thr Cys Gln Asp Ile Phe Lys Glu Thr Asn Ala Thr Tyr Pro Ser Ser
    530                 535                 540

Asp Val Pro Cys Asp Ala Thr Leu Thr Glu Lys Ser Phe Glu Thr Asp
545                 550                 555                 560

Met Asn Leu Asn Phe Gln Asn Leu Leu Val Met Val Leu Arg Ile Leu
                565                 570                 575

Leu Leu Lys Val Ala Gly Phe Asn Leu Leu Met Thr Leu Arg Leu Trp
            580                 585                 590

Ser Ser
```

<210> SEQ ID NO 174
<211> LENGTH: 1785
<212> TYPE: DNA
<213> ORGANISM: Artificial Sequence
<220> FEATURE:
<223> OTHER INFORMATION: Synthetic Construct

<400> SEQUENCE: 174

```
atgctgctgc ttctgctgct tctggggcca ggctccgggc ttggtgctgt cgtctctcaa      60

catccgagct gggttatctg taagagtgga acctctgtga agatcgagtg ccgttccctg     120

gactttcagg ccacaactat gttttggtat cgtcagttcc cgaaacagag tctcatgctg     180

atggcaactt ccaatgaggg ctccaaggcc acatacgagc aaggcgtcga gaaggacaag     240
```

```
tttctcatca accatgcaag cctgaccttg tccactctga cagtgaccag tgcccatcct    300

gaagacagca gcttctacat ctgcagtgct ccgtggctag cggggttgta caatgagcag    360

ttcttcgggc cagggacacg gctcaccgtg ctagaggatc tgagaaatgt gactccaccc    420

aaggtctcct tgtttgagcc atcaaaagca gagattgcaa acaaacaaaa ggctaccctc    480

gtgtgcttgg ccaggggctt cttccctgac cacgtggagc tgagctggtg ggtgaatggc    540

aaggaggtcc acagtggggt cagcacggac cctcaggcct acaaggagag caattatagc    600

tactgcctga gcagccgcct gagggtctct gctaccttct ggcacaatcc tcgcaaccac    660

ttccgctgcc aagtgcagtt ccatgggctt tcagaggagg acaagtggcc agagggctca    720

cccaaacctg tcacacagaa catcagtgca gaggcctggg gccgagcaga ctgtgggatt    780

acctcagcat cctatcaaca aggggtcttg tctgccacca tcctctatga gatcctgcta    840

gggaaagcca ccctgtatgc tgtgcttgtc agtacactgg tggtgatggc tatggtcaaa    900

agaaaaaatt caggaagcgg cgccacgaac ttctctctgt taaagcaagc aggagacgtg    960

gaagaaaacc ccggtcccat gctcctggag cttatcccac tgctggggat acattttgtc   1020

ctgagaactg ccagagccca gtcagtgacc cagcctgaca tccacatcac tgtctctgaa   1080

ggagcctcac tggagttgag atgtaactat tcctatgggg caacacctta tctcttctgg   1140

tatgtccagt cccccggcca aggcctccag ctgctcctga agtacttttc aggagacact   1200

ctggttcaag gcattaaagg ctttgaggct gaatttaaga ggagtcaatc ttccttcaac   1260

ctgaggaaac cctctgtgca ttggagtgat gctgctgagt acttctgtgc tgtgtatcag   1320

ggagcccaga agctggtatt tggccaagga accaggctga ctatcaaccc aaatatccag   1380

aacccagaac ctgctgtgta ccagttaaaa gatcctcggt ctcaggacag caccctctgc   1440

ctgttcaccg actttgactc ccaaatcaat gtgccgaaaa ccatggaatc tggaacgttc   1500

atcactgaca aaactgtgct ggacatgaaa gctatggatt ccaagagcaa tggggccatt   1560

gcctggagca accagacaag cttcacctgc caagatatct tcaaagagac caacgccacc   1620

taccccagtt cagacgttcc ctgtgatgcc acgttgactg agaaaagctt tgaaacagat   1680

atgaacctaa actttcaaaa cctgctggtt atggttctcc gaatcctcct gctgaaagta   1740

gccggattta acctgctcat gacgctgagg ctgtggtcca gttga                   1785
```

```
<210> SEQ ID NO 175
<211> LENGTH: 623
<212> TYPE: PRT
<213> ORGANISM: Artificial Sequence
<220> FEATURE:
<223> OTHER INFORMATION: Synthetic Construct

<400> SEQUENCE: 175

Met Glu Ala Val Val Thr Thr Leu Pro Arg Glu Gly Gly Val Arg Pro
1               5                   10                  15

Ser Arg Lys Met Leu Leu Leu Leu Leu Leu Leu Gly Pro Gly Ser Gly
            20                  25                  30

Leu Gly Ala Val Val Ser Gln His Pro Ser Trp Val Ile Cys Lys Ser
        35                  40                  45

Gly Thr Ser Val Lys Ile Glu Cys Arg Ser Leu Asp Phe Gln Ala Thr
    50                  55                  60

Thr Met Phe Trp Tyr Arg Gln Phe Pro Lys Gln Ser Leu Met Leu Met
65                  70                  75                  80

Ala Thr Ser Asn Glu Gly Ser Lys Ala Thr Tyr Glu Gln Gly Val Glu
```

```
                85                  90                  95

Lys Asp Lys Phe Leu Ile Asn His Ala Ser Leu Thr Leu Ser Thr Leu
            100                 105                 110

Thr Val Thr Ser Ala His Pro Glu Asp Ser Ser Phe Tyr Ile Cys Ser
        115                 120                 125

Ala Pro Trp Leu Ala Gly Leu Tyr Asn Glu Gln Phe Phe Gly Pro Gly
    130                 135                 140

Thr Arg Leu Thr Val Leu Glu Asp Leu Lys Asn Val Phe Pro Pro Glu
145                 150                 155                 160

Val Ala Val Phe Glu Pro Ser Glu Ala Glu Ile Ser His Thr Gln Lys
                165                 170                 175

Ala Thr Leu Val Cys Leu Ala Thr Gly Phe Tyr Pro Asp His Val Glu
            180                 185                 190

Leu Ser Trp Trp Val Asn Gly Lys Glu Val His Ser Gly Val Ser Thr
        195                 200                 205

Asp Pro Gln Pro Leu Lys Glu Gln Pro Ala Leu Asn Asp Ser Arg Tyr
    210                 215                 220

Cys Leu Ser Ser Arg Leu Arg Val Ser Ala Thr Phe Trp Gln Asn Pro
225                 230                 235                 240

Arg Asn His Phe Arg Cys Gln Val Gln Phe Tyr Gly Leu Ser Glu Asn
                245                 250                 255

Asp Glu Trp Thr Gln Asp Arg Ala Lys Pro Val Thr Gln Ile Val Ser
            260                 265                 270

Ala Glu Ala Trp Gly Arg Ala Asp Cys Gly Phe Thr Ser Glu Ser Tyr
        275                 280                 285

Gln Gln Gly Val Leu Ser Ala Thr Ile Leu Tyr Glu Ile Leu Leu Gly
    290                 295                 300

Lys Ala Thr Leu Tyr Ala Val Leu Val Ser Ala Leu Val Leu Met Ala
305                 310                 315                 320

Met Val Lys Arg Lys Asp Ser Arg Gly Gly Ser Gly Ala Thr Asn Phe
                325                 330                 335

Ser Leu Leu Lys Gln Ala Gly Asp Val Glu Glu Asn Pro Gly Pro Met
            340                 345                 350

Leu Leu Glu Leu Ile Pro Leu Leu Gly Ile His Phe Val Leu Arg Thr
        355                 360                 365

Ala Arg Ala Gln Ser Val Thr Gln Pro Asp Ile His Ile Thr Val Ser
    370                 375                 380

Glu Gly Ala Ser Leu Glu Leu Arg Cys Asn Tyr Ser Tyr Gly Ala Thr
385                 390                 395                 400

Pro Tyr Leu Phe Trp Tyr Val Gln Ser Pro Gly Gln Gly Leu Gln Leu
                405                 410                 415

Leu Leu Lys Tyr Phe Ser Gly Asp Thr Leu Val Gln Gly Ile Lys Gly
            420                 425                 430

Phe Glu Ala Glu Phe Lys Arg Ser Gln Ser Ser Phe Asn Leu Arg Lys
        435                 440                 445

Pro Ser Val His Trp Ser Asp Ala Ala Glu Tyr Phe Cys Ala Val Tyr
    450                 455                 460

Gln Gly Ala Gln Lys Leu Val Phe Gly Gln Gly Thr Arg Leu Thr Ile
465                 470                 475                 480

Asn Pro Asn Ile Gln Asn Pro Asp Pro Ala Val Tyr Gln Leu Arg Asp
                485                 490                 495

Ser Lys Ser Ser Asp Lys Ser Val Cys Leu Phe Thr Asp Phe Asp Ser
            500                 505                 510
```

```
Gln Thr Asn Val Ser Gln Ser Lys Asp Ser Asp Val Tyr Ile Thr Asp
        515                 520                 525

Lys Thr Val Leu Asp Met Arg Ser Met Asp Phe Lys Ser Asn Ser Ala
    530                 535                 540

Val Ala Trp Ser Asn Lys Ser Asp Phe Ala Cys Ala Asn Ala Phe Asn
545                 550                 555                 560

Asn Ser Ile Ile Pro Glu Asp Thr Phe Phe Pro Ser Pro Glu Ser Ser
                565                 570                 575

Cys Asp Val Lys Leu Val Glu Lys Ser Phe Glu Thr Asp Thr Asn Leu
            580                 585                 590

Asn Phe Gln Asn Leu Ser Val Ile Gly Phe Arg Ile Leu Leu Leu Lys
        595                 600                 605

Val Ala Gly Phe Asn Leu Leu Met Thr Leu Arg Leu Trp Ser Ser
    610                 615                 620
```

<210> SEQ ID NO 176
<211> LENGTH: 1872
<212> TYPE: DNA
<213> ORGANISM: Artificial Sequence
<220> FEATURE:
<223> OTHER INFORMATION: Synthetic Construct

<400> SEQUENCE: 176

```
atggaggcag tggtcacaac tctccccaga gaaggtggtg tgaggccatc acggaagatg     60

ctgctgcttc tgctgcttct ggggccaggc tccgggcttg gtgctgtcgt ctctcaacat    120

ccgagctggg ttatctgtaa gagtggaacc tctgtgaaga tcgagtgccg ttccctggac    180

tttcaggcca caactatgtt ttggtatcgt cagttcccga aacagagtct catgctgatg    240

gcaacttcca atgagggctc caaggccaca tacgagcaag gcgtcgagaa ggacaagttt    300

ctcatcaacc atgcaagcct gaccttgtcc actctgacag tgaccagtgc ccatcctgaa    360

gacagcagct tctacatctg cagtgctccg tggctagcgg ggttgtacaa tgagcagttc    420

ttcgggccag ggacacggct caccgtgcta gaggacctga aaaacgtgtt cccacccgag    480

gtcgctgtgt ttgagccatc agaagcagag atctcccaca cccaaaaggc cacactggtg    540

tgcctggcca caggcttcta ccccgaccac gtggagctga gctggtgggt gaatgggaag    600

gaggtgcaca gtggggtcag cacagacccg cagcccctca aggagcagcc cgccctcaat    660

gactccagat actgcctgag cagccgcctg agggtctcgg ccaccttctg gcagaacccc    720

cgcaaccact tccgctgtca agtccagttc tacgggctct cggagaatga cgagtggacc    780

caggataggg ccaaacctgt cacccagatc gtcagcgccg aggcctgggg tagagcagac    840

tgtggcttca cctccgagtc ttaccagcaa ggggtcctgt ctgccaccat cctctatgag    900

atcttgctag ggaaggccac cttgtatgcc gtgctggtca gtgccctcgt gctgatggcc    960

atggtcaaga gaaaggattc cagaggcgga agcggcgcca cgaacttctc tctgttaaag   1020

caagcaggag acgtggaaga aaaccccggt cccatgctcc tggagcttat cccactgctg   1080

gggatacatt ttgtcctgag aactgccaga gcccagtcag tgacccagcc tgacatccac   1140

atcactgtct ctgaaggagc ctcactggag ttgagatgta actattccta tggggcaaca   1200

ccttatctct tctggtatgt ccagtccccc ggccaaggcc tccagctgct cctgaagtac   1260

ttttcaggag acactctggt tcaaggcatt aaaggctttg aggctgaatt taagaggagt   1320

caatcttcct tcaacctgag gaaaccctct gtgcattgga gtgatgctgc tgagtacttc   1380

tgtgctgtgt atcagggagc ccagaagctg gtatttggcc aaggaaccag gctgactatc   1440
```

aacccaaata tccagaaccc tgaccctgcc gtgtaccagc tgagagactc taaatccagt 1500
gacaagtctg tctgcctatt caccgatttt gattctcaaa caaatgtgtc acaaagtaag 1560
gattctgatg tgtatatcac agacaaaact gtgctagaca tgaggtctat ggacttcaag 1620
agcaacagtg ctgtggcctg gagcaacaaa tctgactttg catgtgcaaa cgccttcaac 1680
aacagcatta ttccagaaga caccttcttc cccagcccag aaagttcctg tgatgtcaag 1740
ctggtcgaga aaagctttga aacagatacg aacctaaact ttcaaaacct gtcagtgatt 1800
gggttccgaa tcctcctcct gaaagtggcc gggtttaatc tgctcatgac gctgcggctg 1860
tggtccagct ga 1872

<210> SEQ ID NO 177
<211> LENGTH: 613
<212> TYPE: PRT
<213> ORGANISM: Artificial Sequence
<220> FEATURE:
<223> OTHER INFORMATION: Synthetic Construct

<400> SEQUENCE: 177

Met Glu Ala Val Val Thr Thr Leu Pro Arg Glu Gly Gly Val Arg Pro
1 5 10 15

Ser Arg Lys Met Leu Leu Leu Leu Leu Leu Leu Gly Pro Gly Ser Gly
20 25 30

Leu Gly Ala Val Val Ser Gln His Pro Ser Trp Val Ile Cys Lys Ser
35 40 45

Gly Thr Ser Val Lys Ile Glu Cys Arg Ser Leu Asp Phe Gln Ala Thr
50 55 60

Thr Met Phe Trp Tyr Arg Gln Phe Pro Lys Gln Ser Leu Met Leu Met
65 70 75 80

Ala Thr Ser Asn Glu Gly Ser Lys Ala Thr Tyr Glu Gln Gly Val Glu
85 90 95

Lys Asp Lys Phe Leu Ile Asn His Ala Ser Leu Thr Leu Ser Thr Leu
100 105 110

Thr Val Thr Ser Ala His Pro Glu Asp Ser Ser Phe Tyr Ile Cys Ser
115 120 125

Ala Pro Trp Leu Ala Gly Leu Tyr Asn Glu Gln Phe Phe Gly Pro Gly
130 135 140

Thr Arg Leu Thr Val Leu Glu Asp Leu Arg Asn Val Thr Pro Pro Lys
145 150 155 160

Val Ser Leu Phe Glu Pro Ser Lys Ala Glu Ile Ala Asn Lys Gln Lys
165 170 175

Ala Thr Leu Val Cys Leu Ala Arg Gly Phe Phe Pro Asp His Val Glu
180 185 190

Leu Ser Trp Trp Val Asn Gly Lys Glu Val His Ser Gly Val Ser Thr
195 200 205

Asp Pro Gln Ala Tyr Lys Glu Ser Asn Tyr Ser Tyr Cys Leu Ser Ser
210 215 220

Arg Leu Arg Val Ser Ala Thr Phe Trp His Asn Pro Arg Asn His Phe
225 230 235 240

Arg Cys Gln Val Gln Phe His Gly Leu Ser Glu Glu Asp Lys Trp Pro
245 250 255

Glu Gly Ser Pro Lys Pro Val Thr Gln Asn Ile Ser Ala Glu Ala Trp
260 265 270

Gly Arg Ala Asp Cys Gly Ile Thr Ser Ala Ser Tyr Gln Gln Gly Val

```
        275                 280                 285

Leu Ser Ala Thr Ile Leu Tyr Glu Ile Leu Leu Gly Lys Ala Thr Leu
    290                 295                 300

Tyr Ala Val Leu Val Ser Thr Leu Val Val Met Ala Met Val Lys Arg
305                 310                 315                 320

Lys Asn Ser Gly Ser Gly Ala Thr Asn Phe Ser Leu Leu Lys Gln Ala
                325                 330                 335

Gly Asp Val Glu Glu Asn Pro Gly Pro Met Leu Leu Glu Leu Ile Pro
            340                 345                 350

Leu Leu Gly Ile His Phe Val Leu Arg Thr Ala Arg Ala Gln Ser Val
        355                 360                 365

Thr Gln Pro Asp Ile His Ile Thr Val Ser Glu Gly Ala Ser Leu Glu
    370                 375                 380

Leu Arg Cys Asn Tyr Ser Tyr Gly Ala Thr Pro Tyr Leu Phe Trp Tyr
385                 390                 395                 400

Val Gln Ser Pro Gly Gln Gly Leu Gln Leu Leu Leu Lys Tyr Phe Ser
                405                 410                 415

Gly Asp Thr Leu Val Gln Gly Ile Lys Gly Phe Glu Ala Glu Phe Lys
            420                 425                 430

Arg Ser Gln Ser Ser Phe Asn Leu Arg Lys Pro Ser Val His Trp Ser
        435                 440                 445

Asp Ala Ala Glu Tyr Phe Cys Ala Val Tyr Gln Gly Ala Gln Lys Leu
    450                 455                 460

Val Phe Gly Gln Gly Thr Arg Leu Thr Ile Asn Pro Asn Ile Gln Asn
465                 470                 475                 480

Pro Glu Pro Ala Val Tyr Gln Leu Lys Asp Pro Arg Ser Gln Asp Ser
                485                 490                 495

Thr Leu Cys Leu Phe Thr Asp Phe Asp Ser Gln Ile Asn Val Pro Lys
            500                 505                 510

Thr Met Glu Ser Gly Thr Phe Ile Thr Asp Lys Thr Val Leu Asp Met
        515                 520                 525

Lys Ala Met Asp Ser Lys Ser Asn Gly Ala Ile Ala Trp Ser Asn Gln
    530                 535                 540

Thr Ser Phe Thr Cys Gln Asp Ile Phe Lys Glu Thr Asn Ala Thr Tyr
545                 550                 555                 560

Pro Ser Ser Asp Val Pro Cys Asp Ala Thr Leu Thr Glu Lys Ser Phe
                565                 570                 575

Glu Thr Asp Met Asn Leu Asn Phe Gln Asn Leu Leu Val Met Val Leu
            580                 585                 590

Arg Ile Leu Leu Leu Lys Val Ala Gly Phe Asn Leu Leu Met Thr Leu
        595                 600                 605

Arg Leu Trp Ser Ser
    610
```

<210> SEQ ID NO 178
<211> LENGTH: 1842
<212> TYPE: DNA
<213> ORGANISM: Artificial Sequence
<220> FEATURE:
<223> OTHER INFORMATION: Synthetic Construct

<400> SEQUENCE: 178

```
atggaggcag tggtcacaac tctccccaga gaaggtggtg tgaggccatc acggaagatg     60

ctgctgcttc tgctgcttct ggggccaggc tccgggcttg gtgctgtcgt ctctcaacat    120
```

-continued

```
ccgagctggg ttatctgtaa gagtggaacc tctgtgaaga tcgagtgccg ttccctggac    180
tttcaggcca caactatgtt ttggtatcgt cagttcccga aacagagtct catgctgatg    240
gcaacttcca atgagggctc caaggccaca tacgagcaag gcgtcgagaa ggacaagttt    300
ctcatcaacc atgcaagcct gaccttgtcc actctgacag tgaccagtgc ccatcctgaa    360
gacagcagct tctacatctg cagtgctccg tggctagcgg ggttgtacaa tgagcagttc    420
ttcgggccag ggacacggct caccgtgcta gaggatctga gaaatgtgac tccacccaag    480
gtctccttgt ttgagccatc aaaagcagag attgcaaaca aacaaaaggc taccctcgtg    540
tgcttggcca ggggcttctt ccctgaccac gtggagctga gctggtgggt gaatggcaag    600
gaggtccaca gtggggtcag cacggaccct caggcctaca aggagagcaa ttatagctac    660
tgcctgagca gccgcctgag ggtctctgct accttctggc acaatcctcg caaccacttc    720
cgctgccaag tgcagttcca tgggctttca gaggaggaca agtggccaga gggctcaccc    780
aaacctgtca cacagaacat cagtgcagag gcctggggcc gagcagactg tgggattacc    840
tcagcatcct atcaacaagg ggtcttgtct gccaccatcc tctatgagat cctgctaggg    900
aaagccaccc tgtatgctgt gcttgtcagt acactggtgg tgatggctat ggtcaaaaga    960
aaaaattcag gaagcggcgc cacgaacttc tctctgttaa agcaagcagg agacgtggaa   1020
gaaaaccccg gtcccatgct cctggagctt atcccactgc tggggataca ttttgtcctg   1080
agaactgcca gagcccagtc agtgacccag cctgacatcc acatcactgt ctctgaagga   1140
gcctcactgg agttgagatg taactattcc tatggggcaa caccttatct cttctggtat   1200
gtccagtccc ccggccaagg cctccagctg ctcctgaagt acttttcagg agacactctg   1260
gttcaaggca ttaaaggctt tgaggctgaa tttaagagga gtcaatcttc cttcaacctg   1320
aggaaaccct ctgtgcattg gagtgatgct gctgagtact tctgtgctgt gtatcaggga   1380
gcccagaagc tggtatttgg ccaaggaacc aggctgacta tcaacccaaa tatccagaac   1440
ccagaacctg ctgtgtacca gttaaaagat cctcggtctc aggacagcac cctctgcctg   1500
ttcaccgact ttgactccca aatcaatgtg ccgaaaacca tggaatctgg aacgttcatc   1560
actgacaaaa ctgtgctgga catgaaagct atggattcca agagcaatgg ggccattgcc   1620
tggagcaacc agacaagctt cacctgccaa gatatcttca aagagaccaa cgccacctac   1680
cccagttcag acgttccctg tgatgccacg ttgactgaga aaagctttga aacagatatg   1740
aacctaaact ttcaaaacct gctggttatg gttctccgaa tcctcctgct gaaagtagcc   1800
ggatttaacc tgctcatgac gctgaggctg tggtccagtt ga                      1842
```

<210> SEQ ID NO 179
<211> LENGTH: 608
<212> TYPE: PRT
<213> ORGANISM: Artificial Sequence
<220> FEATURE:
<223> OTHER INFORMATION: Synthetic Construct

<400> SEQUENCE: 179

```
Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60
```

```
Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Asp Pro Ala Thr Ser His Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly Gly Ser Gly Ala Thr Asn Phe Ser
305                 310                 315                 320

Leu Leu Lys Gln Ala Gly Asp Val Glu Glu Asn Pro Gly Pro Met Met
                325                 330                 335

Lys Ser Leu Arg Val Leu Leu Val Ile Leu Trp Leu Gln Leu Ser Trp
            340                 345                 350

Val Trp Ser Gln Gln Lys Glu Val Glu Gln Asp Pro Gly Pro Leu Ser
        355                 360                 365

Val Pro Glu Gly Ala Ile Val Ser Leu Asn Cys Thr Tyr Ser Asn Ser
    370                 375                 380

Ala Phe Gln Tyr Phe Met Trp Tyr Arg Gln Tyr Ser Arg Lys Gly Pro
385                 390                 395                 400

Glu Leu Leu Met Tyr Thr Tyr Ser Ser Gly Asn Lys Glu Asp Gly Arg
                405                 410                 415

Phe Thr Ala Gln Val Asp Lys Ser Ser Lys Tyr Ile Ser Leu Phe Ile
            420                 425                 430

Arg Asp Ser Gln Pro Ser Asp Ser Ala Thr Tyr Leu Cys Ala Phe Tyr
        435                 440                 445

Ala Gly Asn Asn Arg Lys Leu Ile Trp Gly Leu Gly Thr Ser Leu Ala
    450                 455                 460

Val Asn Pro Asn Ile Gln Asn Pro Asp Pro Ala Val Tyr Gln Leu Arg
465                 470                 475                 480
```

```
Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
        515                 520                 525

Ala Val Ala Trp Ser Asn Lys Ser Asp Phe Ala Cys Ala Asn Ala Phe
    530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
        595                 600                 605


<210> SEQ ID NO 180
<211> LENGTH: 1827
<212> TYPE: DNA
<213> ORGANISM: Artificial Sequence
<220> FEATURE:
<223> OTHER INFORMATION: Synthetic Construct

<400> SEQUENCE: 180

atgagcaacc aggtgctctg ctgtgtggtc ctttgtttcc tgggagcaaa caccgtggat     60

ggtggaatca ctcagtcccc aaagtacctg ttcagaaagg aaggacagaa tgtgaccctg    120

agttgtgaac agaatttgaa ccacgatgcc atgtactggt accgacagga cccagggcaa    180

gggctgagat tgatctacta ctcacagata gtaaatgact ttcagaaagg agatatagct    240

gaagggtaca gcgtctctcg ggagaagaag gaatcctttc ctctcactgt gacatcggcc    300

caaaagaacc cgacagcttt ctatctctgt gccagtagta tagatccggc gactagtcat    360

gagcagttct tcgggccagg gacacggctc accgtgctag aggacctgaa aaacgtgttc    420

ccacccgagg tcgctgtgtt tgagccatca gaagcagaga tctcccacac ccaaaaggcc    480

acactggtgt gcctggccac aggcttctac cccgaccacg tggagctgag ctggtgggtg    540

aatgggaagg aggtgcacag tggggtcagc acagacccgc agcccctcaa ggagcagccc    600

gccctcaatg actccagata ctgcctgagc agccgcctga gggtctcggc caccttctgg    660

cagaaccccc gcaaccactt ccgctgtcaa gtccagttct acgggctctc ggagaatgac    720

gagtggaccc aggatagggc caaacctgtc acccagatcg tcagcgccga ggcctggggt    780

agagcagact gtggcttcac ctccgagtct taccagcaag ggtcctgtc tgccaccatc    840

ctctatgaga tcttgctagg gaaggccacc ttgtatgccg tgctggtcag tgccctcgtg    900

ctgatggcca tggtcaagag aaaggattcc agaggcggaa gcggcgccac gaacttctct    960

ctgttaaagc aagcaggaga cgtggaagaa aaccccggtc ccatgatgaa atccttgaga   1020

gttttactgg tgatcctgtg gcttcagtta agctgggttt ggagccaaca gaaggaggtg   1080

gagcaggatc ctggaccact cagtgttcca gagggagcca ttgtttctct caactgcact   1140

tacagcaaca gtgcttttca atacttcatg tggtacagac agtattccag aaaaggccct   1200

gagttgctga tgtacacata ctccagtggt aacaaagaag atggaaggtt tacagcacag   1260

gtcgataaat ccagcaagta tatctccttg ttcatcagag actcacagcc cagtgattca   1320

gccacctacc tctgtgcatt ctatgctggc aacaaccgta agctgatttg ggattggga   1380
```

acaagcctgg cagtaaatcc gaatatccag aaccctgacc ctgccgtgta ccagctgaga 1440
gactctaaat ccagtgacaa gtctgtctgc ctattcaccg attttgattc tcaaacaaat 1500
gtgtcacaaa gtaaggattc tgatgtgtat atcacagaca aaactgtgct agacatgagg 1560
tctatggact tcaagagcaa cagtgctgtg gcctggagca acaaatctga ctttgcatgt 1620
gcaaacgcct tcaacaacag cattattcca gaagacacct tcttccccag cccagaaagt 1680
tcctgtgatg tcaagctggt cgagaaaagc tttgaaacag atacgaacct aaactttcaa 1740
aacctgtcag tgattgggtt ccgaatcctc ctcctgaaag tggccgggtt taatctgctc 1800
atgacgctgc ggctgtggtc cagctga 1827

<210> SEQ ID NO 181
<211> LENGTH: 598
<212> TYPE: PRT
<213> ORGANISM: Artificial Sequence
<220> FEATURE:
<223> OTHER INFORMATION: Synthetic Construct

<400> SEQUENCE: 181

Met Ser Asn Gln Val Leu Cys Cys Val Val Leu Cys Phe Leu Gly Ala
1 5 10 15

Asn Thr Val Asp Gly Gly Ile Thr Gln Ser Pro Lys Tyr Leu Phe Arg
20 25 30

Lys Glu Gly Gln Asn Val Thr Leu Ser Cys Glu Gln Asn Leu Asn His
35 40 45

Asp Ala Met Tyr Trp Tyr Arg Gln Asp Pro Gly Gln Gly Leu Arg Leu
50 55 60

Ile Tyr Tyr Ser Gln Ile Val Asn Asp Phe Gln Lys Gly Asp Ile Ala
65 70 75 80

Glu Gly Tyr Ser Val Ser Arg Glu Lys Lys Glu Ser Phe Pro Leu Thr
85 90 95

Val Thr Ser Ala Gln Lys Asn Pro Thr Ala Phe Tyr Leu Cys Ala Ser
100 105 110

Ser Ile Asp Pro Ala Thr Ser His Glu Gln Phe Phe Gly Pro Gly Thr
115 120 125

Arg Leu Thr Val Leu Glu Asp Leu Arg Asn Val Thr Pro Pro Lys Val
130 135 140

Ser Leu Phe Glu Pro Ser Lys Ala Glu Ile Ala Asn Lys Gln Lys Ala
145 150 155 160

Thr Leu Val Cys Leu Ala Arg Gly Phe Phe Pro Asp His Val Glu Leu
165 170 175

Ser Trp Trp Val Asn Gly Lys Glu Val His Ser Gly Val Ser Thr Asp
180 185 190

Pro Gln Ala Tyr Lys Glu Ser Asn Tyr Ser Tyr Cys Leu Ser Ser Arg
195 200 205

Leu Arg Val Ser Ala Thr Phe Trp His Asn Pro Arg Asn His Phe Arg
210 215 220

Cys Gln Val Gln Phe His Gly Leu Ser Glu Glu Asp Lys Trp Pro Glu
225 230 235 240

Gly Ser Pro Lys Pro Val Thr Gln Asn Ile Ser Ala Glu Ala Trp Gly
245 250 255

Arg Ala Asp Cys Gly Ile Thr Ser Ala Ser Tyr Gln Gln Gly Val Leu
260 265 270

Ser Ala Thr Ile Leu Tyr Glu Ile Leu Leu Gly Lys Ala Thr Leu Tyr

```
        275                 280                 285

Ala Val Leu Val Ser Thr Leu Val Val Met Ala Met Val Lys Arg Lys
    290                 295                 300

Asn Ser Gly Ser Gly Ala Thr Asn Phe Ser Leu Leu Lys Gln Ala Gly
305                 310                 315                 320

Asp Val Glu Glu Asn Pro Gly Pro Met Met Lys Ser Leu Arg Val Leu
                325                 330                 335

Leu Val Ile Leu Trp Leu Gln Leu Ser Trp Val Trp Ser Gln Gln Lys
            340                 345                 350

Glu Val Glu Gln Asp Pro Gly Pro Leu Ser Val Pro Glu Gly Ala Ile
        355                 360                 365

Val Ser Leu Asn Cys Thr Tyr Ser Asn Ser Ala Phe Gln Tyr Phe Met
    370                 375                 380

Trp Tyr Arg Gln Tyr Ser Arg Lys Gly Pro Glu Leu Leu Met Tyr Thr
385                 390                 395                 400

Tyr Ser Ser Gly Asn Lys Glu Asp Gly Arg Phe Thr Ala Gln Val Asp
                405                 410                 415

Lys Ser Ser Lys Tyr Ile Ser Leu Phe Ile Arg Asp Ser Gln Pro Ser
            420                 425                 430

Asp Ser Ala Thr Tyr Leu Cys Ala Phe Tyr Ala Gly Asn Asn Arg Lys
        435                 440                 445

Leu Ile Trp Gly Leu Gly Thr Ser Leu Ala Val Asn Pro Asn Ile Gln
    450                 455                 460

Asn Pro Glu Pro Ala Val Tyr Gln Leu Lys Asp Pro Arg Ser Gln Asp
465                 470                 475                 480

Ser Thr Leu Cys Leu Phe Thr Asp Phe Asp Ser Gln Ile Asn Val Pro
                485                 490                 495

Lys Thr Met Glu Ser Gly Thr Phe Ile Thr Asp Lys Thr Val Leu Asp
            500                 505                 510

Met Lys Ala Met Asp Ser Lys Ser Asn Gly Ala Ile Ala Trp Ser Asn
        515                 520                 525

Gln Thr Ser Phe Thr Cys Gln Asp Ile Phe Lys Glu Thr Asn Ala Thr
    530                 535                 540

Tyr Pro Ser Ser Asp Val Pro Cys Asp Ala Thr Leu Thr Glu Lys Ser
545                 550                 555                 560

Phe Glu Thr Asp Met Asn Leu Asn Phe Gln Asn Leu Leu Val Met Val
                565                 570                 575

Leu Arg Ile Leu Leu Leu Lys Val Ala Gly Phe Asn Leu Leu Met Thr
            580                 585                 590

Leu Arg Leu Trp Ser Ser
        595
```

<210> SEQ ID NO 182
<211> LENGTH: 1797
<212> TYPE: DNA
<213> ORGANISM: Artificial Sequence
<220> FEATURE:
<223> OTHER INFORMATION: Synthetic Construct

<400> SEQUENCE: 182

```
atgagcaacc aggtgctctg ctgtgtggtc ctttgtttcc tgggagcaaa caccgtggat      60

ggtggaatca ctcagtcccc aaagtacctg ttcagaaagg aaggacagaa tgtgaccctg     120

agttgtgaac agaatttgaa ccacgatgcc atgtactggt accgacagga cccagggcaa     180

gggctgagat tgatctacta ctcacagata gtaaatgact ttcagaaagg agatatagct     240
```

```
gaagggtaca gcgtctctcg ggagaagaag gaatcctttc ctctcactgt gacatcggcc    300

caaaagaacc cgacagcttt ctatctctgt gccagtagta tagatccggc gactagtcat    360

gagcagttct tcgggccagg gacacggctc accgtgctag aggatctgag aaatgtgact    420

ccacccaagg tctccttgtt tgagccatca aaagcagaga ttgcaaacaa acaaaaggct    480

accctcgtgt gcttggccag gggcttcttc cctgaccacg tggagctgag ctggtgggtg    540

aatggcaagg aggtccacag tggggtcagc acggaccctc aggcctacaa ggagagcaat    600

tatagctact gcctgagcag ccgcctgagg gtctctgcta ccttctggca caatcctcgc    660

aaccacttcc gctgccaagt gcagttccat gggctttcag aggaggacaa gtggccagag    720

ggctcaccca aacctgtcac acagaacatc agtgcagagg cctggggccg agcagactgt    780

gggattacct cagcatccta tcaacaaggg gtcttgtctg ccaccatcct ctatgagatc    840

ctgctaggga aagccaccct gtatgctgtg cttgtcagta cactggtggt gatggctatg    900

gtcaaaagaa aaaattcagg aagcggcgcc acgaacttct ctctgttaaa gcaagcagga    960

gacgtggaag aaaaccccgg tcccatgatg aaatccttga gagttttact ggtgatcctg   1020

tggcttcagt taagctgggt ttggagccaa cagaaggagg tggagcagga tcctggacca   1080

ctcagtgttc cagagggagc cattgtttct ctcaactgca cttacagcaa cagtgctttt   1140

caatacttca tgtggtacag acagtattcc agaaaaggcc ctgagttgct gatgtacaca   1200

tactccagtg gtaacaaaga agatggaagg tttacagcac aggtcgataa atccagcaag   1260

tatatctcct tgttcatcag agactcacag cccagtgatt cagccaccta cctctgtgca   1320

ttctatgctg gcaacaaccg taagctgatt tggggattgg gaacaagcct ggcagtaaat   1380

ccgaatatcc agaacccaga acctgctgtg taccagttaa aagatcctcg gtctcaggac   1440

agcaccctct gcctgttcac cgactttgac tcccaaatca atgtgccgaa aaccatggaa   1500

tctggaacgt tcatcactga caaaactgtg ctggacatga aagctatgga ttccaagagc   1560

aatggggcca ttgcctggag caaccagaca agcttcacct gccaagatat cttcaaagag   1620

accaacgcca cctaccccag ttcagacgtt ccctgtgatg ccacgttgac tgagaaaagc   1680

tttgaaacag atatgaacct aaactttcaa aacctgctgg ttatggttct ccgaatcctc   1740

ctgctgaaag tagccggatt taacctgctc atgacgctga ggctgtggtc cagttga      1797
```

<210> SEQ ID NO 183
<211> LENGTH: 606
<212> TYPE: PRT
<213> ORGANISM: Artificial Sequence
<220> FEATURE:
<223> OTHER INFORMATION: Synthetic Construct

<400> SEQUENCE: 183

```
Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
```

```
                85                  90                  95

Val Thr Ser Ala Gln Lys Asn Pro Thr Ala Phe Tyr Leu Cys Ala Ser
            100                 105                 110

Ser Met Asp Ala Ala Leu Gly Glu Lys Leu Phe Phe Gly Ser Gly Thr
        115                 120                 125

Gln Leu Ser Val Leu Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe Gly Ser Gly Ala Thr Asn Phe Ser Leu Leu
305                 310                 315                 320

Lys Gln Ala Gly Asp Val Glu Glu Asn Pro Gly Pro Met Met Lys Ser
                325                 330                 335

Leu Arg Val Leu Leu Val Ile Leu Trp Leu Gln Leu Ser Trp Val Trp
            340                 345                 350

Ser Gln Gln Lys Glu Val Glu Gln Asp Pro Gly Pro Leu Ser Val Pro
        355                 360                 365

Glu Gly Ala Ile Val Ser Leu Asn Cys Thr Tyr Ser Asn Ser Ala Phe
    370                 375                 380

Gln Tyr Phe Met Trp Tyr Arg Gln Tyr Ser Arg Lys Gly Pro Glu Leu
385                 390                 395                 400

Leu Met Tyr Thr Tyr Ser Ser Gly Asn Lys Glu Asp Gly Arg Phe Thr
                405                 410                 415

Ala Gln Val Asp Lys Ser Ser Lys Tyr Ile Ser Leu Phe Ile Arg Asp
            420                 425                 430

Ser Gln Pro Ser Asp Ser Ala Thr Tyr Leu Cys Ala Met Ser Pro Arg
        435                 440                 445

Ser Gly Tyr Ala Leu Asn Phe Gly Lys Gly Thr Ser Leu Leu Val Thr
    450                 455                 460

Pro His Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510
```

```
Thr Val Leu Asp Met Arg Ser Met Asp Phe Lys Ser Asn Ser Ala Val
        515                 520                 525

Ala Trp Ser Asn Lys Ser Asp Phe Ala Cys Ala Asn Ala Phe Asn Asn
    530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser
        595                 600                 605


<210> SEQ ID NO 184
<211> LENGTH: 1821
<212> TYPE: DNA
<213> ORGANISM: Artificial Sequence
<220> FEATURE:
<223> OTHER INFORMATION: Synthetic Construct

<400> SEQUENCE: 184

atgagcaacc aggtgctctg ctgtgtggtc ctttgtttcc tgggagcaaa caccgtggat      60

ggtggaatca ctcagtcccc aaagtacctg ttcagaaagg aaggacagaa tgtgaccctg     120

agttgtgaac agaatttgaa ccacgatgcc atgtactggt accgacagga cccagggcaa     180

gggctgagat tgatctacta ctcacagata gtaaatgact ttcagaaagg agatatagct     240

gaagggtaca gcgtctctcg ggagaagaag gaatcctttc ctctcactgt gacatcggcc     300

caaaagaacc cgacagcttt ctatctctgt gccagtagta tggacgccgc cttgggtgaa     360

aaactgtttt ttggcagtgg aacccagctc tctgtcttgg aggacctgaa caaggtgttc     420

ccacccgagg tcgctgtgtt tgagccatca gaagcagaga tctcccacac ccaaaaggcc     480

acactggtgt gcctggccac aggcttcttc cccgaccacg tggagctgag ctggtgggtg     540

aatgggaagg aggtgcacag tggggtcagc acggacccgc agcccctcaa ggagcagccc     600

gccctcaatg actccagata ctgcctgagc agccgcctga gggtctcggc caccttctgg     660

cagaaccccc gcaaccactt ccgctgtcaa gtccagttct acgggctctc ggagaatgac     720

gagtggaccc aggatagggc caaacccgtc acccagatcg tcagcgccga ggcctggggt     780

agagcagact gtggctttac ctcggtgtcc taccagcaag ggtcctgtc tgccaccatc     840

ctctatgaga tcctgctagg gaaggccacc ctgtatgctg tgctggtcag cgcccttgtg     900

ttgatggcca tggtcaagag aaaggatttc ggaagcggcg ccacgaactt ctctctgtta     960

aagcaagcag gagacgtgga agaaaacccc ggtcccatga tgaaatcctt gagagtttta    1020

ctggtgatcc tgtggcttca gttaagctgg gtttggagcc aacagaagga ggtggagcag    1080

gatcctggac cactcagtgt tccagaggga gccattgttt ctctcaactg cacttacagc    1140

aacagtgctt ttcaatactt catgtggtac agacagtatt ccagaaaagg ccctgagttg    1200

ctgatgtaca catactccag tggtaacaaa gaagatggaa ggtttacagc acaggtcgat    1260

aaatccagca agtatatctc cttgttcatc agagactcac agcccagtga ttcagccacc    1320

tacctctgtg caatgagccc tcggagcggg tatgcactca acttcggcaa aggcacctcg    1380

ctgttggtca caccccatat ccagaaccct gaccctgccg tgtaccagct gagagactct    1440

aaatccagtg acaagtctgt ctgcctattc accgattttg attctcaaac aaatgtgtca    1500
```

caaagtaagg attctgatgt gtatatcaca gacaaaactg tgctagacat gaggtctatg 1560
gacttcaaga gcaacagtgc tgtggcctgg agcaacaaat ctgactttgc atgtgcaaac 1620
gccttcaaca acagcattat tccagaagac accttcttcc ccagcccaga aagttcctgt 1680
gatgtcaagc tggtcgagaa aagctttgaa acagatacga acctaaactt tcaaaacctg 1740
tcagtgattg ggttccgaat cctcctcctg aaagtggccg ggtttaatct gctcatgacg 1800
ctgcggctgt ggtccagctg a 1821

<210> SEQ ID NO 185
<211> LENGTH: 598
<212> TYPE: PRT
<213> ORGANISM: Artificial Sequence
<220> FEATURE:
<223> OTHER INFORMATION: Synthetic Construct

<400> SEQUENCE: 185

Met Ser Asn Gln Val Leu Cys Cys Val Val Leu Cys Phe Leu Gly Ala
1 5 10 15

Asn Thr Val Asp Gly Gly Ile Thr Gln Ser Pro Lys Tyr Leu Phe Arg
20 25 30

Lys Glu Gly Gln Asn Val Thr Leu Ser Cys Glu Gln Asn Leu Asn His
35 40 45

Asp Ala Met Tyr Trp Tyr Arg Gln Asp Pro Gly Gln Gly Leu Arg Leu
50 55 60

Ile Tyr Tyr Ser Gln Ile Val Asn Asp Phe Gln Lys Gly Asp Ile Ala
65 70 75 80

Glu Gly Tyr Ser Val Ser Arg Glu Lys Lys Glu Ser Phe Pro Leu Thr
85 90 95

Val Thr Ser Ala Gln Lys Asn Pro Thr Ala Phe Tyr Leu Cys Ala Ser
100 105 110

Ser Met Asp Ala Ala Leu Gly Glu Lys Leu Phe Phe Gly Ser Gly Thr
115 120 125

Gln Leu Ser Val Leu Glu Asp Leu Arg Asn Val Thr Pro Pro Lys Val
130 135 140

Ser Leu Phe Glu Pro Ser Lys Ala Glu Ile Ala Asn Lys Gln Lys Ala
145 150 155 160

Thr Leu Val Cys Leu Ala Arg Gly Phe Phe Pro Asp His Val Glu Leu
165 170 175

Ser Trp Trp Val Asn Gly Lys Glu Val His Ser Gly Val Ser Thr Asp
180 185 190

Pro Gln Ala Tyr Lys Glu Ser Asn Tyr Ser Tyr Cys Leu Ser Ser Arg
195 200 205

Leu Arg Val Ser Ala Thr Phe Trp His Asn Pro Arg Asn His Phe Arg
210 215 220

Cys Gln Val Gln Phe His Gly Leu Ser Glu Glu Asp Lys Trp Pro Glu
225 230 235 240

Gly Ser Pro Lys Pro Val Thr Gln Asn Ile Ser Ala Glu Ala Trp Gly
245 250 255

Arg Ala Asp Cys Gly Ile Thr Ser Ala Ser Tyr Gln Gln Gly Val Leu
260 265 270

Ser Ala Thr Ile Leu Tyr Glu Ile Leu Leu Gly Lys Ala Thr Leu Tyr
275 280 285

Ala Val Leu Val Ser Thr Leu Val Val Met Ala Met Val Lys Arg Lys
290 295 300

```
Asn Ser Gly Ser Gly Ala Thr Asn Phe Ser Leu Leu Lys Gln Ala Gly
305                 310                 315                 320

Asp Val Glu Glu Asn Pro Gly Pro Met Met Lys Ser Leu Arg Val Leu
                325                 330                 335

Leu Val Ile Leu Trp Leu Gln Leu Ser Trp Val Trp Ser Gln Gln Lys
            340                 345                 350

Glu Val Glu Gln Asp Pro Gly Pro Leu Ser Val Pro Glu Gly Ala Ile
        355                 360                 365

Val Ser Leu Asn Cys Thr Tyr Ser Asn Ser Ala Phe Gln Tyr Phe Met
    370                 375                 380

Trp Tyr Arg Gln Tyr Ser Arg Lys Gly Pro Glu Leu Leu Met Tyr Thr
385                 390                 395                 400

Tyr Ser Ser Gly Asn Lys Glu Asp Gly Arg Phe Thr Ala Gln Val Asp
                405                 410                 415

Lys Ser Ser Lys Tyr Ile Ser Leu Phe Ile Arg Asp Ser Gln Pro Ser
            420                 425                 430

Asp Ser Ala Thr Tyr Leu Cys Ala Met Ser Pro Arg Ser Gly Tyr Ala
        435                 440                 445

Leu Asn Phe Gly Lys Gly Thr Ser Leu Leu Val Thr Pro His Ile Gln
    450                 455                 460

Asn Pro Glu Pro Ala Val Tyr Gln Leu Lys Asp Pro Arg Ser Gln Asp
465                 470                 475                 480

Ser Thr Leu Cys Leu Phe Thr Asp Phe Asp Ser Gln Ile Asn Val Pro
                485                 490                 495

Lys Thr Met Glu Ser Gly Thr Phe Ile Thr Asp Lys Thr Val Leu Asp
            500                 505                 510

Met Lys Ala Met Asp Ser Lys Ser Asn Gly Ala Ile Ala Trp Ser Asn
        515                 520                 525

Gln Thr Ser Phe Thr Cys Gln Asp Ile Phe Lys Glu Thr Asn Ala Thr
    530                 535                 540

Tyr Pro Ser Ser Asp Val Pro Cys Asp Ala Thr Leu Thr Glu Lys Ser
545                 550                 555                 560

Phe Glu Thr Asp Met Asn Leu Asn Phe Gln Asn Leu Leu Val Met Val
                565                 570                 575

Leu Arg Ile Leu Leu Leu Lys Val Ala Gly Phe Asn Leu Leu Met Thr
            580                 585                 590

Leu Arg Leu Trp Ser Ser
        595


<210> SEQ ID NO 186
<211> LENGTH: 1797
<212> TYPE: DNA
<213> ORGANISM: Artificial Sequence
<220> FEATURE:
<223> OTHER INFORMATION: Synthetic Construct

<400> SEQUENCE: 186

atgagcaacc aggtgctctg ctgtgtggtc ctttgtttcc tgggagcaaa caccgtggat      60

ggtggaatca ctcagtcccc aaagtacctg ttcagaaagg aaggacagaa tgtgaccctg     120

agttgtgaac agaatttgaa ccacgatgcc atgtactggt accgacagga cccagggcaa     180

gggctgagat tgatctacta ctcacagata gtaaatgact ttcagaaagg agatatagct     240

gaagggtaca gcgtctctcg ggagaagaag gaatcctttc ctctcactgt gacatcggcc     300

caaaagaacc cgacagcttt ctatctctgt gccagtagta tggacgccgc cttgggtgaa     360
```

-continued

```
aaactgtttt ttggcagtgg aacccagctc tctgtcttgg aggatctgag aaatgtgact    420

ccacccaagg tctccttgtt tgagccatca aaagcagaga ttgcaaacaa acaaaaggct    480

accctcgtgt gcttggccag gggcttcttc cctgaccacg tggagctgag ctggtgggtg    540

aatggcaagg aggtccacag tggggtcagc acggaccctc aggcctacaa ggagagcaat    600

tatagctact gcctgagcag ccgcctgagg gtctctgcta ccttctggca caatcctcgc    660

aaccacttcc gctgccaagt gcagttccat gggctttcag aggaggacaa gtggccagag    720

ggctcaccca aacctgtcac acagaacatc agtgcagagg cctggggccg agcagactgt    780

gggattacct cagcatccta tcaacaaggg gtcttgtctg ccaccatcct ctatgagatc    840

ctgctaggga aagccaccct gtatgctgtg cttgtcagta cactggtggt gatggctatg    900

gtcaaaagaa aaaattcagg aagcggcgcc acgaacttct ctctgttaaa gcaagcagga    960

gacgtggaag aaaaccccgg tcccatgatg aaatccttga gagttttact ggtgatcctg   1020

tggcttcagt taagctgggt ttggagccaa cagaaggagg tggagcagga tcctggacca   1080

ctcagtgttc cagagggagc cattgtttct ctcaactgca cttacagcaa cagtgctttt   1140

caatacttca tgtggtacag acagtattcc agaaaaggcc ctgagttgct gatgtacaca   1200

tactccagtg gtaacaaaga agatggaagg tttacagcac aggtcgataa atccagcaag   1260

tatatctcct tgttcatcag agactcacag cccagtgatt cagccaccta cctctgtgca   1320

atgagccctc ggagcgggta tgcactcaac ttcggcaaag gcacctcgct gttggtcaca   1380

ccccatatcc agaacccaga acctgctgtg taccagttaa aagatcctcg gtctcaggac   1440

agcaccctct gcctgttcac cgactttgac tcccaaatca atgtgccgaa aaccatggaa   1500

tctggaacgt tcatcactga caaaactgtg ctggacatga aagctatgga ttccaagagc   1560

aatggggcca ttgcctggag caaccagaca agcttcacct gccaagatat cttcaaagag   1620

accaacgcca cctaccccag ttcagacgtt ccctgtgatg ccacgttgac tgagaaaagc   1680

tttgaaacag atatgaacct aaactttcaa aacctgctgg ttatggttct ccgaatcctc   1740

ctgctgaaag tagccggatt taacctgctc atgacgctga ggctgtggtc cagttga      1797


<210> SEQ ID NO 187
<211> LENGTH: 606
<212> TYPE: PRT
<213> ORGANISM: Artificial Sequence
<220> FEATURE:
<223> OTHER INFORMATION: Synthetic Construct

<400> SEQUENCE: 187

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110
```

```
Ser Val Glu Trp Gly Thr Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Asn Tyr
                325                 330                 335

Ser Pro Gly Leu Val Ser Leu Ile Leu Leu Leu Leu Gly Arg Thr Arg
            340                 345                 350

Gly Asn Ser Val Thr Gln Met Glu Gly Pro Val Thr Leu Ser Glu Glu
        355                 360                 365

Ala Phe Leu Thr Ile Asn Cys Thr Tyr Thr Ala Thr Gly Tyr Pro Ser
    370                 375                 380

Leu Phe Trp Tyr Val Gln Tyr Pro Gly Glu Gly Leu Gln Leu Leu Leu
385                 390                 395                 400

Lys Ala Thr Lys Ala Asp Asp Lys Gly Ser Asn Lys Gly Phe Glu Ala
                405                 410                 415

Thr Tyr Arg Lys Glu Thr Thr Ser Phe His Leu Glu Lys Gly Ser Val
            420                 425                 430

Gln Val Ser Asp Ser Ala Val Tyr Phe Cys Ala Leu Arg Ser Gly Gly
        435                 440                 445

Ser Asn Tyr Lys Leu Thr Phe Gly Lys Gly Thr Leu Leu Thr Val Asn
    450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
        515                 520                 525

Ala Trp Ser Asn Lys Ser Asp Phe Ala Cys Ala Asn Ala Phe Asn Asn
```

```
    530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser
        595                 600                 605


<210> SEQ ID NO 188
<211> LENGTH: 1821
<212> TYPE: DNA
<213> ORGANISM: Artificial Sequence
<220> FEATURE:
<223> OTHER INFORMATION: Synthetic Construct

<400> SEQUENCE: 188

atgggcttca ggctcctctg ctgtgtggcc ttttgtctcc tgggagcagg cccagtggat     60

tctggagtca cacaaacccc aaagcacctg atcacagcaa ctggacagcg agtgacgctg    120

agatgctccc ctaggtctgg agacctctct gtgtactggt accaacagag cctggaccag    180

ggcctccagt tcctcattca gtattataat ggagaagaga gagcaaaagg aaacattctt    240

gaacgattct ccgcacaaca gttccctgac ttgcactctg aactaaacct gagctctctg    300

gagctggggg actcagcttt gtatttctgt gccagcagcg tagaatgggg tacctacgag    360

cagtacttcg ggccgggcac caggctcacg gtcacagagg acctgaaaaa cgtgttccca    420

cccgaggtcg ctgtgtttga gccatcagaa gcagagatct cccacaccca aaaggccaca    480

ctggtgtgcc tggccacagg cttctacccc gaccacgtgg agctgagctg gtgggtgaat    540

gggaaggagg tgcacagtgg ggtcagcaca gacccgcagc ccctcaagga gcagcccgcc    600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acctgtcacc cagatcgtca gcgccgaggc ctggggtaga    780

gcagactgtg gcttcacctc cgagtcttac cagcaagggg tcctgtctgc caccatcctc    840

tatgagatct tgctagggaa ggccaccttg tatgccgtgc tggtcagtgc cctcgtgctg    900

atggccatgg tcaagagaaa ggattccaga ggcggaagcg gcgccacgaa cttctctctg    960

ttaaagcaag caggagacgt ggaagaaaac cccggtccca tgaactattc tccaggctta   1020

gtatctctga tactcttact gcttggaaga acccgtggaa attcagtgac ccagatggaa   1080

gggccagtga ctctctcaga agaggccttc ctgactataa actgcacgta cacagccaca   1140

ggataccctt cccttttctg gtatgtccaa tatcctggag aaggtctaca gctcctcctg   1200

aaagccacga aggctgatga caagggaagc aacaaaggtt ttgaagccac ataccgtaaa   1260

gaaaccactt ctttccactt ggagaaaggc tcagttcaag tgtcagactc agcggtgtac   1320

ttctgtgctc tgaggagtgg aggtagcaac tataaactga catttggaaa aggaactctc   1380

ttaaccgtga atccaaatat ccagaaccct gaccctgccg tgtaccagct gagagactct   1440

aaatccagtg acaagtctgt ctgcctattc accgattttg attctcaaac aaatgtgtca   1500

caaagtaagg attctgatgt gtatatcaca gacaaaactg tgctagacat gaggtctatg   1560

gacttcaaga gcaacagtgc tgtggcctgg agcaacaaat ctgactttgc atgtgcaaac   1620

gccttcaaca acagcattat tccagaagac accttcttcc ccagcccaga aagttcctgt   1680
```

gatgtcaagc tggtcgagaa aagctttgaa acagatacga acctaaactt tcaaaacctg 1740
tcagtgattg ggttccgaat cctcctcctg aaagtggccg ggtttaatct gctcatgacg 1800
ctgcggctgt ggtccagctg a 1821

<210> SEQ ID NO 189
<211> LENGTH: 596
<212> TYPE: PRT
<213> ORGANISM: Artificial Sequence
<220> FEATURE:
<223> OTHER INFORMATION: Synthetic Construct

<400> SEQUENCE: 189

Met Gly Phe Arg Leu Leu Cys Cys Val Ala Phe Cys Leu Leu Gly Ala
1 5 10 15

Gly Pro Val Asp Ser Gly Val Thr Gln Thr Pro Lys His Leu Ile Thr
20 25 30

Ala Thr Gly Gln Arg Val Thr Leu Arg Cys Ser Pro Arg Ser Gly Asp
35 40 45

Leu Ser Val Tyr Trp Tyr Gln Gln Ser Leu Asp Gln Gly Leu Gln Phe
50 55 60

Leu Ile Gln Tyr Tyr Asn Gly Glu Glu Arg Ala Lys Gly Asn Ile Leu
65 70 75 80

Glu Arg Phe Ser Ala Gln Gln Phe Pro Asp Leu His Ser Glu Leu Asn
85 90 95

Leu Ser Ser Leu Glu Leu Gly Asp Ser Ala Leu Tyr Phe Cys Ala Ser
100 105 110

Ser Val Glu Trp Gly Thr Tyr Glu Gln Tyr Phe Gly Pro Gly Thr Arg
115 120 125

Leu Thr Val Thr Glu Asp Leu Arg Asn Val Thr Pro Pro Lys Val Ser
130 135 140

Leu Phe Glu Pro Ser Lys Ala Glu Ile Ala Asn Lys Gln Lys Ala Thr
145 150 155 160

Leu Val Cys Leu Ala Arg Gly Phe Phe Pro Asp His Val Glu Leu Ser
165 170 175

Trp Trp Val Asn Gly Lys Glu Val His Ser Gly Val Ser Thr Asp Pro
180 185 190

Gln Ala Tyr Lys Glu Ser Asn Tyr Ser Tyr Cys Leu Ser Ser Arg Leu
195 200 205

Arg Val Ser Ala Thr Phe Trp His Asn Pro Arg Asn His Phe Arg Cys
210 215 220

Gln Val Gln Phe His Gly Leu Ser Glu Glu Asp Lys Trp Pro Glu Gly
225 230 235 240

Ser Pro Lys Pro Val Thr Gln Asn Ile Ser Ala Glu Ala Trp Gly Arg
245 250 255

Ala Asp Cys Gly Ile Thr Ser Ala Ser Tyr Gln Gln Gly Val Leu Ser
260 265 270

Ala Thr Ile Leu Tyr Glu Ile Leu Leu Gly Lys Ala Thr Leu Tyr Ala
275 280 285

Val Leu Val Ser Thr Leu Val Val Met Ala Met Val Lys Arg Lys Asn
290 295 300

Ser Gly Ser Gly Ala Thr Asn Phe Ser Leu Leu Lys Gln Ala Gly Asp
305 310 315 320

Val Glu Glu Asn Pro Gly Pro Met Asn Tyr Ser Pro Gly Leu Val Ser
325 330 335

```
Leu Ile Leu Leu Leu Leu Gly Arg Thr Arg Gly Asn Ser Val Thr Gln
            340                 345                 350

Met Glu Gly Pro Val Thr Leu Ser Glu Glu Ala Phe Leu Thr Ile Asn
        355                 360                 365

Cys Thr Tyr Thr Ala Thr Gly Tyr Pro Ser Leu Phe Trp Tyr Val Gln
    370                 375                 380

Tyr Pro Gly Glu Gly Leu Gln Leu Leu Leu Lys Ala Thr Lys Ala Asp
385                 390                 395                 400

Asp Lys Gly Ser Asn Lys Gly Phe Glu Ala Thr Tyr Arg Lys Glu Thr
                405                 410                 415

Thr Ser Phe His Leu Glu Lys Gly Ser Val Gln Val Ser Asp Ser Ala
            420                 425                 430

Val Tyr Phe Cys Ala Leu Arg Ser Gly Gly Ser Asn Tyr Lys Leu Thr
        435                 440                 445

Phe Gly Lys Gly Thr Leu Leu Thr Val Asn Pro Asn Ile Gln Asn Pro
    450                 455                 460

Glu Pro Ala Val Tyr Gln Leu Lys Asp Pro Arg Ser Gln Asp Ser Thr
465                 470                 475                 480

Leu Cys Leu Phe Thr Asp Phe Asp Ser Gln Ile Asn Val Pro Lys Thr
                485                 490                 495

Met Glu Ser Gly Thr Phe Ile Thr Asp Lys Thr Val Leu Asp Met Lys
            500                 505                 510

Ala Met Asp Ser Lys Ser Asn Gly Ala Ile Ala Trp Ser Asn Gln Thr
        515                 520                 525

Ser Phe Thr Cys Gln Asp Ile Phe Lys Glu Thr Asn Ala Thr Tyr Pro
    530                 535                 540

Ser Ser Asp Val Pro Cys Asp Ala Thr Leu Thr Glu Lys Ser Phe Glu
545                 550                 555                 560

Thr Asp Met Asn Leu Asn Phe Gln Asn Leu Leu Val Met Val Leu Arg
                565                 570                 575

Ile Leu Leu Leu Lys Val Ala Gly Phe Asn Leu Leu Met Thr Leu Arg
            580                 585                 590

Leu Trp Ser Ser
        595


<210> SEQ ID NO 190
<211> LENGTH: 1791
<212> TYPE: DNA
<213> ORGANISM: Artificial Sequence
<220> FEATURE:
<223> OTHER INFORMATION: Synthetic Construct

<400> SEQUENCE: 190

atgggcttca ggctcctctg ctgtgtggcc ttttgtctcc tgggagcagg cccagtggat      60

tctggagtca cacaaacccc aaagcacctg atcacagcaa ctggacagcg agtgacgctg     120

agatgctccc ctaggtctgg agacctctct gtgtactggt accaacagag cctggaccag     180

ggcctccagt tcctcattca gtattataat ggagaagaga gagcaaaagg aaacattctt     240

gaacgattct ccgcacaaca gttccctgac ttgcactctg aactaaacct gagctctctg     300

gagctggggg actcagcttt gtatttctgt gccagcagcg tagaatgggg tacctacgag     360

cagtacttcg ggccgggcac caggctcacg gtcacagagg atctgagaaa tgtgactcca     420

cccaaggtct ccttgtttga gccatcaaaa gcagagattg caaacaaaca aaaggctacc     480

ctcgtgtgct tggccagggg cttcttccct gaccacgtgg agctgagctg gtgggtgaat     540
```

```
ggcaaggagg tccacagtgg ggtcagcacg gaccctcagg cctacaagga gagcaattat    600

agctactgcc tgagcagccg cctgagggtc tctgctacct tctggcacaa tcctcgcaac    660

cacttccgct gccaagtgca gttccatggg ctttcagagg aggacaagtg gccagagggc    720

tcacccaaac ctgtcacaca gaacatcagt gcagaggcct ggggccgagc agactgtggg    780

attacctcag catcctatca acaaggggtc ttgtctgcca ccatcctcta tgagatcctg    840

ctagggaaag ccaccctgta tgctgtgctt gtcagtacac tggtggtgat ggctatggtc    900

aaaagaaaaa attcaggaag cggcgccacg aacttctctc tgttaaagca agcaggagac    960

gtggaagaaa accccggtcc catgaactat tctccaggct tagtatctct gatactctta   1020

ctgcttggaa gaacccgtgg aaattcagtg acccagatgg aagggccagt gactctctca   1080

gaagaggcct tcctgactat aaactgcacg tacacagcca caggataccc ttcccttttc   1140

tggtatgtcc aatatcctgg agaaggtcta cagctcctcc tgaaagccac gaaggctgat   1200

gacaagggaa gcaacaaagg ttttgaagcc acataccgta aagaaaccac ttctttccac   1260

ttggagaaag gctcagttca agtgtcagac tcagcggtgt acttctgtgc tctgaggagt   1320

ggaggtagca actataaact gacatttgga aaaggaactc tcttaaccgt gaatccaaat   1380

atccagaacc cagaacctgc tgtgtaccag ttaaaagatc ctcggtctca ggacagcacc   1440

ctctgcctgt tcaccgactt tgactcccaa atcaatgtgc cgaaaaccat ggaatctgga   1500

acgttcatca ctgacaaaac tgtgctggac atgaaagcta tggattccaa gagcaatggg   1560

gccattgcct ggagcaacca gacaagcttc acctgccaag atatcttcaa agagaccaac   1620

gccacctacc ccagttcaga cgttccctgt gatgccacgt tgactgagaa aagctttgaa   1680

acagatatga acctaaactt tcaaaacctg ctggttatgg ttctccgaat cctcctgctg   1740

aaagtagccg gatttaacct gctcatgacg ctgaggctgt ggtccagttg a            1791
```

<210> SEQ ID NO 191
<211> LENGTH: 612
<212> TYPE: PRT
<213> ORGANISM: Artificial Sequence
<220> FEATURE:
<223> OTHER INFORMATION: Synthetic Construct

<400> SEQUENCE: 191

```
Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Ala Gly Gly Pro Ala Glu Thr Gln Tyr Phe Gly Pro
        115                 120                 125

Gly Thr Arg Leu Leu Val Leu Glu Asp Leu Lys Asn Val Phe Pro Pro
    130                 135                 140
```

-continued

```
Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Leu Leu Leu Leu Val Pro Val Leu Glu Val Ile Phe Thr Leu Gly
            340                 345                 350

Gly Thr Arg Ala Gln Ser Val Thr Gln Leu Asp Ser His Val Ser Val
        355                 360                 365

Ser Glu Gly Thr Pro Val Leu Leu Arg Cys Asn Tyr Ser Ser Ser Tyr
    370                 375                 380

Ser Pro Ser Leu Phe Trp Tyr Val Gln His Pro Asn Lys Gly Leu Gln
385                 390                 395                 400

Leu Leu Leu Lys Tyr Thr Ser Ala Ala Thr Leu Val Lys Gly Ile Asn
                405                 410                 415

Gly Phe Glu Ala Glu Phe Lys Lys Ser Glu Thr Ser Phe His Leu Thr
            420                 425                 430

Lys Pro Ser Ala His Met Ser Asp Ala Ala Glu Tyr Phe Cys Val Val
        435                 440                 445

Ser Ala Ile Gly Tyr Ser Ser Ala Ser Lys Ile Ile Phe Gly Ser Gly
    450                 455                 460

Thr Arg Leu Ser Ile Arg Pro Asn Ile Gln Asn Pro Asp Pro Ala Val
465                 470                 475                 480

Tyr Gln Leu Arg Asp Ser Lys Ser Ser Asp Lys Ser Val Cys Leu Phe
                485                 490                 495

Thr Asp Phe Asp Ser Gln Thr Asn Val Ser Gln Ser Lys Asp Ser Asp
            500                 505                 510

Val Tyr Ile Thr Asp Lys Thr Val Leu Asp Met Arg Ser Met Asp Phe
        515                 520                 525

Lys Ser Asn Ser Ala Val Ala Trp Ser Asn Lys Ser Asp Phe Ala Cys
    530                 535                 540

Ala Asn Ala Phe Asn Asn Ser Ile Ile Pro Glu Asp Thr Phe Phe Pro
545                 550                 555                 560
```

-continued

```
Ser Pro Glu Ser Ser Cys Asp Val Lys Leu Val Glu Lys Ser Phe Glu
                565                 570                 575

Thr Asp Thr Asn Leu Asn Phe Gln Asn Leu Ser Val Ile Gly Phe Arg
            580                 585                 590

Ile Leu Leu Leu Lys Val Ala Gly Phe Asn Leu Leu Met Thr Leu Arg
        595                 600                 605

Leu Trp Ser Ser
    610


<210> SEQ ID NO 192
<211> LENGTH: 1839
<212> TYPE: DNA
<213> ORGANISM: Artificial Sequence
<220> FEATURE:
<223> OTHER INFORMATION: Synthetic Construct

<400> SEQUENCE: 192

atgggcacca gcctcctctg ctggatggcc ctgtgtctcc tgggggcaga tcacgcagat      60

actggagtct cccagaaccc cagacacaag atcacaaaga ggggacagaa tgtaactttc     120

aggtgtgatc caatttctga acacaaccgc ctttattggt accgacagac cctggggcag     180

ggcccagagt ttctgactta cttccagaat gaagctcaac tagaaaaatc aaggctgctc     240

agtgatcggt tctctgcaga gaggcctaag ggatctttct ccaccttgga gatccagcgc     300

acagagcagg gggactcggc catgtatctc tgtgccagca gcttagttgc gggagggccc     360

gcagagaccc agtacttcgg gccaggcacg cggctcctgg tgctcgagga cctgaaaaac     420

gtgttcccac ccgaggtcgc tgtgtttgag ccatcagaag cagagatctc ccacacccaa     480

aaggccacac tggtgtgcct ggccacaggc ttctaccccg accacgtgga gctgagctgg     540

tgggtgaatg ggaaggaggt gcacagtggg gtcagcacag acccgcagcc cctcaaggag     600

cagcccgccc tcaatgactc cagatactgc ctgagcagcc gcctgagggt ctcggccacc     660

ttctggcaga acccccgcaa ccacttccgc tgtcaagtcc agttctacgg gctctcggag     720

aatgacgagt ggacccagga tagggccaaa cctgtcaccc agatcgtcag cgccgaggcc     780

tggggtagag cagactgtgg cttcacctcc gagtcttacc agcaaggggt cctgtctgcc     840

accatcctct atgagatctt gctagggaag gccaccttgt atgccgtgct ggtcagtgcc     900

ctcgtgctga tggccatggt caagagaaag gattccagag gcggaagcgg cgccacgaac     960

ttctctctgt taaagcaagc aggagacgtg gaagaaaacc ccggtcccat gctcctgctg    1020

ctcgtcccag tgctcgaggt gatttttact ctgggaggaa ccagagccca gtcggtgacc    1080

cagcttgaca gccacgtctc tgtctctgaa ggaaccccgg tgctgctgag gtgcaactac    1140

tcatcttctt attcaccatc tctcttctgg tatgtgcaac accccaacaa aggactccag    1200

cttctcctga agtacacatc agcggccacc ctggttaaag gcatcaacgg ttttgaggct    1260

gaatttaaga agagtgaaac ctccttccac ctgacgaaac cctcagccca tatgagcgac    1320

gcggctgagt acttctgtgt tgtgagtgcc attgggtaca gcagtgcttc caagataatc    1380

tttggatcag ggaccagact cagcatccgg ccaaatatcc agaaccctga ccctgccgtg    1440

taccagctga gagactctaa atccagtgac aagtctgtct gcctattcac cgattttgat    1500

tctcaaacaa atgtgtcaca aagtaaggat tctgatgtgt atatcacaga caaaactgtg    1560

ctagacatga ggtctatgga cttcaagagc aacagtgctg tggcctggag caacaaatct    1620

gactttgcat gtgcaaacgc cttcaacaac agcattattc cagaagacac cttcttcccc    1680

agcccagaaa gttcctgtga tgtcaagctg gtcgagaaaa gctttgaaac agatacgaac    1740
```

ctaaactttc aaaacctgtc agtgattggg ttccgaatcc tcctcctgaa agtggccggg 1800
tttaatctgc tcatgacgct gcggctgtgg tccagctga 1839

<210> SEQ ID NO 193
<211> LENGTH: 602
<212> TYPE: PRT
<213> ORGANISM: Artificial Sequence
<220> FEATURE:
<223> OTHER INFORMATION: Synthetic Construct

<400> SEQUENCE: 193

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Ala Gly Gly Pro Ala Glu Thr Gln Tyr Phe Gly Pro
        115                 120                 125

Gly Thr Arg Leu Leu Val Leu Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
    290                 295                 300

Arg Lys Asn Ser Gly Ser Gly Ala Thr Asn Phe Ser Leu Leu Lys Gln
305                 310                 315                 320

Ala Gly Asp Val Glu Glu Asn Pro Gly Pro Met Leu Leu Leu Leu Val
                325                 330                 335

Pro Val Leu Glu Val Ile Phe Thr Leu Gly Gly Thr Arg Ala Gln Ser

```
            340                 345                 350

Val Thr Gln Leu Asp Ser His Val Ser Val Ser Glu Gly Thr Pro Val
        355                 360                 365

Leu Leu Arg Cys Asn Tyr Ser Ser Ser Tyr Ser Pro Ser Leu Phe Trp
    370                 375                 380

Tyr Val Gln His Pro Asn Lys Gly Leu Gln Leu Leu Leu Lys Tyr Thr
385                 390                 395                 400

Ser Ala Ala Thr Leu Val Lys Gly Ile Asn Gly Phe Glu Ala Glu Phe
                405                 410                 415

Lys Lys Ser Glu Thr Ser Phe His Leu Thr Lys Pro Ser Ala His Met
            420                 425                 430

Ser Asp Ala Ala Glu Tyr Phe Cys Val Val Ser Ala Ile Gly Tyr Ser
        435                 440                 445

Ser Ala Ser Lys Ile Ile Phe Gly Ser Gly Thr Arg Leu Ser Ile Arg
    450                 455                 460

Pro Asn Ile Gln Asn Pro Glu Pro Ala Val Tyr Gln Leu Lys Asp Pro
465                 470                 475                 480

Arg Ser Gln Asp Ser Thr Leu Cys Leu Phe Thr Asp Phe Asp Ser Gln
                485                 490                 495

Ile Asn Val Pro Lys Thr Met Glu Ser Gly Thr Phe Ile Thr Asp Lys
            500                 505                 510

Thr Val Leu Asp Met Lys Ala Met Asp Ser Lys Ser Asn Gly Ala Ile
        515                 520                 525

Ala Trp Ser Asn Gln Thr Ser Phe Thr Cys Gln Asp Ile Phe Lys Glu
    530                 535                 540

Thr Asn Ala Thr Tyr Pro Ser Ser Asp Val Pro Cys Asp Ala Thr Leu
545                 550                 555                 560

Thr Glu Lys Ser Phe Glu Thr Asp Met Asn Leu Asn Phe Gln Asn Leu
                565                 570                 575

Leu Val Met Val Leu Arg Ile Leu Leu Leu Lys Val Ala Gly Phe Asn
            580                 585                 590

Leu Leu Met Thr Leu Arg Leu Trp Ser Ser
        595                 600
```

<210> SEQ ID NO 194
<211> LENGTH: 1809
<212> TYPE: DNA
<213> ORGANISM: Artificial Sequence
<220> FEATURE:
<223> OTHER INFORMATION: Synthetic Construct

<400> SEQUENCE: 194

```
atgggcacca gcctcctctg ctggatggcc ctgtgtctcc tgggggcaga tcacgcagat      60

actggagtct cccagaaccc cagacacaag atcacaaaga ggggacagaa tgtaactttc     120

aggtgtgatc caatttctga acacaaccgc ctttattggt accgacagac cctggggcag     180

ggcccagagt ttctgactta cttccagaat gaagctcaac tagaaaaatc aaggctgctc     240

agtgatcggt tctctgcaga gaggcctaag ggatctttct ccaccttgga gatccagcgc     300

acagagcagg gggactcggc catgtatctc tgtgccagca gcttagttgc gggagggccc     360

gcagagaccc agtacttcgg gccaggcacg cggctcctgg tgctcgagga tctgagaaat     420

gtgactccac ccaaggtctc cttgtttgag ccatcaaaag cagagattgc aaacaaacaa     480

aaggctaccc tcgtgtgctt ggccaggggc ttcttccctg accacgtgga gctgagctgg     540

tgggtgaatg gcaaggaggt ccacagtggg gtcagcacgg accctcaggc ctacaaggag     600
```

```
agcaattata gctactgcct gagcagccgc ctgagggtct ctgctacctt ctggcacaat    660

cctcgcaacc acttccgctg ccaagtgcag ttccatgggc tttcagagga ggacaagtgg    720

ccagagggct cacccaaacc tgtcacacag aacatcagtg cagaggcctg gggccgagca    780

gactgtggga ttacctcagc atcctatcaa caaggggtct tgtctgccac catcctctat    840

gagatcctgc tagggaaagc caccctgtat gctgtgcttg tcagtacact ggtggtgatg    900

gctatggtca aaagaaaaaa ttcaggaagc ggcgccacga acttctctct gttaaagcaa    960

gcaggagacg tggaagaaaa ccccggtccc atgctcctgc tgctcgtccc agtgctcgag   1020

gtgattttta ctctgggagg aaccagagcc cagtcggtga cccagcttga cagccacgtc   1080

tctgtctctg aaggaacccc ggtgctgctg aggtgcaact actcatcttc ttattcacca   1140

tctctcttct ggtatgtgca acaccccaac aaaggactcc agcttctcct gaagtacaca   1200

tcagcggcca ccctggttaa aggcatcaac ggttttgagg ctgaatttaa gaagagtgaa   1260

acctccttcc acctgacgaa accctcagcc catatgagcg acgcggctga gtacttctgt   1320

gttgtgagtg ccattgggta cagcagtgct tccaagataa tctttggatc agggaccaga   1380

ctcagcatcc ggccaaatat ccagaaccca gaacctgctg tgtaccagtt aaaagatcct   1440

cggtctcagg acagcaccct ctgcctgttc accgactttg actcccaaat caatgtgccg   1500

aaaaccatgg aatctggaac gttcatcact gacaaaactg tgctggacat gaaagctatg   1560

gattccaaga gcaatggggc cattgcctgg agcaaccaga caagcttcac ctgccaagat   1620

atcttcaaag agaccaacgc cacctacccc agttcagacg ttccctgtga tgccacgttg   1680

actgagaaaa gctttgaaac agatatgaac ctaaactttc aaaacctgct ggttatggtt   1740

ctccgaatcc tcctgctgaa agtagccgga tttaacctgc tcatgacgct gaggctgtgg   1800

tccagttga                                                           1809
```

<210> SEQ ID NO 195
<211> LENGTH: 21
<212> TYPE: PRT
<213> ORGANISM: Artificial Sequence
<220> FEATURE:
<223> OTHER INFORMATION: Synthetic Construct

<400> SEQUENCE: 195

```
Gly Ser Gly Glu Gly Arg Gly Ser Leu Leu Thr Cys Gly Asp Val Glu
1               5                   10                  15

Glu Asn Pro Gly Pro
            20
```

<210> SEQ ID NO 196
<211> LENGTH: 23
<212> TYPE: PRT
<213> ORGANISM: Artificial Sequence
<220> FEATURE:
<223> OTHER INFORMATION: Synthetic Construct

<400> SEQUENCE: 196

```
Gly Ser Gly Gln Cys Thr Asn Tyr Ala Leu Leu Lys Leu Ala Gly Asp
1               5                   10                  15

Val Glu Ser Asn Pro Gly Pro
            20
```

<210> SEQ ID NO 197
<211> LENGTH: 25
<212> TYPE: PRT

<213> ORGANISM: Artificial Sequence
<220> FEATURE:
<223> OTHER INFORMATION: Synthetic Construct

<400> SEQUENCE: 197

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 198
<211> LENGTH: 140
<212> TYPE: PRT
<213> ORGANISM: Artificial Sequence
<220> FEATURE:
<223> OTHER INFORMATION: Synthetic Construct

<400> SEQUENCE: 198

Ile Gln Asn Pro Asp Pro Ala Val Tyr Gln Leu Arg Asp Ser Lys Ser
1 5 10 15

Ser Asp Lys Ser Val Cys Leu Phe Thr Asp Phe Asp Ser Gln Thr Asn
20 25 30

Val Ser Gln Ser Lys Asp Ser Asp Val Tyr Ile Thr Asp Lys Thr Val
35 40 45

Leu Asp Met Arg Ser Met Asp Phe Lys Ser Asn Ser Ala Val Ala Trp
50 55 60

Ser Asn Lys Ser Asp Phe Ala Cys Ala Asn Ala Phe Asn Asn Ser Ile
65 70 75 80

Ile Pro Glu Asp Thr Phe Phe Pro Ser Pro Glu Ser Ser Cys Asp Val
85 90 95

Lys Leu Val Glu Lys Ser Phe Glu Thr Asp Thr Asn Leu Asn Phe Gln
100 105 110

Asn Leu Ser Val Ile Gly Phe Arg Ile Leu Leu Leu Lys Val Ala Gly
115 120 125

Phe Asn Leu Leu Met Thr Leu Arg Leu Trp Ser Ser
130 135 140

<210> SEQ ID NO 199
<211> LENGTH: 423
<212> TYPE: DNA
<213> ORGANISM: Artificial Sequence
<220> FEATURE:
<223> OTHER INFORMATION: Synthetic Construct

<400> SEQUENCE: 199
atccagaacc ctgaccctgc cgtgtaccag ctgagagact ctaaatccag tgacaagtct 60
gtctgcctat tcaccgattt tgattctcaa acaaatgtgt cacaaagtaa ggattctgat 120
gtgtatatca cagacaaaac tgtgctagac atgaggtcta tggacttcaa gagcaacagt 180
gctgtggcct ggagcaacaa atctgacttt gcatgtgcaa acgccttcaa caacagcatt 240
attccagaag acaccttctt ccccagccca gaaagttcct gtgatgtcaa gctggtcgag 300
aaaagctttg aaacagatac gaacctaaac tttcaaaacc tgtcagtgat tgggttccga 360
atcctcctcc tgaaagtggc cgggtttaat ctgctcatga cgctgcggct gtggtccagc 420
tga 423

<210> SEQ ID NO 200
<211> LENGTH: 136
<212> TYPE: PRT

<213> ORGANISM: Artificial Sequence
<220> FEATURE:
<223> OTHER INFORMATION: Synthetic Construct

<400> SEQUENCE: 200

```
Ile Gln Asn Pro Glu Pro Ala Val Tyr Gln Leu Lys Asp Pro Arg Ser
1               5                   10                  15

Gln Asp Ser Thr Leu Cys Leu Phe Thr Asp Phe Asp Ser Gln Ile Asn
            20                  25                  30

Val Pro Lys Thr Met Glu Ser Gly Thr Phe Ile Thr Asp Lys Thr Val
        35                  40                  45

Leu Asp Met Lys Ala Met Asp Ser Lys Ser Asn Gly Ala Ile Ala Trp
    50                  55                  60

Ser Asn Gln Thr Ser Phe Thr Cys Gln Asp Ile Phe Lys Glu Thr Asn
65                  70                  75                  80

Ala Thr Tyr Pro Ser Ser Asp Val Pro Cys Asp Ala Thr Leu Thr Glu
                85                  90                  95

Lys Ser Phe Glu Thr Asp Met Asn Leu Asn Phe Gln Asn Leu Leu Val
            100                 105                 110

Met Val Leu Arg Ile Leu Leu Leu Lys Val Ala Gly Phe Asn Leu Leu
        115                 120                 125

Met Thr Leu Arg Leu Trp Ser Ser
    130                 135
```

<210> SEQ ID NO 201
<211> LENGTH: 411
<212> TYPE: DNA
<213> ORGANISM: Artificial Sequence
<220> FEATURE:
<223> OTHER INFORMATION: Synthetic Construct

<400> SEQUENCE: 201

```
atccagaacc cagaacctgc tgtgtaccag ttaaaagatc ctcggtctca ggacagcacc     60

ctctgcctgt tcaccgactt tgactcccaa atcaatgtgc cgaaaaccat ggaatctgga    120

acgttcatca ctgacaaaac tgtgctggac atgaaagcta tggattccaa gagcaatggg    180

gccattgcct ggagcaacca gacaagcttc acctgccaag atatcttcaa agagaccaac    240

gccacctacc ccagttcaga cgttccctgt gatgccacgt tgactgagaa aagctttgaa    300

acagatatga acctaaactt tcaaaacctg ctggttatgg ttctccgaat cctcctgctg    360

aaagtagccg gatttaacct gctcatgacg ctgaggctgt ggtccagttg a             411
```

<210> SEQ ID NO 202
<211> LENGTH: 177
<212> TYPE: PRT
<213> ORGANISM: Artificial Sequence
<220> FEATURE:
<223> OTHER INFORMATION: Synthetic Construct

<400> SEQUENCE: 202

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60
```

Glu Gln Pro Ala Leu Asn Asp Ser Arg Tyr Cys Leu Ser Ser Arg Leu
65 70 75 80

Arg Val Ser Ala Thr Phe Trp Gln Asn Pro Arg Asn His Phe Arg Cys
85 90 95

Gln Val Gln Phe Tyr Gly Leu Ser Glu Asn Asp Glu Trp Thr Gln Asp
100 105 110

Arg Ala Lys Pro Val Thr Gln Ile Val Ser Ala Glu Ala Trp Gly Arg
115 120 125

Ala Asp Cys Gly Phe Thr Ser Val Ser Tyr Gln Gln Gly Val Leu Ser
130 135 140

Ala Thr Ile Leu Tyr Glu Ile Leu Leu Gly Lys Ala Thr Leu Tyr Ala
145 150 155 160

Val Leu Val Ser Ala Leu Val Leu Met Ala Met Val Lys Arg Lys Asp
165 170 175

Phe

<210> SEQ ID NO 203
<211> LENGTH: 530
<212> TYPE: DNA
<213> ORGANISM: Artificial Sequence
<220> FEATURE:
<223> OTHER INFORMATION: Synthetic Construct

<400> SEQUENCE: 203
aggacctgaa caaggtgttc ccacccgagg tcgctgtgtt tgagccatca gaagcagaga 60
tctcccacac ccaaaaggcc acactggtgt gcctggccac aggcttcttc cccgaccacg 120
tggagctgag ctggtgggtg aatgggaagg aggtgcacag tggggtcagc acggacccgc 180
agcccctcaa ggagcagccc gccctcaatg actccagata ctgcctgagc agccgcctga 240
gggtctcggc caccttctgg cagaaccccc gcaaccactt ccgctgtcaa gtccagttct 300
acgggctctc ggagaatgac gagtggaccc aggatagggc caaacccgtc acccagatcg 360
tcagcgccga ggcctggggt agagcagact gtggctttac ctcggtgtcc taccagcaag 420 ggtcctgtc tgccaccatc ctctatgaga tcctgctagg gaaggccacc ctgtatgctg 480
tgctggtcag cgcccttgtg ttgatggcca tggtcaagag aaaggatttc 530

<210> SEQ ID NO 204
<211> LENGTH: 178
<212> TYPE: PRT
<213> ORGANISM: Artificial Sequence
<220> FEATURE:
<223> OTHER INFORMATION: Synthetic Construct

<400> SEQUENCE: 204

Asp Leu Lys Asn Val Phe Pro Pro Glu Val Ala Val Phe Glu Pro Ser
1 5 10 15

Glu Ala Glu Ile Ser His Thr Gln Lys Ala Thr Leu Val Cys Leu Ala
20 25 30

Thr Gly Phe Tyr Pro Asp His Val Glu Leu Ser Trp Trp Val Asn Gly
35 40 45

Lys Glu Val His Ser Gly Val Ser Thr Asp Pro Gln Pro Leu Lys Glu
50 55 60

Gln Pro Ala Leu Asn Asp Ser Arg Tyr Cys Leu Ser Ser Arg Leu Arg
65 70 75 80

Val Ser Ala Thr Phe Trp Gln Asn Pro Arg Asn His Phe Arg Cys Gln
85 90 95

Val Gln Phe Tyr Gly Leu Ser Glu Asn Asp Glu Trp Thr Gln Asp Arg
100 105 110

Ala Lys Pro Val Thr Gln Ile Val Ser Ala Glu Ala Trp Gly Arg Ala
115 120 125

Asp Cys Gly Phe Thr Ser Glu Ser Tyr Gln Gln Gly Val Leu Ser Ala
130 135 140

Thr Ile Leu Tyr Glu Ile Leu Leu Gly Lys Ala Thr Leu Tyr Ala Val
145 150 155 160

Leu Val Ser Ala Leu Val Leu Met Ala Met Val Lys Arg Lys Asp Ser
165 170 175

Arg Gly

<210> SEQ ID NO 205
<211> LENGTH: 534
<212> TYPE: DNA
<213> ORGANISM: Artificial Sequence
<220> FEATURE:
<223> OTHER INFORMATION: Synthetic Construct

<400> SEQUENCE: 205
gacctgaaaa acgtgttccc acccgaggtc gctgtgtttg agccatcaga agcagagatc 60
tcccacaccc aaaaggccac actggtgtgc ctggccacag gcttctaccc cgaccacgtg 120
gagctgagct ggtgggtgaa tgggaaggag gtgcacagtg ggtcagcac agacccgcag 180 cccctcaagg agcagcccgc cctcaatgac tccagatact gcctgagcag ccgcctgagg 240
gtctcggcca ccttctggca gaacccccgc aaccacttcc gctgtcaagt ccagttctac 300
gggctctcgg agaatgacga gtggacccag gatagggcca aacctgtcac ccagatcgtc 360
agcgccgagg cctggggtag agcagactgt ggcttcacct ccgagtctta ccagcaaggg 420
gtcctgtctg ccaccatcct ctatgagatc ttgctaggga aggccacctt gtatgccgtg 480
ctggtcagtg ccctcgtgct gatggccatg gtcaagagaa aggattccag aggc 534

<210> SEQ ID NO 206
<211> LENGTH: 172
<212> TYPE: PRT
<213> ORGANISM: Artificial Sequence
<220> FEATURE:
<223> OTHER INFORMATION: Synthetic Construct

<400> SEQUENCE: 206

Asp Leu Arg Asn Val Thr Pro Pro Lys Val Ser Leu Phe Glu Pro Ser
1 5 10 15

Lys Ala Glu Ile Ala Asn Lys Gln Lys Ala Thr Leu Val Cys Leu Ala
20 25 30

Arg Gly Phe Phe Pro Asp His Val Glu Leu Ser Trp Trp Val Asn Gly
35 40 45

Lys Glu Val His Ser Gly Val Ser Thr Asp Pro Gln Ala Tyr Lys Glu
50 55 60

Ser Asn Tyr Ser Tyr Cys Leu Ser Ser Arg Leu Arg Val Ser Ala Thr
65 70 75 80

Phe Trp His Asn Pro Arg Asn His Phe Arg Cys Gln Val Gln Phe His
85 90 95

Gly Leu Ser Glu Glu Asp Lys Trp Pro Glu Gly Ser Pro Lys Pro Val
100 105 110

Thr Gln Asn Ile Ser Ala Glu Ala Trp Gly Arg Ala Asp Cys Gly Ile
115 120 125

Thr Ser Ala Ser Tyr Gln Gln Gly Val Leu Ser Ala Thr Ile Leu Tyr
130 135 140

Glu Ile Leu Leu Gly Lys Ala Thr Leu Tyr Ala Val Leu Val Ser Thr
145 150 155 160

Leu Val Val Met Ala Met Val Lys Arg Lys Asn Ser
165 170

<210> SEQ ID NO 207
<211> LENGTH: 516
<212> TYPE: DNA
<213> ORGANISM: Artificial Sequence
<220> FEATURE:
<223> OTHER INFORMATION: Synthetic Construct

<400> SEQUENCE: 207
gatctgagaa atgtgactcc acccaaggtc tccttgtttg agccatcaaa agcagagatt 60
gcaaacaaac aaaaggctac cctcgtgtgc ttggccaggg gcttcttccc tgaccacgtg 120
gagctgagct ggtgggtgaa tggcaaggag gtccacagtg ggtcagcac ggaccctcag 180 gcctacaagg agagcaatta tagctactgc ctgagcagcc gcctgagggt ctctgctacc 240
ttctggcaca atcctcgcaa ccacttccgc tgccaagtgc agttccatgg gctttcagag 300
gaggacaagt ggccagaggg ctcacccaaa cctgtcacac agaacatcag tgcagaggcc 360
tggggccgag cagactgtgg gattacctca gcatcctatc aacaaggggt cttgtctgcc 420
accatcctct atgagatcct gctagggaaa gccaccctgt atgctgtgct tgtcagtaca 480
ctggtggtga tggctatggt caaaagaaaa aattca 516

<210> SEQ ID NO 208
<211> LENGTH: 128
<212> TYPE: PRT
<213> ORGANISM: Artificial Sequence
<220> FEATURE:
<223> OTHER INFORMATION: Synthetic Construct

<400> SEQUENCE: 208

Met Leu Cys Ser Leu Leu Ala Leu Leu Leu Gly Thr Phe Phe Gly Val
1 5 10 15

Arg Ser Gln Thr Ile His Gln Trp Pro Ala Thr Leu Val Gln Pro Val
20 25 30

Gly Ser Pro Leu Ser Leu Glu Cys Thr Val Glu Gly Thr Ser Asn Pro
35 40 45

Asn Leu Tyr Trp Tyr Arg Gln Ala Ala Gly Arg Gly Leu Gln Leu Leu
50 55 60

Phe Tyr Ser Val Gly Ile Gly Gln Ile Ser Ser Glu Val Pro Gln Asn
65 70 75 80

Leu Ser Ala Ser Arg Pro Gln Asp Arg Gln Phe Ile Leu Ser Ser Lys
85 90 95

Lys Leu Leu Leu Ser Asp Ser Gly Phe Tyr Leu Cys Ala Trp Ala Arg
100 105 110

Ser Arg Glu Leu Phe Phe Gly Glu Gly Ser Arg Leu Thr Val Leu Glu
115 120 125

<210> SEQ ID NO 209
<211> LENGTH: 384
<212> TYPE: DNA
<213> ORGANISM: Artificial Sequence
<220> FEATURE:
<223> OTHER INFORMATION: Synthetic Construct

<400> SEQUENCE: 209
atgctctgct ctctccttgc ccttctcctg ggcactttct ttggggtcag atctcagact 60
attcatcaat ggccagcgac cctggtgcag cctgtgggca gcccgctctc tctggagtgc 120
actgtggagg gaacatcaaa ccccaaccta tactggtacc gacaggctgc aggcaggggc 180
ctccagctgc tcttctactc cgttggtatt ggccagatca gctctgaggt gccccagaat 240
ctctcagcct ccagacccca ggaccggcag ttcatcctga gttctaagaa gctccttctc 300
agtgactctg gcttctatct ctgtgcctgg gcgaggagca gggagctgtt ttttggagaa 360
ggctctaggc tgaccgtact ggag 384

<210> SEQ ID NO 210
<211> LENGTH: 132
<212> TYPE: PRT
<213> ORGANISM: Artificial Sequence
<220> FEATURE:
<223> OTHER INFORMATION: Synthetic Construct

<400> SEQUENCE: 210

Met Lys Pro Thr Leu Ile Ser Val Leu Val Ile Ile Phe Ile Leu Arg
1 5 10 15

Gly Thr Arg Ala Gln Arg Val Thr Gln Pro Glu Lys Leu Leu Ser Val
20 25 30

Phe Lys Gly Ala Pro Val Glu Leu Lys Cys Asn Tyr Ser Tyr Ser Gly
35 40 45

Ser Pro Glu Leu Phe Trp Tyr Val Gln Tyr Ser Arg Gln Arg Leu Gln
50 55 60

Leu Leu Leu Arg His Ile Ser Arg Glu Ser Ile Lys Gly Phe Thr Ala
65 70 75 80

Asp Leu Asn Lys Gly Glu Thr Ser Phe His Leu Lys Lys Pro Phe Ala
85 90 95

Gln Glu Glu Asp Ser Ala Met Tyr Tyr Cys Ala Leu Ser Ala Leu Pro
100 105 110

Tyr Asn Gln Gly Gly Lys Leu Ile Phe Gly Gln Gly Thr Glu Leu Ser
115 120 125

Val Lys Pro Asn
130

<210> SEQ ID NO 211
<211> LENGTH: 396
<212> TYPE: DNA
<213> ORGANISM: Artificial Sequence
<220> FEATURE:
<223> OTHER INFORMATION: Synthetic Construct

<400> SEQUENCE: 211
atgaagccca ccctcatctc agtgcttgtg ataatattta tactcagagg aacaagagcc 60
cagagagtga ctcagcccga gaagctcctc tctgtcttta aaggggcccc agtggagctg 120
aagtgcaact attcctattc tgggagtcct gaactcttct ggtatgtcca gtactccaga 180
caacgcctcc agttactctt gagacacatc tctagagaga gcatcaaagg cttcactgct 240
gaccttaaca aaggcgagac atctttccac ctgaagaaac catttgctca agaggaagac 300
tcagccatgt attactgtgc tctaagtgcc ctcccctata accagggagg aaagcttatc 360
ttcggacagg gaacggagtt atctgtgaaa cccaat 396

<210> SEQ ID NO 212

```
<211> LENGTH: 129
<212> TYPE: PRT
<213> ORGANISM: Artificial Sequence
<220> FEATURE:
<223> OTHER INFORMATION: Synthetic Construct

<400> SEQUENCE: 212

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Arg Asp Thr Glu Ala Phe Phe Gly Gln Gly Thr Arg Leu Thr Val
        115                 120                 125

Val


<210> SEQ ID NO 213
<211> LENGTH: 388
<212> TYPE: DNA
<213> ORGANISM: Artificial Sequence
<220> FEATURE:
<223> OTHER INFORMATION: Synthetic Construct

<400> SEQUENCE: 213

atgggcacca ggctcctctg ctgggcggcc ctctgtctcc tgggagcaga actcacagaa      60

gctggagttg cccagtctcc cagatataag attatagaga aaaggcagag tgtggctttt     120

tggtgcaatc ctatatctgg ccatgctacc ctttactggt accagcagat cctgggacag     180

ggcccaaagc ttctgattca gtttcagaat aacggtgtag tggatgattc acagttgcct     240

aaggatcgat tttctgcaga gaggctcaaa ggagtagact ccactctcaa gatccagcct     300

gcaaagcttg aggactcggc cgtgtatctc tgtgccagca gggacactga agctttcttt     360

ggacaaggca ccagactcac agttgtag                                        388


<210> SEQ ID NO 214
<211> LENGTH: 128
<212> TYPE: PRT
<213> ORGANISM: Artificial Sequence
<220> FEATURE:
<223> OTHER INFORMATION: Synthetic Construct

<400> SEQUENCE: 214

Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60
```

```
Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Ala Trp Tyr Asn
            100                 105                 110

Asn Asn Asp Met Arg Phe Gly Ala Gly Thr Arg Leu Thr Val Lys Pro
        115                 120                 125


<210> SEQ ID NO 215
<211> LENGTH: 385
<212> TYPE: DNA
<213> ORGANISM: Artificial Sequence
<220> FEATURE:
<223> OTHER INFORMATION: Synthetic Construct

<400> SEQUENCE: 215

atgaggctgg tggcaagagt aactgtgttt ctgacctttg gaactataat tgatgctaag      60

accacccagc ccccctccat ggattgcgct gaaggaagag ctgcaaacct gccttgtaat     120

cactctacca tcagtggaaa tgagtatgtg tattggtatc gacagattca ctcccagggg     180

ccacagtata tcattcatgg tctaaaaaac aatgaaacca atgaaatggc ctctctgatc     240

atcacagaag acagaaagtc cagcaccttg atcctgcccc acgctacgct gagagacact     300

gctgtgtact attgcatcgt cagagcttgg tacaataaca atgacatgcg ctttggagca     360

gggaccagac tgacagtaaa accaa                                           385


<210> SEQ ID NO 216
<211> LENGTH: 133
<212> TYPE: PRT
<213> ORGANISM: Artificial Sequence
<220> FEATURE:
<223> OTHER INFORMATION: Synthetic Construct

<400> SEQUENCE: 216

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Glu Trp Gly Thr Tyr Glu Gln Tyr Phe Gly Pro Gly Thr Arg
        115                 120                 125

Leu Thr Val Thr Glu
    130


<210> SEQ ID NO 217
<211> LENGTH: 399
<212> TYPE: DNA
<213> ORGANISM: Artificial Sequence
```

<220> FEATURE:
<223> OTHER INFORMATION: Synthetic Construct

<400> SEQUENCE: 217

```
atgggcttca ggctcctctg ctgtgtggcc ttttgtctcc tgggagcagg cccagtggat     60

tctggagtca cacaaacccc aaagcacctg atcacagcaa ctggacagcg agtgacgctg    120

agatgctccc ctaggtctgg agacctctct gtgtactggt accaacagag cctggaccag    180

ggcctccagt tcctcattca gtattataat ggagaagaga gagcaaaagg aaacattctt    240

gaacgattct ccgcacaaca gttccctgac ttgcactctg aactaaacct gagctctctg    300

gagctggggg actcagcttt gtatttctgt gccagcagcg tagaatgggg tacctacgag    360

cagtacttcg ggccgggcac caggctcacg gtcacagag                           399
```

<210> SEQ ID NO 218
<211> LENGTH: 133
<212> TYPE: PRT
<213> ORGANISM: Artificial Sequence
<220> FEATURE:
<223> OTHER INFORMATION: Synthetic Construct

<400> SEQUENCE: 218

```
Met Asn Tyr Ser Pro Gly Leu Val Ser Leu Ile Leu Leu Leu Leu Gly
1               5                   10                  15

Arg Thr Arg Gly Asn Ser Val Thr Gln Met Glu Gly Pro Val Thr Leu
            20                  25                  30

Ser Glu Glu Ala Phe Leu Thr Ile Asn Cys Thr Tyr Thr Ala Thr Gly
        35                  40                  45

Tyr Pro Ser Leu Phe Trp Tyr Val Gln Tyr Pro Gly Glu Gly Leu Gln
    50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Leu Arg
            100                 105                 110

Ser Gly Gly Ser Asn Tyr Lys Leu Thr Phe Gly Lys Gly Thr Leu Leu
        115                 120                 125

Thr Val Asn Pro Asn
    130
```

<210> SEQ ID NO 219
<211> LENGTH: 399
<212> TYPE: DNA
<213> ORGANISM: Artificial Sequence
<220> FEATURE:
<223> OTHER INFORMATION: Synthetic Construct

<400> SEQUENCE: 219

```
atgaactatt ctccaggctt agtatctctg atactcttac tgcttggaag aacccgtgga     60

aattcagtga cccagatgga agggccagtg actctctcag aagaggcctt cctgactata    120

aactgcacgt acacagccac aggataccct tccctttttct ggtatgtcca atatcctgga    180

gaaggtctac agctcctcct gaaagccacg aaggctgatg acaagggaag caacaaaggt    240

tttgaagcca cataccgtaa agaaaccact tctttccact tggagaaagg ctcagttcaa    300

gtgtcagact cagcggtgta cttctgtgct ctgaggagtg gaggtagcaa ctataaactg    360

acatttggaa aaggaactct cttaaccgtg aatccaaat                           399
```

<210> SEQ ID NO 220
<211> LENGTH: 133
<212> TYPE: PRT
<213> ORGANISM: Artificial Sequence
<220> FEATURE:
<223> OTHER INFORMATION: Synthetic Construct

<400> SEQUENCE: 220

Met Ser Ile Gly Leu Leu Cys Cys Ala Ala Leu Ser Leu Leu Trp Ala
1 5 10 15

Gly Pro Val Asn Ala Gly Val Thr Gln Thr Pro Lys Phe Gln Val Leu
20 25 30

Lys Thr Gly Gln Ser Met Thr Leu Gln Cys Ala Gln Asp Met Asn His
35 40 45

Glu Tyr Met Ser Trp Tyr Arg Gln Asp Pro Gly Met Gly Leu Arg Leu
50 55 60

Ile His Tyr Ser Val Gly Ala Gly Ile Thr Asp Gln Gly Glu Val Pro
65 70 75 80

Asn Gly Tyr Asn Val Ser Arg Ser Thr Thr Glu Asp Phe Pro Leu Arg
85 90 95

Leu Leu Ser Ala Ala Pro Ser Gln Thr Ser Val Tyr Phe Cys Ala Ser
100 105 110

Ser Ser Trp Asp Arg Asp Gln Pro Gln His Phe Gly Asp Gly Thr Arg
115 120 125

Leu Ser Ile Leu Glu
130

<210> SEQ ID NO 221
<211> LENGTH: 399
<212> TYPE: DNA
<213> ORGANISM: Artificial Sequence
<220> FEATURE:
<223> OTHER INFORMATION: Synthetic Construct

<400> SEQUENCE: 221
atgagcatcg gcctcctgtg ctgtgcagcc ttgtctctcc tgtgggcagg tccagtgaat 60
gctggtgtca ctcagacccc aaaattccag gtcctgaaga caggacagag catgacactg 120
cagtgtgccc aggatatgaa ccatgaatac atgtcctggt atcgacaaga cccaggcatg 180
gggctgaggc tgattcatta ctcagttggt gctggtatca ctgaccaagg agaagtcccc 240
aatggctaca atgtctccag atcaaccaca gaggatttcc cgctcaggct gctgtcggct 300
gctccctccc agacatctgt gtacttctgt gccagcagtt catgggacag ggatcagccc 360
cagcattttg gtgatgggac tcgactctcc atcctagag 399

<210> SEQ ID NO 222
<211> LENGTH: 127
<212> TYPE: PRT
<213> ORGANISM: Artificial Sequence
<220> FEATURE:
<223> OTHER INFORMATION: Synthetic Construct

<400> SEQUENCE: 222

Met Leu Leu Ile Thr Ser Met Leu Val Leu Trp Met Gln Leu Ser Gln
1 5 10 15

Val Asn Gly Gln Gln Val Met Gln Ile Pro Gln Tyr Gln His Val Gln
20 25 30

Glu Gly Glu Asp Phe Thr Thr Tyr Cys Asn Ser Ser Thr Thr Leu Ser

-continued

```
        35                  40                  45

Asn Ile Gln Trp Tyr Lys Gln Arg Pro Gly Gly His Pro Val Phe Leu
    50                  55                  60

Ile Gln Leu Val Lys Ser Gly Glu Val Lys Lys Gln Lys Arg Leu Thr
65                  70                  75                  80

Phe Gln Phe Gly Glu Ala Lys Lys Asn Ser Ser Leu His Ile Thr Ala
                85                  90                  95

Thr Gln Thr Thr Asp Val Gly Thr Tyr Phe Cys Ala Gly Pro Gly Asn
            100                 105                 110

Gln Phe Tyr Phe Gly Thr Gly Thr Ser Leu Thr Val Ile Pro Asn
        115                 120                 125


<210> SEQ ID NO 223
<211> LENGTH: 381
<212> TYPE: DNA
<213> ORGANISM: Artificial Sequence
<220> FEATURE:
<223> OTHER INFORMATION: Synthetic Construct

<400> SEQUENCE: 223

atgctactca tcacatcaat gttggtctta tggatgcaat tgtcacaggt gaatggacaa      60

caggtaatgc aaattcctca gtaccagcat gtacaagaag gagaggactt caccacgtac     120

tgcaattcct caactacttt aagcaatata cagtggtata agcaaaggcc tggtggacat     180

cccgtttttt tgatacagtt agtgaagagt ggagaagtga agaagcagaa aagactgaca     240

tttcagtttg gagaagcaaa aaagaacagc tccctgcaca tcacagccac ccagactaca     300

gatgtaggaa cctacttctg tgcagggccc ggtaaccagt tctattttgg gacagggaca     360

agtttgacgg tcattccaaa t                                               381


<210> SEQ ID NO 224
<211> LENGTH: 134
<212> TYPE: PRT
<213> ORGANISM: Artificial Sequence
<220> FEATURE:
<223> OTHER INFORMATION: Synthetic Construct

<400> SEQUENCE: 224

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Met Asp Ala Ala Leu Gly Glu Lys Leu Phe Phe Gly Ser Gly Thr
        115                 120                 125

Gln Leu Ser Val Leu Glu
    130
```

<210> SEQ ID NO 225
<211> LENGTH: 402
<212> TYPE: DNA
<213> ORGANISM: Artificial Sequence
<220> FEATURE:
<223> OTHER INFORMATION: Synthetic Construct

<400> SEQUENCE: 225

```
atgagcaacc aggtgctctg ctgtgtggtc ctttgtttcc tgggagcaaa caccgtggat     60

ggtggaatca ctcagtcccc aaagtacctg ttcagaaagg aaggacagaa tgtgaccctg    120

agttgtgaac agaatttgaa ccacgatgcc atgtactggt accgacagga cccagggcaa    180

gggctgagat tgatctacta ctcacagata gtaaatgact ttcagaaagg agatatagct    240

gaagggtaca gcgtctctcg ggagaagaag gaatcctttc ctctcactgt gacatcggcc    300

caaaagaacc cgacagcttt ctatctctgt gccagtagta tggacgccgc cttgggtgaa    360

aaactgtttt ttggcagtgg aacccagctc tctgtcttgg ag                       402
```

<210> SEQ ID NO 226
<211> LENGTH: 134
<212> TYPE: PRT
<213> ORGANISM: Artificial Sequence
<220> FEATURE:
<223> OTHER INFORMATION: Synthetic Construct

<400> SEQUENCE: 226

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Pro Arg Ser Gly Tyr Ala Leu Asn Phe Gly Lys Gly Thr Ser
        115                 120                 125

Leu Leu Val Thr Pro His
    130
```

<210> SEQ ID NO 227
<211> LENGTH: 402
<212> TYPE: DNA
<213> ORGANISM: Artificial Sequence
<220> FEATURE:
<223> OTHER INFORMATION: Synthetic Construct

<400> SEQUENCE: 227

```
atgatgaaat ccttgagagt ttttactggtg atcctgtggc ttcagttaag ctgggtttgg     60

agccaacaga aggaggtgga gcaggatcct ggaccactca gtgttccaga gggagccatt    120

gtttctctca actgcactta cagcaacagt gcttttcaat acttcatgtg gtacagacag    180

tattccagaa aaggccctga gttgctgatg tacacatact ccagtggtaa caaagaagat    240

ggaaggttta cagcacaggt cgataaatcc agcaagtata tctccttgtt catcagagac    300
```

tcacagccca gtgattcagc cacctacctc tgtgcaatga gccctcggag cgggtatgca 360
ctcaacttcg gcaaaggcac ctcgctgttg gtcacacccc at 402

<210> SEQ ID NO 228
<211> LENGTH: 136
<212> TYPE: PRT
<213> ORGANISM: Artificial Sequence
<220> FEATURE:
<223> OTHER INFORMATION: Synthetic Construct

<400> SEQUENCE: 228

Met Gly Thr Ser Leu Leu Cys Trp Met Ala Leu Cys Leu Leu Gly Ala
1 5 10 15

Asp His Ala Asp Thr Gly Val Ser Gln Asn Pro Arg His Lys Ile Thr
20 25 30

Lys Arg Gly Gln Asn Val Thr Phe Arg Cys Asp Pro Ile Ser Glu His
35 40 45

Asn Arg Leu Tyr Trp Tyr Arg Gln Thr Leu Gly Gln Gly Pro Glu Phe
50 55 60

Leu Thr Tyr Phe Gln Asn Glu Ala Gln Leu Glu Lys Ser Arg Leu Leu
65 70 75 80

Ser Asp Arg Phe Ser Ala Glu Arg Pro Lys Gly Ser Phe Ser Thr Leu
85 90 95

Glu Ile Gln Arg Thr Glu Gln Gly Asp Ser Ala Met Tyr Leu Cys Ala
100 105 110

Ser Ser Leu Val Ala Gly Gly Pro Ala Glu Thr Gln Tyr Phe Gly Pro
115 120 125

Gly Thr Arg Leu Leu Val Leu Glu
130 135

<210> SEQ ID NO 229
<211> LENGTH: 408
<212> TYPE: DNA
<213> ORGANISM: Artificial Sequence
<220> FEATURE:
<223> OTHER INFORMATION: Synthetic Construct

<400> SEQUENCE: 229
atgggcacca gcctcctctg ctggatggcc ctgtgtctcc tgggggcaga tcacgcagat 60
actggagtct cccagaaccc cagacacaag atcacaaaga ggggacagaa tgtaactttc 120
aggtgtgatc caatttctga acacaaccgc ctttattggt accgacagac cctggggcag 180
ggcccagagt ttctgactta cttccagaat gaagctcaac tagaaaaatc aaggctgctc 240
agtgatcggt tctctgcaga gaggcctaag ggatctttct ccaccttgga gatccagcgc 300
acagagcagg gggactcggc catgtatctc tgtgccagca gcttagttgc gggagggccc 360
gcagagaccc agtacttcgg gccaggcacg cggctcctgg tgctcgag 408

<210> SEQ ID NO 230
<211> LENGTH: 136
<212> TYPE: PRT
<213> ORGANISM: Artificial Sequence
<220> FEATURE:
<223> OTHER INFORMATION: Synthetic Construct

<400> SEQUENCE: 230

Met Leu Leu Leu Leu Val Pro Val Leu Glu Val Ile Phe Thr Leu Gly
1 5 10 15

-continued

```
Gly Thr Arg Ala Gln Ser Val Thr Gln Leu Asp Ser His Val Ser Val
            20                  25                  30

Ser Glu Gly Thr Pro Val Leu Leu Arg Cys Asn Tyr Ser Ser Ser Tyr
        35                  40                  45

Ser Pro Ser Leu Phe Trp Tyr Val Gln His Pro Asn Lys Gly Leu Gln
    50                  55                  60

Leu Leu Leu Lys Tyr Thr Ser Ala Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Val Val
            100                 105                 110

Ser Ala Ile Gly Tyr Ser Ser Ala Ser Lys Ile Ile Phe Gly Ser Gly
        115                 120                 125

Thr Arg Leu Ser Ile Arg Pro Asn
    130                 135
```

<210> SEQ ID NO 231
<211> LENGTH: 408
<212> TYPE: DNA
<213> ORGANISM: Artificial Sequence
<220> FEATURE:
<223> OTHER INFORMATION: Synthetic Construct

<400> SEQUENCE: 231

```
atgctcctgc tgctcgtccc agtgctcgag gtgattttta ctctgggagg aaccagagcc     60

cagtcggtga cccagcttga cagccacgtc tctgtctctg aaggaacccc ggtgctgctg    120

aggtgcaact actcatcttc ttattcacca tctctcttct ggtatgtgca acaccccaac    180

aaaggactcc agcttctcct gaagtacaca tcagcggcca ccctggttaa aggcatcaac    240

ggttttgagg ctgaatttaa gaagagtgaa acctccttcc acctgacgaa accctcagcc    300

catatgagcg acgcggctga gtacttctgt gttgtgagtg ccattgggta cagcagtgct    360

tccaagataa tctttggatc agggaccaga ctcagcatcc ggccaaat                 408
```

<210> SEQ ID NO 232
<211> LENGTH: 133
<212> TYPE: PRT
<213> ORGANISM: Artificial Sequence
<220> FEATURE:
<223> OTHER INFORMATION: Synthetic Construct

<400> SEQUENCE: 232

```
Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110
```

Ser Ile Asp Pro Ala Thr Ser His Glu Gln Phe Phe Gly Pro Gly Thr
115 120 125

Arg Leu Thr Val Leu
130

<210> SEQ ID NO 233
<211> LENGTH: 398
<212> TYPE: DNA
<213> ORGANISM: Artificial Sequence
<220> FEATURE:
<223> OTHER INFORMATION: Synthetic Construct

<400> SEQUENCE: 233
atgagcaacc aggtgctctg ctgtgtggtc ctttgtttcc tgggagcaaa caccgtggat 60
ggtggaatca ctcagtcccc aaagtacctg ttcagaaagg aaggacagaa tgtgaccctg 120
agttgtgaac agaatttgaa ccacgatgcc atgtactggt accgacagga cccagggcaa 180
gggctgagat tgatctacta ctcacagata gtaaatgact ttcagaaagg agatatagct 240
gaagggtaca gcgtctctcg ggagaagaag gaatcctttc ctctcactgt gacatcggcc 300
caaaagaacc cgacagcttt ctatctctgt gccagtagta tagatccggc gactagtcat 360
gagcagttct tcgggccagg gacacggctc accgtgct 398

<210> SEQ ID NO 234
<211> LENGTH: 133
<212> TYPE: PRT
<213> ORGANISM: Artificial Sequence
<220> FEATURE:
<223> OTHER INFORMATION: Synthetic Construct

<400> SEQUENCE: 234

Met Met Lys Ser Leu Arg Val Leu Leu Val Ile Leu Trp Leu Gln Leu
1 5 10 15

Ser Trp Val Trp Ser Gln Gln Lys Glu Val Glu Gln Asp Pro Gly Pro
20 25 30

Leu Ser Val Pro Glu Gly Ala Ile Val Ser Leu Asn Cys Thr Tyr Ser
35 40 45

Asn Ser Ala Phe Gln Tyr Phe Met Trp Tyr Arg Gln Tyr Ser Arg Lys
50 55 60

Gly Pro Glu Leu Leu Met Tyr Thr Tyr Ser Ser Gly Asn Lys Glu Asp
65 70 75 80

Gly Arg Phe Thr Ala Gln Val Asp Lys Ser Ser Lys Tyr Ile Ser Leu
85 90 95

Phe Ile Arg Asp Ser Gln Pro Ser Asp Ser Ala Thr Tyr Leu Cys Ala
100 105 110

Phe Tyr Ala Gly Asn Asn Arg Lys Leu Ile Trp Gly Leu Gly Thr Ser
115 120 125

Leu Ala Val Asn Pro
130

<210> SEQ ID NO 235
<211> LENGTH: 400
<212> TYPE: DNA
<213> ORGANISM: Artificial Sequence
<220> FEATURE:
<223> OTHER INFORMATION: Synthetic Construct

<400> SEQUENCE: 235
atgatgaaat ccttgagagt tttactggtg atcctgtggc ttcagttaag ctgggtttgg 60
agccaacaga aggaggtgga gcaggatcct ggaccactca gtgttccaga gggagccatt 120
gtttctctca actgcactta cagcaacagt gcttttcaat acttcatgtg gtacagacag 180
tattccagaa aaggccctga gttgctgatg tacacatact ccagtggtaa caaagaagat 240
ggaaggttta cagcacaggt cgataaatcc agcaagtata tctccttgtt catcagagac 300
tcacagccca gtgattcagc cacctacctc tgtgcattct atgctggcaa caaccgtaag 360
ctgatttggg gattgggaac aagcctggca gtaaatccga 400

<210> SEQ ID NO 236
<211> LENGTH: 133
<212> TYPE: PRT
<213> ORGANISM: Artificial Sequence
<220> FEATURE:
<223> OTHER INFORMATION: Synthetic Construct

<400> SEQUENCE: 236

Met Leu Leu Leu Leu Leu Leu Leu Gly Pro Ala Gly Ser Gly Leu Gly
1 5 10 15

Ala Val Val Ser Gln His Pro Ser Arg Val Ile Cys Lys Ser Gly Thr
20 25 30

Ser Val Lys Ile Glu Cys Arg Ser Leu Asp Phe Gln Ala Thr Thr Met
35 40 45

Phe Trp Tyr Arg Gln Phe Pro Lys Lys Ser Leu Met Leu Met Ala Thr
50 55 60

Ser Asn Glu Gly Ser Lys Ala Thr Tyr Glu Gln Gly Val Glu Lys Asp
65 70 75 80

Lys Phe Leu Ile Asn His Ala Ser Leu Thr Leu Ser Thr Leu Thr Val
85 90 95

Thr Ser Ala His Pro Glu Asp Ser Ser Phe Tyr Ile Cys Ser Ala Leu
100 105 110

Glu Gly Thr Ser Gly Lys Glu Thr Gln Tyr Phe Gly Pro Gly Thr Arg
115 120 125

Leu Leu Val Leu Glu
130

<210> SEQ ID NO 237
<211> LENGTH: 399
<212> TYPE: DNA
<213> ORGANISM: Artificial Sequence
<220> FEATURE:
<223> OTHER INFORMATION: Synthetic Construct

<400> SEQUENCE: 237
atgctgctgc ttctgctgct tctggggcca gcaggctccg ggcttggtgc tgtcgtctct 60
caacatccga gcagggttat ctgtaagagt ggaacctctg tgaagatcga gtgccgttcc 120
ctggactttc aggccacaac tatgttttgg tatcgtcagt tcccgaaaaa gagtctcatg 180
ctgatggcaa cttccaatga gggctccaag gccacatacg agcaaggcgt cgagaaggac 240
aagtttctca tcaaccatgc aagcctgacc ttgtccactc tgacagtgac cagtgcccat 300
cctgaagaca gcagcttcta catctgcagt gctttagagg ggactagcgg gaaagagacc 360
cagtacttcg ggccaggcac gcggctcctg gtgctcgag 399

<210> SEQ ID NO 238
<211> LENGTH: 133
<212> TYPE: PRT
<213> ORGANISM: Artificial Sequence
<220> FEATURE:

<223> OTHER INFORMATION: Synthetic Construct

<400> SEQUENCE: 238

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Met Lys Asp Ser Ser Tyr Lys Leu Ile Phe Gly Ser Gly Thr Arg Leu
        115                 120                 125

Leu Val Arg Pro Asp
    130

<210> SEQ ID NO 239
<211> LENGTH: 399
<212> TYPE: DNA
<213> ORGANISM: Artificial Sequence
<220> FEATURE:
<223> OTHER INFORMATION: Synthetic Construct

<400> SEQUENCE: 239
atgatatcct tgagagtttt actggtgatc ctgtggcttc agttaagctg ggtttggagc 60
caacggaagg aggtggagca ggatcctgga cccttcaatg ttccagaggg agccactgtc 120
gctttcaact gtacttacag caacagtgct tctcagtctt tcttctggta cagacaggat 180
tgcaggaaag aacctaagtt gctgatgtcc gtatactcca gtggtaatga agatggaagg 240
tttacagcac agctcaatag agccagccag tatatttccc tgctcatcag agactccaag 300
ctcagtgatt cagccaccta cctctgtgtg gtgaacatga aggatagcag ctataaattg 360
atcttcggga gtgggaccag actgctggtc aggcctgat 399

<210> SEQ ID NO 240
<211> LENGTH: 131
<212> TYPE: PRT
<213> ORGANISM: Artificial Sequence
<220> FEATURE:
<223> OTHER INFORMATION: Synthetic Construct

<400> SEQUENCE: 240

Met Leu Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Lys Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
85 90 95

Thr Ser Ala His Pro Glu Asp Ser Ser Phe Tyr Ile Cys Ser Ala His
100 105 110

Glu Arg Ile Thr Asp Thr Gln Tyr Phe Gly Pro Gly Thr Arg Leu Thr
115 120 125

Val Leu Glu
130

<210> SEQ ID NO 241
<211> LENGTH: 393
<212> TYPE: DNA
<213> ORGANISM: Artificial Sequence
<220> FEATURE:
<223> OTHER INFORMATION: Synthetic Construct

<400> SEQUENCE: 241
atgctgctgc ttctgctgct tctggggcca gcaggctccg ggcttggtgc tgtcgtctct 60
caacatccga gcagggttat ctgtaagagt ggaacctctg tgaagatcga gtgccgttcc 120
ctggactttc aggccacaac tatgttttgg tatcgtcagt tcccgaaaaa gagtctcatg 180
ctgatggcaa cttccaatga gggctccaag gccacatacg agcaaggcgt cgagaaggac 240
aagtttctca tcaaccatgc aagcctgacc ttgtccactc tgacagtgac cagtgcccat 300
cctgaagaca gcagcttcta catctgcagt gcccatgagc ggatcacaga tacgcagtat 360
tttggcccag gcacccggct gacagtgctc gag 393

<210> SEQ ID NO 242
<211> LENGTH: 133
<212> TYPE: PRT
<213> ORGANISM: Artificial Sequence
<220> FEATURE:
<223> OTHER INFORMATION: Synthetic Construct

<400> SEQUENCE: 242

Met Ile Ser Leu Arg Val Leu Leu Val Ile Leu Trp Leu Gln Leu Ser
1 5 10 15

Trp Val Trp Ser Gln Arg Lys Glu Val Glu Gln Asp Pro Gly Pro Phe
20 25 30

Asn Val Pro Glu Gly Ala Thr Val Ala Phe Asn Cys Thr Tyr Ser Asn
35 40 45

Ser Ala Ser Gln Ser Phe Phe Trp Tyr Arg Gln Asp Cys Arg Lys Glu
50 55 60

Pro Lys Leu Leu Met Ser Val Tyr Ser Ser Gly Asn Glu Asp Gly Arg
65 70 75 80

Phe Thr Ala Gln Leu Asn Arg Ala Ser Gln Tyr Ile Ser Leu Leu Ile
85 90 95

Arg Asp Ser Lys Leu Ser Asp Ser Ala Thr Tyr Leu Cys Val Val Asn
100 105 110

Met Arg Asp Ser Ser Tyr Lys Leu Ile Phe Gly Ser Gly Thr Arg Leu
115 120 125

Leu Val Arg Pro Asp
130

<210> SEQ ID NO 243
<211> LENGTH: 399
<212> TYPE: DNA
<213> ORGANISM: Artificial Sequence
<220> FEATURE:
<223> OTHER INFORMATION: Synthetic Construct

<400> SEQUENCE: 243
atgatatcct tgagagtttt actggtgatc ctgtggcttc agttaagctg ggtttggagc 60
caacggaagg aggtggagca ggatcctgga cccttcaatg ttccagaggg agccactgtc 120
gctttcaact gtacttacag caacagtgct tctcagtctt tcttctggta cagacaggat 180
tgcaggaaag aacctaagtt gctgatgtcc gtatactcca gtggtaatga agatggaagg 240
tttacagcac agctcaatag agccagccag tatatttccc tgctcatcag agactccaag 300
ctcagtgatt cagccaccta cctctgtgtg gtgaacatga gggatagcag ctataaattg 360
atcttcggga gtgggaccag actgctggtc aggcctgat 399

<210> SEQ ID NO 244
<211> LENGTH: 132
<212> TYPE: PRT
<213> ORGANISM: Artificial Sequence
<220> FEATURE:
<223> OTHER INFORMATION: Synthetic Construct

<400> SEQUENCE: 244

Met Leu Leu Leu Leu Leu Leu Leu Gly Pro Gly Ser Gly Leu Gly Ala
1 5 10 15

Val Val Ser Gln His Pro Ser Trp Val Ile Cys Lys Ser Gly Thr Ser
20 25 30

Val Lys Ile Glu Cys Arg Ser Leu Asp Phe Gln Ala Thr Thr Met Phe
35 40 45

Trp Tyr Arg Gln Phe Pro Lys Gln Ser Leu Met Leu Met Ala Thr Ser
50 55 60

Asn Glu Gly Ser Lys Ala Thr Tyr Glu Gln Gly Val Glu Lys Asp Lys
65 70 75 80

Phe Leu Ile Asn His Ala Ser Leu Thr Leu Ser Thr Leu Thr Val Thr
85 90 95

Ser Ala His Pro Glu Asp Ser Ser Phe Tyr Ile Cys Ser Ala Pro Trp
100 105 110

Leu Ala Gly Leu Tyr Asn Glu Gln Phe Phe Gly Pro Gly Thr Arg Leu
115 120 125

Thr Val Leu Glu
130

<210> SEQ ID NO 245
<211> LENGTH: 396
<212> TYPE: DNA
<213> ORGANISM: Artificial Sequence
<220> FEATURE:
<223> OTHER INFORMATION: Synthetic Construct

<400> SEQUENCE: 245
atgctgctgc ttctgctgct tctggggcca ggctccgggc ttggtgctgt cgtctctcaa 60
catccgagct gggttatctg taagagtgga acctctgtga agatcgagtg ccgttccctg 120
gactttcagg ccacaactat gttttggtat cgtcagttcc cgaaacagag tctcatgctg 180
atggcaactt ccaatgaggg ctccaaggcc acatacgagc aaggcgtcga gaaggacaag 240
tttctcatca accatgcaag cctgaccttg tccactctga cagtgaccag tgcccatcct 300
gaagacagca gcttctacat ctgcagtgct ccgtggctag cggggttgta caatgagcag 360
ttcttcgggc cagggacacg gctcaccgtg ctagag 396

<210> SEQ ID NO 246
<211> LENGTH: 178
<212> TYPE: PRT
<213> ORGANISM: Artificial Sequence
<220> FEATURE:
<223> OTHER INFORMATION: Synthetic Construct

<400> SEQUENCE: 246

Asp Leu Lys Asn Val Phe Pro Pro Glu Val Ala Val Phe Glu Pro Ser
1 5 10 15

Glu Ala Glu Ile Ser His Thr Gln Lys Ala Thr Leu Val Cys Leu Ala
20 25 30

Thr Gly Phe Tyr Pro Asp His Val Glu Leu Ser Trp Trp Val Asn Gly
35 40 45

Lys Glu Val His Ser Gly Val Ser Thr Asp Pro Gln Pro Leu Lys Glu
50 55 60

Gln Pro Ala Leu Asn Asp Ser Arg Tyr Cys Leu Ser Ser Arg Leu Arg
65 70 75 80

Val Ser Ala Thr Phe Trp Gln Asn Pro Arg Asn His Phe Arg Cys Gln
85 90 95

Val Gln Phe Tyr Gly Leu Ser Glu Asn Asp Glu Trp Thr Gln Asp Arg
100 105 110

Ala Lys Pro Val Thr Gln Ile Val Ser Ala Glu Ala Trp Gly Arg Ala
115 120 125

Asp Cys Gly Phe Thr Ser Glu Ser Tyr Gln Gln Gly Val Leu Ser Ala
130 135 140

Thr Ile Leu Tyr Glu Ile Leu Leu Gly Lys Ala Thr Leu Tyr Ala Val
145 150 155 160

Leu Val Ser Ala Leu Val Leu Met Ala Met Val Lys Arg Lys Asp Ser
165 170 175

Arg Gly

<210> SEQ ID NO 247
<211> LENGTH: 534
<212> TYPE: DNA
<213> ORGANISM: Artificial Sequence
<220> FEATURE:
<223> OTHER INFORMATION: Synthetic Construct

<400> SEQUENCE: 247
gacctgaaaa acgtgttccc acccgaggtc gctgtgtttg agccatcaga agcagagatc 60
tcccacaccc aaaaggccac actggtgtgc ctggccacag gcttctaccc cgaccacgtg 120
gagctgagct ggtgggtgaa tgggaaggag gtgcacagtg ggtcagcac agacccgcag 180 cccctcaagg agcagcccgc cctcaatgac tccagatact gcctgagcag ccgcctgagg 240
gtctcggcca ccttctggca gaacccccgc aaccacttcc gctgtcaagt ccagttctac 300
gggctctcgg agaatgacga gtggacccag gatagggcca aacctgtcac ccagatcgtc 360
agcgccgagg cctggggtag agcagactgt ggcttcacct ccgagtctta ccagcaaggg 420
gtcctgtctg ccaccatcct ctatgagatc ttgctaggga aggccacctt gtatgccgtg 480
ctggtcagtg ccctcgtgct gatggccatg gtcaagagaa aggattccag aggc 534

<210> SEQ ID NO 248
<211> LENGTH: 15
<212> TYPE: PRT
<213> ORGANISM: Artificial Sequence
<220> FEATURE:
<223> OTHER INFORMATION: Synthetic Construct

<400> SEQUENCE: 248

Gln Leu Phe Leu Asn Thr Leu Ser Phe Val Cys Pro Trp Cys Ala
1 5 10 15

<210> SEQ ID NO 249
<211> LENGTH: 15
<212> TYPE: PRT
<213> ORGANISM: Artificial Sequence
<220> FEATURE:
<223> OTHER INFORMATION: Synthetic Construct

<400> SEQUENCE: 249

Leu Asn Thr Leu Ser Phe Val Cys Pro Trp Cys Ala Ser Gln Gln
1 5 10 15

<210> SEQ ID NO 250
<211> LENGTH: 15
<212> TYPE: PRT
<213> ORGANISM: Artificial Sequence
<220> FEATURE:
<223> OTHER INFORMATION: Synthetic Construct

<400> SEQUENCE: 250

Met Cys Lys Gly Leu Ala Ala Leu Pro His Ser Cys Leu Glu Arg
1 5 10 15

<210> SEQ ID NO 251
<211> LENGTH: 15
<212> TYPE: PRT
<213> ORGANISM: Artificial Sequence
<220> FEATURE:
<223> OTHER INFORMATION: Synthetic Construct

<400> SEQUENCE: 251

Leu Ala Ala Leu Pro His Ser Cys Leu Glu Arg Ala Lys Glu Ile
1 5 10 15

<210> SEQ ID NO 252
<211> LENGTH: 15
<212> TYPE: PRT
<213> ORGANISM: Artificial Sequence
<220> FEATURE:
<223> OTHER INFORMATION: Synthetic Construct

<400> SEQUENCE: 252

Pro His Ser Cys Leu Glu Arg Ala Lys Glu Ile Lys Ile Lys Leu
1 5 10 15

<210> SEQ ID NO 253
<211> LENGTH: 15
<212> TYPE: PRT
<213> ORGANISM: Artificial Sequence
<220> FEATURE:
<223> OTHER INFORMATION: Synthetic Construct

<400> SEQUENCE: 253

Leu Glu Arg Ala Lys Glu Ile Lys Ile Lys Leu Gly Ile Leu Leu
1 5 10 15

<210> SEQ ID NO 254
<211> LENGTH: 6
<212> TYPE: PRT
<213> ORGANISM: Artificial Sequence
<220> FEATURE:

<223> OTHER INFORMATION: Synthetic Construct

<400> SEQUENCE: 254

Thr Ile Ser Gly Asn Glu
1               5

<210> SEQ ID NO 255
<211> LENGTH: 5
<212> TYPE: PRT
<213> ORGANISM: Artificial Sequence
<220> FEATURE:
<223> OTHER INFORMATION: Synthetic Construct

<400> SEQUENCE: 255

Gly Leu Lys Asn Asn
1               5

<210> SEQ ID NO 256
<211> LENGTH: 5
<212> TYPE: PRT
<213> ORGANISM: Artificial Sequence
<220> FEATURE:
<223> OTHER INFORMATION: Synthetic Construct

<400> SEQUENCE: 256

Ser Gly His Ala Thr
1               5

<210> SEQ ID NO 257
<211> LENGTH: 7
<212> TYPE: PRT
<213> ORGANISM: Artificial Sequence
<220> FEATURE:
<223> OTHER INFORMATION: Synthetic Construct

<400> SEQUENCE: 257

Gln Phe Gln Asn Asn Gly Val
1               5

<210> SEQ ID NO 258
<211> LENGTH: 6
<212> TYPE: PRT
<213> ORGANISM: Artificial Sequence
<220> FEATURE:
<223> OTHER INFORMATION: Synthetic Construct

<400> SEQUENCE: 258

Asn Ser Ala Ser Gln Ser
1               5

<210> SEQ ID NO 259
<211> LENGTH: 6
<212> TYPE: PRT
<213> ORGANISM: Artificial Sequence
<220> FEATURE:
<223> OTHER INFORMATION: Synthetic Construct

<400> SEQUENCE: 259

Val Tyr Ser Ser Gly Asn
1               5

<210> SEQ ID NO 260
<211> LENGTH: 6
<212> TYPE: PRT
<213> ORGANISM: Artificial Sequence
<220> FEATURE:
<223> OTHER INFORMATION: Synthetic Construct

<400> SEQUENCE: 260

Asp Phe Gln Ala Thr Thr
1               5

<210> SEQ ID NO 261
<211> LENGTH: 7
<212> TYPE: PRT
<213> ORGANISM: Artificial Sequence
<220> FEATURE:
<223> OTHER INFORMATION: Synthetic Construct

<400> SEQUENCE: 261

Ser Asn Glu Gly Ser Lys Ala
1               5

<210> SEQ ID NO 262
<211> LENGTH: 6
<212> TYPE: PRT
<213> ORGANISM: Artificial Sequence
<220> FEATURE:
<223> OTHER INFORMATION: Synthetic Construct

<400> SEQUENCE: 262

Asn Ser Ala Ser Gln Ser
1               5

<210> SEQ ID NO 263
<211> LENGTH: 6
<212> TYPE: PRT
<213> ORGANISM: Artificial Sequence
<220> FEATURE:
<223> OTHER INFORMATION: Synthetic Construct

<400> SEQUENCE: 263

Val Tyr Ser Ser Gly Asn
1               5

<210> SEQ ID NO 264
<211> LENGTH: 6
<212> TYPE: PRT
<213> ORGANISM: Artificial Sequence
<220> FEATURE:
<223> OTHER INFORMATION: Synthetic Construct

<400> SEQUENCE: 264

Asp Phe Gln Ala Thr Thr
1               5

<210> SEQ ID NO 265
<211> LENGTH: 7
<212> TYPE: PRT
<213> ORGANISM: Artificial Sequence
<220> FEATURE:
<223> OTHER INFORMATION: Synthetic Construct

<400> SEQUENCE: 265

Ser Asn Glu Gly Ser Lys Ala
1               5

<210> SEQ ID NO 266
<211> LENGTH: 5
<212> TYPE: PRT
<213> ORGANISM: Artificial Sequence
<220> FEATURE:
<223> OTHER INFORMATION: Synthetic Construct

<400> SEQUENCE: 266

Thr Thr Leu Ser Asn
1 5

<210> SEQ ID NO 267
<211> LENGTH: 7
<212> TYPE: PRT
<213> ORGANISM: Artificial Sequence
<220> FEATURE:
<223> OTHER INFORMATION: Synthetic Construct

<400> SEQUENCE: 267

Leu Val Lys Ser Gly Glu Val
1 5

<210> SEQ ID NO 268
<211> LENGTH: 5
<212> TYPE: PRT
<213> ORGANISM: Artificial Sequence
<220> FEATURE:
<223> OTHER INFORMATION: Synthetic Construct

<400> SEQUENCE: 268

Met Asn His Glu Tyr
1 5

<210> SEQ ID NO 269
<211> LENGTH: 6
<212> TYPE: PRT
<213> ORGANISM: Artificial Sequence
<220> FEATURE:
<223> OTHER INFORMATION: Synthetic Construct

<400> SEQUENCE: 269

Ser Val Gly Ala Gly Ile
1 5

<210> SEQ ID NO 270
<211> LENGTH: 6
<212> TYPE: PRT
<213> ORGANISM: Artificial Sequence
<220> FEATURE:
<223> OTHER INFORMATION: Synthetic Construct

<400> SEQUENCE: 270

Tyr Ser Gly Ser Pro Glu
1 5

<210> SEQ ID NO 271
<211> LENGTH: 4
<212> TYPE: PRT
<213> ORGANISM: Artificial Sequence
<220> FEATURE:
<223> OTHER INFORMATION: Synthetic Construct

<400> SEQUENCE: 271

His Ile Ser Arg
1

<210> SEQ ID NO 272
<211> LENGTH: 6
<212> TYPE: PRT
<213> ORGANISM: Artificial Sequence
<220> FEATURE:
<223> OTHER INFORMATION: Synthetic Construct

<400> SEQUENCE: 272

Gly Thr Ser Asn Pro Asn
1 5

<210> SEQ ID NO 273
<211> LENGTH: 5
<212> TYPE: PRT
<213> ORGANISM: Artificial Sequence
<220> FEATURE:
<223> OTHER INFORMATION: Synthetic Construct

<400> SEQUENCE: 273

Ser Val Gly Ile Gly
1 5

<210> SEQ ID NO 274
<211> LENGTH: 6
<212> TYPE: PRT
<213> ORGANISM: Artificial Sequence
<220> FEATURE:
<223> OTHER INFORMATION: Synthetic Construct

<400> SEQUENCE: 274

Asn Ser Ala Phe Gln Tyr
1 5

<210> SEQ ID NO 275
<211> LENGTH: 6
<212> TYPE: PRT
<213> ORGANISM: Artificial Sequence
<220> FEATURE:
<223> OTHER INFORMATION: Synthetic Construct

<400> SEQUENCE: 275

Thr Tyr Ser Ser Gly Asn
1 5

<210> SEQ ID NO 276
<211> LENGTH: 4
<212> TYPE: PRT
<213> ORGANISM: Artificial Sequence
<220> FEATURE:
<223> OTHER INFORMATION: Synthetic Construct

<400> SEQUENCE: 276

Leu Asn His Asp
1

<210> SEQ ID NO 277
<211> LENGTH: 6
<212> TYPE: PRT
<213> ORGANISM: Artificial Sequence
<220> FEATURE:
<223> OTHER INFORMATION: Synthetic Construct

<400> SEQUENCE: 277

Ser Gln Ile Val Asn Asp
1 5

<210> SEQ ID NO 278
<211> LENGTH: 6
<212> TYPE: PRT
<213> ORGANISM: Artificial Sequence
<220> FEATURE:
<223> OTHER INFORMATION: Synthetic Construct

<400> SEQUENCE: 278

Asn Ser Ala Phe Gln Tyr
1 5

<210> SEQ ID NO 279
<211> LENGTH: 6
<212> TYPE: PRT
<213> ORGANISM: Artificial Sequence
<220> FEATURE:
<223> OTHER INFORMATION: Synthetic Construct

<400> SEQUENCE: 279

Thr Tyr Ser Ser Gly Asn
1 5

<210> SEQ ID NO 280
<211> LENGTH: 5
<212> TYPE: PRT
<213> ORGANISM: Artificial Sequence
<220> FEATURE:
<223> OTHER INFORMATION: Synthetic Construct

<400> SEQUENCE: 280

Leu Asn His Asp Ala
1 5

<210> SEQ ID NO 281
<211> LENGTH: 6
<212> TYPE: PRT
<213> ORGANISM: Artificial Sequence
<220> FEATURE:
<223> OTHER INFORMATION: Synthetic Construct

<400> SEQUENCE: 281

Ser Gln Ile Val Asn Asp
1 5

<210> SEQ ID NO 282
<211> LENGTH: 6
<212> TYPE: PRT
<213> ORGANISM: Artificial Sequence
<220> FEATURE:
<223> OTHER INFORMATION: Synthetic Construct

<400> SEQUENCE: 282

Ala Thr Gly Tyr Pro Ser
1 5

<210> SEQ ID NO 283
<211> LENGTH: 7
<212> TYPE: PRT
<213> ORGANISM: Artificial Sequence
<220> FEATURE:
<223> OTHER INFORMATION: Synthetic Construct

<400> SEQUENCE: 283

Ala Thr Lys Ala Asp Asp Lys
1 5

<210> SEQ ID NO 284
<211> LENGTH: 5
<212> TYPE: PRT
<213> ORGANISM: Artificial Sequence
<220> FEATURE:
<223> OTHER INFORMATION: Synthetic Construct

<400> SEQUENCE: 284

Ser Gly Asp Leu Ser 1 5

<210> SEQ ID NO 285
<211> LENGTH: 5
<212> TYPE: PRT
<213> ORGANISM: Artificial Sequence
<220> FEATURE:
<223> OTHER INFORMATION: Synthetic Construct

<400> SEQUENCE: 285

Tyr Tyr Asn Gly Glu
1 5

<210> SEQ ID NO 286
<211> LENGTH: 6
<212> TYPE: PRT
<213> ORGANISM: Artificial Sequence
<220> FEATURE:
<223> OTHER INFORMATION: Synthetic Construct

<400> SEQUENCE: 286

Tyr Gly Ala Thr Pro Tyr
1 5

<210> SEQ ID NO 287
<211> LENGTH: 8
<212> TYPE: PRT
<213> ORGANISM: Artificial Sequence
<220> FEATURE:
<223> OTHER INFORMATION: Synthetic Construct

<400> SEQUENCE: 287

Tyr Phe Ser Gly Asp Thr Leu Val
1 5

<210> SEQ ID NO 288
<211> LENGTH: 6
<212> TYPE: PRT
<213> ORGANISM: Artificial Sequence
<220> FEATURE:
<223> OTHER INFORMATION: Synthetic Construct

<400> SEQUENCE: 288

Asp Phe Gln Ala Thr Thr
1 5

<210> SEQ ID NO 289
<211> LENGTH: 7
<212> TYPE: PRT
<213> ORGANISM: Artificial Sequence
<220> FEATURE:
<223> OTHER INFORMATION: Synthetic Construct

<400> SEQUENCE: 289

Ser Asn Glu Gly Ser Lys Ala
1 5

<210> SEQ ID NO 290
<211> LENGTH: 6
<212> TYPE: PRT
<213> ORGANISM: Artificial Sequence
<220> FEATURE:
<223> OTHER INFORMATION: Synthetic Construct

<400> SEQUENCE: 290

Ser Ser Tyr Ser Pro Ser
1 5

-continued

<210> SEQ ID NO 291
<211> LENGTH: 8
<212> TYPE: PRT
<213> ORGANISM: Artificial Sequence
<220> FEATURE:
<223> OTHER INFORMATION: Synthetic Construct

<400> SEQUENCE: 291

Tyr Thr Ser Ala Ala Thr Leu Val
1 5

<210> SEQ ID NO 292
<211> LENGTH: 5
<212> TYPE: PRT
<213> ORGANISM: Artificial Sequence
<220> FEATURE:
<223> OTHER INFORMATION: Synthetic Construct

<400> SEQUENCE: 292

Ser Glu His Asn Arg
1 5

<210> SEQ ID NO 293
<211> LENGTH: 6
<212> TYPE: PRT
<213> ORGANISM: Artificial Sequence
<220> FEATURE:
<223> OTHER INFORMATION: Synthetic Construct

<400> SEQUENCE: 293

Phe Gln Asn Glu Ala Gln
1 5

METHODS OF OBTAINING TUMOR-SPECIFIC T CELL RECEPTORS

CROSS-REFERENCE TO RELATED APPLICATIONS

This application is a divisional application of U.S. application Ser. No. 17/047,059, which adopts the international filing date of Apr. 12, 2019, now U.S. Pat. No. 11,390,659, which is a national phase filing under 35 U.S.C. § 371 of International Application No. PCT/US2019/082408, filed internationally on Apr. 12, 2019, which claims the priority benefit of International Patent Application No. PCT/CN2018/082947, filed Apr. 13, 2018, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing file name: 776902000310SEQLIST.TXT, date recorded: Jun. 15, 2022, size: 442,179 bytes).

FIELD OF THE INVENTION

The present invention relates to the field of cancer immunotherapy. In particular, this invention provides methods of obtaining TCRs, tumor-specific TCRs, engineered immune cells, pharmaceutical compositions and kits for treating cancer.

BACKGROUND OF THE INVENTION

Unlike hematological cancer, solid tumors lack cell surface antigens to be recognized by typical Chimeric Antigen Receptors (CARs). Intracellular antigens from solid tumors must be presented by HLA molecules as HLA-antigen epitope complexes on the cell surface, which are specifically recognized by T cell receptors (TCRs) on the surface of tumor-specific T cells, thereby eliciting anti-tumor cytotoxicity by the tumor-specific T cells.

By February 2018, there are 75 clinical trials on adoptive immune cells engineered with tumor-specific TCRs for treating cancer. Targets include tumor-associated antigens, tumor-associated viral antigens and neoantigens. Indicates include many common types of solid tumors. Examples of TCR-T cells currently in clinical trials include TCR-Ts targeting WT1/HLA-A*0201 complex (Juno Therapeutics) for treating acute myeloid leukemia (AML) and non-small cell lung cancer; TCR-Ts targeting MAGE-A3/A6/HLA-DPB1*0401 complex (Kite) for treating malignant solid tumors; and TCR-Ts targeting MAGE-A4/HLA-A*0201 (Adaptimmune) for treating malignant solid tumors.

The disclosures of all publications, patents, patent applications and published patent applications referred to herein are hereby incorporated herein by reference in their entirety.

BRIEF SUMMARY OF THE INVENTION

The present invention provides methods, compositions and kits for obtaining one or more T cell receptors (TCRs) that specifically recognize a tumor antigen peptide from an individual that has clinically benefitted from an immunotherapy such as Multiple Antigen Specific Cell Therapy ("MASCT").

One aspect of the present application provides a method of obtaining a plurality of T cell receptors (TCRs) specifically recognizing a target tumor antigen peptide, comprising: a) a first co-culturing step comprising co-culturing a first population of dendritic cells (DCs) loaded with the target tumor antigen peptide with a population of T cells from an individual to obtain a first co-culture; b) an enrichment step comprising subjecting the first co-culture to an enrichment process to obtain enriched activated T cells; c) a second co-culturing step comprising co-culturing the enriched activated T cells with a second population of DCs loaded with the target tumor antigen peptide to obtain a population of tumor antigen-specific T cells, wherein at least about 10% of the tumor antigen-specific T cells specifically responds to the target tumor antigen peptide; and d) a sequencing step, comprising subjecting the tumor antigen-specific T cells to next-generation sequencing to identify a plurality of pairs of genes encoding TCRα and TCRβ, thereby providing the plurality of T cell receptors based on paired genes encoding TCRα and TCRβ; wherein the individual has clinically benefitted from a Multiple Antigen Specific Cell Therapy (MASCT) comprising administering to the individual an effective amount of activated T cells prepared by co-culturing a population of T cells with a population of dendritic cells loaded with a plurality of tumor antigen peptides comprising the target tumor antigen peptide. In some embodiments, the first co-culturing step is carried out for about 1 to about 3 days prior to the enrichment step. In some embodiments, the ratio between the population of T cells to the first population of DCs loaded with the target tumor antigen peptide is no more than about 30:1 (such as about 10:1 to about 20:1, or about 15:1 or about 20:1). In some embodiments, the population of T cells in the first co-culturing step is present in PBMCs. In some embodiments, the first population of DCs loaded with the target tumor antigen peptide and the population of T cells are co-cultured in a first co-culture medium comprising one or more cytokines (e.g., IL-2 or a plurality of cytokines) and an immune checkpoint inhibitor. In some embodiments, the first co-culture medium comprises IL-2, IL-7, IL-15 and IL-21 and an anti-PD-1 antibody. In some embodiments, the first co-culture medium comprises IL-2 and an anti-PD-1 antibody.

In some embodiments according to any one of the methods described above, the enrichment step comprises contacting the first co-culture with antigen presenting cells (APCs) loaded with the target tumor antigen peptide to obtain a stimulated co-culture, and isolating from the stimulated co-culture an enriched population of activated T cells using a ligand that specifically recognizes a cytokine. In some embodiments, the cytokine is IFNγ. In some embodiments, the ratio between the enriched population of activated T cells and the second population of DCs loaded with the target tumor antigen peptide is about 1:1 to about 20:1. In some embodiments, the enriched population of activated T cells and the second population of DCs loaded with the target tumor antigen peptide are co-cultured for about 12 to 25 days.

In some embodiments according to any one of the methods described above, the second co-culturing step comprises co-culturing the second population of DCs loaded with the target tumor antigen peptide with the enriched population of activated T cells in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells. In some embodiments, the anti-CD3 antibody is added to the second co-culture no more than about 3 days after the second co-culturing step starts. In some embodiments, the anti-CD3 antibody is OKT3. In some embodiments, the one or more cytokines is added to the second co-culture no more than about 3 days (e.g., about 2 days) after the second co-culturing step starts. In some embodiments, the one or cytokines comprises IL-2. In some embodiments, the immune checkpoint inhibitor is an anti-PD-1 antibody (e.g., SHR-1210). In some embodiments, the initial second co-culture medium comprises IL-2, IL-7, IL-15 and IL-21 and an anti-PD-1 antibody.

In some embodiments according to any one of the methods described above, the method further comprises a third co-culturing step comprising co-culturing a population of the tumor antigen-specific T cells with a population of antigen presenting cells (APCs) loaded with target tumor antigen peptide to obtain a second population of tumor antigen-specific T cells, wherein the second population of tumor antigen-specific T cells are subjected to next-generation sequencing in the sequencing step. In some embodiments, the APCs are PBMCs, DCs, or cell line APCs. In some embodiments, the ratio between the population of tumor antigen-specific T cells and the population of APCs loaded with the target tumor antigen peptide is about 1:1 to about 20:1. In some embodiments, the population of tumor antigen-specific T cells and the population of APCs loaded with the target tumor antigen peptide are co-cultured for about 5 to 9 days. In some embodiments, the population of tumor antigen-specific T cells and the population of APCs loaded with the target tumor antigen peptide are co-cultured in a third co-culture medium comprising one or more cytokines (such as IL-2 or a plurality of cytokines) and an anti-CD3 antibody. In some embodiments, the third co-culture medium comprises IL-2, IL-7, IL-15 and OKT3. In some embodiments, the third co-culture medium comprises IL-2 and OKT3. In some embodiments, the third co-culturing step is repeated (e.g., once, twice or three times).

In some embodiments according to any one of the methods described above, the plurality of tumor antigen peptides is a plurality of synthetic tumor antigen peptides. In some embodiments, the plurality of tumor antigen peptides is not obtained from a cell sample.

In some embodiments according to any one of the methods described above, the plurality of tumor antigen peptides comprises general tumor antigen peptide(s), cancer-type specific antigen peptide(s), and/or neoantigen peptides. In some embodiments, the plurality of tumor antigen peptides comprises one or more neoantigen peptides. In some embodiments, the plurality of tumor antigen peptides comprises (e.g., consists of) neoantigen peptides. In some embodiments, the plurality of tumor antigen peptides comprises at least about 5 (e.g., at least about 10, 20, 30, 40 or more) different tumor antigen peptides.

In some embodiments according to any one of the methods described above, the target tumor antigen peptide is derived from a tumor antigen selected from the group consisting of hTERT, p53, Survivin, NY-ESO-1, CEA, CCND1, RGS5, MMP7, VEGFR1, VEGFR2, MUC1, HER2, MAGE-A1, MAGE-A3, CDCA1, WT1, KRAS, PARP4, MLL3, MTHFR, HPV16-E6, HPV16-E7, HPV18-E6, HPV18-E7, HPV58-E6, HPV58-E7, HBcAg, HBV polymerase, GPC3, SSX, and AFP.

In some embodiments according to any one of the methods described above, the method further comprises identifying a target tumor epitope from the target tumor antigen peptide, wherein the target tumor epitope elicits specific response by the enriched population of activated T cells, and contacting a population of APCs with the target tumor epitope to obtain the population of APCs loaded with the target tumor antigen peptide.

In some embodiments according to any one of the methods described above, the next-generation sequencing is single cell sequencing. In some embodiments, the next-generation sequencing is bulk sequencing. In some embodiments, the sequencing step comprises sequencing a bulk sample of the tumor antigen-specific T cells, and single-cell sequencing of a plurality of the tumor antigen-specific T cells. In some embodiments, the sequencing step comprises bulk sequencing of a first portion of the tumor antigen-specific T cells to provide a plurality of genes encoding TCRα and TCRβ, and single-cell sequencing of a second portion of the tumor antigen-specific T cells providing cognate pairing information of the plurality of genes encoding TCRα and TCRβ, thereby providing a plurality of TCRs based on paired genes encoding TCRα and TCRβ. In some embodiments, the tumor antigen-specific T cells are stimulated with APCs loaded with the target tumor antigen peptide prior to the next-generation sequencing.

In some embodiments according to any one of the methods described above, the individual has partial response (PR), complete response (CR), or stable disease (SD) after receiving the MASCT. In some embodiments, the MASCT comprises: co-culturing a population of DCs loaded with a plurality of tumor antigen peptides comprising the target tumor antigen peptide and a population of T cells to obtain a population of activated T cells. In some embodiments, the MASCT comprises: (i) co-culturing a population of DCs loaded with a plurality of tumor antigen peptides comprising the target tumor antigen peptide and a population of T cells in an initial co-culture medium comprising one or more (e.g., a plurality of cytokines) and an immune checkpoint inhibitor to provide a co-culture; and (ii) adding an anti-CD3 antibody to the co-culture at about 3 to 7 days after the co-culturing starts, thereby obtaining the population of activated T cells. In some embodiments, the MASCT comprises: (i) contacting a population of DCs with a plurality of tumor antigen peptides comprising the target tumor antigen peptide to obtain a population of DCs loaded with the plurality of tumor antigen peptides; and (ii) culturing the population of DCs loaded with the plurality of tumor antigen peptides in a DC maturation medium comprising MPLA. In some embodiments, the DC maturation medium comprises INFγ, MPLA and PGE2. In some embodiments, the MASCT comprises administering to the individual an effective amount of the DCs loaded with the plurality of tumor antigen peptides. In some embodiments, the individual has previously received the MASCT for at least three times.

In some embodiments according to any one of the methods described above, TCRs specifically recognizing a plurality of target tumor antigen peptides are obtained in parallel.

In some embodiments according to any one of the methods described above, the method further comprises expressing each pair of genes encoding TCRα and TCRβ in a host immune cell to provide an engineered immune cell expressing a TCR, and assessing response of the engineered immune cell to the target tumor antigen peptide. Further provided is a method of obtaining a TCR specifically recognizing a target tumor antigen peptide using the method above, wherein the TCR is selected based on the response of the engineered immune cell expressing the TCR to the target tumor antigen peptide. In some embodiments, the method further comprises determining HLA restriction of the TCR. In some embodiments, the TCR has a HLA haplotype restriction that is predominant in Asians. In some embodiments, the method further comprises affinity maturation of the TCR. In some embodiments, the method further comprises enhancing the paring of the TCRα and TCRβ chains in the TCR. In some embodiments, the method further comprises enhancing the expression of the TCR. In some embodiments, the target tumor antigen peptide is derived from CEA, RSG-5 or HPV18-E7.

Also provided is a tumor-specific TCR obtained using any one of the methods described above.

Another aspect of the present application provides a tumor-specific TCR comprising: (a) a TCRα chain comprising a complementary determining region (CDR) 3 having at least about 90% sequence identity to any one of the amino acid sequences of SEQ ID NOs: 4, 10, and 16; and a TCRβ chain comprising a CDR3 comprising an amino acid sequence having at least about 90% sequence identity to any one of the amino acid sequences of SEQ ID NOs: 7, 13, and 19; (b) a TCRα chain comprising a complementary determining region (CDR) 3 having at least about 90% sequence identity to any one of the amino acid sequences of SEQ ID NOs: 22, 28, 34, 40, 46, and 52; and a TCRβ chain comprising a CDR3 comprising an amino acid sequence having at least about 90% sequence identity to any one of the amino acid sequences of SEQ ID NOs: 7, 13, 19, 25, 31, 37, 43, 49, and 55; or (c) a TCRα chain comprising a complementary determining region (CDR) 3 having at least about 90% sequence identity to any one of the amino acid sequences of SEQ ID NOs: 58, 64, 70, 76, 87 and 93; and a TCRβ chain comprising a CDR3 comprising an amino acid sequence having at least about 90% sequence identity to any one of the amino acid sequences of SEQ ID NOs: 61, 67, 73, 79, 90 and 96.

In some embodiments, the tumor-specific TCR comprises: (a) a TCRα chain comprising a CDR3 comprising the amino acid sequence of SEQ ID NO: 4, and a TCRβ chain comprising a CDR3 comprising the amino acid sequence of SEQ ID NO: 7; (b) a TCRα chain comprising a CDR3 comprising the amino acid sequence of SEQ ID NO: 10, and a TCRβ chain comprising a CDR3 comprising the amino acid sequence of SEQ ID NO: 13; (c) a TCRα chain comprising a CDR3 comprising the amino acid sequence of SEQ ID NO: 16, and a TCRβ chain comprising a CDR3 comprising the amino acid sequence of SEQ ID NO: 19; (d) a TCRα chain comprising a CDR3 comprising the amino acid sequence of SEQ ID NO: 22, and a TCRβ chain comprising a CDR3 comprising the amino acid sequence of SEQ ID NO: 25; (e) a TCRα chain comprising a CDR3 comprising the amino acid sequence of SEQ ID NO: 28, and a TCRβ chain comprising a CDR3 comprising the amino acid sequence of SEQ ID NO: 31; (f) a TCRα chain comprising a CDR3 comprising the amino acid sequence of SEQ ID NO: 34, and a TCRβ chain comprising a CDR3 comprising the amino acid sequence of SEQ ID NO: 37; (g) a TCRα chain comprising a CDR3 comprising the amino acid sequence of SEQ ID NO: 40, and a TCRβ chain comprising a CDR3 comprising the amino acid sequence of SEQ ID NO: 43; (h) a TCRα chain comprising a CDR3 comprising the amino acid sequence of SEQ ID NO: 46, and a TCRβ chain comprising a CDR3 comprising the amino acid sequence of SEQ ID NO: 49; (i) a TCRα chain comprising a CDR3 comprising the amino acid sequence of SEQ ID NO: 52, and a TCRβ chain comprising a CDR3 comprising the amino acid sequence of SEQ ID NO: 55; (j) a TCRα chain comprising a CDR3 comprising the amino acid sequence of SEQ ID NO: 58, and a TCRβ chain comprising a CDR3 comprising the amino acid sequence of SEQ ID NO: 61; (k) a TCRα chain comprising a CDR3 comprising the amino acid sequence of SEQ ID NO: 64, and a TCRβ chain comprising a CDR3 comprising the amino acid sequence of SEQ ID NO: 67; (l) a TCRα chain comprising a CDR3 comprising the amino acid sequence of SEQ ID NO: 70, and a TCRβ chain comprising a CDR3 comprising the amino acid sequence of SEQ ID NO: 73; (m) a TCRα chain comprising a CDR3 comprising the amino acid sequence of SEQ ID NO: 76, and a TCRβ chain comprising a CDR3 comprising the amino acid sequence of SEQ ID NO: 79; (n) a TCRα chain comprising a CDR3 comprising the amino acid sequence of SEQ ID NO: 87, and a TCRβ chain comprising a CDR3 comprising the amino acid sequence of SEQ ID NO: 90; or (o) a TCRα chain comprising a CDR3 comprising the amino acid sequence of SEQ ID NO: 93, and a TCRβ chain comprising a CDR3 comprising the amino acid sequence of SEQ ID NO: 96.

Further provided is a tumor-specific TCR comprising: (a) a TCRα chain comprising CDRs of any one of the amino acid sequences of SEQ ID NOs: 5, 11 and 17, and a TCRβ chain comprising CDRs of any one of the amino acid sequences of SEQ ID NOs: 8, 14 and 20; (b) a TCRα chain comprising CDRs of any one of the amino acid sequences of SEQ ID NOs: 23, 29, 35, 41, 47 and 53, and a TCRβ chain comprising CDRs of any one of the amino acid sequences of SEQ ID NOs: 26, 32, 38, 44, 50 and 56; or (c) a TCRα chain comprising CDRs of any one of the amino acid sequences of SEQ ID NOs: 59, 65, 71, 77, 88 and 94, and a TCRβ chain comprising CDRs of any one of the amino acid sequences of SEQ ID NOs: 62, 68, 74, 80, 91 and 97.

In some embodiments according to any one of the tumor-specific TCRs described above, the tumor-specific TCR is a human TCR. In some embodiments, the tumor-specific TCR is a chimeric TCR, such as a murinized TCR, e.g., a TCR comprising murine constant regions of TCRα and β chains.

In some embodiments according to any one of the tumor-specific TCRs described above, the tumor-specific TCR comprises: (a) a TCRα chain comprising an amino acid sequence having at least about 80% identity to any one of the amino acid sequences of SEQ ID NOs: 5, 11 and 17, and a TCRβ chain comprising an amino acid sequence having at least about 80% identity to any one of the amino acid sequences of SEQ ID NOs: 8, 14 and 20; (b) a TCRα chain comprising an amino acid sequence having at least about 80% identity to any one of the amino acid sequences of SEQ ID NOs: 23, 29, 35, 41, 47 and 53, and a TCRβ chain comprising an amino acid sequence having at least about 80% identity to any one of the amino acid sequences of SEQ ID NOs: 26, 32, 38, 44, 50 and 56; or (c) a TCRα chain comprising an amino acid sequence having at least about 80% identity to any one of the amino acid sequences of SEQ ID NOs: 59, 65, 71, 77, 88 and 94, and a TCRβ chain comprising an amino acid sequence having at least about 80% identity to any one of the amino acid sequences of SEQ ID NOs: 62, 68, 74, 80, 91 and 97.

Also provided is an isolated nucleic acid encoding the TCRα chain and/or the TCRβ chain of the tumor-specific TCR according to any one of the tumor-specific TCRs described above, a vector comprising the isolated nucleic acid(s).

One aspect of the present application provides an engineered immune cell comprising the tumor-specific TCR according to any one of the tumor-specific TCRs, the isolated nucleic acids, or the vectors described above.

In some embodiments, the immune cell is a T cell. In some embodiments, there is provided a pharmaceutical composition comprising the engineered immune cell according to any one of the engineered immune cells described above, and a pharmaceutically acceptable carrier.

In some embodiments, there is provided a method of treating a cancer in an individual, comprising administering to the individual an effective amount of the pharmaceutical composition according to any one of the pharmaceutical compositions described above.

In some embodiments, there is provided a library of tumor-specific TCRs obtained using the method according to any one of the methods described above.

Further provided are kits, medicines, and articles of manufacture comprising any one of the compositions (such as isolated nucleic acids, vectors and engineered immune cells) as described above.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE DRAWINGS

FIG. 3B shows consistently strong immune response by the patient's PBMCs against the HPV18-E7, RGS-5 and CEA peptides.

FIG. 12 summarizes the numbers of unique clonotypes of TCRα and TCRβ sequences that may be specific for CEA, RGS5 and HPV18-E7 peptides respectively from tumor-antigen specific T cell preparations using different samples of PBMCs from a patient who has clinically benefitted from MASCT. The clonotypes were selected based on the expression frequency patterns in the various samples as shown in FIG. 11. The results were obtained by next-generation sequencing of bulk T cell samples.

FIGS. 25A-25B show compositions and sequences of exemplary TCR constructs.

FIGS. 28A-28C show validation results of 09B12 and related TCR constructs. The sequences in FIG. 28B are, from top to bottom: SEQ ID NO 86, and aa1-15, aa5-19, aa9-23, aa13-27, aa16-30 of SEQ ID NO 86, and SEQ ID NO 85.

FIGS. 29A-29C show validation results of 09E01 and related TCR constructs.

DETAILED DESCRIPTION OF THE INVENTION

Figure 1:
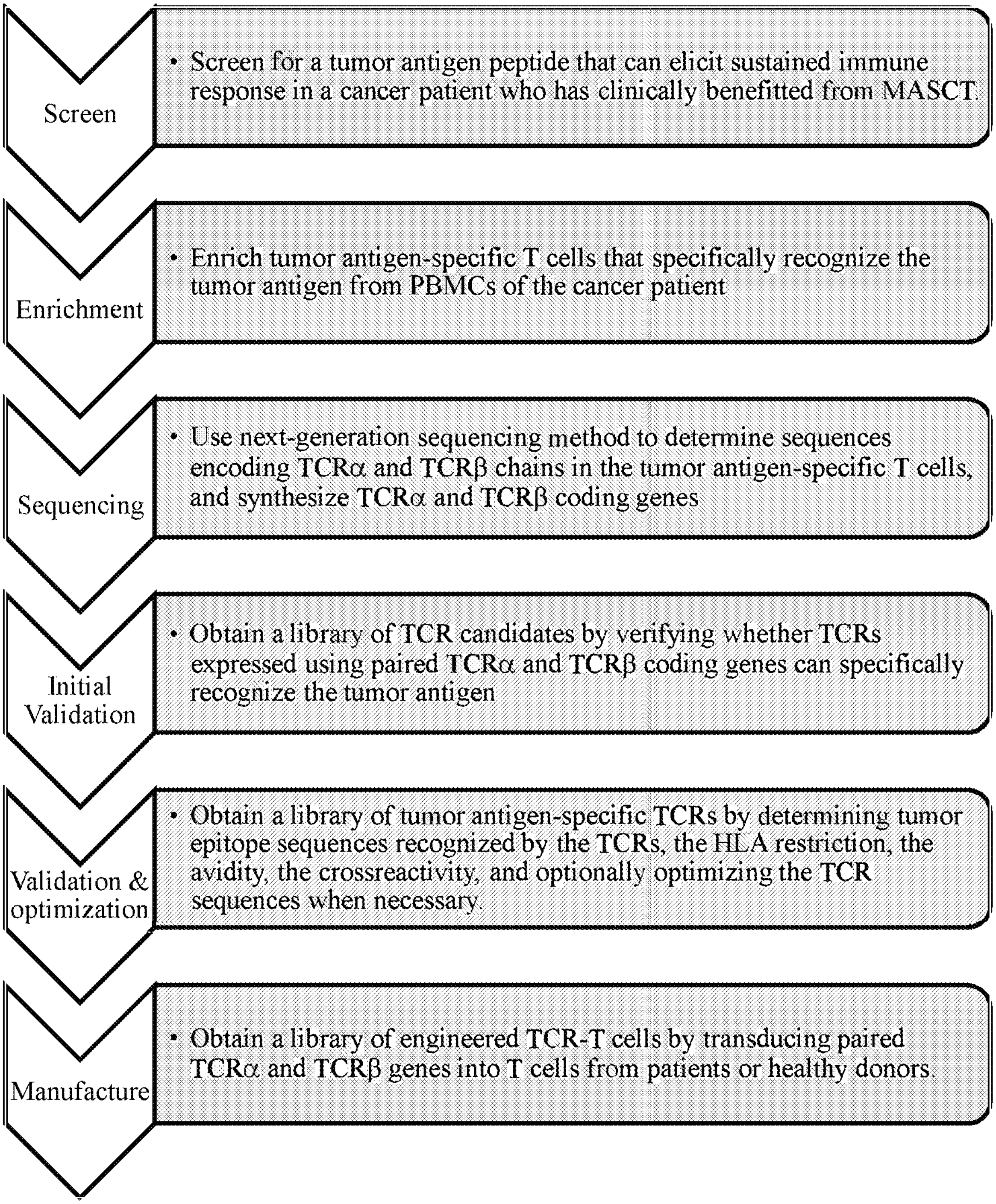
FIG. 1 shows an overview of an exemplary method for cloning a plurality of TCRs specifically recognizing a target tumor antigen peptide.

The present application provides a platform for cloning a plurality of T cell receptors (TCRs) specifically recognizing one or more tumor antigen peptides using PBMCs or T cells from an individual who has clinically benefitted from an immunotherapy, such as Multiple Antigen Specific Cell Therapy ("MASCT"). The methods described herein comprise enrichment of activated T cells from a co-culture of T cells with antigen-loaded dendritic cells ("DCs"), followed by co-culturing of the enriched activated T cells with antigen-loaded DCs to provide tumor antigen-specific T cells for bulk and/or single-cell sequencing to obtain a plurality of paired TCRα and TCRβ genes. The source of T cells, as well as the enrichment and co-culturing steps in the methods described herein contribute to the high percentage (e.g., at least about 1% or higher for bulk sequencing of T cell samples, or at least 10% or higher for single-T cell sequencing) of tumor antigen-specific T cells that respond specifically to the target tumor antigen peptide, which is essential for obtaining cognate pairing information for the TCRα and TCRβ genes of predominant TCR clonotypes by next-generation sequencing. Tumor specific TCRs, engineered immune cells expressing the TCRs and methods of treating cancer using the engineered immune cells are also provided.

TCRs currently under development and in clinical trials in the field are typically cloned from PBMCs of healthy human donors, which are stimulated with pre-determined tumor antigen epitope peptides. As a result, clinical response in patients treated with T cells expressing such TCRs is unpredictable. In contrast, the TCRs of the present application are obtained from individuals who have clinically benefitted from MASCT treatment, indicating anti-tumor potential of TCRs targeting the tumor antigen epitope(s) contained in the target tumor antigen peptides.

Additionally, currently known TCRs cloned from PBMCs of healthy human donors have low affinity to their target tumor antigen epitope-HLA complexes. Optimization of the amino acid sequences of the TCRα and TCRβ chains are needed to improve the affinity of the TCRs, which increases the risk of cross-reaction of the TCRs, off-target side effects and severe toxicity. In contrast, because the TCRs of the present application are cloned with cancer patients who have demonstrated clinical response, the TCRs described herein may not require affinity optimization, and thus promises improved safety profile in the clinics.

In some embodiments, TCRs are cloned from individuals of a racial group in order to provide TCRs having HLA restrictions that reflect the predominant HLA haplotypes of the racial group. Most of the TCRs in clinical trials today are HLA-restrictive for haplotypes, such as HLA-DPB1*0401 and HLA-A*0201, that are predominant in Caucasian populations. The methods described herein may be used to obtain TCRs that are HLA-restrictive for any a racial group of interest, including, for example, HLA-A*1101 or HLA-A*2402-restrictive TCRs that may be more efficacious for treatment of Asian patients.

Accordingly, one aspect of the present application provides a method of obtaining a plurality of T cell receptors (TCRs) specifically recognizing a target tumor antigen peptide, comprising: a) a first co-culturing step comprising co-culturing a first population of dendritic cells (DCs)

loaded with the target tumor antigen peptide with a population of T cells from an individual to obtain a first co-culture; b) an enrichment step comprising subjecting the first co-culture to an enrichment process to obtain enriched activated T cells; c) a second co-culturing step comprising co-culturing the enriched activated T cells with a second population of DCs loaded with the target tumor antigen peptide to obtain a population of tumor antigen-specific T cells, wherein at least about 10% (e.g., at least about 20%, or at least about 50%) of the tumor antigen-specific T cells specifically responds to the target tumor antigen peptide; and d) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; wherein the individual has clinically benefitted from a Multiple Antigen Specific Cell Therapy ("MASCT") comprising administering to the individual an effective amount of activated T cells prepared by co-culturing a population of T cells with a population of dendritic cells loaded with a plurality of tumor antigen peptides comprising the target tumor antigen peptide. In some embodiments, TCRs specifically recognizing a plurality of target tumor antigens are obtained in parallel in the method.

I. Definitions

Terms are used herein as generally used in the art, unless otherwise defined as follows.

As used herein, "a plurality of tumor antigen peptides," "multiple tumor antigen peptides," "a pool of tumor antigen peptides" and "a tumor antigen peptides pool" are used interchangeably to refer to a combination of two or more tumor antigen peptides.

As used herein, "antigen presenting cells loaded with a plurality of tumor antigen peptides" and "antigen presenting cells loaded with one or more tumor antigen peptides" are also referred to as "antigen-loaded antigen presenting cells." Antigen presenting cells ("APCs") loaded with a plurality of tumor antigen peptides are APCs that have enhanced presentation of one or more tumor antigen peptides or fragments thereof among the plurality of tumor antigen peptides. In some embodiments, the antigen-loaded APCs are antigen-loaded DCs. In some embodiments, the antigen-loaded APCs are antigen-loaded PBMCs.

As used herein, "activated T cells" refer to a population of monoclonal (e.g. encoding the same TCR) or polyclonal (e.g. with clones encoding different TCRs) T cells that have T cell receptors that recognize at least one tumor antigen peptide. Activated T cells may contain one or more subtypes of T cells, including, but not limited to, cytotoxic T cells, helper T cells, natural killer T cells, γδ T cells, regulatory T cells, and memory T cells.

"Tumor antigen-specific T cells" and "tumor specific T cells" are used herein interchangeably.

As used herein, "T cell receptor" or "TCR" refers to an endogenous or engineered T cell receptor comprising an extracellular antigen binding domain that binds to a specific antigen epitope bound in an MHC molecule. A TCR may comprise a TCRα polypeptide chain and a TCRβ polypeptide chain. "Tumor-specific TCR" refers to a TCR that specifically recognizes a tumor antigen expressed by a tumor cell. "TCR-T" refers to a T cell that expresses a recombinant TCR.

As used herein, "immune checkpoint inhibitor" refers to an agent (including an antibody) that inhibits or blocks an inhibitory immune checkpoint molecule on an immune cell (such as T cell) or a tumor cell. "Immune checkpoint molecules" include molecules that turn up an immune signal (i.e., "co-stimulatory molecules"), or molecules that turn down an immune signal (i.e., "inhibitory immune checkpoint molecules") against a tumor cell.

As used herein, "treatment" or "treating" is an approach for obtaining beneficial or desired results including clinical results. For purposes of this invention, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread (e.g., metastasis) of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The terms "individual," "subject" and "patient" are used interchangeably herein to describe a mammal, including humans. An individual includes, but is not limited to, human, bovine, horse, feline, canine, rodent, or primate. In some embodiments, the individual is human. In some embodiments, an individual suffers from a disease, such as cancer. In some embodiments, the individual is in need of treatment.

As is understood in the art, an "effective amount" refers to an amount of a composition (e.g. antigen-loaded DCs, activated T cells or engineered immune cells expressing TCRs) sufficient to produce a desired therapeutic outcome (e.g., reducing the severity or duration of, stabilizing the severity of, or eliminating one or more symptoms of cancer). For therapeutic use, beneficial or desired results include, e.g., decreasing one or more symptoms resulting from the disease (biochemical, histologic and/or behavioral), including its complications and intermediate pathological phenotypes presented during development of the disease, increasing the quality of life of those suffering from the disease, decreasing the dose of other medications required to treat the disease, enhancing effect of another medication, delaying the progression of the disease, and/or prolonging survival of patients.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "combination therapy" means that a first agent is administered in conjunction with another agent. "In conjunction with" refers to administration of one treatment modality in addition to another treatment modality, such as administration of a composition described herein (e.g. antigen-loaded DCs, activated T cells or engineered immune cells expressing TCRs) in addition to administration of another agent (such as an immune checkpoint inhibitor) to the same individual. As such, "in conjunction with" refers to administration of one treatment modality before, during, or after delivery of the other treatment modality to the individual. Such combinations are considered to be part of a single treatment regimen or regime.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to an individual without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The following definitions may be used to evaluate response based on target lesions: "complete response" or "CR" refers to disappearance of all target lesions; "partial response" or "PR" refers to at least a 30% decrease in the sum of the longest diameters (SLD) of target lesions, taking as reference the baseline SLD; "stable disease" or "SD" refers to neither sufficient shrinkage of target lesions to qualify for PR, nor sufficient increase to qualify for PD, taking as reference the nadir SLD since the treatment started; and "progressive disease" or "PD" refers to at least a 20% increase in the SLD of target lesions, taking as reference the nadir SLD recorded since the treatment started, or, the presence of one or more new lesions.

The following definitions of response assessments may be used to evaluate anon-target lesion: "complete response" or "CR" refers to disappearance of all non-target lesions; "stable disease" or "SD" refers to the persistence of one or more non-target lesions not qualifying for CR or PD; and "progressive disease" or "PD" refers to the "unequivocal progression" of existing non-target lesion(s) or appearance of one or more new lesion(s) is considered progressive disease (if PD for the individual is to be assessed for a time point based solely on the progression of non-target lesion(s), then additional criteria are required to be fulfilled.

As used herein, the terms "cell", "cell line", and "cell culture" are used interchangeably and all such designations include progeny. It is understood that all progeny may not be precisely identical in DNA content, due to deliberate or inadvertent mutations. Variant progeny that have the same function or biological activity as the original cells are included.

The term "peptide" refers to a polymer of amino acids no more than about 100 amino acids (including fragments of a protein), which may be linear or branched, comprise modified amino acids, and/or be interrupted by non-amino acids. The term also encompasses an amino acid polymer that has been modified naturally or by intervention, including, for example, disulfide bond formation, glycosylation, lipidation, acetylation, phosphorylation, or any other manipulation or modification. Also included within this term are, for example, peptides containing one or more analogs of an amino acid (including, for example, unnatural amino acids, etc.), as well as other modifications known in the art. The peptides described herein may be naturally-occurring, i.e., obtained or derived from a natural source (e.g., blood) or synthesized (e.g., chemically synthesized or by synthesized by recombinant DNA techniques).

The term "antibody" used herein is used in the broadest sense and specifically covers monoclonal antibodies (including full length monoclonal antibodies), multispecific antibodies (e.g., bispecific antibodies), and antibody fragments so long as they exhibit the desired biological activity.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragments.

As use herein, the term "specifically binds to," "recognizes," "specifically recognizes," "targets," or is "specific for" refers to measurable and reproducible interactions such as binding between a target and an antibody, or a receptor and a ligand, or a receptor and an epitope/MHC complex, which is determinative of the presence of the target in the presence of a heterogeneous population of molecules including biological molecules. For example, a TCR that binds to or specifically binds to a target epitope is a TCR that binds the target epitope/MHC complex with greater affinity, avidity, more readily, and/or with greater duration than it binds to other epitope/MHC complexes. In one embodiment, the extent of binding of a TCR to an unrelated epitope/MHC complex is less than about 10% of the binding of the TCR to the target epitope/MHC complex as measured, e.g., by a radioimmunoassay (RIA). In certain embodiments, a TCR that specifically binds to a target epitope (i.e., target epitope/MHC complex) has a dissociation constant (Kd) of ≤1 μM, ≤100 nM, ≤10 nM, ≤1 nM, or ≤0.1 nM. In certain embodiments, a TCR specifically binds to an epitope on a protein that is conserved among the protein from different species. In another embodiment, specific binding can include, but does not require exclusive binding.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

The term "about X-Y" used herein has the same meaning as "about X to about Y."

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "an," and "the" include plural referents unless the context clearly dictates otherwise.

II. Methods of Obtaining Tumor-Specific TCRs

The present application provides methods of obtaining a plurality of T cell receptors (TCRs) specifically recognizing one or more target tumor antigen peptides from PBMCs or T cells of an individual that has clinically benefitted from an immunotherapy. In some embodiments, the immunotherapy is adoptive T cell therapy comprising administering to the individual an effective amount of activated T cells that specifically recognizes the target tumor antigen peptides or fragments thereof. In some embodiments, the immunotherapy is Multiple Antigen Specific Cell Therapy ("MASCT") comprising administering to the individual an effective amount of activated T cells prepared by co-culturing a population of T cells with a population of dendritic cells loaded with a plurality of tumor antigen peptides comprising one or more target tumor antigen peptides. In some embodiments, TCRs specifically recognizing a single target tumor antigen peptide or a fragment thereof (e.g., a target tumor epitope) are obtained. In some embodiments, TCRs specifically recognizing a plurality of target tumor antigen peptides are obtained simultaneously using the method.

In some embodiments, there is provided a method of obtaining a plurality of TCRs specifically recognizing a target tumor antigen peptide, comprising: subjecting a population of tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; wherein at least about 10% (e.g., at least about 20%, or at least about 50%) of the tumor antigen-specific T cells specifically responds to the target tumor antigen peptide; wherein the population of tumor antigen-specific T cells is prepared by: i) a first co-culturing step comprising co-culturing a first population of DCs loaded with the target tumor antigen peptide with a population of T cells from an individual to obtain a first co-culture; ii) an enrichment step comprising subjecting the first co-culture to an enrichment process to obtain enriched activated T cells; and iii) a second co-culturing step comprising co-culturing the enriched activated T cells with a second population of DCs loaded with the target tumor antigen peptide to obtain a population of tumor antigen-specific T cells; and wherein the individual has clinically benefitted from a Multiple Antigen Specific Cell Therapy ("MASCT") comprising administering to the individual an effective amount of activated T cells prepared by co-culturing a population of T cells with a population of DCs loaded with a plurality of tumor antigen peptides comprising the target tumor antigen peptide.

In some embodiments, there is provided a method of obtaining a plurality of TCRs specifically recognizing a target tumor antigen peptide, comprising: a) co-culturing an enriched population of activated T cells with a second population of DCs loaded with the target tumor antigen peptide to obtain a population of tumor antigen-specific T cells, wherein at least about 10% (e.g., at least about 20%, or at least about 50%) of the tumor antigen-specific T cells specifically responds to the target tumor antigen peptide; and b) subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; wherein the enriched population of activated T cells is prepared by: i) a first co-culturing step comprising co-culturing a first population of DCs loaded with the target tumor antigen peptide with a population of T cells from an individual to obtain a first co-culture; and ii) an enrichment step comprising subjecting the first co-culture to an enrichment process to obtain enriched activated T cells; and wherein the individual has clinically benefitted from a Multiple Antigen Specific Cell Therapy ("MASCT") comprising administering to the individual an effective amount of activated T cells prepared by co-culturing a population of T cells with a population of DCs loaded with a plurality of tumor antigen peptides comprising the target tumor antigen peptide.

In some embodiments, there is provided a method of obtaining a plurality of TCRs specifically recognizing a target tumor antigen peptide, comprising: a) subjecting the a first co-culture comprising a first population of DCs loaded with the target tumor antigen peptide and a population of T cells from an individual to an enrichment process to obtain enriched activated T cells; b) co-culturing the enriched activated T cells with a second population of DCs loaded with the target tumor antigen peptide to obtain a population of tumor antigen-specific T cells, wherein at least about 10% (e.g., at least about 20%, or at least about 50%) of the tumor antigen-specific T cells specifically responds to the target tumor antigen peptide; and c) subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; and wherein the individual has clinically benefitted from a Multiple Antigen Specific Cell Therapy ("MASCT") comprising administering to the individual an effective amount of activated T cells prepared by co-culturing a population of T cells with a population of DCs loaded with a plurality of tumor antigen peptides comprising the target tumor antigen peptide.

In some embodiments, there is provided a method of obtaining a plurality of TCRs specifically recognizing a target tumor antigen peptide, comprising: a) a first co-culturing step comprising co-culturing a first population of DCs loaded with the target tumor antigen peptide with a population of T cells from an individual to obtain a first co-culture; b) an enrichment step comprising subjecting the first co-culture to an enrichment process to obtain enriched activated T cells; c) a second co-culturing step comprising co-culturing the enriched activated T cells with a second population of DCs loaded with the target tumor antigen peptide to obtain a population of tumor antigen-specific T cells, wherein at least about 10% (e.g., at least about 20%, or at least about 50%) of the tumor antigen-specific T cells specifically responds to the target tumor antigen peptide; and d) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; wherein the individual has clinically benefitted from a Multiple Antigen Specific Cell Therapy ("MASCT") comprising administering to the individual an effective amount of activated T cells prepared by co-culturing a population of T cells with a population of DCs loaded with a plurality of tumor antigen peptides comprising the target tumor antigen peptide. In some embodiments, the first co-culturing step is carried out for about 1 to about 3 days prior to the enrichment step. In some embodiments, the ratio between the population of T cells to the first population of antigen-loaded DCs is no more than about 30:1 (e.g., about 20:1, 15:1 or 10:1). In some embodiments, the population of T cells in the first co-culturing step is present in PBMCs. In some embodiments, the first population of DCs loaded with the target tumor antigen peptide and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody, such as SHR-1210). In some embodiments, the first co-culture medium comprises IL-2 and an anti-PD-1 antibody. In some embodiments, the ratio between the enriched population of activated T cells and the second population of DCs loaded with the target tumor antigen peptide is about 1:1 to about 20:1 (e.g., about 1:1, 2:1 or 4:1). In some embodiments, the enriched population of activated T cells and the second population of DCs loaded with the target tumor antigen peptide are co-cultured for about 12 to 25 days. In some embodiments, the individual has response (PR), complete response (CR), or stable disease (SD) for at least about 6 months (e.g., at least about 1 year, 2 years, or more) after receiving the MASCT.

In some embodiments, there is provided a method of obtaining a plurality of TCRs specifically recognizing a target tumor antigen peptide, comprising: a) a first co-culturing step comprising co-culturing a first population of DCs loaded with the target tumor antigen peptide with a population of T cells from an individual to obtain a first co-culture; b) an enrichment step comprising contacting the first co-culture with APCs (e.g., DCs or PBMCs) loaded with the target tumor antigen peptide to obtain a stimulated co-culture, and isolating from the stimulated co-culture an enriched population of activated T cells using a ligand that specifically recognizes a cytokine or cell surface molecule; c) a second co-culturing step comprising co-culturing the enriched activated T cells with a second population of DCs loaded with the target tumor antigen peptide to obtain a population of tumor antigen-specific T cells, wherein at least about 10% (e.g., at least about 20%, or at least about 50%) of the tumor antigen-specific T cells specifically responds to the target tumor antigen peptide; and d) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; wherein the individual has clinically benefitted from a Multiple Antigen Specific Cell Therapy ("MASCT") comprising administering to the individual an effective amount of activated T cells prepared by co-culturing a population of T cells with a population of DCs loaded with a plurality of tumor antigen peptides comprising the target tumor antigen peptide. In some embodiments, the enrichment step comprises contacting the first co-culture with APCs (e.g., DCs or PBMCs) loaded with the target tumor antigen peptide to obtain a stimulated co-culture, and isolating from the stimulated co-culture an enriched population of activated T cells using a ligand that specifically recognizes IFNγ. In some embodiments, the first co-culturing step is carried out for about 1 to about 3 days prior to the enrichment step. In some embodiments, the ratio between the population of T cells to the first population of antigen-loaded DCs is no more than about 30:1 (e.g., about 20:1, 15:1 or 10:1). In some embodiments, the population of T cells in the first co-culturing step is present in PBMCs. In some embodiments, the first population of DCs loaded with the target tumor antigen peptide and the population of T cells are co-cultured in a first co-culture medium comprising a plurality of cytokines (e.g., IL-2, IL-7, IL-15 and IL-21) and an immune checkpoint inhibitor (e.g., anti-PD-1 antibody, such as SHR-1210). In some embodiments, the ratio between the enriched population of activated T cells and the second population of DCs loaded with the target tumor antigen peptide is about 1:1 to about 20:1 (e.g., about 1:1, 2:1 or 4:1). In some embodiments, the enriched population of activated T cells and the second population of DCs loaded with the target tumor antigen peptide are co-cultured for about 12 to 25 days. In some embodiments, the individual has response (PR), complete response (CR), or stable disease (SD) after receiving the MASCT.

In some embodiments, there is provided a method of obtaining a plurality of TCRs specifically recognizing a target tumor antigen peptide, comprising: a) a first co-culturing step comprising co-culturing a first population of DCs loaded with the target tumor antigen peptide with a population of T cells from an individual to obtain a first co-culture; b) an enrichment step comprising subjecting the first co-culture to an enrichment process to obtain enriched activated T cells; c) a second co-culturing step co-culturing a second population of DCs loaded with the target tumor antigen peptide with the enriched population of activated T cells in an initial second co-culture medium comprising an immune checkpoint inhibitor and optionally one or more cytokines (e.g., a plurality of cytokines) to provide a second co-culture; and adding an anti-CD3 (e.g., OKT-3) antibody and optionally one or more cytokines to the second co-culture to obtain a population of tumor antigen-specific T cells, wherein at least about 10% (e.g., at least about 20%, or at least about 50%) of the tumor antigen-specific T cells specifically responds to the target tumor antigen peptide; and d) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; wherein the individual has clinically benefitted from a Multiple Antigen Specific Cell Therapy ("MASCT") comprising administering to the individual an effective amount of activated T cells prepared by co-culturing a population of T cells with a population of DCs loaded with a plurality of tumor antigen peptides comprising the target tumor antigen peptide. In some embodiments, the first co-culturing step is carried out for about 1 to about 3 days prior to the enrichment step. In some embodiments, the ratio between the population of T cells to the first population of antigen-loaded DCs is no more than about 30:1 (e.g., about 20:1, 15:1 or 10:1). In some embodiments, the population of T cells in the first co-culturing step is present in PBMCs. In some embodiments, the first population of DCs loaded with the target tumor antigen peptide and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody, such as SHR-1210). In some embodiments, the enrichment step comprises contacting the first co-culture with APCs (e.g., DCs or PBMCs) loaded with the target tumor antigen peptide to obtain a stimulated co-culture, and isolating from the stimulated co-culture an enriched population of activated T cells using a ligand that specifically recognizes a cytokine (e.g., IFNγ) or a cell surface molecule. In some embodiments, the ratio between the enriched population of activated T cells and the second population of DCs loaded with the target tumor antigen peptide is about 1:1 to about 20:1 (e.g., about 1:1, 2:1 or 4:1). In some embodiments, the enriched population of activated T cells and the second population of DCs loaded with the target tumor antigen peptide are co-cultured for about 12 to 25 days. In some embodiments, the anti-CD3 antibody is added to the second co-culture no more than about 3 days (e.g., about 2 days) after the second co-culturing step starts. In some embodiments, the initial second co-culture medium comprises IL-2, IL-7, IL-15 and IL-21 and an anti-PD-1 antibody. In some embodiments, the individual has response (PR), complete response (CR), or stable disease (SD) after receiving the MASCT.

In some embodiments, there is provided a method of obtaining a plurality of TCRs specifically recognizing a target tumor antigen peptide, comprising: a) a first co-culturing step comprising co-culturing a first population of DCs loaded with the target tumor antigen peptide with a population of T cells from an individual to obtain a first co-culture; b) an enrichment step comprising subjecting the first co-culture to an enrichment process to obtain enriched activated T cells; c) a second co-culturing step comprising co-culturing the enriched activated T cells with a second population of DCs loaded with the target tumor antigen peptide to obtain a population of tumor antigen-specific T cells; d) a third co-culturing step comprising co-culturing a population of the tumor antigen-specific T cells with a population of APCs (e.g., PBMCs, DCs, or cell line APCs) loaded with target tumor antigen peptide to obtain a second population of tumor antigen-specific T cells, wherein at least about 10% (e.g., at least about 20%, or at least about 50%) of the tumor antigen-specific T cells specifically responds to the target tumor antigen peptide; and e) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; wherein the individual has clinically benefitted from a Multiple Antigen Specific Cell Therapy ("MASCT") comprising administering to the individual an effective amount of activated T cells prepared by co-culturing a population of T cells with a population of DCs loaded with a plurality of tumor antigen peptides comprising the target tumor antigen peptide. In some embodiments, the first co-culturing step is carried out for about 1 to about 3 days prior to the enrichment step. In some embodiments, the ratio between the population of T cells to the first population of antigen-loaded DCs is no more than about 30:1 (e.g., about 20:1, 15:1 or 10:1). In some embodiments, the population of T cells in the first co-culturing step is present in PBMCs. In some embodiments, the first population of DCs loaded with the target tumor antigen peptide and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody, such as SHR-1210). In some embodiments, the enrichment step comprises contacting the first co-culture with APCs (e.g., DCs or PBMCs) loaded with the target tumor antigen peptide to obtain a stimulated co-culture, and isolating from the stimulated co-culture an enriched population of activated T cells using a ligand that specifically recognizes a cytokine (e.g., IFNγ) or a cell surface molecule. In some embodiments, the ratio between the enriched population of activated T cells and the second population of DCs loaded with the target tumor antigen peptide is about 1:1 to about 20:1 (e.g., about 1:1, 2:1 or 4:1). In some embodiments, the enriched population of activated T cells and the second population of DCs loaded with the target tumor antigen peptide are co-cultured for about 12 to 25 days. In some embodiments, the second co-culturing step comprises co-culturing the second population of DCs loaded with the target tumor antigen peptide with the enriched population of activated T cells in an initial second co-culture medium comprising an immune checkpoint inhibitor and optionally one or more cytokines (e.g., a plurality of cytokines) to provide a second co-culture; and adding an anti-CD3 antibody (e.g., OKT-3) and optionally one or more cytokines to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the initial second co-culture medium comprises IL-2, IL-7, IL-15 and IL-21 and an anti-PD-1 antibody. In some embodiments, the ratio between the population of tumor antigen-specific T cells and the population of APCs loaded with the target tumor antigen peptide is about 1:1 to about 20:1 (e.g., about 4:1). In some embodiments, the population of tumor antigen-specific T cells and the population of APCs loaded with the target tumor antigen peptide are co-cultured for about 5 to 9 days (e.g., about 7 days). In some embodiments, the population of tumor antigen-specific T cells and the population of APCs loaded with the target tumor antigen peptide are co-cultured in a third co-culture medium comprising one or more cytokines (such as IL-2 or a plurality of cytokines, e.g., IL-2, IL-7, IL-15) and an anti-CD3 antibody (e.g., OKT3). In some embodiments, the third co-culturing step is repeated (e.g., once or twice). In some embodiments, the individual has response (PR), complete response (CR), or stable disease (SD) after receiving the MASCT.

In some embodiments, there is provided a method of obtaining a plurality of TCRs specifically recognizing a target tumor antigen peptide, comprising: a) a first co-culturing step comprising co-culturing a first population of DCs loaded with the target tumor antigen peptide with a population of T cells from an individual to obtain a first co-culture; b) an enrichment step comprising contacting the first co-culture with APCs (e.g., PBMCs or DCs) loaded with the target tumor antigen peptide to obtain a stimulated co-culture, and isolating from the stimulated co-culture an enriched population of activated T cells using a ligand that specifically recognizes a cytokine (e.g., IFNγ); c) a second co-culturing step comprising co-culturing a second population of DCs loaded with the target tumor antigen peptide with the enriched population of activated T cells in an initial second co-culture medium comprising an immune checkpoint inhibitor and optionally one or more cytokines (e.g., a plurality of cytokines) to provide a second co-culture; and adding an anti-CD3 antibody (e.g., OKT-3) and optionally one or more cytokines to the second co-culture to obtain a population of tumor antigen-specific T cells; d) a third co-culturing step comprising co-culturing a population of the tumor antigen-specific T cells with a first population of APCs (e.g., PBMCs, DCs, or cell line APCs) loaded with target tumor antigen peptide for about 5 to 9 days (e.g., 7 days), adding to the third co-culture a second population of APCs (e.g., PBMCs, DCs, or cell line APCs) loaded with target tumor antigen peptide and culturing for about 5 to 9 days (e.g., 7 days), and adding to the co-culture a third population of APCs (e.g., PBMCs, DCs, or cell line APCs) loaded with target tumor antigen peptide and culturing for about 5 to 9 days (e.g., 7 days) to obtain a second population of tumor antigen-specific T cells, wherein at least about 10% (e.g., at least about 20%, or at least about 50%) of the tumor antigen-specific T cells specifically responds to the target tumor antigen peptide; and e) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; wherein the individual has clinically benefitted from a Multiple Antigen Specific Cell Therapy ("MASCT") comprising administering to the individual an effective amount of activated T cells prepared by co-culturing a population of T cells with a population of DCs loaded with a plurality of tumor antigen peptides comprising the target tumor antigen peptide. In some embodiments, the first co-culturing step is carried out for about 1 to about 3 days prior to the enrichment step. In some embodiments, the ratio between the population of T cells to the first population of antigen-loaded DCs is no more than about 30:1 (e.g., about 20:1, 15:1 or 10:1). In some embodiments, the population of T cells in the first co-culturing step is present in PBMCs. In some embodiments, the first population of DCs loaded with the target tumor antigen peptide and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody, such as SHR-1210). In some embodiments, the ratio between the enriched population of activated T cells and the second population of DCs loaded with the target tumor antigen peptide is about 1:1 to about 20:1 (e.g., about 1:1, 2:1 or 4:1). In some embodiments, the enriched population of activated T cells and the second population of DCs loaded with the target tumor antigen peptide are co-cultured for about 12 to 25 days. In some embodiments, the anti-CD3 antibody is added to the second co-culture no more than about 3 days (e.g., about 2 days) after the second co-culturing step starts. In some embodiments, the initial second co-culture medium comprises IL-2, IL-7, IL-15 and IL-21 and an anti-PD-1 antibody. In some embodiments, the ratio between the population of tumor antigen-specific T cells and the first population of APCs loaded with the target tumor antigen peptide is about 1:1 to about 20:1 (e.g., about 4:1). In some embodiments, the population of tumor antigen-specific T cells and the APCs loaded with the target tumor antigen peptide are co-cultured in a third co-culture medium comprising one or more cytokines (such as IL-2 or a plurality of cytokines, e.g., IL-2, IL-7, IL-15) and an anti-CD3 antibody (e.g., OKT3). In some embodiments, the individual has response (PR), complete response (CR), or stable disease (SD) after receiving the MASCT.

In some embodiments, there is provided a method of obtaining a plurality of TCRs specifically recognizing a target tumor antigen peptide, comprising: a) a first co-culturing step comprising co-culturing a first population of DCs loaded with the target tumor antigen peptide with a population of T cells from an individual to obtain a first co-culture; b) an enrichment step comprising subjecting the first co-culture to an enrichment process to obtain enriched activated T cells; c) a second co-culturing step comprising co-culturing the enriched activated T cells with a second population of DCs loaded with the target tumor antigen peptide to obtain a population of tumor antigen-specific T cells; d) a screening step comprising identifying a target tumor epitope from the target tumor antigen peptide, wherein the target tumor epitope elicits specific response by the enriched population of activated T cells, and contacting a population of APCs (e.g., PBMCs, DCs, or cell line APCs) with the target tumor epitope to obtain a population of APCs loaded with the target tumor antigen peptide; e) a third co-culturing step comprising co-culturing a population of the tumor antigen-specific T cells with the population of APCs loaded with target tumor antigen peptide to obtain a second population of tumor antigen-specific T cells, wherein at least about 10% (e.g., at least about 20%, or at least about 50%) of the tumor antigen-specific T cells specifically responds to the target tumor antigen peptide; and f) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; wherein the individual has clinically benefitted from a Multiple Antigen Specific Cell Therapy ("MASCT") comprising administering to the individual an effective amount of activated T cells prepared by co-culturing a population of T cells with a population of DCs loaded with a plurality of tumor antigen peptides comprising the target tumor antigen peptide. In some embodiments, the first co-culturing step is carried out for about 1 to about 3 days prior to the enrichment step. In some embodiments, the ratio between the population of T cells to the first population of antigen-loaded DCs is no more than about 30:1 (e.g., about 20:1, 15:1 or 10:1). In some embodiments, the population of T cells in the first co-culturing step is present in PBMCs. In some embodiments, the first population of DCs loaded with the target tumor antigen peptide and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody, such as SHR-1210). In some embodiments, the enrichment step comprises contacting the first co-culture with APCs (e.g., DCs or PBMCs) loaded with the target tumor antigen peptide to obtain a stimulated co-culture, and isolating from the stimulated co-culture an enriched population of activated T cells using a ligand that specifically recognizes a cytokine (e.g., IFNγ) or a cell surface molecule. In some embodiments, the ratio between the enriched population of activated T cells and the second population of DCs loaded with the target tumor antigen peptide is about 1:1 to about 20:1 (e.g., about 1:1, 2:1 or 4:1). In some embodiments, the enriched population of activated T cells and the second population of DCs loaded with the target tumor antigen peptide are co-cultured for about 12 to 25 days. In some embodiments, the second co-culturing step comprises co-culturing the second population of DCs loaded with the target tumor antigen peptide with the enriched population of activated T cells in an initial second co-culture medium comprising an immune checkpoint inhibitor and optionally one or more cytokines (e.g., a plurality of cytokines) to provide a second co-culture; and adding an anti-CD3 antibody (e.g., OKT-3) and optionally one or more cytokines to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the initial second co-culture medium comprises IL-2, IL-7, IL-15 and IL-21 and an anti-PD-1 antibody. In some embodiments, the ratio between the population of tumor antigen-specific T cells and the population of APCs loaded with the target tumor antigen peptide is about 1:1 to about 20:1 (e.g., about 4:1). In some embodiments, the population of tumor antigen-specific T cells and the population of APCs loaded with the target tumor antigen peptide are co-cultured for about 5 to 9 days (e.g., about 7 days). In some embodiments, the population of tumor antigen-specific T cells and the population of APCs loaded with the target tumor antigen peptide are co-cultured in a third co-culture medium comprising one or more cytokines (such as IL-2 or a plurality of cytokines, e.g., IL-2, IL-7, IL-15) and an anti-CD3 antibody (e.g., OKT3). In some embodiments, the third co-culturing step is repeated (e.g., once or twice). In some embodiments, the individual has response (PR), complete response (CR), or stable disease (SD) after receiving the MASCT.

Any one of the methods described herein may be used to obtain TCRs specifically recognizing a plurality of target tumor antigen peptides in parallel by using APCs (e.g., PBMCs or DCs) loaded with a plurality of target tumor antigen peptides in the first co-culturing step, the enrichment step and the second co-culturing step. In some embodiments, APCs (e.g., PBMCs, DCs or cell line APCs) loaded with individual target tumor antigen peptides are used in the third co-culturing step to prepare individual populations of tumor antigen-specific T cells for sequencing. In some embodiments, APCs (e.g., PBMCs, DCs or cell line APCs) loaded with the plurality of target tumor antigen peptides are used in the third co-culturing step to prepare a pooled population of tumor antigen-specific T cells for sequencing. In some embodiments, TCRs specifically recognizing at least about any one of 2, 3, 4, 5, 6, 7, 8, 9, 10, 20, 30, 40, or more target tumor antigen peptides are obtained using the method.

Thus, in some embodiments, there is provided a method of obtaining a plurality of TCRs specifically recognizing a plurality of target tumor antigen peptides, comprising: a) a first co-culturing step comprising co-culturing a first population of DCs loaded with the plurality of target tumor antigen peptides with a population of T cells from an individual to obtain a first co-culture; b) an enrichment step comprising subjecting the co-culture to an enrichment process to obtain enriched activated T cells; c) a second co-culturing step comprising co-culturing the enriched activated T cells with a second population of DCs loaded with the plurality of target tumor antigen peptides to obtain a population of tumor antigen-specific T cells, wherein at least about 10% (e.g., at least about 20%, or at least about 50%) of the tumor antigen-specific T cells specifically responds to one or more target tumor antigen peptides from the plurality of target tumor antigen peptides; and d) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ; wherein the individual has clinically benefitted from a Multiple Antigen Specific Cell Therapy ("MASCT") comprising administering to the individual an effective amount of activated T cells prepared by co-culturing a population of T cells with a population of DCs loaded with a plurality of tumor antigen peptides comprising the target tumor antigen peptides. In some embodiments, the first co-culturing step is carried out for about 1 to about 3 days prior to the enrichment step. In some embodiments, the ratio between the population of T cells to the first population of antigen-loaded DCs is no more than about 30:1 (e.g., about 20:1, 15:1 or 10:1). In some embodiments, the population of T cells in the first co-culturing step is present in PBMCs. In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody, such as SHR-1210). In some embodiments, the enrichment step comprises contacting the first co-culture with APCs (e.g., DCs or PBMCs) loaded with the plurality of target tumor antigen peptides to obtain a stimulated co-culture, and isolating from the stimulated co-culture an enriched population of activated T cells using a ligand that specifically recognizes a cytokine (e.g., IFNγ) or a cell surface molecule. In some embodiments, the ratio between the enriched population of activated T cells and the second population of antigen-loaded DCs is about 1:1 to about 20:1 (e.g., about 1:1, 2:1 or 4:1). In some embodiments, the enriched population of activated T cells and the second population of antigen-loaded DCs are co-cultured for about 12 to 25 days. In some embodiments, the second co-culturing step comprises co-culturing the second population of antigen-loaded DCs with the enriched population of activated T cells in an initial second co-culture medium comprising an immune checkpoint inhibitor and optionally one or more cytokines (e.g., a plurality of cytokines) to provide a second co-culture; and adding an anti-CD3 antibody (e.g., OKT-3) and optionally one or more cytokines to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the initial second co-culture medium comprises IL-2, IL-7, IL-15 and IL-21 and an anti-PD-1 antibody. In some embodiments, the ratio between the population of tumor antigen-specific T cells and the population of antigen-loaded APCs is about 1:1 to about 20:1 (e.g., about 4:1). In some embodiments, the method further comprises a third co-culturing step comprising co-culturing a population of the tumor antigen-specific T cells with a population of APCs (e.g., PBMCs, DCs, or cell line APCs) loaded with one or more target tumor antigen peptides from the plurality of the tumor antigen peptides to obtain a second population of tumor antigen-specific T cells, wherein the second population of tumor antigen-specific T cells are subjected to next-generation sequencing in the sequencing step. In some embodiments, the population of tumor antigen-specific T cells and the population of antigen-loaded APCs are co-cultured for about 5 to 9 days (e.g., about 7 days). In some embodiments, the population of tumor antigen-specific T cells and the population of antigen-loaded APCs are co-cultured in a third co-culture medium comprising one or more cytokines (such as IL-2 or a plurality of cytokines, e.g., IL-2, IL-7, IL-15) and an anti-CD3 antibody (e.g., OKT3). In some embodiments, the third co-culturing step is repeated (e.g., once or twice). In some embodiments, the method further comprises identifying a target tumor epitope from the target tumor antigen peptide, wherein the target tumor epitope elicits specific response by the enriched population of activated T cells, and contacting a population of APCs with the target tumor epitope to obtain the population of APCs loaded with the target tumor antigen peptide. In some embodiments, the individual has response (PR), complete response (CR), or stable disease (SD) after receiving the MASCT.

The TCRs can be cloned from any individual who has clinically benefitted from a MASCT, including any one or combinations of the MASCT methods described in the "MASCT" subsection. In some embodiments, the individual has a partial response (PR) for at least 6 about months (e.g., at least about 1 year, 2 years, or more) after receiving the MASCT. In some embodiments, the individual has a complete response (CR) for at least 6 about months (e.g., at least about 1 year, 2 years, or more) after receiving the MASCT. In some embodiments, the individual has a stable disease (SD) after receiving the MASCT.

In some embodiments, there is provided a method of obtaining a plurality of TCRs specifically recognizing a target tumor antigen peptide, comprising: a) optionally administering to the individual an effective amount of DCs loaded with a plurality of tumor antigen peptides comprising the target tumor antigen peptide; b) co-culturing a population of DCs loaded with the plurality of tumor antigen peptides and a first population of T cells to obtain a population of activated T cells; c) administering to the individual an effective amount of the activated T cells; d) obtaining a second population of T cells from the individual after achieving PR, CR, or SD after the administration of the activated T cells; e) a first co-culturing step comprising co-culturing a first population of DCs loaded with the target tumor antigen peptide with the second population of T cells to obtain a first co-culture; f) an enrichment step comprising subjecting the co-culture to an enrichment process to obtain enriched activated T cells; g) a second co-culturing step comprising co-culturing the enriched activated T cells with a second population of DCs loaded with the target tumor antigen peptide to obtain a population of tumor antigen-specific T cells, wherein at least about 10% (e.g., at least about 20%, or at least about 50%) of the tumor antigen-specific T cells specifically responds to the target tumor antigen peptide; and h) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ. In some embodiments, the first co-culturing step is carried out for about 1 to about 3 days prior to the enrichment step. In some embodiments, the ratio between the population of T cells to the first population of antigen-loaded DCs is no more than about 30:1 (e.g., about 20:1, 15:1 or 10:1). In some embodiments, the second population of T cells in the first co-culturing step is present in PBMCs. In some embodiments, the first population of antigen-loaded DCs and the second population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody, such as SHR-1210). In some embodiments, the enrichment step comprises contacting the first co-culture with APCs (e.g., DCs or PBMCs) loaded with the plurality of target tumor antigen peptides to obtain a stimulated co-culture, and isolating from the stimulated co-culture an enriched population of activated T cells using a ligand that specifically recognizes a cytokine (e.g., IFNγ) or a cell surface molecule. In some embodiments, the ratio between the enriched population of activated T cells and the second population of antigen-loaded DCs is about 1:1 to about 20:1 (e.g., about 1:1, 2:1 or 4:1). In some embodiments, the enriched population of activated T cells and the second population of antigen-loaded DCs are co-cultured for about 12 to 25 days. In some embodiments, the second co-culturing step comprises co-culturing the second population of antigen-loaded DCs with the enriched population of activated T cells in an initial second co-culture medium comprising an immune checkpoint inhibitor and optionally one or more cytokines (e.g., a plurality of cytokines) to provide a second co-culture; and adding an anti-CD3 antibody (e.g., OKT-3) and optionally one or more cytokines to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the initial second co-culture medium comprises IL-2, IL-7, IL-15 and IL-21 and an anti-PD-1 antibody. In some embodiments, the ratio between the population of tumor antigen-specific T cells and the population of antigen-loaded APCs is about 1:1 to about 20:1 (e.g., about 4:1). In some embodiments, the method further comprises a third co-culturing step comprising co-culturing a population of the tumor antigen-specific T cells with a population of APCs (e.g., PBMCs, DCs, or cell line APCs) loaded with one or more target tumor antigen peptides from the plurality of the tumor antigen peptides to obtain a second population of tumor antigen-specific T cells, wherein the second population of tumor antigen-specific T cells are subjected to next-generation sequencing in the sequencing step. In some embodiments, the population of tumor antigen-specific T cells and the population of antigen-loaded APCs are co-cultured for about 5 to 9 days (e.g., about 7 days). In some embodiments, the population of tumor antigen-specific T cells and the population of antigen-loaded APCs are co-cultured in a third co-culture medium comprising one or more cytokines (such as IL-2 or a plurality of cytokines, e.g., IL-2, IL-7, IL-15) and an anti-CD3 antibody (e.g., OKT3). In some embodiments, the third co-culturing step is repeated (e.g., once or twice). In some embodiments, the method further comprises identifying a target tumor epitope from the target tumor antigen peptide, wherein the target tumor epitope elicits specific response by the enriched population of activated T cells, and contacting a population of APCs with the target tumor epitope to obtain the population of APCs loaded with the target tumor antigen peptide.

In some embodiments, there is provided a method of obtaining a plurality of TCRs specifically recognizing a target tumor antigen peptide, comprising: a) contacting a population of DCs with a plurality of tumor antigen peptides comprising the target tumor antigen peptide to obtain a population of DCs loaded with the plurality of tumor antigen peptides; b) culturing the population of DCs loaded with the plurality of tumor antigen peptides in a DC maturation medium comprising MPLA; c) optionally administering to the individual an effective amount of the DCs loaded with the plurality of tumor antigen peptides; d) co-culturing a population of DCs loaded with the plurality of tumor antigen peptides and a first population of T cells to obtain a population of activated T cells; e) administering to the individual an effective amount of the activated T cells; f) obtaining a second population of T cells from the individual after achieving PR, CR, or SD after the administration of the activated T cells; g) a first co-culturing step comprising co-culturing a first population of DCs loaded with the target tumor antigen peptide with the second population of T cells to obtain a first co-culture; h) an enrichment step comprising subjecting the co-culture to an enrichment process to obtain enriched activated T cells; i) a second co-culturing step comprising co-culturing the enriched activated T cells with a second population of DCs loaded with the target tumor antigen peptide to obtain a population of tumor antigen-specific T cells, wherein at least about 10% (e.g., at least about 20%, or at least about 50%) of the tumor antigen-specific T cells specifically responds to the target tumor antigen peptide; and j) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ. In some embodiments, the DC maturation medium comprises INFγ, MPLA and PGE2. In some embodiments, the first co-culturing step is carried out for about 1 to about 3 days prior to the enrichment step. In some embodiments, the ratio between the population of T cells to the first population of antigen-loaded DCs is no more than about 30:1 (e.g., about 20:1, 15:1 or 10:1). In some embodiments, the second population of T cells in the first co-culturing step is present in PBMCs. In some embodiments, the first population of antigen-loaded DCs and the second population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody, such as SHR-1210). In some embodiments, the enrichment step comprises contacting the first co-culture with APCs (e.g., DCs or PBMCs) loaded with the plurality of target tumor antigen peptides to obtain a stimulated co-culture, and isolating from the stimulated co-culture an enriched population of activated T cells using a ligand that specifically recognizes a cytokine (e.g., IFNγ) or a cell surface molecule. In some embodiments, the ratio between the enriched population of activated T cells and the second population of antigen-loaded DCs is about 1:1 to about 20:1 (e.g., about 1:1, 2:1 or 4:1). In some embodiments, the enriched population of activated T cells and the second population of antigen-loaded DCs are co-cultured for about 12 to 25 days. In some embodiments, the second co-culturing step comprises co-culturing the second population of antigen-loaded DCs with the enriched population of activated T cells in an initial second co-culture medium comprising an immune checkpoint inhibitor and optionally one or more cytokines (e.g., a plurality of cytokines) to provide a second co-culture; and adding an anti-CD3 antibody (e.g., OKT-3) and optionally one or more cytokines to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the initial second co-culture medium comprises IL-2, IL-7, IL-15 and IL-21 and an anti-PD-1 antibody. In some embodiments, the ratio between the population of tumor antigen-specific T cells and the population of antigen-loaded APCs is about 1:1 to about 20:1 (e.g., about 4:1). In some embodiments, the method further comprises a third co-culturing step comprising co-culturing a population of the tumor antigen-specific T cells with a population of APCs (e.g., PBMCs, DCs, or cell line APCs) loaded with one or more target tumor antigen peptides from the plurality of the tumor antigen peptides to obtain a second population of tumor antigen-specific T cells, wherein the second population of tumor antigen-specific T cells are subjected to next-generation sequencing in the sequencing step. In some embodiments, the population of tumor antigen-specific T cells and the population of antigen-loaded APCs are co-cultured for about 5 to 9 days (e.g., about 7 days). In some embodiments, the population of tumor antigen-specific T cells and the population of antigen-loaded APCs are co-cultured in a third co-culture medium comprising one or more cytokines (such as IL-2 or a plurality of cytokines, e.g., IL-2, IL-7, IL-15) and an anti-CD3 antibody (e.g., OKT3). In some embodiments, the third co-culturing step is repeated (e.g., once or twice). In some embodiments, the method further comprises identifying a target tumor epitope from the target tumor antigen peptide, wherein the target tumor epitope elicits specific response by the enriched population of activated T cells, and contacting a population of APCs with the target tumor epitope to obtain the population of APCs loaded with the target tumor antigen peptide.

In some embodiments, there is provided a method of obtaining a plurality of TCRs specifically recognizing a target tumor antigen peptide, comprising: a) optionally administering to the individual an effective amount of the DCs loaded with the plurality of tumor antigen peptides; b) co-culturing a population of DCs loaded with the plurality of tumor antigen peptides and a first population of T cells in an initial co-culture medium comprising one or more cytokines (such as IL-2 or a plurality of cytokines, e.g., IL-2, IL-7, IL-15 and IL-21) and an immune checkpoint inhibitor to provide a co-culture; and adding an anti-CD3 antibody to the co-culture at about 3 to 7 days (e.g., about 5 days) after the co-culturing starts, thereby obtaining the population of activated T cells; c) administering to the individual an effective amount of the activated T cells; d) obtaining a second population of T cells from the individual after achieving PR, CR, or SD after the administration of the activated T cells; e) a first co-culturing step comprising co-culturing a first population of DCs loaded with the target tumor antigen peptide with the second population of T cells to obtain a first co-culture; f) an enrichment step comprising subjecting the co-culture to an enrichment process to obtain enriched activated T cells; g) a second co-culturing step comprising co-culturing the enriched activated T cells with a second population of DCs loaded with the target tumor antigen peptide to obtain a population of tumor antigen-specific T cells, wherein at least about 10% (e.g., at least about 20%, or at least about 50%) of the tumor antigen-specific T cells specifically responds to the target tumor antigen peptide; and h) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ. In some embodiments, the ratio between the population of T cells to the first population of antigen-loaded DCs is no more than about 30:1 (e.g., about 20:1, 15:1 or 10:1). In some embodiments, the second population of T cells in the first co-culturing step is present in PBMCs. In some embodiments, the first population of antigen-loaded DCs and the second population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody, such as SHR-1210). In some embodiments, the enrichment step comprises contacting the first co-culture with APCs (e.g., DCs or PBMCs) loaded with the plurality of target tumor antigen peptides to obtain a stimulated co-culture, and isolating from the stimulated co-culture an enriched population of activated T cells using a ligand that specifically recognizes a cytokine (e.g., IFNγ) or a cell surface molecule. In some embodiments, the ratio between the enriched population of activated T cells and the second population of antigen-loaded DCs is about 1:1 to about 20:1 (e.g., about 1:1, 2:1 or 4:1). In some embodiments, the enriched population of activated T cells and the second population of antigen-loaded DCs are co-cultured for about 12 to 25 days. In some embodiments, the second co-culturing step comprises co-culturing the second population of antigen-loaded DCs with the enriched population of activated T cells in an initial second co-culture medium comprising an immune checkpoint inhibitor and optionally one or more cytokines (e.g., a plurality of cytokines) to provide a second co-culture; and adding an anti-CD3 antibody (e.g., OKT-3) and optionally one or more cytokines to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the initial second co-culture medium comprises IL-2, IL-7, IL-15 and IL-21 and an anti-PD-1 antibody. In some embodiments, the ratio between the population of tumor antigen-specific T cells and the population of antigen-loaded APCs is about 1:1 to about 20:1 (e.g., about 4:1). In some embodiments, the method further comprises a third co-culturing step comprising co-culturing a population of the tumor antigen-specific T cells with a population of APCs (e.g., PBMCs, DCs, or cell line APCs) loaded with one or more target tumor antigen peptides from the plurality of the tumor antigen peptides to obtain a second population of tumor antigen-specific T cells, wherein the second population of tumor antigen-specific T cells are subjected to next-generation sequencing in the sequencing step. In some embodiments, the population of tumor antigen-specific T cells and the population of antigen-loaded APCs are co-cultured for about 5 to 9 days (e.g., about 7 days). In some embodiments, the population of tumor antigen-specific T cells and the population of antigen-loaded APCs are co-cultured in a third co-culture medium comprising one or more cytokines (such as IL-2 or a plurality of cytokines, e.g., IL-2, IL-7, IL-15) and an anti-CD3 antibody (e.g., OKT3). In some embodiments, the third co-culturing step is repeated (e.g., once or twice). In some embodiments, the method further comprises identifying a target tumor epitope from the target tumor antigen peptide, wherein the target tumor epitope elicits specific response by the enriched population of activated T cells, and contacting a population of APCs with the target tumor epitope to obtain the population of APCs loaded with the target tumor antigen peptide.

In some embodiments, there is provided a method of obtaining a plurality of TCRs specifically recognizing a target tumor antigen peptide, comprising: a) contacting a population of DCs with a plurality of tumor antigen peptides comprising the target tumor antigen peptide to obtain a population of DCs loaded with the plurality of tumor antigen peptides; b) culturing the population of DCs loaded with the plurality of tumor antigen peptides in a DC maturation medium comprising MPLA; c) optionally administering to the individual an effective amount of the DCs loaded with the plurality of tumor antigen peptides; d) co-culturing a population of DCs loaded with the plurality of tumor antigen peptides and a first population of T cells in an initial co-culture medium comprising one or more cytokines (such as IL-2 or a plurality of cytokines) and an immune checkpoint inhibitor to provide a co-culture; and adding an anti-CD3 antibody to the co-culture at about 3 to 7 days (e.g., about 5 days) after the co-culturing starts, thereby obtaining the population of activated T cells; e) administering to the individual an effective amount of the activated T cells; f) obtaining a second population of T cells from the individual after achieving PR, CR, or SD after the administration of the activated T cells; g) a first co-culturing step comprising co-culturing a first population of DCs loaded with the target tumor antigen peptide with the second population of T cells to obtain a first co-culture; h) an enrichment step comprising subjecting the co-culture to an enrichment process to obtain enriched activated T cells; i) a second co-culturing step comprising co-culturing the enriched activated T cells with a second population of DCs loaded with the target tumor antigen peptide to obtain a population of tumor antigen-specific T cells, wherein at least about 10% (e.g., at least about 20%, or at least about 50%) of the tumor antigen-specific T cells specifically responds to the target tumor antigen peptide; and j) a sequencing step, comprising subjecting the tumor antigen-specific T cells to next-generation sequencing (e.g., single-cell sequencing) to identify a plurality of pairs of genes encoding TCRα and TCRβ, thereby providing the plurality of T cell receptors based on paired genes encoding TCRα and TCRβ. In some embodiments, the DC maturation medium comprises INFγ, MPLA and PGE2. In some embodiments, the first co-culturing step is carried out for about 1 to about 3 days prior to the enrichment step. In some embodiments, the ratio between the population of T cells to the first population of antigen-loaded DCs is no more than about 30:1 (e.g., about 20:1, 15:1 or 10:1). In some embodiments, the second population of T cells in the first co-culturing step is present in PBMCs. In some embodiments, the first population of antigen-loaded DCs and the second population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody, such as SHR-1210). In some embodiments, the enrichment step comprises contacting the first co-culture with APCs (e.g., DCs or PBMCs) loaded with the plurality of target tumor antigen peptides to obtain a stimulated co-culture, and isolating from the stimulated co-culture an enriched population of activated T cells using a ligand that specifically recognizes a cytokine (e.g., IFNγ) or a cell surface molecule. In some embodiments, the ratio between the enriched population of activated T cells and the second population of antigen-loaded DCs is about 1:1 to about 20:1 (e.g., about 1:1, 2:1 or 4:1). In some embodiments, the enriched population of activated T cells and the second population of antigen-loaded DCs are co-cultured for about 12 to 25 days. In some embodiments, the second co-culturing step comprises co-culturing the second population of antigen-loaded DCs with the enriched population of activated T cells in an initial second co-culture medium comprising one or more cytokines (such as IL-2 or a plurality of cytokines) and an immune checkpoint inhibitor to provide a second co-culture; and adding an anti-CD3 antibody (e.g., OKT-3) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the initial second co-culture medium comprises IL-2, IL-7, IL-15 and IL-21 and an anti-PD-1 antibody. In some embodiments, the ratio between the population of tumor antigen-specific T cells and the population of antigen-loaded APCs is about 1:1 to about 20:1 (e.g., about 4:1). In some embodiments, the method further comprises a third co-culturing step comprising co-culturing a population of the tumor antigen-specific T cells with a population of APCs (e.g., PBMCs, DCs, or cell line APCs) loaded with one or more target tumor antigen peptides from the plurality of the tumor antigen peptides to obtain a second population of tumor antigen-specific T cells, wherein the second population of tumor antigen-specific T cells are subjected to next-generation sequencing in the sequencing step. In some embodiments, the population of tumor antigen-specific T cells and the population of antigen-loaded APCs are co-cultured for about 5 to 9 days (e.g., about 7 days). In some embodiments, the population of tumor antigen-specific T cells and the population of antigen-loaded APCs are co-cultured in a third co-culture medium comprising one or more cytokines (such as IL-2 or a plurality of cytokines, e.g., IL-2, IL-7, IL-15) and an anti-CD3 antibody (e.g., OKT3). In some embodiments, the third co-culturing step is repeated (e.g., once or twice). In some embodiments, the method further comprises identifying a target tumor epitope from the target tumor antigen peptide, wherein the target tumor epitope elicits specific response by the enriched population of activated T cells, and contacting a population of APCs with the target tumor epitope to obtain the population of APCs loaded with the target tumor antigen peptide.

In some embodiments, the TCR is cloned from an individual that responds to the MASCT method, for example, an individual having reduced CTC number or a low CTC number after the MASCT, an individual having a clinical evaluation of Stable Disease (SD), Complete Response (CR), or Partial Response (PR). In some embodiments, the individual remains PR, CR or SD for at least about 6 months (e.g., at least about 1 year, 2 years, or more). In some embodiments, the individual has a strong specific immune response against the target tumor antigen peptide. Specific immune response against a target tumor antigen peptide may be determined using any known methods in the art, for example, by measuring levels of cytotoxic factor (such as perform or granzyme B), or cytokine release (such as IFNγ or TNFα) from T cells (or PBMCs) after stimulation by the target tumor antigen peptide. An antibody-based assay, such as ELISPOT, may be used to quantify the cytotoxic factor, or cytokine (such as IFNγ) levels. In some embodiments, the cytokine (such as IFNγ) release level from T cells (or PBMCs) in response to a target tumor antigen peptide is normalized to a reference, such as a baseline cytokine release level, or a nonspecific cytokine release level of from T cells (or PBMCs) in response to an irrelevant peptide, to provide a cytokine (such as IFNγ) fold change value. In some embodiments, a cytokine (such as IFNγ) fold change value of more than about any of 1.2, 1.5, 2, 2.5, 3, 4, 5, 6, 8, 10, or more in an ELISPOT assay indicate strong specific immune response against the target tumor antigen peptide. In some embodiments, the method of cloning a TCR further comprises determining the specific immune response of each of the plurality of tumor antigen peptides in the individual, such as in a PBMC sample of the individual.

The T cell may be isolated from a biological sample from the individual after receiving the MASCT. In some embodiments, the biological sample is obtained from the individual after one cycle of MASCT. In some embodiments, the biological sample is obtained from the individual after at least any of 2, 3, 4, 5, or more cycles of MASCT. In some embodiments, the biological sample is obtained from the individual after at least about any of 1 week, 2 weeks, 3 weeks, 4 weeks 5 weeks, 6 weeks, 2 months, or 3 months after receiving the MASCT. In some embodiments, the biological sample is obtained from the individual after no more than about any of 6 months, 3 months, 2 months, 1 month, or less after receiving the MASCT. In some embodiments, the biological sample is a blood sample. In some embodiments, the biological sample is a PBMC sample. In some embodiments, the biological sample is a T cell sample. In some embodiments, the biological sample is a tumor sample containing CTLs. T cells may be isolated from the biological sample using any known methods in the art, for example, by flow cytometry or centrifugation methods. In some embodiments, a plurality of T cells obtained from the biological sample are screened for their specific immune response against the plurality of tumor antigen peptides, for example, by staining with multimers (such as pentamers or dextramers), or by determining the level of cytotoxic factor (such as perform or granzyme B), or cytokine release (such as IFNγ or TNFα) by the cell.

The target tumor antigen peptide that the T cell specifically recognizes can be any tumor antigen peptide or fragment thereof from the tumor antigen peptide pool(s) used for the MASCT. In some embodiments, the target tumor antigen peptide comprises an MHC-I restricted epitope. In some embodiments, the target tumor antigen peptide comprises an MHC-II restricted epitope. In some embodiments, the target tumor antigen peptide is a general cancer tumor antigen peptide. In some embodiments, the target tumor antigen peptide is a cancer-type specific tumor antigen peptide. In some embodiments, the target tumor antigen peptide is a neoantigen peptide. In some embodiments, the target tumor antigen peptide is derived from a tumor antigen selected from the group consisting of hTERT, p53, Survivin, NY-ESO-1, CEA, CCND1, RGS5, MMP7, VEGFR1, VEGFR2, MUC1, HER2, MAGE-A1, MAGE-A3, CDCA1, WT1, KRAS, PARP4, MLL3, MTHFR, HPV16-E6, HPV16-E7, HPV18-E6, HPV18-E7, HPV58-E6, HPV58-E7, HBcAg, HBV polymerase, GPC3, SSX, and AFP. In some embodiments, the target tumor antigen peptide comprises an epitope derived from CEA, RGS5 or HPV18-E7.

Any known next-generation sequencing methods can be used to sequence the tumor antigen-specific T cells to provide a plurality of pairs of genes encoding TCRα and TCRβ. In some embodiments, the next-generation sequencing is single-cell next generation sequencing. In some embodiments, the next-generation sequencing is bulk next-generation sequencing. In some embodiments, the sequencing step comprises next-generation sequencing of immune repertoire of TCRs of the tumor antigen-specific T cells. In some embodiments, the sequencing step comprises amplification of genes encoding TCRα and TCRβ from the tumor antigen-specific T cells (e.g., single cells or a population of cells) to provide a sample of amplified nucleic acids, and subjecting the amplified nucleic acids to next-generation sequencing. In some embodiments, the genes encoding TCRα and TCRβ are amplified using PCR methods with primers that specifically annealing to known TCR variable domains. In some embodiments, amplicon rescued multiplex PCR (or arm-PCR) is used to amplify the genes encoding TCRα and TCRβ. See, for example, U.S. Pat. No. 7,999,092. In some embodiments, the tumor antigen-specific T cells are subjected to both bulk next-generation sequencing data and single-cell next generation sequencing to identify a plurality of pairs of genes encoding TCRα and TCRβ. In some embodiments, the sequencing step comprises bulk sequencing of a first portion of the tumor antigen-specific T cells to provide a plurality of genes encoding TCRα and TCRβ, and single-cell sequencing of a second portion of the tumor antigen-specific T cells providing cognate pairing information of the plurality of genes encoding TCRα and TCRβ, thereby providing a plurality of TCRs based on paired genes encoding TCRα and TCRβ.

Commercial kits and services are available for single-cell next generation sequencing of TCRs, including, but not limited to IPAR® (iReportoire), IMMUNOSEQ™ (Adaptive Biotech), SMARTER® human TCRa/b profiling kit (Clontech), ION AMPLISEQ® Immune Repertoire and Assay Plus (Thermofisher). For example, the IPAR® method including two steps of PCR amplification followed by next-generation sequencing. Briefly, a sample of tumor antigen-specific T cells is subject to single cell plating in one or more 96-well plates. In the first PCR step, RT-PCR is performed in each of the wells of the 96 well-plates with nested, multiplex primers covering both the alpha and beta locus of TCR with communal forward and reverse binding sites included on the 5'-end of the inside primers. Included on the C-region gene primer is an in-line barcode, which serves as a plate identifier so that multiple 96-well plates may be multiplexed on a sequencing flow cell. After the RT-PCR, the products are rescued. A second PCR is performed with dual-indexed primers that complete the adaptors introduced during the first PCR and provide plate positional information. In this step, each well, and thus each single cell, is uniquely barcoded. In some cases, bulk next-generation_sequencing of each chain is also performed on RNA from remaining cells (those cells not subjected to single cell plating). Sequencing data is analyzed using the IPAR® Analyzer software, which also facilitates easy comparisons of single-cell sequencing data to the bulk sequencing data. Cognate pairing information of genes encoding TCRα and TCRβ is obtained based on the data in each well as determined by the IPAR® Analyzer. Also, see, for example, iPair Analyzer User's Guide, iRepertoire Inc. (docs.wixstatic.com/ugd/c9f231_3c322d131c084e908eea039c42304ff7.pdf), the contents of which are incorporated herein by reference.

In some embodiments, the tumor antigen-specific T cells are stimulated with APCs (e.g., PBMCs, DCs, or cell line APCs) loaded with the target tumor antigen peptide (i.e., stimulated tumor antigen-specific T cells) prior to the next-generation sequencing. In some embodiments, the tumor antigen-specific T cells stimulated with the APCs loaded with the target tumor antigen peptide are sorted to isolate IFNγ$^+$ T cells for the next-generation sequencing. In some embodiments, a control population of T cells are subject to the next-generation sequencing to provide a baseline TCRα and TCRβ clonotype profile. In some embodiments, the control population of T cells are unstimulated PBMCs from the individual. In some embodiments, the control population of T cells are tumor antigen-specific T cells that are stimulated with one or more irrelevant peptides. In some embodiments, TCRα and TCRβ genes that are only identified in the sequencing data of stimulated tumor antigen-specific T cells, but not in the sequencing data of the control population of T cells are selected to provide tumor-specific TCRs. In some embodiments, TCRα and TCRβ genes that are present at a frequency at least about any one of 2×, 5×, 10×, 20×, 50×, 100×, 1000× or more in the sequencing data of stimulated tumor antigen-specific T cells than in the sequencing data of the control population of T cells are selected to provide tumor-specific TCRs.

In some embodiments, a plurality of population of T cells (e.g., PBMCs) from the individual is obtained at different time after the MASCT treatment. The TCRα and TCRβ genes consistently identified from the tumor antigen-specific T cells prepared using each population of T cells are selected to provide tumor-specific TCRs. In some embodiments, if a TCRα and a TCRβ genes are found in the sequencing data of two or more (such as 2, 3, 4, 5, 6 or more) populations of tumor antigen-specific T cells prepared using different samples of T cells from the individual, and the TCRα and TCRβ genes are paired by single-cell sequencing, then the pair of TCRα and TCRβ genes is selected to provide a tumor-specific TCR.

Any one of the methods described herein may comprise one or more of the followings steps: (i) expressing each pair of genes encoding TCRα and TCRβ in a host immune cell to provide an engineered immune cell expressing a TCR, and assessing response of the engineered immune cell to the target tumor antigen peptide; (ii) determining the antigen epitope recognized by each TCR; (iii) determining HLA restriction (including MHC I or MHC II restriction, and optionally HLA haplotype restriction) of each TCR; (iv) determining the avidity and cross-reactivity of each TCR; (v) affinity maturation of each TCR; (vi) enhancing the paring of the TCRα and TCRβ chains in each TCR; and (vii) enhancing the expression of each TCR. An overview of an exemplary method of obtaining a plurality of TCRs specifically recognizing a target tumor antigen peptide from an individual who has clinically benefitted from a MASCT is shown in FIG. 1.

In some embodiments, isolated nucleic acids comprising each pair of TCRα and TCRβ genes are synthesized. In some embodiments, for each pair of TCRα and TCRβ genes, a first isolated nucleic acid encoding the TCRα gene and a second isolated nucleic acid encoding the TCRβ gene are synthesized. In some embodiments, the TCRα and TCRβ genes are codon optimized (e.g., for expression in human cells). In some embodiments, each of the TCRα and TCRβ genes is operably linked to a promoter. In some embodiments, the TCRα and TCRβ genes are operably linked to the same promoter. In some embodiments, the TCRα and TCRβ genes are operably linked to different promoters. In some embodiments, the isolated nucleic acids are incorporated in a vector, such as a viral vector, for example, a lentiviral vector.

In some embodiments, the isolated nucleic acids is transduced (such as by a viral vector, or by physical or chemical methods) into a host immune cell (such as T cell) to express the TCR encoded by the TCRα and TCRβ genes. In some embodiments, the host immune cell is a CD3$^+$ cell. In some embodiments, the host immune cell is a T cell. In some embodiments, the host immune cell is selected from the group consisting of a PBMC, a cytotoxic T cell, a helper T cell, a natural killer T cell, and a regulatory T cell. In some embodiments, the host immune cell expressing the TCR is assayed for specific immune response to the target tumor antigen peptide for validation. In some embodiments, the host immune cell is derived from a cell line. In some embodiments, the host immune cell is a primary cell. In some embodiments, the host immune cell is derived from a cancer patient. In some embodiments, the host immune cell is derived from a healthy donor.

Further provided is a method of obtaining a TCR specifically recognizing a target tumor antigen peptide using any one of the method of obtaining a plurality of TCRs specifically recognizing a target tumor antigen peptide as described herein, wherein the TCR is selected based on the response of an engineered immune cell expressing the TCR to the target tumor antigen peptide.

HLA restriction of the TCRs may be determined using any known methods in the art. See, for example, Larche M. *Methods Mol. Med.* (2008), 138:57-72. In some embodiments, the TCR is MHC class I restricted. In some embodiments, the TCR is MHC class II restricted. In some embodiments, the tumor-specific TCR has a HLA haplotype restriction that is predominant in certain a racial groups, including, but not limited to, Africans, African Americans, Asians, Caucasians, Europeans, Hispanics, Pacific Islanders, etc. In some embodiments, the TCR has a HLA haplotype restriction that is predominant in Asians, for example, HLA-A*1101 or HLA-A*2402-restricted TCR. In some embodiments, the TCR has a HLA haplotype restriction that is predominant in Caucasians, e.g., HLA-DPB1*0401 or HLA-A*0201-restricted TCR.

The TCRs obtained herein may be further engineered to improve the physical/chemical properties and/or functions of the TCRs. For example, the engineered tumor-specific TCRs may have enhanced expression level, improved stability, enhanced binding affinity to the MHC-target tumor-specific antigen peptide complexes, and/or enhanced signaling. In some embodiments, the TCRs are engineered based on the MHC subtype of the individual receiving immunotherapy treatment using the TCRs. In some embodiments, the engineering comprises mutating one or more positions in the variable regions of a TCR. In some embodiments, the engineering comprises providing a fusion protein comprising one or more domains or fragments of the TCR. In some embodiments, the TCRα and TCRβ chains of a TCR may be engineered to have enhanced pairing. Any known methods in the art for epitope determining, affinity maturation, avidity and cross-reactivity determination, expression enhancement, and pairing enhancement may be used.

It is intended that any of the steps and parameters described herein for preparing the antigen-loaded APCs, the first, second and third co-culturing steps, the enrichment step, the sequencing step, the MASCT, etc., can be combined with each other as if each and every combination is individually described.

Methods for Preparing Tumor Antigen-Specific T Cells

The present application provides methods of preparing a population of T cells for TCR cloning, comprising: co-culturing a population of enriched activated T cells or a population of stock tumor antigen-specific T cells with a population of antigen-presenting cells (APCs) loaded with one or more target tumor antigen peptides (referred herein as "antigen-loaded APCs"), wherein the population of enriched activated T cells or the population of stock tumor antigen-specific T cells is obtained from an individual who has clinically benefitted from a MASCT, and wherein at least about 10% (e.g., at least 20% or 50%) of the population of T cells for TCR cloning specifically responds to the target tumor antigen peptide. In some embodiments, the tumor-antigen specific T cells are obtained using any one of the methods described in International Patent Application No. PCT/CN2018/082945, which is incorporated herein in reference by its entirety.

In some embodiments, there is provided a method of preparing a population of T cells for TCR cloning, comprising: co-culturing an enriched population of activated T cells with a population of DCs loaded with a target tumor antigen peptide, wherein the enriched population of activated T cells is prepared by subjecting a first co-culture to an enrichment process, and wherein the first co-culture comprises a population of T cells and a first population of DCs loaded with the tumor antigen peptide, wherein the population of T cells in the first co-culture is obtained from an individual who has clinically benefitted from a MASCT, and wherein at least about 10% (e.g., at least 20% or 50%) of the population of T cells for TCR cloning specifically responds to the target tumor antigen peptide. In some embodiments, the ratio between the enriched population of activated T cells and the population of antigen-loaded DCs is about 1:1 to about 20:1 (e.g., about 1:1 or about 2:1). In some embodiments, the enriched population of activated T cells and the population of antigen-loaded DCs are co-cultured for about 12 to 25 days. In some embodiments, the method comprises co-culturing the population of antigen-loaded DCs with the enriched population of activated T cells in an initial co-culture medium comprising one or more cytokines (such as IL-2 or a plurality of cytokines) and an immune checkpoint inhibitor (e.g., anti-PD-1 antibody) to provide a co-culture; and adding an anti-CD3 antibody (e.g., OKT-3) and optionally one or more cytokines to the co-culture to obtain a population of tumor antigen-specific T cells. In some embodiments, the anti-CD3 antibody is added to the co-culture no more than about 3 days (e.g., about 2 days) after the co-culturing step starts.

In some embodiments, there is provided a method of preparing a population of T cells for TCR cloning, comprising: a) subjecting a first co-culture to an enrichment process to obtain an enriched population of activated T cells, wherein the first co-culture comprises a first population of DCs loaded with a target tumor antigen peptide and a population of T cells; and b) co-culturing the enriched population of activated T cells with a second population of DCs loaded with the target tumor antigen peptide to obtain a population of T cells for TCR cloning, wherein the population of T cells in step a) is obtained from an individual who has clinically benefitted from a MASCT, and wherein at least about 10% (e.g., at least 20% or 50%) of the population of T cells for TCR cloning specifically responds to the target tumor antigen peptide. In some embodiments, the enrichment process comprises contacting the first co-culture with APCs (e.g., PBMCs) loaded with the target tumor antigen peptide to obtain a stimulated co-culture, and isolating an enriched population of activated T cells from the stimulated co-culture using a ligand that specifically recognizes a cytokine (such as IFNγ) or a cell surface molecule. In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days.

In some embodiments, the method comprises co-culturing the second population of antigen-loaded DCs with the population of T cells in an initial second co-culture medium comprising one or more cytokines (such as IL-2 or a plurality of cytokines and an immune checkpoint inhibitor (e.g., anti-PD-1 antibody) to provide a second co-culture; and adding an anti-CD3 antibody (e.g., OKT3) to the second co-culture to obtain a population of tumor antigen-specific T cells. In some embodiments, the anti-CD3 antibody is added to the second co-culture no more than about 3 days (e.g., about 2 days) after the second co-culturing step starts.

In some embodiments, there is provided a method of preparing a population of T cells for TCR cloning, comprising: a) a first co-culturing step, comprising co-culturing a first population of DCs loaded with a target tumor antigen peptide with a population of T cells to obtain a first co-culture comprising activated T cells; b) an enrichment step, comprising subjecting the first co-culture to an enrichment process to obtain an enriched population of activated T cells; and c) a second co-culturing step, comprising co-culturing the enriched population of activated T cells with a second population of DCs loaded with the target tumor antigen peptide to obtain a population of T cells for TCR cloning, wherein the population of T cells in the first co-culturing step is obtained from an individual who has clinically benefitted from a MASCT, and wherein at least about 10% (e.g., at least 20% or 50%) of the population of T cells for TCR cloning specifically responds to the target tumor antigen peptide. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody). In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days. In some embodiments, the method comprises co-culturing the second population of antigen-loaded DCs with the population of T cells in an initial second co-culture medium comprising one or more cytokines (such as IL-2 or a plurality of cytokines) and an immune checkpoint inhibitor (e.g., anti-PD-1 antibody) to provide a second co-culture; and adding an anti-CD3 antibody (e.g., OKT3) to the second co-culture to obtain a population of tumor antigen-specific T cells. In some embodiments, the anti-CD3 antibody is added to the second co-culture no more than about 3 days (e.g., about 2 days) after the second co-culturing step starts.

In some embodiments, there is provided a method of preparing a population of T cells for TCR cloning, comprising: a) a first co-culturing step, comprising co-culturing a first population of DCs loaded with a target tumor antigen peptide with a population of T cells to obtain a first co-culture comprising activated T cells; b) an enrichment step, comprising contacting the first co-culture with APCs (e.g., PBMCs) loaded with the target tumor antigen peptide to obtain a stimulated co-culture, and isolating an enriched population of activated T cells from the stimulated co-culture using a ligand that specifically recognizes a cytokine (such as IFNγ) or a cell surface molecule; and c) a second co-culturing step, comprising co-culturing the enriched population of activated T cells with a second population of DCs loaded with the target tumor antigen peptide to obtain a population of T cells for TCR cloning, wherein the population of T cells in the first co-culturing step is obtained from an individual who has clinically benefitted from a MASCT, and wherein at least about 10% (e.g., at least 20% or 50%) of the population of T cells for TCR cloning specifically responds to the target tumor antigen peptide. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody). In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days. In some embodiments, the method comprises co-culturing the second population of antigen-loaded DCs with the population of T cells in an initial second co-culture medium comprising one or more cytokines (such as IL-2 or a plurality of cytokines) and an immune checkpoint inhibitor (e.g., anti-PD-1 antibody) to provide a second co-culture; and adding an anti-CD3 antibody (e.g., OKT3) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the population of T cells in the first co-culturing step is present in a population of PBMCs.

In some embodiments, there is provided a method of preparing a population of T cells for TCR cloning, comprising: a) a first co-culturing step, comprising co-culturing a first population of DCs loaded with a target tumor antigen peptide with a population of T cells to obtain a first co-culture comprising activated T cells; b) an enrichment step, comprising subjecting the first co-culture to an enrichment process to obtain an enriched population of activated T cells; and c) a second co-culturing step, comprising co-culturing the enriched population of activated T cells with a second population of DCs loaded with the target tumor antigen peptide in an initial second co-culture medium comprising one or more cytokines (such as IL-2 or a plurality of cytokines) and an immune checkpoint inhibitor (e.g., anti-PD-1 antibody) to obtain a second co-culture, and adding an anti-CD3 antibody (e.g., OKT3) to the second co-culture to obtain a population of T cells for TCR cloning, wherein the population of T cells in the first co-culturing step is obtained from an individual who has clinically benefitted from a MASCT, and wherein at least about 10% (e.g., at least 20% or 50%) of the population of T cells for TCR cloning specifically responds to the target tumor antigen peptide. In some embodiments, the anti-CD3 antibody is added to the second co-culture no more than about 3 days (e.g., about 2 days) after the second co-culturing step starts. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody). In some embodiments, the enrichment process comprises contacting the first co-culture with APCs (e.g., PBMCs) loaded with the target tumor antigen peptide to obtain a stimulated co-culture, and isolating an enriched population of activated T cells from the stimulated co-culture using a ligand that specifically recognizes a cytokine (such as IFNγ) or a cell surface molecule. In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days. In some embodiments, the population of T cells in the first co-culturing step is present in a population of PBMCs.

In some embodiments, there is provided a method of preparing a population of T cells for TCR cloning, comprising: a) contacting a first population of DCs with a target tumor antigen peptide to obtain a first population of DCs loaded with the target tumor antigen peptide; b) a first co-culturing step, comprising co-culturing the first population of DCs loaded with the target tumor antigen peptide with a population of T cells to obtain a first co-culture comprising activated T cells; c) an enrichment step, comprising subjecting the first co-culture to an enrichment process to obtain an enriched population of activated T cells; d) contacting a second population of dendritic cells with the target tumor antigen peptide to obtain a second population of DCs loaded with the target tumor antigen peptide; and e) a second co-culturing step, comprising co-culturing the enriched population of activated T cells with the second population of DCs loaded with the target tumor antigen peptide in an initial second co-culture medium comprising one or more cytokines (such as IL-2 or a plurality of cytokines) and an immune checkpoint inhibitor (e.g., anti-PD-1 antibody) to obtain a second co-culture, and adding an anti-CD3 antibody (e.g., OKT3) to the second co-culture to obtain a population of T cells for TCR cloning, wherein the population of T cells in the first co-culturing step is obtained from an individual who has clinically benefitted from a MASCT, and wherein at least about 10% (e.g., at least 20% or 50%) of the population of T cells for TCR cloning specifically responds to the target tumor antigen peptide. In some embodiments, the anti-CD3 antibody is added to the second co-culture no more than about 3 days (e.g., about 2 days) after the second co-culturing step starts. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody). In some embodiments, the enrichment process comprises contacting the first co-culture with APCs (e.g., PBMCs) loaded with the target tumor antigen peptide to obtain a stimulated co-culture, and isolating an enriched population of activated T cells from the stimulated co-culture using a ligand that specifically recognizes a cytokine (such as IFNγ) or a cell surface molecule. In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days. In some embodiments, the population of T cells in the first co-culturing step is present in a population of PBMCs.

In some embodiments, there is provided a method of preparing a population of T cells for TCR cloning, comprising a) contacting a first population of DCs with a target tumor antigen peptide to obtain a first population of DCs loaded with the target tumor antigen peptide; b) culturing the first population of DCs loaded with the target tumor antigen peptide in a DC maturation medium comprising a toll-like receptor (TLR) agonist; c) a first co-culturing step, comprising co-culturing the first population of DCs loaded with the target tumor antigen peptide with the population of T cells in a first co-culture medium comprising one or more cytokines (such as IL-2 or a plurality of cytokines, e.g., IL-2, IL-7, IL-15 and IL-21), an immune checkpoint inhibitor (e.g., anti-PD-1 antibody) to obtain a first co-culture comprising activated T cells; d) an enrichment step, comprising contacting the first co-culture with PBMCs loaded with the target tumor antigen peptide to obtain a stimulated co-culture, and isolating an enriched population of activated T cells from the stimulated co-culture using a ligand that specifically recognizes a cytokine (such as IFNγ) or a cell surface molecule; e) contacting a second population of DCs with the target tumor antigen peptide to obtain a second population of antigen-loaded DCs; f) culturing the second population of antigen-loaded DCs in a DC maturation medium comprising a toll-like receptor (TLR) agonist; and g) a second co-culturing step, comprising co-culturing the enriched population of activated T cells with the second population of DCs loaded with the target tumor antigen peptide in a second initial co-culture medium comprising one or more cytokines (such as IL-2 or a plurality of cytokines) and an immune checkpoint inhibitor (e.g., anti-PD-1 antibody) to obtain a second co-culture, and adding an anti-CD3 antibody (e.g., OKT3) to the second co-culture to provide a population of T cells for TCR cloning, wherein the population of T cells in the first co-culturing step is obtained from an individual who has clinically benefitted from a MASCT, and wherein at least about 10% (e.g., at least 20% or 50%) of the population of T cells for TCR cloning specifically responds to the target tumor antigen peptide. In some embodiments, the anti-CD3 antibody is added to the second co-culture no more than about 3 days (e.g., about 2 days) after the second co-culturing step starts. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody).

In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days. In some embodiments, the population of T cells in the first co-culturing step is present in a population of PBMCs. In some embodiments, the DC maturation medium comprises INFγ, MPLA and PGE2. In some embodiments, the first population of DCs and/or the second population of DCs is obtained by inducing differentiation of a population of monocytes from PBMCs.

In some embodiments, there is provided a method of preparing a population of T cells for TCR cloning, comprising: co-culturing a population of tumor antigen-specific T cells with a population of APCs (e.g., PBMCs, DCs, or cell line APCs) loaded with one or more target tumor antigen peptides. In some embodiments, the population of tumor antigen-specific T cells is obtained using any one of the methods of preparing T cells for cloning TCR described above. In some embodiments, the population of tumor antigen-specific T cells is obtained from the PBMCs of an individual that has clinically benefitted from a MASCT. In some embodiments, the ratio between the population of tumor antigen-specific T cells and the population of antigen-loaded APCs is about 1:1 to about 20:1 (e.g., about 1:1, 1:2 or 1:4). In some embodiments, the population of tumor antigen-specific T cells and the population of antigen-loaded APCs are co-cultured for about 5 to 9 (e.g., about 7) days. In some embodiments, the population of tumor antigen-specific T cells and the population of antigen-loaded APCs are co-cultured in a third co-culture medium comprising one or more cytokines (such as IL-2 or a plurality of cytokines, e.g., IL-2, IL-7, IL-15) and an anti-CD3 antibody (e.g., OKT3). In some embodiments, the co-culturing is repeated, e.g., once or twice. In some embodiments, the population of the tumor antigen-specific T cells is obtained from a frozen stock of the tumor antigen-specific T cells.

In some embodiments, there is provided a method of preparing a population of T cells for TCR cloning, comprising: a) a first co-culturing step, comprising co-culturing a first population of DCs loaded with a target tumor antigen peptide with a population of T cells to obtain a first co-culture comprising activated T cells; b) an enrichment step, comprising subjecting the first co-culture to an enrichment process to obtain an enriched population of activated T cells; c) a second co-culturing step, comprising co-culturing the enriched population of activated T cells with a second population of DCs loaded with the target tumor antigen peptide to obtain a first population of tumor antigen-specific T cells; d) a third co-culturing step, comprising co-culturing a subpopulation of tumor antigen-specific T cells from the first population of tumor antigen-specific T cells with a third population of APCs (e.g., DCs, PBMCs, or cell line APCs such as LCL) loaded with the target tumor antigen peptide, thereby providing a population of T cells for TCR cloning, wherein the population of T cells in the first co-culturing step is obtained from an individual who has clinically benefitted from a MASCT, and wherein at least about 10% (e.g., at least 20% or 50%) of the population of T cells for TCR cloning specifically responds to the target tumor antigen peptide. In some embodiments, the ratio between the subpopulation of tumor antigen-specific T cells and the third population of antigen-loaded DCs is about 1:1 to about 20:1 (e.g., about 1:1, 1:2 or 1:4). In some embodiments, the subpopulation of tumor antigen-specific T cells and the third population of antigen-loaded DCs are co-cultured for about 5 to 9 (e.g., about 7) days. In some embodiments, the subpopulation of tumor antigen-specific T cells and the third population of antigen-loaded DCs are co-cultured in a third co-culture medium comprising one or more cytokines (such as IL-2 or a plurality of cytokines, e.g., IL-2, IL-7, IL-15) and an anti-CD3 antibody (e.g., OKT3). In some embodiments, the third co-culturing step is repeated, e.g., once, twice or three times. In some embodiments, the subpopulation of tumor antigen-specific T cells is obtained from a frozen stock of the first population of tumor antigen-specific T cells. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody). In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days. In some embodiments, the method comprises co-culturing the second population of antigen-loaded DCs with the population of T cells in an initial second co-culture medium comprising one or more cytokines (such as IL-2 or a plurality of cytokines) and an immune checkpoint inhibitor (e.g., anti-PD-1 antibody) to provide a second co-culture; and adding an anti-CD3 antibody (e.g., OKT3) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the population of T cells in the first co-culturing step is present in a population of PBMCs.

Exemplary methods for preparing T cells for TCR cloning or for preparing tumor antigen-specific T cells are illustrated in FIGS. 4, 7 and 15A-15B and described in Examples 2-3.

Figure 4:
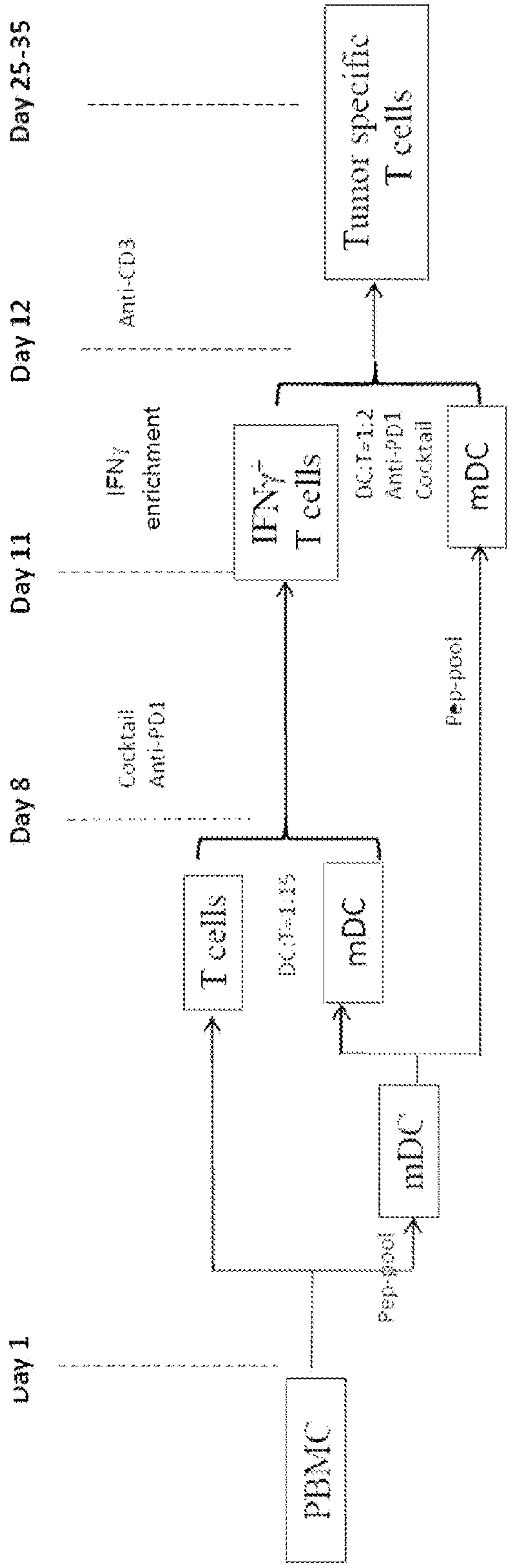
FIG. 4 shows an exemplary method ("Method 2") for preparing tumor antigen-specific T cells as described in Example 2.
Figure 7:
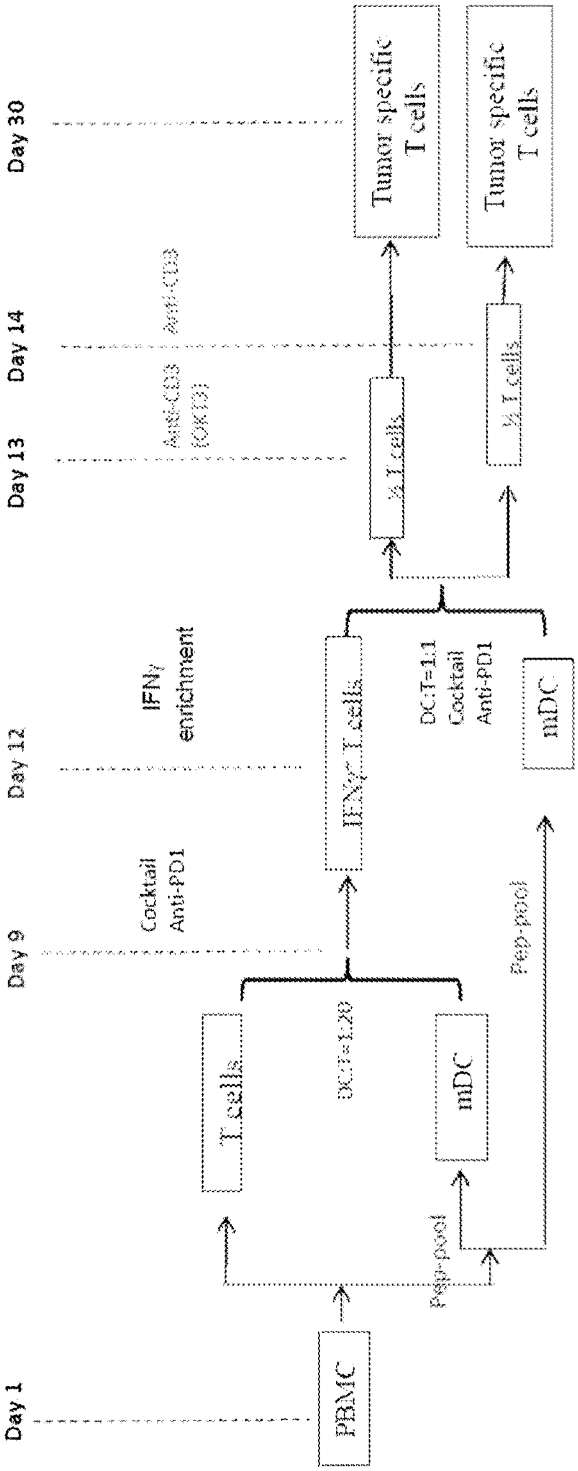
FIG. 7 shows optimization of the exemplary method of FIG. 4 ("Method 2m") for preparing tumor antigen-specific T cells as described in Example 2.

In some embodiments, there is provided a method of preparing a population of T cells for TCR cloning, comprising: (a) contacting a population of DCs derived from a population of PBMCs from an individual with a target tumor antigen peptide to obtain antigen-loaded DCs; (b) a first co-culture step comprising co-culturing a population of T cells (e.g., present in PBMCs) and a first population of the antigen-loaded DCs in an initial first co-culture medium comprising one or more cytokines (such as IL-2 or a plurality of cytokines) and an immune checkpoint inhibitor (e.g., anti-PD-1 antibody); (c) an enrichment step comprising contacting the first co-culture with PBMCs loaded with the target tumor antigen peptide to obtain a stimulated co-culture, and isolating an enriched population of activated T cells from the stimulated co-culture using a ligand that specifically recognizes a cytokine (such as IFNγ) to obtain an enriched population of activated T cells; (d) a second co-culture step comprising co-culturing the enriched population of activated T cells and a second population of the antigen-loaded DCs in an initial second co-culture medium comprising one or more cytokines (such as IL-2 or a plurality of cytokines) and an immune checkpoint inhibitor (e.g., anti-PD-1 antibody) to obtain a second co-culture, and adding an anti-CD3 antibody (e.g., OKT3) to the second co-culture about 1 day to about 3 days (e.g., about 2 days) after the second co-culture starts, thereby providing a population of T cells for TCR cloning, wherein the population of T cells in the first co-culturing step is obtained from an individual who has clinically benefitted from a MASCT, and wherein at least about 10% (e.g., at least 20% or 50%) of the population of T cells for TCR cloning specifically responds to the target tumor antigen peptide. In some embodiments, the antigen-loaded DCs are cultured in a DC maturation medium comprising a toll-like receptor (TLR) agonist. In some embodiments, the DC maturation medium comprises INFγ, MPLA and PGE2. In some embodiments, the antigen-loaded DCs are cultured in the DC maturation medium for about 8 to about 12 days. In some embodiments, the ratio between the population of T cells and the first population of the antigen-loaded DCs is about 20:1. In some embodiments, the population of T cells and the population of antigen-loaded DCs are co-cultured for about 2-3 days. In some embodiments, the ratio between the enriched population of activated T cells and the second population of antigen-loaded DCs is about 1:1. In some embodiments, the enriched population of activated T cells and the second population of antigen-loaded DCs are co-cultured for about 15-20 days (e.g., about 16 days). Exemplary methods are shown in FIGS. 4 and 7.

Figure 15A:
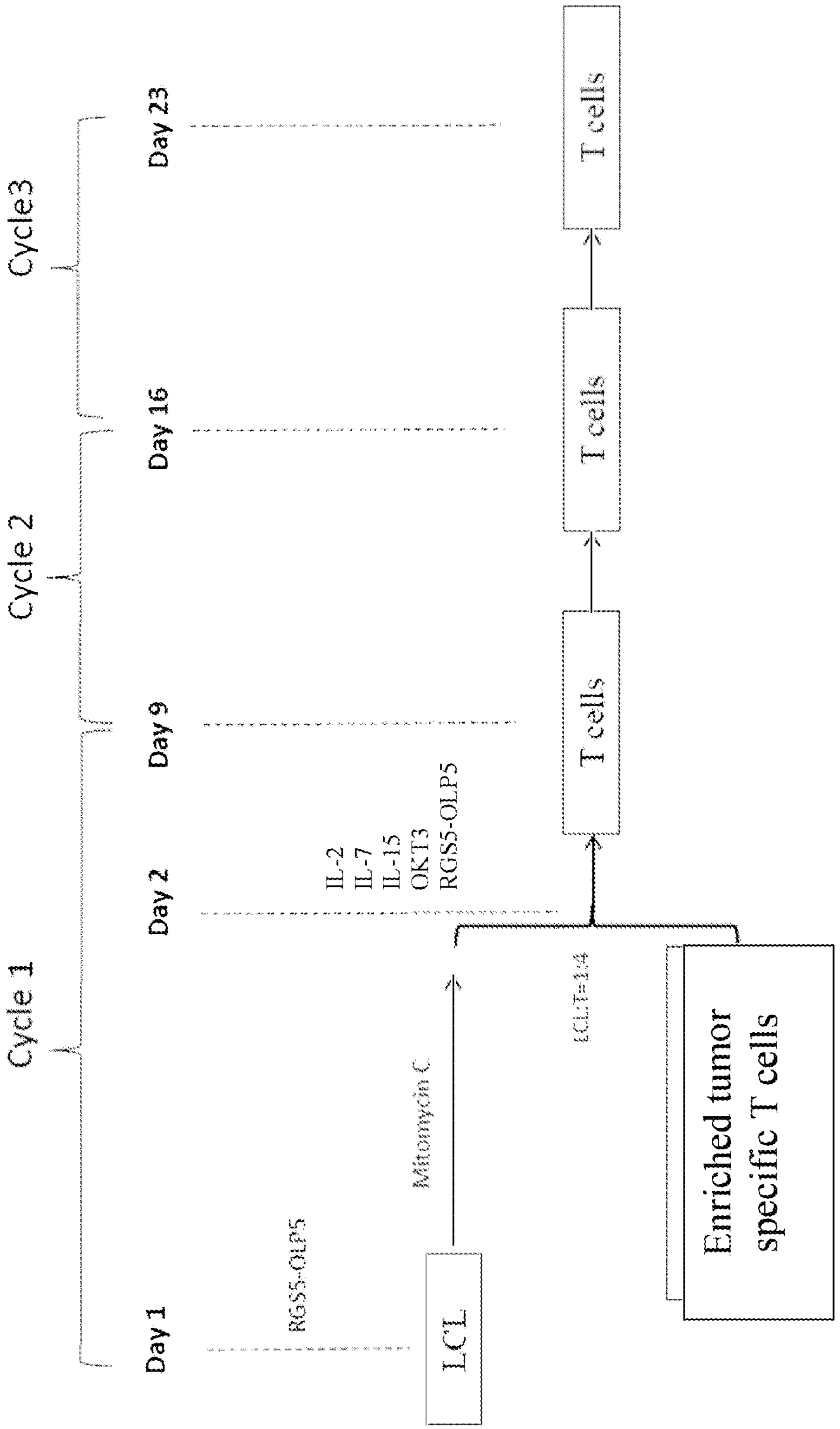
FIGS. 15A-15B show exemplary methods for preparing tumor antigen-specific T cells from a frozen stock of tumor antigen-specific T cells prepared by Method 2 or Method 2m as described in Example 3.
Figure 15B:
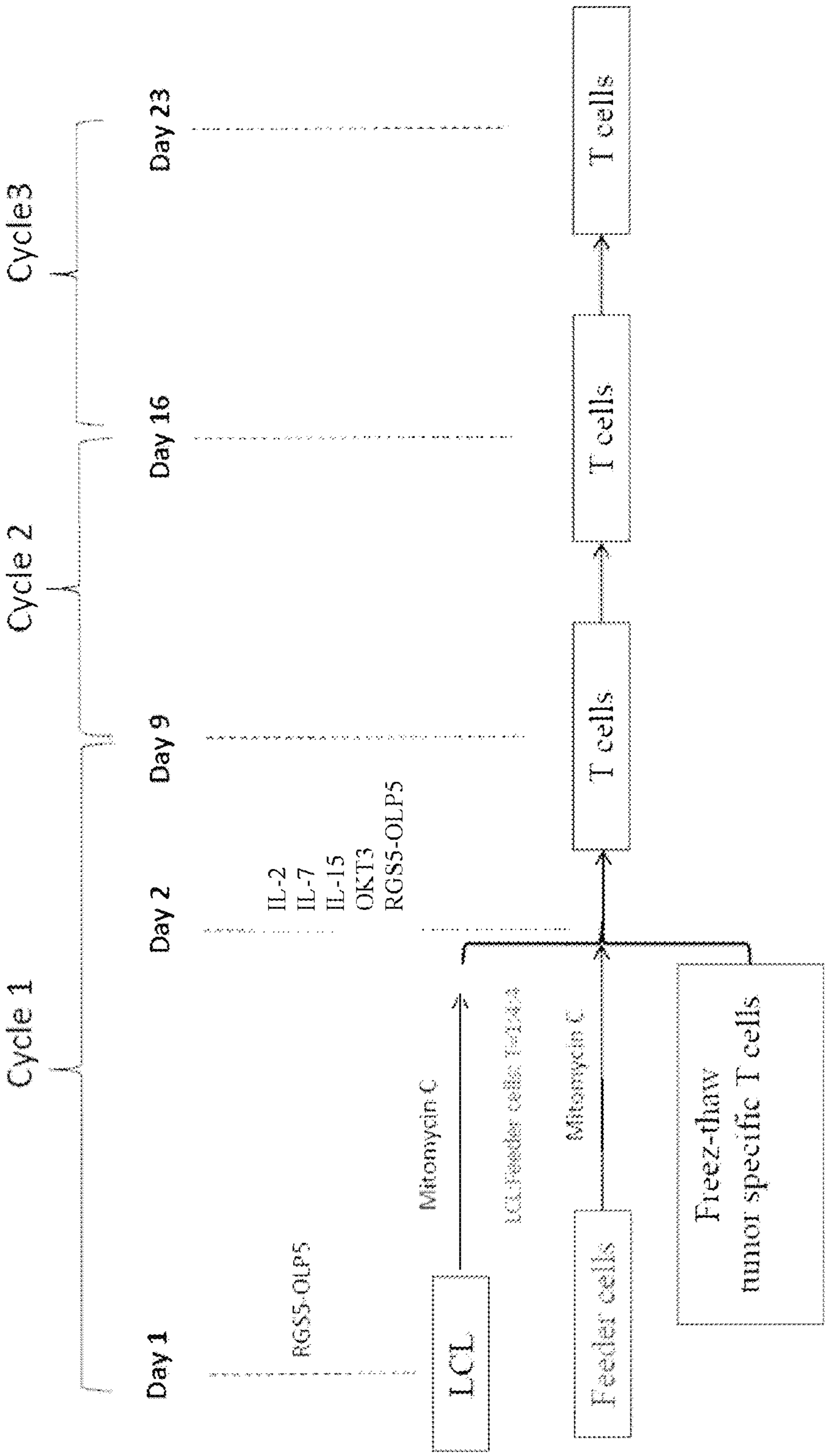

In some embodiments, there is provided a method of preparing a population of T cells for TCR cloning, comprising: (a) co-culturing a population of tumor-antigen specific T cells with a first population of APCs (e.g., PBMCs, DCs, or cell line APCs) loaded with a target tumor antigen peptide for about 5 to 9 days (e.g., about 7 days) in a co-culture medium comprising one or more cytokines (such as IL-2 or a plurality of cytokines) and an anti-CD3 antibody to obtain a first population of tumor antigen-specific T cells; and (b) co-culturing the first population of tumor antigen-specific T cells with a second population of APCs loaded with the target tumor antigen peptide for about 5 to 9 days (e.g., about 7 days), thereby providing a second population of tumor antigen-specific T cells for TCR cloning, wherein the population of tumor antigen-specific T cells is obtained from an individual who has clinically benefitted from a MASCT, and wherein at least about 10% (e.g., at least 20% or 50%) of the population of T cells for TCR cloning specifically responds to the target tumor antigen peptide. In some embodiments, the stimulation step is repeated once or twice. In some embodiments, the method further comprises: co-culturing the second population of tumor antigen-specific T cells with a third population of APCs loaded with the tumor antigen-specific T cells for about 5 to 9 days (e.g., about 7 days), thereby providing a third population of tumor antigen-specific T cells. In some embodiments, the APCs are LCL cells with or without feeder cells. In some embodiments, the APCs are DCs. In some embodiments, the co-culture medium comprises IL-2, IL-7, IL-15 and OKT3. In some embodiments, the ratio between the antigen-loaded APCs and the first, second or third population of tumor antigen-specific T cells is about 1:1 to about 1:10 (e.g., about 1:4). Exemplary methods are shown in FIGS. 15A-15B.

The tumor antigen-specific T cells used for the sequencing step have a high percentage of T cells that specifically responds to the target tumor antigen peptide or epitope thereof. For example, at least about any one of 20%, 30%, 40%, 50%, 60%, 70%, 80%, 90% or higher of the tumor antigen-specific T cells used for the sequencing step specifically respond to the target tumor antigen peptide or epitope thereof. In some embodiments, any one of about 20-90%, 20-50%, 50-95%, 20-80%, 50-70%, 40-60%, or 40%-80% of the tumor antigen-specific T cells used for the sequencing step specifically respond to the target tumor antigen peptide or epitope thereof. Because T cells express a large number of TCRα and TCRβ clonotypes, a high percentage of T cells that can specifically respond to the tumor antigen peptide is important for obtaining successful cognate pairing information of the TCRα and TCRβ genes.

In some embodiments, the tumor antigen-specific T cells in any embodiment of the isolated population of cells are capable of eliciting specific immune response to the one or more tumor antigen peptides in vivo or ex vivo. In some embodiments, the tumor antigen-specific T cells are capable of increasing cytotoxic T cell activity in a human individual against more than one tumor antigen peptides. In some embodiments, the tumor antigen-specific T cells are characterized by high expression or secretion level of pro-inflammatory signal molecules, upon stimulation by the one or more tumor antigen peptides. In some embodiments, the expression or secretion level is determined by comparing the expression or secretion level of a molecule (such as a pro-inflammatory signal molecule) of the tumor antigen-specific T cells upon stimulation with the one or more tumor antigen peptides to the expression or secretion level upon stimulation with an irrelevant peptide. In some embodiments, the control expression or secretion level of a molecule is the expression or secretion level of the molecule in a control population of T cells measured under the same assay conditions. In some embodiments, the control population of T cells is a population of T cells induced by one or more irrelevant peptides (such as peptides not corresponding to T cell receptor antigens, or random peptides). In some embodiments, the control expression or secretion level of a molecule is an average or median expression or secretion level of the molecule in a plurality of control populations of T cells. In some embodiments, a high level of expression or secretion of a molecule in the tumor antigen-specific T cells is at least about any of 1.5, 2, 2.5, 3, 4, 5, 10, 20, 50, 100, 1000, or more times of the control expression or secretion level.

In some embodiments, upon stimulation with the target tumor antigen peptide, the tumor antigen-specific T cells express a plurality of pro-inflammatory molecules, such as IFNγ, TNFα, granzyme B, perform, or any combination thereof. In some embodiments, at least about any one of 10%, 20%, 30%, 40%, 50%, 60%, 70%, 80%, 90% or higher percentage of tumor antigen-specific T cells that secrete INF-γ upon stimulation with the target tumor antigen peptide. In some embodiments, at least about any one of 10%, 20%, 30%, 40%, 50%, 60%, 70%, 80%, 90% or higher percentage of tumor antigen-specific T cells secrete TNF-α upon stimulation with the target tumor antigen peptide.

In some embodiments, the tumor antigen-specific T cells are prepared by steps comprising: (a) contacting a population of DCs derived from a population of PBMCs from an individual with a target tumor antigen peptide to obtain a first population of antigen-loaded DCs; (b) a first co-culture step comprising co-culturing a population of T cells (e.g., present in PBMCs) and the first population of antigen-loaded DCs in an initial first co-culture medium comprising one or more cytokines (such as IL-2 or a plurality of cytokines) and an immune checkpoint inhibitor (e.g., anti-PD-1 antibody), and adding an anti-CD3 antibody to the first co-culture no more than about 7 days (e.g., about 5 days) after the first-co-culture starts to obtain a first co-culture; (c) an enrichment step comprising contacting the first co-culture with PBMCs loaded with the target tumor antigen peptide to obtain a stimulated co-culture, and isolating an enriched population of activated T cells from the stimulated co-culture using a ligand that specifically recognizes a cytokine (such as IFNγ) to obtain an enriched population of activated T cells; (d) a second co-culture step comprising co-culturing the enriched population of activated T cells and a second population of DCs loaded with the target tumor antigen peptide in a co-culture medium comprising one or more cytokines (such as IL-2 or a plurality of cytokines), an immune checkpoint inhibitor (e.g., anti-PD-1 antibody) and an anti-CD3 antibody, thereby providing the tumor antigen-specific T cells. In some embodiments, the ratio between the population of T cells and the first population of antigen-loaded DCs is about 20:1. In some embodiments, the population of T cells and the population of antigen-loaded DCs are co-cultured for about 13-14 days. In some embodiments, the ratio between the enriched population of activated T cells and the second population of antigen-loaded DCs is about 2:1. In some embodiments, the enriched population of activated T cells and the second population of antigen-loaded DCs are co-cultured for about 9-13 days.

In some embodiments, the tumor antigen-specific T cells are prepared by steps comprising: (a) contacting a population of DCs derived from a population of PBMCs from an individual with a target tumor antigen peptide to obtain antigen-loaded DCs; (b) a first co-culture step comprising co-culturing a population of T cells (e.g., present in PBMCs) and a first population of the antigen-loaded DCs in an initial first co-culture medium comprising one or more cytokines (such as IL-2 or a plurality of cytokines) and an immune checkpoint inhibitor (e.g., anti-PD-1 antibody); (c) an enrichment step comprising contacting the first co-culture with PBMCs loaded with the target tumor antigen peptide to obtain a stimulated co-culture, and isolating an enriched population of activated T cells from the stimulated co-culture using a ligand that specifically recognizes a cytokine (such as IFNγ) to obtain an enriched population of activated T cells; (d) a second co-culture step comprising co-culturing the enriched population of activated T cells and a second population of the antigen-loaded DCs in a co-culture medium comprising one or more cytokines (such as IL-2 or a plurality of cytokines), an immune checkpoint inhibitor (e.g., anti-PD-1 antibody) and an anti-CD3 antibody, thereby providing the tumor antigen-specific T cells. In some embodiments, the antigen-loaded DCs are cultured in a DC maturation medium comprising a toll-like receptor (TLR) agonist. In some embodiments, the DC maturation medium comprises INFγ, MPLA and PGE2. In some embodiments, the antigen-loaded DCs are cultured in the DC maturation medium for about 8 to about 12 days. In some embodiments, the ratio between the population of T cells and the first population of the antigen-loaded DCs is about 15:1. In some embodiments, the population of T cells and the population of antigen-loaded DCs are co-cultured for about 3-4 days. In some embodiments, the ratio between the enriched population of activated T cells and the second population of antigen-loaded DCs is about 2:1. In some embodiments, the enriched population of activated T cells and the second population of antigen-loaded DCs are co-cultured for about 13-23 days.

In some embodiments, the tumor antigen-specific T cells are prepared by steps comprising: (a) contacting a population of DCs derived from a population of PBMCs from an individual with a target tumor antigen peptide to obtain antigen-loaded DCs; (b) a first co-culture step comprising co-culturing a population of T cells (e.g., present in PBMCs) and a first population of the antigen-loaded dendritic cells in an initial first co-culture medium comprising one or more cytokines (such as IL-2 or a plurality of cytokines) and an immune checkpoint inhibitor (e.g., anti-PD-1 antibody); (c) an enrichment step comprising contacting the first co-culture with PBMCs loaded with the target tumor antigen peptide to obtain a stimulated co-culture, and isolating an enriched population of activated T cells from the stimulated co-culture using a ligand that specifically recognizes a cytokine (such as IFNγ) to obtain an enriched population of activated T cells; (d) a second co-culture step comprising co-culturing the enriched population of activated T cells and a second population of the antigen-loaded DCs in an initial second co-culture medium comprising one or more cytokines (such as IL-2 or a plurality of cytokines) and an immune checkpoint inhibitor (e.g., anti-PD-1 antibody) to obtain a second co-culture, and adding an anti-CD3 antibody (e.g., OKT3) to the second co-culture about 1 day to about 3 days (e.g., about 2 days) after the second co-culture starts, thereby providing the tumor antigen-specific T cells. In some embodiments, the antigen-loaded DCs are cultured in a DC maturation medium comprising a toll-like receptor (TLR) agonist. In some embodiments, the DC maturation medium comprises INFγ, MPLA and PGE2. In some embodiments, the antigen-loaded DCs are cultured in the DC maturation medium for about 8 to about 12 days. In some embodiments, the ratio between the population of T cells and the first population of the antigen-loaded DCs is about 20:1. In some embodiments, the population of T cells and the population of antigen-loaded DCs are co-cultured for about 2-3 days. In some embodiments, the ratio between the enriched population of activated T cells and the second population of antigen-loaded DCs is about 1:1. In some embodiments, the enriched population of activated T cells and the second population of antigen-loaded DCs are co-cultured for about 15-20 days (e.g., about 16 days).

In some embodiments, the tumor antigen-specific T cells are prepared by steps comprising: (a) contacting a population of DCs derived from a population of PBMCs from an individual with a target tumor antigen peptide to obtain antigen-loaded DCs; (b) a first co-culture step comprising co-culturing a population of T cells (e.g., present in PBMCs) and a first population of the antigen-loaded DCs in an initial first co-culture medium comprising one or more cytokines (such as IL-2 or a plurality of cytokines) and an immune checkpoint inhibitor (e.g., anti-PD-1 antibody); (c) an enrichment step comprising contacting the first co-culture with PBMCs loaded with the target tumor antigen peptide to obtain a stimulated co-culture, and isolating an enriched population of activated T cells from the stimulated co-culture using a ligand that specifically recognizes a cytokine (such as IFNγ) to obtain an enriched population of activated T cells; (d) a second co-culture step comprising co-culturing the enriched population of activated T cells and a second population of the antigen-loaded DCs in an initial second co-culture medium comprising one or more cytokines (such as IL-2 or a plurality of cytokines) and an immune checkpoint inhibitor (e.g., anti-PD-1 antibody) to obtain a second co-culture, and adding an anti-CD3 antibody (e.g., OKT3) to the second co-culture about 1 day to about 3 days (e.g., about 2 days) after the second co-culture starts, thereby providing the tumor antigen-specific T cells. In some embodiments, the antigen-loaded DCs are cultured in a DC maturation medium comprising a toll-like receptor (TLR) agonist. In some embodiments, the DC maturation medium comprises INFγ, MPLA and PGE2. In some embodiments, the antigen-loaded DCs are cultured in the DC maturation medium for about 8 to about 12 days. In some embodiments, the ratio between the population of T cells and the first population of the antigen-loaded DCs is about 20:1. In some embodiments, the population of T cells and the population of antigen-loaded DCs are co-cultured for about 2-3 days. In some embodiments, the ratio between the enriched population of activated T cells and the second population of antigen-loaded DCs is about 1:1. In some embodiments, the enriched population of activated T cells and the second population of antigen-loaded DCs are co-cultured for about 15-20 days (e.g., about 16 days).

In some embodiments, the method uses PBMC obtained from an individual who has previously received an immunotherapy (e.g., MASCT) to prepare tumor-antigen specific T cells used in the sequencing step.

In some embodiments, the method comprises: a) contacting a first population of PBMCs from the individual with the target tumor antigen peptide to provide a population of PBMCs loaded with the target tumor antigen peptide; b) subjecting the population of PBMCs loaded with the target tumor antigen peptide to an enrichment process to provide an enriched population of activated T cells; c) optionally contacting a population of APCs (e.g., PBMCs, or DCs) with the target tumor antigen peptide to provide a population of antigen-loaded APCs; d) a co-culturing step, comprising co-culturing the enriched population of activated T cells with the population of antigen-loaded APCs to obtain a population of tumor antigen-specific T cells. In some embodiments, the PBMCs are contacted with the target tumor antigen peptide for no more than about 5, 4, 3, 2, or 1 day prior to the enrichment process. In some embodiments, the enrichment process comprises contacting the first co-culture with PBMCs loaded with the target tumor antigen peptide to obtain a stimulated co-culture, and isolating an enriched population of activated T cells from the stimulated co-culture using a ligand that specifically recognizes a cytokine (such as IFNγ) or a cell surface molecule. In some embodiments, the co-culturing step comprises co-culturing the enriched population of activated T cells with the population of antigen-loaded APCs in a co-culture medium comprising one or more cytokines (such as IL-2 or a plurality of cytokines), an immune checkpoint inhibitor, and an anti-CD3 antibody. In some embodiments, the co-culturing step comprises co-culturing the enriched population of activated T cells with the population of antigen-loaded APCs in an initial co-culture medium comprising one or more cytokines (such as IL-2 or a plurality of cytokines) and an immune checkpoint inhibitor to provide a co-culture, and adding an anti-CD3 antibody to the co-culture. In some embodiments, the anti-CD3 antibody is added to the co-culture at about 1-3 days after the co-culturing starts. In some embodiments, the enriched population of activated T cells and the population of antigen-loaded APCs are co-cultured for a total of about 12-25 days.

In some embodiments, the PBMCs are freshly obtained. In some embodiments, the PBMCs are obtained by thawing a frozen stock of PBMCs. In some embodiments, the PBMCs are autologous, i.e. obtained from the individual being treated. In some embodiments, the PBMCs are contacted with cytokines, such as IL-2, GM-CSF, or the like, to induce differentiation, maturation, or proliferation of certain cells (such as DCs, T cells, or combination thereof) in the PBMCs concurrently or after the contacting step.

In some embodiments, the tumor antigen-specific T cells are prepared by steps comprising: (a) contacting a population of PBMCs with a target tumor antigen peptide to obtain a population of stimulated PBMCs; (b) isolating an enriched population of activated T cells from the population of stimulated PBMCs using a ligand that specifically recognizes a cytokine (such as IFNγ) to obtain an enriched population of activated T cells; and (c) a co-culture step comprising co-culturing the enriched population of activated T cells and a population of DCs loaded with a target tumor antigen peptide in an initial co-culture medium comprising one or more cytokines (such as IL-2 or a plurality of cytokines) and an immune checkpoint inhibitor (e.g., anti-PD-1 antibody) to obtain a first co-culture, and adding an anti-CD3 antibody (e.g., OKT3) to the first co-culture about 1 day to about 3 days (e.g., about 1 day or 2 days) after the first co-culture starts, thereby providing the tumor antigen-specific T cells. In some embodiments, the PBMCs are from a frozen stock. In some embodiments, the PBMCs are freshly obtained from the individual. In some embodiments, the antigen-loaded DCs are prepared by contacting a population of PBMCs with a target tumor antigen peptide. In some embodiments, the ratio between the enriched population of activated T cells and the population of antigen-loaded DCs is about 1:1. In some embodiments, the enriched population of activated T cells and the population of antigen-loaded DCs are co-cultured for about 7 to about 21 days.

Co-Culturing

The methods described herein and the MASCT methods comprise one or more (such as 1, 2, 3, or more) co-culturing steps. In some embodiments, the method comprises a first co-culturing step, comprising co-culturing a population of T cells with a population of DCs loaded with the target tumor antigen peptide. In some embodiments, in the first co-culturing step, the population of T cells is co-cultured with the first population of antigen-loaded DCs for no more than about 7 days, such as about any one of 1, 2, 3, 4, 5, 6, or 7 days. In some embodiments, the population of T cells is co-cultured with the first population of antigen-loaded DCs for about 1-3 days, such as about 2-3 days.

In some embodiments, the first co-culturing step comprises co-culturing a first population of antigen-loaded DCs and the population of T cells in a first co-culture medium comprising one or more cytokines (such as a plurality of cytokines) and an immune checkpoint inhibitor. In some embodiments, the first co-culture medium comprises an anti-CD3 antibody. In some embodiments, the first co-culture medium does not comprise an anti-CD3 antibody. In some embodiments, the first co-culturing step comprises co-culturing a first population of antigen-loaded DCs and the population of T cells in a first initial co-culture medium comprising one or more cytokines (such as a plurality of cytokines) and an immune checkpoint inhibitor to provide a first co-culture; and adding an anti-CD3 antibody to the first co-culture.

In some embodiments, the method comprises a second co-culturing step, comprising co-culturing an enriched population of activated T cells with a population of DCs loaded with the target tumor antigen peptide. In some embodiments, in the second co-culturing step, the enriched population of activated T cells and the second population of antigen-loaded DCs are co-cultured for a total of at least about any one of 2, 4, 6, 8, 10, 12, 14, 16, 18, 20, 22, 24, 26, 28, or 30 days. In some embodiments, the enriched population of activated T cells is co-cultured with the second population of antigen-loaded DCs for about 12 days to about 25 days, such as about any one of 12-15, 15-18, 18-21, 15-20, 20-25, 15, 18, 19, 20, 21, or 22 days.

In some embodiments, the enriched population of activated T cells and the second population of antigen-loaded DCs are co-cultured in the presence of the anti-CD3 antibody for at least about any one of 1, 2, 3, 4, 5, 6, 7, 8, 9, 10, 12, 15, 20, 25 or more days. In some embodiments, the enriched population of activated T cells and the second population of antigen-loaded DCs are co-cultured in the presence of the anti-CD3 antibody for about any one of 8-18, 10-20, 1-25, or 12-25 days. In some embodiments, the enriched population of activated T cells and the second population of antigen-loaded DCs are initially co-cultured without an anti-CD3 antibody for about 1-5 days, such as about 1, 2, or 3 days.

In some embodiments, the second co-culturing step comprises co-culturing a second population of antigen-loaded DCs and the enriched population of activated T cells in a second co-culture medium comprising one or more cytokines (e.g., a plurality of cytokines), an immune checkpoint inhibitor. In some embodiments, the second co-culture medium comprises an anti-CD3 antibody. In some embodiments, the second co-culture medium does not comprise an anti-CD3 antibody. In some embodiments, the second co-culturing step comprises co-culturing a second population of antigen-loaded DCs and the enriched population of activated T cells in a second initial co-culture medium comprising one or more cytokines (e.g., a plurality of cytokines) and an immune checkpoint inhibitor to provide a second co-culture; and adding an anti-CD3 antibody to the second co-culture.

In some embodiments, the method of preparing tumor antigen-specific T cells comprises: (1) a first co-culturing step, comprising co-culturing a population of T cells with a first population of DCs loaded with a plurality of tumor antigen peptides, and (2) a second co-culturing step, comprising co-culturing an enriched population of activated T cells with a second population of DCs loaded with one or more tumor antigen peptides from the plurality of tumor antigen peptides.

In some embodiments, the method comprises a third co-culturing step, comprising co-culturing a population of tumor antigen-specific T cells with a population of APCs (e.g., PBMCs such as fixed PBMCs, DCs, or cell line APCs such as LCL) loaded with the target tumor antigen peptide (or an epitope thereof). In some embodiments, the third co-culturing step is repeated for one or more times (such as 1, 2, 3, 4, 5, 6 or more) times to obtain further populations of tumor antigen-specific T cells. In some embodiments, repeating the third co-culturing step comprising co-culturing a portion of the tumor antigen-specific T cells obtained from the third co-culturing step with a second population of antigen-loaded APCs (e.g., PBMCs such as fixed PBMCs, DCs, or cell line APCs such as LCL). In some embodiments, repeating the third co-culturing step comprising adding to the third co-culture a fresh population of antigen-loaded APCs (e.g., PBMCs such as fixed PBMCs, DCs, or cell line APCs such as LCL) at an interval of every about 5-9 days (e.g., about 7 days).

In some embodiments, in the third co-culturing step, the population of tumor antigen-specific T cells and the population of antigen-loaded APCs (e.g., PBMCs such as fixed PBMCs, DCs, or cell line APCs such as LCL) are co-cultured for at least about any one of 2, 4, 6, 8, 10, 12, 14, 16, 18, 20, or 14 days. In some embodiments, the population of tumor antigen-specific T cells and the population of antigen-loaded APCs (e.g., PBMCs such as fixed PBMCs, DCs, or cell line APCs such as LCL) are co-cultured for about 5 days to about 15 days, such as about any one of 5-9, 7-10, 10-12, 12-15, 7, 8, 9, 10, 11, 12, 13, or 15 days.

In some embodiments, the third co-culturing step comprises co-culturing a population of antigen-loaded APCs (e.g., PBMCs such as fixed PBMCs, DCs, or cell line APCs such as LCL) and a population of tumor antigen-specific T cells in a third co-culture medium comprising one or more cytokines (e.g., a plurality of cytokines) and an immune checkpoint inhibitor. In some embodiments, the third co-culture medium does not comprise an anti-CD3 antibody. In some embodiments, the third co-culture medium comprises an anti-CD3 antibody. In some embodiments, the third co-culturing step comprises co-culturing a population of antigen-loaded APCs (e.g., PBMCs such as fixed PBMCs, DCs, or cell line APCs such as LCL) and a population of tumor antigen-specific T cells in a third initial co-culture medium comprising one or more cytokines (e.g., a plurality of cytokines) and an immune checkpoint inhibitor to provide a third co-culture; and adding an anti-CD3 antibody to the third co-culture.

The co-culture medium or the initial co-culture medium for each co-culturing step may be the same or different. Unless indicated otherwise, "co-culture medium" as discussed in the subsection "Co-culturing" includes the first, second and third co-culture medium; "Initial co-culture medium" as discussed in this subsection includes the first, second and third initial co-culture medium. In some embodiments, the co-culture medium (including the initial co-culture medium) comprises one or more (e.g., 1, 2, 3, 4, 5, or more) cytokines. In some embodiments, the co-culture medium (including the initial co-culture medium) comprises a plurality of cytokines (also referred herein as "cytokine cocktail"). Exemplary cytokines include, but are not limited to, IL-2, IL-7, IL-15, IL-21 and the like. In some embodiments, the co-culture medium (including the initial co-culture medium) comprises IL-2. In some embodiments, the co-culture medium (including the initial co-culture medium) comprises IL-2, IL-7, IL-15 and IL-21. In some embodiments, the IL-2 is present at a concentration of at least about any of 50, 100, 200, 300, 400, 500, 600, 700, 800, 900, 1000, 2000, 5000, 6000 or higher IU/ml in the co-culture medium (including the initial co-culture medium). In some embodiments, the IL-2 is present at a concentration of no more than about any one of 1000, 500, 200, 100, 50, 20, or lower IU/ml in the co-culture medium (including the initial co-culture medium). In some embodiments, the first co-culture medium comprises IL-2 at a concentration of no more than about 200 IU/mL (such as about 150, 100 or 50 IU/ml). In some embodiments, the second co-culture medium comprises IL-2 at a concentration of at least about 2000 IU/mL (such as about 3000, 5000, or 6000 IU/mL). In some embodiments, the IL-7 is present at a concentration of at least about any one of 1, 2, 5, 10, 20, 50 or 100 ng/mL in the co-culture medium (including the initial co-culture medium). In some embodiments, the IL-15 is present at a concentration of at least about any one of 1, 2, 5, 10, 20, 50 or 100 ng/mL in the co-culture medium (including the initial co-culture medium). The cytokines may facilitate activation, maturation, and/or proliferation of the T cells, to prime T cells for later differentiation into memory T cells, and/or suppress the percentage of $T_{REG}$ in the co-culture.

In some embodiments, the co-culture medium (including the initial co-culture medium) comprises one or more (such as any of 1, 2, 3, or more) immune checkpoint inhibitors. Any known immune checkpoint inhibitors may be used. In some embodiments, the immune checkpoint inhibitor is a natural or engineered ligand of an inhibitory immune checkpoint molecule, including, for example, ligands of CTLA-4 (e.g., B7.1, B7.2), ligands of TIM-3 (e.g., Galectin-9), ligands of A2a Receptor (e.g., adenosine, Regadenoson), ligands of LAG-3 (e.g., MHC class I or MHC class II molecules), ligands of BTLA (e.g., HVEM, B7-H4), ligands of KIR (e.g., MHC class I or MHC class II molecules), ligands of PD-1 (e.g., PD-L1, PD-L2), ligands of IDO (e.g., NKTR-218, Indoximod, NLG919), and ligands of CD47 (e.g., SIRP-alpha receptor). The immune checkpoint inhibitors may be of any suitable molecular modality, including, but not limited to, small molecules, nucleic acids (such as DNA, RNAi, or aptamer), peptides, or proteins (such as antibodies).

In some embodiments, the immune checkpoint inhibitor is an antibody (such as antagonist antibody) that targets an inhibitory immune checkpoint protein selected from the group consisting of anti-CTLA-4 (e.g., Ipilimumab, Tremelimumab, KAHR-102), anti-TIM-3 (e.g., F38-2E2, ENUM005), anti-LAG-3 (e.g., BMS-986016, IMP701, IMP321, C9B7W), anti-KIR (e.g., Lirilumab and IPH2101), anti-PD-1 (e.g., Nivolumab, Pidilizumab, Pembrolizumab, BMS-936559, atezolizumab, Pembrolizumab, MK-3475, AMP-224, AMP-514, STI-A1110, TSR-042, SHR1210), anti-PD-L1 (e.g., KY-1003 (EP20120194977), MCLA-145, RG7446, BMS-936559, MEDI-4736, MSB0010718C, AUR-012, STI-A1010, PCT/US2001/020964, MPDL3280A, AMP-224, Dapirolizumab pegol (CDP-7657), MEDI-4920), anti-CD73 (e.g., AR-42 (OSU-HDAC42, HDAC-42, AR42, AR 42, OSU-HDAC 42, OSU-HDAC-42, NSC D736012, HDAC-42, HDAC 42, HDAC42, NSCD736012, NSC-D736012), MEDI-9447), anti-B7-H3 (e.g., MGA271, DS-5573a, 8H9), anti-CD47 (e.g., CC-90002, TTI-621, VLST-007), anti-BTLA, anti-VISTA, anti-A2aR, anti-B7-1, anti-B7-H4, anti-CD52 (such as alemtuzumab), anti-IL-10, anti-IL-35, and anti-TGF-β (such as Fresolumimab). In some embodiments, the antibody is a monoclonal antibody. In some embodiments, the antibody is a full-length antibody. In some embodiments, the antibody is an antigen-binding fragment selected from the group consisting of Fab, Fab', $F(ab')_2$, Fv, scFv, BiTE, nanobody, and other antigen-binding subsequences of the full length antibody or engineered combinations thereof. In some embodiments, the antibody is a human antibody, a humanized antibody, or a chimeric antibody. In some embodiments, the antibody is a bispecific or multispecific antibody.

In some embodiments, the immune checkpoint inhibitor is an inhibitor of PD-1. In some embodiments, the immune checkpoint inhibitor is an anti-PD-1 antibody. Exemplary anti-PD-1 antibodies include, but are not limited to, Nivolumab, pembrolizumab, pidilizumab, BMS-936559, and atezolizumab, Pembrolizumab, MK-3475, AMP-224, AMP-514, STI-A1110, TSR-042, and SHR-1210. In some embodiments, the immune checkpoint inhibitor is nivolumab (for example, OPDIVO®). In some embodiments, the immune checkpoint inhibitor is Pembrolizumab (for example, KEYTRUDA®). In some embodiments, the immune checkpoint inhibitor is SHR-1210. In some embodiments, the initial co-culture medium comprises IL-2, IL-7, IL-15, IL-21 and an anti-PD-1 antibody (e.g., SHR-1210).

A suitable concentration of the immune checkpoint inhibitor (e.g., anti-PD-1 antibody) in the co-culture medium (including the initial co-culture medium) include, but are not limited to, at least about any of 1, 2, 5, 10, 15, 20, 25 or more μg/mL. In some embodiments, the immune checkpoint inhibitor (e.g., anti-PD-1 antibody) is present in the co-culture medium (including the initial co-culture medium) is any one of about 1 μg/mL to about 10 μg/mL, about 10 μg/mL to about 20 μg/mL, about 1 μg/mL to about 25 μg/mL, or about 5 μg/mL to about 20 μg/mL.

The anti-CD3 antibody may be present in the co-culture at the time the co-culturing starts, or added to the co-culture after the co-culturing of the antigen-loaded DCs and the T cells, the enriched activated T cells, or the population of tumor antigen-specific T cells starts. In some embodiments, the anti-CD3 antibody is included in the co-culture medium (including the initial co-culture medium). In some embodiments, the initial co-culture medium does not comprise the anti-CD3 antibody.

In some embodiments, the anti-CD3 antibody is added to the second co-culture comprising the enriched population of activated T cells and the second population of antigen-loaded DCs at no more than about any one of 5, 4, 3, 2, or 1 day(s) after the second co-culturing starts. In some embodiments, the anti-CD3 antibody is added to the second co-culture comprising the enriched population of activated T cells and the second population of antigen-loaded DCs about 1, 2, or 3 days after the second co-culturing starts. Any suitable anti-CD3 antibody may be used, including, but not limited to OKT3.

The T cells (e.g., T cells, enriched population of activated T cells, or tumor antigen-specific T cells) and antigen-loaded APCs (such as PBMCs, DCs or cell line APCs) may be present in the co-cultures at an appropriate ratio in terms of the number of cells. In some embodiments, the ratio between the population of T cells to the first population of antigen-loaded DCs in the first co-culturing step is no more than about any one of 30:1, 25:1, 20:1, 15:1, 10:1, 8:1, or 5:1. In some embodiments, the ratio between the population of T cells to the first population of antigen-loaded DCs in the first co-culturing step is at least about any one of 5:1, 8:1, 10:1, 15:1, 20:1, 25:1, or more. In some embodiments, the ratio between the population of T cells to the first population of antigen-loaded DCs in the first co-culturing step is any one of about 5:1 to about 10:1, about 5:1 to about 20:1, about 10:1 to about 20:1, about 20:1 to about 30:1, or about 5:1 to about 30:1. In some embodiments, the ratio between the enriched population of T cells and the second population of antigen-loaded DCs is at least about any one of 1:1, 2:1, 3:1, 4:1, 5:1, 6:1, 7:1, 8:1, 9:1, or 10:1. In some embodiments, the ratio between the enriched population of T cells and the second population of antigen-loaded DCs is no more than about any one of 10:1, 9:1, 8:1, 7:1, 6:1, 5:1, 4:1, 3:1, 2:1 or 1:1. In some embodiments, the ratio between the enriched population of T cells and the second population of antigen-loaded DCs is any one of about 1:1 to about 20:1, about 1:1 to about 10:1, about 1:1 to about 5:1, about 5:1 to about 10:1, about 10:1 to about 15:1, about 15:1 to about 20:1, about 10:1 to about 20:1, about 1:1 to about 1:3, about 1:1 to about 2:1, or about 2:1 to about 5:1. In some embodiments, the ratio between the population of tumor antigen-specific T cells and the population of antigen-loaded APCs (e.g., PBMCs such as fixed PBMCs, DCs, or cell line APCs) is at least about any one of 1:1, 2:1, 3:1, 4:1, 5:1, 6:1, 7:1, 8:1, 9:1, or 10:1. In some embodiments, the ratio between the population of tumor antigen-specific T cells and the population of antigen-loaded APCs (e.g., PBMCs such as fixed PBMCs, DCs or cell line APCs) is no more than about any one of 10:1, 9:1, 8:1, 7:1, 6:1, 5:1, 4:1, 3:1, 2:1 or 1:1. In some embodiments, the ratio between the population of tumor antigen-specific T cells and the population of antigen-loaded APCs (e.g., PBMCs such as fixed PBMCs, DCs, or cell line APCs) is any one of about 1:1 to about 20:1, about 1:1 to about 10:1, about 1:1 to about 5:1, about 5:1 to about 10:1, about 10:1 to about 15:1, about 15:1 to about 20:1, about 10:1 to about 20:1, about 1:3 to about 3:1, about 1:1 to about 3:1, about 1:1 to about 2:1, or about 2:1 to about 5:1.

In some embodiments, the T cells and the APCs (e.g., PBMCs, DCs, or cell line APCs) are derived from the same individual, e.g., the individual who has clinically benefitted from the MASCT. In some embodiments, the APCs (e.g., PBMCs, DCs, or cell line APCs) are not derived from the individual who has clinically benefitted from the MASCT. In some embodiments, the T cells, the APCs (e.g., PBMCs, DCs, or cell line APCs) or both are derived from autologous sources, e.g., from the individual that receives the engineered immune cells expressing the TCR. In some embodiments, the T cells, the APCs (e.g., PBMCs, DCs, or cell line APCs) or both are derived from allogenic sources.

In some embodiments, the T cells and/or the APCs (e.g., PBMCs or DCs) are obtained from an individual who has previously received an immunotherapy. In some embodiments, the individual is immunologically responsive to the immunotherapy. "Immunologically responsive" to an immunotherapy means that the individual has developed specific immune response to one or more tumor antigens in response to the immunotherapy. In some embodiments, the T cells and/or the APCs (e.g., PBMCs or DCs) are obtained from an individual who has clinically benefitted from the immunotherapy. An individual who "clinically benefitted" from a therapy has demonstrated a clinical response to the therapy as assessed by a physician. Exemplary clinical responses include, but are not limited to, complete response ("CR"), partial response ("PR"), and stable disease ("SD"). Immunotherapies, include, but are not limited to, immune checkpoint inhibitors, adoptive immune cell therapy (e.g., adoptive T cell therapy, CIK, TIL, CAR-T, and TCR-T therapies), cancer vaccine, oncolytic viruses and combinations thereof. In some embodiments, the T cells and/or the APCs (e.g., PBMCs or DCs) are obtained from an individual who has previously received a MASCT. In some embodiments, the individual is capable of developing a specific immune response against a tumor antigen peptide in the MASCT. Specific immune response against a tumor antigen peptide can be determined using known assays in the art, such as ELISPOT assays. In some embodiments, the individual has clinically benefitted from the MASCT. In some embodiments, the individual has tumor antigen-specific immune response(s). In some embodiments, the individual has tumor antigen-specific immune responses and clinically benefitted from a MASCT.

The population of T cells used in any embodiment of the methods described herein may be derived from a variety of sources. A convenient source of T cells is from the PBMCs of the human peripheral blood. The population of T cells may be isolated from the PBMCs, or alternatively, a population of PBMCs enriched with T cells (such as by addition of T cell specific antibodies and cytokines) can be used in the co-culture. In some embodiments, the population of T cells used in the first co-culturing step is obtained from the peripheral blood mononuclear cells (PBMCs). In some embodiments, the PBMCs are obtained by density gradient centrifugation of a sample of peripheral blood. In some embodiments, the population of T cells used in the first co-culturing step is present in the PBMCs.

Enrichment of Activated T Cells

The methods described herein comprise an enrichment step comprising enriching activated T cells from a co-culture comprising a first population of antigen-loaded DCs and a population of T cells. In some embodiments, the method comprises an enrichment step comprising enriching activated T cells from PBMCs stimulated with the target tumor antigen peptide or fragments thereof.

In some embodiments, the enrichment process comprises selecting activated T cells based on one or more (such as any one of 1, 2, 3, or more) biomarkers of T cell activation from the co-culture in response to stimulation by the target tumor antigen peptide or fragments thereof. In some embodiments, APCs (such as PBMCs) loaded with the target tumor antigen peptide are used to stimulate the activated T cells in the co-culture. In some embodiments, the enrichment process comprises isolating activated T cells expressing one or more biomarkers, such as cell surface molecules or secreted molecules, from the co-culture.

In some embodiments, the enrichment process comprises isolating activated T cells expressing or secreting one or more cytokines from the co-culture that has been stimulated by the target tumor antigen peptide or fragments thereof. In some embodiments, the enrichment step comprises contacting the first co-culture with antigen-loaded PBMCs to obtain a stimulated co-culture, and isolating an enriched population of activated T cells from the stimulated co-culture using a ligand that specifically recognizes a cytokine. Exemplary cytokines include, but are not limited to, IFNγ and TNFα. Ligands that specifically recognize the cytokine, such as antibodies or receptors for the cytokine, can be used to isolate the enriched population of activated T cells. In some embodiments, the enrichment step comprises contacting the first co-culture with antigen-loaded PBMCs to obtain a stimulated co-culture, and isolating an enriched population of activated T cells from the stimulated co-culture using a ligand that specifically recognizes a cell surface molecule, such as 4-1BB (also known as CD137).

In some embodiments, the method comprises contacting the co-culture with PBMCs loaded with the target tumor antigen peptide or fragments thereof to obtain a stimulated co-culture, and isolating an enriched population of activated T cells from the stimulated co-culture using a ligand that specifically recognizes a cytokine or a cell surface molecule. In some embodiments, the cytokine is IFNγ. In some embodiments, the cell surface molecule is 4-1BB.

In some embodiments, the enrichment process comprises isolating activated T cells secreting IFNγ from the co-culture upon stimulation by the target tumor antigen peptide or fragments thereof. In some embodiments, the enrichment process comprises isolating $CD3^+IFN\gamma^+$ cells from the co-culture upon stimulation by the target tumor antigen peptide or fragments thereof. In some embodiments, the enrichment process comprises: (1) contacting the co-culture comprising a first population of DCs loaded with the target tumor antigen peptide or fragments thereof and a population of T cells with the PBMCs loaded with the target tumor antigen peptide or fragments thereof for about 10-24 hours (such as about 1 day) to obtain a stimulated co-culture; and (2) isolating activated T cells using a ligand that specifically recognizes IFNγ from the stimulated co-culture. In some embodiments, the first population of antigen-loaded DCs and the population of T cells have been co-cultured for about 1-7 days (such as about 2-3 days) prior to the contacting with the antigen-loaded PBMCs. In some embodiments, the co-culture and the antigen-loaded PBMCs are contacted for at least about any one of 2, 4, 6, 12, 18, 24 or more hours prior to the isolating. Activated T cells expressing a cytokine (such as IFNγ) can be isolated or enriched from the stimulated co-culture using any known methods in the art. For example, commercial kits are available for isolating T cells that secrete IFNγ, including IFNγ Secretion Assay-Cell Enrichment and Detection Kit from Miltenyi Biotec. In some embodiments, the activated T cells secreting IFNγ are isolated by: (1) contacting the co-culture with an IFNγ catch reagent that specifically binds to a cell surface antigen on T cells and IFNγ; (2) contacting the IFNγ catch reagent treated co-culture with an anti-IFNγ antibody (e.g., an anti-IFNγ antibody conjugated to R-phycoerthrin or PE); (3) contacting the anti-IFNγ antibody treated co-culture with a magnetic bead comprising a secondary antibody that recognizes the anti-IFNγ antibody (e.g., an anti-PE antibody); and (4) isolating the magnetic beads using a magnetic field (e.g., using a MACSm separator column), thereby obtaining an enriched population of activated T cells.

In some embodiments, the activated T cells expressing a cell surface biomarker are isolated by: (1) contacting the co-culture with a fluorescently labeled antibody against the cell surface biomarker; and (2) isolating cells bound to the fluorescently labeled antibody from the co-culture by flow cytometry.

Antigen Loading of APCs

The methods described herein and the MASCT methods use APCs (such as PBMCs, dendritic cells, or cell line APCs) loaded with one or more tumor antigen peptides. In some embodiments, the antigen-loaded APCs (e.g., antigen-loaded DCs) are freshly prepared for one or more of the co-culturing steps. In some embodiments, the antigen-loaded APCs (e.g., antigen-loaded DCs) are freshly prepared for each co-culturing step. In some embodiments, the antigen-loaded APCs (e.g., antigen-loaded DCs) are prepared, cultured in a DC maturation medium, and used for one or more co-culturing or stimulation steps. The antigen-loaded DCs used in the first, second and third co-culturing steps may be obtained from a single batch or separate batches of antigen-loaded DCs. Unless indicated otherwise, the features described in this section for the APCs (e.g., DCs) apply to all APCs (e.g., DCs) used in each of the co-culturing steps; and the methods and features described in this section for the antigen-loaded APCs (e.g., DCs) apply to the first population, the second population, and the third population of antigen-loaded DCs and other types of APCs. APCs include, but are not limited to, PBMCs, DCs, B cells, or macrophages. The APCs described herein can be primary cells or derived from cell lines. In some embodiments, the APCs are PBMCs. In some embodiments, the APCs are fixed PBMCs. Fixing PBMCs can destroy the proliferation capacity of the PBMCs, while maintaining the antigen presenting capacity of PBMCs.

The antigen-loaded DCs used in each co-culturing step may be loaded with the same pool of tumor antigen peptides or different pool of tumor antigen peptides. In some embodiments, the first population of DCs in the first co-culturing step is loaded with the same pool of tumor antigen peptides used to load the second population of DCs in the second co-culturing step. In some embodiments, the second population of DCs in the second co-culturing step is loaded with a subset of the pool of tumor antigen peptides used to load the first population of DCs in the first co-culturing step. In some embodiments, the third population of DCs in the third co-culturing step is loaded with a subset of the pool of tumor antigen peptides used to load the first population of DCs in the first co-culturing step and/or the second population of DCs in the second co-culturing step. In some embodiments, the subset of the pool of tumor antigen peptides includes fragments of the tumor antigen peptides and combinations thereof. In some embodiments, a single tumor antigen peptide (i.e., the target tumor antigen peptide) or fragment thereof is used to load the APCs (such as DCs) used in the second and third co-culturing steps.

In some embodiments, the first population of antigen-loaded DCs used in the first co-culturing step is prepared using the plurality of tumor antigen peptides that the individual used in previous MASCTs. In some embodiments, the first population of antigen-loaded DCs used in the first co-culturing step is prepared using one or more tumor antigen peptides that the individual has specific immune response to in previous MASCTs. In some embodiments, individual tumor antigen peptides from one or more target tumor antigen peptides or fragments thereof, and combinations thereof are screened (e.g., by ELISPOT) for specific immune response by PBMCs, activated T cells, or tumor antigen-specific T cells derived from an individual to identify one or more target tumor antigen peptides (including fragments thereof) for use in subsequent preparation of tumor antigen-specific T cells.

In some embodiments, prior to each co-culturing step, the method comprises one or more of the following steps: (1) obtaining PBMCs from an individual; (2) obtaining a population of monocytes from the PBMCs; (3) inducing differentiation of the population of monocytes into immature DCs; (4) contacting the immature DCs with one or more tumor antigen peptides to obtain a population of antigen-loaded DCs; and (5) culturing the population of antigen-loaded DCs in a DC maturation medium comprising a TLR agonist (such as MPLA).

In some embodiments, the antigen-loaded DCs are prepared by: (a) contacting a population of DCs with one or more tumor antigen peptides to obtain a population of antigen-loaded DCs, and (b) culturing the population of antigen-loaded DCs in a DC maturation medium comprising a toll-like receptor (TLR) agonist. Exemplary TLR agonists include, but are not limited to, MPLA (monophosphoryl lipid A), Poly I:C, resquimod, gardiquimod, and CL075. Cytokines and other appropriate molecules, such as INFγ and PGE2 (prostaglandin E2) may be further included in the culturing media in the maturation step.

In some embodiments, the antigen-loaded DCs are prepared by: (a) contacting a population of DCs with one or more tumor antigen peptides to obtain a population of antigen-loaded DCs, and (b) culturing the population of antigen-loaded DCs in a DC maturation medium comprising MPLA, INFγ and PGE2.

In some embodiments, the antigen-loaded DCs are prepared by: (a) inducing differentiation of a population of monocytes into immature DCs; (b) contacting a population of immature DCs with one or more tumor antigen peptides to obtain a population of antigen-loaded DCs; and (c) culturing the population of the antigen-loaded DCs in a DC maturation medium comprising MPLA, INFγ and PGE2. In some embodiments, the population of monocytes is obtained from PBMCs.

In some embodiments, the antigen-loaded PBMCs are prepared by contacting a population of PBMCs with one or more tumor antigen peptides. In some embodiments, antigen-loaded cell line APCs are prepared by contacting a population of cell line APCs (e.g., LCL) with one or more tumor antigen peptides.

The DC maturation medium may comprise a suitable concentration of MPLA, INFγ and/or PGE2. In some embodiments, the DC maturation medium comprises MPLA at a concentration of at least about 0.5 μg/mL, such as at least about any one of 1, 2, 3, 4, 5, 6, 7, 8, 9, 10 or more g/mL. In some embodiments, the DC maturation medium comprises MPLA at a concentration of any one of about 0.5-10, 1-5, 5-10, or 2.5-7.5 μg/mL. In some embodiments, the DC maturation medium comprises INFγ at a concentration of at least about 100 IU/mL, such as at least about any one of 150, 200, 250, 300, 400, 500, 600, 800, 1000 or more IU/mL. In some embodiments, the DC maturation medium comprises INFγ at a concentration of about any one of 100-1000, 100-250, 250-500, 500-1000, or 250-750 IU/mL. In some embodiments, the DC maturation medium comprises PGE2 at a concentration of at least about 0.1 μg/mL, such as at least about any one of 0.15, 0.2, 0.25, 0.3, 0.4, 0.5, or more μg/mL. In some embodiments, the DC maturation medium comprises PGE2 at a concentration of about any one of 0.1-0.5, 0.1-0.3, 0.25-0.5 or 0.2-0.4 μg/mL.

The immature DCs loaded with one or more tumor antigen peptides may be induced by TLR agonists to mature for at least about any one of 1, 2, 3, 4, 5, 6, 7, 8, 9, 10, 15, or 20 days. In some embodiments, the DCs loaded with one or more tumor antigen peptides are induced to mature for about 8, 9, 10, 11, or 12 days.

In some embodiments, the antigen-loaded DCs are mature DCs that present one or more tumor antigen peptides. The mature DCs prepared by any of the methods described herein may present at least about any one of 1, 5, 10, 15, 20, 25, 30, 35, 40, 50 or more tumor antigen peptides. Compared to naïve DCs, or DCs that have not been loaded with a plurality of tumor antigen peptides, the multiple-antigen loaded DCs may have enhanced level of presentation for at least about any of 1, 5, 10, 15, 20, 25, 30, 35, 40, 50 or more tumor antigen peptides. In some embodiments, the mature DCs have enhanced level of presentation for more than 10 tumor antigen peptides. In some embodiments, the mature DCs have enhanced level of presentation of about any of 1, 2, 3, 4, 5, 6, 7, 8, 9, 10, 11, 12, 13, 14, or more tumor antigen peptides derived from proteins selected from the group consisting of hTERT, p53, Survivin, NY-ESO-1, CEA, CCND1, RGS5, MMP7, VEGFR1, VEGFR2, MUC1, HER2, MAGE-A1, MAGE-A3, CDCA1, WT1, KRAS, PARP4, MLL3, MTHFR, HPV16-E6, HPV16-E7, HPV18-E6, HPV18-E7, HPV58-E6, HPV58-E7, HBcAg, HBV polymerase, GPC3, SSX, and AFP.

In some embodiments, the antigen-loaded APCs (e.g., DCs, PBMCs, or cell line APCs) are prepared by pulsing one or more tumor antigen peptides into a population of APCs. In some embodiments, the antigen-loaded DCs are prepared by pulsing one or more tumor antigen peptides into a population of DCs, such as immature DCs, or DCs contained in or derived (such as differentiated) from the PBMCs. As known in the art, pulsing refers to a process of mixing cells, such as APCs (e.g., PBMCs or DCs, or cell line APCs), with a solution containing antigen peptides, and optionally subsequently removing the antigen peptides from the mixture. The population of DCs may be contacted with one or more tumor antigen peptides for seconds, minutes, or hours, such as about at least any one of 30 seconds, 1 minute, 5 minutes, 10 minutes, 15 minutes, 20 minutes, 30 minutes, 1 hour, 5 hours, 10 hours, 12 hours, 14 hours, 16 hours, 18 hours, 20 hours, 22 hours, 1 day, 2 days, 3 days, 4 days, 5 days, 6 days, one week, 10 days, or more. The concentration of each tumor antigen peptide used in the contacting step may be at least about any one of 0.1, 0.5, 1, 2, 3, 5, or 10 μg/mL. In some embodiments, the concentration of the tumor antigen peptides is about 0.1-200 μg/mL, including for example about any of 0.1-0.5, 0.5-1, 1-10, 10-50, 50-100, 100-150, or 150-200 μg/mL.

In some embodiments, the population of APCs (e.g., DCs or PBMCs, or cell line APCs) is contacted with one or more tumor antigen peptides in the presence of a composition that facilitates the uptake of the one or more tumor antigen peptides by the APCs (e.g., DCs or PBMCs, or cell line APCs). In some embodiments, compounds, materials or compositions may be included in a solution of the one or more tumor antigen peptides to facilitate peptide uptake by the APCs (e.g., DCs or PBMCs, or cell line APCs). Compounds, materials or compositions that facilitate the uptake of the one or more tumor antigen peptides by the APCs (e.g., DCs or PBMCs, or cell line APCs) include, but are not limited to, lipid molecules and peptides with multiple positively charged amino acids. In some embodiments, more than about any of 50%, 60%, 70%, 80%, 90%, or 95% of the tumor antigen peptides are uptaken by the population of APCs (e.g., DCs or PBMCs, or cell line APCs). In some embodiments, more than about any of 50%, 60%, 70%, 80%, 90%, or 95% of the APCs (e.g., DCs or PBMCs, or cell line APCs) in the population uptake at least one tumor antigen peptide.

Dendritic cells (such as immature DCs) may be obtained from various sources, including autologous sources, i.e. from the individual receiving the TCR treatment. A convenient source of DCs is the PBMCs from the peripheral blood. For example, monocytes, a type of white blood cells, are abundant in PBMCs, comprising about 5-30% of total PBMCs. Monocytes can be induced to differentiate into DCs, such as immature DCs, using cytokines. In some embodiments, the immature DCs are prepared by obtaining a population of PBMCs, obtaining a population of monocytes from the population of PBMCs, and contacting the population of monocytes with one or more cytokines (e.g., a plurality of cytokines) to obtain a population of immature DCs. Exemplary cytokines that may be used to induce differentiation of monocytes include, but are not limited to, GM-CSF and IL-4, with conditions (such as concentrations, temperature, $CO_2$ level etc.) known in the art.

The adherent fraction of PBMCs contains the majority of monocytes in PBMCs. In some embodiments, the monocytes from the adherent fraction of PBMCs are contacted with cytokines to obtain a population of immature DCs. PBMCs can be conveniently obtained by centrifugation of a sample of peripheral blood, or using apheresis methods to collect from an individual. In some embodiments, the population of PBMCs is obtained by density gradient centrifugation of a sample of human peripheral blood. In some embodiments, the sample is from the individual that receives the multiple-antigen loaded DCs, activated T cells, engineered immune cells expressing TCR, or other immunotherapeutic compositions prepared using the multiple-antigen loaded DCs.

Tumor Antigen Peptides

The methods described herein and the MASCT methods use one or more tumor antigen peptides (including the target tumor antigen peptide) to prepare antigen-loaded APCs (such as antigen-loaded DCs), activated T cells and tumor antigen-specific T cells that can trigger specific immune response ex vivo and in vivo. In some embodiments, the plurality of tumor antigen peptides is a plurality of synthetic tumor antigen peptides. In some embodiments, the plurality of tumor antigen peptides is not obtained from a cell sample, such as a lysed cell composition. As used herein, "one or more tumor antigen peptides from a plurality of tumor antigen peptides" refers to a sub-selection or all tumor antigen peptides in the plurality of tumor antigen peptides, including fragments of the tumor antigen peptides and combinations thereof. The features and parameters described in this subsection are applicable to the target tumor antigen peptide(s).

In some embodiments, each tumor antigen peptide comprises at least about any one of 1, 2, 3, 4, 5, or 10 epitopes from a single protein antigen (including a neoantigen). In some embodiments, each tumor antigen peptide in the plurality of tumor antigen peptides comprises at least one epitope recognizable by a T cell receptor. In some embodiments, the plurality of tumor antigen peptides comprises at least one tumor antigen peptide that comprises at least 2 epitopes from a single protein antigen. The tumor antigen peptide can be a naturally derived peptide fragment from a protein antigen containing one or more epitopes, or an artificially designed peptide with one or more natural epitope sequences, wherein a linker peptide can optionally be placed in between adjacent epitope sequences. In some preferred embodiments, the epitopes contained in the same tumor antigen peptide are derived from the same protein antigen.

The tumor antigen peptide may contain at least one MHC-I epitope, at least one MHC-II epitope, or both MHC-I epitope(s) and MHC-II epitope(s). In some embodiments, the plurality of tumor antigen peptides comprises at least one peptide comprising an MHC-I epitope. In some embodiments, the plurality of tumor antigen peptides comprises at least one peptide comprising an MHC-II epitope. In some embodiments, at least one tumor antigen peptide in the plurality of tumor antigen peptides comprises both MHC-I and MHC-II epitopes.

Special design strategies can be applied to the sequence of the tumor antigen peptides (including neoantigen peptides) in order to optimize the immune response to DCs loaded with the tumor antigen peptides. Typically, a peptide longer than the exact epitope peptide can increase uptake of the peptide into DCs. In some embodiments, an MHC-I or MHC-II epitope sequence is extended at the N terminus or the C terminus or both termini according to the natural sequence of the protein harboring the epitope to obtain an extended sequence, wherein the extended sequence is amenable for presentation by both class I and class II MHC molecules, and by different subtypes of MHC molecules in different individuals. In some embodiments, the epitope sequence is extended at one or both termini by at least about any one of 1, 2, 3, 4, 5, 6, 7, 8, 9, 10, 12, 15, or 20 amino acid residues to generate the extended epitope. In some embodiments, the peptides comprising an MHC-I or MHC-II epitope further comprise additional amino acids flanking the epitope at the N-terminus, the C-terminus, or both. In some embodiments, each tumor antigen peptide in the plurality of tumor antigen peptides is at least about any one of 10, 15, 20, 25, 30, 35, 40, 45, 50, 60, 70, 80, 90, or 100 amino acids long. Different tumor antigen peptides in the plurality of tumor antigen peptides may have the same length, or different lengths. In some embodiments, the plurality of tumor antigen peptides is each about 20-40 amino acids long.

In some embodiments, the amino acid sequences of one or more epitope peptides used to design a tumor antigen peptide in the present application are based on sequences known in the art or available in public databases, such as the Peptide Database (Vigneron N. et al. *Cancer Immunity,* 13:15 (2013)).

In some embodiments, the amino acid sequences of one or more epitope peptides are predicted based on the sequence of the antigen protein using a bioinformatics tool for T cell epitope prediction. Exemplary bioinformatics tools for T cell epitope prediction are known in the art, for example, see Yang X. and Yu X. (2009) "An introduction to epitope prediction methods and software" *Rev. Med. Virol.* 19(2): 77-96. In some embodiments, the sequence of the antigen protein is known in the art or available in public databases. In some embodiments, the sequence of the antigen protein is determined by sequencing a sample (such as a tumor sample) of the individual being treated.

The present application contemplates tumor antigen peptides derived from any tumor antigens and epitopes known in the art, including neoantigens and neoepitopes, or specially developed or predicted using bioinformatics tools by the inventors.

In some embodiments, the plurality of tumor antigen peptides comprises a first core group of general tumor antigen peptides. In some embodiments, the plurality of tumor antigen peptides further comprises a second group of cancer-type specific antigen peptides. In some embodiments, the plurality of tumor antigen peptides comprises one or more neoantigen peptides. In some embodiments, neoantigen peptides are cancer-type specific antigen peptides. In some embodiments, the plurality of tumor antigen peptides consists of the first core group of general tumor antigen peptides. In some embodiments, the plurality of tumor antigen peptides consists of the first core group of general tumor antigen peptides and the second group of cancer-type specific antigen peptides. In some embodiments, the plurality of tumor antigen peptides consists of neoantigen peptides only. In some embodiments, the plurality of tumor antigen peptides comprises a first core group of general tumor antigen peptides and one or more neoantigen peptides. In some embodiments, the plurality of tumor antigen peptides comprises a first core group of general tumor antigen peptides, a second group of cancer-type specific antigen peptides, and one or more neoantigen peptides.

In some embodiments, the plurality of tumor antigen peptides comprises a first core group of general tumor antigen peptides. In some embodiments, the plurality of tumor antigen peptides further comprises a second group of cancer-type specific antigen peptides. In some embodiments, the plurality of tumor antigen peptides comprises one or more neoantigen peptides. In some embodiments, neoantigen peptides are cancer-type specific antigen peptides. In some embodiments, the plurality of tumor antigen peptides consists of the first core group of general tumor antigen peptides. In some embodiments, the plurality of tumor antigen peptides consists of the first core group of general tumor antigen peptides and the second group of cancer-type specific antigen peptides. In some embodiments, the plurality of tumor antigen peptides consists of neoantigen peptides only. In some embodiments, the plurality of tumor antigen peptides comprises a first core group of general tumor antigen peptides and one or more neoantigen peptides. In some embodiments, the plurality of tumor antigen peptides comprises a first core group of general tumor antigen peptides, a second group of cancer-type specific antigen peptides, and one or more neoantigen peptides.

The first core group of general tumor antigen peptides is derived from tumor antigens commonly overexpressed by a variety of cancers of different types. Therefore, the first core group of general tumor antigen peptides is useful to prepare dendritic cells and/or activated T cells for treating individuals with different cancer types. For example, in some embodiments, the first core group of general tumor antigen peptides is useful for methods described herein for treating a variety of cancers, such as lung cancer, colon cancer, gastric cancer, prostate cancer, melanoma, lymphoma, pancreatic cancer, ovarian cancer, breast cancer, glioma, esophageal cancer, nasopharyngeal carcinoma, cervical cancer, renal carcinoma, or hepatocellular carcinoma. Exemplary tumor antigen peptides of the first core group include, but are not limited to, peptides derived from hTERT, p53, Survivin, NY-ESO-1, CEA, CCND1, MET, MUC1, Her2, MAGEA1, MAGEA3, WT-1, RGS5, MMP7, VEGFR (such as VEGFR1 and VEGFR2), and CDCA1. The first core group may comprise peptides derived from at least about any one of 1, 2, 5, 10, 15, 20, 25, 30, 40, 50, 60, 70, 80 or more tumor antigens. The first core group may comprise at least about any one of 1, 2, 5, 10, 15, 20, 25, 30, 40, 50, 60, 70, 80 or more general tumor antigen peptides. In some embodiments, the first core group comprises more than one general tumor antigen peptides. In some embodiments, the first core group comprises about 10 to about 20 general tumor antigen peptides.

The second group of cancer-type specific antigen peptides is derived from tumor antigens that are overexpressed only in one or a limited number of cancer types. Therefore, the second group of cancer-type specific antigen peptides is useful to prepare dendritic cells and/or activated T cells for treating individuals with a particular type of cancer. Exemplary cancer-type specific antigen peptides for treating hepatocellular carcinoma (HCC) include, but are not limited to, peptides derived from SSX, AFP, and GPC3. In some embodiments, one or more cancer-specific antigen peptide is a virus-specific antigen peptide derived from a virus that can induce cancer, or relates to cancer development in the individual when infecting the individual. In some embodiments, the virus-specific antigen peptide is specific to the subtype of the virus infecting the individual. Exemplary virus-specific antigen peptides for treating an HCC patient with concurrent infection of HBV include, but are not limited to, peptides derived from HBV core antigen (HBcAg), and HBV DNA polymerase. In some embodiments, the second group comprises virus-specific antigen peptides derived from HBV antigens, wherein the method is to treat hepatocellular carcinoma in an individual. In some embodiments, the second group comprises virus-specific antigen peptides derived from HPV antigens, wherein the method is to treat cervical cancer in an individual. In some embodiments, the second group comprises virus-specific antigen peptides derived from EBV antigens, wherein the method is to treat nasopharyngeal carcinoma in an individual. The second group of cancer-type specific antigen peptides may comprise peptides derived from at least about any one of 1, 2, 5, 10, 15, 20, 25, 30, 40, 50 or more cancer-type specific antigens. The second group of cancer-type specific antigen peptides may comprise at least about any one of 1, 2, 5, 10, 15, 20, 25, 30, 40, 50 or more cancer-type specific antigen peptides. In some embodiments, the second group comprises more than one cancer-type specific antigen peptides. In some embodiments, the second group comprises about 1 to about 10 cancer-type specific antigen peptides. In some embodiments, the type of cancer targeted by the cancer-type specific antigen peptides is selected from the group consisting essentially of hepatocellular carcinoma, cervical cancer, nasopharyngeal carcinoma, endometrial cancer, colorectal cancer, breast cancer, endometrial cancer, and lymphoma.

In some embodiments, the plurality of tumor antigen peptides comprises one or more (such as any of 1, 2, 3, 4, 5, 6, 7, 8, 9, 10 or more) neoantigen peptides. In some embodiments, the plurality of tumor antigen peptides consists of neoantigen peptides. In some embodiments, the plurality of tumor antigen peptides comprises neoantigen peptides and no general tumor antigen peptides. In some embodiments, the plurality of tumor antigen peptides comprises one or more general tumor antigen peptides and one or more neoantigen peptides. In some embodiments, the plurality of tumor antigen peptides comprises one or more general tumor antigen peptides, one or more cancer-type specific antigen peptides, and one or more neoantigen peptides. The neoantigen peptides are derived from neoantigens. Neoantigens are newly acquired and expressed antigens present in tumor cells of the individual, such as the individual being treated for cancer. In some embodiments, neoantigens are derived from mutant protein antigens that are only present in cancer cells, but absent in normal cells. Neoantigens may be uniquely present in the tumor cells (such as all tumor cells or a portion of tumor cells) of the individual being treated for cancer, or present in individuals having similar types of cancer as the individual being treated. In some embodiments, the neoantigen is a clonal neoantigen. In some embodiments, the neoantigen is a subclonal neoantigen. In some embodiments, the neoantigen is present in at least about any of 10%, 20%, 30%, 40%, 50%, 60%, 70%, 80%, 90%, 95% or more tumor cells in the individual. In some embodiments, the neoantigen peptide comprises an MHC-I restricted neoepitope. In some embodiments, the neoantigen peptide comprises an MHC-II restricted neoepitope. In some embodiments, the neoantigen peptide is designed to facilitate presentation of the neoepitope by both class I and class II MHC molecules, for example, by extending the neoepitope at both the N- and the C-termini. Exemplary neoantigen peptides include, but are not limited to, neoepitope derived from mutant KRAS (e.g., $KRAS^{G12A}$), PARP4 (e.g., $PARP4^{T1170I}$), MLL3 (e.g., $MLL3^{C988F}$), and MTHFR (e.g., $MTHFR^{A222V}$).

Neoantigen peptides can be selected based on the genetic profile of one or more tumor sites of the individual being treated, and neoantigens are not expressed in normal tissues. In some embodiments, the genetic profile of the tumor sample comprises sequence information of the full genome. In some embodiments, the genetic profile of the tumor sample comprises sequence information of the exome. In some embodiments, the genetic profile of the tumor sample comprises sequence information of cancer-associated genes.

Neoantigen peptides suitable for use in the present application may be derived from any mutant proteins, such as those encoded by mutant cancer-associated genes, in the tumor cells. In some embodiments, the neoantigen peptide comprises a single neoepitope derived from a cancer-associated gene. In some embodiments, the neoantigen peptide comprises more than one (such as 2, 3, or more) neoepitope derived from a cancer-associated gene. In some embodiments, the neoantigen peptide comprises more than one (such as 2, 3, or more) neoepitope derived from more than one (such as 2, 3, or more) cancer-associated genes. In some embodiments, the plurality of tumor antigens comprises a plurality of neoantigen peptides derived from a single cancer-associated gene. In some embodiments, the plurality of tumor antigens comprises a plurality of neoantigen peptides derived from more than one (such as any of 2, 3, 4, 5, or more) cancer-associated genes.

Cancer-associated genes are genes that are overexpressed in cancer cells, but expressed at low levels in normal cells. Exemplary cancer-associated genes include, but are not limited to, ABL1, AKT1, AKT2, AKT3, ALK, ALOX12B, APC, AR, ARAF, ARID1A, ARID1B, ARID2, ASXL1, ATM, ATRX, AURKA, AURKB, AXL, B2M, BAP1, BCL2, BCL2L1, BCL2L12, BCL6, BCOR, BCORL1, BLM, BMPR1A, BRAF, BRCA1, BRCA2, BRD4, BRIP1, BUB1B, CADM2, CARD11, CBL, CBLB, CCND1, CCND2, CCND3, CCNE1, CD274, CD58, CD79B, CDC73, CDH1, CDK1, CDK2, CDK4, CDK5, CDK6, CDK9, CDKN1A, CDKN1B, CDKN1C, CDKN2A, CDKN2B, CDKN2C, CEBPA, CHEK2, CIITA, CREBBP, CRKL, CRLF2, CRTC1, CRTC2, CSF1R, CSF3R, CTNNB1, CUX1, CYLD, DDB2, DDR2, DEPDC5, DICER1, DIS3, DMD, DNMT3A, EED, EGFR, EP300, EPHA3, EPHA5, EPHA7, ERBB2, ERBB3, ERBB4, ERCC2, ERCC3, ERCC4, ERCC5, ESR1, ETV1, ETV4, ETV5, ETV6, EWSR1, EXT1, EXT2, EZH2, FAM46C, FANCA, FANCC, FANCD2, FANCE, FANCF, FANCG, FAS, FBXW7, FGFR1, FGFR2, FGFR3, FGFR4, FH, FKBP9, FLCN, FLT1, FLT3, FLT4, FUS, GATA3, GATA4, GATA6, GLI1, GLI2, GLI3, GNA11, GNAQ, GNAS, GNB2L1, GPC3, GSTM5, H3F3A, HNF1A, HRAS, ID3, IDH1, IDH2, IGF1R, IKZF1, IKZF3, INSIG1, JAK2, JAK3, KCNIP1, KDM5C, KDM6A, KDM6B, KDR, KEAP1, KIT, KRAS, LINC00894, LMO1, LMO2, LMO3, MAP2K1, MAP2K4, MAP3K1, MAPK1, MCL1, MDM2, MDM4, MECOM, MEF2B, MEN1, MET, MITF, MLH1, MLL (KMT2A), MLL2 (KTM2D), MPL, MSH2, MSH6, MTOR, MUTYH, MYB, MYBL1, MYC, MYCL1 (MYCL), MYCN, MYD88, NBN, NEGR1, NF1, NF2, NFE2L2, NFKBIA, NFKBIZ, NKX2-1, NOTCH1, NOTCH2, NPM1, NPRL2, NPRL3, NRAS, NTRK1, NTRK2, NTRK3, PALB2, PARK2, PAX5, PBRM1, PDCD1LG2, PDGFRA, PDGFRB, PHF6, PHOX2B, PIK3C2B, PIK3CA, PIK3R1, PIM1, PMS1, PMS2, PNRC1, PRAME, PRDM1, PRF1, PRKAR1A, PRKCI, PRKCZ, PRKDC, PRPF40B, PRPF8, PSMD13, PTCH1, PTEN, PTK2, PTPN11, PTPRD, QKI, RAD21, RAF1, RARA, RB1, RBL2, RECQL4, REL, RET, RFWD2, RHEB, RHPN2, ROS1, RPL26, RUNX1, SBDS, SDHA, SDHAF2, SDHB, SDHC, SDHD, SETBP1, SETD2, SF1, SF3B1, SH2B3, SLITRK6, SMAD2, SMAD4, SMARCA4, SMARCB1, SMC1A, SMC3, SMO, SOCS1, SOX2, SOX9, SQSTM1, SRC, SRSF2, STAG1, STAG2, STAT3, STAT6, STK11, SUFU, SUZ12, SYK, TCF3, TCF7L1, TCF7L2, TERC, TERT, TET2, TLR4, TNFAIP3, TP53, TSC1, TSC2, U2AF1, VHL, WRN, WT1, XPA, XPC, XPO1, ZNF217, ZNF708, and ZRSR2.

In some embodiments, the plurality of tumor antigen peptides comprises at least one (such as at least about any of 1, 2, 3, 4, 5, 6, 7, 8, 9, 10, 11, 12, 13, 14, 15 or more) tumor antigen peptide each comprising one or more epitopes encoded by a cancer-associated gene selected from the group consisting of hTERT, p53, Survivin, NY-ESO-1, CEA, CCND1, RGS5, MMP7, VEGFR1, VEGFR2, MUC1, HER2, MAGE-A1, MAGE-A3, CDCA1, WT1, KRAS, PARP4, MLL3, MTHFR, HPV16-E6, HPV16-E7, HPV18-E6, HPV18-E7, HPV58-E6, HPV58-E7, HBcAg, HBV polymerase, GPC3, SSX, and AFP. In some embodiments, the plurality of tumor antigen peptides comprises at least 10 tumor antigen peptides. In some embodiments, the plurality of tumor antigen peptides comprises tumor antigen peptides derived from hTERT, p53, Survivin, NY-ESO-1, CEA, CCND1, MUC1, Her2, MAGEA1, MAGEA3, WT-1, RGS5, VEGFR1, VEGFR2, and CDCA1.

In some embodiments, the one or more tumor antigen peptides is present in a composition having at least about any one of 95%, 96%, 97%, 98%, 99%, 99.9% or higher percentage of the tumor antigen peptides. In some embodiments, the purity of the one or more tumor antigen peptides is at least about 98%. In some embodiments, the solubility of the one or more tumor antigen peptides in the medium for pulsing the tumor antigen peptides into the DCs is at least about any one of 80%, 85%, 90%, 95%, 98%, 99%, 99.9% or higher. In some embodiments, the one or more tumor antigen peptides is about 100% soluble in the medium for pulsing the tumor antigen peptides into the APCs.

MASCT

The TCRs described herein are obtained from the PBMCs or T cells of an individual who has clinically benefitted from a MASCT. In some embodiments, the individual has developed specific response to the target tumor antigen peptide(s) or fragments thereof used in the methods described herein, for example, as determined by ELISPOT.

As used herein, "MASCT" or "Multiple Antigen Specific Cell Therapy" refers to methods of adoptive T cells therapy comprising administering to an individual an effective amount of activated T cells prepared by co-culturing a population of T cells with a population of DCs loaded with a plurality of tumor antigen peptides. MASCT methods have been described, for example, in International Patent Application Publication No. WO2016145578A1, International Patent Application Nos. PCT/CN2018/081338, and PCT/CN2019/080535, the contents of which are incorporated herein by reference in their entirety. First-generation MASCT, precision MASCT, PBMC-based MASCT, customized MASCT, neoantigen-based MASCT, improved MASCT, and combination therapy with MASCT (e.g., immune checkpoint inhibitor and MASCT) are all within the scope of MASCT of the present application. Any suitable features and parameters for preparation of antigen-loaded DCs, preparation of activated T cells, enrichment steps, and co-culturing steps described in the present application or in International Patent Applications WO2016145578A1, PCT/CN2018/081338 and PCT/CN2019/080535 may be combined in a MASCT treatment.

The individual may have received a single type of MASCT, or a combination of different types of MASCT, for example, customized MASCT and improved MASCT. The individual may have received one or more cycles of the MASCT. In some embodiments, the individual has received at least about any one of 2, 5, 10, 15, 20 or more cycles of MASCT. In some embodiments, the individual has received MASCT over at least about any one of 3 months, 6 months, 9 months, 12 months, 2 years, 3 years or longer.

In some embodiments, the MASCT comprises: (i) co-culturing a population of DCs loaded with a plurality of tumor antigen peptides comprising the target tumor antigen peptide(s) and a population of T cells to obtain a population of activated T cells, and (ii) administering to the individual an effective amount of the activated T cells. In some embodiments, the MASCT comprises administering to the individual an effective amount of the DCs loaded with the plurality of tumor antigen peptides.

In some embodiments, the MASCT comprises: (i) co-culturing a population of DCs loaded with a plurality of tumor antigen peptides comprising the target tumor antigen peptide and a population of T cells in an initial co-culture medium comprising one or more cytokines (e.g., a plurality of cytokines) and an immune checkpoint inhibitor to provide a co-culture; (ii) adding an anti-CD3 antibody to the co-culture at about 3 to 7 days after the co-culturing starts to obtain the population of activated T cells; and (iii) administering to the individual an effective amount of the activated T cells. In some embodiments, the MASCT comprises administering to the individual an effective amount of the DCs loaded with the plurality of tumor antigen peptides.

In some embodiments, the MASCT comprises: (i) contacting a population of DCs with a plurality of tumor antigen peptides comprising the target tumor antigen peptide to obtain a population of DCs loaded with the plurality of tumor antigen peptides; (ii) culturing the population of DCs loaded with the plurality of tumor antigen peptides in a DC maturation medium comprising MPLA; (iii) co-culturing the population of DCs loaded with the plurality of tumor antigen peptides and a population of T cells to obtain a population of activated T cells, and (iv) administering to the individual an effective amount of the activated T cells. In some embodiments, the DC maturation medium comprises INFγ, MPLA and PGE2. In some embodiments, the MASCT comprises administering to the individual an effective amount of the DCs loaded with the plurality of tumor antigen peptides.

In some embodiments, the MASCT comprises: (i) contacting a population of DCs with a plurality of tumor antigen peptides comprising the target tumor antigen peptide to obtain a population of DCs loaded with the plurality of tumor antigen peptides; (ii) culturing the population of DCs loaded with the plurality of tumor antigen peptides in a DC maturation medium comprising MPLA; (iii) co-culturing the population of DCs loaded with the plurality of tumor antigen peptides and a population of T cells in an initial co-culture medium comprising one or more cytokines (e.g., a plurality of cytokines) and an immune checkpoint inhibitor to provide a co-culture; (iv) adding an anti-CD3 antibody to the co-culture at about 3 to 7 days after the co-culturing starts to obtain the population of activated T cells; and (V) administering to the individual an effective amount of the activated T cells. In some embodiments, the DC maturation medium comprises INFγ, MPLA and PGE2. In some embodiments, the MASCT comprises administering to the individual an effective amount of the DCs loaded with the plurality of tumor antigen peptides.

In some embodiments, the MASCT comprises administering to the individual an effective amount of activated T cells, wherein the activated T cells are prepared by co-culturing a population of T cells with a population of antigen presenting cells (such as DCs) loaded with a plurality of tumor antigen peptides. In some embodiments, the activated T cells are administered intravenously. In some embodiments, the activated T cells are administered for at least three times. In some embodiments, the individual has previously been administered an effective amount of antigen presenting cells loaded with the plurality of tumor antigen peptides. In some embodiments, the method comprises administering to the individual an effective amount of antigen presenting cells (such as DCs) loaded with the plurality of tumor antigen peptides. In some embodiments, the antigen presenting cells are administered about 7 days to about 21 days (such as about 7 days to about 14 days, or about 14 days to about 21 days) prior to the administration of the activated T cells. In some embodiments, the antigen presenting cells are administered for at least three times. In some embodiments, the antigen presenting cells are administered subcutaneously, intradermally or intravenously. In some embodiments, the activated T cells and the population of antigen presenting cells are from the same individual. In some embodiments, the activated T cells and/or the population of antigen presenting cells are from the individual being treated. In some embodiments, the population of antigen presenting cells is a population of DCs, B cells, or macrophages. In some embodiments, the antigen presenting cells are DCs. In some embodiments, the MASCT further comprises administering to the individual an effective amount of an immune checkpoint inhibitor. In some embodiments, the activated T cells and the immune checkpoint inhibitor are administered simultaneously, such as in the same composition. In some embodiments, the activated T cells and the immune checkpoint inhibitor are administered sequentially.

In some embodiments, the MASCT comprises: (a) administering to the individual an effective amount of DCs loaded with a plurality of tumor antigen peptides; (b) co-culturing a population of DCs loaded with the plurality of tumor antigen peptides and a population of T cells to obtain a population of activated T cells; and (c) administering to the individual an effective amount of the activated T cells. In some embodiments, the interval between the administration of the DCs and the administration of the activated T cells is about 7 days to about 21 days (such as about 7 days to about 14 days, about 14 days to about 21 days, about 10 days or about 14 days). In some embodiments, the DCs loaded with the plurality of tumor antigen peptides are administered subcutaneously. In some embodiments, the DCs loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of DCs loaded with the plurality of tumor antigen peptides for about 7 days to about 21 days (such as about 7 days to about 10 days, about 10 days to about 15 days, about 15 days to about 21 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-1, PD-L1, or CTLA-4) prior to and/or during the co-culturing. In some embodiments, the population of DCs loaded with the plurality of tumor antigen peptides is prepared by contacting a population of DCs with the plurality of tumor antigen peptides. In some embodiments, the population of T cells and the population of DCs are derived from the same individual. In some embodiments, the population of T cells, the population of DCs, the population of PBMCs, or any combination thereof is derived from the individual being treated. In some embodiments, the MASCT further comprises administering to the individual an effective amount of an immune checkpoint inhibitor. In some embodiments, the activated T cells and the immune checkpoint inhibitor are administered simultaneously, such as in the same composition. In some embodiments, the activated T cells and the immune checkpoint inhibitor are administered sequentially.

In some embodiments, the MASCT comprises: (a) inducing differentiation of a population of monocytes into a population of DCs; (b) contacting the population of DCs with a plurality of tumor antigen peptides to obtain a population of DCs loaded with the plurality of tumor antigen peptides; (c) administering to the individual an effective amount of the DCs loaded with the plurality of tumor antigen peptides; (d) co-culturing the population of DCs loaded with the plurality of tumor antigen peptides and a population of non-adherent PBMCs to obtain the population of activated T cells; and (e) administering to the individual an effective amount of the activated T cells, wherein the population of monocytes and the population of non-adherent PBMCs are obtained from a population of PBMCs. In some embodiments, the interval between the administration of the DCs and the administration of the activated T cells is about 7 days to about 21 days (such as about 7 days to about 14 days, about 14 days to about 21 days, about 10 days or about 14 days). In some embodiments, the DCs loaded with the plurality of tumor antigen peptides are administered subcutaneously. In some embodiments, the DCs loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, about 14 days to about 21 days, or about 10 days). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of non-adherent PBMCs is contacted with an immune checkpoint inhibitor (such as an inhibitor of PD-1, PD-L1, or CTLA-4) prior to and/or during the co-culturing. In some embodiments, the population of PBMCs is obtained from the individual being treated. In some embodiments, the MASCT further comprises administering to the individual an effective amount of an immune checkpoint inhibitor. In some embodiments, the activated T cells and the immune checkpoint inhibitor are administered simultaneously, such as in the same composition. In some embodiments, the activated T cells and the immune checkpoint inhibitor are administered sequentially.

In some embodiments, the MASCT comprises: contacting a population of peripheral blood mononuclear cells (PBMCs) with a plurality of tumor antigen peptides to obtain a population of activated PBMCs, and administering to the individual an effective amount of the activated PBMCs. In some embodiments, the population of PBMCs is contacted with the plurality of tumor antigen peptides in the presence of a composition that facilitates the uptake of the plurality of tumor antigen peptides by antigen presenting cells (such as DCs) in the PBMCs. In some embodiments, the population of PBMCs is contacted with the plurality of tumor antigen peptides in the presence of an immune checkpoint inhibitor, such as an inhibitor of PD-1, PD-L1, CTLA-4, IDO, TIM-3, BTLA, VISTA, and LAG-3. In some embodiments, the population of activated PBMCs is contacted with IL-2. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the MASCT further comprises administering to the individual an effective amount of an immune checkpoint inhibitor. In some embodiments, the activated T cells and the immune checkpoint inhibitor are administered simultaneously, such as in the same composition. In some embodiments, the activated T cells and the immune checkpoint inhibitor are administered sequentially.

In some embodiments, the MASCT comprises: (a) co-culturing a population of DCs loaded with a plurality of tumor antigen peptides and a population of T cells in an initial co-culture medium comprising one or more cytokines (e.g., a plurality of cytokines) and an immune checkpoint inhibitor to provide a co-culture; b) adding an anti-CD3 antibody to the co-culture at about 3 to 7 days after the co-culturing starts, thereby obtaining the population of activated T cells; and (c) administering to the individual an effective amount of the activated T cells. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 μg/mL. In some embodiments, the anti-CD3 antibody is added to the co-culture at about 5 days after the co-culturing starts. In some embodiments, the population of DCs loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of DCs and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of DCs loaded with the plurality of tumor antigen peptides. In some embodiments, the DCs loaded with the plurality of tumor antigen peptides are administered for at least three times. In some embodiments, the DCs loaded with the plurality of tumor antigen peptides are administered subcutaneously, intradermally or intravenously.

In some embodiments, the MASCT comprises: a) contacting a population of DCs with a plurality of tumor antigen peptides to obtain a population of DCs loaded with the plurality of tumor antigen peptides; b) culturing the population of DCs loaded with the plurality of tumor antigen peptides in a DC maturation medium comprising MPLA; c) co-culturing the population of DCs loaded with the plurality of tumor antigen peptides and a population of T cells, thereby obtaining the population of activated T cells; and d) administering to the individual an effective amount of the activated T cells. In some embodiments, step c) comprises co-culturing the population of DCs loaded with the plurality of tumor antigen peptides and a population of T cells in a co-culture medium comprising an interleukin cocktail, an immune checkpoint inhibitor and an anti-CD3 antibody. In some embodiments, the population of DCs loaded with the plurality of tumor antigen peptides and the population of T cells are co-cultured for at least about 10 days in the presence of the anti-CD3 antibody. In some embodiments, the DC maturation medium comprises INFγ and MPLA. In some embodiments, the DC maturation medium further comprises PGE2. In some embodiments, the MPLA is present in the DC maturation medium at a concentration of at least about 0.5 μg/mL. In some embodiments, the INFγ is present in the DC maturation medium at a concentration of at least about 100 IU/mL. In some embodiments, the PGE2 is present in the DC maturation medium at a concentration of at least about 0.1 μg/mL. In some embodiments, the plurality of cytokines comprises IL-2, IL-7, IL-15 and IL-21. In some embodiments, the IL-2 is present in the co-culture medium at a concentration of at least about 500 IU/mL. In some embodiments, the immune checkpoint inhibitor is an anti-PD-1 antibody. In some embodiments, the anti-PD-1 antibody is present in the co-culture medium at a concentration of at least about 10 μg/mL. In some embodiments, the population of DCs loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of DCs and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of DCs loaded with the plurality of tumor antigen peptides. In some embodiments, the DCs loaded with the plurality of tumor antigen peptides are administered for at least three times. In some embodiments, the DCs loaded with the plurality of tumor antigen peptides are administered subcutaneously, intradermally or intravenously.

In some embodiments, the MASCT comprises: a) contacting a population of DCs with a plurality of tumor antigen peptides to obtain a population of DCs loaded with the plurality of tumor antigen peptides; b) co-culturing the population of DCs loaded with the plurality of tumor antigen peptides and a population of T cells in an initial co-culture medium comprising one or more cytokines (e.g., a plurality of cytokines) and an immune checkpoint inhibitor to provide a co-culture; c) adding an anti-CD3 antibody to the co-culture at about 3 to 7 days after the co-culturing starts, thereby obtaining the population of activated T cells; and d) administering to the individual an effective amount of the activated T cells. In some embodiments, step (a) further comprises culturing the population of DCs loaded with the plurality of tumor antigen peptides in a DC maturation medium comprising a toll-like receptor (TLR) agonist. In some embodiments, the TLR agonist is selected from the group consisting of MPLA, Poly I:C, resquimod, gardiquimod, and CL075. In some embodiments, the DC maturation medium comprises PGE2. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 μg/mL. In some embodiments, the anti-CD3 antibody is added to the co-culture at about 5 days after the co-culturing starts. In some embodiments, the population of DCs loaded with the plurality of tumor antigen peptides and the population of T cells are co-cultured for at least about 10 days in the presence of the anti-CD3 antibody. In some embodiments, the population of DCs and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of DCs loaded with the plurality of tumor antigen peptides. In some embodiments, the DCs loaded with the plurality of tumor antigen peptides are administered for at least three times. In some embodiments, the DCs loaded with the plurality of tumor antigen peptides are administered subcutaneously, intradermally or intravenously.

In some embodiments, the MASCT comprises: a) contacting a population of DCs with a plurality of tumor antigen peptides to obtain a population of DCs loaded with the plurality of tumor antigen peptides; b) culturing the population of DCs loaded with the plurality of tumor antigen peptides in a DC maturation medium comprising MPLA; c) co-culturing the population of DCs loaded with the plurality of tumor antigen peptides and a population of T cells in an initial co-culture medium comprising one or more cytokines (e.g., a plurality of cytokines) and an immune checkpoint inhibitor to provide a co-culture; d) adding an anti-CD3 antibody to the co-culture, thereby obtaining the population of activated T cells; and e) administering to the individual an effective amount of the activated T cells. In some embodiments, the anti-CD3 antibody is added to the co-culture when the co-culturing starts. In some embodiments, the anti-CD3 antibody is added to the co-culture after the co-culturing starts. In some embodiments, the DC maturation medium comprises INFγ and MPLA. In some embodiments, the DC maturation medium further comprises PGE2. In some embodiments, the MPLA is present in the DC maturation medium at a concentration of at least about 0.5 μg/mL. In some embodiments, the INFγ is present in the DC maturation medium at a concentration of at least about 100 IU/mL. In some embodiments, the PGE2 is present in the DC maturation medium at a concentration of at least about 0.1 μg/mL. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 μg/mL. In some embodiments, the population of DCs loaded with the plurality of tumor antigen peptides and the population of T cells are co-cultured for at least about 10 days in the presence of the anti-CD3 antibody. In some embodiments, the population of DCs and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of DCs loaded with the plurality of tumor antigen peptides. In some embodiments, the DCs loaded with the plurality of tumor antigen peptides are administered for at least three times. In some embodiments, the DCs loaded with the plurality of tumor antigen peptides are administered subcutaneously, intradermally or intravenously.

In some embodiments, the MASCT comprises: a) contacting a population of DCs with a plurality of tumor antigen peptides to obtain a population of DCs loaded with the plurality of tumor antigen peptides; b) culturing the population of DCs loaded with the plurality of tumor antigen peptides in a DC maturation medium comprising MPLA, INFγ and PGE2; c) co-culturing the population of DCs loaded with the plurality of tumor antigen peptides and a population of T cells in an initial co-culture medium comprising a plurality of cytokines comprising IL-2, IL-7, IL-15 and IL-21 and an anti-PD-1 antibody to provide a co-culture; d) adding an anti-CD3 antibody to the co-culture at about 3 to 7 days (e.g., about 5 days) after the co-culturing starts, thereby obtaining the population of activated T cells; and e) administering to the individual an effective amount of the activated T cells. In some embodiments, the MPLA is present in the DC maturation medium at a concentration of at least about 0.5 μg/mL. In some embodiments, the INFγ is present in the DC maturation medium at a concentration of at least about 100 IU/mL. In some embodiments, the PGE2 is present in the DC maturation medium at a concentration of at least about 0.1 μg/mL. In some embodiments, the IL-2 is present in the initial co-culture medium at a concentration of at least about 500 IU/mL. In some embodiments, the anti-PD-1 antibody is present in the initial co-culture medium at a concentration of at least about 10 μg/mL. In some embodiments, the population of DCs loaded with the plurality of tumor antigen peptides and the population of T cells are co-cultured for at least about 10 days in the presence of the anti-CD3 antibody. In some embodiments, the population of DCs and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of DCs loaded with the plurality of tumor antigen peptides. In some embodiments, the DCs loaded with the plurality of tumor antigen peptides are administered for at least three times. In some embodiments, the DCs loaded with the plurality of tumor antigen peptides are administered subcutaneously, intradermally or intravenously.

Generally, dosages, schedules, and routes of administration of the activated T cells and the population of DCs loaded with the plurality of tumor antigen peptides described herein may be determined according to the size and condition of the individual, and according to standard pharmaceutical practice. Exemplary routes of administration include intravenous, intra-arterial, intraperitoneal, intrapulmonary, intravesicular, intramuscular, intra-tracheal, subcutaneous, intraocular, intrathecal, or transdermal. In some embodiments, the DCs loaded with the plurality of tumor antigen peptides are administered subcutaneously. In some embodiments, the activated T cells are administered intravenously.

The dose of the cells administered to an individual may vary according to, for example, the particular type of cells being administered, the route of administration, and the particular type and stage of cancer being treated. The amount should be sufficient to produce a desirable response, such as a therapeutic response against cancer, but without severe toxicity or adverse events. In some embodiments, the amount of the activated T cells or the DCs to be administered is a therapeutically effective amount. In some embodiments, the amount of the cells (such as multiple-antigen loaded DCs, or the activated T cells) is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same individual prior to treatment or compared to the corresponding activity in other individuals not receiving the treatment. Standard methods can be used to measure the magnitude of this effect, such as in vitro assays with purified enzyme, cell-based assays, animal models, or human testing.

In some embodiments, the antigen-loaded dendritic cells are administered at a dose at least about any one of $1\times10^5$, $5\times10^5$, $1\times10^6$, $1.5\times10^6$, $2\times10^6$, $3\times10^6$, $4\times10^6$, $5\times10^6$, $6\times10^6$, $7\times10^6$, $8\times10^6$, $9\times10^6$, $1\times10^7$ or $5\times10^7$ cells/individual. In some embodiments, the antigen-loaded dendritic cells are administered at a dose about any one of $1\times10^5$-$5\times10^5$, $5\times10^5$-$1\times10^6$, $1\times10^6$-$2\times10^6$, $2\times10^6$-$3\times10^6$, $3\times10^6$-$4\times10^6$, $4\times10^6$-$5\times10^6$, $5\times10^6$-$6\times10^6$, $6\times10^6$-$7\times10^6$, $7\times10^6$-$8\times10^6$, $8\times10^6$-$1\times10^8$, $1\times10^6$-$3\times10^6$, $3\times10^6$-$5\times10^6$, $5\times10^6$-$7\times10^6$, $2\times10^6$-$2\times10^7$, $5\times10^6$-$2\times10^7$, or $1\times10^6$-$2\times10^7$ cells/individual. In some embodiments, the antigen-loaded dendritic cells are administered at a dose of at least about $1\times10^6$ cells/individual. In some embodiments, the antigen-loaded dendritic cells are administered at a dose of about $1.5\times10^6$ to about $1.5\times10^7$ cells/individual.

In some embodiments, the antigen-loaded dendritic cells are administered at a dose at least about any one of $1\times10^4$, $2.5\times10^4$, $5\times10^4$, $1\times10^5$, $2\times10^5$, $2.5\times10^5$, $4\times10^5$, $6\times10^5$, $8\times10^5$, $1\times10^6$, $2\times10^6$ or $1\times10^7$ cells/kg. In some embodiments, the antigen-loaded dendritic cells are administered at a dose about any one of $1\times10^4$-$5\times10^4$, $5\times10^4$-$1\times10^5$, $1\times10^5$-$2\times10^5$, $2\times10^5$-$4\times10^5$, $4\times10^5$-$6\times10^5$, $6\times10^5$-$8\times10^5$, $8\times10^5$-$1\times10^6$, $1\times10^6$-$2\times10^6$, $2\times10^6$-$1\times10^7$, $1\times10^4$-$1\times10^5$, $1\times10^5$-$1\times10^6$, $1\times10^6$-$1\times10^7$, $1\times10^4$-$1\times10^6$, or $1\times10^5$-$1\times10^7$ cells/kg. In some embodiments, the antigen-loaded dendritic cells are administered at a dose of at least about $2\times10^5$ cells/kg. In some embodiments, the antigen-loaded dendritic cells are administered at a dose of about $2.5\times10^4$ to about $2.5\times10^5$ cells/kg.

In some embodiments, the activated T cells are administered at a dose of at least about any one of $1\times10^8$, $5\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $1.5\times10^{10}$, $2\times10^{10}$, or $5\times10^{10}$ cells/individual. In some embodiments, the activated T cells are administered at a dose of about any one of $1\times10^8$-$5\times10^8$, $5\times10^8$-$1\times10^9$, $1\times10^9$-$5\times10^9$, $5\times10^9$-$1\times10^{10}$, $3\times10^9$-$7\times10^9$, $1\times10^{10}$-$2\times10^{10}$, or $1\times10^9$-$1\times10^{10}$ cells/individual. In some embodiments, the activated T cells are administered at a dose of at least about $3\times10^9$ cells/individual. In some embodiments, the activated T cells are administered at a dose of about $1\times10^9$ to about $1\times10^{10}$ cells/individual.

In some embodiments, the activated T cells are administered at a dose of at least about any one of $1\times10^7$, $2\times10^7$, $4\times10^7$, $6\times10^7$, $8\times10^7$, $1\times10^1$, $2\times10^8$, $4\times10^8$, $6\times10^8$, $8\times10^8$, $1\times10^9$ cells/kg. In some embodiments, the activated T cells are administered at a dose of about any one of $1\times10^7$-$1\times10^8$, $1\times10^7$-$5\times10^7$, $2\times10^7$-$4\times10^7$, $5\times10^7$-$1\times10^8$, $1\times10^8$-$2\times10^8$, $5\times10^7$-$1\times10^8$, $1\times10^8$-$2\times10^8$, $2\times10^8$-$5\times10^8$, $1\times10^8$-$1\times10$, or $1\times10^7$-$1\times10^9$ cells/kg. In some embodiments, the activated T cells are administered at a dose of at least about $6\times10^7$ cells/kg. In some embodiments, the activated T cells are administered at a dose of about $1.5\times10^7$ to about $2\times10^8$ cells/kg.

The MASCT can be used in monotherapy as well as in combination therapy with another agent. For example, any of the treatment methods described herein may be combined with administration of one or more (such as any of 1, 2, 3, 4, or more) immune checkpoint inhibitors. In some embodiments, the immune checkpoint inhibitor is selected from the group consisting of inhibitors of PD-1, PD-L1, CTLA-4, IDO, TIM-3, BTLA, VISTA, and LAG-3.

In some embodiments, the immune checkpoint inhibitor is an inhibitor of PD-1. In some embodiments, the immune checkpoint inhibitor is an anti-PD-1 antibody. Exemplary anti-PD-1 antibodies include, but are not limited to, Nivolumab, pembrolizumab, pidilizumab, BMS-936559, and atezolizumab, Pembrolizumab, MK-3475, AMP-224, AMP-514, STI-A1110, and TSR-042. In some embodiments, the immune checkpoint inhibitor is nivolumab (for example, OPDIVO®). In some embodiments, the immune checkpoint inhibitor is Pembrolizumab (for example, KEYTRUDA©). In some embodiments, the immune checkpoint inhibitor is SHR-1210.

In some embodiments, the immune checkpoint inhibitor is an inhibitor of PD-L1. In some embodiments, the immune checkpoint inhibitor is an anti-PD-L1 antibody. Exemplary anti-PD-L1 antibodies include, but are not limited to, KY-1003, MCLA-145, RG7446, BMS935559, MPDL3280A, MEDI4736, Avelumab, or STI-A1010.

In some embodiments, the immune checkpoint inhibitor is an inhibitor of CTLA-4. In some embodiments, the immune checkpoint inhibitor is an anti-CTLA-4 antibody. Exemplary anti-CTLA-4 antibodies include, but are not limited to, Ipilimumab, Tremelimumab, and KAHR-102. In some embodiments, the immune checkpoint inhibitor is Ipilimumab (for example, YERVOY®).

In some embodiments, the activated T cells and the immune checkpoint inhibitor are administered simultaneously. In some embodiments, the activated T cells and the immune checkpoint inhibitor are administered in a single composition. In some embodiments, the immune checkpoint inhibitor is present in the first, second or third co-culture. In some embodiments, the activated T cells and the immune checkpoint inhibitor are admixed prior to (such as immediately prior to) the administration. In some embodiments, the activated T cells and the immune checkpoint inhibitor are administered simultaneously via separate compositions.

In some embodiments, the activated T cells and the immune checkpoint inhibitor are administered sequentially. In some embodiments, the immune checkpoint inhibitor is administered prior to the administration of the activated T cells. In some embodiments, the immune checkpoint inhibitor is administered after the administration of the activated T cells.

Exemplary routes of administration of the immune checkpoint inhibitor include, but are not limited to, intratumoral, intravesical, intramuscular, intraperitoneal, intravenous, intra-arterial, intracranial, intrapleural, subcutaneous, and epidermal routes, or be delivered into lymph glands, body spaces, organs or tissues known to contain such live cancer cells. In some embodiments, the immune checkpoint inhibitor is administered intravenously. In some embodiments, the immune checkpoint inhibitor is administered by infusion. In some embodiments, the immune checkpoint inhibitor is infused over at least about any of 10 minutes, 30 minutes, 1 hour, 2 hours, 4 hours, 6 hours, or more. In some embodiments, the immune checkpoint inhibitor is administered via the same administration route as the activated T cells. In some embodiments, the immune checkpoint inhibitor is administered via a different administration route as the activated T cells.

Suitable dose of the immune checkpoint inhibitor include, but are not limited to, about any one of 1 $mg/m^2$, 5 $mg/m^2$, 10 $mg/m^2$, 20 $mg/m^2$, 50 $mg/m^2$, 100 $mg/m^2$, 200 $mg/m^2$, 300 $mg/m^2$, 400 $mg/m^2$, 500 $mg/m^2$, 750 $mg/m^2$, 1000 $mg/m^2$, or more. In some embodiments, the dose of immune checkpoint inhibitor is any one of about 1 to about 5 $mg/m^2$, about 5 to about 10 $mg/m^2$, about 10 to about 20 $mg/m^2$, about 20 to about 50 $mg/m^2$, about 50 to about 100 $mg/m^2$, about 100 $mg/m^2$ to about 200 $mg/m^2$, about 200 to about 300 $mg/m^2$, about 300 to about 400 $mg/m^2$, about 400 to about 500 $mg/m^2$, about 500 to about 750 $mg/m^2$, or about 750 to about 1000 $mg/m^2$. In some embodiments, the dose of immune checkpoint inhibitor is about any one of 1 μg/kg, 2 μg/kg, 5 μg/kg, 10 μg/kg, 20 μg/kg, 50 μg/kg, 0.1 mg/kg, 0.2 mg/kg, 0.3 mg/kg, 0.4 mg/kg, 0.5 mg/kg, 1 mg/kg, 2 mg/kg, 5 mg/kg, 10 mg/kg, 20 mg/kg, 50 mg/kg, 100 mg/kg, or more. In some embodiments, the dose of the immune checkpoint inhibitor is any one of about 1 μg/kg to about 5 μg/kg, about 5 μg/kg to about 10 μg/kg, about 10 μg/kg to about 50 μg/kg, about 50 μg/kg to about 0.1 mg/kg, about 0.1 mg/kg to about 0.2 mg/kg, about 0.2 mg/kg to about 0.3 mg/kg, about 0.3 mg/kg to about 0.4 mg/kg, about 0.4 mg/kg to about 0.5 mg/kg, about 0.5 mg/kg to about 1 mg/kg, about 1 mg/kg to about 5 mg/kg, about 5 mg/kg to about 10 mg/kg, about 10 mg/kg to about 20 mg/kg, about 20 mg/kg to about 50 mg/kg, about 50 mg/kg to about 100 mg/kg, or about 1 mg/kg to about 100 mg/kg.

In some embodiments, the immune checkpoint inhibitor is administered daily. In some embodiments, the immune checkpoint inhibitor is administered is administered at least about any one of 1×, 2×, 3×, 4×, 5×, 6×, or 7× (i.e., daily) a week. In some embodiments, the immune checkpoint inhibitor is administered weekly. In some embodiments, the immune checkpoint inhibitor is administered weekly without break; weekly, two out of three weeks; weekly three out of four weeks; once every two weeks; once every 3 weeks; once every 4 weeks; once every 6 weeks; once every 8 weeks, monthly, or every two to 12 months. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, the immune checkpoint inhibitor is administered once every 3 months. In some embodiments, there is no break in the dosing schedule. In some embodiments, the interval between each administration is no more than about a week. In some embodiments, the immune checkpoint inhibitor is administered with the same dosing schedule as the activated T cells. In some embodiments, the immune checkpoint inhibitor is administered with a different dosing schedule as the activated T cells.

In some embodiments, the immune checkpoint inhibitor is administered in every MASCT treatment cycle. For example, the immune checkpoint inhibitor may be administered about any of 1, 2, 3, 4, 5, 6, or more times every MASCT treatment cycle. In some embodiments, the immune checkpoint inhibitor is not administered in every MASCT treatment cycle. For example, the immune checkpoint inhibitor may be administered about once every 1, 2, 3, 4, 5, or more MASCT treatment cycles.

The administration of the immune checkpoint inhibitor can be over an extended period of time, such as from about a month up to about seven years. In some embodiments, the immune checkpoint inhibitor is administered over a period of at least about any one of 1, 2, 3, 4, 5, 6, 7, 8, 9, 10, 11, 12, 18, 24, 30, 36, 48, 60, 72, or 84 months. In some embodiments, the immune checkpoint inhibitor is administered for a single time. In some embodiments, the immune checkpoint inhibitor is administered repeatedly. In some embodiments, the immune checkpoint inhibitor is administered repeatedly until disease progression.

In some embodiments, the MASCT is particularly suitable for an individual with a low total mutation load in the cancer of the individual. In some embodiments, the MASCT is particularly suitable for an individual with a low mutation load in the cancer-associated genes in the cancer of the individual. In some embodiments, the MASCT is particularly suitable for an individual with a low mutation load in immune genes related to T cell response in the cancer of the individual. In some embodiments, the MASCT is particularly suitable for an individual with a low mutation load in the MHC genes in the cancer of the individual. The mutation load may be mutation load in all cancer cells, or a subset of cancer cells, such as a primary or metastatic tumor site, for example, cells in a tumor biopsy sample.

In some embodiments, a low mutation load of one or more genes is a low number of mutations accumulated on the one or more genes. In some embodiments, a total number of no more than about any of 500, 400, 300, 200, 100, 50, 40, 30, 20, 10, 5 or fewer mutations indicate a low mutation load. In some embodiments, no more than about any of 50, 40, 30, 25, 20, 15, 14, 13, 12, 11, 10, 9, 8, 7, 6, 5, 4, 3, 2 or 1 mutations in the one or more MHC genes indicate a low mutation load of the one or more MHC genes. In some embodiments, a low mutation load of one or more genes is a low ratio between the number of mutations accumulated on the one or more genes (such as MHC genes) and the total number of mutations in a selected set of genes (such as cancer-associated genes) or the full genome.

In some embodiments, the one or more MHC genes comprise MHC class I genes (or loci). In some embodiments, the one or more MHC genes comprise MHC class II genes (or loci). In some embodiments, wherein the individual is a human individual, the one or more MHC genes are selected from the group consisting of HLA-A, HLA-B, HLA-C and B2M.

Exemplary mutations include, but are not limited to, deletion, frameshift, insertion, indel, missense mutation, nonsense mutation, point mutation, copy number variation, single nucleotide variation (SNV), silent mutation, splice site mutation, splice variant, gene fusion, and translocation. In some embodiments, the copy number variation of the MHC gene is caused by structural rearrangement of the genome, including deletions, duplications, inversion, and translocation of a chromosome or a fragment thereof. In some embodiments, the mutations in the one or more MHC genes are selected from point mutations, frameshift mutations, gene fusions, and copy number variations. In some embodiments, the mutations are in the protein-coding region of the MHC genes. In some embodiments, the mutation is a nonsynonymous mutation. In some embodiments, the mutation is not a polymorphism. In some embodiments, the mutation is present in normal cells of the individual. In some embodiments, the mutation is not present in normal cells of the individual. In some embodiments, the mutation affects the physiochemical or functional properties, such as stability or binding affinity, of the MHC molecule encoded by the affected gene. In some embodiments, the mutation results in an irreversible deficiency in the MHC molecule. In some embodiments, the mutation reduces the binding affinity of the MHC molecule to T cell epitopes and/or T cell receptors. In some embodiments, the mutation is a loss-of-function mutation. In some embodiments, the mutation results in reversible deficiency in the MHC molecule. In some embodiments, the mutation does not affect the binding affinity of the MHC molecule to T cell epitopes and/or T cell receptors. In some embodiments, the mutation is a somatic mutation. In some embodiments, the mutation is a germline mutation.

The mutations counted towards the mutation load may be present in all cancer cells or in a subset of cancer cells. In some embodiments, the mutations are present in all cancer cells in the individual. In some embodiments, the mutations are present in all cancer cells of a tumor site. In some embodiments, the mutations are clonal. In some embodiments, the mutations are subclonal. In some embodiments, the mutations are present in at least about any of 10%, 20%, 30%, 40%, 50%, 60%, 70%, 80%, 90%, 95%, or more cancer cells of the individual.

The mutations in certain MHC genes and/or in certain domains or positions of the one or more MHC genes may have more profound influence on the clinical response of the individual to the treatment methods described herein. For example, loss-of-function mutations may occur in the leader peptide sequence, a3 domain (which binds the CD8 co-receptor of T cells), a1 peptide binding domain, or a2 peptide binding domain of the HLA molecule; see, for example, Shukla S. et al. *Nature Biotechnology* 33, 1152-1158 (2015), incorporated herein by reference. Mutations in B2M (β2-macroglobulin) gene may also promote tumor escape phenotypes. See, for example, Monica B et al. *Cancer Immunol. Immu.*, (2012) 61: 1359-1371. In some embodiments, presence of any number (such as 1, 2, 3, 4, 5, or more) of mutations in the functional regions of the one or more MHC genes, such as the leader peptide sequence, a1 domain, a2 domain, or a3 domain, indicates a high mutation load. In some embodiments, presence of any number (such as 1, 2, 3, 4, 5, or more) loss-of-function mutations in the one or more MHC genes (such as HLA-A, HLA-B or HLA-C genes in human individuals) indicates a high mutation load. In some embodiments, a low mutation load in the one or more MHC genes comprises no mutation in the functional regions, including leader peptide sequence, a1 domain (for example, residues in direct contact with the CD8 co-receptor), a2 domain, and a3 domain (for example, residues in direct contact with the epitope), of the one or more MHC genes (such as HLA-A, HLA-B or HLA-C genes). In some embodiments, presence of any number of mutations (such as loss-of-function mutations) in the B2M gene indicates a high mutation load. In some embodiments, a low mutation load in the one or more MHC genes comprises no mutation in the B2M gene.

The mutation load of one or more genes (such as MHC genes) may be determined by any known methods in the art, including, but not limited to, genomic DNA sequencing, exome sequencing, or other DNA sequencing-based methods using Sanger sequencing or next generation sequencing platforms; polymerase chain reaction assays; in situ hybridization assays; and DNA microarrays.

In some embodiments, the mutation load of the one or more MHC genes is determined by sequencing a tumor sample from the individual. In some embodiments, the sequencing is next generation sequencing. In some embodiments, the sequencing is full genome sequencing. In some embodiments, the sequencing is exome sequencing, such as whole exome sequencing ("WES"). In some embodiments, the sequencing is RNA sequencing. In some embodiments, the sequencing is targeted sequencing of candidate genes, such as cancer-associated genes plus HLA genes. For example, ONCOGXONE™ Plus (Admera Health), are available to sequence cancer-associated genes and HLA loci with high sequencing depth. In some embodiments, the same sequencing data can be used to determine the mutation load of the one or more MHC genes and to identify neoantigens in the individual.

In some embodiments, the tumor sample is a tissue sample. In some embodiments, the tumor sample is a tumor biopsy sample, such as fine needle aspiration of tumor cells or laparoscopy obtained tumor cells (such as including tumor stroma). In some embodiments, the tumor sample is freshly obtained. In some embodiments, the tumor sample is frozen. In some embodiments, the tumor sample is a Formaldehyde Fixed-Paraffin Embedded (FFPE) sample. In some embodiments, the tumor sample is a cell sample. In some embodiments, the tumor sample comprises a circulating metastatic cancer cell. In some embodiments, the tumor sample is obtained by sorting circulating tumor cells (CTCs) from blood. In some embodiments, nucleic acids (such as DNA and/or RNA) are extracted from the tumor sample for the sequencing analysis. In some embodiments, the sequencing data of the tumor sample is compared to the sequencing data of a reference sample, such as a sample of a healthy tissue from the same individual, or a sample of a healthy individual, to identify mutations and determine mutation load in the tumor cells. In some embodiments, the sequencing data of the tumor sample is compared to the reference sequences from a genome database to identify mutations and determine mutation load in the tumor cells.

Any of the MASCT methods may comprise using one or more neoantigen peptides in the plurality of tumor antigen peptides. In some embodiments, the MASCT further comprises the steps of selecting the individual for the method of treating based on having one or more (such as at least 5)

neoantigens in the individual, and/or the steps of: (i) identifying a neoantigen of the individual; and (ii) incorporating a neoantigen peptide derived from the neoantigen in the plurality of tumor antigen peptides for use in the treatment method.

In some embodiments, the MASCT comprises: (a) identifying a neoantigen of the individual; (b) incorporating a neoantigen peptide in a plurality of tumor antigen peptides, wherein the neoantigen peptide comprises a neoepitope in the neoantigen; (c) optionally administering an effective amount of DCs loaded with the plurality of tumor antigen peptides; (d) preparing a population of activated T cells by co-culturing the antigen-loaded DCs with a population of T cells; and (e) administering to the individual an effective amount of activated T cells, wherein the individual has one or more neoantigens.

The individual may have any number (such as at least about any one of 1, 2, 4, 5, 6, 7, 8, 9, 10, 11, 12, 13, 14, 15, 20, 50, 100 or more) of neoantigens in order to benefit from the MASCT method using a plurality of tumor antigen peptides comprising a neoantigen peptide. In some embodiments, the MASCT method is particularly suitable for an individual having at least about any one of 4, 5, 6, 7, 8, 10, 15, 20, 50, 100 or more neoantigens. In some embodiments, the neoantigen comprises one or more neoepitopes. In some embodiments, the MASCT method is particularly suitable for an individual having at least about any one of 4, 5, 6, 7, 8, 10, 15, 20, 50, 100 or more neoepitopes. In some embodiments, the T cell epitopes are MHC-I restricted epitopes. In some embodiments, the neoepitope has a higher affinity to the MHC molecules of the individual than the corresponding wildtype T cell epitope. In some embodiments, the neoepitope has higher affinity to a model T cell receptor than the corresponding wildtype T cell epitope. In some embodiments, the neoantigen (or neoepitope) is a clonal neoantigen. In some embodiments, the neoantigen (or neoepitope) is a subclonal neoantigen. In some embodiments, the neoantigen (or neoepitope) is present in at least about any one of 10%, 20%, 30%, 40%, 50%, 60%, 70%, 80%, 90%, 95% or more tumor cells in the individual.

The number of neoantigens may be combined with other biomarkers or selection criteria to select an individual for any one of the MASCT methods described herein. In some embodiments, the MASCT method is particularly suitable for an individual with a low mutation load (such as in one or more MHC genes) in the cancer cells, and/or have at least about any of 4, 5, 6, 7, 8, 10 or more neoantigens (such as neoantigens with high affinity MHC-I restricted neoepitopes).

Any number (such as any of 1, 2, 3, 4, 5, 6, 7, 8, 9, 10, or more) of neoantigen peptides may be designed based on the neoantigens of the individual and to be incorporated in the plurality of tumor antigen peptides for use in any of the treatment methods described herein. In some embodiments, the plurality of tumor antigen peptides comprises a single neoantigen peptide. In some embodiments, the plurality of tumor antigen peptides comprises a plurality of neoantigen peptides. Each neoantigen peptide may comprise one or more neoepitopes from a neoantigen of the individual. In some embodiments, the neoepitope is a T cell epitope. Methods of designing a neoantigen peptide based on a neoantigen are described in the section "Plurality of tumor antigen peptides."

The neoantigens in the individual may be identified using any known methods in the art. In some embodiments, the neoantigen is identified based on the genetic profile of a tumor sample from the individual. Each neoantigen comprises one or more neoepitopes. In some embodiments, the one or more neoepitopes in the neoantigen are identified based on the genetic profile of the tumor sample. Any known genetic profiling methods, such as next generation sequencing (NGS) methods, microarrays, or proteomic methods may be used to provide the genetic profile of the tumor sample.

In some embodiments, the neoantigen is identified by sequencing a tumor sample from the individual. In some embodiments, the sequencing is next generation sequencing. In some embodiments, the sequencing is full-genome sequencing. In some embodiments, the sequencing is exome sequencing, such as whole exome sequencing ("WES"). In some embodiments, the sequencing is RNA sequencing. In some embodiments, the sequencing is targeted sequencing of candidate genes, such as cancer-associated genes. Many commercial NGS cancer panels, for example, ONCOGX-ONE™ Plus (Admera Health), are available to sequence cancer-associated genes with high sequencing depth.

In some embodiments, the tumor sample is a tissue sample. In some embodiments, the tumor sample is a tumor biopsy sample, such as fine needle aspiration of tumor cells or laparoscopy obtained tumor cells (such as including tumor stroma). In some embodiments, the tumor sample is freshly obtained. In some embodiments, the tumor sample is frozen. In some embodiments, the tumor sample is a Formaldehyde Fixed-Paraffin Embedded (FFPE) sample. In some embodiments, the tumor sample is a cell sample. In some embodiments, the tumor sample comprises a circulating metastatic cancer cell. In some embodiments, the tumor sample is obtained by sorting circulating tumor cells (CTCs) from blood. In some embodiments, nucleic acids (such as DNA and/or RNA) are extracted from the tumor sample for the sequencing analysis. In some embodiments, proteins are extracted from the tumor sample for the sequencing analysis.

In some embodiments, the genetic profile of the tumor sample is compared to the genetic profile of a reference sample, such as a sample of a healthy tissue from the same individual, or a sample of a healthy individual, to identify candidate mutant genes in the tumor cells. In some embodiments, the genetic profile of the tumor sample is compared to the reference sequences from a genome database to identify candidate mutant genes in the tumor cells. In some embodiments, the candidate mutant genes are cancer-associated genes. In some embodiments, each candidate mutant gene comprises one or more mutations, such as nonsynonymous substitutions, indel (insertion or deletion), or gene fusion, which may give rise to a neoantigen. Common Single Nucleotide Polymorphisms (SNPs) are excluded from the candidate mutations.

In some embodiments, neoepitopes in neoantigens are identified from the candidate mutant proteins. In some embodiments, the neoepitopes are predicted in silico. Exemplary bioinformatics tools for T cell epitope prediction are known in the art, for example, see Yang X. and Yu X. (2009) "An introduction to epitope prediction methods and software" *Rev. Med. Virol.* 19(2): 77-96. Factors considered in the T cell epitope prediction algorithms include, but are not limited to, MHC subtype of the individual, sequence-derived physiochemical properties of the T cell epitope, MHC binding motifs, proteasomal cleavage pattern, transporter associated with antigen processing (TAP) transport efficiency, MHC binding affinity, peptide-MHC stability, and T-cell receptor binding affinity. In some embodiments, the neoepitope is an MHC-I restricted epitope. In some embodiments, the neoepitope is an MHC-II restricted epitope.

In some embodiments, the neoepitope has high affinity to the MHC molecules of the individual. In some embodiments, the method further comprises determining the MHC subtype of the individual, for example, from the sequencing data, to identify one or more MHC molecules of the individual. In some embodiments, the method further comprises determining the affinity of the neoepitope to an MHC molecule, such as an MHC class I molecule. In some embodiments, the method comprises determining the affinity of the neoepitope to one or more MHC (such as MHC class I) molecules of the individual. In some embodiments, the affinity of the neoepitope to one or more MHC molecules of the individual is compared to the affinity of the corresponding wildtype epitope to the one or more MHC molecules of the individual. In some embodiments, the neoepitope is selected for having a higher (such as at least about any of 1.5, 2, 5, 10, 15, 20, 25, 50, 100, or more times) affinity to the one or more MHC molecules (such as MHC-I molecules) of the individual than the corresponding wildtype epitope. In some embodiments, the MHC binding affinity is predicted in silico using any known tools or methods in the art. In some embodiments, the MHC binding affinity is determined experimentally, such as using an in vitro binding assay.

In some embodiments, the MASCT further comprises determining the affinity of the complex comprising the neoepitope and an MHC molecule (such as an MHC class I molecule of the individual) to a T cell receptor. In some embodiments, the affinity of the complex comprising the neoepitope and the MHC molecule to the T cell receptor is compared to that of the complex comprising the corresponding wildtype epitope and the MHC molecule. In some embodiments, the MHC molecule is from the individual. In some embodiments, the T cell receptor is on the surface of one or more T cells of the individual. In some embodiments, the neoepitope is selected for having a higher (such as at least about any one of 1.5, 2, 5, 10, 15, 20, 25, 50, 100, or more times) affinity in a complex comprising the neoepitope and an MHC molecule to a T cell receptor model than the corresponding wildtype epitope. In some embodiments, the TCR binding affinity is predicted in silico using any known tools or methods in the art. In some embodiments, the TCR binding affinity is determined experimentally, for example, by determining the T cell response against the neoepitope.

In some embodiments, the neoantigen (or the neoepitope) is identified further based on the expression level of the neoantigen (or the neoepitope) in the tumor sample. Expression level of the neoantigen (or the neoepitope) may be determined using any methods for quantification of mRNA or protein levels known in the art, such as RT-PCR, antibody-based assays, mass spectrometry. In some embodiments, the expression level of the neoantigen (or the neoepitope) is determined from the sequencing data of the tumor sample. In some embodiments, the neoantigen (or the neoepitope) is expressed in the tumor cells at a level of at least about any one of 10, 20, 50, 100, 200, 500, 1000, 2000, 5000, $10^4$, or more copies per cell. In some embodiments, the neoantigen (or the neoepitope) is expressed at a level of more than about any one of 1.5, 2, 5, 10, 20, 50, 100, or more times than the corresponding wildtype protein (or the corresponding wildtype epitope) in the tumor cells.

In some embodiments, the neoantigen peptide is selected or identified by the steps comprising: (a) sequencing a tumor sample from the individual to identify a neoantigen; (b) identifying a neoepitope in the neoantigen; optionally (c) determining the MHC subtype of the individual (e.g., using the sequencing data) to identify an MHC molecule of the individual; optionally (d) determining the affinity of the neoepitope to the MHC molecule of the individual; optionally (e) determining the affinity of the complex comprising the neoepitope and the MHC molecule to a T cell receptor; and (f) obtaining a peptide comprising the neoepitope to provide the neoantigen peptide. In some embodiments, the neoepitope has higher affinity to the MHC molecule (such as MHC-I molecule) of the individual and/or higher affinity in the complex comprising the neoepitope and the MHC molecule to the TCR as compared to the complex comprising the corresponding wildtype T cell epitope and the MHC molecule. In some embodiments, the neoepitope is extended at the N terminus or the C terminus or both termini according to the natural sequence of the neoantigen harboring the epitope to obtain an extended sequence, wherein the extended sequence is amenable for presentation by both class I and class II MHC molecules. Any of the treatment methods described herein using one or more neoantigen peptides may further comprise any one or more of the neoantigen selection/identification steps.

Any of the treatment methods and the MASCT methods described herein may further comprise a monitoring step after the individual receives the treatment. Post-treatment monitoring may be beneficial for adjusting the treatment regimen of the individual to optimize treatment outcome.

For example, the plurality of tumor antigen peptides described herein may be adjusted or customized based on the specific immune response of the individual against each of the plurality of tumor antigen peptides and/or the clinical response of the individual to the activated T cells in order to provide a plurality of customized tumor antigen peptides, which may be used for repeated treatments. In some embodiments, tumor antigen peptides that do not elicit a strong specific immune response can be removed from the antigen peptide pool for future preparations of the pulsed DCs or activated T cells.

Specific immune response against one or more tumor antigen peptides may be determined using any known methods in the art, for example, by measuring levels of cytotoxic factor (such as perforin or granzyme B), or cytokine release (such as IFNγ or TNFα) from T cells (or PBMCs) after stimulation by the individual tumor antigen peptide. An antibody-based assay, such as ELISPOT, may be used to quantify the cytotoxic factor, or cytokine (such as IFNγ) levels. In some embodiments, the cytokine (such as IFNγ) release level from T cells (or PBMCs) in response to a tumor antigen peptide is normalized to a reference, such as a baseline cytokine release level, or a nonspecific cytokine release level of from T cells (or PBMCs) in response to an irrelevant peptide, to provide a cytokine (such as IFNγ) fold change value. In some embodiments, a cytokine (such as IFNγ) fold change value of more than about any one of 1.2, 1.5, 2, 2.5, 3, 4, 5, 6, 8, 10, or more in an ELISPOT assay indicate strong specific immune response against the tumor antigen peptide. In some embodiments, a tumor antigen peptide with a cytokine (such as IFNγ) fold change value of less than about any one of 10, 8, 6, 5, 4, 3, 2.5, 2, 1.5, 1.2 or less in an ELISPOT assay is removed from the plurality of tumor antigen peptides to provide a plurality of customized tumor antigen peptides for future treatments.

Clinical response of the individual to the treatment methods described herein may be assessed by known methods in the art by a physician, such as by imaging methods, blood tests, biomarker assessment, and biopsy. In some embodiments, the clinical response is monitored by determining the number of circulating tumor cells (CTC) in the individual before and after receiving the activated T cells. In some embodiments, the CTCs have detached from a primary tumor and circulate in a bodily fluid. In some embodiments, the CTCs have detached from a primary tumor and circulate in the bloodstream. In some embodiments, the CTCs are an indication of metastasis. CTC numbers can be determined by a variety of methods known in the art, including, but not limited to, CellSearch method, Epic Science method, isoflux, and maintrac. In some embodiments, the number of single CTCs, including specific subtypes of CTCs, in a blood sample of the individual is determined. In some embodiments, a number of more than about any of 10, 20, 50, 100, 150, 200, 300 or more of single CTCs per mL of the blood sample in the individual after receiving the treatment indicates an increased risk of metastasis, and/or poor clinical response to the treatment method. In some embodiments, an increased number (such as at least about any one of 1.5, 2, 3, 4, 5, 10, or more fold increase) of single CTCs of the individual after receiving the treatment compared to before receiving the treatment indicates poor clinical response to the treatment method. In some embodiments, the number of CTC clusters in a blood sample of the individual is determined. In some embodiments, detection of at least about any of 1, 5, 10, 50, 100, or more CTC clusters in a blood sample of the individual after receiving the treatment indicates an increased risk of metastasis, and/or poor clinical response to the treatment. In some embodiments, an increased number (such as at least about any one of 1.5, 2, 3, 4, 5, 10, or more fold increase) of CTC clusters of the individual after receiving the treatment compared to before receiving the treatment indicates poor clinical response to the treatment.

III. Tumor-Specific TCRs

Also provided herein are tumor-specific TCRs obtained using any one of the methods described in Section II. In some embodiments, the tumor-specific TCR specifically recognizes CEA, RSG-5 or HPV18-E7. Nucleic acids and vectors encoding the tumor-specific TCRs, engineered immune cells expressing the tumor-specific TCRs are also within the scope of this application.

Exemplary Tumor-Specific TCRs

Exemplary TCRs identified using the methods described herein are shown in Table 1 below. The V, J, C segments are named according to IMGT database. Other nomenclature and segment delineation algorithms known in the art may be used. For example, according to IMGT, a TCR chain comprises a FR1 from amino acid position 1 to 26, a CDR1 from amino acid position 27 to 38, a FR2 from amino acid position 39 to 55, a CDR2 from amino acid position 56 to 65, a FR3 from amino acid position 66 to 104, and a CDR3 from amino acid position 105 to 117 (for rearranged V-J-Genes and V-D-J-genes), and a FR4 from amino acid position 118 to 129. See, for example, Lefranc, M.-P., The Immunologist, 7, 132-136 (1999), and world wide web.imgt.org/IMGTScientificChart/Nomenclature/IMGT-FRCDRdefinition.html. CDR1, CDR2 and CDR3 of exemplary TCRs are shown in the "SEQUENCE LISTING" section and in Table 5.

TABLE 1

Exemplary tumor-specific TCRs

| | | | | | | | SEQ ID NO. | | | | | |
|---|---|---|---|---|---|---|---|---|---|---|---|---|
| | | | | | | | | | Full chain | | Variable region | |
| TCR ID | Clone # | Antigen | TCR chain | V | J | C | Epitope | CDR3 | amino acid | nucleic acid | amino acid | nucleic acid |
| | 1 | CEA | Alpha | TRAV26-1*01 | TRAJ48*01 | Cα | | 4 | 5 | 6 | | |
| | | | Beta | TRBV18*01 | TRBJ1-2*01 | Cβ1 | | 7 | 8 | 9 | | |
| | 2 | | Alpha | TRAV16*01 | TRAJ27*01 | Cα | | 10 | 11 | 12 | | |
| | | | Beta | TRBV2*01 | TRBJ1-3*01 | Cβ1 | | 13 | 14 | 15 | | |
| | 3 | | Alpha | TRAV23/DV6*01 | TRAJ20*01 | Cα | | 16 | 17 | 18 | | |
| | | | Beta | TRBV18*01 | TRBJ1-4*01 | Cβ1 | | 19 | 20 | 21 | | |
| | 1 | RGS5 | Alpha | TRAV38-2/DV8*01 | TRAJ20*01 | Cα | | 22 | 23 | 24 | | |
| | | | Beta | TRBV19*01 | TRBJ2-1*01 | Cβ2 | | 25 | 26 | 27 | | |
| P09E06 | 2 | | Alpha | TRAV26-1*01 | TRAJ43*01 | Cα | 82 | 28 | 29 | 30 | 214 | 215 |
| | | | Beta | TRBV11-2*01 | TRBJ1-1*01 | Cβ1 | | 31 | 32 | 33 | 212 | 213 |
| 09D01 | 3 | | Alpha | TRAV12-1*01 | TRAJ12*01 | Cα | 82 | 34 | 35 | 36 | 242 | 243 |
| | | | Beta | TRBV20-1*05 | TRBJ2-3*01 | Cβ2 | | 37 | 38 | 39 | 240 | 241 |
| 09H05 | 4 | | Alpha | TRAV12-1*01 | TRAJ12*01 | Cα | 82 | 40 | 41 | 42 | 238 | 239 |
| | | | Beta | TRBV20-1*05 | TRBJ2-5*01 | Cβ2 | | 43 | 44 | 45 | 236 | 237 |
| 09E01 | 5 | | Alpha | TRAV25*01 | TRAJ49*01 | Cα | 83 | 46 | 47 | 48 | 222 | 223 |
| | | | Beta | TRBV6-5*01 | TRBJ1-5*01 | Cβ1 | | 49 | 50 | 51 | 220 | 221 |
| 09B03 | 6 | | Alpha | TRAV16*01 | TRAJ23*01 | Cα | 82 | 52 | 53 | 54 | 210 | 211 |
| | | | Beta | TRBV30*01# | TRBJ2-2*01 | Cβ2 | | 55 | 56 | 57 | 208 | 209 |
| P09B08 | 1 | HPV18E7 | Alpha | TRAV12-3 | TRAJ38*01 | Cα | 85 | 58 | 59 | 60 | 234 | 235 |
| | | | Beta | TRBV19*01 | TRBJ2-1*01 | Cβ2 | | 61 | 62 | 63 | 232 | 233 |
| | 2 | | Alpha | TRAV16*01 | TRAJ43*01 | Cα | | 64 | 65 | 66 | | |
| | | | Beta | TRBV7-9*01 | TRBJ2-1*01 | Cβ2 | | 67 | 68 | 69 | | |
| 10F04 | 3 | | Alpha | TRAV12-3*01 | TRAJ41*01 | Cα | 85 | 70 | 71 | 72 | 226 | 227 |
| | | | Beta | TRBV19*01 | TRBJ1-4*01 | Cβ1 | | 73 | 74 | 75 | 224 | 225 |
| 09B12 | 4 | | Alpha | TRAV9-2*01 | TRAJ53*01 | Cα | 85 | 76 | 77 | 78 | 218 | 219 |
| | | | Beta | TRBV9*01 | TRBJ2-7*01 | Cβ2 | | 79 | 80 | 81 | 216 | 217 |
| 33A02 | 5 | | Alpha | TRAV8-3*02 | TRAJ54*01 | Cα | 84 | 87 | 88 | 89 | 246 | 247 |
| | | | Beta | TRBV20-1*01 | TRBJ2-1*01 | Cβ2 | | 90 | 91 | 92 | 244 | 245 |
| 33D05 | 6 | | Alpha | TRAV8-2*01 | TRAJ3*01 | Cα | 86 | 93 | 94 | 95 | 230 | 231 |
| | | | Beta | TRBV7-9*01 | TRBJ2-5*01 | Cβ2 | | 96 | 97 | 98 | 228 | 229 |

In some embodiments, there is provided an antigen recognizing construct (e.g., a TCR) specifically binds to an epitope of a CEA peptide comprising the amino acid sequence of SEQ ID NO: 1.

In some embodiments, there is provided an antigen recognizing construct (e.g., a TCR) specifically binds to an epitope of RGS5, such as human RGS5, for example, amino acids 1-30 or amino acids 16-30 of human RGS5. In some embodiments, there is provided an antigen recognizing construct (e.g., a TCR) specifically binds to an epitope of a RGS5 peptide comprising the amino acid sequence of SEQ ID NO: 2. In some embodiments, there is provided an antigen recognizing construct (e.g., a TCR) specifically binds to an epitope of RGS5 comprising the amino acid sequence of SEQ ID NO: 82. In some embodiments, there is provided an antigen recognizing construct (e.g., a TCR) specifically binds to an epitope of RGS5 comprising the amino acid sequence of SEQ ID NO: 83.

In some embodiments, there is provided an antigen recognizing construct (e.g., a TCR) specifically binds to an epitope of HPV18-E7, such as human HPV18-E7, for example, amino acids 80-94, 76-105, or 84-102 of human HPV18-E7. In some embodiments, there is provided an antigen recognizing construct (e.g., a TCR) specifically binds to an epitope of a HPV18-E7 peptide comprising the amino acid sequence of SEQ ID NO: 3. In some embodiments, there is provided an antigen recognizing construct (e.g., a TCR) specifically binds to an epitope of HPV18-E7 comprising the amino acid sequence of SEQ ID NO: 84. In some embodiments, there is provided an antigen recognizing construct (e.g., a TCR) specifically binds to an epitope of HPV18-E7 comprising the amino acid sequence of SEQ ID NO: 85. In some embodiments, there is provided an antigen recognizing construct (e.g., a TCR) specifically binds to an epitope of HPV18-E7 comprising the amino acid sequence of SEQ ID NO: 86.

Also provided are isolated tumor epitopes comprising any one of the amino acid sequences of SEQ ID NOs: 82-86.

In some embodiments, there is provided a tumor-specific antigen binding construct (e.g. tumor-specific TCR) comprising the amino acid sequence of any one of SEQ ID NOs: 4, 7, 10, 13, 16, 19, 22, 25, 28, 31, 34, 37, 40, 43, 46, 49, 52, 55, 58, 61, 64, 67, 70, 73, 76, 79, 87, 90, 93 and 96. In some embodiments, there is provided a tumor-specific antigen binding construct (e.g. tumor-specific TCR) comprising: (a) a first amino acid sequence having at least about 90% sequence identity (e.g., 100% identity) to any one of the amino acid sequences of SEQ ID NOs: 4, 10, and 16; and a second amino acid sequence having at least about 90% sequence identity (e.g., 100% identity) to any one of the amino acid sequences of SEQ ID NOs: 7, 13, and 19; (b) a first amino acid sequence having at least about 90% sequence identity (e.g., 100% identity) to any one of the amino acid sequences of SEQ ID NOs: 22, 28, 34, 40, 46, and 52; and a second amino acid sequence having at least about 90% sequence identity (e.g., 100% identity) to any one of the amino acid sequences of SEQ ID NOs: 7, 13, 19, 25, 31, 37, 43, 49, and 55; or (c) a first amino acid sequence having at least about 90% sequence identity (e.g., 100% identity) to any one of the amino acid sequences of SEQ ID NOs: 58, 64, 70, 76, 87, and 93; and a second amino acid sequence having at least about 90% sequence identity (e.g., 100% identity) to any one of the amino acid sequences of SEQ ID NOs: 61, 67, 73, 79, 90 and 96.

In some embodiments, there is provided a tumor-specific antigen binding construct (e.g. tumor-specific TCR) comprising: (a) a first amino acid sequence having at least about 90% sequence identity (e.g., 100% identity) to SEQ ID NO: 4, and a second amino acid sequence having at least about 90% sequence identity (e.g., 100% identity) to SEQ ID NO: 7; (b) a first amino acid sequence having at least about 90% sequence identity (e.g., 100% identity) to SEQ ID NO: 10, and a second amino acid sequence having at least about 90% sequence identity (e.g., 100% identity) to SEQ ID NO: 13; (c) a first amino acid sequence having at least about 90% sequence identity (e.g., 100% identity) to SEQ ID NO: 16, and a second amino acid sequence having at least about 90% sequence identity (e.g., 100% identity) to SEQ ID NO: 19; (d) a first amino acid sequence having at least about 90% sequence identity (e.g., 100% identity) to SEQ ID NO: 22, and a second amino acid sequence having at least about 90% sequence identity (e.g., 100% identity) to SEQ ID NO: 25; (e) a first amino acid sequence having at least about 90% sequence identity (e.g., 100% identity) to SEQ ID NO: 28, and a second amino acid sequence having at least about 90% sequence identity (e.g., 100% identity) to SEQ ID NO: 31; (f) a first amino acid sequence having at least about 90% sequence identity (e.g., 100% identity) to SEQ ID NO: 34, and a second amino acid sequence having at least about 90% sequence identity (e.g., 100% identity) to SEQ ID NO: 37; (g) a first amino acid sequence having at least about 90% sequence identity (e.g., 100% identity) to SEQ ID NO: 40, and a second amino acid sequence having at least about 90% sequence identity (e.g., 100% identity) to SEQ ID NO: 43; (h) a first amino acid sequence having at least about 90% sequence identity (e.g., 100% identity) to SEQ ID NO: 46, and a second amino acid sequence having at least about 90% sequence identity (e.g., 100% identity) to SEQ ID NO: 49; (i) a first amino acid sequence having at least about 90% sequence identity (e.g., 100% identity) to SEQ ID NO: 52, and a second amino acid sequence having at least about 90% sequence identity (e.g., 100% identity) to SEQ ID NO: 55; (j) a first amino acid sequence having at least about 90% sequence identity (e.g., 100% identity) to SEQ ID NO: 58, and a second amino acid sequence having at least about 90% sequence identity (e.g., 100% identity) to SEQ ID NO: 61; (k) a first amino acid sequence having at least about 90% sequence identity (e.g., 100% identity) to SEQ ID NO: 64, and a second amino acid sequence having at least about 90% sequence identity (e.g., 100% identity) to SEQ ID NO: 67; (l) a first amino acid sequence having at least about 90% sequence identity (e.g., 100% identity) to SEQ ID NO: 70, and a second amino acid sequence having at least about 90% sequence identity (e.g., 100% identity) to SEQ ID NO: 73; (m) a first amino acid sequence having at least about 90% sequence identity (e.g., 100% identity) to SEQ ID NO: 76, and a second amino acid sequence having at least about 90% sequence identity (e.g., 100% identity) to SEQ ID NO: 79; (n) a first amino acid sequence having at least about 90% sequence identity (e.g., 100% identity) to SEQ ID NO: 87, and a second amino acid sequence having at least about 90% sequence identity (e.g., 100% identity) to SEQ ID NO: 90; or (o) a first amino acid sequence having at least about 90% sequence identity (e.g., 100% identity) to SEQ ID NO: 93, and a second amino acid sequence having at least about 90% sequence identity (e.g., 100% identity) to SEQ ID NO: 96. In some embodiments, the antigen-binding construct of any one of (a)-(c) specifically binds to an epitope of a CEA peptide comprising the amino acid sequence of SEQ ID NO: 1. In some embodiments, the antigen-binding construct of any one of (d)-(i) specifically binds to an epitope of a RGS-5 peptide comprising the amino acid sequence of SEQ ID NO: 2. In some embodiments, the antigen-binding construct of any one of (e)-(g) and (i) specifically binds to a RGS-5 epitope comprising the amino acid sequence of SEQ ID NO: 82. In some embodiments, the antigen-binding construct of (h) specifically binds to a RGS-5 epitope comprising the amino acid sequence of SEQ ID NO: 83. In some embodiments, the antigen-binding construct of any one of (j)-(o) specifically binds an epitope of a HPV18-E7 peptide comprising the amino acid sequence of SEQ ID NO: 3. In some embodiments, the antigen-binding construct of (n) specifically binds to a HPV18-E7 epitope comprising the amino acid sequence of SEQ ID NO: 84. In some embodiments, the antigen-binding construct of any one of (j), (l) and (m) specifically binds to a HPV18-E7 epitope comprising the amino acid sequence of SEQ ID NO: 85. In some embodiments, the antigen-binding construct of (o) specifically binds to a HPV18-E7 epitope comprising the amino acid sequence of SEQ ID NO: 86.

In some embodiments, there is provided a tumor-specific antigen binding construct (e.g. tumor-specific TCR) comprising a CDR3 comprising the amino acid sequence of any one of SEQ ID NOs: 4, 7, 10, 13, 16, 19, 22, 25, 28, 31, 34, 37, 40, 43, 46, 49, 52, 55, 58, 61, 64, 67, 70, 73, 76, 79, 87, 90, 93 and 96. In some embodiments, there is provided a tumor-specific TCR, comprising: (a) a TCRα chain comprising a complementary determining region (CDR) 3 having at least about 90% sequence identity (e.g., 100% identity) to any one of the amino acid sequences of SEQ ID NOs: 4, 10, and 16; and a TCRβ chain comprising a CDR3 comprising an amino acid sequence having at least about 90% sequence identity (e.g., 100% identity) to any one of the amino acid sequences of SEQ ID NOs: 7, 13, and 19; (b) a TCRα chain comprising a complementary determining region (CDR) 3 comprising an amino acid sequence having at least about 90% sequence identity (e.g., 100% identity) to any one of the amino acid sequences of SEQ ID NOs: 22, 28, 34, 40, 46, and 52; and a TCRβ chain comprising a CDR3 comprising an amino acid sequence having at least about 90% sequence identity (e.g., 100% identity) to any one of the amino acid sequences of SEQ ID NOs: 7, 13, 19, 25, 31, 37, 43, 49, and 55; or (c) a TCRα chain comprising a complementary determining region (CDR) 3 comprising an amino acid sequence having at least about 90% sequence identity (e.g., 100% identity) to any one of the amino acid sequences of SEQ ID NOs: 58, 64, 70, 76, 87 and 93; and a TCRβ chain comprising a CDR3 comprising an amino acid sequence having at least about 90% sequence identity (e.g., 100% identity) to any one of the amino acid sequences of SEQ ID NOs: 61, 67, 73, 79, 90 and 96.

In some embodiments, there is provided a tumor-specific TCR, comprising: (a) a TCRα chain comprising a CDR3 an amino acid sequence having at least about 90% sequence identity (e.g., 100% identity) to SEQ ID NO: 4, and a TCRβ chain comprising a CDR3 comprising an amino acid sequence having at least about 90% sequence identity (e.g., 100% identity) to SEQ ID NO: 7; (b) a TCRα chain comprising a CDR3 comprising an amino acid sequence having at least about 90% sequence identity (e.g., 100% identity) to SEQ ID NO: 10, and a TCRβ chain comprising a CDR3 comprising an amino acid sequence having at least about 90% sequence identity (e.g., 100% identity) to SEQ ID NO: 13; (c) a TCRα chain comprising a CDR3 comprising an amino acid sequence having at least about 90% sequence identity (e.g., 100% identity) to SEQ ID NO: 16, and a TCRβ chain comprising a CDR3 comprising an amino acid sequence having at least about 90% sequence identity (e.g., 100% identity) to SEQ ID NO: 19; (d) a TCRα chain comprising a CDR3 comprising an amino acid sequence having at least about 90% sequence identity (e.g., 100% identity) to SEQ ID NO: 22, and a TCRβ chain comprising a CDR3 comprising an amino acid sequence having at least about 90% sequence identity (e.g., 100% identity) to SEQ ID NO: 25; (e) a TCRα chain comprising a CDR3 comprising an amino acid sequence having at least about 90% sequence identity (e.g., 100% identity) to SEQ ID NO: 28, and a TCRβ chain comprising a CDR3 comprising an amino acid sequence having at least about 90% sequence identity (e.g., 100% identity) to SEQ ID NO: 31; (f) a TCRα chain comprising a CDR3 comprising an amino acid sequence having at least about 90% sequence identity (e.g., 100% identity) to SEQ ID NO: 34, and a TCRβ chain comprising a CDR3 comprising an amino acid sequence having at least about 90% sequence identity (e.g., 100% identity) to SEQ ID NO: 37; (g) a TCRα chain comprising a CDR3 comprising an amino acid sequence having at least about 90% sequence identity (e.g., 100% identity) to SEQ ID NO: 40, and a TCRβ chain comprising a CDR3 comprising an amino acid sequence having at least about 90% sequence identity (e.g., 100% identity) to SEQ ID NO: 43; (h) a TCRα chain comprising a CDR3 comprising an amino acid sequence having at least about 90% sequence identity (e.g., 100% identity) to SEQ ID NO: 46, and a TCRβ chain comprising a CDR3 comprising an amino acid sequence having at least about 90% sequence identity (e.g., 100% identity) to SEQ ID NO: 49; (i) a TCRα chain comprising a CDR3 comprising an amino acid sequence having at least about 90% sequence identity (e.g., 100% identity) to SEQ ID NO: 52, and a TCRβ chain comprising a CDR3 comprising an amino acid sequence having at least about 90% sequence identity (e.g., 100% identity) to SEQ ID NO: 55; (j) a TCRα chain comprising a CDR3 comprising an amino acid sequence having at least about 90% sequence identity (e.g., 100% identity) to SEQ ID NO: 58, and a TCRβ chain comprising a CDR3 comprising an amino acid sequence having at least about 90% sequence identity (e.g., 100% identity) to SEQ ID NO: 61; (k) a TCRα chain comprising a CDR3 comprising an amino acid sequence having at least about 90% sequence identity (e.g., 100% identity) to SEQ ID NO: 64, and a TCRβ chain comprising a CDR3 comprising an amino acid sequence having at least about 90% sequence identity (e.g., 100% identity) to SEQ ID NO: 67; (l) a TCRα chain comprising a CDR3 comprising an amino acid sequence having at least about 90% sequence identity (e.g., 100% identity) to SEQ ID NO: 70, and a TCRβ chain comprising a CDR3 comprising an amino acid sequence having at least about 90% sequence identity (e.g., 100% identity) to SEQ ID NO: 73; (m) a TCRα chain comprising a CDR3 comprising an amino acid sequence having at least about 90% sequence identity (e.g., 100% identity) to SEQ ID NO: 76, and a TCRβ chain comprising a CDR3 comprising an amino acid sequence having at least about 90% sequence identity (e.g., 100% identity) to SEQ ID NO: 79; (n) a TCRα chain comprising a CDR3 comprising an amino acid sequence having at least about 90% sequence identity (e.g., 100% identity) to SEQ ID NO: 87, and a TCRβ chain comprising a CDR3 comprising an amino acid sequence having at least about 90% sequence identity (e.g., 100% identity) to SEQ ID NO: 90; or (o) a TCRα chain comprising a CDR3 comprising an amino acid sequence having at least about 90% sequence identity (e.g., 100% identity) to SEQ ID NO: 93, and a TCRβ chain comprising a CDR3 comprising an amino acid sequence having at least about 90% sequence identity (e.g., 100% identity) to SEQ ID NO: 96. In some embodiments, the tumor-specific TCR of any one of (a)-(c) specifically binds to an epitope of a CEA peptide comprising the amino acid sequence of SEQ ID NO: 1. In some embodiments, the tumor-specific TCR of any one of (d)-(i) specifically binds to an epitope of a RGS-5 peptide comprising the amino acid sequence of SEQ ID NO: 2. In some embodiments, the tumor-specific TCR of any one of (e)-(g) and (i) specifically binds to a RGS-5 epitope comprising the amino acid sequence of SEQ ID NO: 82. In some embodiments, the tumor-specific TCR of (h) specifically binds to a RGS-5 epitope comprising the amino acid sequence of SEQ ID NO: 83. In some embodiments, the tumor-specific TCR of any one of (j)-(o) specifically binds an epitope of a HPV18-E7 peptide comprising the amino acid sequence of SEQ ID NO: 3. In some embodiments, the tumor-specific TCR of (n) specifically binds to a HPV18-E7 epitope comprising the amino acid sequence of SEQ ID NO: 84. In some embodiments, the tumor-specific TCR of any one of (j), (l) and (m) specifically binds to a HPV18-E7 epitope comprising the amino acid sequence of SEQ ID NO: 85. In some embodiments, the tumor-specific TCR of (o) specifically binds to a HPV18-E7 epitope comprising the amino acid sequence of SEQ ID NO: 86.

Any of the tumor-specific TCRs described herein may comprise a V element and/or a J element. Any suitable V and J elements may be applicable, see, for example, the IMGT database. Table 1 shows exemplary combinations of the V element and J elements. In some embodiments, the tumor-specific TCR comprises: a TCRα chain comprising a TRAV element of any one of SEQ ID NOs: 5, 11, 17, 23, 29, 35, 41, 47, 53, 59, 65, 71, 77, 88, and 94, or a variant thereof; and a TCRβ chain comprising a TRBV element of any one of the amino acid sequences of SEQ ID NOs: 8, 14, 20, 26, 32, 38, 44, 56, 62, 68, 74, 80, 91 and 97 or a variant thereof. In some embodiments, the tumor-specific TCR comprises: a TCRα chain comprising a TRAJ element of any one of SEQ ID NOs: 5, 11, 17, 23, 29, 35, 41, 47, 53, 59, 65, 71, 77, 88, and 94, or a variant thereof; and a TCRβ chain comprising a TRBJ element of any one of the amino acid sequences of SEQ ID NOs: 8, 14, 20, 26, 32, 38, 44, 56, 62, 68, 74, 80, 91 and 97, or a variant thereof.

In some embodiments, there is provided a tumor-specific TCR, comprising: (a) a TCRα chain comprising CDRs of any one of the amino acid sequences of SEQ ID NOs: 5, 11 and 17, and a TCRβ chain comprising CDRs of any one of the amino acid sequences of SEQ ID NOs: 8, 14 and 20; (b) a TCRα chain comprising CDRs of any one of the amino acid sequences of SEQ ID NOs: 23, 29, 35, 41, 47 and 53, and a TCRβ chain comprising CDRs of any one of the amino acid sequences of SEQ ID NOs: 26, 32, 38, 44, 50 and 56; or (c) a TCRα chain comprising CDRs of any one of the amino acid sequences of SEQ ID NOs: 59, 65, 71, 77, 88 and 94, and a TCRβ chain comprising CDRs of any one of the amino acid sequences of SEQ ID NOs: 62, 68, 74, 80, 91 and 97.

The tumor-specific TCRs described herein also comprise TCR constant domains. In some embodiments, the tumor-specific TCR comprises: a TCRα chain comprising a TCRα constant domain (TRAC) of any one of SEQ ID NOs: 5, 11, 17, 23, 29, 35, 41, 47, 53, 59, 65, 71, 77, 88 and 94, or a variant thereof; and a TCRβ chain comprising a TCRβ constant domain (TRBC) of any one of the amino acid sequences of SEQ ID NOs: 8, 14, 20, 26, 32, 38, 44, 56, 62, 68, 74, 80, 91 and 97, or a variant thereof. In some embodiments, the tumor-specific TCR comprises a human TRAC and a human TRBC, such as human Cα and human Cβ1 or human Cα and human Cβ2. In some embodiments, the tumor-specific TCR comprises: a TCRα chain comprising a TRAC comprising the amino acid sequence of SEQ ID NO: 198, or a variant thereof; and a TCRβ chain comprising a TRBC comprising the amino acid sequence of SEQ ID NO: 202 or 204. In some embodiments, the tumor-specific TCR comprises a murine TRAC and a murine TRBC, such as murine Ca and murine Cβ1. In some embodiment, the murine TRAC comprises a modification at position 117 (e.g., S117L) and/or 110 (e.g., G110V). In some embodiments, the tumor-specific TCR comprises: a TCRα chain comprising a TRAC comprising the amino acid sequence of SEQ ID NO: 200, or a variant thereof; and a TCRβ chain comprising a TRBC comprising the amino acid sequence of SEQ ID NO: 206.

In some embodiments, the tumor-specific TCR is a human TCR. In some embodiments, the tumor-specific TCR is a chimeric TCR, such as a murinized TCR, e.g., a TCR comprising murine constant regions of TCRα and β chains. In some embodiments, the tumor-specific TCR comprises human TCR variable regions and TCR constant regions from a non-human species, such as mouse.

In some embodiments, there is provided a tumor-specific TCR, comprising: (a) a TCRα chain comprising an amino acid sequence having at least about 80% identity (e.g., at least about any one of 85%, 90%, 95%, 98% or higher identity, or having 100% identity) to any one of the amino acid sequences of SEQ ID NOs: 5, 11 and 17, and a TCRβ chain comprising an amino acid sequence having at least about 80% identity (e.g., at least about any one of 85%, 90%, 95%, 98% or higher identity, or having 100% identity) to any one of the amino acid sequences of SEQ ID NOs: 8, 14 and 20; (b) a TCRα chain comprising an amino acid sequence having at least about 80% identity (e.g., at least about any one of 85%, 90%, 95%, 98% or higher identity, or having 100% identity) to any one of the amino acid sequences of SEQ ID NOs: 23, 29, 35, 41, 47 and 53, and a TCRβ chain comprising an amino acid sequence having at least about 80% identity (e.g., at least about any one of 85%, 90%, 95%, 98% or higher identity, or having 100% identity) to any one of the amino acid sequences of SEQ ID NOs: 26, 32, 38, 44, 50 and 56; or (c) a TCRα chain comprising an amino acid sequence having at least about 80% identity (e.g., at least about any one of 85%, 90%, 95%, 98% or higher identity, or having 100% identity) to any one of the amino acid sequences of SEQ ID NOs: 59, 65, 71, 77, 88 and 94, and a TCRβ chain comprising an amino acid sequence having at least about 80% identity (e.g., at least about any one of 85%, 90%, 95%, 98% or higher identity, or having 100% identity) to any one of the amino acid sequences of SEQ ID NOs: 62, 68, 74, 80 and 91 and 97.

In some embodiments, there is provided a tumor-specific TCR, comprising: (a) a TCRα chain comprising an amino acid sequence having at least about 80% identity (e.g., at least about any one of 85%, 90%, 95%, 98% or higher identity, or having 100% identity) to SEQ ID NO: 5; a TCRβ chain comprising an amino acid sequence having at least about 80% identity (e.g., at least about any one of 85%, 90%, 95%, 98% or higher identity, or having 100% identity) to SEQ ID NO: 8; (b) a TCRα chain comprising an amino acid sequence having at least about 80% identity (e.g., at least about any one of 85%, 90%, 95%, 98% or higher identity, or having 100% identity) to SEQ ID NO: 11; a TCRβ chain comprising an amino acid sequence having at least about 80% identity (e.g., at least about any one of 85%, 90%, 95%, 98% or higher identity, or having 100% identity) to SEQ ID NO: 14; (c) a TCRα chain comprising an amino acid sequence having at least about 80% identity (e.g., at least about any one of 85%, 90%, 95%, 98% or higher identity, or having 100% identity) to SEQ ID NO: 17; a TCRβ chain comprising an amino acid sequence having at least about 80% identity (e.g., at least about any one of 85%, 90%, 95%, 98% or higher identity, or having 100% identity) to SEQ ID NO: 20; (d) a TCRα chain comprising an amino acid sequence having at least about 80% identity (e.g., at least about any one of 85%, 90%, 95%, 98% or higher identity, or having 100% identity) to SEQ ID NO: 23; a TCRβ chain comprising an amino acid sequence having at least about 80% identity (e.g., at least about any one of 85%, 90%, 95%, 98% or higher identity, or having 100% identity) to SEQ ID NO: 26; (e) a TCRα chain comprising an amino acid sequence having at least about 80% identity (e.g., at least about any one of 85%, 90%, 95%, 98% or higher identity, or having 100% identity) to SEQ ID NO: 29; a TCRβ chain comprising an amino acid sequence having at least about 80% identity (e.g., at least about any one of 85%, 90%, 95%, 98% or higher identity, or having 100% identity) to SEQ ID NO: 32; (f) a TCRα chain comprising an amino acid sequence having at least about 80% identity (e.g., at least about any one of 85%, 90%, 95%, 98% or higher identity, or having 100% identity) to SEQ ID NO: 35; a TCRβ chain comprising an amino acid sequence having at least about 80% identity (e.g., at least about any one of 85%, 90%, 95%, 98% or higher identity, or having 100% identity) to SEQ ID NO: 38; (g) a TCRα chain comprising an amino acid sequence having at least about 80% identity (e.g., at least about any one of 85%, 90%, 95%, 98% or higher identity, or having 100% identity) to SEQ ID NO: 41; a TCRβ chain comprising an amino acid sequence having at least about 80% identity (e.g., at least about any one of 85%, 90%, 95%, 98% or higher identity, or having 100% identity) to SEQ ID NO: 44; (h) a TCRα chain comprising an amino acid sequence having at least about 80% identity (e.g., at least about any one of 85%, 90%, 95%, 98% or higher identity, or having 100% identity) to SEQ ID NO: 47; a TCRβ chain comprising an amino acid sequence having at least about 80% identity (e.g., at least about any one of 85%, 90%, 95%, 98% or higher identity, or having 100% identity) to SEQ ID NO: 50; (i) a TCRα chain comprising an amino acid sequence having at least about 80% identity (e.g., at least about any one of 85%, 90%, 95%, 98% or higher identity, or having 100% identity) to SEQ ID NO: 53; a TCRβ chain comprising an amino acid sequence having at least about 80% identity (e.g., at least about any one of 85%, 90%, 95%, 98% or higher identity, or having 100% identity) to SEQ ID NO: 56; (j) a TCRα chain comprising an amino acid sequence having at least about 80% identity (e.g., at least about any one of 85%, 90%, 95%, 98% or higher identity, or having 100% identity) to SEQ ID NO: 59; a TCRβ chain comprising an amino acid sequence having at least about 80% identity (e.g., at least about any one of 85%, 90%, 95%, 98% or higher identity, or having 100% identity) to SEQ ID NO: 62; (k) a TCRα chain comprising an amino acid sequence having at least about 80% identity (e.g., at least about any one of 85%, 90%, 95%, 98% or higher identity, or having 100% identity) to SEQ ID NO: 65; a TCRβ chain comprising an amino acid sequence having at least about 80% identity (e.g., at least about any one of 85%, 90%, 95%, 98% or higher identity, or having 100% identity) to SEQ ID NO: 68; (l) a TCRα chain comprising an amino acid sequence having at least about 80% identity (e.g., at least about any one of 85%, 90%, 95%, 98% or higher identity, or having 100% identity) to SEQ ID NO: 71; a TCRβ chain comprising an amino acid sequence having at least about 80% identity (e.g., at least about any one of 85%, 90%, 95%, 98% or higher identity, or having 100% identity) to SEQ ID NO: 74; (m) a TCRα chain comprising an amino acid sequence having at least about 80% identity (e.g., at least about any one of 85%, 90%, 95%, 98% or higher identity, or having 100% identity) to SEQ ID NO: 77; a TCRβ chain comprising an amino acid sequence having at least about 80% identity (e.g., at least about any one of 85%, 90%, 95%, 98% or higher identity, or having 100% identity) to SEQ ID NO: 80; (n) a TCRα chain comprising an amino acid sequence having at least about 80% identity (e.g., at least about any one of 85%, 90%, 95%, 98% or higher identity, or having 100% identity) to SEQ ID NO: 88; a TCRβ chain comprising an amino acid sequence having at least about 80% identity (e.g., at least about any one of 85%, 90%, 95%, 98% or higher identity, or having 100% identity) to SEQ ID NO: 91; or (o) a TCRα chain comprising an amino acid sequence having at least about 80% identity (e.g., at least about any one of 85%, 90%, 95%, 98% or higher identity, or having 100% identity) to SEQ ID NO: 94; a TCRβ chain comprising an amino acid sequence having at least about 80% identity (e.g., at least about any one of 85%, 90%, 95%, 98% or higher identity, or having 100% identity) to SEQ ID NO: 97. In some embodiments, the tumor-specific TCR of any one of (a)-(c) specifically binds to an epitope of a CEA peptide comprising the amino acid sequence of SEQ ID NO: 1. In some embodiments, the tumor-specific TCR of any one of (d)-(i) specifically binds to an epitope of a RGS-5 peptide comprising the amino acid sequence of SEQ ID NO: 2. In some embodiments, the tumor-specific TCR of any one of (e)-(g) and (i) specifically binds to a RGS-5 epitope comprising the amino acid sequence of SEQ ID NO: 82. In some embodiments, the tumor-specific TCR of (h) specifically binds to a RGS-5 epitope comprising the amino acid sequence of SEQ ID NO: 83. In some embodiments, the tumor-specific TCR of any one of (j)-(o) specifically binds an epitope of a HPV18-E7 peptide comprising the amino acid sequence of SEQ ID NO: 3. In some embodiments, the tumor-specific TCR of (n) specifically binds to a HPV18-E7 epitope comprising the amino acid sequence of SEQ ID NO: 84. In some embodiments, the tumor-specific TCR of any one of (j), (l) and (m) specifically binds to a HPV18-E7 epitope comprising the amino acid sequence of SEQ ID NO: 85. In some embodiments, the tumor-specific TCR of (o) specifically binds to a HPV18-E7 epitope comprising the amino acid sequence of SEQ ID NO: 86.

In some embodiments, there is provided an antigen recognizing construct (e.g., a TCR) specifically binds to an MHC/RGS5 epitope complex, wherein the RGS5 epitope comprises the amino acid sequence of SEQ ID NO: 82, and wherein the MHC is HLA-DPA1*02:02/DPB1*05:01. In some embodiments, the antigen recognizing construct comprises a TCRα chain comprising a CDR3 comprising SEQ ID NO: 28, and a TCRβ chain comprising a CDR3 comprising SEQ ID NO: 31. In some embodiments, the antigen recognizing construct comprises a TCRα chain comprising a CDR1 comprising the amino acid sequence of SEQ ID NO: 254, a CDR2 comprising the amino acid sequence of SEQ ID NO: 255, and a CDR3 comprising the amino acid sequence of SEQ ID NO: 28; and a TCRβ chain comprising a CDR1 comprising the amino acid sequence of SEQ ID NO: 256, a CDR2 comprising the amino acid sequence of SEQ ID NO: 257, and a CDR3 comprising the amino acid sequence of SEQ ID NO: 31. In some embodiments, the antigen recognizing construct comprises a TCRα chain comprising CDR1, CDR2 and CDR3 of SEQ ID NO: 214; a TCRβ chain comprising CDR1, CDR2 and CDR3 of SEQ ID NO: 212. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 214; a TCRβ chain comprising an amino acid sequence having at least about 80% identity (e.g., at least about any one of 85%, 90%, 95%, 98% or higher identity, or having 100% identity) to SEQ ID NO: 212. In some embodiments, the antigen recognizing construct is a human TCR. In some embodiments, the antigen recognizing construct is a chimeric TCR, such as murinized TCR, e.g., a TCR comprising murine constant regions of TCRα and β chains. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 29; a TCRβ chain comprising an amino acid sequence having at least about 80% identity (e.g., at least about any one of 85%, 90%, 95%, 98% or higher identity, or having 100% identity) to SEQ ID NO: 32. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 103; a TCRβ chain comprising an amino acid sequence having at least about 80% identity (e.g., at least about any one of 85%, 90%, 95%, 98% or higher identity, or having 100% identity) to SEQ ID NO: 105. In some embodiments, the antigen recognizing construct comprises the amino acid sequence of SEQ ID NO: 147 or 149.

In some embodiments, there is provided an antigen recognizing construct (e.g., a TCR) specifically binds to an MHC/RGS5 epitope complex, wherein the RGS5 epitope comprises the amino acid sequence of SEQ ID NO: 82, and wherein the MHC is HLA-DRA/DRB1*09:01 or HLA-DRA/DRB4*01:03. In some embodiments, the antigen recognizing construct comprises a TCRα chain comprising a CDR3 comprising SEQ ID NO: 34, and a TCRβ chain comprising a CDR3 comprising SEQ ID NO: 37. In some embodiments, the antigen recognizing construct comprises a TCRα chain comprising a CDR1 comprising the amino acid sequence of SEQ ID NO: 258, a CDR2 comprising the amino acid sequence of SEQ ID NO: 259, and a CDR3 comprising the amino acid sequence of SEQ ID NO: 34; and a TCRβ chain comprising a CDR1 comprising the amino acid sequence of SEQ ID NO: 260, a CDR2 comprising the amino acid sequence of SEQ ID NO: 261, and a CDR3 comprising the amino acid sequence of SEQ ID NO: 37. In some embodiments, the antigen recognizing construct comprises a TCRα chain comprising CDR1, CDR2 and CDR3 of SEQ ID NO: 242; a TCRβ chain comprising CDR1, CDR2 and CDR3 of SEQ ID NO: 240. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 242; a TCRβ chain comprising an amino acid sequence having at least about 80% identity (e.g., at least about any one of 85%, 90%, 95%, 98% or higher identity, or having 100% identity) to SEQ ID NO: 240. In some embodiments, the antigen recognizing construct is a human TCR. In some embodiments, the antigen recognizing construct is a chimeric TCR, such as murinized TCR, e.g., a TCR comprising murine constant regions of TCRα and β chains. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 35; a TCRβ chain comprising an amino acid sequence having at least about 80% identity (e.g., at least about any one of 85%, 90%, 95%, 98% or higher identity, or having 100% identity) to SEQ ID NO: 38. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: $10^7$; a TCRβ chain comprising an amino acid sequence having at least about 80% identity (e.g., at least about any one of 85%, 90%, 95%, 98% or higher identity, or having 100% identity) to SEQ ID NO: $10^9$. In some embodiments, the antigen recognizing construct comprises the amino acid sequence of any one of SEQ ID NOs: 151, 153, 155 and 157.

In some embodiments, there is provided an antigen recognizing construct (e.g., a TCR) specifically binds to an MHC/RGS5 epitope complex, wherein the RGS5 epitope comprises the amino acid sequence of SEQ ID NO: 82, and wherein the MHC is HLA-DRA/DRB1*09:01 or HLA-DRA/DRB4*01:03. In some embodiments, the antigen recognizing construct comprises a TCRα chain comprising a CDR3 comprising SEQ ID NO: 40, and a TCRβ chain comprising a CDR3 comprising SEQ ID NO: 43. In some embodiments, the antigen recognizing construct comprises a TCRα chain comprising a CDR1 comprising the amino acid sequence of SEQ ID NO: 262, a CDR2 comprising the amino acid sequence of SEQ ID NO: 263, and a CDR3 comprising the amino acid sequence of SEQ ID NO: 40; and a TCRβ chain comprising a CDR1 comprising the amino acid sequence of SEQ ID NO: 264, a CDR2 comprising the amino acid sequence of SEQ ID NO: 265, and a CDR3 comprising the amino acid sequence of SEQ ID NO: 43. In some embodiments, the antigen recognizing construct comprises a TCRα chain comprising CDR1, CDR2 and CDR3 of SEQ ID NO: 238; a TCRβ chain comprising CDR1, CDR2 and CDR3 of SEQ ID NO: 236. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 238; a TCRβ chain comprising an amino acid sequence having at least about 80% identity (e.g., at least about any one of 85%, 90%, 95%, 98% or higher identity, or having 100% identity) to SEQ ID NO: 236. In some embodiments, the antigen recognizing construct is a human TCR. In some embodiments, the antigen recognizing construct is a chimeric TCR, such as murinized TCR, e.g., a TCR comprising murine constant regions of TCRα and β chains. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 41; a TCRβ chain comprising an amino acid sequence having at least about 80% identity (e.g., at least about any one of 85%, 90%, 95%, 98% or higher identity, or having 100% identity) to SEQ ID NO: 44. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 111; a TCRβ chain comprising an amino acid sequence having at least about 80% identity (e.g., at least about any one of 85%, 90%, 95%, 98% or higher identity, or having 100% identity) to SEQ ID NO: 113. In some embodiments, the antigen recognizing construct comprises the amino acid sequence of any one of SEQ ID NOs: 159, 161, 163 and 165.

In some embodiments, there is provided an antigen recognizing construct (e.g., a TCR) specifically binds to an MHC/RGS5 epitope complex, wherein the RGS5 epitope comprises the amino acid sequence of SEQ ID NO: 83, and wherein the MHC is HLA-DRA/DRB1*09:01 or HLA-DRA/DRB4*01:03. In some embodiments, the antigen recognizing construct comprises a TCRα chain comprising a CDR3 comprising SEQ ID NO: 46, and a TCRβ chain comprising a CDR3 comprising SEQ ID NO: 49. In some embodiments, the antigen recognizing construct comprises a TCRα chain comprising a CDR1 comprising the amino acid sequence of SEQ ID NO: 266, a CDR2 comprising the amino acid sequence of SEQ ID NO: 267, and a CDR3 comprising the amino acid sequence of SEQ ID NO: 46; and a TCRβ chain comprising a CDR1 comprising the amino acid sequence of SEQ ID NO: 268, a CDR2 comprising the amino acid sequence of SEQ ID NO: 269, and a CDR3 comprising the amino acid sequence of SEQ ID NO: 49. In some embodiments, the antigen recognizing construct comprises a TCRα chain comprising CDR1, CDR2 and CDR3 of SEQ ID NO: 222; a TCRβ chain comprising CDR1, CDR2 and CDR3 of SEQ ID NO: 220. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 222; a TCRβ chain comprising an amino acid sequence having at least about 80% identity (e.g., at least about any one of 85%, 90%, 95%, 98% or higher identity, or having 100% identity) to SEQ ID NO: 220. In some embodiments, the antigen recognizing construct is a human TCR. In some embodiments, the antigen recognizing construct is a murinized TCR, e.g., a TCR comprising murine constant regions of TCRα and β chains. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 47; a TCRβ chain comprising an amino acid sequence having at least about 80% identity (e.g., at least about any one of 85%, 90%, 95%, 98% or higher identity, or having 100% identity) to SEQ ID NO: 50. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 115; a TCRβ chain comprising an amino acid sequence having at least about 80% identity (e.g., at least about any one of 85%, 90%, 95%, 98% or higher identity, or having 100% identity) to SEQ ID NO: 117. In some embodiments, the antigen recognizing construct comprises the amino acid sequence of any one of SEQ ID NOs: 167 and 169.

In some embodiments, there is provided an antigen recognizing construct (e.g., a TCR) specifically binds to an MHC/RGS5 epitope complex, wherein the RGS5 epitope comprises the amino acid sequence of SEQ ID NO: 82, and wherein the MHC is HLA-DPA1*02:02/DPB1*05:01. In some embodiments, the antigen recognizing construct comprises a TCRα chain comprising a CDR3 comprising SEQ ID NO: 52, and a TCRβ chain comprising a CDR3 comprising SEQ ID NO: 55. In some embodiments, the antigen recognizing construct comprises a TCRα chain comprising a CDR1 comprising the amino acid sequence of SEQ ID NO: 270, a CDR2 comprising the amino acid sequence of SEQ ID NO: 271, and a CDR3 comprising the amino acid sequence of SEQ ID NO: 52; and a TCRβ chain comprising a CDR1 comprising the amino acid sequence of SEQ ID NO: 272, a CDR2 comprising the amino acid sequence of SEQ ID NO: 273, and a CDR3 comprising the amino acid sequence of SEQ ID NO: 55. In some embodiments, the antigen recognizing construct comprises a TCRα chain comprising CDR1, CDR2 and CDR3 of SEQ ID NO: 210; a TCRβ chain comprising CDR1, CDR2 and CDR3 of SEQ ID NO: 208. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 210; a TCRβ chain comprising an amino acid sequence having at least about 80% identity (e.g., at least about any one of 85%, 90%, 95%, 98% or higher identity, or having 100% identity) to SEQ ID NO: 208. In some embodiments, the antigen recognizing construct is a human TCR. In some embodiments, the antigen recognizing construct is a chimeric TCR, such as murinized TCR, e.g., a TCR comprising murine constant regions of TCRα and β chains. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 53; a TCRβ chain comprising an amino acid sequence having at least about 80% identity (e.g., at least about any one of 85%, 90%, 95%, 98% or higher identity, or having 100% identity) to SEQ ID NO: 56. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 119; a TCRβ chain comprising an amino acid sequence having at least about 80% identity (e.g., at least about any one of 85%, 90%, 95%, 98% or higher identity, or having 100% identity) to SEQ ID NO: 121. In some embodiments, the antigen recognizing construct comprises the amino acid sequence of any one of SEQ ID NOs: 143 and 145.

In some embodiments, there is provided an antigen recognizing construct (e.g., a TCR) specifically binds to an MHC/HPV18-E7 epitope complex, wherein the HPV18-E7 epitope comprises the amino acid sequence of SEQ ID NO: 85, and wherein the MHC is HLA-DRA/DRB1*09:01. In some embodiments, the antigen recognizing construct comprises a TCRα chain comprising a CDR3 comprising SEQ ID NO: 58, and a TCRβ chain comprising a CDR3 comprising SEQ ID NO: 61. In some embodiments, the antigen recognizing construct comprises a TCRα chain comprising a CDR1 comprising the amino acid sequence of SEQ ID NO: 274, a CDR2 comprising the amino acid sequence of SEQ ID NO: 275, and a CDR3 comprising the amino acid sequence of SEQ ID NO: 58; and a TCRβ chain comprising a CDR1 comprising the amino acid sequence of SEQ ID NO: 276, a CDR2 comprising the amino acid sequence of SEQ ID NO: 277, and a CDR3 comprising the amino acid sequence of SEQ ID NO: 61. In some embodiments, the antigen recognizing construct comprises a TCRα chain comprising CDR1, CDR2 and CDR3 of SEQ ID NO: 234; a TCRβ chain comprising CDR1, CDR2 and CDR3 of SEQ ID NO: 232. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 234; a TCRβ chain comprising an amino acid sequence having at least about 80% identity (e.g., at least about any one of 85%, 90%, 95%, 98% or higher identity, or having 100% identity)

to SEQ ID NO: 232. In some embodiments, the antigen recognizing construct is a human TCR. In some embodiments, the antigen recognizing construct is a chimeric TCR, such as a murinized TCR, e.g., a TCR comprising murine constant regions of TCRα and β chains. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 59; a TCRβ chain comprising an amino acid sequence having at least about 80% identity (e.g., at least about any one of 85%, 90%, 95%, 98% or higher identity, or having 100% identity) to SEQ ID NO: 62. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 123; a TCRβ chain comprising an amino acid sequence having at least about 80% identity (e.g., at least about any one of 85%, 90%, 95%, 98% or higher identity, or having 100% identity) to SEQ ID NO: 125. In some embodiments, the antigen recognizing construct comprises the amino acid sequence of any one of SEQ ID NOs: 179 and 181.

In some embodiments, there is provided an antigen recognizing construct (e.g., a TCR) specifically binds to an MHC/HPV18-E7 epitope complex, wherein the HPV18-E7 epitope comprises the amino acid sequence of SEQ ID NO: 85, and wherein the MHC is HLA-DRA/DRB1*09:01 or HLA-DRA/DRB4*01:03. In some embodiments, the antigen recognizing construct comprises a TCRα chain comprising a CDR3 comprising SEQ ID NO: 70, and a TCRβ chain comprising a CDR3 comprising SEQ ID NO: 73. In some embodiments, the antigen recognizing construct comprises a TCRα chain comprising a CDR1 comprising the amino acid sequence of SEQ ID NO: 278, a CDR2 comprising the amino acid sequence of SEQ ID NO: 279, and a CDR3 comprising the amino acid sequence of SEQ ID NO: 70; and a TCRβ chain comprising a CDR1 comprising the amino acid sequence of SEQ ID NO: 280, a CDR2 comprising the amino acid sequence of SEQ ID NO: 281, and a CDR3 comprising the amino acid sequence of SEQ ID NO: 73. In some embodiments, the antigen recognizing construct comprises a TCRα chain comprising CDR1, CDR2 and CDR3 of SEQ ID NO:226; a TCRβ chain comprising CDR1, CDR2 and CDR3 of SEQ ID NO: 224. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 226; a TCRβ chain comprising an amino acid sequence having at least about 80% identity (e.g., at least about any one of 85%, 90%, 95%, 98% or higher identity, or having 100% identity) to SEQ ID NO: 224. In some embodiments, the antigen recognizing construct is a human TCR. In some embodiments, the antigen recognizing construct is a chimeric TCR, such as a murinized TCR, e.g., a TCR comprising murine constant regions of TCRα and β chains. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 71; a TCRβ chain comprising an amino acid sequence having at least about 80% identity (e.g., at least about any one of 85%, 90%, 95%, 98% or higher identity, or having 100% identity) to SEQ ID NO: 74. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 127; a TCRβ chain comprising an amino acid sequence having at least about 80% identity (e.g., at least about any one of 85%, 90%, 95%, 98% or higher identity, or having 100% identity) to SEQ ID NO: 129. In some embodiments, the antigen recognizing construct comprises the amino acid sequence of any one of SEQ ID NOs: 183 and 185.

In some embodiments, there is provided an antigen recognizing construct (e.g., a TCR) specifically binds to an MHC/HPV18-E7 epitope complex, wherein the HPV18-E7 epitope comprises the amino acid sequence of SEQ ID NO: 85, and wherein the MHC is HLA-II. In some embodiments, the antigen recognizing construct comprises a TCRα chain comprising a CDR3 comprising SEQ ID NO: 76, and a TCRβ chain comprising a CDR3 comprising SEQ ID NO: 79. In some embodiments, the antigen recognizing construct comprises a TCRα chain comprising a CDR1 comprising the amino acid sequence of SEQ ID NO: 282, a CDR2 comprising the amino acid sequence of SEQ ID NO: 283, and a CDR3 comprising the amino acid sequence of SEQ ID NO: 76; and a TCRβ chain comprising a CDR1 comprising the amino acid sequence of SEQ ID NO: 284, a CDR2 comprising the amino acid sequence of SEQ ID NO: 285, and a CDR3 comprising the amino acid sequence of SEQ ID NO: 79. In some embodiments, the antigen recognizing construct comprises a TCRα chain comprising CDR1, CDR2 and CDR3 of SEQ ID NO: 218; a TCRβ chain comprising CDR1, CDR2 and CDR3 of SEQ ID NO: 216. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 218; a TCRβ chain comprising an amino acid sequence having at least about 80% identity (e.g., at least about any one of 85%, 90%, 95%, 98% or higher identity, or having 100% identity) to SEQ ID NO: 216. In some embodiments, the antigen recognizing construct is a human TCR. In some embodiments, the antigen recognizing construct is a chimeric TCR, such as a murinized TCR, e.g., a TCR comprising murine constant regions of TCRα and β chains. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 77; a TCRβ chain comprising an amino acid sequence having at least about 80% identity (e.g., at least about any one of 85%, 90%, 95%, 98% or higher identity, or having 100% identity) to SEQ ID NO: 80. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 131; a TCRβ chain comprising an amino acid sequence having at least about 80% identity (e.g., at least about any one of 85%, 90%, 95%, 98% or higher identity, or having 100% identity) to SEQ ID NO: 133. In some embodiments, the antigen recognizing construct comprises the amino acid sequence of any one of SEQ ID NOs: 187 and 189.

In some embodiments, there is provided an antigen recognizing construct (e.g., a TCR) specifically binds to an MHC/HPV18-E7 epitope complex, wherein the HPV18-E7 epitope comprises the amino acid sequence of SEQ ID NO: 84, and wherein the MHC is HLA-DRA/DRB1*09:01. In some embodiments, the antigen recognizing construct comprises a TCRα chain comprising a CDR3 comprising SEQ ID NO: 87, and a TCRβ chain comprising a CDR3 comprising SEQ ID NO: 90. In some embodiments, the antigen recognizing construct comprises a TCRα chain comprising a CDR1 comprising the amino acid sequence of SEQ ID NO: 286, a CDR2 comprising the amino acid sequence of SEQ ID NO: 287, and a CDR3 comprising the amino acid sequence of SEQ ID NO: 87; and a TCRβ chain comprising a CDR1 comprising the amino acid sequence of SEQ ID NO: 288, a CDR2 comprising the amino acid sequence of SEQ ID NO: 289, and a CDR3 comprising the amino acid sequence of SEQ ID NO: 90. In some embodiments, the antigen recognizing construct comprises a TCRα chain comprising CDR1, CDR2 and CDR3 of SEQ ID NO: 246; a TCRβ chain comprising CDR1, CDR2 and CDR3 of SEQ ID NO: 244. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 246; a TCRβ chain comprising an amino acid sequence having at least about 80% identity (e.g., at least about any one of 85%, 90%, 95%, 98% or higher identity, or having 100% identity) to SEQ ID NO: 244. In some embodiments, the antigen recognizing construct is a human TCR. In some embodiments, the antigen recognizing construct is a chimeric TCR, such as a murinized TCR, e.g., a TCR comprising murine constant regions of TCRα and β chains. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 88; a TCRβ chain comprising an amino acid sequence having at least about 80% identity (e.g., at least about any one of 85%, 90%, 95%, 98% or higher identity, or having 100% identity) to SEQ ID NO: 91. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 135; a TCRβ chain comprising an amino acid sequence having at least about 80% identity (e.g., at least about any one of 85%, 90%, 95%, 98% or higher identity, or having 100% identity) to SEQ ID NO: 137. In some embodiments, the antigen recognizing construct comprises the amino acid sequence of any one of SEQ ID NOs: 171, 173, 175 and 177.

In some embodiments, there is provided an antigen recognizing construct (e.g., a TCR) specifically binds to an MHC/HPV18-E7 epitope complex, wherein the HPV18-E7 epitope comprises the amino acid sequence of SEQ ID NO: 86, and wherein the MHC is HLA-DPA1*02:02/DPB1*05:01, HLA-DPA1*01:03/DPB1*02:01, or HLA-DPA1*01:03/DPB1*05:01. In some embodiments, the antigen recognizing construct comprises a TCRα chain comprising a CDR3 comprising SEQ ID NO: 93, and a TCRβ chain comprising a CDR3 comprising SEQ ID NO: 96. In some embodiments, the antigen recognizing construct comprises a TCRα chain comprising a CDR1 comprising the amino acid sequence of SEQ ID NO: 290, a CDR2 comprising the amino acid sequence of SEQ ID NO: 291, and a CDR3 comprising the amino acid sequence of SEQ ID NO: 93; and a TCRβ chain comprising a CDR1 comprising the amino acid sequence of SEQ ID NO: 292, a CDR2 comprising the amino acid sequence of SEQ ID NO: 293, and a CDR3 comprising the amino acid sequence of SEQ ID NO: 96. In some embodiments, the antigen recognizing construct comprises a TCRα chain comprising CDR1, CDR2 and CDR3 of SEQ ID NO: 230; a TCRβ chain comprising CDR1, CDR2 and CDR3 of SEQ ID NO: 228. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 230; a TCRβ chain comprising an amino acid sequence having at least about 80% identity (e.g., at least about any one of 85%, 90%, 95%, 98% or higher identity, or having 100% identity) to SEQ ID NO: 228. In some embodiments, the antigen recognizing construct is a human TCR. In some embodiments, the antigen recognizing construct is a chimeric TCR, such as a murinized TCR, e.g., a TCR comprising murine constant regions of TCRα and β chains. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 94; a TCRβ chain comprising an amino acid sequence having at least about 80% identity (e.g., at least about any one of 85%, 90%, 95%, 98% or higher identity, or having 100% identity) to SEQ ID NO: 97. In some embodiments, the antigen recognizing construct comprises a TCRα chain comprising an amino acid sequence having at least about 80% identity (e.g., at least about any one of 85%, 90%, 95%, 98% or higher identity, or having 100% identity) to SEQ ID NO: 139; a TCRβ chain comprising an amino acid sequence having at least about 80% identity (e.g., at least about any one of 85%, 90%, 95%, 98% or higher identity, or having 100% identity) to SEQ ID NO: 141. In some embodiments, the antigen recognizing construct comprises the amino acid sequence of any one of SEQ ID NOs: 191 and 193.

Naturally occurring TCRs are heterodimeric receptors composed of αβ or γδ chains that pair on the surface of a T cell. Each α, β, γ, and δ chain is composed of two Ig-like domains: a variable domain (V) that confers antigen recognition through the complementarity determining regions (CDR), followed by a constant domain (C) that is anchored to cell membrane by a connecting peptide and a transmembrane (TM) region. The TM region associates with the invariant subunits of the CD3 signaling apparatus. Each of the V domains has three CDRs. These CDRs interact with a complex between an antigenic peptide bound to a protein encoded by the major histocompatibility complex (pMHC) (Davis and Bjorkman (1988) Nature, 334, 395-402; Davis et al. (1998) Annu Rev Immunol, 16, 523-544; Murphy (2012), xix, 868 p.).

"Homology" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are "homologous" at that position. The "percent of homology" or "percent sequence identity" between two sequences is a function of the number of matching or homologous positions shared by the two sequences divided by the number of positions compared times 100, considering any conservative substitutions as part of the sequence identity. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5): 1792-1797, 2004; Edgar, R. C., *BMC Bioinformatics* 5(1): 113, 2004).

Also provided are epitopes, and MHC/epitope complexes that any one of the TCRs described herein recognizes. Further provided are TCRs that competitively bind to the same MHC/epitope complex as any one of the TCRs described herein.

HLA Restriction

The tumor-specific TCRs described herein are MHC class I or MHC class II restricted. In some embodiments, the tumor-specific TCR is restricted to a HLA haplotype. In some embodiments, the tumor-specific TCR has a HLA haplotype restriction that is predominant in Asians. FIGS. 25A-25B show HLA restrictions of exemplary TCRs.

MHC class I proteins are one of two primary classes of major histocompatibility complex (MHC) molecules (the other being MHC class II) and are found on nearly every nucleated cell of the body. Their function is to display fragments of proteins from within the cell to T cells; healthy cells will be ignored, while cells containing foreign or mutated proteins will be attacked by the immune system. Because MHC class I proteins present peptides derived from cytosolic proteins, the pathway of MHC class I presentation is often called the cytosolic or endogenous pathway. Class I MHC molecules bind peptides generated mainly from degradation of cytosolic proteins by the proteasome. The MHC I:peptide complex is then inserted into the plasma membrane of the cell. The peptide is bound to the extracellular part of the class I MHC molecule. Thus, the function of the class I MHC is to display intracellular proteins to cytotoxic T cells (CTLs). However, class I MHC can also present peptides generated from exogenous proteins, in a process known as cross-presentation.

MHC class I proteins consist of two polypeptide chains, α and β2-microglobulin (β2M). The two chains are linked noncovalently via interaction of β2M and the α3 domain. Only the α chain is polymorphic and encoded by a HLA gene, while the β2M subunit is not polymorphic and encoded by the β-2 microglobulin gene. The α3 domain is plasma membrane-spanning and interacts with the CD8 co-receptor of T-cells. The α3-CD8 interaction holds the MHC I molecule in place while the T cell receptor (TCR) on the surface of the cytotoxic T cell binds its α1-α2 heterodimer ligand, and checks the coupled peptide for antigenicity. The α1 and α2 domains fold to make up a groove for peptides to bind. MHC class I proteins bind peptides that are 8-10 amino acid in length.

MHC class II molecules are a family of molecules normally found only on antigen-presenting cells such as dendritic cells, mononuclear phagocytes, some endothelial cells, thymic epithelial cells, and B cells. The antigens presented by class II peptides are derived from extracellular proteins (not cytosolic as in class I); hence, the MHC class II-dependent pathway of antigen presentation is called the endocytic or exogenous pathway. Loading of an MHC class II molecule occurs by phagocytosis; extracellular proteins are endocytosed, digested in lysosomes, and the resulting epitopic peptide fragments are loaded onto MHC class II molecules prior to their migration to the cell surface.

Like MHC class I molecules, class II molecules are also heterodimers, but in this case consist of two homogenous peptides, an a and R chain. The subdesignation α1, α2, etc. refers to separate domains within the HLA gene; each domain is usually encoded by a different exon within the gene, and some genes have further domains that encode leader sequences, transmembrane sequences, etc. Because the antigen-binding groove of MHC class II molecules is open at both ends while the corresponding groove on class I molecules is closed at each end, the antigens presented by MHC class II molecules are longer, generally between 15 and 24 amino acid residues long.

The human leukocyte antigen (HLA) genes are the human versions of the MHC genes. The three major MHC class I proteins in humans are HLA-A, HLA-B, and HLA-C, while the 3 minor ones are HLA-E, HLA-F, and HLA-G. The three major MHC class II proteins involved in antigen presentation in humans are HLA-DP, HLDA-DQ, and HLA-DR, while the other MHC class II proteins, HLA-DM and HLA-DO, are involved in the internal processing and loading of antigens. HLA-A is ranked among the genes in humans with the fastest-evolving coding sequence. As of December 2013, there were 2432 known HLA-A alleles coding for 1740 active proteins and 117 null proteins. The HLA-A gene is located on the short arm of chromosome 6 and encodes the larger, α-chain, constituent of HLA-A. Variation of HLA-A α-chain is key to HLA function. This variation promotes genetic diversity in the population. Since each HLA has a different affinity for peptides of certain structures, greater variety of HLAs means greater variety of antigens to be 'presented' on the cell surface, enhancing the likelihood that a subset of the population will be resistant to any given foreign invader. This decreases the likelihood that a single pathogen has the capability to wipe out the entire human population. Each individual can express up to two types of HLA-A, one from each of their parents. Some individuals will inherit the same HLA-A from both parents, decreasing their individual HLA diversity; however, the majority of individuals will receive two different copies of HLA-A. This same pattern follows for all HLA groups. In other words, a person can only express either one or two of the 2432 known HLA-A alleles.

All alleles receive at least a four digit classification, e.g., HLA-A*02:12. The A signifies which HLA gene the allele belongs to. There are many HLA-A alleles, so that classification by serotype simplifies categorization. The next pair of digits indicates this assignment. For example, HLA-A*02:02, HLA-A*02:04, and HLA-A*02:324 are all members of the A2 serotype (designated by the *02 prefix). This group is the primary factor responsible for HLA compatibility. All numbers after this cannot be determined by serotyping and are designated through gene sequencing. The second set of digits indicates what HLA protein is produced. These are assigned in order of discovery and as of December 2013 there are 456 different HLA-A02 proteins known (assigned names HLA-A*02:01 to HLA-A*02:456). The shortest possible HLA name includes both of these details. Each extension beyond that signifies a nucleotide change that may or may not change the protein.

In some embodiments, the tumor-specific TCR specifically binds to a complex comprising the target tumor antigen peptide and an MHC class I protein, wherein the MHC class I protein is HLA-A, HLA-B, HLA-C, HLA-E, HLA-F, or HLA-G. In some embodiments, the MHC class I protein is HLA-A, HLA-B, or HLA-C. In some embodiments, the MHC class I protein is HLA-A. In some embodiments, the MHC class I protein is HLA-B. In some embodiments, the MHC class I protein is HLA-C. In some embodiments, the MHC class I protein is HLA-A01, HLA-A02, HLA-A03, HLA-A09, HLA-A10, HLA-A11, HLA-A19, HLA-A23, HLA-A24, HLA-A25, HLA-A26, HLA-A28, HLA-A29, HLA-A30, HLA-A31, HLA-A32, HLA-A33, HLA-A34, HLA-A36, HLA-A43, HLA-A66, HLA-A68, HLA-A69, HLA-A74, or HLA-A80. In some embodiments, the MHC class I protein is HLA-A02. In some embodiments, the MHC class I protein is any one of HLA-A*02:01-555, such as HLA-A*02:01, HLA-A*02:02, HLA-A*02:03, HLA-A*02:04, HLA-A*02:05, HLA-A*02:06, HLA-A*02:07, HLA-A*02:08, HLA-A*02:09, HLA-A*02:10, HLA-A*02:11, HLA-A*02:12, HLA-A*02:13, HLA-A*02:14, HLA-A*02:15, HLA-A*02:16, HLA-A*02:17, HLA-A*02:18, HLA-A*02:19, HLA-A*02:20, HLA-A*02:21, HLA-A*02:22, or HLA-A*02:24. In some embodiments, the MHC class I protein is HLA-A*02:01. HLA-A*02:01 is expressed in 39-46% of all Caucasians. Tumor-specific TCRs having HLA-A*02:01 restriction may be especially suitable for treating Caucasian patients. In some embodiments, the MHC class I protein is HLA-A*1101. HLA-A*1101 is expressed in about 25-30% of all Chinese. Tumor-specific TCRs having HLA-A*1101 restriction may be especially suitable for treating Chinese patients.

In some embodiments, the tumor-specific TCR specifically binds to a complex comprising the target tumor antigen peptide and an MHC class II protein, wherein the MHC class II protein is HLA-DP, HLA-DQ, or HLA-DR. In some embodiments, the MHC class II protein is HLA-DP. In some embodiments, the MHC class II protein is HLA-DQ. In some embodiments, the MHC class II protein is HLA-DR. In some embodiments, the MHC class II protein is HLA-DPB1*0401. HLA-DPB1*0401 is expressed in 35-40% of all Caucasians. Tumor-specific TCRs having HLA-DPB1*0401 restriction may be especially suitable for treating Caucasian patients.

Variants

In some embodiments, amino acid sequence variants of the tumor-specific antigen binding constructs (e.g., tumor-specific TCRs) provided herein are contemplated. For example, it may be desirable to improve the binding affinity and/or other biological properties of the tumor-specific antigen binding constructs (e.g., tumor-specific TCRs). Amino acid sequence variants of a tumor-specific TCR may be prepared by introducing appropriate modifications into the nucleotide sequence(s) encoding the TCRα or TCRβ chain of the tumor-specific TCR, or by peptide synthesis. Such modifications include, for example, deletions from, and/or insertions into and/or substitutions of residues within the amino acid sequences of the tumor-specific TCR. Any combination of deletion, insertion, and substitution can be made to arrive at the final construct, provided that the final construct possesses the desired characteristics, e.g., antigen-binding.

In some embodiments, tumor-specific antigen binding construct (e.g., tumor-specific TCR) variants having one or more amino acid substitutions are provided. Sites of interest for substitutional mutagenesis include the CDRs and FRs. Amino acid substitutions may be introduced into a tumor-specific TCR of interest and the products screened for a desired activity, e.g., retained/improved antigen binding or decreased immunogenicity.

Conservative substitutions are shown in Table 2 below.

TABLE 2

CONSERVATIVE SUBSTITITIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

a. hydrophobic: Norleucine, Met, Ala, Val, Leu, Ile;
b. neutral hydrophilic: Cys, Ser, Thr, Asn, Gln;
c. acidic: Asp, Glu;
d. basic: His, Lys, Arg;
e. residues that influence chain orientation: Gly, Pro;
f. aromatic: Trp, Tyr, Phe.

Non-conservative substitutions will entail exchanging a member of one of these classes for another class.

An exemplary substitutional variant is an affinity matured tumor-specific TCR, which may be conveniently generated, e.g., using phage display-based affinity maturation techniques. Briefly, one or more CDR residues are mutated and the variant tumor-specific TCR moieties displayed on phage and screened for a particular biological activity (e.g., binding affinity). Alterations (e.g., substitutions) may be made in CDRs, e.g., to improve tumor-specific TCR affinity.

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any tumor-specific TCR variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling.

In some embodiments, substitutions, insertions, or deletions may occur within one or more CDRs so long as such alterations do not substantially reduce the ability of the tumor-specific TCR to bind antigen. For example, conservative alterations (e.g., conservative substitutions as provided herein) that do not substantially reduce binding affinity may be made in CDRs. In some embodiments of the variant TCRα or TCRβ sequences provided above, each CDR either is unaltered, or contains no more than one, two or three amino acid substitutions.

Amino acid sequence insertions include amino- and/or carboxyl-terminal fusions ranging in length from one residue to polypeptides containing a hundred or more residues, as well as intrasequence insertions of single or multiple amino acid residues. In some embodiments, the tumor-specific TCR construct comprises a leader sequence at the N-terminus of the TCRα chain or the TCRβ chain. In some embodiments, the leader sequence comprises the amino acid sequence of SEQ ID NO: 101.

In some embodiments, there is provided a tumor specific TCR construct comprising a polypeptide comprising a TCRα chain polypeptide, a self-cleavable linker, and a TCRβ chain polypeptide. In some embodiments, the self-cleavable linker is a P2A peptide, a T2A peptide, a E2A peptide, or a F2A peptide. In some embodiments, the self-cleavable linker comprises any one of the amino acid sequences of SEQ ID NOs: 99, 195, 196 and 197.

Antigen binding fragments and derivatives of the tumor-specific TCRs described herein are also contemplated.

Nucleic Acids

In some embodiments, according to any of the tumor-specific TCRs described herein, there is provided a nucleic acid (or a set of nucleic acids) encoding the tumor-specific TCR. The present invention also provides vectors in which one or more nucleic acids of the present invention is incorporated.

In some embodiments, there is provided an isolated nucleic acid encoding the tumor-specific TCR or components or derivatives thereof (such as the TCRα chain, the TCRβ chain, the tumor-specific TCR, or the tumor-specific TCR construct). In some embodiments, there is provided an expression vector encoding the tumor-specific TCR or components or derivatives thereof (such as the TCRα chain, the TCRβ chain, the tumor-specific TCR, or the tumor-specific TCR construct). In some embodiments, there is provided an isolated host cell expressing the tumor-specific TCR or components or derivatives thereof (such as the TCRα chain, the TCRβ chain, the tumor-specific TCR, or the tumor-specific TCR construct).

Nucleic acid sequences encoding exemplary tumor-specific TCRs are shown in Table 1 and FIGS. 25A-25B. In some embodiments, there is provided an isolated nucleic acid encoding a TCRα comprising a nucleic acid sequence having at least about 80% identity (e.g., at least about any one of 85%, 90%, 95%, 98% or higher identity, or having 100% identity) to any one of the nucleic acid sequences of SEQ ID NOs: 6, 12, 18, 24, 30, 36, 42, 48, 54, 60, 66, 72, 78, 89, and 95. In some embodiments, there is provided an isolated nucleic acid encoding a TCRβ comprising a nucleic acid sequence having at least about 80% identity (e.g., at least about any one of 85%, 90%, 95%, 98% or higher identity, or having 100% identity) to any one of the nucleic acid sequences of SEQ ID NOs: 9, 15, 21, 27, 33, 39, 45, 51, 57, 63, 69, 75, 81, 92 and 98.

In some embodiments, there is provided one or more vectors comprising: (a) a TCRα chain-encoding nucleic acid comprising a nucleic acid sequence having at least about 80% identity (e.g., at least about any one of 85%, 90%, 95%, 98% or higher identity, or having 100% identity) to any one of the nucleic acid sequences of SEQ ID NOs: 6, 12 and 18, and a TCRβ chain-encoding nucleic acid comprising a nucleic acid sequence having at least about 80% identity (e.g., at least about any one of 85%, 90%, 95%, 98% or higher identity, or having 100% identity) to any one of the nucleic acid sequences of SEQ ID NOs: 9, 15 and 21; (b) a TCRα chain-encoding nucleic acid comprising a nucleic acid sequence having at least about 80% identity (e.g., at least about any one of 85%, 90%, 95%, 98% or higher identity, or having 100% identity) to any one of the nucleic acid sequences of SEQ ID NOs: 24, 30, 36, 42, 48 and 54, and a TCRβ chain-encoding nucleic acid comprising a nucleic acid sequence having at least about 80% identity (e.g., at least about any one of 85%, 90%, 95%, 98% or higher identity, or having 100% identity) to any one of the nucleic acid sequences of SEQ ID NOs: 27, 33, 39, 45, 51 and 57; or (c) a TCRα chain-encoding nucleic acid comprising a nucleic acid sequence having at least about 80% identity (e.g., at least about any one of 85%, 90%, 95%, 98% or higher identity, or having 100% identity) to any one of the nucleic acid sequences of SEQ ID NOs: 60, 66, 72, 78, 89 and 95, and a TCRβ chain-encoding nucleic acid comprising a nucleic acid sequence having at least about 80% identity (e.g., at least about any one of 85%, 90%, 95%, 98% or higher identity, or having 100% identity) to any one of the nucleic acid sequences of SEQ ID NOs: 63, 69, 75, 81, 92 and 98.

In some embodiments, there is provided one or more vectors comprising: (a) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 6; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 9; (b) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 12; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 15; (c) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 18; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 21; (d) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 24; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 27; (e) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 30; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 33; (f) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 36; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 39; (g) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 42; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 45; (h) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 48; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 51; (i) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 54; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 57; (j) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 60; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 63; (k) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 66; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 69; (l) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 72; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 75; (m) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 78; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 81; (n) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 89; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 92; or (o) a TCRα chain-encoding nucleic acid comprising a nucleic acid sequence having at least about 80% identity (e.g., at least about any one of 85%, 90%, 95%, 98% or higher identity, or having 100% identity) to SEQ ID NO: 95; a TCRβ chain-encoding nucleic acid comprising a nucleic acid sequence having at least about 80% identity (e.g., at least about any one of 85%, 90%, 95%, 98% or higher identity, or having 100% identity) to SEQ ID NO: 98.

In some embodiments, there is provided an isolated nucleic acid (such as a vector) comprising a tumor-specific TCR construct, wherein the nucleic acid comprises a nucleic acid sequence having at least about 80% identity (e.g., at least about any one of 85%, 90%, 95%, 98% or higher identity, or having 100% identity) to any one of the nucleic acid sequences selected from the group consisting of SEQ ID NOs: 144, 146, 148, 150, 154, 156, 158, 160, 162, 164, 166, 168, 170, 172, 174, 176, 178, 180, 182, 184, 186, 188, 190, 192 and 194.

In brief summary, the expression of an tumor-specific TCR by a nucleic acid encoding the tumor-specific TCR can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the invention provides a gene therapy vector.

The nucleic acid can be cloned into a number of types of vectors. For example, the nucleic acid can be cloned into a vector including, but not limited to, a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. (1993) Proc. Natl. Acad. Sci. USA 90:5603-5607), synthetic ligand-regulated elements (see, e.g., Spencer, D. M. et al 1993) Science 262: 1019-1024) and ionizing radiation-regulated elements (e.g., see Manome, Y. et al. (1993) Biochemistry 32: 10607-10613; Datta, R. et al. (1992) Proc. Natl. Acad. Sci. USA 89: 1014-10153). Further exemplary inducible promoter systems for use in in vitro or in vivo mammalian systems are reviewed in Gingrich et al. (1998) Annual Rev. Neurosci 21:377-405.

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, there is provided nucleic acid encoding a tumor-specific TCR according to any of the tumor-specific TCRs described herein. In some embodiments, the nucleic acid encoding the tumor-specific TCR comprises a first nucleic acid sequence encoding the TCRα chain of the tumor-specific TCR and a second nucleic acid sequence encoding the TCRβ chain of the tumor-specific TCR. In some embodiments, the first nucleic acid sequence is located on a first vector and the second nucleic acid sequence is located on a second vector. In some embodiments, the first and second nucleic acid sequences are located on the same vector. In some embodiments, the first nucleic acid sequence is fused to the second nucleic acid sequence via a third nucleic acid sequence encoding a self-cleavable linker, such as P2A, T2A, E2A, or F2A peptide. Vectors may be selected, for example, from the group consisting of mammalian expression vectors and viral vectors (such as those derived from retroviruses, adenoviruses, adeno-associated viruses, herpes viruses, and lentiviruses). In some embodiments, the first nucleic acid sequence is under the control of a first promoter and the second nucleic acid sequence is under the control of a second promoter. In some embodiments, the first and second promoters have the same sequence. In some embodiments, the first and second promoters have different sequences. In some embodiments, the first and second nucleic acid sequences are expressed as a single transcript under the control of a single promoter in a multicistronic (such as a bicistronic) vector. See for example Kim, J H, et al., *PLoS One* 6(4): e18556, 2011. In some embodiments, the first, second, and/or single promoters are inducible.

Engineered Immune Cells

In some embodiments, there is provided an engineered immune cell (such as a T cell) expressing a tumor-specific TCR according to any of the tumor-specific TCRs described herein. In some embodiments, the engineered immune cell comprises a nucleic acid encoding the tumor-specific TCR, wherein the tumor-specific TCR is expressed from the nucleic acid and localized to the surface of the engineered immune cell. In some embodiments, the engineered immune cell is a T cell. In some embodiments, the engineered immune cell is selected from the group consisting of a PBMC, a cytotoxic T cell, a helper T cell, a natural killer T cell, and a regulatory T cell. In some embodiments, the engineered immune cell does not express an endogenous TCR.

In some embodiments, there is provided an engineered T cell comprising a tumor-specific TCRs according to any of the tumor-specific TCRs or components or derivatives thereof (such as the TCRα chain, the TCRβ chain, the tumor-specific TCR, or the tumor-specific TCR construct). In some embodiments, the endogenous TCR of the engineered T cell is knocked out. In some embodiments, the engineered T cell is a TCR-T cell. In some embodiments, there is provided a pharmaceutical composition comprising the engineered T cell and a pharmaceutically acceptable excipient. In some embodiments, the engineered T cell is derived from the individual receiving the TCR-T treatment. In some embodiments, the engineered T cell is derived from an allogenic individual.

In some embodiments, the engineered immune cell (e.g., T cell) expresses a plurality (such as about any one of 2, 3, 4, 5, 10, or more) of tumor-specific TCRs obtained using any one of the methods described herein. In some embodiments, the engineered immune cell (e.g., T cell) expresses tumor-specific TCRs specifically recognizing a plurality of target tumor antigen peptides.

The engineered immune cells or pharmaceutical compositions thereof may be useful for treating the individual from whom the tumor-specific TCR is obtained (e.g., as a maintenance therapy), or for treating another individual, such as an allogenic individual, or an individual having the same MHC genotype, HLA haplotype and/or expressing the same epitope on the cancer cells.

Methods of Treatment Using Tumor-Specific TCRs

The present application provides cell-based immunotherapy methods of treating cancer in an individual, comprising administering to the individual an effective amount of an engineered immune cells (e.g., T cells) expressing any one of the tumor-specific TCRs described herein. In some embodiments, the method is used as a maintenance therapy for a previous MASCT received by the individual.

The methods described herein are suitable for treating various cancers, including liquid and solid cancers. In some embodiments, the cancer is selected from the group consisting of hepatocellular carcinoma, cervical cancer, lung cancer, colorectal cancer, lymphoma, renal carcinoma, breast cancer, pancreatic cancer, gastric cancer, esophageal cancer, ovarian cancer, prostate cancer, nasopharyngeal carcinoma, melanoma, endometrial cancer, and brain cancer. The methods are applicable to cancers of all stages, including early stage, advanced stage and metastatic cancer. For example, any one of the CEA-specific TCRs, the RGS5-specific TCRs and HPV18-E7 TCRs described herein may be useful for treating cervical cancer.

In some embodiments, the method reduces the severity of one or more symptoms associated with the cancer by at least about any of 10%, 20%, 30%, 40%, 50%, 60%, 70%, 80%, 90%, 95% or 100% compared to the corresponding symptom in the same individual prior to treatment or compared to the corresponding symptom in other individuals not receiving the treatment method. In some embodiments, the method delays progression of the cancer.

In some embodiments, the method is for treating hepatocellular carcinoma (HCC). In some embodiments, the HCC is early stage HCC, non-metastatic HCC, primary HCC, advanced HCC, locally advanced HCC, metastatic HCC, HCC in remission, or recurrent HCC. In some embodiments, the HCC is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve all lobes of the liver and/or has spread to involve other organs (e.g., lung, lymph nodes, bone). In some embodiments, the HCC is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the HCC is, according to AJCC (American Joint Commission on Cancer) staging criteria, stage T1, T2, T3, or T4 HCC. In some embodiments, the HCC is any one of liver cell carcinomas, fibrolamellar variants of HCC, and mixed hepatocellularcholangiocarcinomas. In some embodiments, the HCC is caused by Hepatitis B Virus (HBV) infection.

In some embodiments, the method is for treating lung cancer. In some embodiments, the lung cancer is a non-small cell lung cancer (NSCLC). Examples of NCSLC include, but are not limited to, large-cell carcinoma (e.g., large-cell neuroendocrine carcinoma, combined large-cell neuroendocrine carcinoma, basaloid carcinoma, lymphoepithelioma-like carcinoma, clear cell carcinoma, and large-cell carcinoma with rhabdoid phenotype), adenocarcinoma (e.g., acinar, papillary (e.g., bronchioloalveolar carcinoma, nonmucinous, mucinous, mixed mucinous and nonmucinous and indeterminate cell type), solid adenocarcinoma with mucin, adenocarcinoma with mixed subtypes, well-differentiated fetal adenocarcinoma, mucinous (colloid) adenocarcinoma, mucinous cystadenocarcinoma, signet ring adenocarcinoma, and clear cell adenocarcinoma), neuroendocrine lung tumors, and squamous cell carcinoma (e.g., papillary, clear cell, small cell, and basaloid). In some embodiments, the NSCLC may be, according to TNM classifications, a stage T tumor (primary tumor), a stage N tumor (regional lymph nodes), or a stage M tumor (distant metastasis).

In some embodiments, the lung cancer is a carcinoid (typical or atypical), adenosquamous carcinoma, cylindroma, or carcinoma of the salivary gland (e.g., adenoid cystic carcinoma or mucoepidermoid carcinoma). In some embodiments, the lung cancer is a carcinoma with pleomorphic, sarcomatoid, or sarcomatous elements (e.g., carcinomas with spindle and/or giant cells, spindle cell carcinoma, giant cell carcinoma, carcinosarcoma, or pulmonary blastoma). In some embodiments, the lung cancer is small cell lung cancer (SCLC; also called oat cell carcinoma). The small cell lung cancer may be limited-stage, extensive stage or recurrent small cell lung cancer. In some embodiments, the individual may be a human who has a gene, genetic mutation, or polymorphism suspected or shown to be associated with lung cancer (e.g., SASH1, LATS1, IGF2R, PARK2, KRAS, PTEN, Kras2, Krag, Pas1, ERCC1, XPD, IL8RA, EGFR, $\alpha_1$-AD, EPHX, MMP1, MMP2, MMP3, MMP12, IL1β, RAS, and/or AKT) or has one or more extra copies of a gene associated with lung cancer.

In some embodiments, the method is for treating cervical cancer. In some embodiments, the cervical cancer is early stage cervical cancer, non-metastatic cervical cancer, locally advanced cervical cancer, metastatic cervical cancer, cervical cancer in remission, unresectable cervical cancer, cervical cancer in an adjuvant setting, or cervical cancer in a neoadjuvant setting. In some embodiments, the cervical cancer is caused by human papillomavirus (HPV) infection. In some embodiments, the cervical cancer may be, according to TNM classifications, a stage T tumor (primary tumor), a stage N tumor (regional lymph nodes), or a stage M tumor (distant metastasis). In some embodiments, the cervical cancer is any of stage 0, stage I (Tis, N0, M0), stage IA (T1a, N0, M0), stage IB (T1b, N0, M0), stage IIA (T2a, N0, M0), stage IIB (T2b, N0, M0), stage IIIA (T3a, N0, M0), stage IIIB (T3b, N0, M0, or T1-3, N1, M0) stage IVA (T4, N0, M0), or stage IVB (T1-T3, N0-N1, M1) cervical cancer. In some embodiments, the cervical cancer is cervical squamous cell carcinoma, cervical adenonocarcinoma, or adenosquamous carcinoma.

In some embodiments, the method is for treating breast cancer. In some embodiments, the breast cancer is early stage breast cancer, non-metastatic breast cancer, locally advanced breast cancer, metastatic breast cancer, hormone receptor positive metastatic breast cancer, breast cancer in remission, breast cancer in an adjuvant setting, ductal carcinoma in situ (DCIS), invasive ductal carcinoma (IDC), or breast cancer in a neoadjuvant setting. In some embodiments, the breast cancer is hormone receptor positive metastatic breast cancer. In some embodiments, the breast cancer (which may be HER2 positive or HER2 negative) is advanced breast cancer. In some embodiments, the breast cancer is ductal carcinoma in situ. In some embodiments, the individual may be a human who has a gene, genetic mutation, or polymorphism associated with breast cancer (e.g., BRCA1, BRCA2, ATM, CHEK2, RAD51, AR, DIRAS3, ERBB2, TP53, AKT, PTEN, and/or PI3K) or has one or more extra copies of a gene (e.g., one or more extra copies of the HER2 gene) associated with breast cancer.

In some embodiments, the method is for treating pancreatic cancer. In some embodiments, the pancreatic cancer includes, but is not limited to, serous microcystic adenoma, intraductal papillary mucinous neoplasm, mucinous cystic neoplasm, solid pseudopapillary neoplasm, pancreatic adenocarcinoma, pancreatic ductal carcinoma, or pancreatoblastoma. In some embodiments, the pancreatic cancer is any of early stage pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, recurrent pancreatic cancer, pancreatic cancer in an adjuvant setting, or pancreatic cancer in a neoadjuvant setting.

In some embodiments, the method is for treating ovarian cancer. In some embodiments, the ovarian cancer is ovarian epithelial cancer. Exemplary ovarian epithelial cancer histological classifications include: serous cystomas (e.g., serous benign cystadenomas, serous cystadenomas with proliferating activity of the epithelial cells and nuclear abnormalities but with no infiltrative destructive growth, or serous cystadenocarcinomas), mucinous cystomas (e.g., mucinous benign cystadenomas, mucinous cystadenomas with proliferating activity of the epithelial cells and nuclear abnormalities but with no infiltrative destructive growth, or mucinous cystadenocarcinomas), endometrioid tumors (e.g., endometrioid benign cysts, endometrioid tumors with proliferating activity of the epithelial cells and nuclear abnormalities but with no infiltrative destructive growth, or endometrioid adenocarcinomas), clear cell (mesonephroid) tumors (e.g., benign clear cell tumors, clear cell tumors with proliferating activity of the epithelial cells and nuclear abnormalities but with no infiltrative destructive growth, or clear cell cystadenocarcinomas), unclassified tumors that cannot be allotted to one of the above groups, or other malignant tumors. In various embodiments, the ovarian epithelial cancer is stage I (e.g., stage IA, IB, or IC), stage II (e.g., stage IIA, IIB, or IIC), stage III (e.g., stage IIIA, IIIB, or IIIC), or stage IV. In some embodiments, the individual may be a human who has a gene, genetic mutation, or polymorphism associated with ovarian cancer (e.g., BRCA1 or BRCA2) or has one or more extra copies of a gene associated with ovarian cancer (e.g., one or more extra copies of the HER2 gene). In some embodiments, the ovarian cancer is an ovarian germ cell tumor. Exemplary histologic subtypes include dysgerminomas or other germ cell tumors (e.g., endodermal sinus tumors such as hepatoid or intestinal tumors, embryonal carcinomas, olyembryomas, choriocarcinomas, teratomas, or mixed form tumors). Exemplary teratomas are immature teratomas, mature teratomas, solid teratomas, and cystic teratomas (e.g., dermoid cysts such as mature cystic teratomas, and dermoid cysts with malignant transformation). Some teratomas are monodermal and highly specialized, such as struma ovarii, carcinoid, struma ovarii and carcinoid, or others (e.g., malignant neuroectodermal and ependymomas). In some embodiments, the ovarian germ cell tumor is stage I (e.g., stage IA, IB, or IC), stage II (e.g., stage IIA, IIB, or IIC), stage III (e.g., stage IIIA, IIIB, or IIIC), or stage IV.

Several viruses are related to cancer in humans. For example, Hepatitis B virus (HBV) can cause chronic infection of the liver, increasing an individual's chance of liver cancer, or hepatocellular carcinoma (HCC). Human papilloma viruses (HPVs) are a group of more than 150 related viruses, which cause papilloma, or warts, when they infect and grow in skin or mucous membranes, such as the mouth, throat, or vagina. Several types of HPV (including types 16, 18, 31, 33, 35, 39, 45, 51, 52, 56, 58, 59 and 6) are known to cause cervical cancer. HPVs also play a role in inducing or causing other cancers of the genitalia, and are linked to some cancers of the mouth and throat. Epstein-Barr virus (EBV) is a type of herpes virus, which chronically infects and remains latent in B lymphocytes. EBV infection increases an individual's risk of developing nasopharyngeal carcinoma and certain types of fast-growing lymphomas such as Burkitt lymphoma. EBV is also linked to Hodgkin lymphoma and some cases of gastric cancer. In addition to causing cancer or increasing risk of developing cancer, viral infections, such as infections with HBV, HPV, and EBV, may result in damage to tissues or organs, which can increase the disease burden of an individual suffering from a cancer, and contribute to cancer progression. It is known in the art that the human body can be induced to mount effective and specific immune response, including cytotoxic T cell response, against several cancer-related viruses, such as HBV, HPV and EBV, including their various subtypes. Therefore, in some embodiments, there is provided a method of treating a virus-related cancer in an individual, comprising administering to the individual an effective amount of an engineered immune cell (such as T cells) expressing any one of the tumor-specific TCRs described herein, wherein the target tumor antigen is derived from the virus. In some embodiments, the cancer is HBV-related hepatocellular carcinoma, HPV-related cervical cancer, or EBV-related nasopharyngeal carcinoma.

The methods of treatment described herein can be used for any one or more of the following purposes: alleviating one or more symptoms of cancer, delaying progression of cancer, shrinking cancer tumor size, disrupting (such as destroying) cancer stroma, inhibiting cancer tumor growth, prolonging overall survival, prolonging disease-free survival, prolonging time to cancer disease progression, preventing or delaying cancer tumor metastasis, reducing (such as eradiating) preexisting cancer tumor metastasis, reducing incidence or burden of preexisting cancer tumor metastasis, preventing recurrence of cancer, and/or improving clinical benefit of cancer.

In some embodiments, there is provided a method of inhibiting cancer cell proliferation (such as tumor growth) in an individual, comprising administering to the individual an effective amount of an engineered immune cells (e.g., T cells) expressing any one of the tumor-specific TCRs described herein. In some embodiments, the method further comprises administering to the individual an effective amount of an effective amount of antigen-loaded DCs. In some embodiments, at least about 10% (including for example at least about any of 20%, 30%, 40%, 60%, 70%, 80%, 90%, or 100%) cell proliferation is inhibited.

In some embodiments, there is provided a method of inhibiting tumor metastasis in an individual, comprising administering to the individual an effective amount of an engineered immune cells (e.g., T cells) expressing any one of the tumor-specific TCRs described herein. In some embodiments, the method further comprises administering to the individual an effective amount of an effective amount of antigen-loaded DCs. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided.

In some embodiments, there is provided a method of reducing tumor size in an individual, comprising administering to the individual an effective amount of an engineered immune cells (e.g., T cells) expressing any one of the tumor-specific TCRs described herein. In some embodiments, the method further comprises administering to the individual an effective amount of an effective amount of antigen-loaded DCs. In some embodiments, the tumor size is reduced at least about 10% (including for example at least about any of 20%, 30%, 40%, 60%, 70%, 80%, 90%, or 100%).

In some embodiments, there is provided a method of prolonging progression-free survival of cancer in an individual, comprising administering to the individual an effective amount of an engineered immune cells (e.g., T cells) expressing any one of the tumor-specific TCRs described herein. In some embodiments, the method further comprises administering to the individual an effective amount of an effective amount of antigen-loaded DCs. In some embodiments, the method prolongs the time to disease progression by at least any of 1, 2, 3, 4, 5, 6, 7, 8, 9, 10, 11, or 12 weeks.

In some embodiments, there is provided a method of prolonging survival of an individual having cancer, comprising administering to the individual an effective amount of an engineered immune cells (e.g., T cells) expressing any one of the tumor-specific TCRs described herein. In some embodiments, the method further comprises administering to the individual an effective amount of an effective amount of antigen-loaded DCs. In some embodiments, the method prolongs the time to disease progression by at least about any one of 1, 2, 3, 4, 5, 6, 7, 8, 9, 10, 11, or 12 weeks. In some embodiments, the method prolongs the survival of the individual by at least about any one of 1, 2, 3, 4, 5, 6, 7, 8, 9, 10, 11, 12, 18, or 24 months.

In some embodiments, there is provided a method of reducing adverse effects (AEs) and severe adverse effects (SAEs) in an individual having cancer, comprising administering to the individual an effective amount of an engineered immune cells (e.g., T cells) expressing any one of the tumor-specific TCRs described herein. In some embodiments, the method further comprises administering to the individual an effective amount of antigen-loaded DCs.

In some embodiments, the method is predictive of and/or results in an objective response (such as a partial response or complete response). In some embodiments, the method is predictive of and/or results in improved quality of life.

Some cancer immunotherapies are associated with immune-related adverse events (irAEs) in additional to common adverse events generally associated with other cancer therapies. IrAEs are usually mechanistically related to either on-target T-cell toxicity against target antigens that are expressed in normal, non-tumor tissue, so called on-target off-tumor effect, or off-target effects such as breaking of self-tolerance or epitope cross-reaction. IrAEs can lead to severe symptoms and conditions on the dermatologic, gastrointestinal, endocrine, hepatic, ocular, neurologic, and other tissues or organs. Typical irAEs reported for cancer immunotherapy methods known in the art include fatal immune-mediated dermatitis, pneumonia, colitis, lymphocytic hypophysitis, pancreatitis, lymphadenopathy, endocrine disorders, CNS toxicity, and the like. In some embodiments, the treatment method is associated with low incidence of adverse events, such as irAEs. In some embodiments, less than about any one of 50%, 40%, 30%, 20%, 10%, 5%, 4%, 3%, 2%, or 1% of individuals experience irAEs, such as irAEs of Grade 2-5.

Generally, dosages, schedules, and routes of administration of the engineered immune cell (such as T cells) expressing any one of the tumor-specific TCRs described herein may be determined according to the size and condition of the individual, and according to standard pharmaceutical practice. Exemplary routes of administration include intravenous, intra-arterial, intraperitoneal, intrapulmonary, intravesicular, intramuscular, intra-tracheal, subcutaneous, intraocular, intrathecal, or transdermal. In some embodiments, the engineered immune cell (such as T cells) expressing the tumor-specific TCR is administered intravenously.

The dose of the cells administered to an individual may vary according to, for example, the particular type of cells being administered, the route of administration, and the particular type and stage of cancer being treated. The amount should be sufficient to produce a desirable response, such as a therapeutic response against cancer, but without severe toxicity or adverse events. In some embodiments, the amount of the engineered immune cell (such as T cells) expressing the tumor-specific TCR to be administered is a therapeutically effective amount. In some embodiments, the amount of the cells is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same individual prior to treatment or compared to the corresponding activity in other individuals not receiving the treatment. Standard methods can be used to measure the magnitude of this effect, such as in vitro assays with purified enzyme, cell-based assays, animal models, or human testing.

In some embodiments, a stabilizing agent or an excipient, such as human albumin, is used together with the engineered immune cell expressing the tumor-specific TCR(s).

The treatment method may comprise a single treatment, or repeated treatments. In some embodiments, the engineered immune cell expressing the tumor-specific TCR is administered for at least about any one of 1, 2, 3, 4, 5, 6, 7, 8, 9, 10, or more than 10 times. In some embodiments, the engineered immune cell expressing the tumor-specific TCR is administered at least 3 times. In some embodiments, the treatment method is repeated once per week, once 2 weeks, once 3 weeks, once 4 weeks, once per month, once per 2 months, once per 3 months, once per 4 months, once per 5 months, once per 6 months, once per 7 months, once per 8 months, once per 9 months, or once per year.

The treatment method provided herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radio-frequency ablation or the like, in an adjuvant setting or a neoadjuvant setting. In some embodiments, the treatment method is used as a first therapy. In some embodiments, there exists no other approved anti-cancer therapy for the individual. In some embodiments, the treatment method is used as a second therapy, wherein the individual has previously received resection, radio-frequency ablation, chemotherapy, radiation therapy, or other types of cancer therapy. In some embodiments, the individual has progressed or has not been able to tolerate standard anti-cancer therapy. In some embodiments, the individual receives other types of cancer therapy prior to, concurrently with, or after receiving the treatment method described herein. For example, the treatment method described herein may precede or follow the other cancer therapy (such as chemotherapy, radiation, surgery or combination thereof) by intervals ranging from minutes, days, weeks to months. In some embodiments, the interval between the first and the second therapy is such that the engineered immune cell (e.g., T cell) expressing the tumor-specific TCR is and the other cancer therapy (such as chemotherapy, radiation, surgery, or combination thereof) would be able to exert an advantageously combined effect on the individual. Additionally, a person having a greater risk of developing a proliferative disease may receive treatments to inhibit and/or delay the development of the disease.

V. Compositions, Kits and Articles of Manufacture

The present application further provides kits, compositions (such as pharmaceutical compositions), and articles of manufacture for use in any embodiment of the methods of obtaining a plurality of TCRs recognizing a target tumor antigen peptide and methods of treatment described herein.

In some embodiments, there is provided a kit useful for cancer immunotherapy, comprising at least 10 tumor antigen peptides. A person skilled in the art may use any combinations of tumor antigen peptides from the first core group and optionally any combinations of cancer-type specific antigen peptides from the second group, and/or neoantigen peptides to load a population of DCs, which can further be used to prepare activated T cells for MASCT, tumor antigen-specific T cells or isolating tumor-specific TCRs for treating cancer in an individual.

In some embodiments, there is provided a kit comprising any one of the tumor-specific TCRs described herein, or nucleic acid(s) or vector encoding the tumor-specific TCR thereof. In some embodiments, there is provided a kit comprising a library of tumor-specific TCRs obtained using any one of the methods described herein with T cells or PBMCs from a plurality of individuals that have clinically benefitted from MASCT, nucleic acids encoding the tumor-specific TCRs thereof, or vectors encoding the tumor-specific TCRs thereof. In some embodiments, the tumor-specific TCRs specifically recognize one or more tumor antigens selected from the group consisting of hTERT, p53, Survivin, NY-ESO-1, CEA, CCND1, RGS5, MMP7, VEGFR1, VEGFR2, MUC1, HER2, MAGE-A1, MAGE-A3, CDCA1, WT1, KRAS, PARP4, MLL3, MTHFR, HPV16-E6, HPV16-E7, HPV18-E6, HPV18-E7, HPV58-E6, HPV58-E7, HBcAg, HBV polymerase, GPC3, SSX, and AFP. In some embodiments, the tumor-specific TCRs have HLA haplotype restriction that is predominant in certain racial groups.

The kit may contain additional components, such as containers, reagents, culturing media, cytokines, immune checkpoint inhibitors, TLR agonists, buffers, antibodies, and the like to facilitate execution of any embodiment of the treatment methods or cell preparation methods described herein. For example, in some embodiments, the kit further comprises a peripheral blood collection and storage apparatus, which can be used to collect an individual's peripheral blood. In some embodiments, the kit further comprises containers and reagents for density gradient centrifugation of peripheral blood, which can be used to isolate PBMCs from a sample of human peripheral blood. In some embodiments, the kit further comprises culturing media, cytokines, or buffers for obtaining DCs from peripheral blood. In some embodiments, the kit further comprises culturing media, TLR agonists (e.g., MPLA), IFNγ, PGE2, reagents and buffers for loading the plurality of tumor antigen peptides into DCs. In some embodiments, the kit further comprises cytokines (e.g., IL-2, IL-7, IL-15 and IL-21), immune checkpoint inhibitors (e.g., anti-PD1 antibody), anti-CD3 antibody (e.g., OKT-3), buffers, or culturing media for co-culturing T cells, enriched activated T cells, or tumor antigen-specific T cells with antigen-loaded APCs (e.g., DCs). In some embodiments, the kit further comprises cell line APCs, such as LCL cells. In some embodiments, the kit further comprises antibodies, magnetic beads, and columns for enriching activated T cells expressing a cytokine (e.g., IFNγ). In some embodiments, the kit further comprises containers, buffers, and reagents for freezing and storing PBMCs or T cells. In some embodiments, the kit further comprises reagents for determining the mutation load (such as in one or more MHC genes) in cancer cells. In some embodiments, the kit further comprises an immune checkpoint inhibitor for combination therapy with the treatment method. In some embodiments, the kit further comprises reagents for identifying a neoantigen (such as by sequencing) in a tumor sample. In some embodiments, the kit further comprises an ELISPOT assay for assessing specific immune response against one or more tumor antigen peptides. In some embodiments, the kit further comprises primers and reagents for amplifying TCR genes, and/or next-generation sequencing of TCR genes. In some embodiments, the kit further comprises immune cells, culturing medium and reagents for preparing engineered immune cells expressing the tumor-specific TCR(s).

The kits of the present application are in suitable packaging. Suitable packaging include, but is not limited to, vials, bottles, jars, flexible packaging (e.g., Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions may also comprise instructions relating to the use of the tumor antigen peptides (and optionally additional components described above). In some embodiments, the kit further comprises an instructional manual, such as a manual describing a protocol of an embodiment of the treatment methods, or an embodiment of the cell preparation methods as described herein. The instructions may also include information on dosage, dosing schedule, and routes of administration of the DCs, the activated T cells, or engineered immune cells expressing the tumor-specific TCR(s) prepared using the kit for the intended treatment. In some embodiments, the kit further comprises instructions for selecting an individual for the treatment method. In some embodiments, the kit further comprises instructions for administering an immune checkpoint inhibitor in combination with the treatment method, including, for example, information on dosage, dosing schedule, and route of administration of the immune checkpoint inhibitor. In some embodiments, the kit further comprises instructions for identifying a neoantigen (such as by sequencing) in a tumor sample. In some embodiments, the kit further comprises instructions for monitoring an individual after receiving the treatment.

The containers may be unit doses, bulk packages (e.g., multi-dose packages) or subunit doses. For example, kits may be provided that contain sufficient tumor antigen peptides as disclosed herein to prepare sufficient tumor antigen-specific T cells, antigen-loaded APCs (such as DCs), and/or engineered immune cells expressing the tumor-specific TCR(s) to provide effective treatment of an individual for an extended period, such as any of 3 weeks, 6 weeks, 9 weeks, 3 months, 4 months, 5 months, 6 months, 8 months, 9 months, 1 year or more.

Kits may also include multiple unit doses of tumor antigen peptides or tumor-specific TCRs (or nucleic acids encoding tumor-specific TCRs) and instructions for use and packaged in quantities sufficient for storage and use in pharmacies, for example, hospital pharmacies and compounding pharmacies.

Further provided are kits, compositions (such as pharmaceutical compositions), and articles of manufacture of any one of the isolated population of cells (such as DCs, activated T cells, or engineered immune cells expressing tumor-specific TCRs) described herein.

The isolated population of cells (such as DCs, activated T cells, or engineered immune cells expressing tumor-specific TCRs) described herein may be used in pharmaceutical compositions or formulations, by combining the isolated population of cells described with a pharmaceutically acceptable carrier, excipients, stabilizing agents and/or other agents, which are known in the art, for use in the methods of treatment, methods of administration, and dosage regimens described herein. In some embodiments, human albumin is used as a pharmaceutically acceptable carrier.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. The final form may be sterile and may also be able to pass readily through an injection device such as a hollow needle. The proper viscosity may be achieved and maintained by the proper choice of solvents or excipients.

The pharmaceutical compositions described herein may include other agents, excipients, or stabilizers to improve properties of the composition. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. In some embodiments, the pharmaceutical composition is formulated to have a pH in the range of about 4.5 to about 9.0, including for example pH ranges of about any one of 5.0 to about 8.0, about 6.5 to about 7.5, or about 6.5 to about 7.0. In some embodiments, the pharmaceutical composition can also be made to be isotonic with blood by the addition of a suitable tonicity modifier, such as glycerol.

In some embodiments, the isolated cell composition (such as DCs, activated T cells, or engineered immune cells expressing tumor-specific TCRs) is suitable for administration to a human. In some embodiments, the compositions (such as pharmaceutical compositions) is suitable for administration to a human by parenteral administration. Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as ampules and vials, and can be stored in a condition requiring only the addition of the sterile liquid excipient methods of treatment, methods of administration, and dosage regimens described herein (i.e., water) for injection, immediately prior to use. In some embodiments, the compositions (such as pharmaceutical compositions) is contained in a single-use vial, such as a single-use sealed vial. In some embodiments, the composition (such as pharmaceutical composition) is contained in a multi-use vial. In some embodiments, the composition (such as pharmaceutical composition) is contained in bulk in a container.

Also provided are unit dosage forms comprising the isolated cell compositions (such as pharmaceutical compositions) and formulations described herein. These unit dosage forms can be stored in a suitable packaging in single or multiple unit dosages and may also be further sterilized and sealed. In some embodiments, the composition (such as pharmaceutical composition) also includes one or more other compounds (or pharmaceutically acceptable salts thereof) that are useful for treating cancer.

The present application further provides kits comprising any of the isolated population of cells, compositions (such as pharmaceutical compositions), formulations, unit dosages, and articles of manufacture described herein for use in the methods of treatment, methods of administration, and dosage regimens described herein.

VI. Exemplary Embodiments

Among the embodiments provided herein are:

1. A method of obtaining a plurality of T cell receptors (TCRs) specifically recognizing a target tumor antigen peptide, comprising:
   a) a first co-culturing step comprising co-culturing a first population of dendritic cells (DCs) loaded with the target tumor antigen peptide with a population of T cells from an individual to obtain a first co-culture;
   b) an enrichment step comprising subjecting the first co-culture to an enrichment process to obtain enriched activated T cells;
   c) a second co-culturing step comprising co-culturing the enriched activated T cells with a second population of DCs loaded with the target tumor antigen peptide to obtain a population of tumor antigen-specific T cells, wherein at least about 10% of the tumor antigen-specific T cells specifically responds to the target tumor antigen peptide; and
   d) a sequencing step, comprising subjecting the tumor antigen-specific T cells to next-generation sequencing to identify a plurality of pairs of genes encoding TCRα and TCRβ, thereby providing the plurality of T cell receptors based on paired genes encoding TCRα and TCRβ;
   wherein the individual has clinically benefitted from a Multiple Antigen Specific Cell Therapy (MASCT) comprising administering to the individual an effective amount of activated T cells prepared by co-culturing a population of T cells with a population of dendritic cells loaded with a plurality of tumor antigen peptides comprising the target tumor antigen peptide.
2. The method of embodiment 1, wherein the first co-culturing step is carried out for about 1 to about 3 days prior to the enrichment step.
3. The method of embodiment 1 or 2, wherein the ratio between the population of T cells to the first population of DCs loaded with the target tumor antigen peptide is no more than about 30:1.
4. The method of any one of embodiments 1-3, wherein the population of T cells in the first co-culturing step is present in PBMCs.
5. The method of any one of embodiments 1-4, wherein the first population of DCs loaded with the target tumor antigen peptide and the population of T cells are co-cultured in a first co-culture medium comprising one or more cytokines (e.g., IL-2 or a plurality of cytokines) and an immune checkpoint inhibitor.
6. The method of embodiment 5, wherein the first co-culture medium comprises IL-2, IL-7, IL-15 and IL-21 and an anti-PD-1 antibody.
7. The method of embodiment 5, wherein the first co-culture medium comprises IL-2 and an anti-PD-1 antibody.
8. The method of any one of embodiments 1-7, wherein the enrichment step comprises contacting the first co-culture with antigen presenting cells (APCs) loaded with the target tumor antigen peptide to obtain a stimulated co-culture, and isolating from the stimulated co-culture an enriched population of activated T cells using a ligand that specifically recognizes a cytokine.
9. The method of embodiment 8, wherein the cytokine is IFNγ.
10. The method of any one of embodiments 1-9, wherein the ratio between the enriched population of activated T cells and the second population of DCs loaded with the target tumor antigen peptide is about 1:1 to about 20:1.
11. The method of any one of embodiments 1-10, wherein the enriched population of activated T cells and the second population of DCs loaded with the target tumor antigen peptide are co-cultured for about 12 to 25 days.
12. The method of any one of embodiments 1-11, wherein the second co-culturing step comprises co-culturing the second population of DCs loaded with the target tumor antigen peptide with the enriched population of activated T cells in an initial second co-culture medium comprising an immune checkpoint inhibitor and optionally one or more cytokines (e.g., IL-2 or a plurality of cytokines) to provide a second co-culture; and adding an anti-CD3 antibody to the second co-culture to obtain a population of tumor antigen-specific T cells.
13. The method of embodiment 12, wherein the anti-CD3 antibody is added to the second co-culture no more than about 3 days (e.g., 2 days) after the second co-culturing step starts.
14. The method of embodiment 12 or 13, wherein the anti-CD3 antibody is OKT3.
15. The method of any one of embodiments 12-14, wherein the initial second co-culture medium comprises IL-2, IL-7, IL-15 and IL-21 and an anti-PD-1 antibody.
16. The method of any one of embodiments 12-14, wherein the second co-culturing step comprises adding one or more cytokines to the second co-culture.
17. The method of embodiment 16, wherein the one or more cytokines comprise IL-2.
18. The method of embodiment 16 or 17, wherein the one or more cytokines is added to the second co-culture no more than about 3 days (e.g., about 2 days) after the second co-culturing step starts.
19. The method of any one of embodiments 12-18, wherein the initial second co-culture medium comprises IL-2 and an anti-PD-1 antibody.
20. The method of any one of embodiments 1-19, further comprising a third co-culturing step comprising co-culturing a population of the tumor antigen-specific T cells with a population of antigen presenting cells (APCs) loaded with target tumor antigen peptide to obtain a second population of tumor antigen-specific T cells, wherein the second population of tumor antigen-specific T cells are subjected to next-generation sequencing in the sequencing step.
21. The method of embodiment 20, wherein the APCs are PBMCs, DCs, or cell line APCs.
22. The method of embodiment 20 or 21, wherein the ratio between the population of tumor antigen-specific T cells and the population of APCs loaded with the target tumor antigen peptide is about 1:1 to about 20:1.
23. The method of any one of embodiments 20-22, wherein the population of tumor antigen-specific T cells and the population of APCs loaded with the target tumor antigen peptide are co-cultured for about 5 to 9 days.
24. The method of any one of embodiments 20-23, wherein the population of tumor antigen-specific T cells and the population of APCs loaded with the target tumor antigen peptide are co-cultured in a third co-culture medium comprising one or more cytokines (e.g., a plurality of cytokines) and an anti-CD3 antibody.

25. The method of embodiment 24, wherein the third co-culture medium comprises IL-2 and OKT3.
26. The method of embodiment 24, wherein the third co-culture medium comprises IL-2, IL-7, IL-15 and OKT3.
27. The method of any one of embodiments 20-26, the third co-culturing step is repeated.
28. The method of any one of embodiments 1-27, wherein the target tumor antigen peptide is derived from a tumor antigen selected from the group consisting of hTERT, p53, Survivin, NY-ESO-1, CEA, CCND1, RGS5, MMP7, VEGFR1, VEGFR2, MUC1, HER2, MAGE-A1, MAGE-A3, CDCA1, WT1, KRAS, PARP4, MLL3, MTHFR, HPV16-E6, HPV16-E7, HPV18-E6, HPV18-E7, HPV58-E6, HPV58-E7, HBcAg, HBV polymerase, GPC3, SSX, and AFP.
29. The method of embodiments 1-28, further comprising identifying a target tumor epitope from the target tumor antigen peptide, wherein the target tumor epitope elicits specific response by the enriched population of activated T cells, and contacting a population of APCs with the target tumor epitope to obtain the population of APCs loaded with the target tumor antigen peptide.
30. The method of any one of embodiments 1-29, wherein the next-generation sequencing is single cell sequencing.
31. The method of any one of embodiments 1-30, wherein the individual has partial response (PR), complete response (CR), or stable disease (SD) after receiving the MASCT; and/or wherein the individual has tumor antigen-specific immune response(s).
32. The method of any one of embodiments 1-31, wherein the MASCT comprises: co-culturing a population of DCs loaded with a plurality of tumor antigen peptides comprising the target tumor antigen peptide and a population of T cells to obtain a population of activated T cells.
33. The method of any one of embodiments 1-32, wherein the MASCT comprises:
   (i) co-culturing a population of DCs loaded with a plurality of tumor antigen peptides comprising the target tumor antigen peptide and a population of T cells in an initial co-culture medium comprising one or more cytokines (e.g., a plurality of cytokines) and an immune checkpoint inhibitor to provide a co-culture; and
   (ii) adding an anti-CD3 antibody to the co-culture at about 3 to 7 days after the co-culturing starts, thereby obtaining the population of activated T cells.
34. The method of any one of embodiments 1-33, wherein the MASCT comprises:
   (i) contacting a population of DCs with a plurality of tumor antigen peptides comprising the target tumor antigen peptide to obtain a population of DCs loaded with the plurality of tumor antigen peptides; and
   (ii) culturing the population of DCs loaded with the plurality of tumor antigen peptides in a DC maturation medium comprising MPLA.
35. The method of embodiment 34, wherein the DC maturation medium comprises INFγ, MPLA and PGE2.
36. The method of any one of embodiments 1-35, wherein the MASCT comprises administering to the individual an effective amount of the DCs loaded with the plurality of tumor antigen peptides.
37. The method of any one of embodiments 1-36, wherein the individual has previously received the MASCT for at least three times.
38. The method of any one of embodiments 1-37, wherein the tumor antigen-specific T cells are stimulated with APCs loaded with the target tumor antigen peptide prior to the next-generation sequencing.
39. The method of any one of embodiments 1-38, wherein TCRs specifically recognizing a plurality of target tumor antigen peptides are obtained in parallel.
40. The method of any one of embodiments 1-39, further comprising expressing each pair of genes encoding TCRα and TCRβ in a host immune cell to provide an engineered immune cell expressing a TCR, and assessing response of the engineered immune cell to the target tumor antigen peptide.
41. A method of obtaining a TCR specifically recognizing a target tumor antigen peptide, comprising the method of embodiment 40, wherein the TCR is selected based on the response of the engineered immune cell expressing the TCR to the target tumor antigen peptide.
42. The method of embodiment 41, further comprising determining HLA restriction of the TCR.
43. The method of embodiment 42, wherein the TCR has a HLA haplotype restriction that is predominant in Asians.
44. The method of any one of embodiments 41-43, further comprising affinity maturation of the TCR.
45. The method of any one of embodiments 41-44, further comprising enhancing the paring of the TCRα and TCRβ chains in the TCR.
46. The method of any one of embodiments 41-45, further comprising enhancing the expression of the TCR.
47. The method of any one of embodiments 41-46, wherein the target tumor antigen peptide is derived from CEA, RSG-5 or HPV18-E7.
48. A tumor-specific TCR obtained using the method of any one of embodiments 1-47.
49. A tumor-specific TCR comprising:
   (a) a TCRα chain comprising a complementary determining region (CDR) 3 having at least about 90% sequence identity to any one of the amino acid sequences of SEQ ID NOs: 4, 10, and 16; and a TCRβ chain comprising a CDR3 comprising an amino acid sequence having at least about 90% sequence identity to any one of the amino acid sequences of SEQ ID NOs: 7, 13, and 19;
   (b) a TCRα chain comprising a complementary determining region (CDR) 3 having at least about 90% sequence identity to any one of the amino acid sequences of SEQ ID NOs: 22, 28, 34, 40, 46, and 52; and a TCRβ chain comprising a CDR3 comprising an amino acid sequence having at least about 90% sequence identity to any one of the amino acid sequences of SEQ ID NOs: 7, 13, 19, 25, 31, 37, 43, 49, and 55; or
   (c) a TCRα chain comprising a complementary determining region (CDR) 3 having at least about 90% sequence identity to any one of the amino acid sequences of SEQ ID NOs: 58, 64, 70, 76, 87 and 93; and a TCRβ chain comprising a CDR3 comprising an amino acid sequence having at least about 90% sequence identity to any one of the amino acid sequences of SEQ ID NOs: 61, 67, 73, 79, 90 and 96.
50. The tumor-specific TCR of embodiment 49, comprising:
   (a) a TCRα chain comprising a CDR3 comprising the amino acid sequence of SEQ ID NO: 4, and a TCRβ chain comprising a CDR3 comprising the amino acid sequence of SEQ ID NO: 7;

(b) a TCRα chain comprising a CDR3 comprising the amino acid sequence of SEQ ID NO: 10, and a TCRβ chain comprising a CDR3 comprising the amino acid sequence of SEQ ID NO: 13;

(c) a TCRα chain comprising a CDR3 comprising the amino acid sequence of SEQ ID NO: 16, and a TCRβ chain comprising a CDR3 comprising the amino acid sequence of SEQ ID NO: 19;

(d) a TCRα chain comprising a CDR3 comprising the amino acid sequence of SEQ ID NO: 22, and a TCRβ chain comprising a CDR3 comprising the amino acid sequence of SEQ ID NO: 25;

(e) a TCRα chain comprising a CDR3 comprising the amino acid sequence of SEQ ID NO: 28, and a TCRβ chain comprising a CDR3 comprising the amino acid sequence of SEQ ID NO: 31;

(f) a TCRα chain comprising a CDR3 comprising the amino acid sequence of SEQ ID NO: 34, and a TCRβ chain comprising a CDR3 comprising the amino acid sequence f SEQ ID NO: 37;

(g) a TCRα chain comprising a CDR3 comprising the amino acid sequence of SEQ ID NO: 40, and a TCRβ chain comprising a CDR3 comprising the amino acid sequence of SEQ ID NO: 43;

(h) a TCRα chain comprising a CDR3 comprising the amino acid sequence of SEQ ID NO: 46, and a TCRβ chain comprising a CDR3 comprising the amino acid sequence of SEQ ID NO: 49;

(i) a TCRα chain comprising a CDR3 comprising the amino acid sequence of SEQ ID NO: 52, and a TCRβ chain comprising a CDR3 comprising the amino acid sequence of SEQ ID NO: 55;

(j) a TCRα chain comprising a CDR3 comprising the amino acid sequence of SEQ ID NO: 58, and a TCRβ chain comprising a CDR3 comprising the amino acid sequence of SEQ ID NO: 61;

(k) a TCRα chain comprising a CDR3 comprising the amino acid sequence of SEQ ID NO: 64, and a TCRβ chain comprising a CDR3 comprising the amino acid sequence of SEQ ID NO: 67;

(l) a TCRα chain comprising a CDR3 comprising the amino acid sequence of SEQ ID NO: 70, and a TCRβ chain comprising a CDR3 comprising the amino acid sequence of SEQ ID NO: 73;

(m) a TCRα chain comprising a CDR3 comprising the amino acid sequence of SEQ ID NO: 76, and a TCRβ chain comprising a CDR3 comprising the amino acid sequence of SEQ ID NO: 79;

(n) a TCRα chain comprising a CDR3 comprising the amino acid sequence of SEQ ID NO: 87, and a TCRβ chain comprising a CDR3 comprising the amino acid sequence of SEQ ID NO: 90; or (o) a TCRα chain comprising a CDR3 comprising the amino acid sequence of SEQ ID NO: 93, and a TCRβ chain comprising a CDR3 comprising the amino acid sequence of SEQ ID NO: 96.

51. A tumor-specific TCR comprising:

(a) a TCRα chain comprising CDRs of any one of the amino acid sequences of SEQ ID NOs: 5, 11 and 17, and a TCRβ chain comprising CDRs of any one of the amino acid sequences of SEQ ID NOs: 8, 14 and 20;

(b) a TCRα chain comprising CDRs of any one of the amino acid sequences of SEQ ID NOs: 23, 29, 35, 41, 47 and 53, and a TCRβ chain comprising CDRs of any one of the amino acid sequences of SEQ ID NOs: 26, 32, 38, 44, 50 and 56; or (c) a TCRα chain comprising CDRs of any one of the amino acid sequences of SEQ ID NOs: 59, 65, 71, 77, 88 and 94, and a TCRβ chain comprising CDRs of any one of the amino acid sequences of SEQ ID NOs: 62, 68, 74, 80, 91 and 97.

52. The tumor-specific TCR of any one of embodiments 49-51, comprising:

(a) a TCRα chain comprising an amino acid sequence having at least about 80% identity to any one of the amino acid sequences of SEQ ID NOs: 5, 11 and 17, and a TCRβ chain comprising an amino acid sequence having at least about 80% identity to any one of the amino acid sequences of SEQ ID NOs: 8, 14 and 20;

(b) a TCRα chain comprising an amino acid sequence having at least about 80% identity to any one of the amino acid sequences of SEQ ID NOs: 23, 29, 35, 41, 47 and 53, and a TCRβ chain comprising an amino acid sequence having at least about 80% identity to any one of the amino acid sequences of SEQ ID NOs: 26, 32, 38, 44, 50 and 56; or (c) a TCRα chain comprising an amino acid sequence having at least about 80% identity to any one of the amino acid sequences of SEQ ID NOs: 59, 65, 71, 77, 88 and 94, and a TCRβ chain comprising an amino acid sequence having at least about 80% identity to any one of the amino acid sequences of SEQ ID NOs: 62, 68, 74, 80, 91 and 97.

53. A tumor-specific TCR that specifically binds to an MHC/RGS5 epitope complex, comprising a TCRα chain comprising a CDR1 comprising the amino acid sequence of SEQ ID NO: 254, a CDR2 comprising the amino acid sequence of SEQ ID NO: 255, and a CDR3 comprising the amino acid sequence of SEQ ID NO: 28; and a TCRβ chain comprising a CDR1 comprising the amino acid sequence of SEQ ID NO: 256, a CDR2 comprising the amino acid sequence of SEQ ID NO: 257, and a CDR3 comprising the amino acid sequence of SEQ ID NO: 31.

54. The tumor-specific TCR of embodiment 53, wherein the RGS5 epitope comprises the amino acid sequence of SEQ ID NO: 82.

55. The tumor-specific TCR of embodiment 53 or 54, wherein the MHC is HLA-DPA1*02:02/DPB1*05:01.

56. A tumor-specific TCR that specifically binds to an MHC/RGS5 epitope complex, comprising a TCRα chain comprising a CDR1 comprising the amino acid sequence of SEQ ID NO: 258, a CDR2 comprising the amino acid sequence of SEQ ID NO: 259, and a CDR3 comprising the amino acid sequence of SEQ ID NO: 34; and a TCRβ chain comprising a CDR1 comprising the amino acid sequence of SEQ ID NO: 260, a CDR2 comprising the amino acid sequence of SEQ ID NO: 261, and a CDR3 comprising the amino acid sequence of SEQ ID NO: 37.

57. The tumor-specific TCR of embodiment 56, wherein the RGS5 epitope comprises the amino acid sequence of SEQ ID NO: 82.

58. The tumor-specific TCR of embodiment 56 or 57, wherein the MHC is HLA-DRA/DRB1*09:01 or HLA-DRA/DRB4*01:03.

59. A tumor-specific TCR that specifically binds to an MHC/RGS5 epitope complex, comprising a TCRα chain comprising a CDR1 comprising the amino acid sequence of SEQ ID NO: 262, a CDR2 comprising the amino acid sequence of SEQ ID NO: 263, and a CDR3 comprising the amino acid sequence of SEQ ID NO:

40; and a TCRβ chain comprising a CDR1 comprising the amino acid sequence of SEQ ID NO: 264, a CDR2 comprising the amino acid sequence of SEQ ID NO: 265, and a CDR3 comprising the amino acid sequence of SEQ ID NO: 43.

60. The tumor-specific TCR of embodiment 59, wherein the RGS5 epitope comprises the amino acid sequence of SEQ ID NO: 82.

61. The tumor-specific TCR of embodiment 59 or 60, wherein the MHC is HLA-DRA/DRB1*09:01 or HLA-DRA/DRB4*01:03.

62. A tumor-specific TCR that specifically binds to an MHC/RGS5 epitope complex, comprising a TCRα chain comprising a CDR1 comprising the amino acid sequence of SEQ ID NO: 266, a CDR2 comprising the amino acid sequence of SEQ ID NO: 267, and a CDR3 comprising the amino acid sequence of SEQ ID NO: 46; and a TCRβ chain comprising a CDR1 comprising the amino acid sequence of SEQ ID NO: 268, a CDR2 comprising the amino acid sequence of SEQ ID NO: 269, and a CDR3 comprising the amino acid sequence of SEQ ID NO: 49.

63. The tumor-specific TCR of embodiment 62, wherein the RGS5 epitope comprises the amino acid sequence of SEQ ID NO: 83.

64. The tumor-specific TCR of embodiment 62 or 63, wherein the MHC is HLA-DRA/DRB1*09:01 or HLA-DRA/DRB4*01:03.

65. A tumor-specific TCR that specifically binds to an MHC/RGS5 epitope complex, comprising a TCRα chain comprising a CDR1 comprising the amino acid sequence of SEQ ID NO: 270, a CDR2 comprising the amino acid sequence of SEQ ID NO: 271, and a CDR3 comprising the amino acid sequence of SEQ ID NO: 52; and a TCRβ chain comprising a CDR1 comprising the amino acid sequence of SEQ ID NO: 272, a CDR2 comprising the amino acid sequence of SEQ ID NO: 273, and a CDR3 comprising the amino acid sequence of SEQ ID NO: 55.

66. The tumor-specific TCR of embodiment 65, wherein the RGS5 epitope comprises the amino acid sequence of SEQ ID NO: 82.

67. The tumor-specific TCR of embodiment 65 or 66, wherein the MHC is HLA-DPA1*02:02/DPB1*05:01.

68. A tumor-specific TCR that specifically binds to an MHC/HPV18-E7 epitope complex, comprising a TCRα chain comprising a CDR1 comprising the amino acid sequence of SEQ ID NO: 274, a CDR2 comprising the amino acid sequence of SEQ ID NO: 275, and a CDR3 comprising the amino acid sequence of SEQ ID NO: 58; and a TCRβ chain comprising a CDR1 comprising the amino acid sequence of SEQ ID NO: 276, a CDR2 comprising the amino acid sequence of SEQ ID NO: 277, and a CDR3 comprising the amino acid sequence of SEQ ID NO: 61.

69. The tumor-specific TCR of embodiment 68, wherein the HPV18-E7 epitope comprises the amino acid sequence of SEQ ID NO: 85.

70. The tumor-specific TCR of embodiment 68 or 69, wherein the MHC is HLA-DRA/DRB1*09:01.

71. A tumor-specific TCR that specifically binds to an MHC/HPV18-E7 epitope complex, comprising a TCRα chain comprising a CDR1 comprising the amino acid sequence of SEQ ID NO: 278, a CDR2 comprising the amino acid sequence of SEQ ID NO: 279, and a CDR3 comprising the amino acid sequence of SEQ ID NO: 70; and a TCRβ chain comprising a CDR1 comprising the amino acid sequence of SEQ ID NO: 280, a CDR2 comprising the amino acid sequence of SEQ ID NO: 281, and a CDR3 comprising the amino acid sequence of SEQ ID NO: 73.

72. The tumor-specific TCR of embodiment 71, wherein the HPV18-E7 epitope comprises the amino acid sequence of SEQ ID NO: 85.

73. The tumor-specific TCR of embodiment 71 or 72, wherein the MHC is HLA-DRA/DRB1*09:01 or HLA-DRA/DRB4*01:03.

74. A tumor-specific TCR that specifically binds to an MHC/HPV18-E7 epitope complex, comprising a TCRα chain comprising a CDR1 comprising the amino acid sequence of SEQ ID NO: 282, a CDR2 comprising the amino acid sequence of SEQ ID NO: 283, and a CDR3 comprising the amino acid sequence of SEQ ID NO: 76; and a TCRβ chain comprising a CDR1 comprising the amino acid sequence of SEQ ID NO: 284, a CDR2 comprising the amino acid sequence of SEQ ID NO: 285, and a CDR3 comprising the amino acid sequence of SEQ ID NO: 79.

75. The tumor-specific TCR of embodiment 74, wherein the HPV18-E7 epitope comprises the amino acid sequence of SEQ ID NO: 85.

76. The tumor-specific TCR of embodiment 74 or 75, wherein the MHC is HLA-II.

77. A tumor-specific TCR that specifically binds to an MHC/HPV18-E7 epitope complex, comprising a TCRα chain comprising a CDR1 comprising the amino acid sequence of SEQ ID NO: 286, a CDR2 comprising the amino acid sequence of SEQ ID NO: 287, and a CDR3 comprising the amino acid sequence of SEQ ID NO: 87; and a TCRβ chain comprising a CDR1 comprising the amino acid sequence of SEQ ID NO: 288, a CDR2 comprising the amino acid sequence of SEQ ID NO: 289, and a CDR3 comprising the amino acid sequence of SEQ ID NO: 90.

78. The tumor-specific TCR of embodiment 77, wherein the HPV18-E7 epitope comprises the amino acid sequence of SEQ ID NO: 84.

79. The tumor-specific TCR of embodiment 77 or 78, wherein the MHC is HLA-DRA/DRB1*09:01.

80. A tumor-specific TCR that specifically binds to an MHC/HPV18-E7 epitope complex, comprising a TCRα chain comprising a CDR1 comprising the amino acid sequence of SEQ ID NO: 290, a CDR2 comprising the amino acid sequence of SEQ ID NO: 291, and a CDR3 comprising the amino acid sequence of SEQ ID NO: 93; and a TCRβ chain comprising a CDR1 comprising the amino acid sequence of SEQ ID NO: 292, a CDR2 comprising the amino acid sequence of SEQ ID NO: 293, and a CDR3 comprising the amino acid sequence of SEQ ID NO: 96.

81. The tumor-specific TCR of embodiment 80, wherein the HPV18-E7 epitope comprises the amino acid sequence of SEQ ID NO: 84.

82. The tumor-specific TCR of embodiment 80 or 81, wherein the MHC is HLA-DPA1*02:02/DPB1*05:01, HLA-DPA1*01:03/DPB1*02:01, or HLA-DPA1*01:03/DPB1*05:01.

83. The tumor-specific TCR of any one of embodiments 49-51 and 53-82, wherein the TCR is a human TCR.

84. The tumor-specific TCR of any one of embodiments 49-51 and 53-82, wherein the TCR is a chimeric TCR, such as a murinized TCR, e.g., a TCR comprising murine constant regions of TCRα and β chains.

85. The tumor-specific TCR of any one of embodiments 49-51 and 53-82, wherein the TCR comprises murine TCR constant regions.
86. An isolated nucleic acid encoding the TCRα chain and/or the TCRβ chain of the tumor-specific TCR of any one of embodiments 48-85.
87. A vector comprising the isolated nucleic acid of embodiment 86.
88. An engineered immune cell comprising the tumor-specific TCR of any one of embodiments 48-85, the isolated nucleic acid of embodiment 86, or the vector of embodiment 87.
89. The engineered immune cell of embodiment 88, wherein the immune cell is a T cell.
90. A pharmaceutical composition comprising the engineered immune cell of embodiment 88 or 89, and a pharmaceutically acceptable carrier.
91. A method of treating a cancer in an individual, comprising administering to the individual an effective amount of the pharmaceutical composition of embodiment 90.
92. A library of tumor-specific TCRs obtained using the method of any one of embodiments 1-47.
93. An epitope of RGS-5 comprising the amino acid sequence of SEQ ID NO: 82 or 83.
94. An epitope of HPV18-E7 comprising the amino acid sequence of SEQ ID NO: 84, 85 or 86.
95. An MHC/epitope complex comprising the epitope of embodiment 93 or 94 and an MHC molecule.

EXAMPLES

The examples below are intended to be purely exemplary of the present application and should therefore not be considered to limit the invention in any way. The following examples and detailed description are offered by way of illustration and not by way of limitation.

Figure 2:
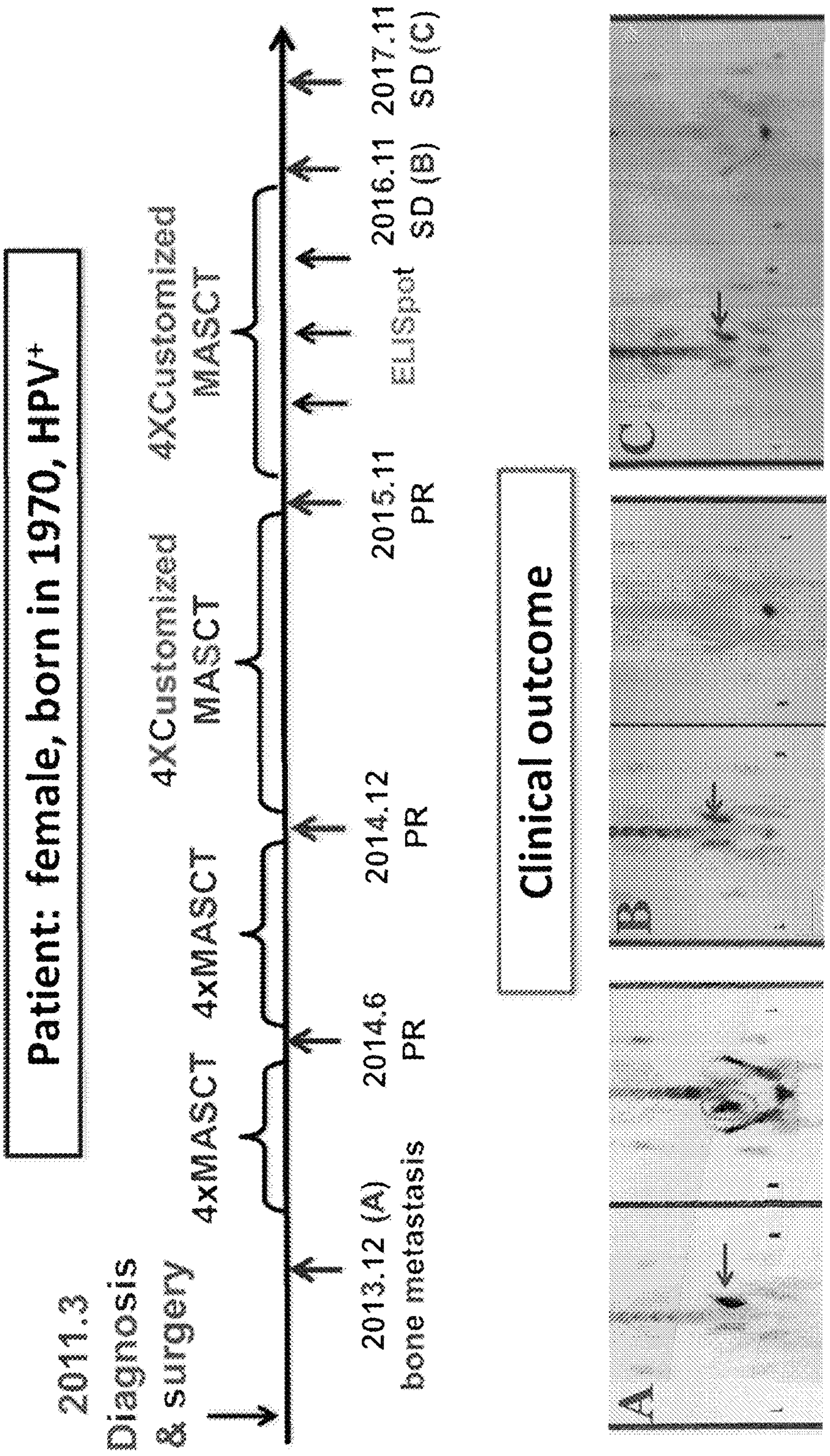
FIG. 2 shows clinical data of a patient with metastatic cervical cancer treated with MASCT. The bottom panel shows ECT results of the patent taken in December 2013 (prior to any MASCT treatments), in November 2016 (after achieving Stable Disease status on MASCT), and in November 2017. The arrows and circles point to the metastasis site on the right sacroiliac joint bone, showing reduction of the metastatic tumor and no additional metastasis in response to MASCT treatments.

Example 1: Specific Immune Response Against Tumor Antigen Peptides in a Patient Treated with MASCT Patient WJ, female, was diagnosed with cervical cancer with vascular invasion at age 41, and was tested positive with Human Papilloma Virus (HPV) DNA. She underwent curative resection, and a five-month chemo-radio therapy. The patient took a second HPV DNA test, and was confirmed to be negative in serum HPV DNA. The clinical history and response of this patient is summarized in FIG. 2.

About two years after the curative resection and chemo-radio therapy, the patient was diagnosed to have metastasis tumor on the right sacroiliac joint bone according to Magnetic Resonance Imaging (MRI) and Emission Computed Tomography (ECT). The patient then received ten local radiotherapy treatments, followed by three MASCT treatment, administered one per month. The MASCT treatment used PBMCs from the patient's own peripheral blood to prepare dendritic cells pulsed with a pool of 18 antigen peptides, including a core group of 12 tumor-associated antigen peptides, as well as a cervical cancer-specific group of 6 antigen peptides derived from viral proteins of HPV. Briefly, monocytes from the patient's PBMCs were differentiated into immature DCs and then pulsed with multiple synthetic peptide antigens including tumor-associated antigens and HPV antigens. The immature DCs were further stimulated by TLR ligands to differentiate into mature DCs (mDCs). Half of mDCs were subcutaneous injected to the patient. Maintaining T cells were prepared by culturing non-adherent PBMCs with anti-CD3 antibody (e.g., OKT3), and IL2. The other half of mDCs was co-cultured with the maintaining T cells for another 7-9 days before infusion. The patient was confirmed to have HLA-A2 serotype (HLA-A0201+).

After four MASCT treatments, the patient's ECT results showed that the right sacroiliac joint bone metastasis was reduced, and no new metastasis was detected, indicating positive treatment outcome of MASCT. The patient received four additional MASCT treatments administered with an interval of about 1 month or 2 months. After a total of 8 MASCT treatments, a sample of the patient's PBMC was obtained and tested with an ELISPOT assay to determine whether the patient had a therapeutically effective MHC-restricted T cell response to the antigen peptide pool and each of the antigen peptides within the pool. The ELISPOT results demonstrated enhanced T-cell response to the cervical carcinoma antigen peptide pool, and individual antigen peptides within both the core group of tumor-specific antigen peptides (such as hTERT, p53, CEA, and RGS5), and the cervical cancer-specific group of tumor antigen peptides (such as HPV-3 and HPV-5). The patient's ECT after a total of 8 MASCT showed further reduction of the right sacroiliac joint bone metastasis, and no new metastasis sites, indicating that the MASCT treatment regimen was successful in reducing tumor burden in the patient and in preventing tumor progression and further metastasis.

Based on the patient's specific immune response, the antigen peptide pool was customized to provide a patient-specific antigen peptide pool by saving the responsive peptides that had induced specific responses and removing the non-responsive peptides that did not induce specific responses. The patient was further treated with four cycles of MASCT prepared using the patient-specific antigen peptide pool (referred herein as "precise MASCT"). After the four precise MASCT, The patient's ECT showed no development of the right sacroiliac joint bone metastasis, and no new metastasis sites.

Figure 3A:
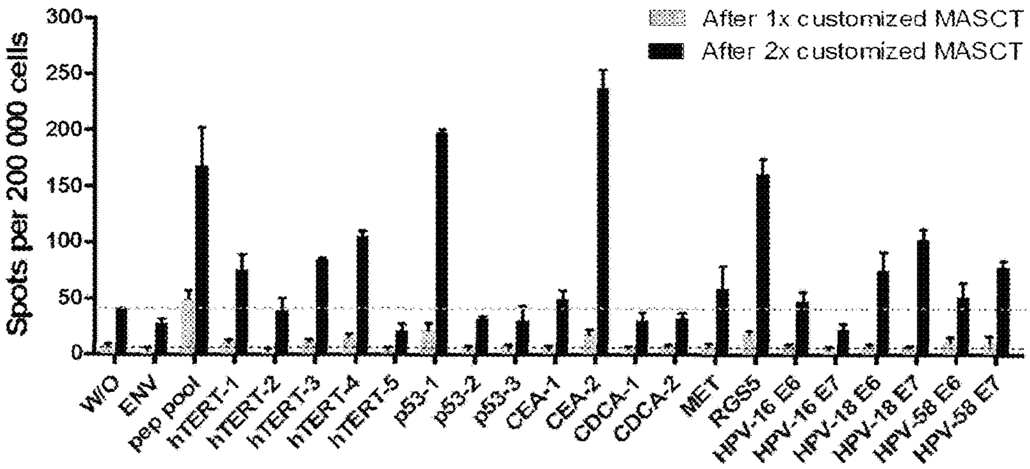
FIGS. 3A-3B show specific immune response by the patient's PBMCs against the cervical carcinoma antigen peptide pool (pep pool), and each tumor antigen peptide in the pool after customized MASCT treatments as determined by ELISPOT. W/O=response without stimulation with any antigen peptide. ENV refers to experiment with an irrelevant peptide. The dotted line indicates a threshold of no elevated immune response as measured by spots per 200,000 cells which reflect IFNγ secretion levels.
Figure 3B:
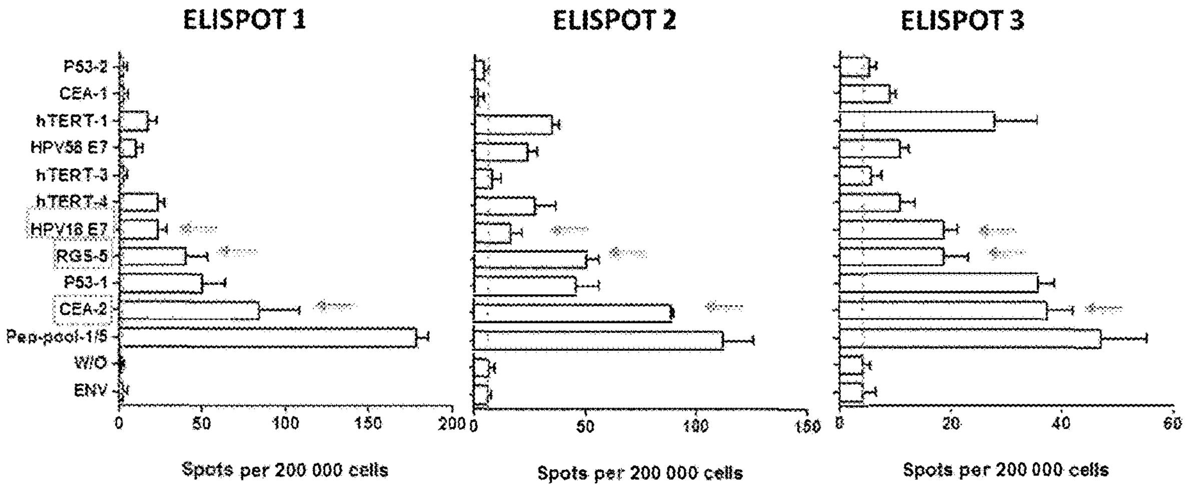

The antigen peptide pool was further adjusted based on the specific immune response of the patient, and the patient was treated with four cycles of a $2^{nd}$ precise MASCT using the further adjusted peptide antigen pool. After the second four cycles of precise MASCT, the patient was evaluated as having stable disease (SD). The patient-specific antigen peptide pool elicited enhanced specific responses as demonstrated by the ELISPOT assay (FIG. 3A). In particular, HPV18-E7 peptide, CEA peptide, and RGS5 peptide consistently yielded the strongest specific response (FIG. 3B).

Adoptive transfer of tumor-specific TCR engineered T cells has shown great efficacy against solid tumors. The clinical benefits of this patient indicated that tumor-specific T cells were expanded in vivo and played an important role to control tumor progression. These T cells may be the good sources to isolate tumor-specific TCRs.

Example 2: Identification of Paired Tumor Antigen Peptide-Specific TCRα and TCRβ Genes from Tumor Antigen-Specific T Cells PBMC samples from the patient in Example 1 were obtained and used as the starting material to prepare tumor antigen-specific T cells in this example. Twelve pairs of tumor antigen-specific TCRα and TCRβ genes (3 pairs for CEA-specific TCRs, 3 pairs for RGS5-specific TCRs, and 6 pairs for HPV18-E7-specific TCRs) were identified by next-generation sequencing of the tumor antigen-specific T cell samples.

Method 2

Cells Preparation

FIG. 4 provides an overview of the protocol of exemplary "Method 2". Briefly, on Day 1, peripheral blood mononuclear cells (PBMCs) from the patient were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed with a peptide pool comprising three tumor antigen peptides derived from CEA, RGS5, and HPV18-E7 (1 μg/mL/peptide), and then cultured in a DC maturation medium to differentiate into mature DCs. On Day 8, PBMCs containing T cells were co-cultured with antigen-loaded mature DCs at a ratio between the T cells and the mature antigen-loaded DCs of about 15:1, and the co-culture medium contained a cytokine cocktail and an anti-PD-1 antibody. On Day 11, the co-culture was stimulated with PBMCs pulsed with the peptide pool. On Day 12, an IFNγ secretion assay-cell enrichment and detection kit (Miltenyi Biotec) was used to isolate a population of IFNγ$^+$ T cells. On Day 12, the IFNγ$^+$ T cells were co-cultured with antigen-loaded mature DCs at a ratio between the T cells and the antigen-loaded mature DCs of about 2:1 in a medium containing a cytokine cocktail, an anti-PD-1 antibody, and an anti-CD3 antibody from Day 12 to Day 25-35 to obtain tumor antigen-specific T cells.

Proliferation Assay

Cell proliferation was assessed using cell samples from Day 1 (PBMCs), Day 8 (start of co-culture), Day 11 (before IFNγ enrichment and after IFNγ enrichment), and Days 17, 21, 25, 27, 31 and 32 (co-culture of IFNγ$^+$ T cells with antigen-loaded mature DCs). The numbers of cells in each sample were counted.

Figure 5:
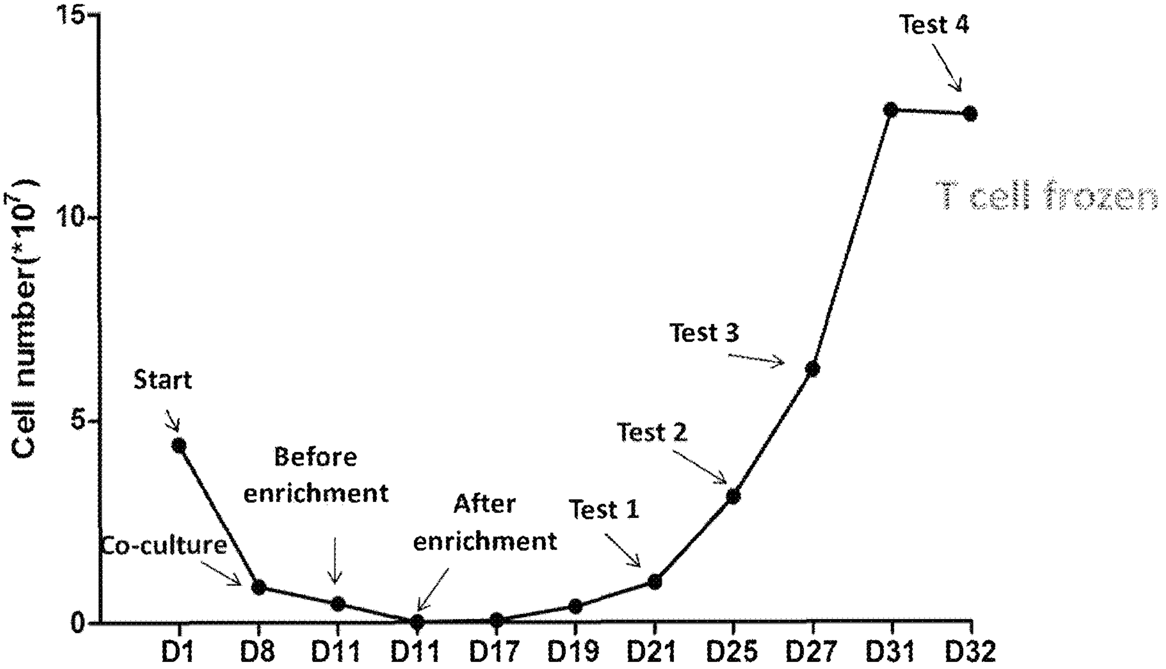
FIG. 5 shows cell proliferation at various time points in the preparation of tumor antigen-specific T cells.

As shown in FIG. 5, the initial co-culture of antigen-loaded mature DCs and T cells yielded a small number of IFNγ$^+$ T cells (Day 11). In the co-culture of enriched IFNγ$^+$ T cells and antigen-loaded mature DCs, the number of cells continued to increase rapidly until Day 31, at which time point the total number of cells in the co-culture plateaued at more than $10^8$.

IFNγ Production by Tumor Antigen-Specific T Cells

Various co-culture samples were each plated (T cells: $1\times10^6$ cells/well; PBMCs: $2.5\times10^5$ cells/well) in AIM-V medium and stimulated with 2 μg/mL of the peptide pool for 4 hours. The IFNγ production levels by tumor antigen-specific T cells in each sample were detected by intracellular cytokine staining and FACS analysis. Cell samples incubated with 10 μg/mL irrelevant peptide were used as negative controls.

Antibodies for cell surface (e.g., anti-human CD3-FITC) or intracellular cytokine (e.g., anti-human IFNγ-APC) staining were obtained from BD Biosciences. Intracellular cytokine staining was performed by fixing and permeabilizing cells with cytofix/cytoperm (BD Biosciences). Flow cytometry was performed using FACS CantoII (BD Biosciences) flow cytometers and data was analyzed with the Flowjo program.

Figure 6A:
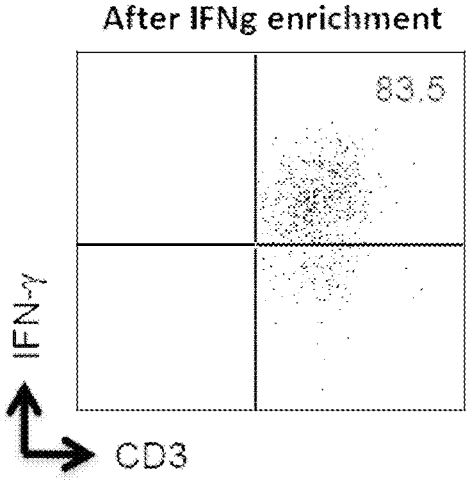
FIGS. 6A-6B shows the percentages of $IFN\gamma^+CD3^+$ tumor antigen-specific T cells in various co-culture samples.
Figure 6B:
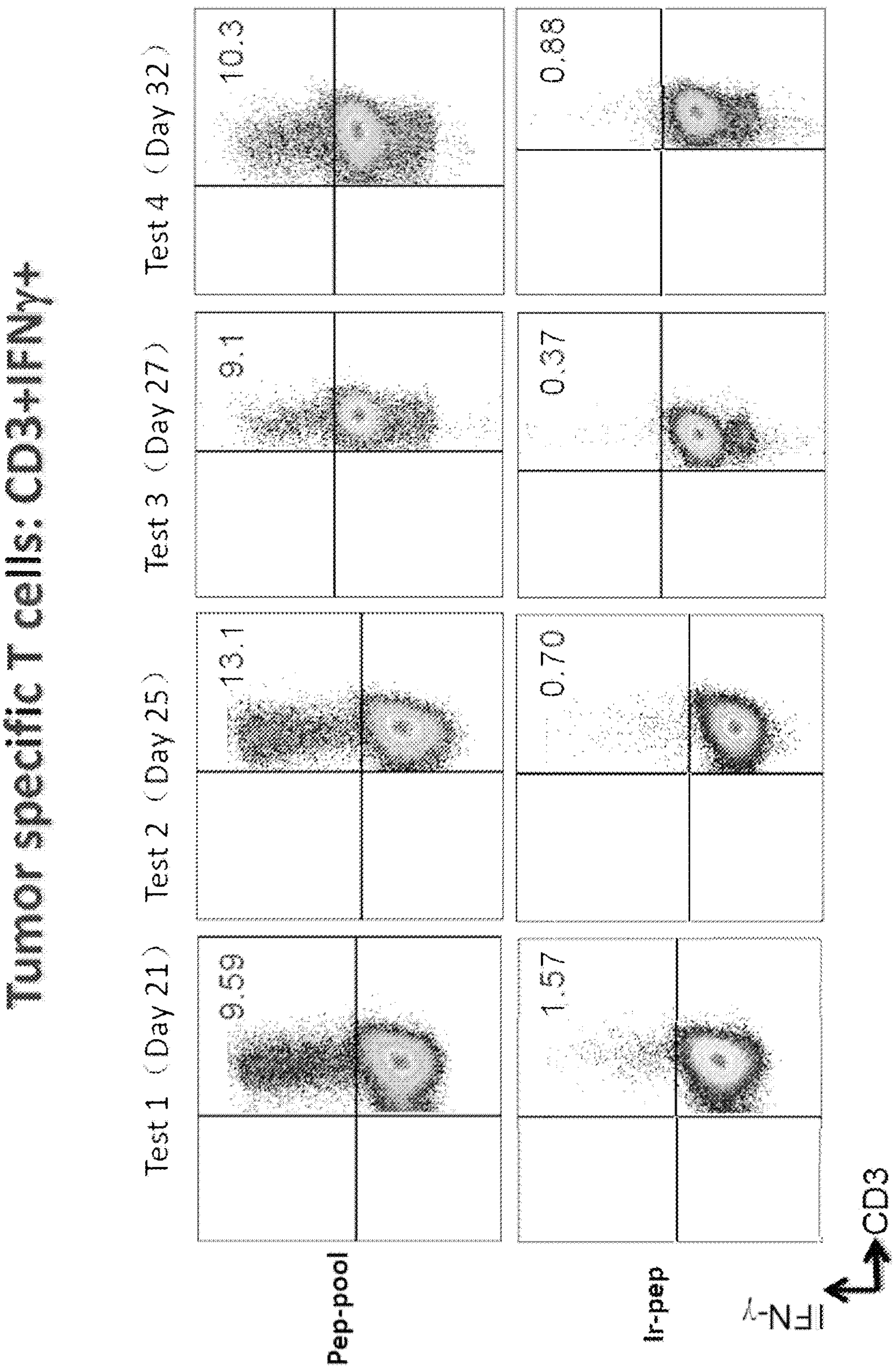

FIGS. 6A-6B show the percentages of tumor antigen-specific T cells in the cell samples as determined by assessing IFNγ$^+$CD3$^+$ cells in response to stimulation by the tumor antigen peptide pool. After the enrichment step, the percentage of tumor antigen-specific T cells in the cell sample reached 83.5%. From Day 21 to Day 32, the co-cultures contained about 10% tumor antigen-specific T cells that produced IFNγ in response to stimulation by the tumor antigen peptide pool. Non-specific T cells that produced IFNγ in response to stimulation by irrelevant peptides constituted less than 1% in the co-cultures on Days 25-32.

Optimization of Method 2 ("Method 2m")

Cells Preparation

FIG. 7 provides an overview of the protocols of exemplary "Method 2m". Briefly, on Day 1, peripheral blood mononuclear cells (PBMCs) from the patient were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed with a peptide pool comprising three tumor antigen peptides derived from CEA, RGS5, and HPV18-E7 (1 μg/mL/peptide), and then cultured in a DC maturation medium to differentiate into mature DCs. On Day 8, PBMCs containing T cells were co-cultured with antigen-loaded mature DCs at a ratio between the T cells and the mature antigen-loaded DCs of about 20:1, and the co-culture medium contained a cytokine cocktail and an anti-PD-1 antibody. On Day 11, the co-culture was stimulated with PBMCs pulsed with the peptide pool. On Day 12, an IFNγ secretion assay-cell enrichment and detection kit (Miltenyi Biotec) was used to isolate a population of IFNγ$^+$ T cells. Meanwhile, the antigen-loaded mature DCs were cultured in the DC maturation medium. On Day 12, the IFNγ$^+$ T cells were co-cultured with antigen-loaded mature DCs at a ratio between the T cells and the antigen-loaded mature DCs of about 1:1 in a medium containing a cytokine cocktail, an anti-PD-1 antibody. On Day 13 or 14, an anti-CD3 antibody (OKT3) was added to the co-culture, which was continued to be cultured to Day 30 to obtain tumor antigen-specific T cells.

Proliferation Assay

Cell proliferation was assessed using cell samples from Day 1 (PBMCs), Day 9 (start of co-culture), Day 12 (before IFNγ enrichment), Day 12 (after IFNγ enrichment), and Days 22 and 30 (co-culture of IFNγ$^+$ T cells with antigen-loaded mature DCs) as described above.

Figure 8:
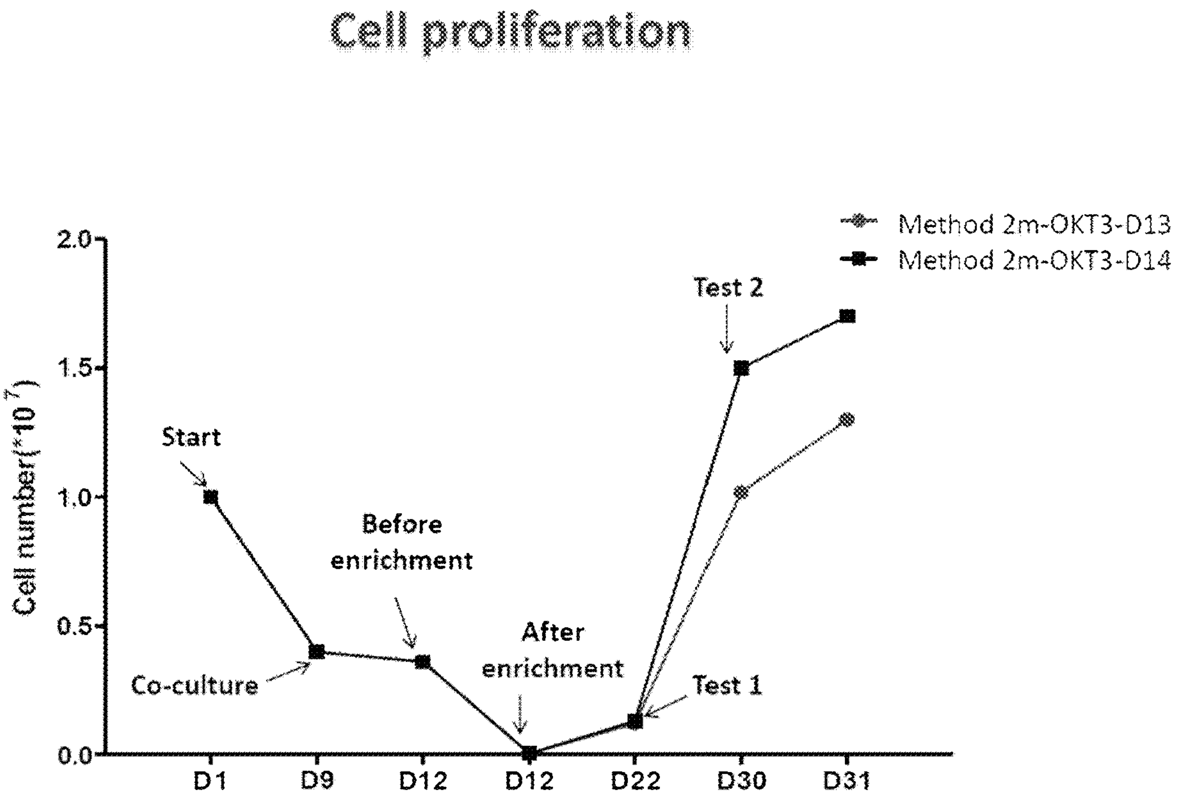
FIG. 8 shows cell proliferation at various time points in the preparation of tumor antigen-specific T cells.

As shown in FIG. 8, the initial co-culture of antigen-loaded mature DCs and T cells yielded a small number of IFNγ$^+$ T cells (Day 12). In the co-culture of enriched IFNγ$^+$ T cells and antigen-loaded mature DCs, the number of cells continued to increase rapidly until Day 31. The method with anti-CD3 antibody added on Day 14 resulted in a higher level of cell proliferation.

IFNγ Production by Tumor Antigen-Specific T Cells

Figure 9A:
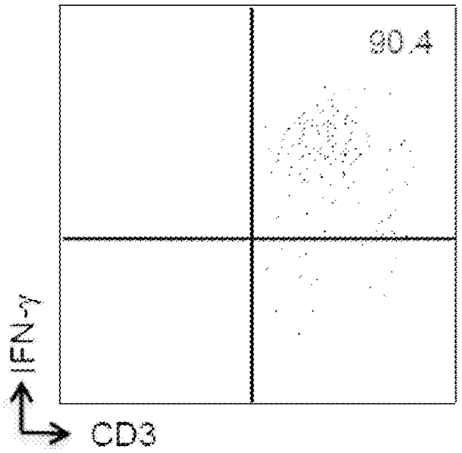
FIGS. 9A-9B show the percentages of $IFN\gamma^+CD3^+$ tumor antigen-specific T cells in various co-culture samples.
Figure 9B:
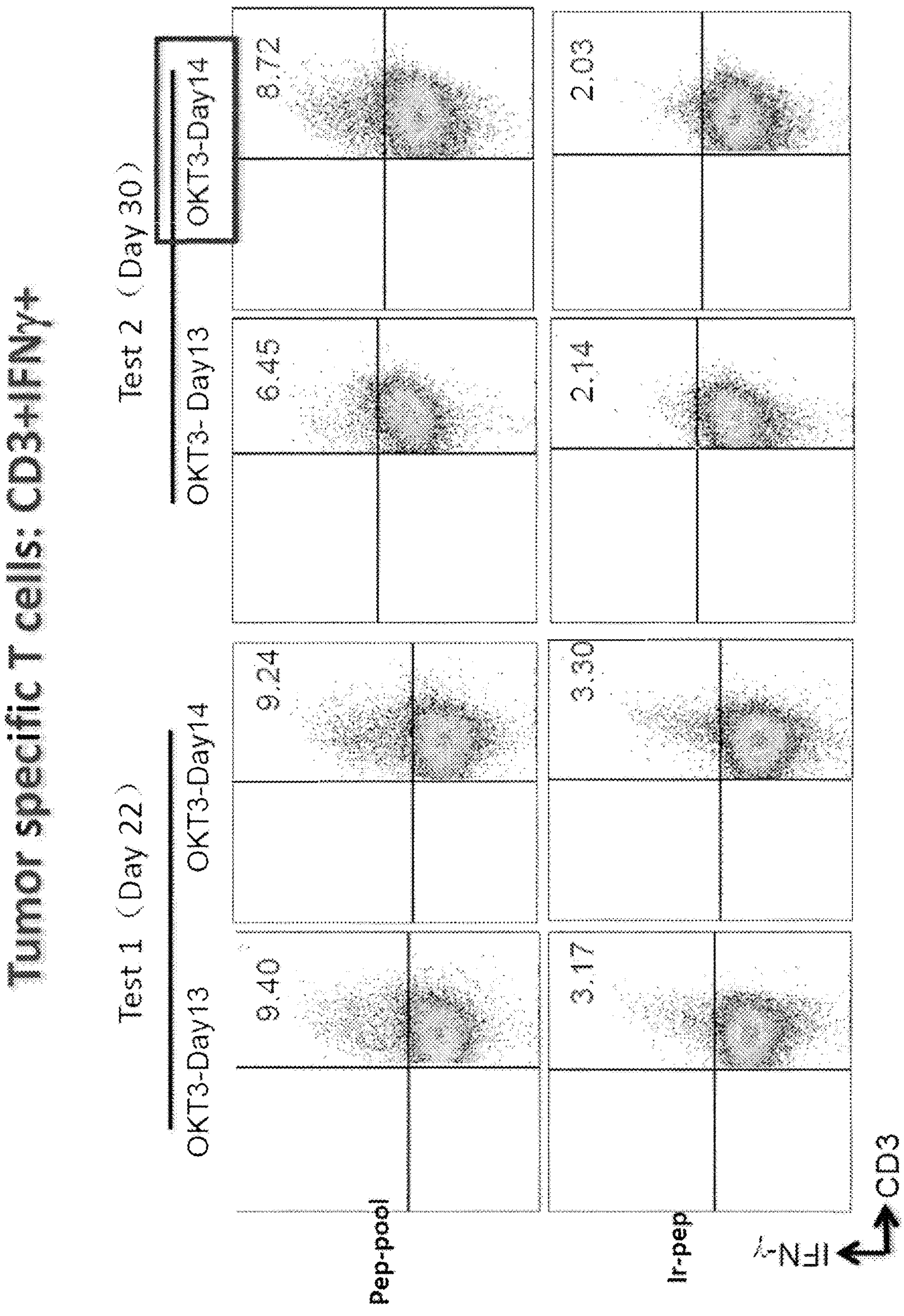
Figure 9C:
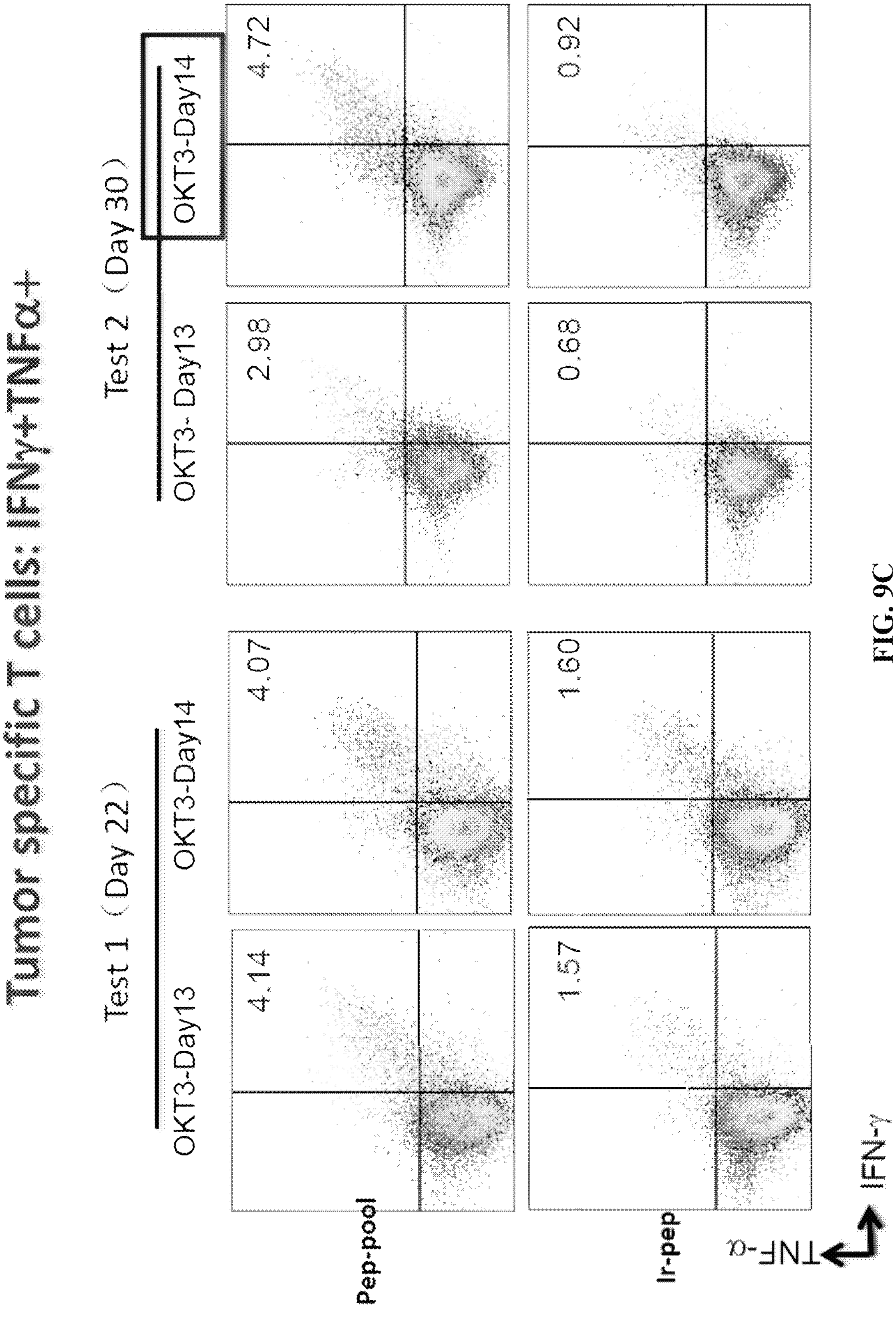
FIG. 9C shows the percentages of $IFN\gamma^+TNF\alpha^+$ tumor antigen-specific T cells in various co-culture samples.

The IFNγ production levels by tumor antigen-specific T cells in various co-culture samples were determined as described above. FIGS. 9A-9B show the percentages of tumor antigen-specific T cells in the cell samples as determined by assessing IFNγ$^+$CD3$^+$ cells in response to stimulation by the tumor antigen peptide pool. After the enrichment step, the percentage of tumor antigen-specific T cells in the cell sample reached 90.4%. From Day 22 to Day 30, the co-cultures contained about 6-10% tumor antigen-specific T cells that produced IFNγ in response to stimulation by the tumor antigen peptide pool. The method with anti-CD3 antibody added on Day 14 yielded a higher percentage of IFNγ$^+$CD3$^+$ cells. Consistent results were obtained by assessing IFNγ$^+$TNFα$^+$ cells (FIG. 9C).

Screen of Subset of Tumor Antigen Peptide Pool

Figure 13:
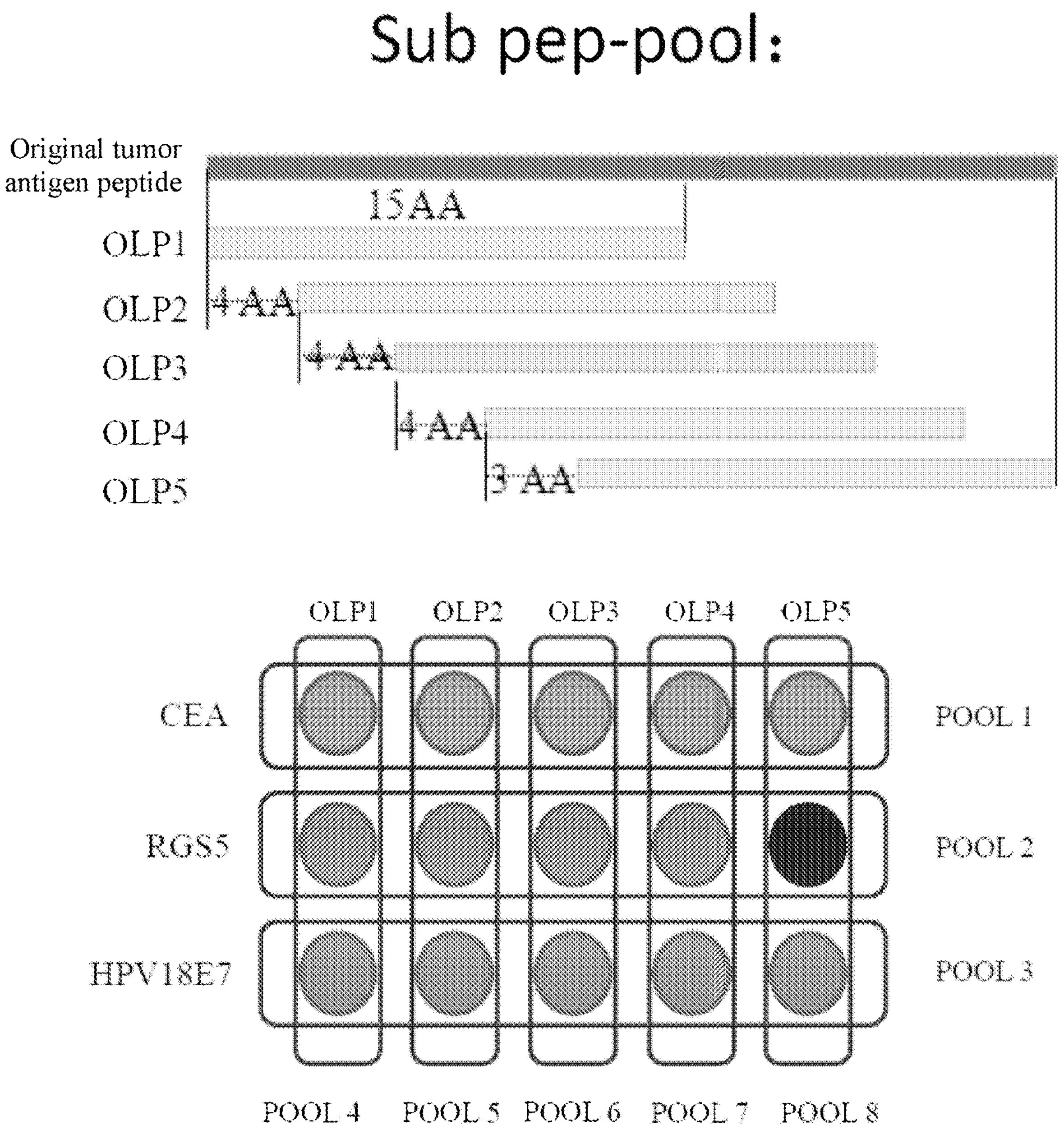
FIG. 13 shows sub-pools of fragments of the HPV18-E7, RGS-5 and CEA peptides, which were screened for specific immune response by tumor antigen-specific T cells. The RGS5-OLP5 peptide was shown to elicit the strongest specific response by the tumor antigen-specific T cells prepared using Method 2 and Method 2m.
Figure 14A:
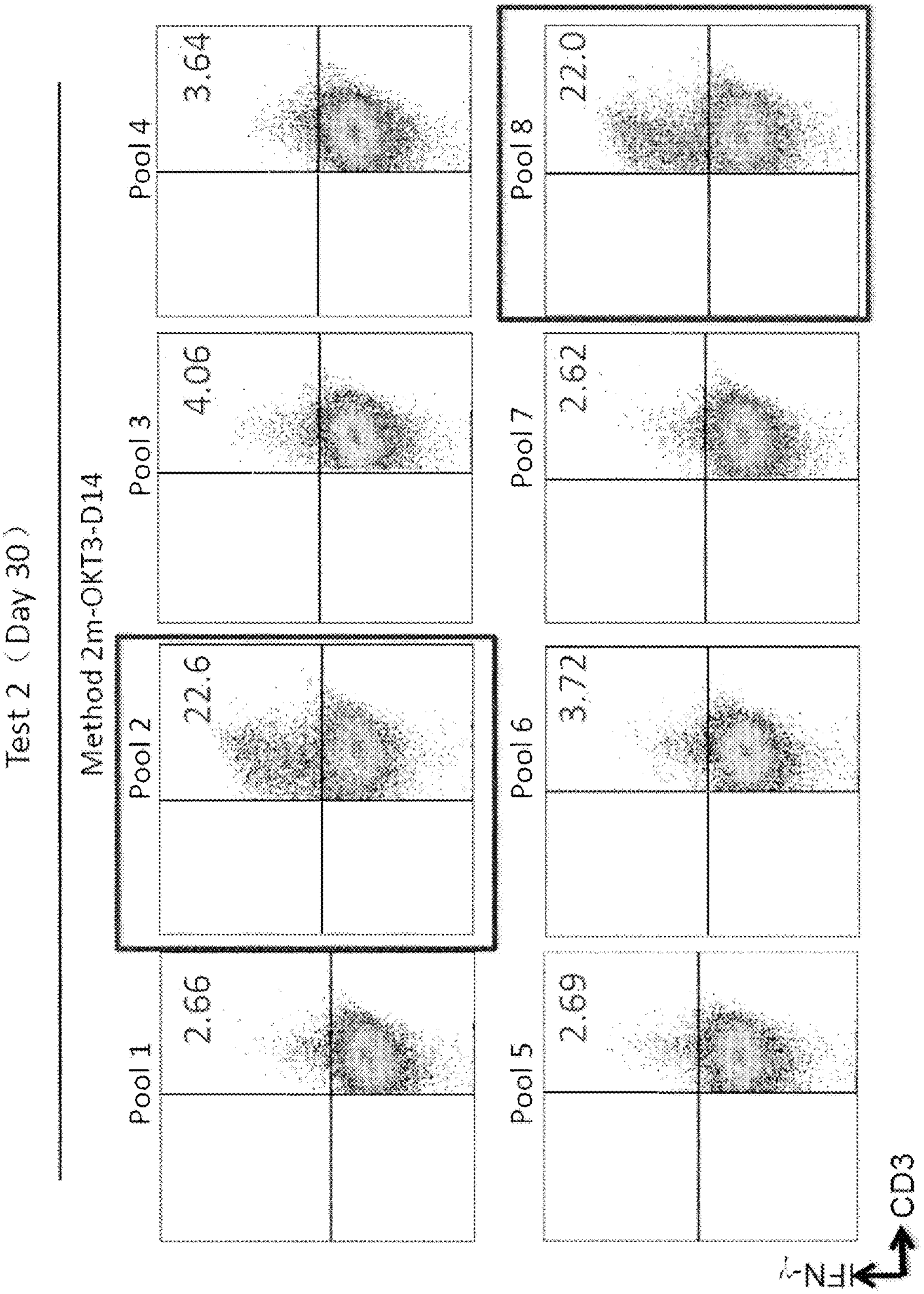
FIG. 14A shows percentages of $IFN\gamma+CD3^+$ tumor antigen-specific T cells after the tumor antigen-specific T cells prepared using Method 2m were stimulated by each of the sub-pool of antigen peptide fragments.
Figure 14B:
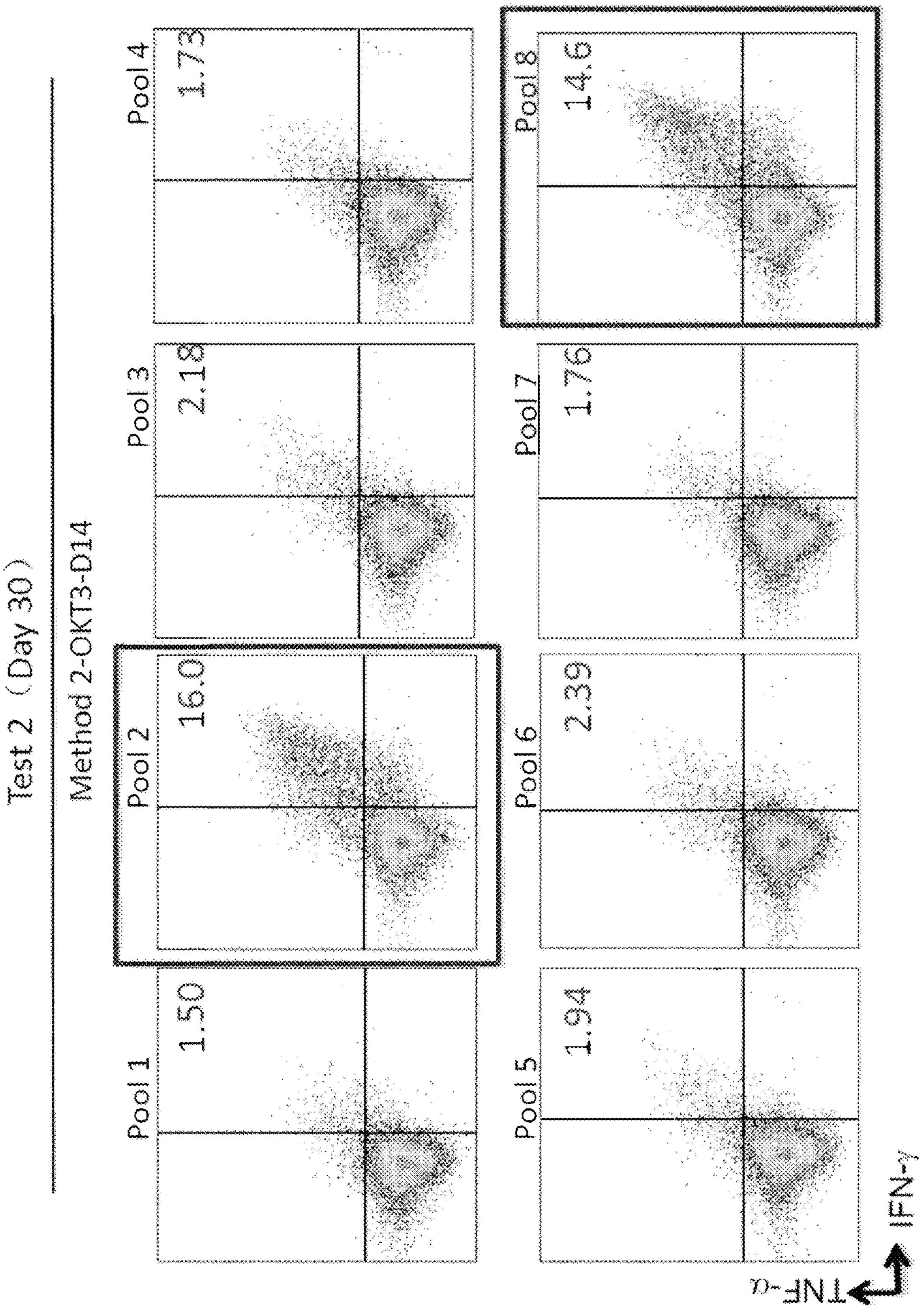
FIG. 14B shows percentages of $IFN\gamma^+TNF\alpha^+$ tumor antigen-specific T cells after the tumor antigen-specific T cells prepared using Method 2 were stimulated by each of the sub-pool of antigen peptide fragments.

Five fragments of each of the three initial tumor antigen peptides, CEA, RGS5 and HPV18-E7, were designed and synthesized. Sub-pools of the initial tumor antigen peptides and their fragments were prepared according to FIG. 13. The tumor antigen-specific T cells obtained on Day 30 were stimulated with each of the sub-pool of tumor antigen peptides, and the percentages of IFNγ$^+$CD3$^+$ cells were determined. As shown in FIGS. 14A-14B, Pool 2 and Pool 8 consistently yielded the highest percentages of IFNγ$^+$ CD3$^+$ cells, which suggests that the RGS5-OLP5 fragment elicited the strongest specific response by the tumor antigen-specific T cells.

Next-Generation Sequencing of Tumor Antigen-Specific T Cells

Four samples of the tumor antigen-specific T cells prepared using Method 2 were obtained and subjected to TCRα and TCRβ amplification coupled to next-generation sequencing. The four samples are: (1) tumor antigen-specific T cells stimulated by the CEA peptide; (2) tumor antigen-specific T cells stimulated by the RGS5 peptide; (3) tumor antigen-specific T cells stimulated by the HPV18-E7 peptide; and (4) INFγ$^+$CD3$^+$ tumor antigen-specific T cells stimulated by the CEA peptide enriched by beads. As a control, a PBMC sample from the same patient was also subjected to the same next-generation sequencing analysis.

Figure 10:
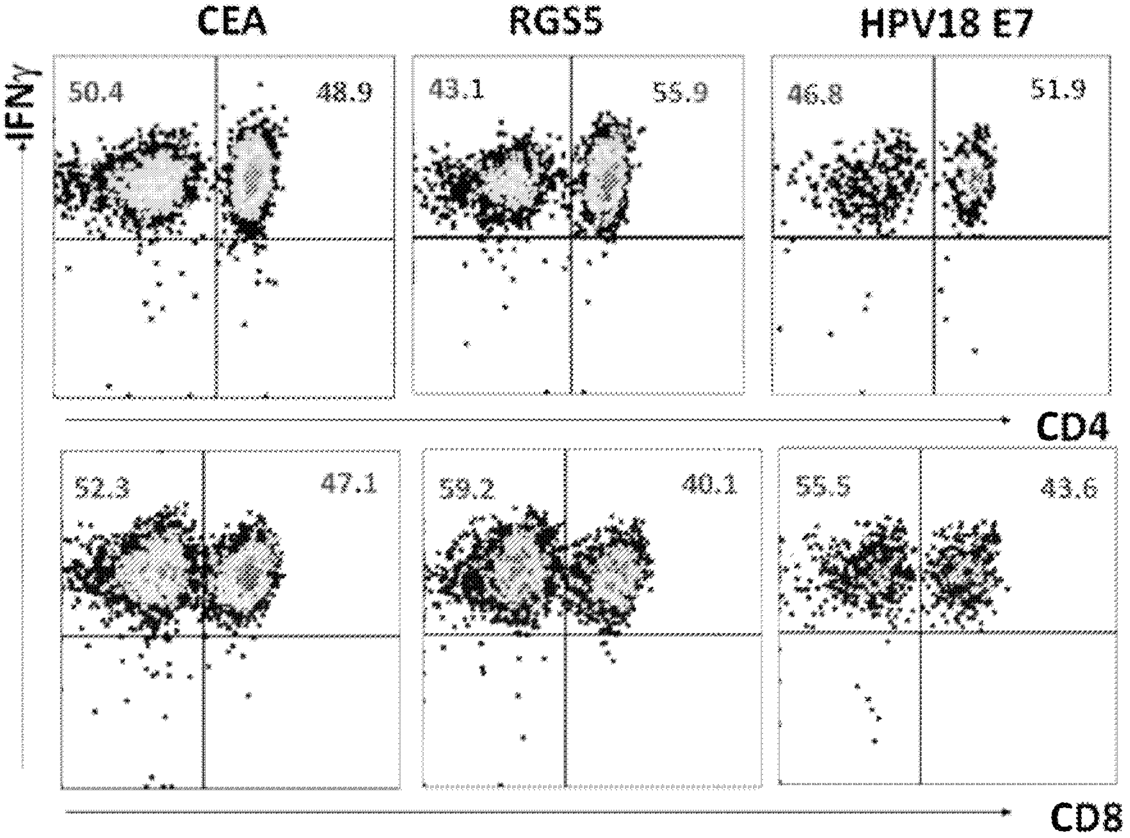
FIG. 10 shows the percentages of $IFN\gamma^+CD4+$ and $IFN\gamma^+CD8^+$ cells in tumor antigen-specific cells stimulated by each of the tumor antigen peptides. The tumor antigen-specific cells were prepared using PBMCs from a patient who has clinically benefitted from MASCT and a pool of tumor antigen peptides derived from CEA, RGS5 and HPV18-E7.

FIG. 10 shows flow cytometry results of tumor antigen-specific T cells stimulated by the CEA, RGS5 and HPV18-E7 peptides respectively. Each sample contained more than 90% of tumor antigen-specific T cells (a combination of CD8$^+$ and CD4$^+$ cells).

Figure 11:
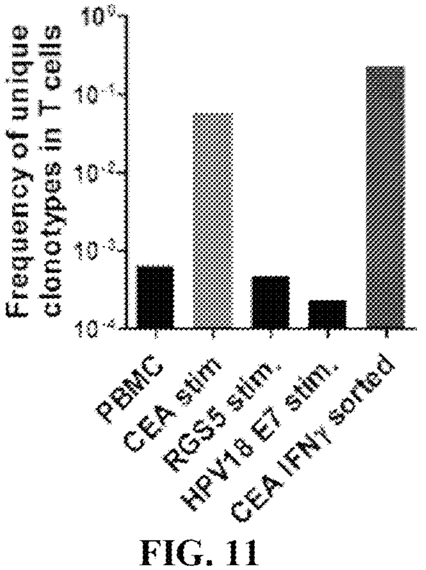
FIG. 11 shows the frequencies of unique TCR clonotypes in various T cell samples determined by next-generation sequencing.

FIG. 11 shows the frequency of unique clonotypes of TCRα and TCRβ sequences in the various samples. Tumor antigen-specific T cells stimulated by specific tumor antigen peptides had increased frequency of unique TCR clonotypes than tumor antigen-specific T cells stimulated with an irrelevant peptide. IFNγ sorted tumor antigen-specific T cells stimulated by tumor antigen peptides showed even higher frequency of unique clonotypes of TCR.

Frozen PBMC samples obtained from the patient at three different time points (T1=June 2016, T2=September 2016, and T3=May 2017) were subjected to the same tumor antigen-specific T cell preparation and sequencing analysis. FIG. 12 shows the frequencies of unique TCRα and TCRβ clonotypes identified from the bulk next-generation sequencing results. Certain TCRα and TCRβ genes were found in corresponding tumor antigen-specific T cell samples derived from two or all three frozen PBMC samples.

Single-cell TCRα and TCRβ amplification coupled to next-generation sequencing using the IPAIR™ technology (iRepertoire, Inc.) was applied to the tumor antigen-specific T cell samples in order to obtain cognate pairing information of the TCRα and TCRβ genes. Three pairs of CEA-specific TCRα and TCRβ genes (clones 1-3), three pairs of RGS5-specific TCRα and TCRβ genes (clones 1-3), and six pairs of HPV18-E7-specific TCRα and TCRβ genes (clones 1-6) were identified, and synthesized. See Table 1 for sequence information of the exemplary TCR clones. Engineered T cells expressing each pair of TCRα and TCRβ genes are prepared, and the TCRs are validated by assessing tumor antigen-specific immune response by the engineered T cells using ELISPOT assay.

Figure 20:
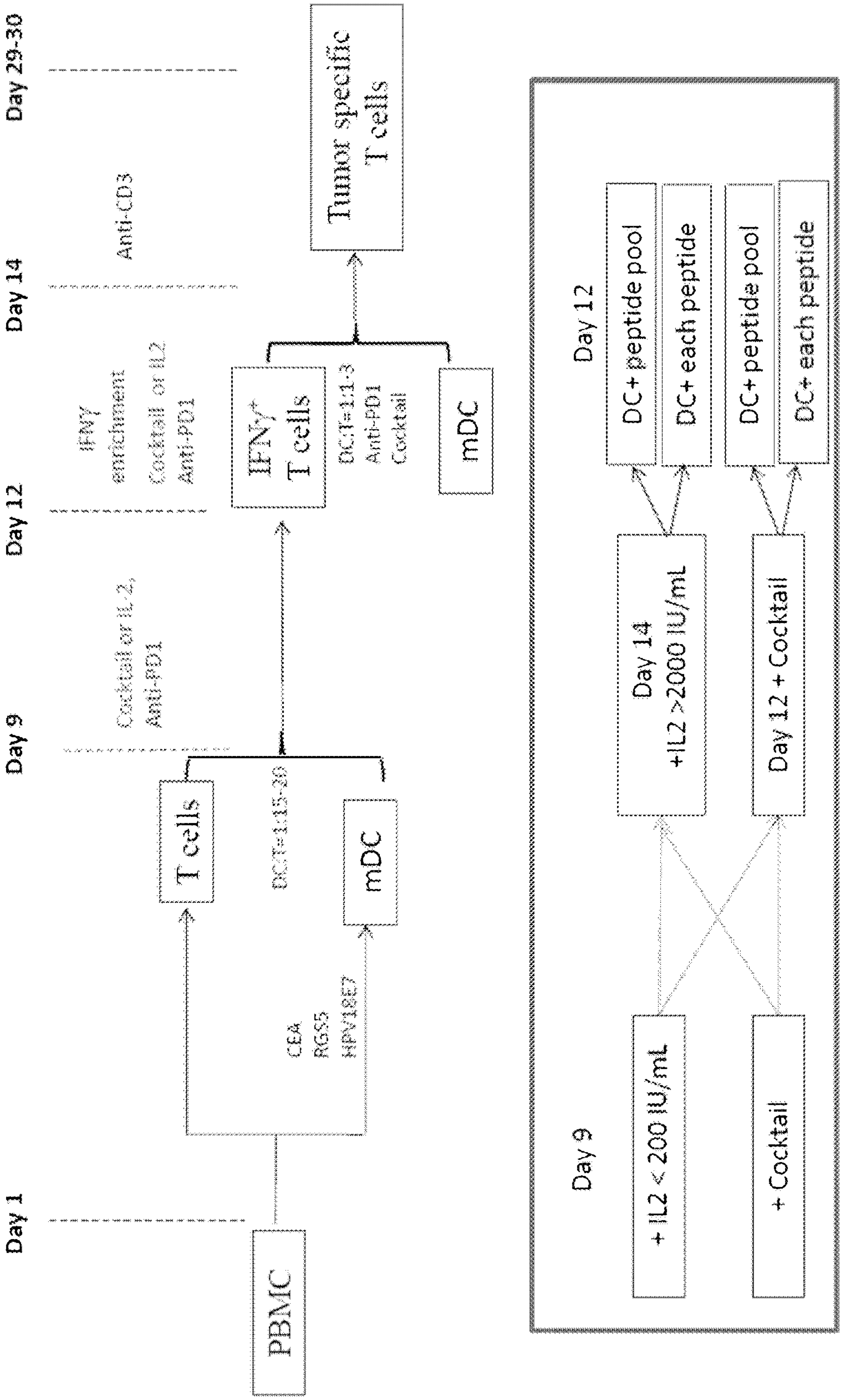
FIG. 20 shows exemplary methods for preparing tumor antigen-specific T cells as described in Example 2.

Comparison of Cytokine Cocktail v. IL-2 and Antigen Peptide Pool v. Single Antigen Peptide Cells Preparation FIG. 20 provides an overview of protocols that compare addition of cytokine cocktail v. IL-2 alone, and stimulation with DC loaded with a pool of antigen peptides v. a single antigen peptide. Briefly, on Day 1, peripheral blood mononuclear cells (PBMCs) from the patient were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed with a peptide pool comprising three tumor antigen peptides derived from CEA, RGS5, and HPV18-E7 (1p g/mL/peptide), and then cultured in a DC maturation medium to differentiate into mature DCs. On Day 9, PBMCs containing T cells were co-cultured with antigen-loaded mature DCs at a ratio between the T cells and the mature antigen-loaded DCs of about 15:1 to about 20:1, and the co-culture medium contained a cytokine cocktail or IL-2 (no more than about 200 IU/mL) and an anti-PD-1 antibody. On Day 11, the co-culture was stimulated with PBMCs pulsed with the peptide pool or each individual peptide. On Day 12, an IFNγ secretion assay-cell enrichment and detection kit (Miltenyi Biotec) was used to isolate a population of IFNγ$^+$ T cells. Meanwhile, the antigen-loaded mature DCs were cultured in the DC maturation medium. The IFNγ$^+$ T cells were co-cultured with antigen-loaded mature DCs at a ratio between the T cells and the antigen-loaded mature DCs of about 1:1 to about 3:1 in a medium containing a cytokine cocktail added on Day 12 or IL-2 alone (at least about 2000 IU/mL) added on Day 14, and an anti-PD-1 antibody. On Day 14, an anti-CD3 antibody (OKT3) was added to the co-culture, which was continued to be cultured to Day 29-30 to obtain tumor antigen-specific T cells.

Proliferation Assay and IFNγ Production by Tumor Antigen-Specific T Cells

Cell proliferation was assessed using cell samples from Day 1 (PBMCs), Day 9 (start of co-culture), Day 12 (before IFNγ enrichment), Day 12 (after IFNγ enrichment), and Days 19, 24 and 29 (co-culture of IFNγ$^+$ T cells with antigen-loaded mature DCs) by methods described in Example 2.

Figure 21A:
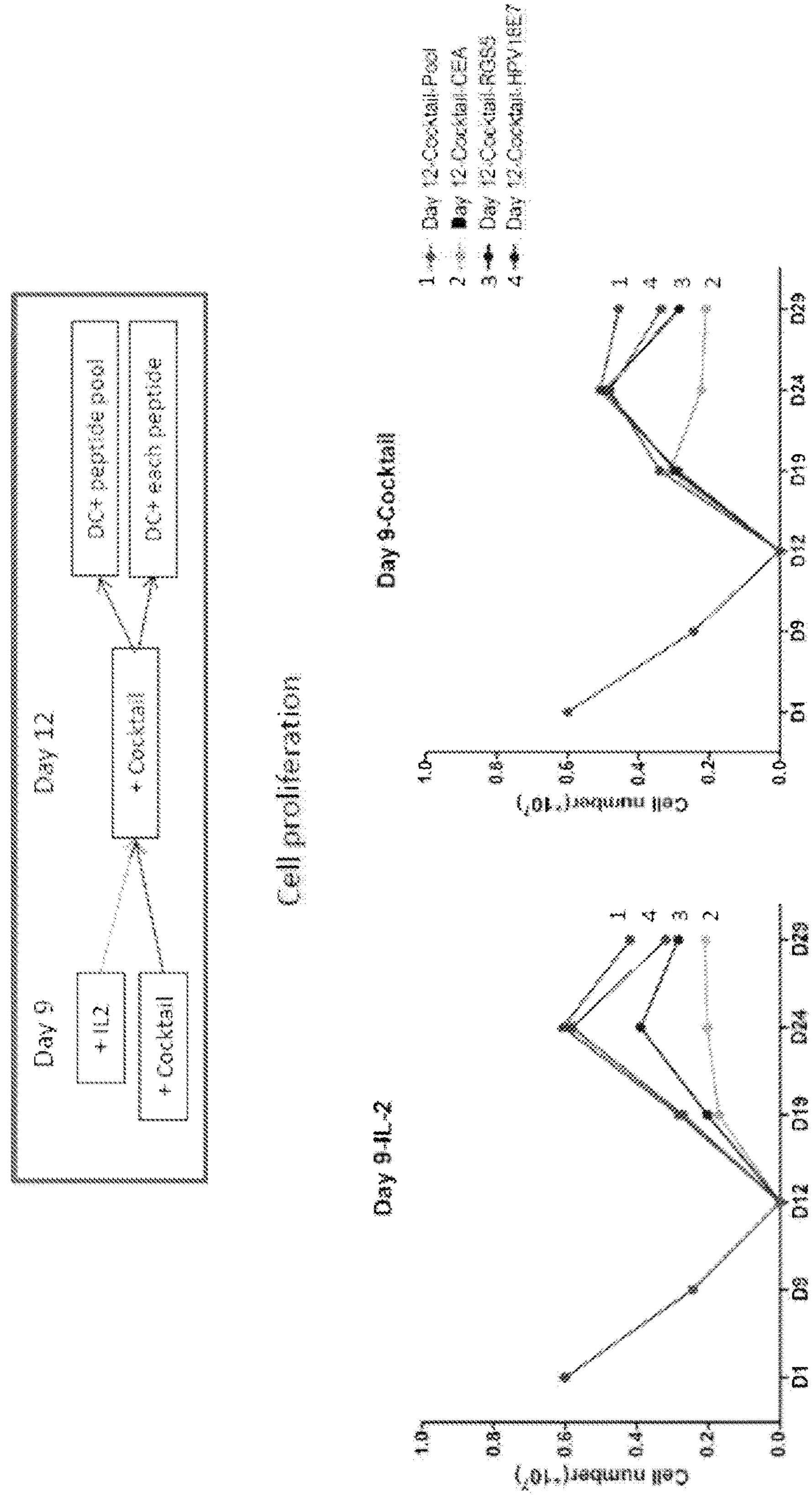
FIG. 21A shows cell proliferation at various time points in the preparation of tumor antigen-specific T cells.

As shown in FIG. 21A, the initial co-culture of antigen-loaded mature DCs and T cells yielded a small number of IFNγ$^+$ T cells (Day 12). In the co-culture of enriched IFNγ$^+$ T cells and antigen-loaded mature DCs, the number of cells continued to increase rapidly until Day 29.

Figure 21B:
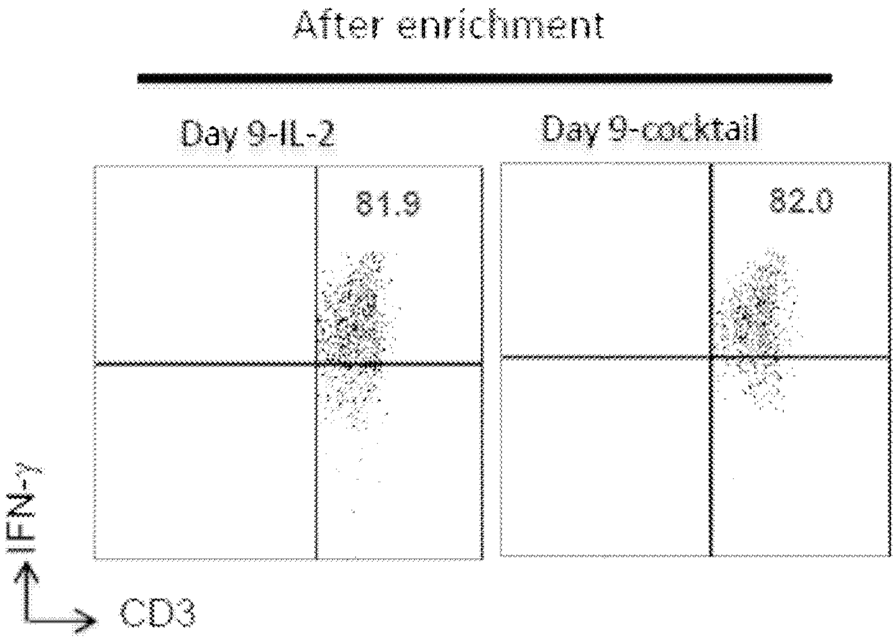
FIG. 21B shows the percentages of $IFN\gamma+CD3^+$ tumor antigen-specific T cells before and after the enrichment step.

The IFNγ production levels by tumor antigen-specific T cells in various co-culture samples were determined by methods described in Example 2. As shown in FIG. 21B, similar percentage of IFNγ$^+$ T cells were obtained after the enrichment step on Day 12 with the cytokine cocktail or IL-2 only added to the co-culture on Day 9.

Table 3 below compares the percentages of tumor-specific T cells in the cell samples on Day 19 (Test 1) and Day 29 (Test 2) as determined by assessing IFNγ$^+$CD3+ and IFNγ$^+$ TNFα$^+$ cells in response to stimulation by the tumor antigen peptide pool or individual antigen peptides. Protocols with cytokine cocktail or IL-2 alone added on Day 9 and co-culture with DCs pulsed with tumor antigen pool or single tumor antigen yield comparable results in terms of T cell proliferation and percentages of tumor-specific T cells.

TABLE 3

Percentages of Tumor-specific T cells in Cell Samples.

| Tumor-specific T cells | b | Test 1 Pool | Test 1 CEA | Test 1 RGS5 | Test 1 HPV18E7 | Test 2 Pool | Test 2 CEA | Test 2 RGS5 | Test 2 HPV18E7 |
|---|---|---|---|---|---|---|---|---|---|
| | | a | | | | | | | |
| Day 9 IL-2 | | | | | | | | | |
| CD3+ | Pool | 9.40 | 0.36 | 2.47 | 6.74 | 8.97 | 0.63 | 2.60 | 5.30 |
| IFNγ+ | CEA | 13.90 | 0.27 | 6.69 | 5.46 | 6.66 | 0.70 | 3.64 | 3.29 |
| (%) | RGS5 | 9.44 | 0.54 | 3.00 | 5.89 | 5.86 | 0.59 | 2.40 | 3.39 |
| | HPV18E7 | 12.65 | 0.50 | 4.44 | 6.05 | 7.16 | 1.31 | 2.50 | 4.39 |
| IFNγ+ | Pool | 4.15 | 0.16 | 1.08 | 4.07 | 5.32 | 0.52 | 2.40 | 3.94 |
| TNFα+ | CEA | 8.96 | 0.21 | 4.25 | 4.07 | 3.76 | 0.64 | 1.85 | 2.69 |
| (%) | RGS5 | 6.38 | 0.29 | 1.36 | 4.61 | 3.81 | 0.37 | 1.66 | 2.80 |
| | HPV18E7 | 7.90 | 0.44 | 2.85 | 3.65 | 4.69 | 0.91 | 1.92 | 2.90 |
| Day 9 Cocktail | | | | | | | | | |
| CD3+ | Pool | 9.96 | 0.68 | 1.82 | 5.72 | 8.13 | 2.51 | 3.80 | 4.30 |
| IFNγ+ | CEA | 11.21 | 0.79 | 5.37 | 5.71 | 5.86 | 0.71 | 2.86 | 4.26 |
| (%) | RGS5 | 9.09 | 0.20 | 2.25 | 5.44 | 8.79 | 1.37 | 4.35 | 6.38 |
| | HPV18E7 | 12.08 | 1.16 | 6.09 | 4.16 | 9.73 | 1.87 | 4.93 | 3.83 |
| IFNγ+ | Pool | 5.33 | 0.56 | 0.89 | 3.54 | 4.07 | 1.06 | 1.91 | 2.42 |
| TNFα+ | CEA | 6.96 | 0.62 | 3.51 | 3.67 | 2.84 | 0.69 | 0.42 | 2.71 |
| (%) | RGS5 | 5.67 | 0.50 | 1.59 | 4.00 | 5.06 | 0.08 | 1.29 | 3.62 |
| | HPV18E7 | 6.48 | 0.69 | 3.84 | 2.30 | 4.63 | 0.62 | 2.56 | 2.52 |

a: stimulation/testing conditions
b: culturing conditions

Figure 22A:
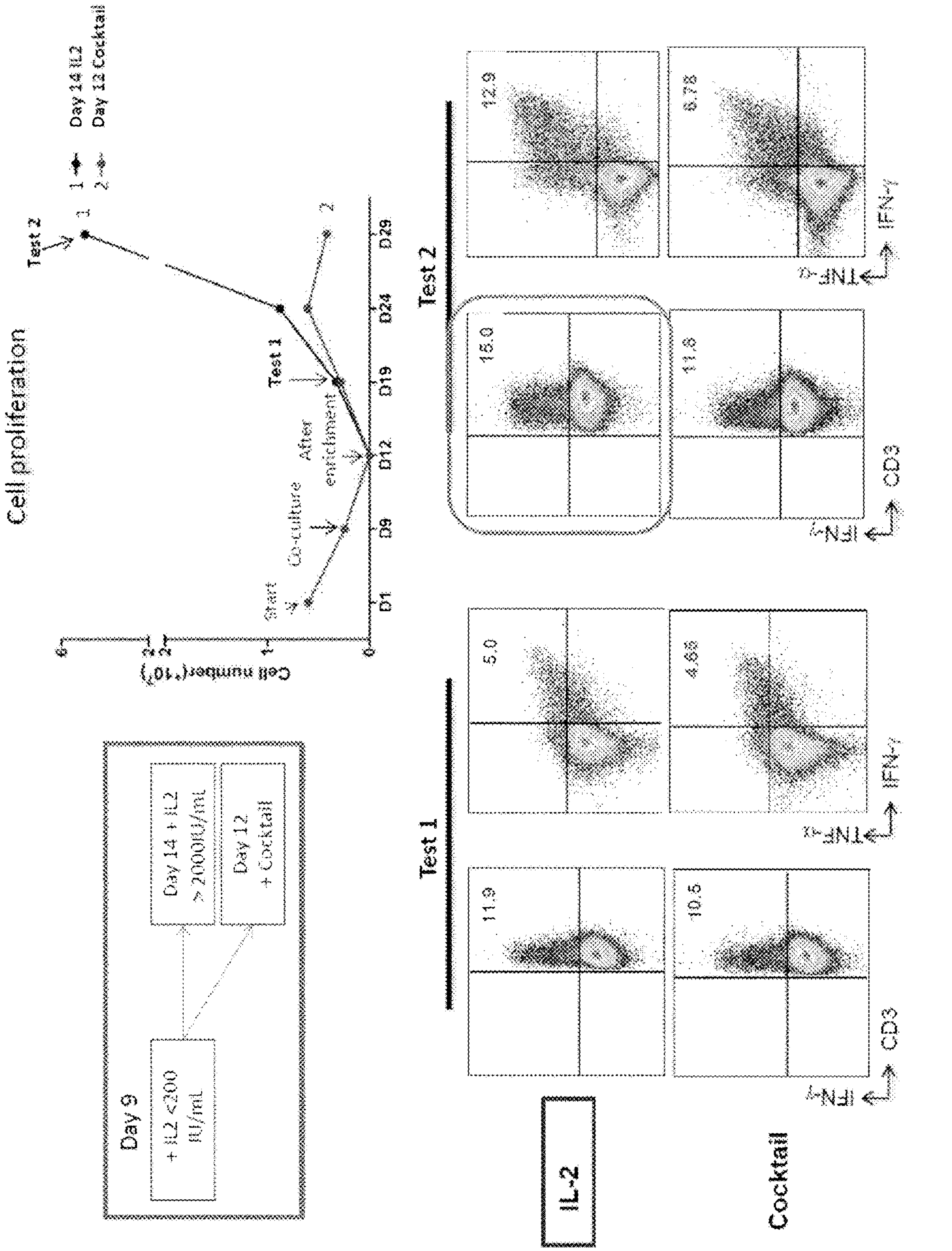
FIGS. 22A-22B show cell proliferation and percentages of tumor antigen-specific T cell populations in various co-culture samples.
Figure 22B:
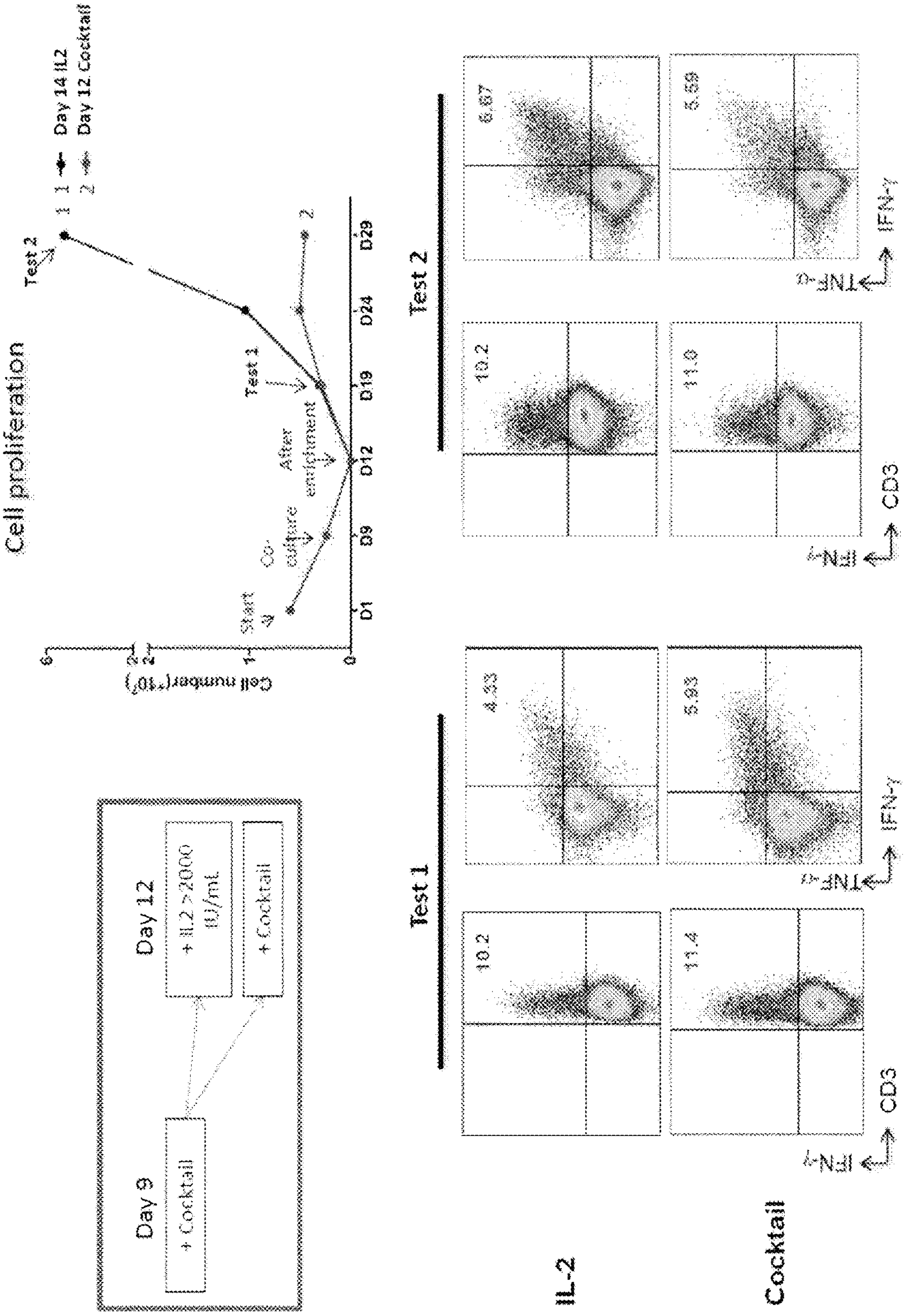

FIGS. 22A-22B compare T cell numbers and percentages of tumor antigen-specific T cells in various co-culture samples using protocols with IL-2 or cytokine cocktail added on Days 9 and 12. The protocol with IL-2 added on Day 9, co-culture with DCs pulsed with the tumor antigen peptide pool on Day 12 and IL-2 added on Day 14 yielded the highest percentage of tumor-antigen-specific T cells on Days 19 and 29.

Example 3: Identification of Paired RGS5-Specific TCRα and TCR$ Genes from Tumor Antigen-Specific T Cells A frozen stock of tumor antigen-specific T cells prepared using Method 2 and Method 2m was used in this example to prepare a population of tumor antigen specific T cells with enhanced percentage (e.g., up to 50%) of RGS5-specific T cells. Three pairs of RGS5-specific TCRα and TCRβ genes were identified by single-cell sequencing of the tumor antigen-specific T cell samples.

Cells Preparation

FIGS. 15A-15B provide an overview of the protocols used in this example. Briefly, a sample of the co-culture containing tumor antigen-specific T cells on Day 32 using Method 2 or on Day 30 using Method 2m described in Example 2 was frozen to provide a frozen stock of tumor antigen-specific T cells. On Day 1 of this experiment, a sample of the frozen stock of tumor antigen-specific T cells was thawed, and co-cultured with LCL cells (an APC cell line) loaded with RGS5-OLP5 (1 μg/mL) in a co-culture medium comprising a cocktail of cytokines (IL-2, IL-7, IL-15), an anti-CD3 antibody (OKT-3) and RGS5-OLP5 until Day 9, with or without feeder cells. The ratio between the tumor antigen-specific T cells and the antigen-loaded LCL cells was about 4:1. The ratio between the tumor antigen-specific T cells, the feeder cells, and the antigen-loaded LCL cells was about 4:4:1. On Days 9 and 16, the cycles were repeated by co-culturing the tumor antigen-specific T cells with antigen-loaded LCL cells with or without the presence of feeder cells.

PBMCs and dendritic cells may be used in place of the LCL cells to provide antigen-loaded APCs. The APCs may be loaded with a single tumor antigen peptide, an epitope fragment of a single tumor antigen peptide, a pool of tumor antigen peptides, or a pool of epitope fragments of tumor antigen peptides.

Proliferation Assay

Cell proliferation was assessed using cell samples from Days 1, 9, 16 and 23 of the co-culture by methods described in Example 2.

Figure 16:
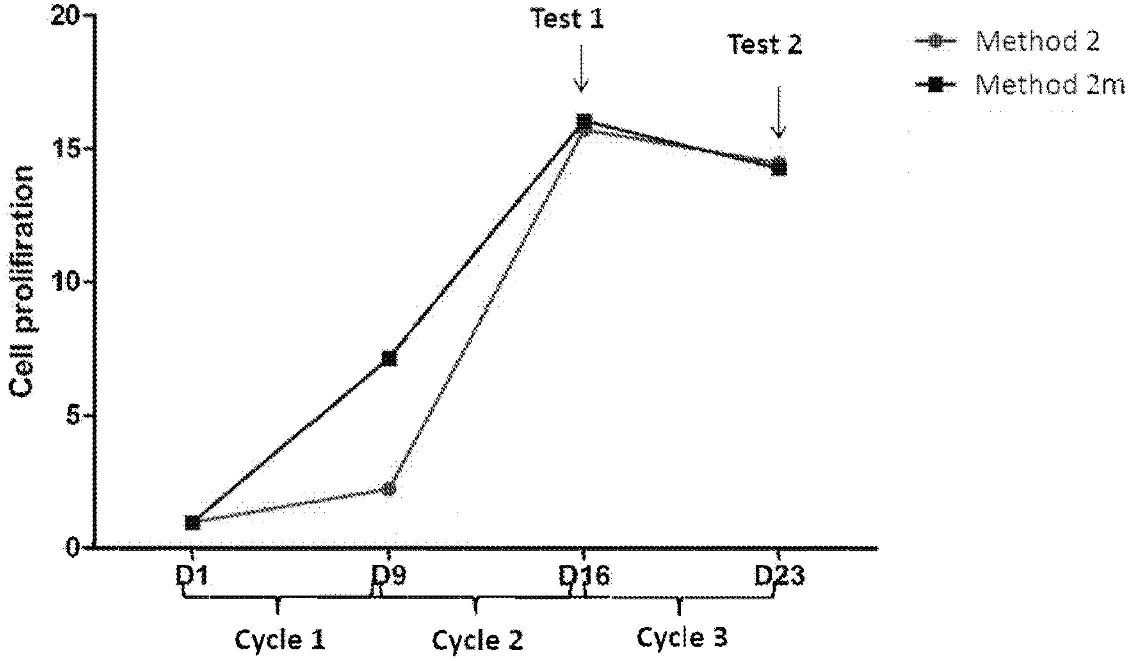
FIG. 16 shows cell proliferation at various time points in the preparation of tumor antigen-specific T cells.

As shown in FIG. 16, cells continued to proliferate when a thawed population of frozen tumor antigen-specific T cells was co-cultured with antigen-loaded LCL cells with or without feeder cells until Day 16. The total cell numbers decreased by Day 23.

Cytokine Production by Tumor Antigen-Specific T Cells

The IFNγ production levels by tumor antigen-specific T cells in various co-culture samples were determined by methods described in Example 2.

Figure 17A:
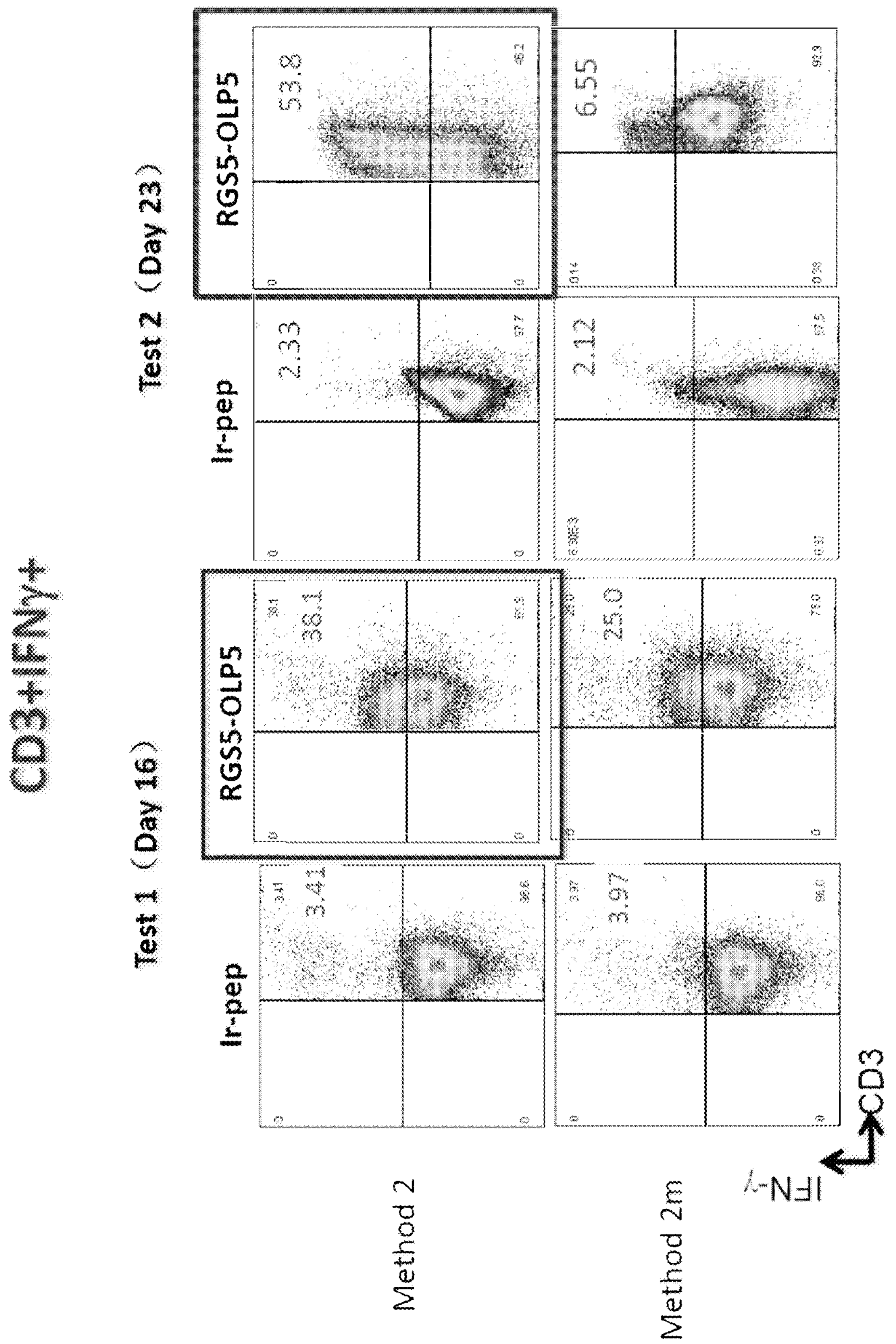
FIG. 17A shows the percentages of $IFN\gamma^+CD3^+$ tumor antigen-specific T cells in various co-culture samples.
Figure 17B:
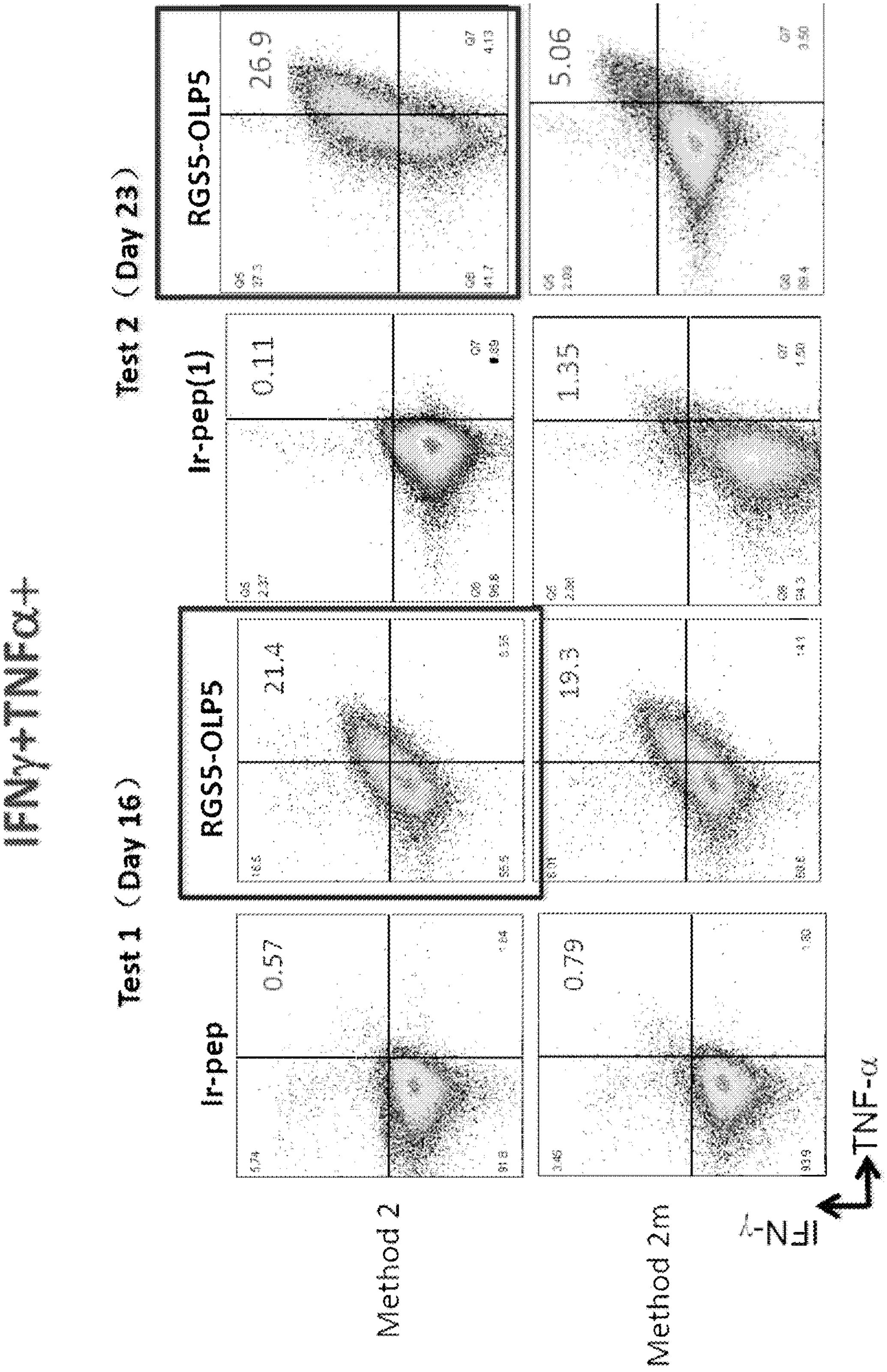
FIG. 17B shows the percentages of $IFN\gamma^+TNF\alpha^+$ tumor antigen-specific T cells in various co-culture samples.

FIG. 17A shows the percentages of tumor antigen-specific T cells in the cell samples as determined by assessing IFNγ$^+$CD3$^+$ cells in response to stimulation by the RGS5-OLP5 peptide. On Day 16, the co-culture derived from a frozen stock of tumor antigen-specific T cells using Method 2m contained about 38.6% tumor antigen-specific T cells that produced IFNγ in response to stimulation by the RGS5-OLP5 peptide. Notably, on Day 23, the co-culture derived from a frozen stock of tumor antigen-specific T cells using Method 2m contained about 53.8% tumor antigen-specific T cells that produced IFNγ in response to stimulation by the RGS5-OLP5 peptide. The co-cultures derived from a frozen stock of tumor antigen-specific T cells using Method 2 yielded lower percentages of tumor antigen-specific T cells that produced IFNγ in response to stimulation by the RGS5-OLP5 peptide on Day 16 and Day 23. Consistent results were obtained by assessing IFNγ$^+$TNFα$^+$ cells (FIG. 17B). These results suggest that repeated stimulation of the tumor antigen-specific T cells with APCs loaded with a tumor antigen peptide could enhance percentage of T cells that specifically respond to the tumor antigen peptide.

Next-Generation Sequencing of Tumor Antigen-Specific T Cells

Three samples of the tumor antigen-specific T cells derived from a frozen stock of tumor antigen-specific T cells prepared using Method 2m were prepared and subjected to bulk and single-cell TCRα and TCRβ amplification coupled to next-generation sequencing using the IPAIR™ technology (iRepertoire, Inc.). The three samples are: (1) tumor antigen-specific T cells stimulated by an irrelevant peptide; (2) tumor antigen-specific T cells stimulated by RGS5-OLP5; and (3) $INF\gamma^+CD3^+$ tumor antigen-specific T cells stimulated by RGS5-OLP5 enriched by beads. As a control, a PBMC sample from the same patient was also subjected to the same next-generation sequencing analysis.

Figure 18A:
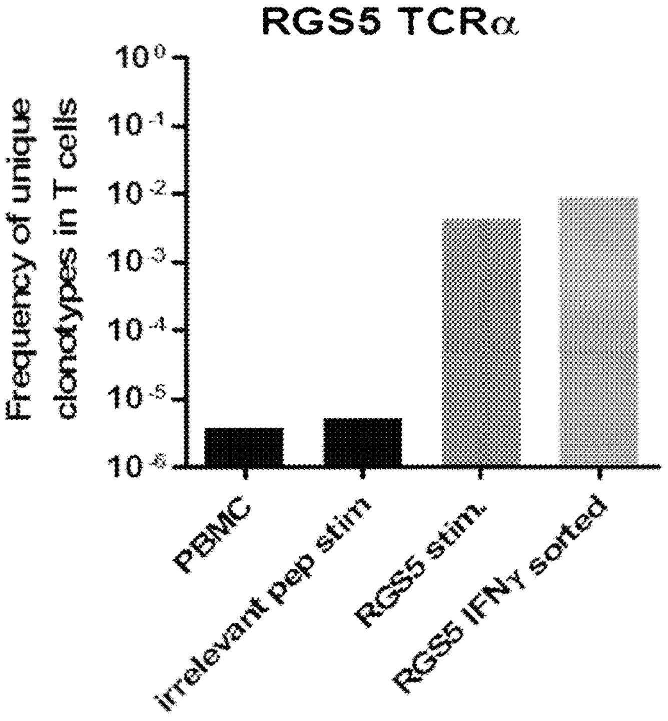
FIG. 18A-18B show the frequencies of unique clonotypes of TCRα and TCRβ in various T cell samples determined by next-generation sequencing.
Figure 18B:
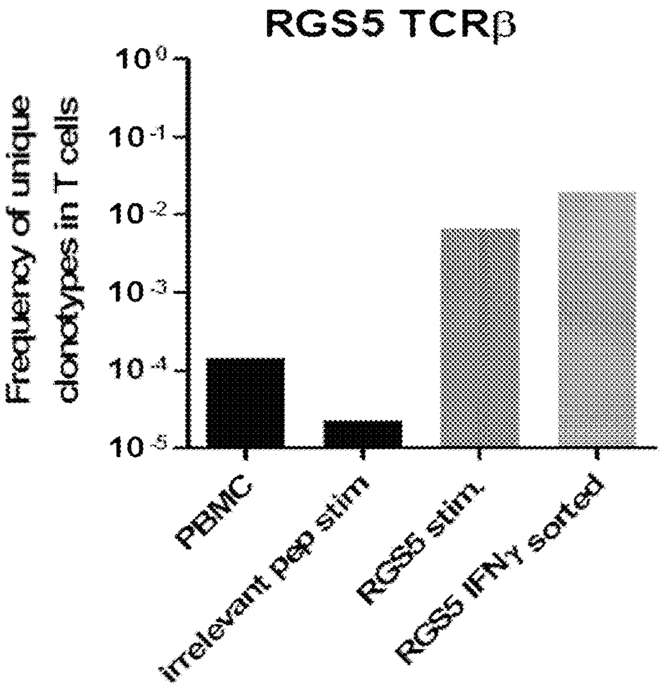

FIGS. 18A and 18B show the frequency of unique clonotypes of TCRα and TCRβ sequences in the various samples. Tumor antigen-specific T cells stimulated by RGS5-OLP5 and INFγ sorted tumor antigen-specific T cells stimulated by RG5-OLP5 have much higher frequency of unique clonotypes of TCRα and TCRβ sequences than the control T cells, i.e., PBMCs and tumor antigen-specific T cells stimulated by an irrelevant peptide.

Figure 19:
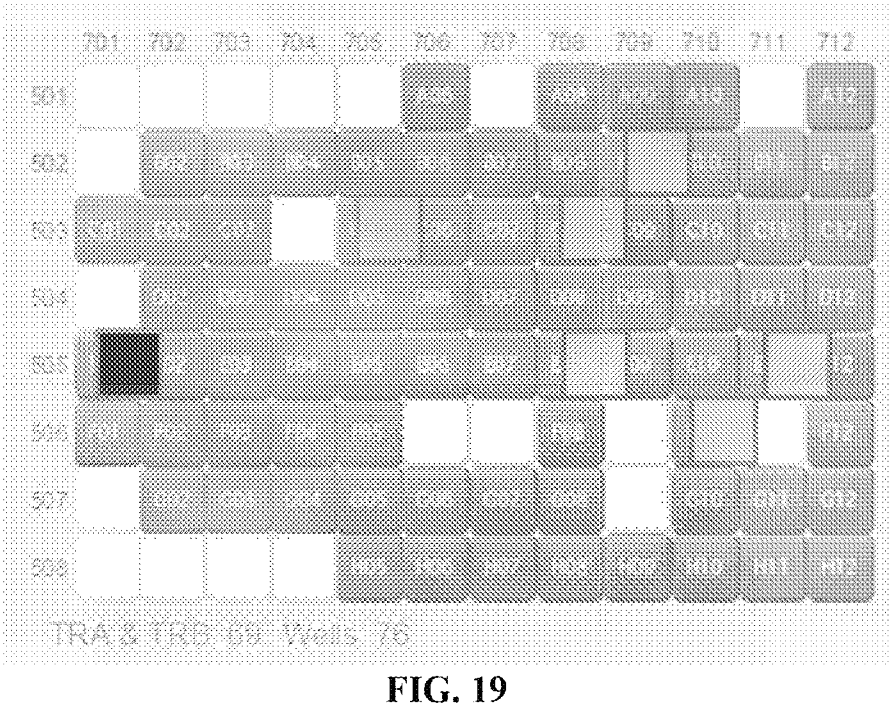
FIG. 19 shows results of TCRα and TCRβ pairing results using iPair Analyzer determined by single-cell sequencing. Wells in a 96-well plate giving rise to successfully paired TCRα and TCRβ sequences are shown in gray and marked with the well position number. Wells giving rise to only TCRβ sequences are shown in light gray and wells giving rise to only TCRα sequences are shown in dark gray.

Notably, using the IPAIR™ Analyzer software, cognate TCRα and TCRβ pairing was achieved for 69 out of 96 single-cell TCRα and TCRβ sequencing samples (FIG. 19). A pair of RGS5-specific TCRα and TCRβ genes (clone 4) was identified from the 96-well plate shown in FIG. 19. Three pairs of RGS5-specific TCRα and TCRβ genes (clones 4-6) from the most predominant clonotypes were identified and synthesized. See Table 1 for detailed information of the exemplary TCR clones. Engineered T cells expressing each pair of RGS5-specific TCRα and TCRβ genes are prepared, and the TCRs are validated by assessing RGS5-specific immune response by the engineered T cells.

Example 4: Validation of RGS5 and HPV18 E7-Specific TCRs

Figure 23:
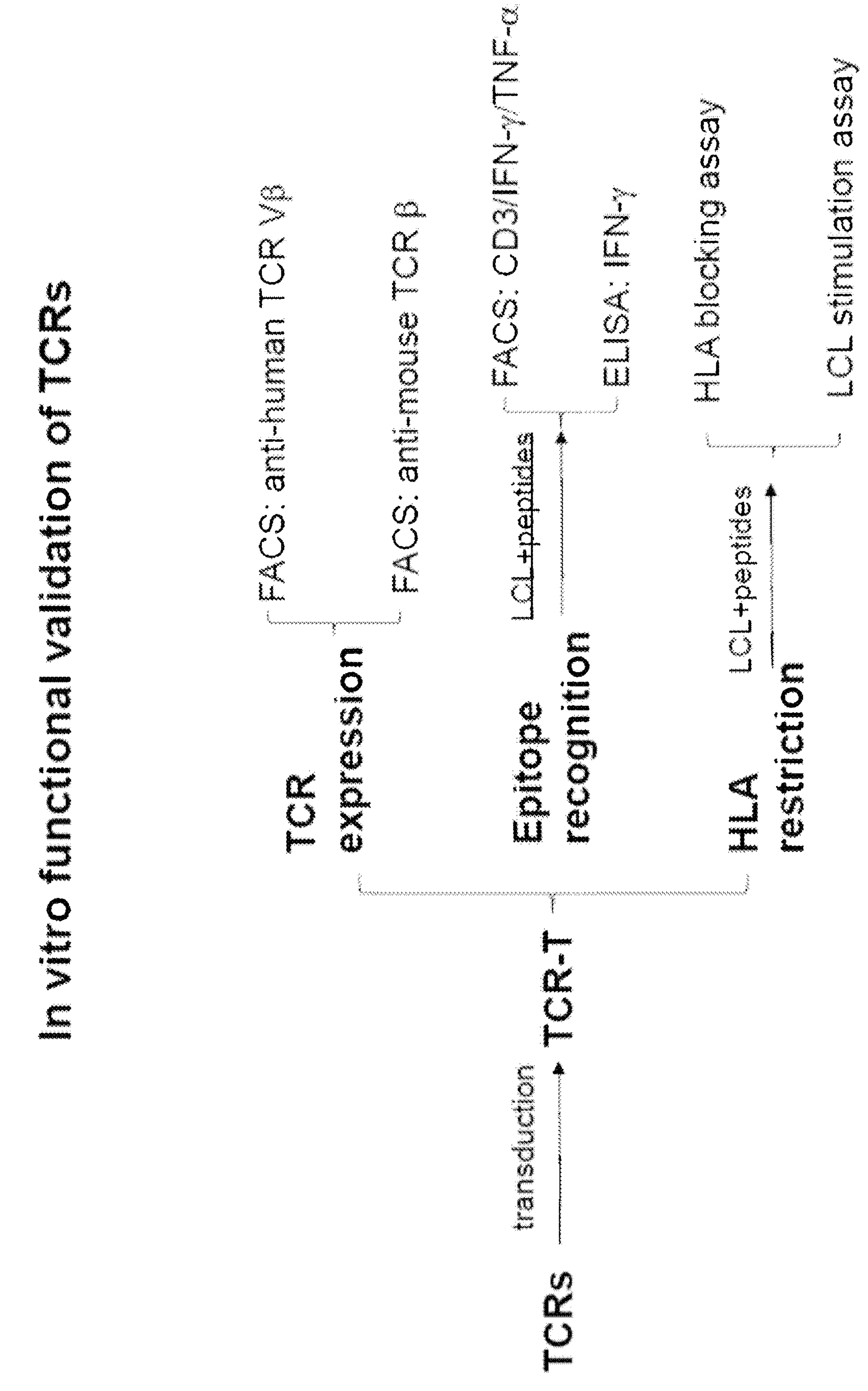
FIG. 23 shows exemplary validation steps for tumor-specific TCRs.

Tumor antigen-specific TCRs identified from Examples 2 and 3 were validated using assays shown in FIG. 23. Five RGS5-specific TCRs and five HPV18-E7-specific TCRs were validated.

Figure 24:
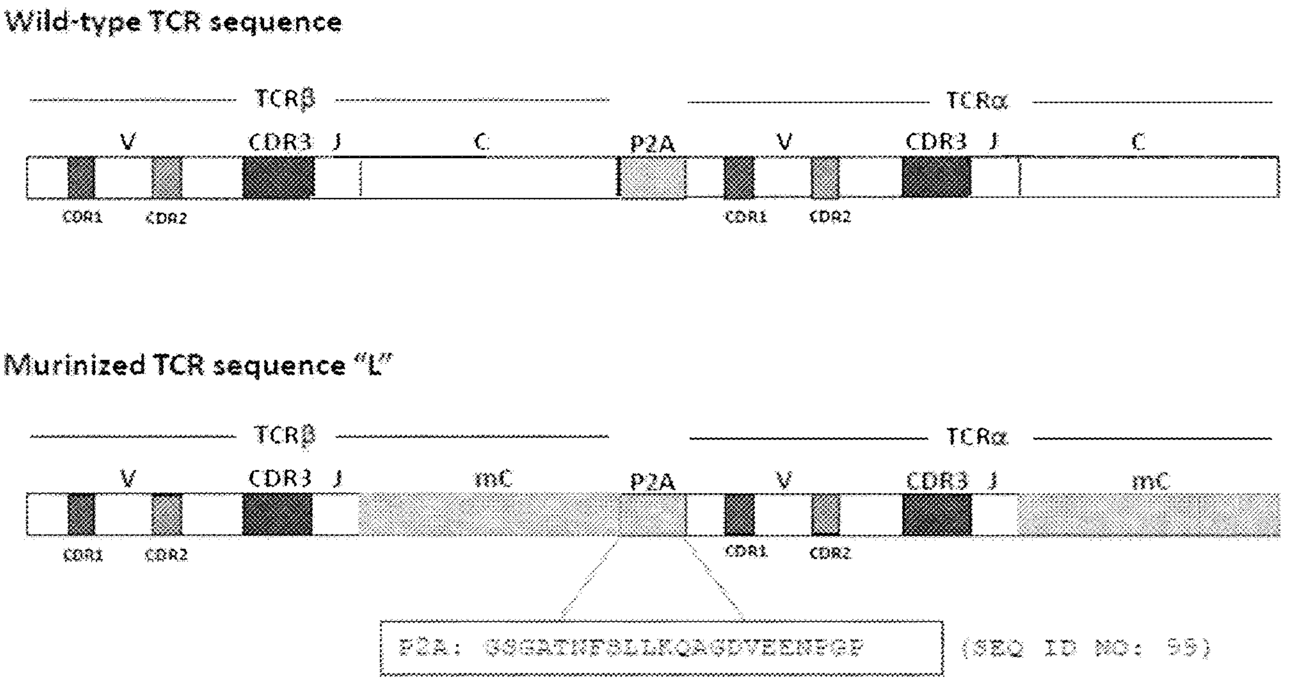
FIG. 24 shows exemplary TCR constructs.
Figure 26A:
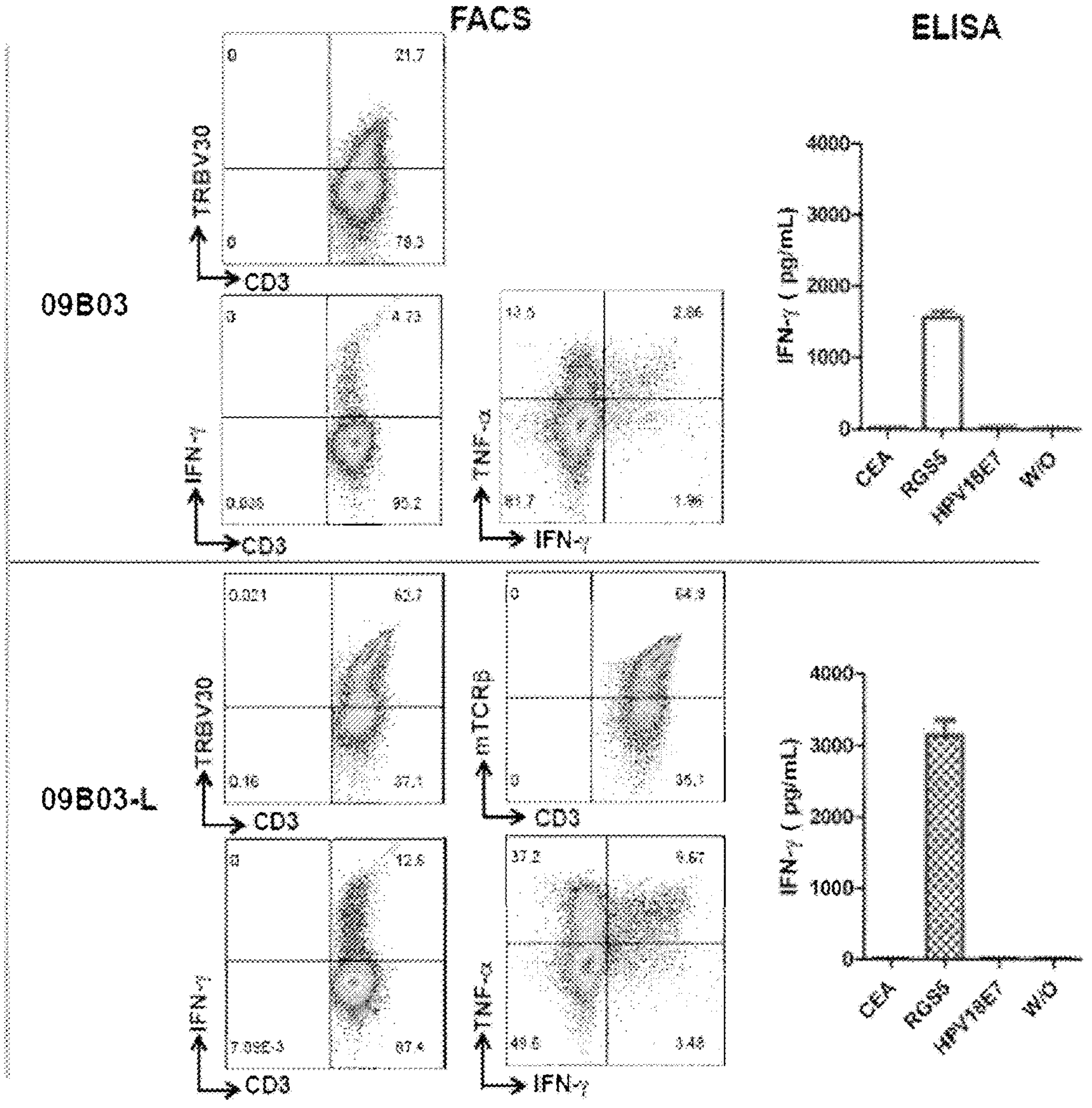
FIGS. 26A-26D show validation results of 09B03 and related TCR constructs. The sequences in FIG. 26B are, from top to bottom: SEQ ID NOs 83, 250, 251, 252, 253, 82 and 82.
Figure 26B:
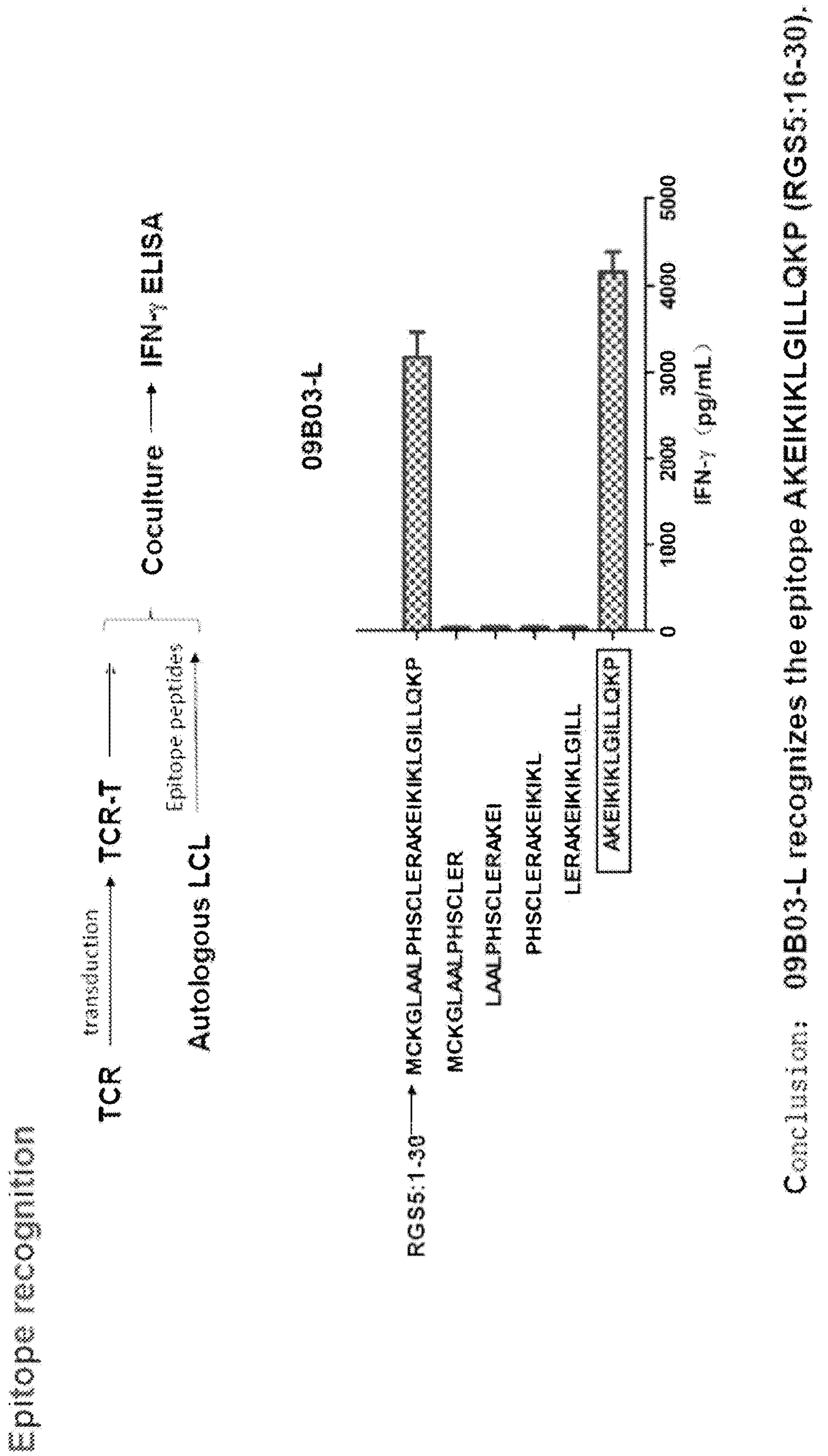
Figure 26C:
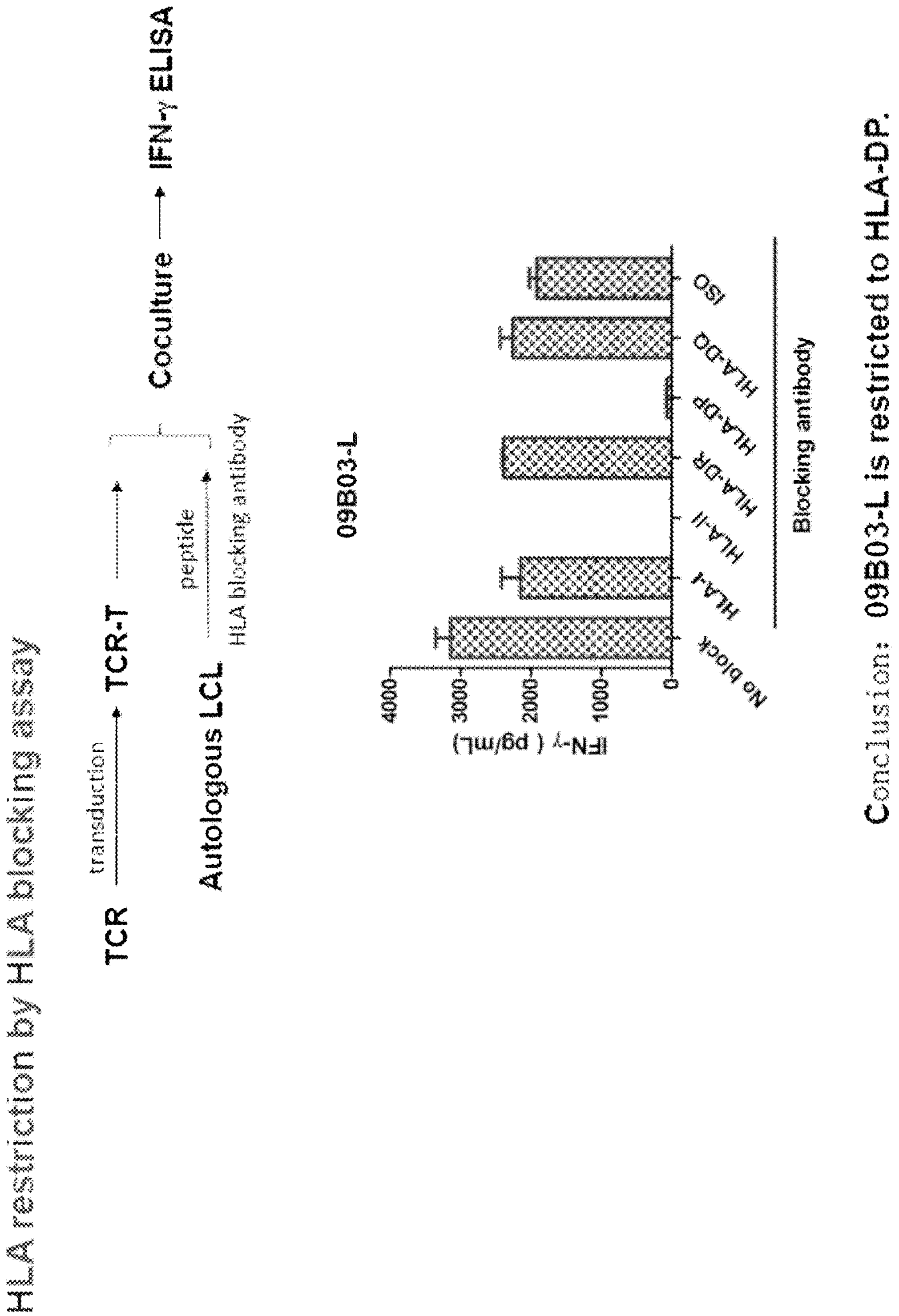
Figure 26D:
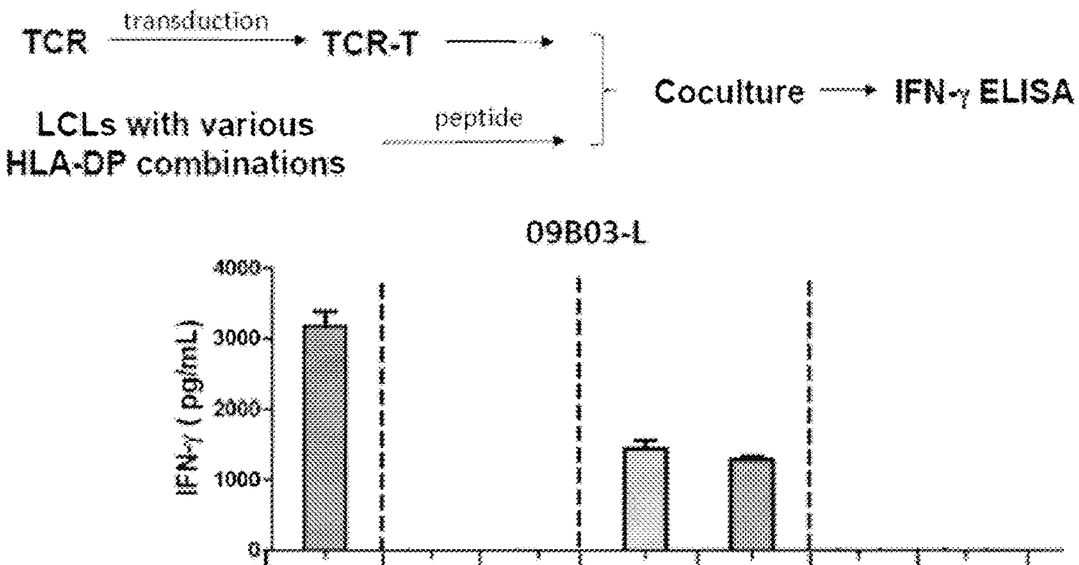
Figure 27A:
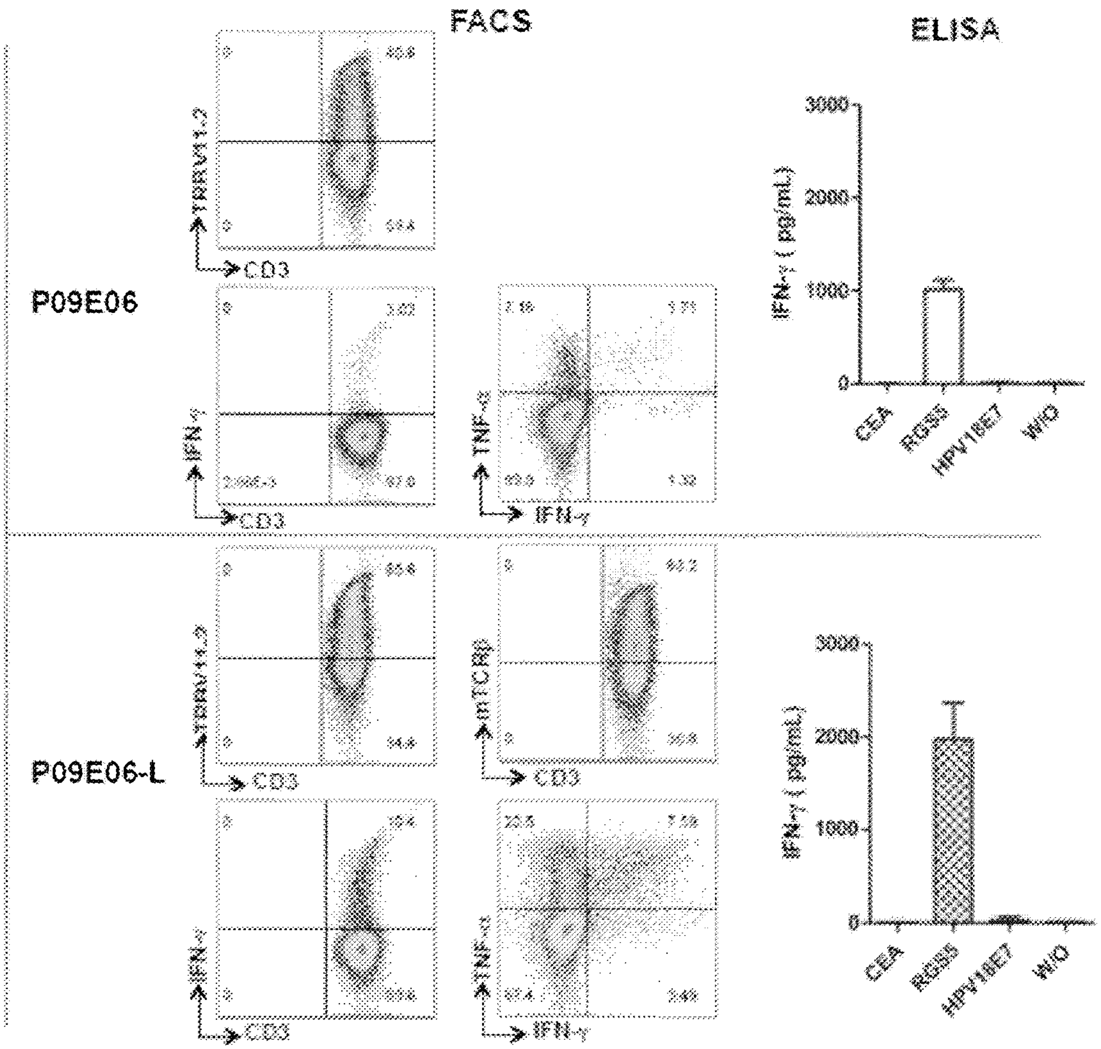
FIGS. 27A-27D show validation results of P09E06 and related TCR constructs. The sequences in FIG. 27B are, from top to bottom: SEQ ID NOs 83, 250, 251, 252, 253, 82 and 82.
Figure 27B:
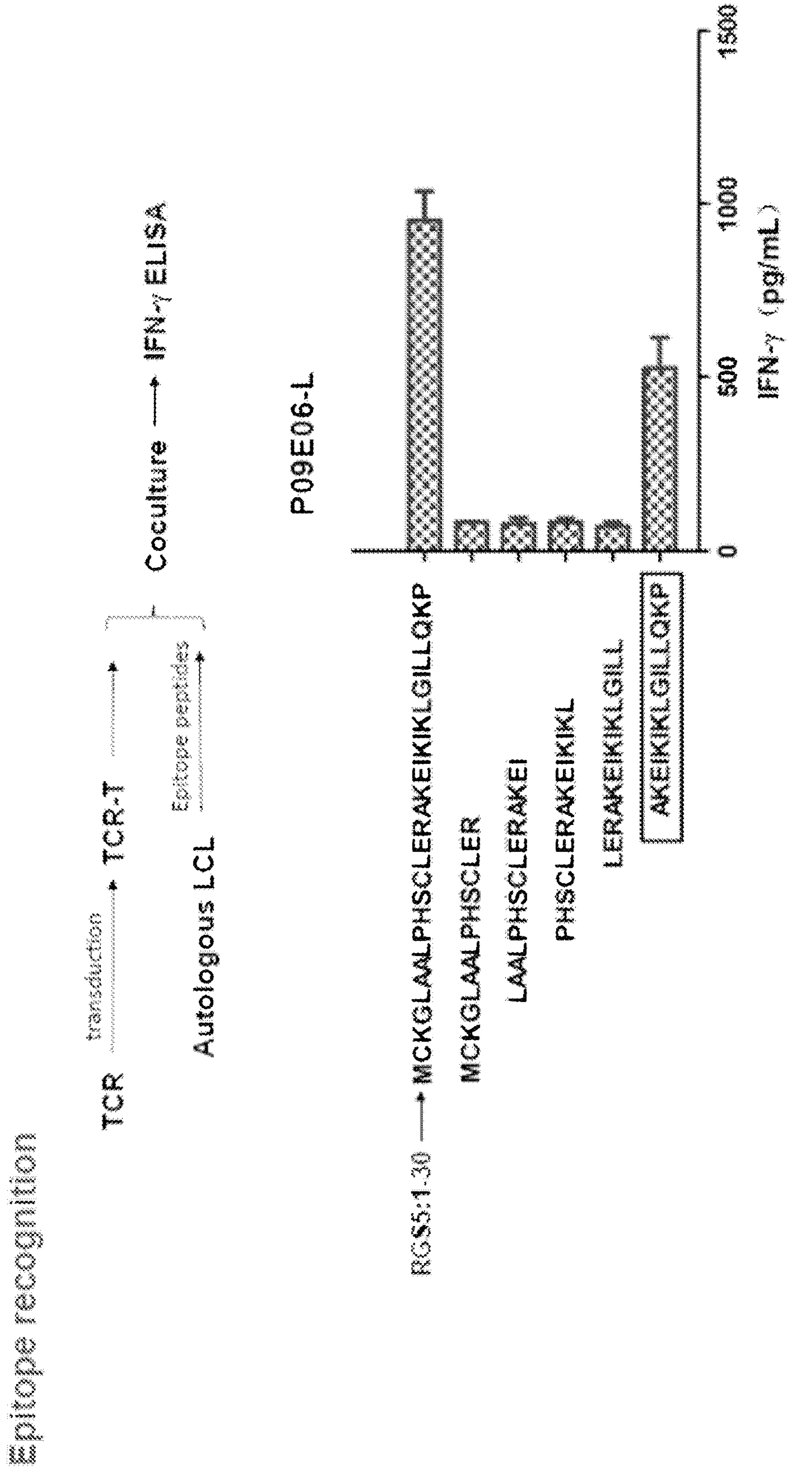
Figure 27C:
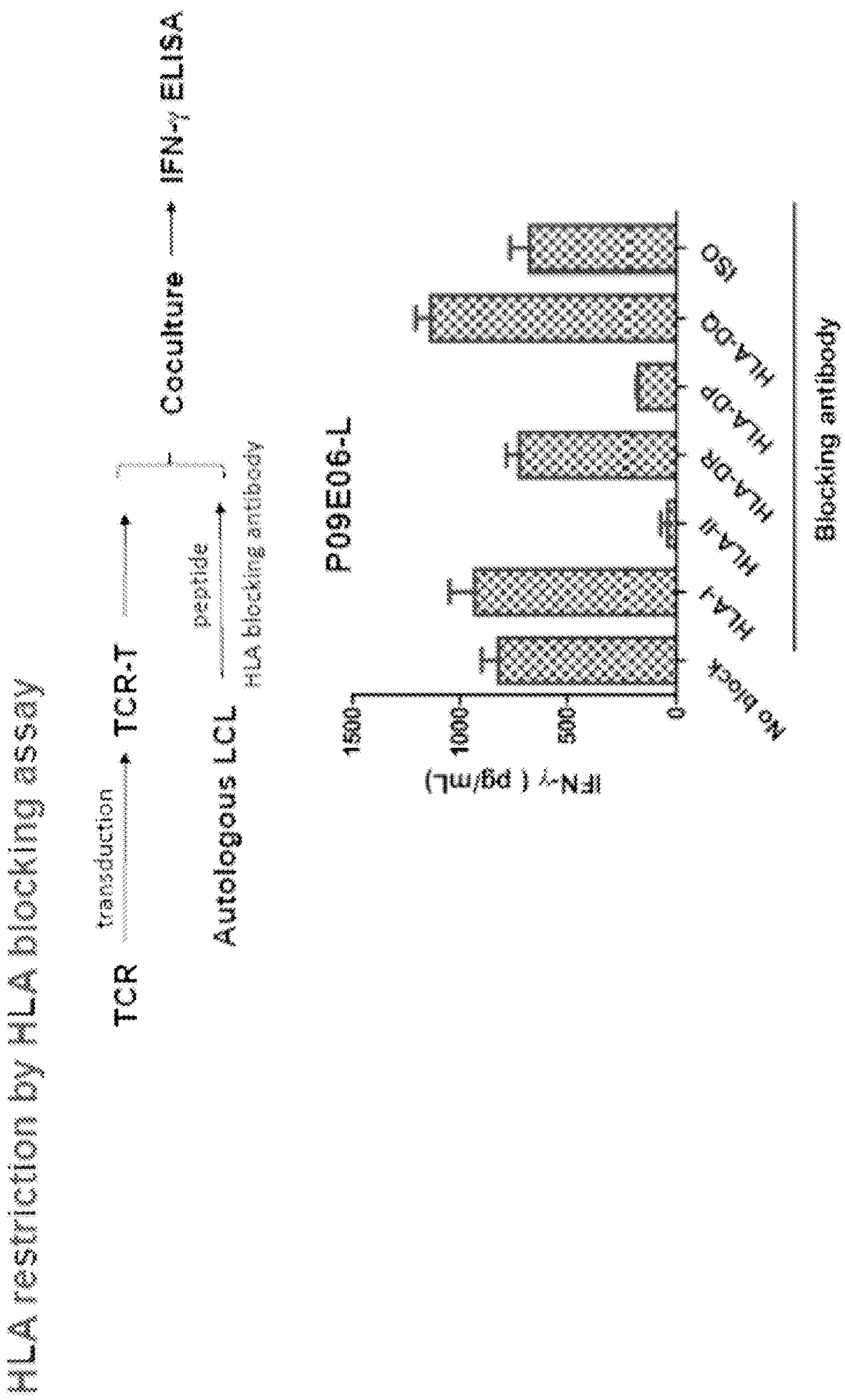
Figure 27D:
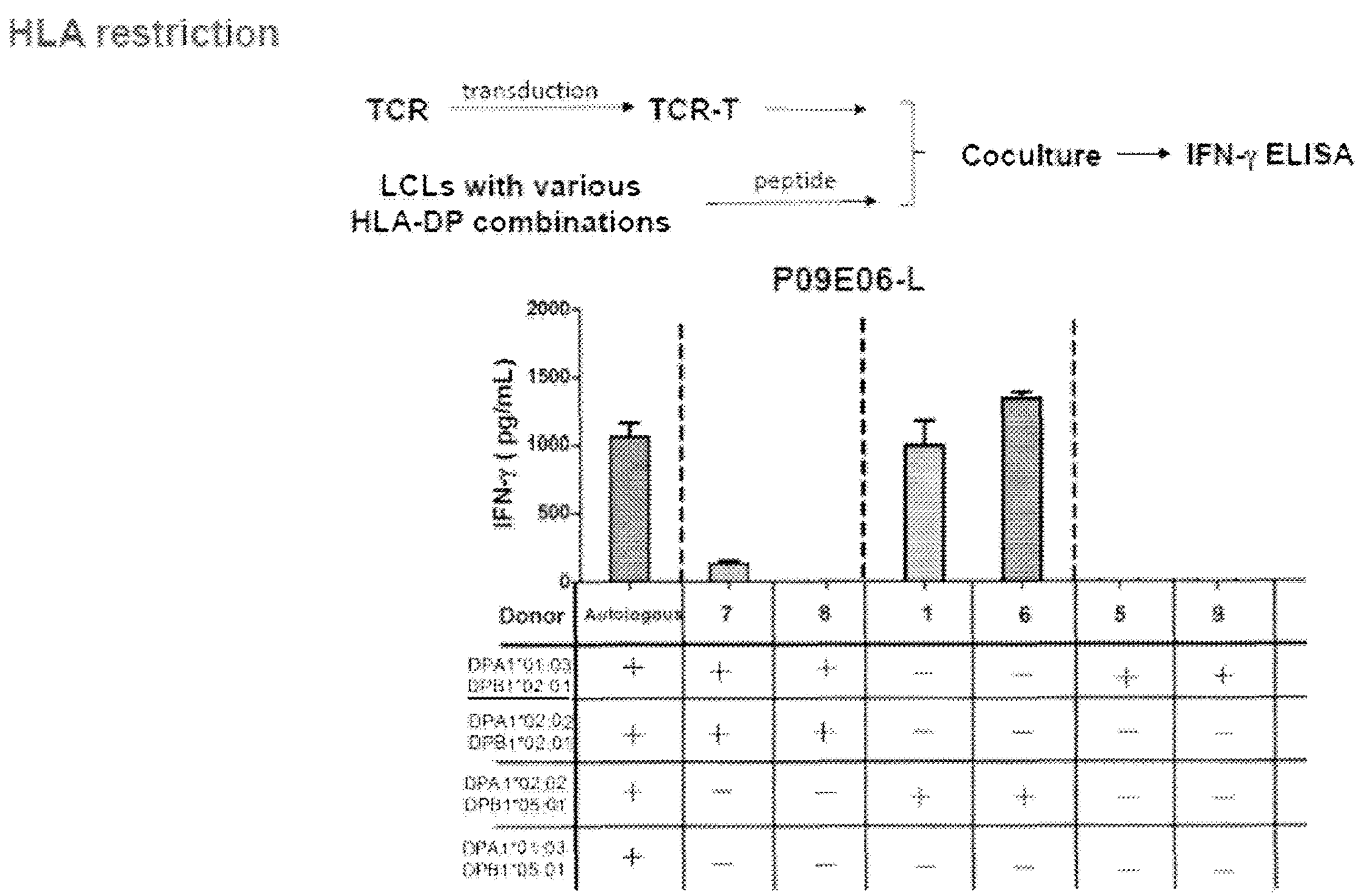
Figure 28A:
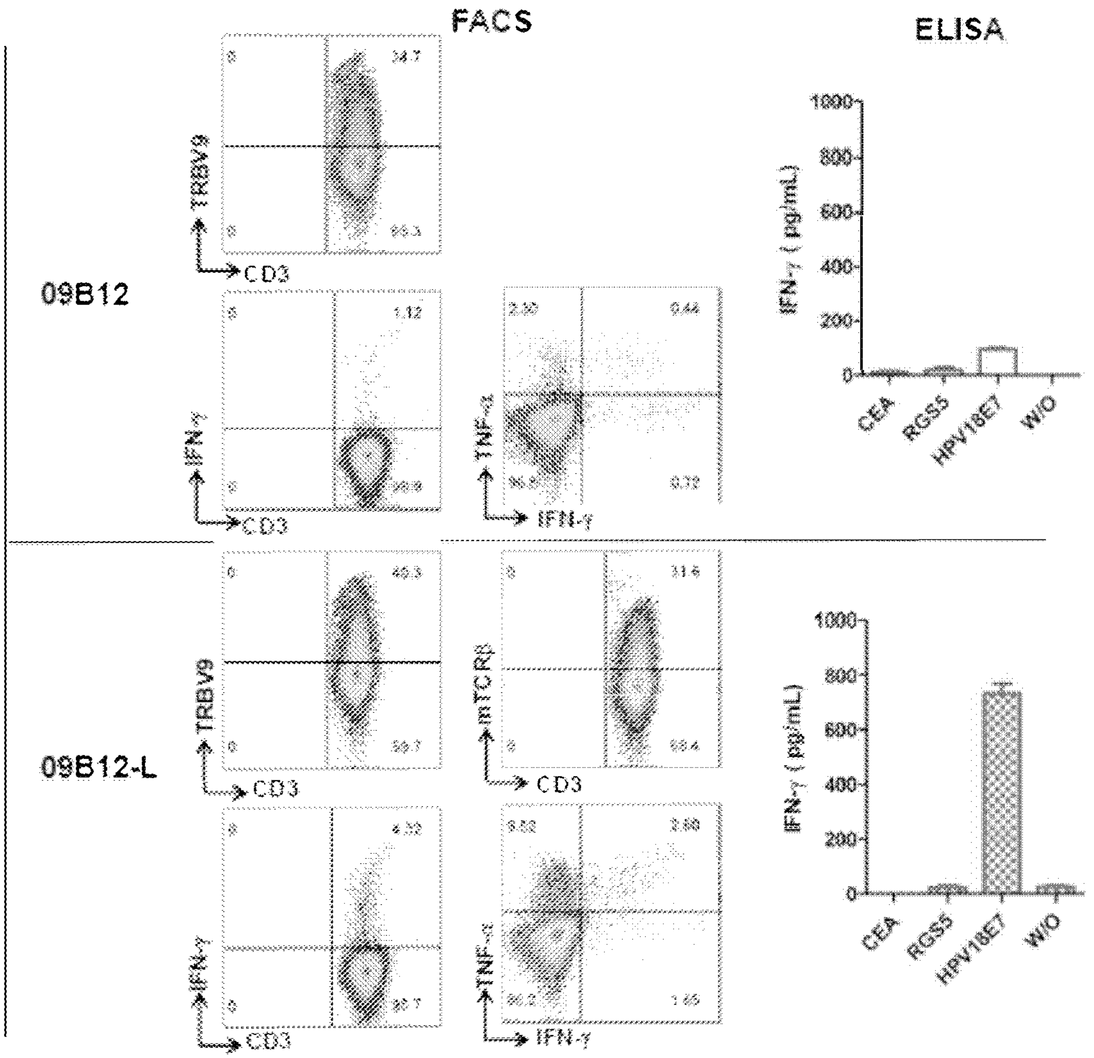
Figure 28B:
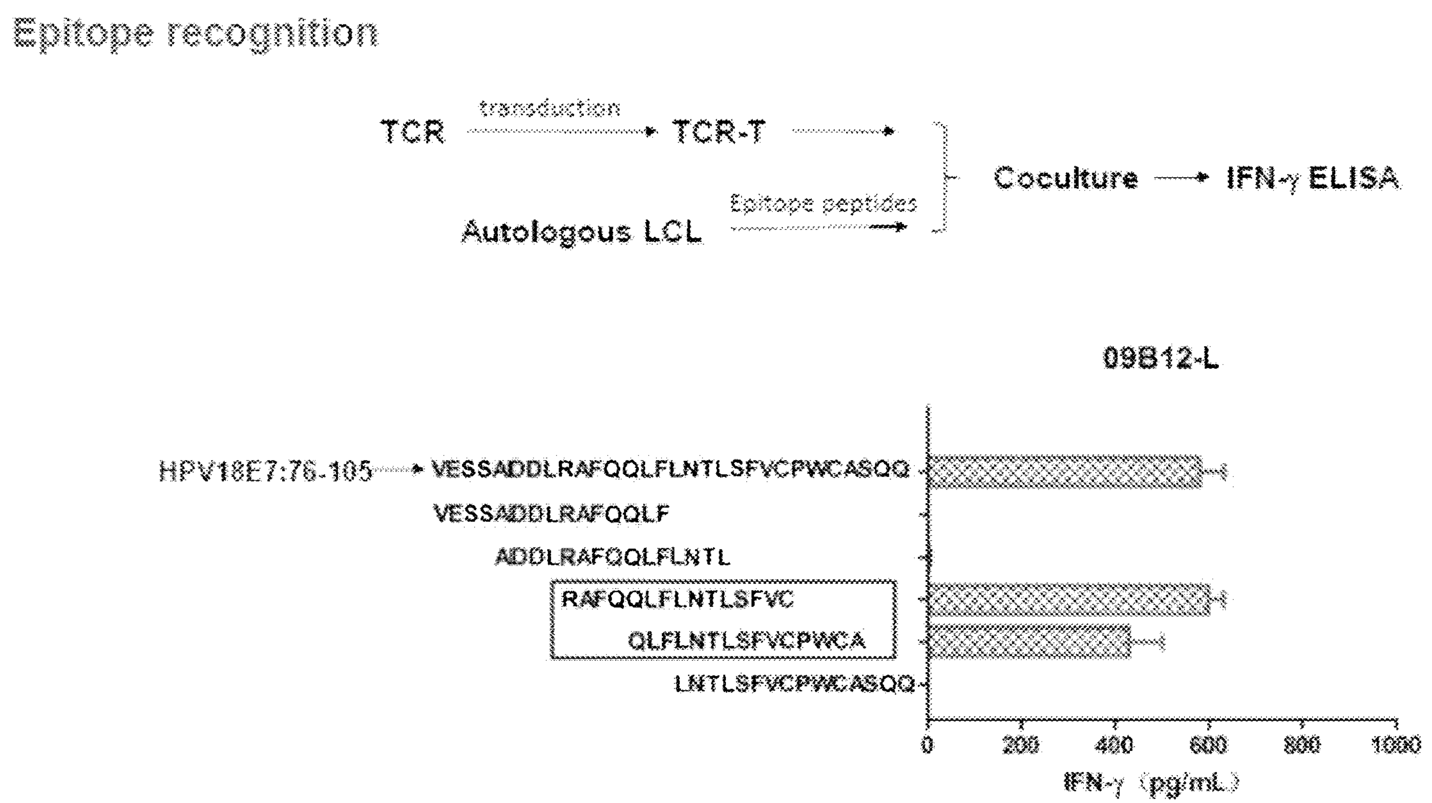
Figure 29B:
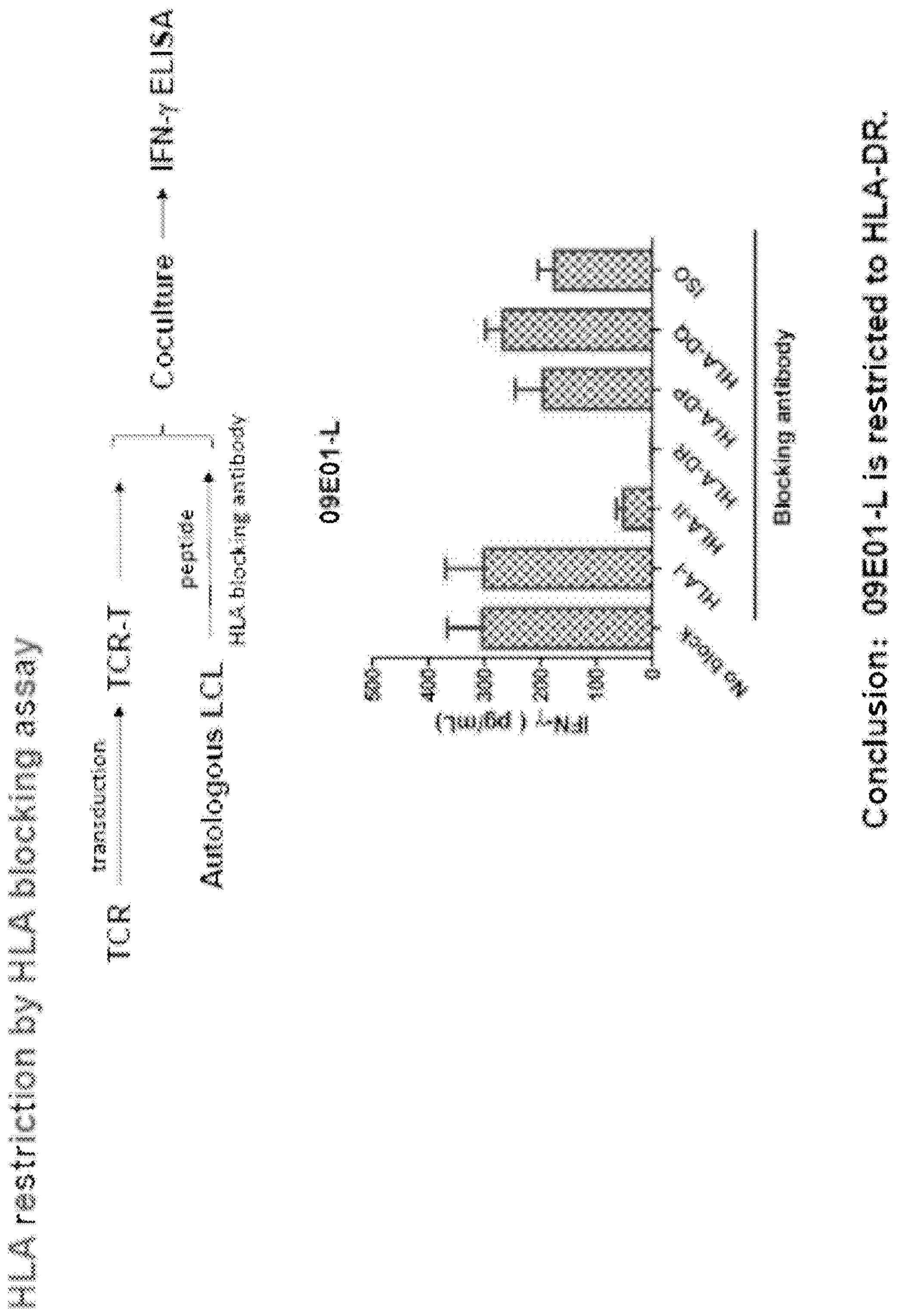
Figure 30A:
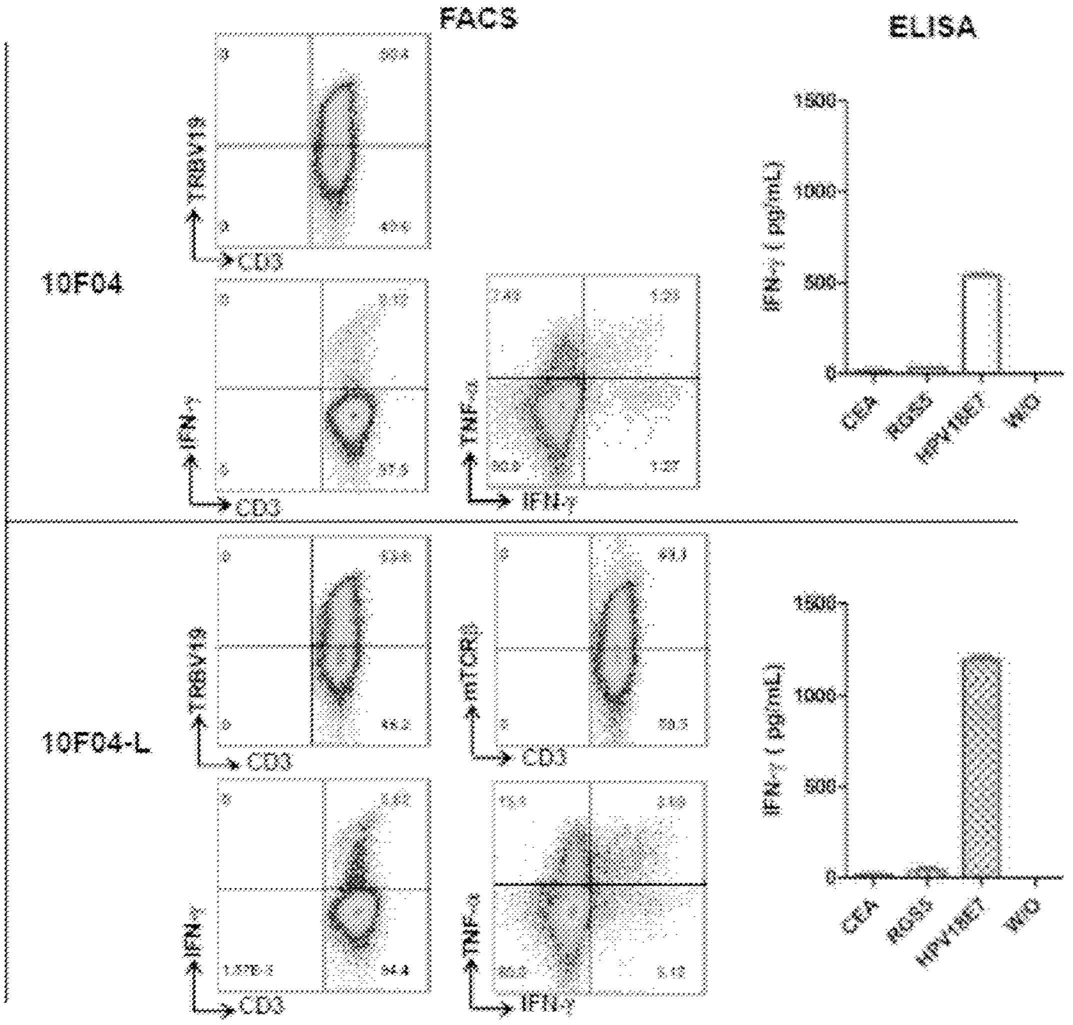
FIGS. 30A-30D show validation results of 10F04 and related TCR constructs. The sequences in FIG. 30B are, from top to bottom: SEQ ID NO 86, and aa1-15, aa5-19, aa9-23, aa13-27, aa16-30 of SEQ ID NO 86, and SEQ ID NO 85.
Figure 30B:
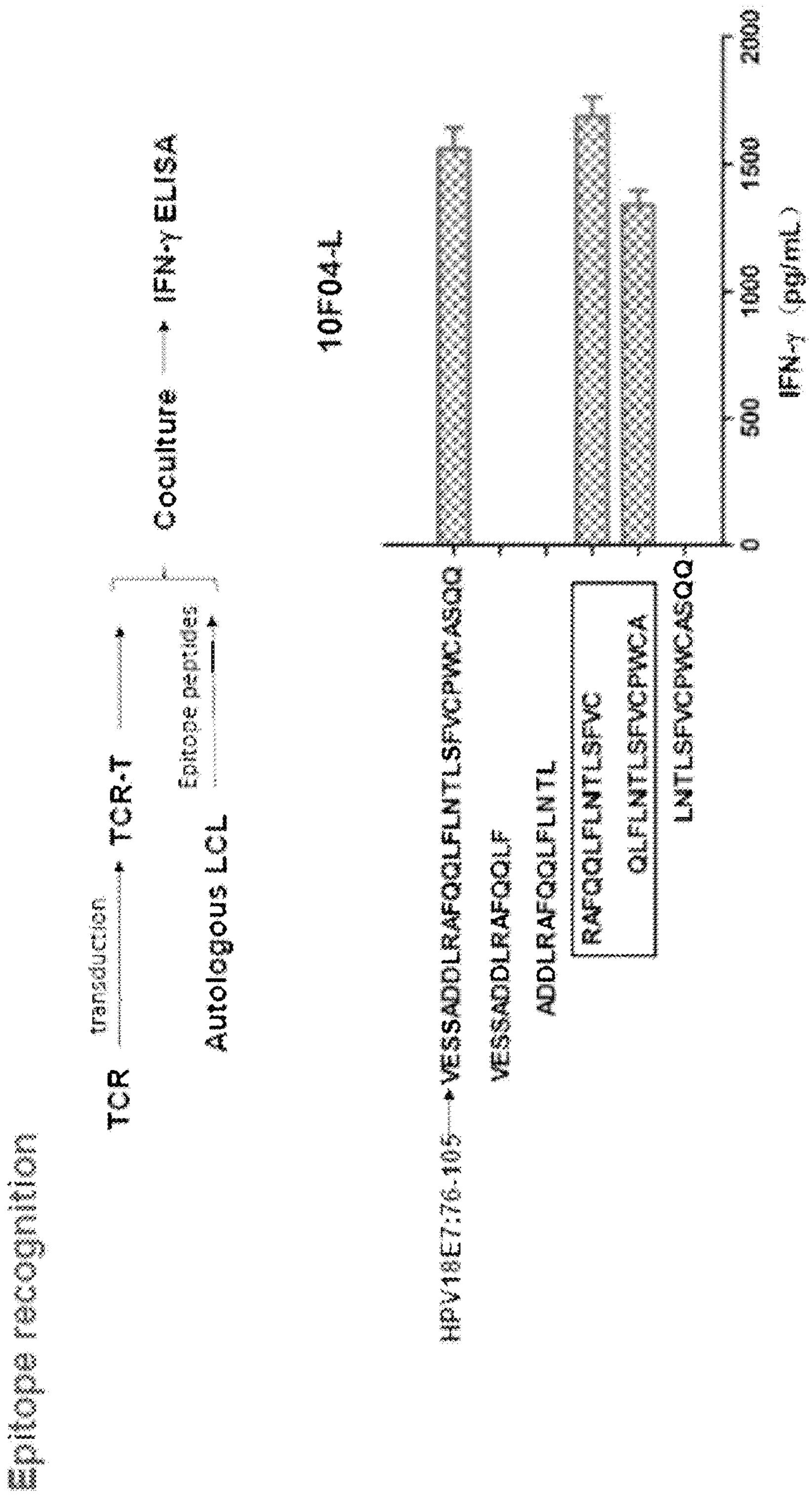
Figure 30C:
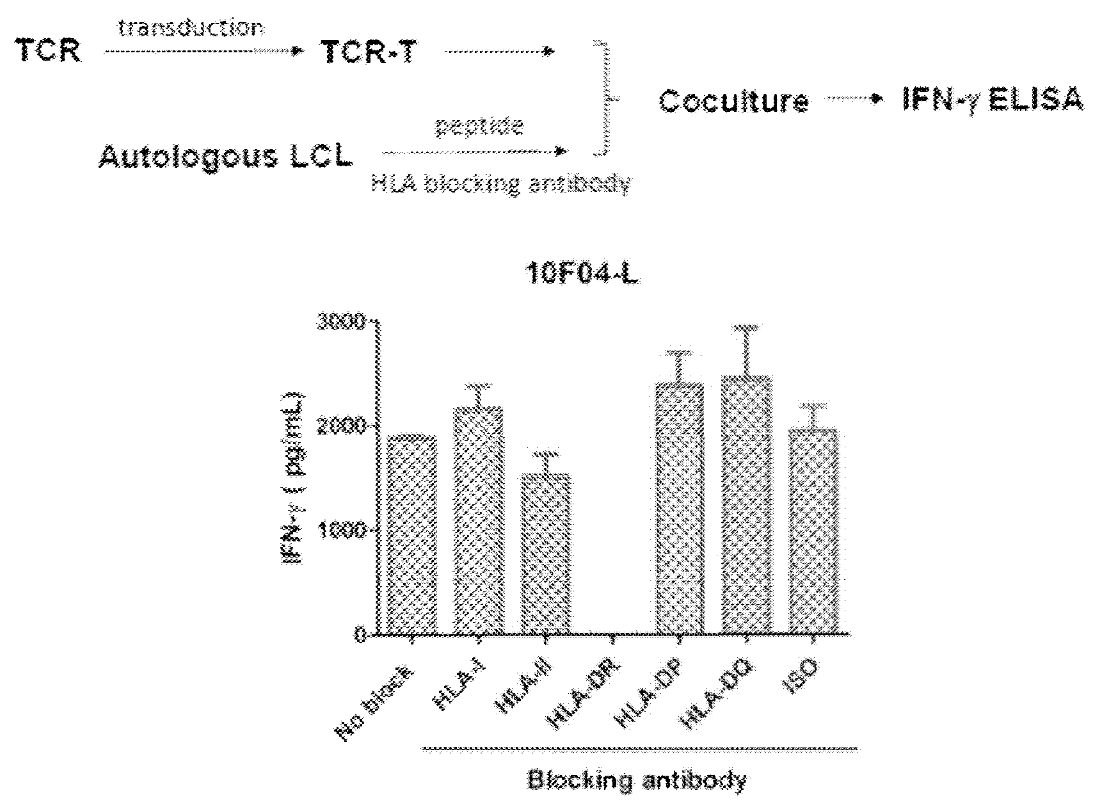
Figure 30D:
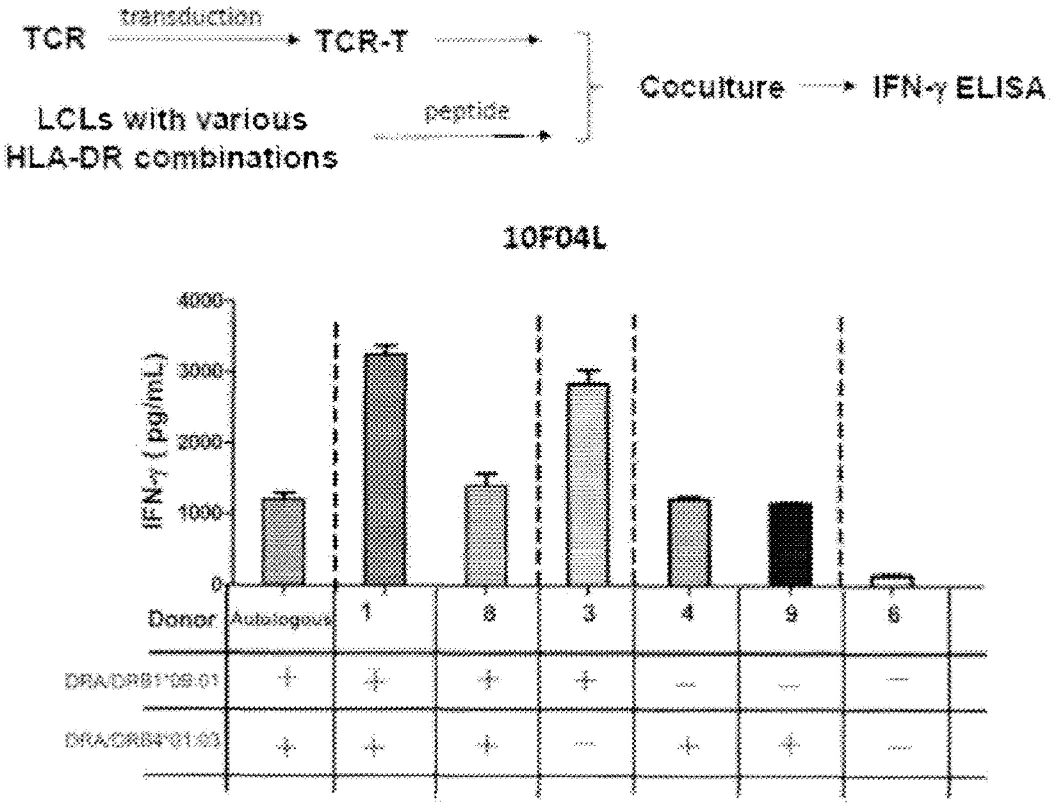
Figure 31A:
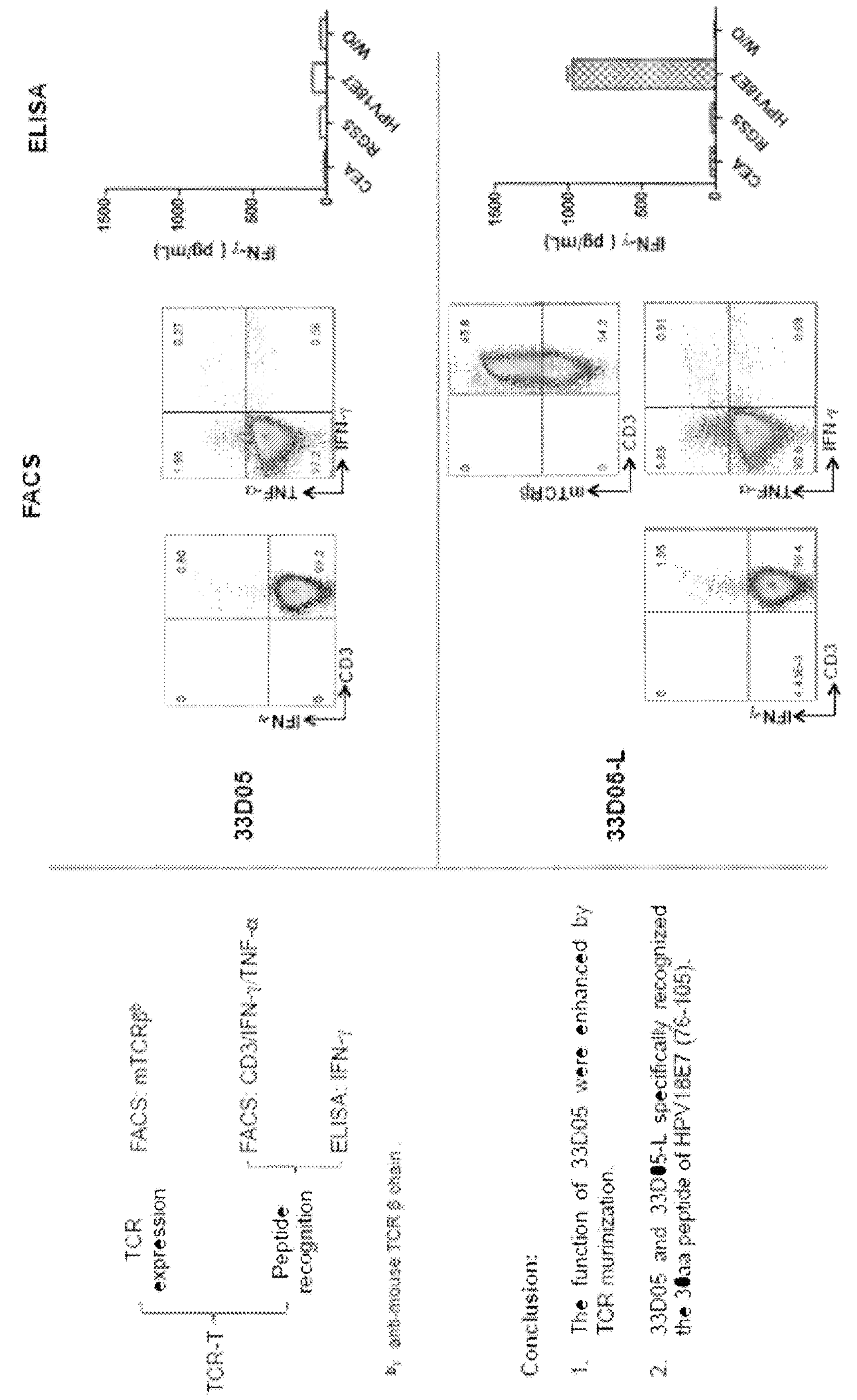
FIGS. 31A-31C show validation results of 33D05 and related TCR constructs.
Figure 31B:
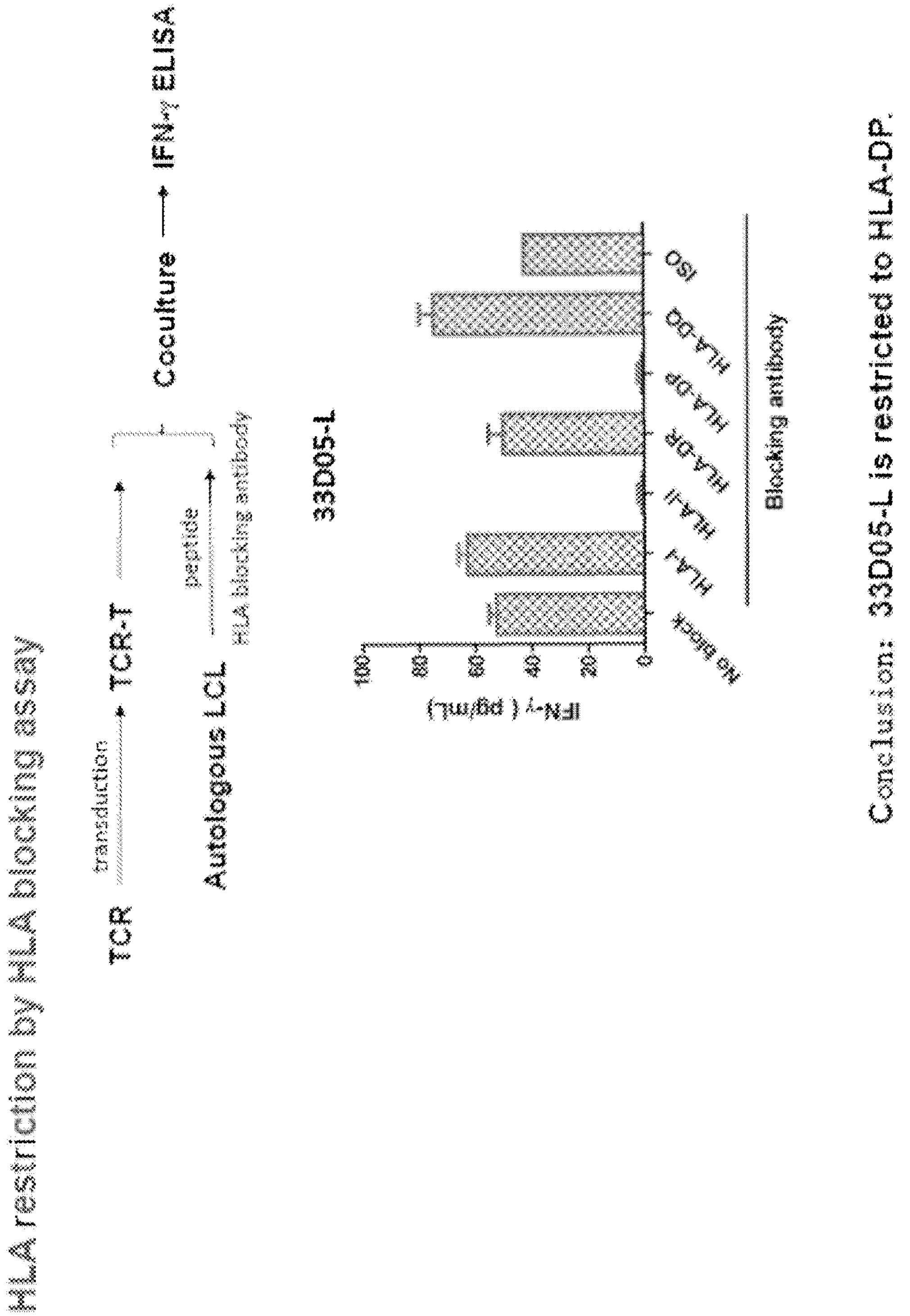
Figure 31C:
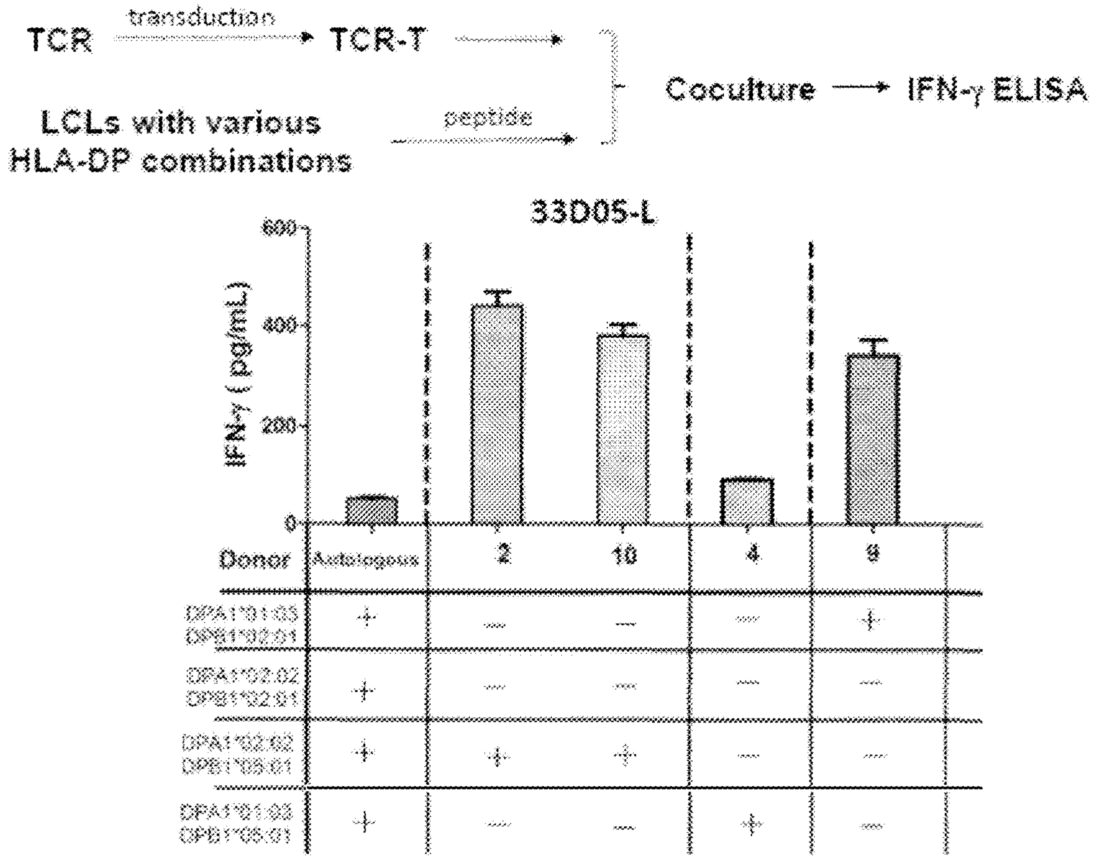
Figure 32A:
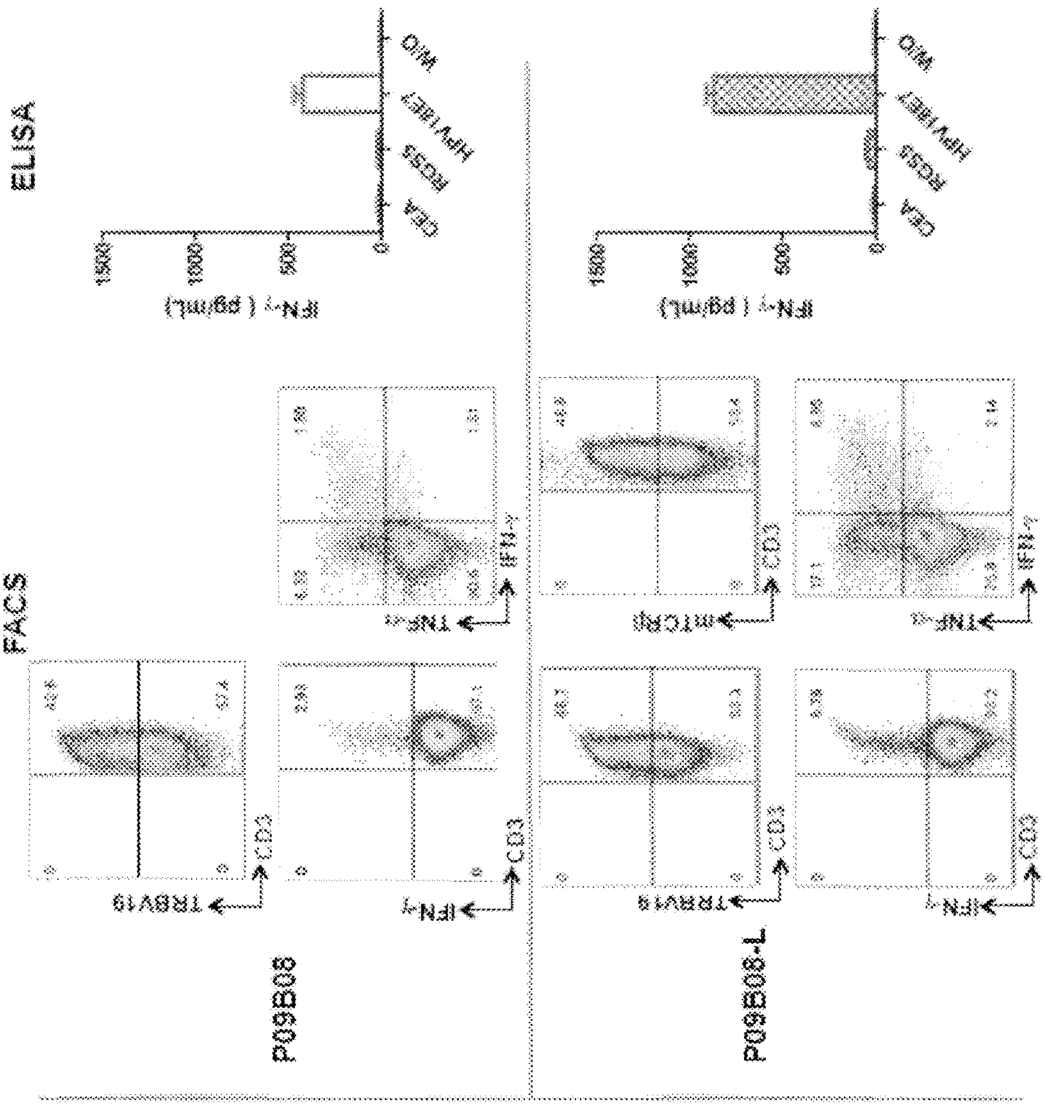
FIGS. 32A-32D show validation results of P09B08 and related TCR constructs. The sequences in FIG. 32B are, from top to bottom: SEQ ID NO 86, and aa1-15, aa5-19, aa9-23, aa13-27, aa16-30 of SEQ ID NO 86, and SEQ ID NO 85.
Figure 32B:
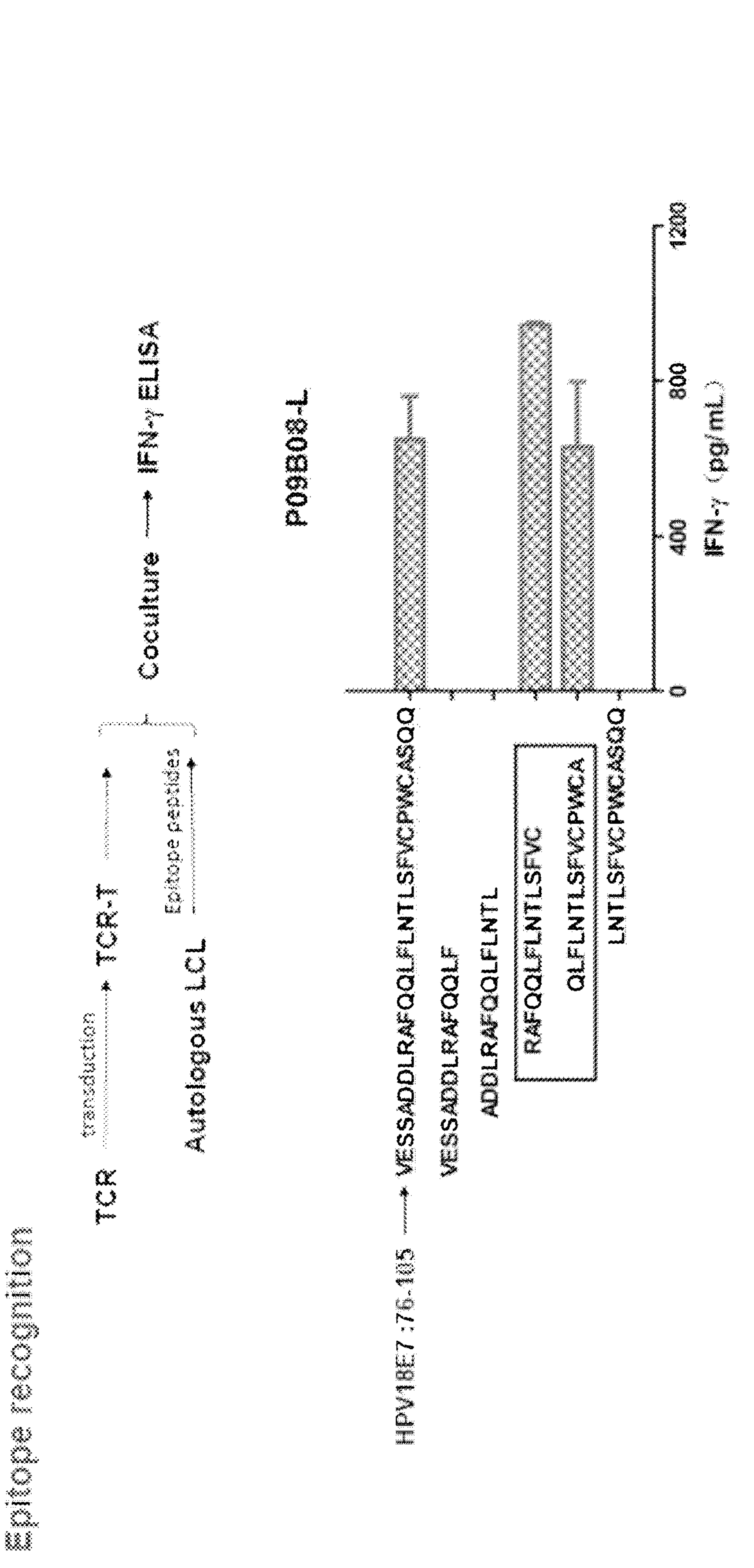
Figure 32C:
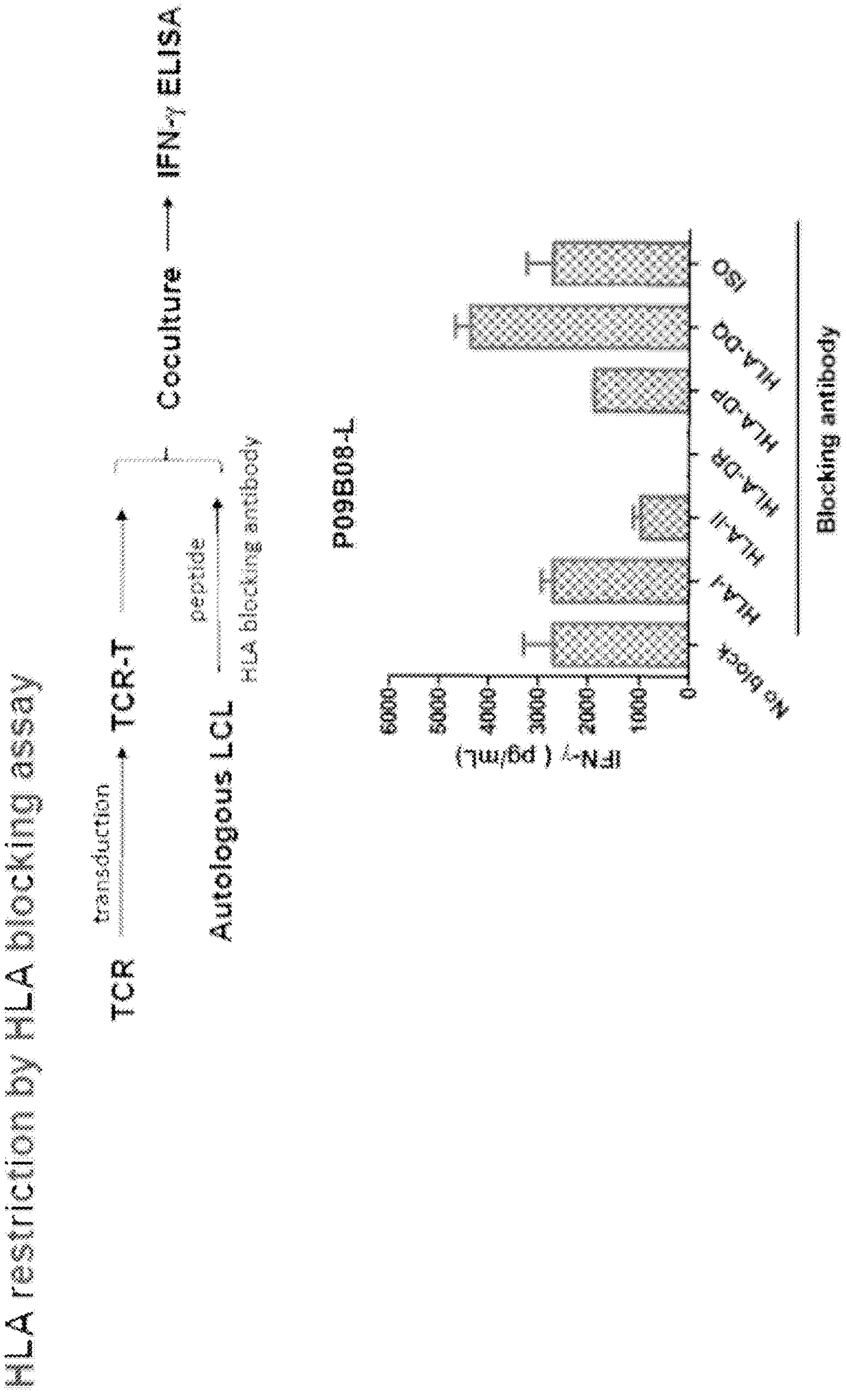
Figure 32D:
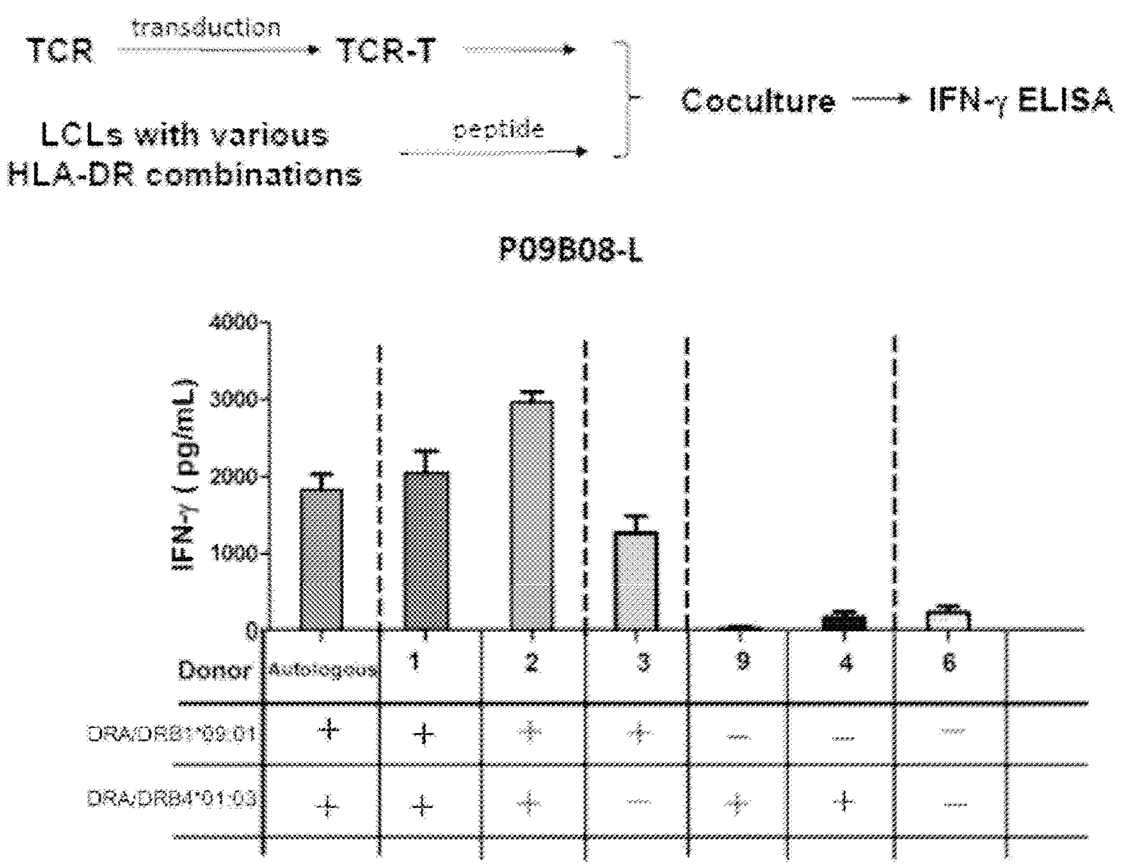
Figure 33A:
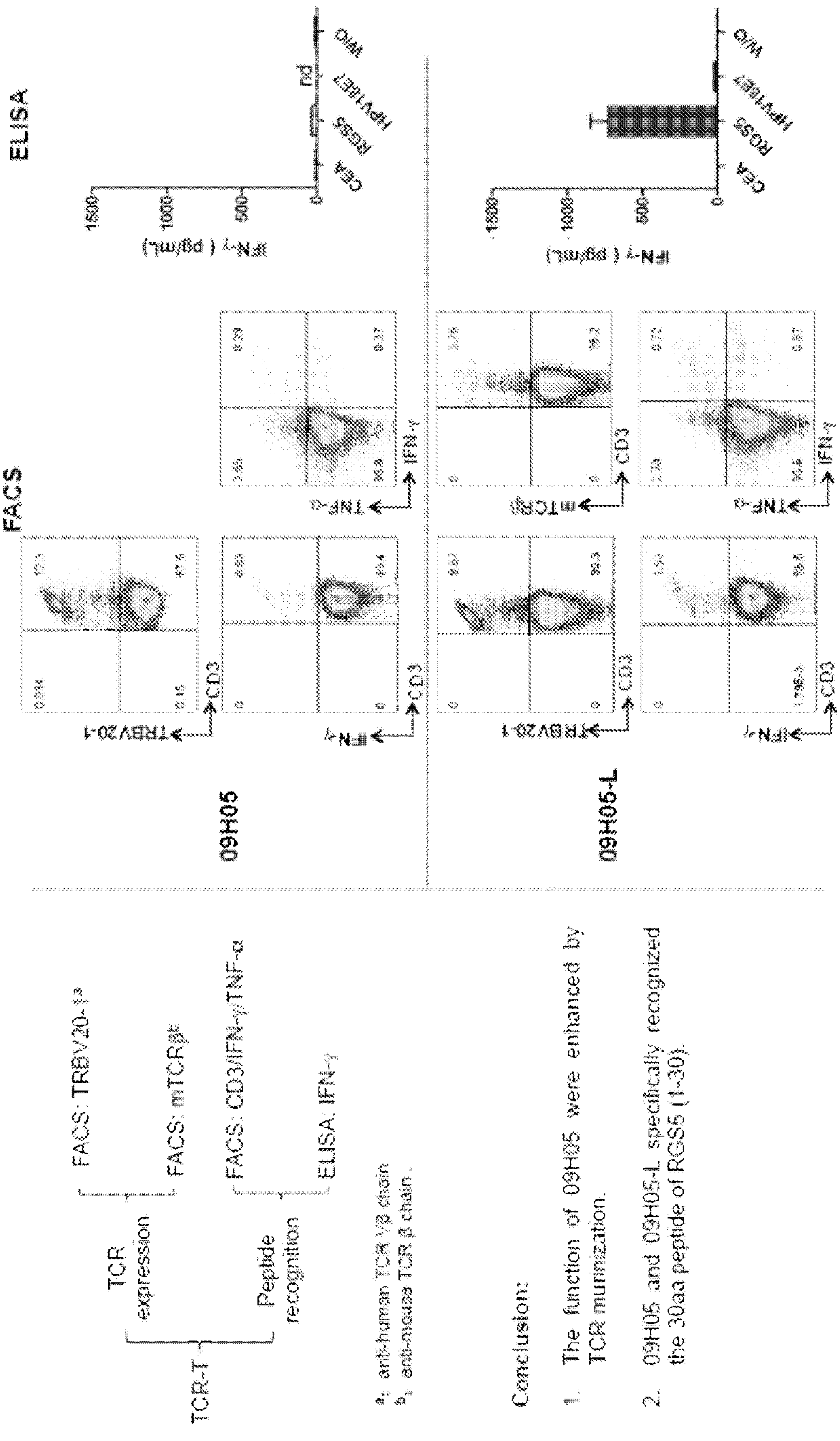
FIGS. 33A-33G show validation results of 09H05 and related TCR constructs. The sequences in FIGS. 33C and 33D are, from top to bottom: SEQ ID NOs 83, 250, 251, 252, 253, 82 and 82.
Figure 33B:
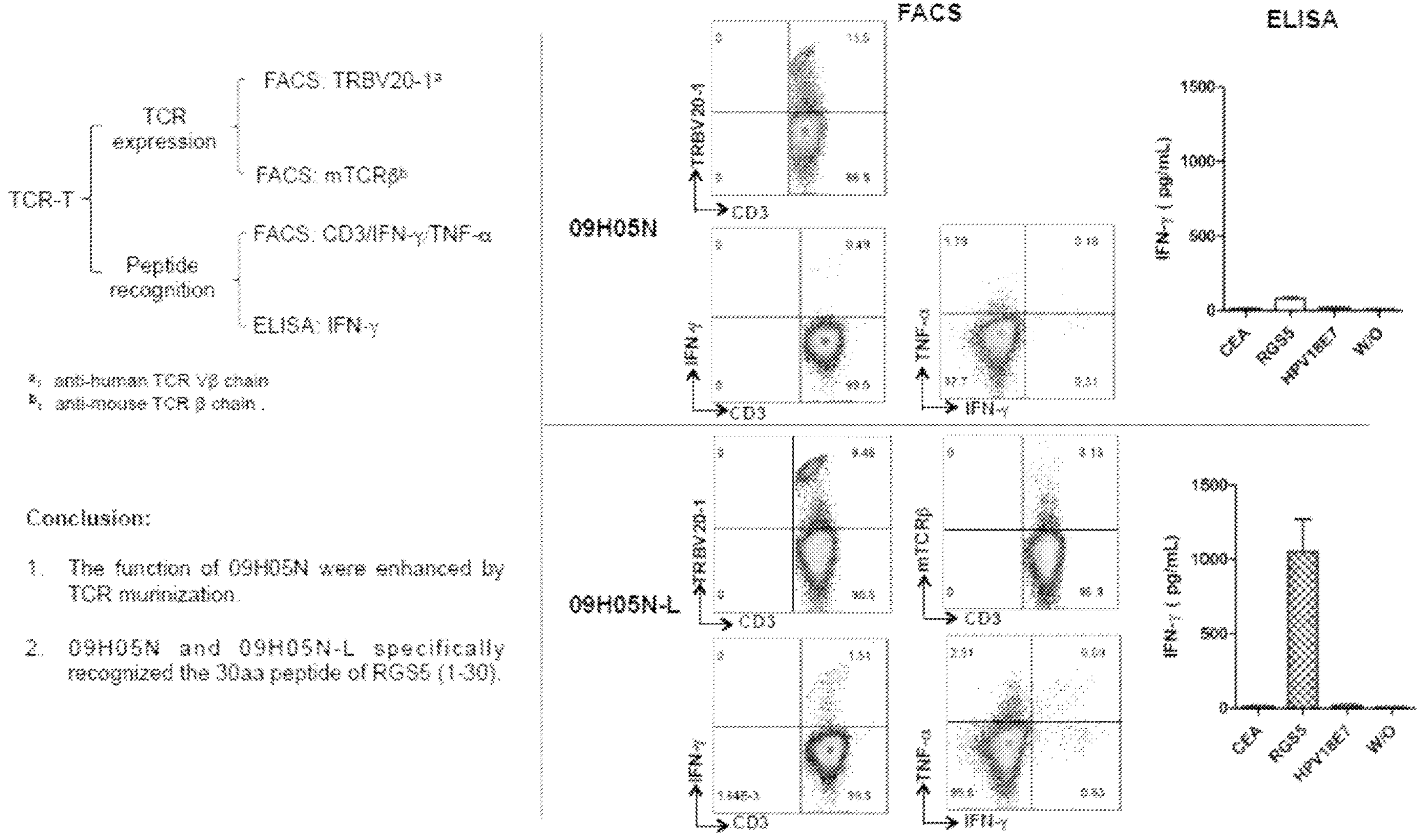
Figure 33C:
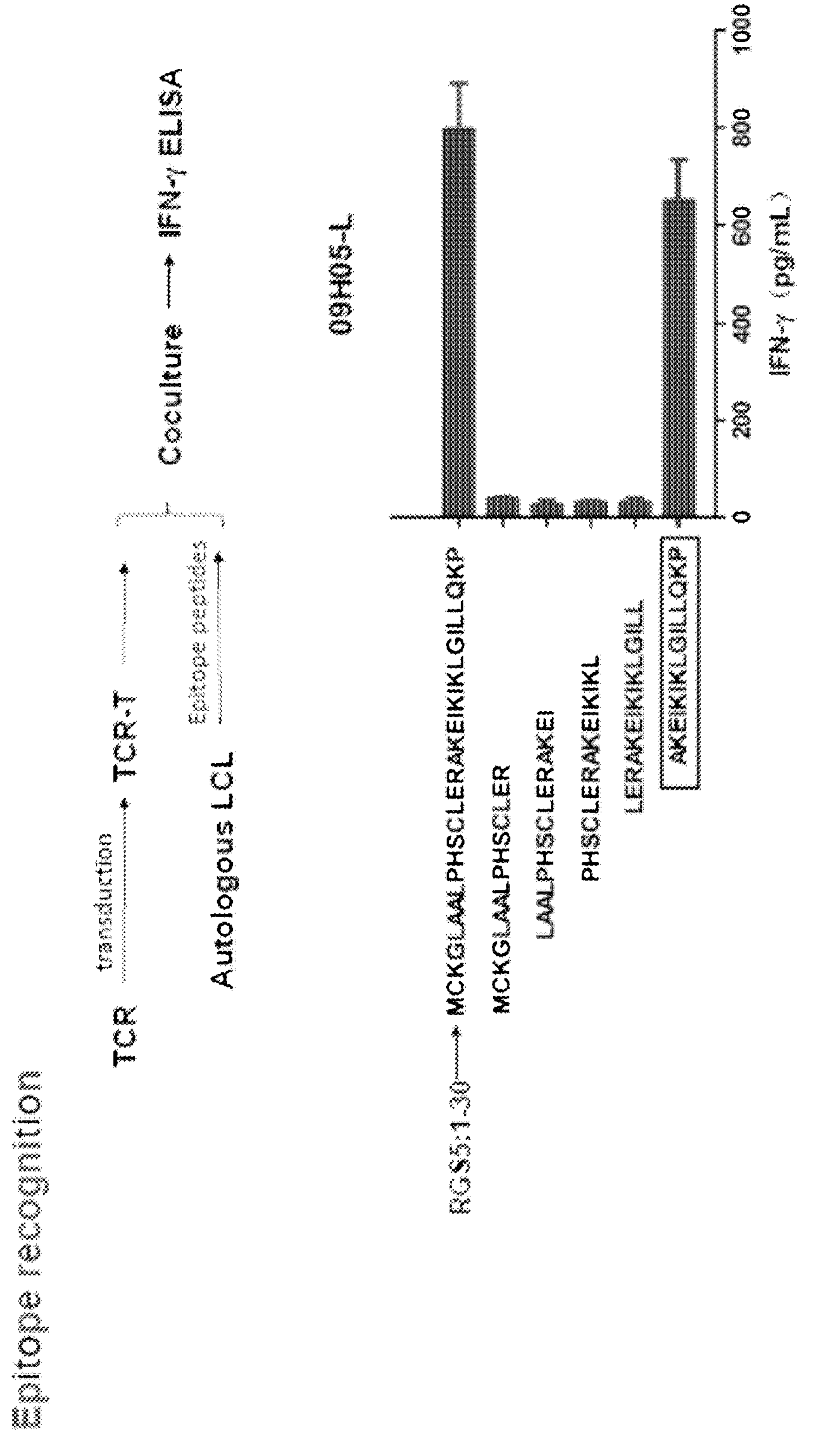
Figure 33D:
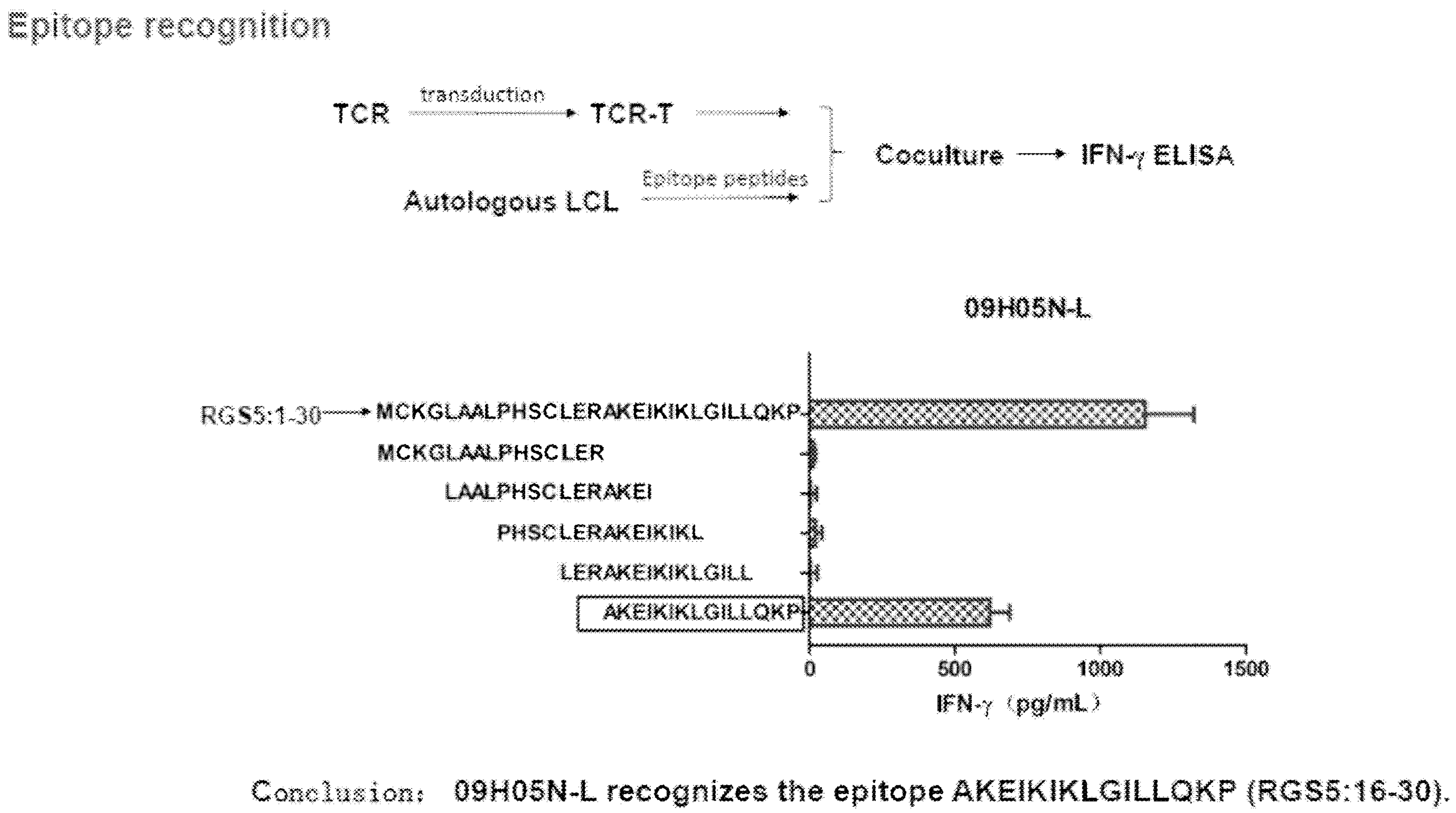
Figure 33E:
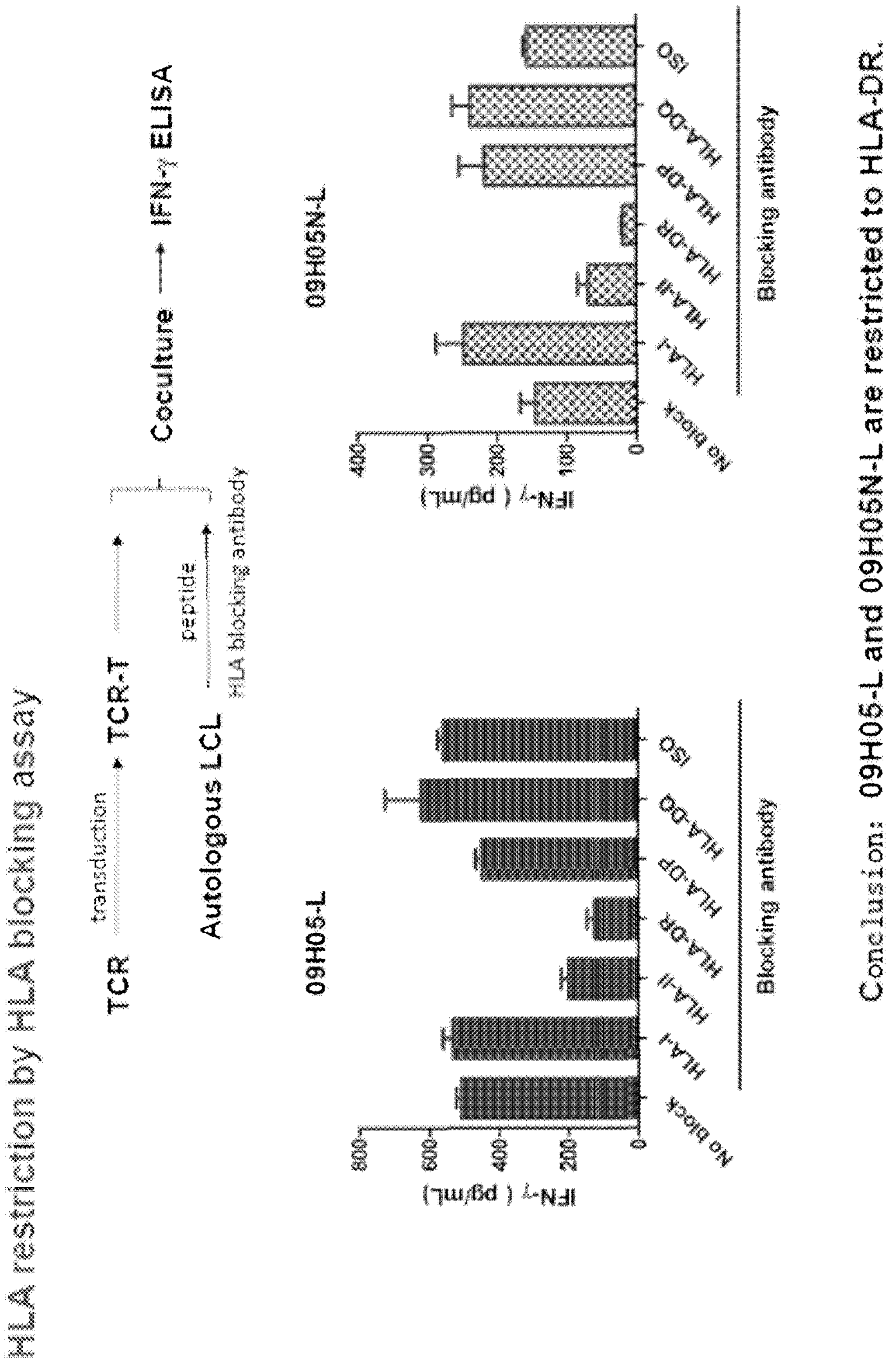
Figure 33F:
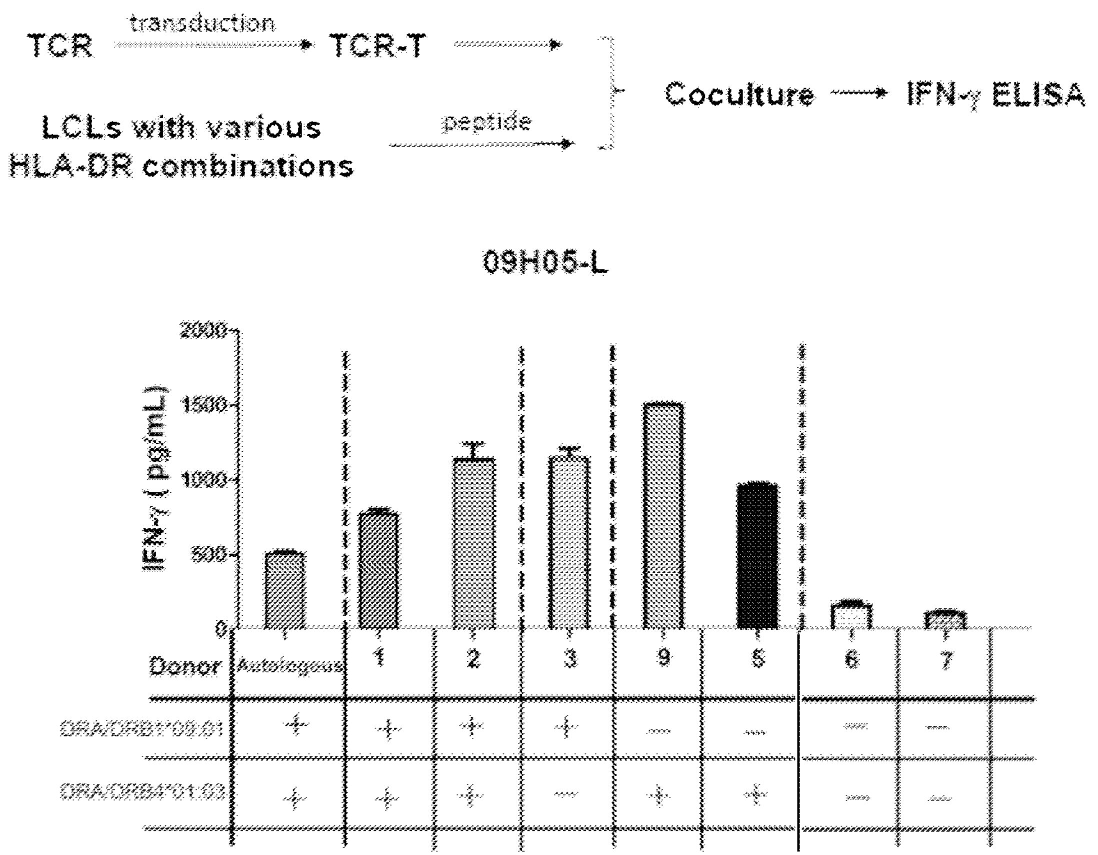
Figure 33G:
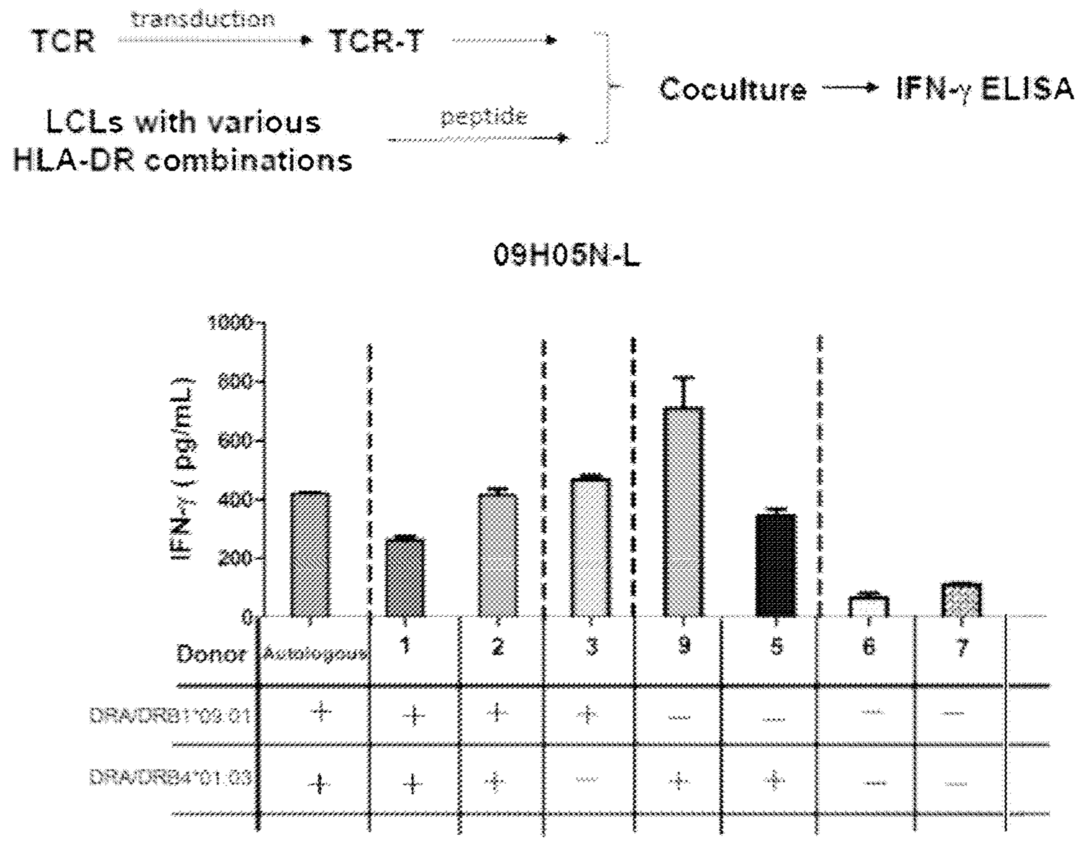
Figure 34A:
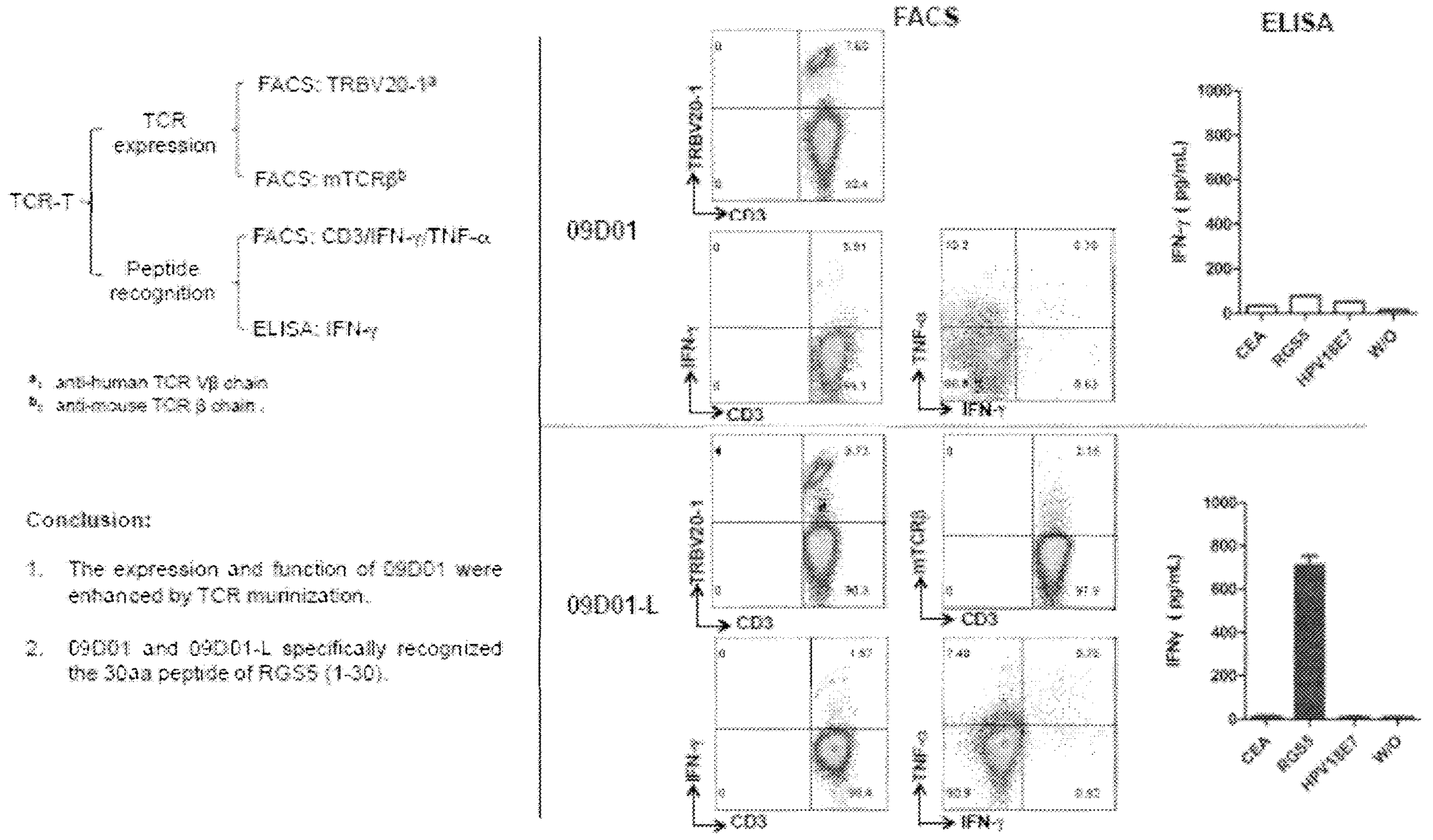
FIGS. 34A-34G show validation results of 09D01 and related TCR constructs. The sequences in FIGS. 34C and 34D are, from top to bottom: SEQ ID NOs 83, 250, 251, 252, 253, 82 and 82.
Figure 34B:
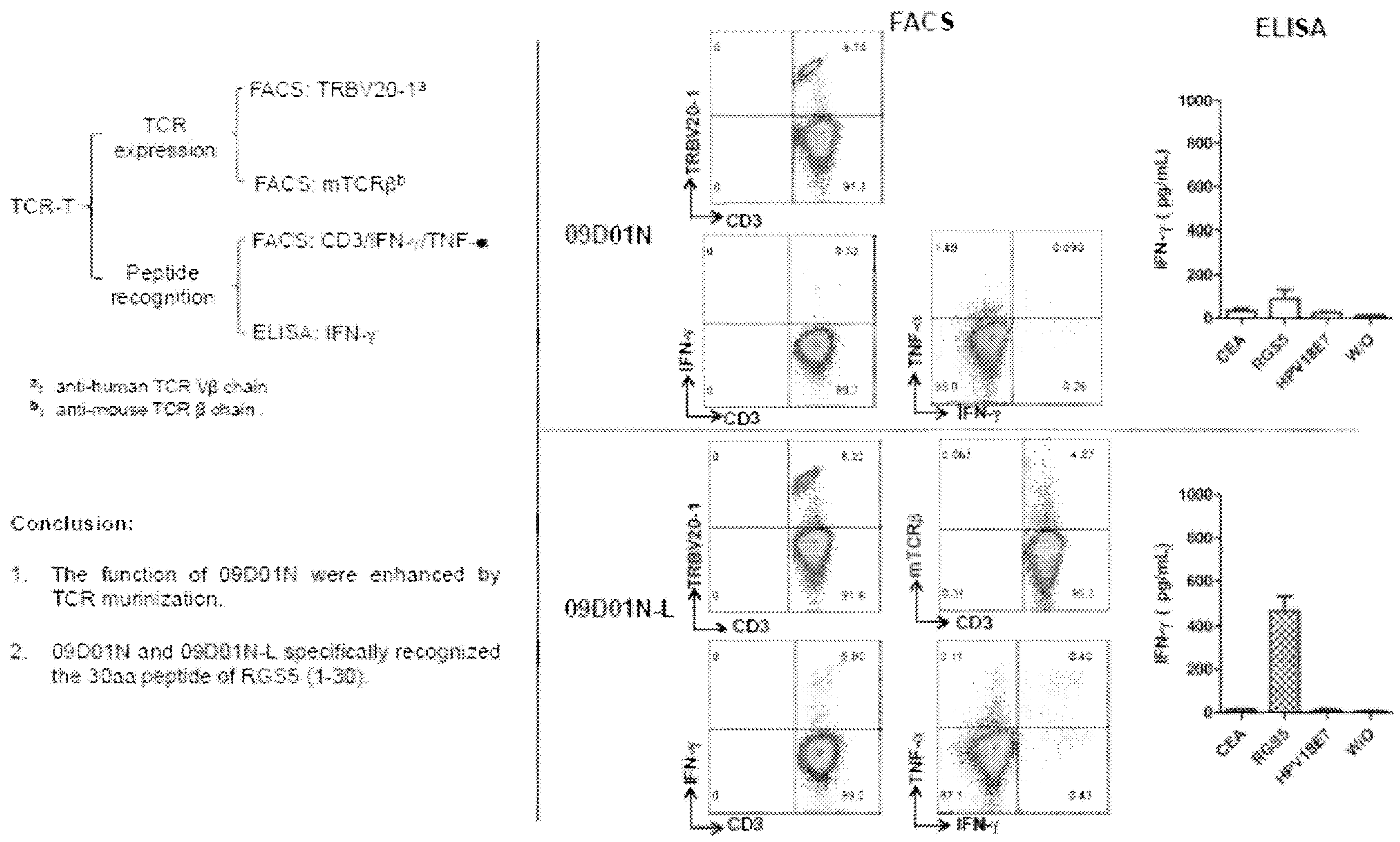
Figure 34C:
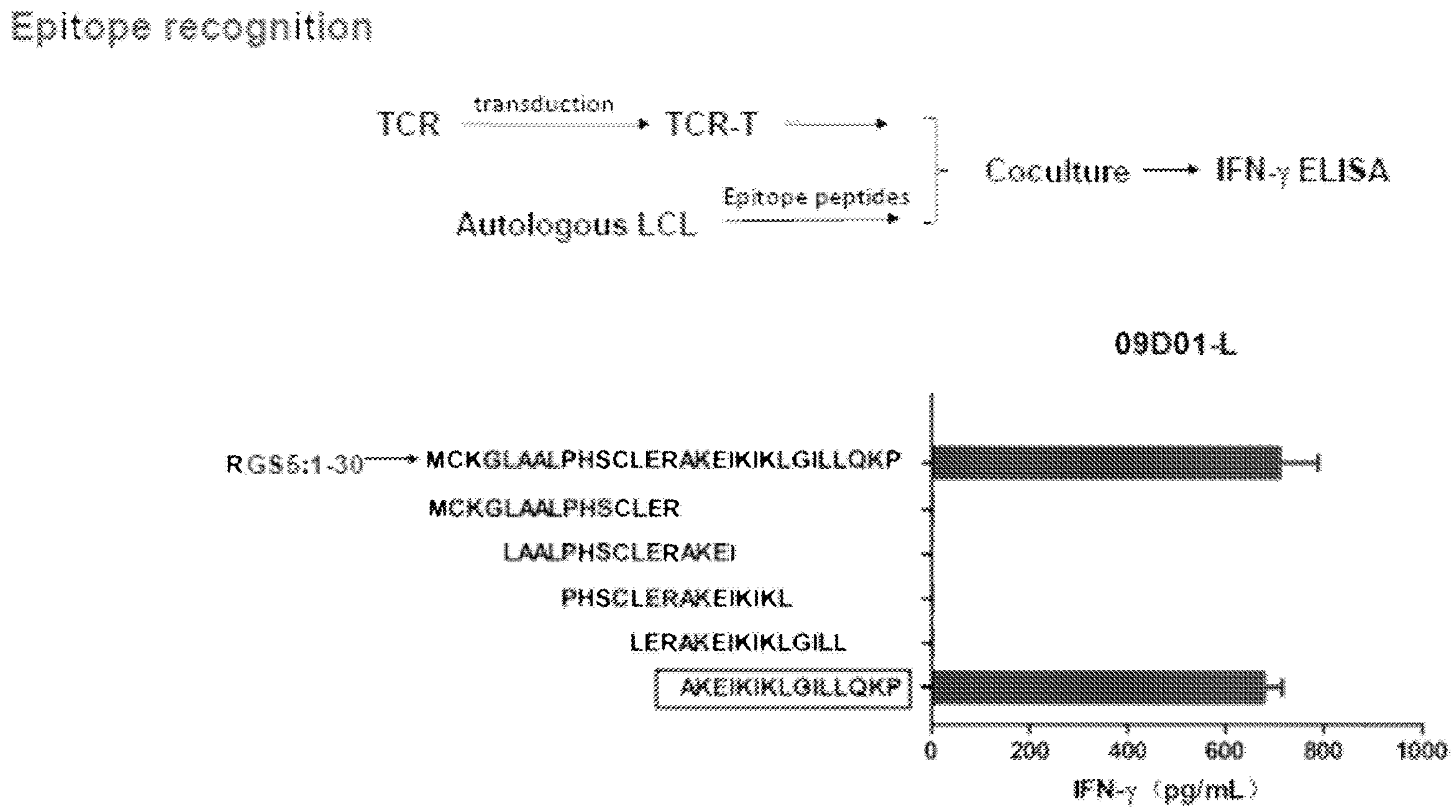
Figure 34D:
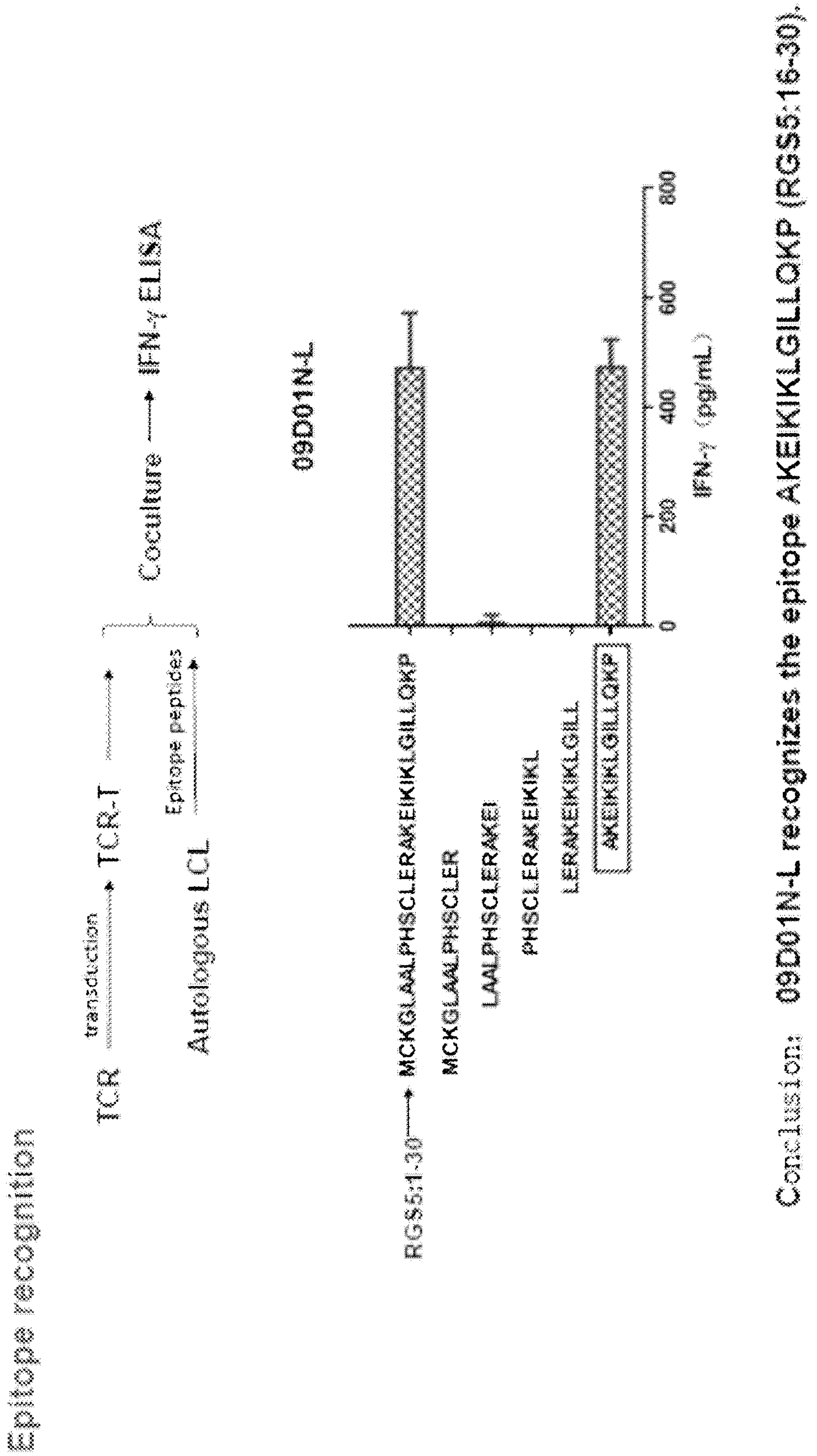
Figure 34E:
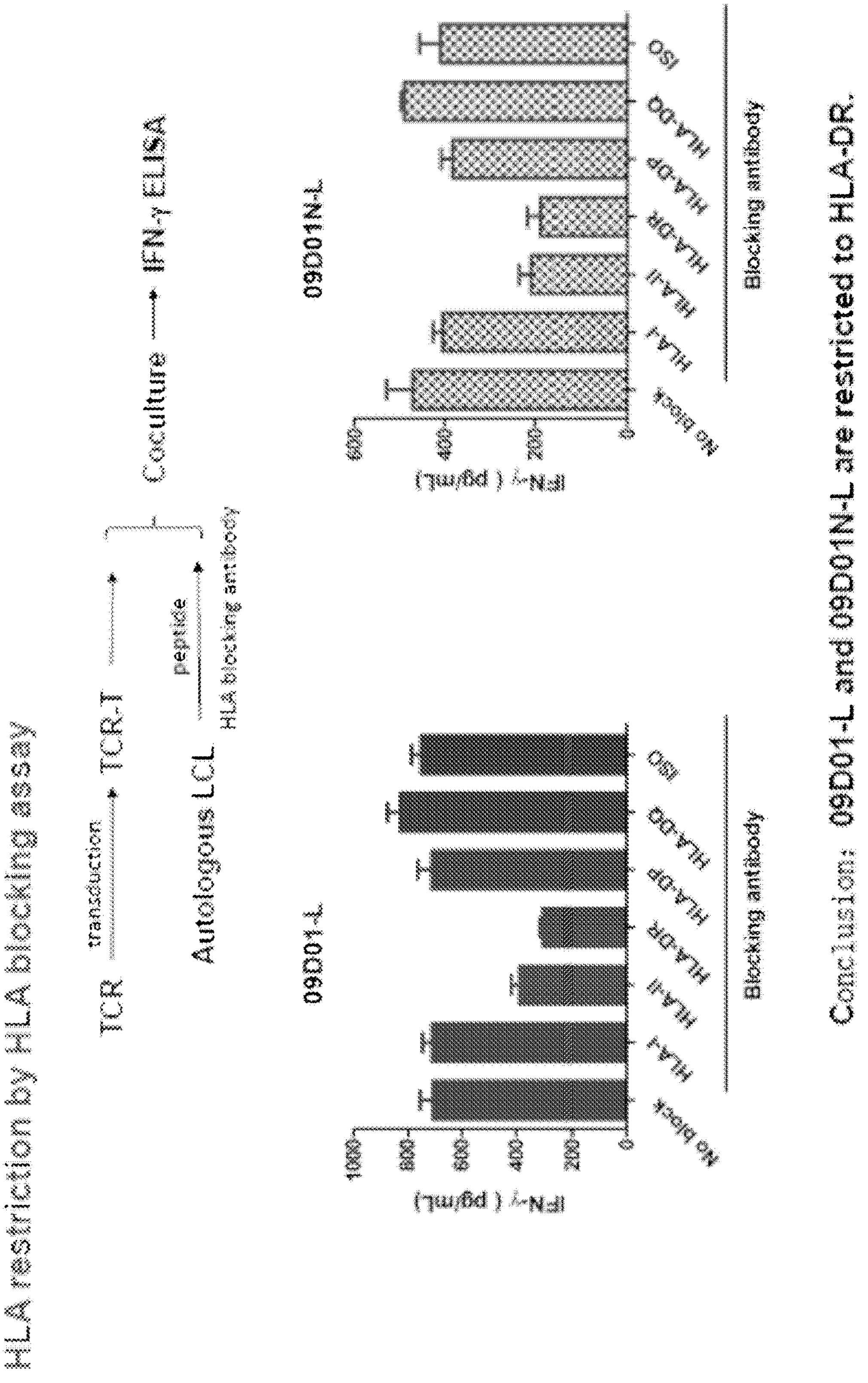
Figure 34F:
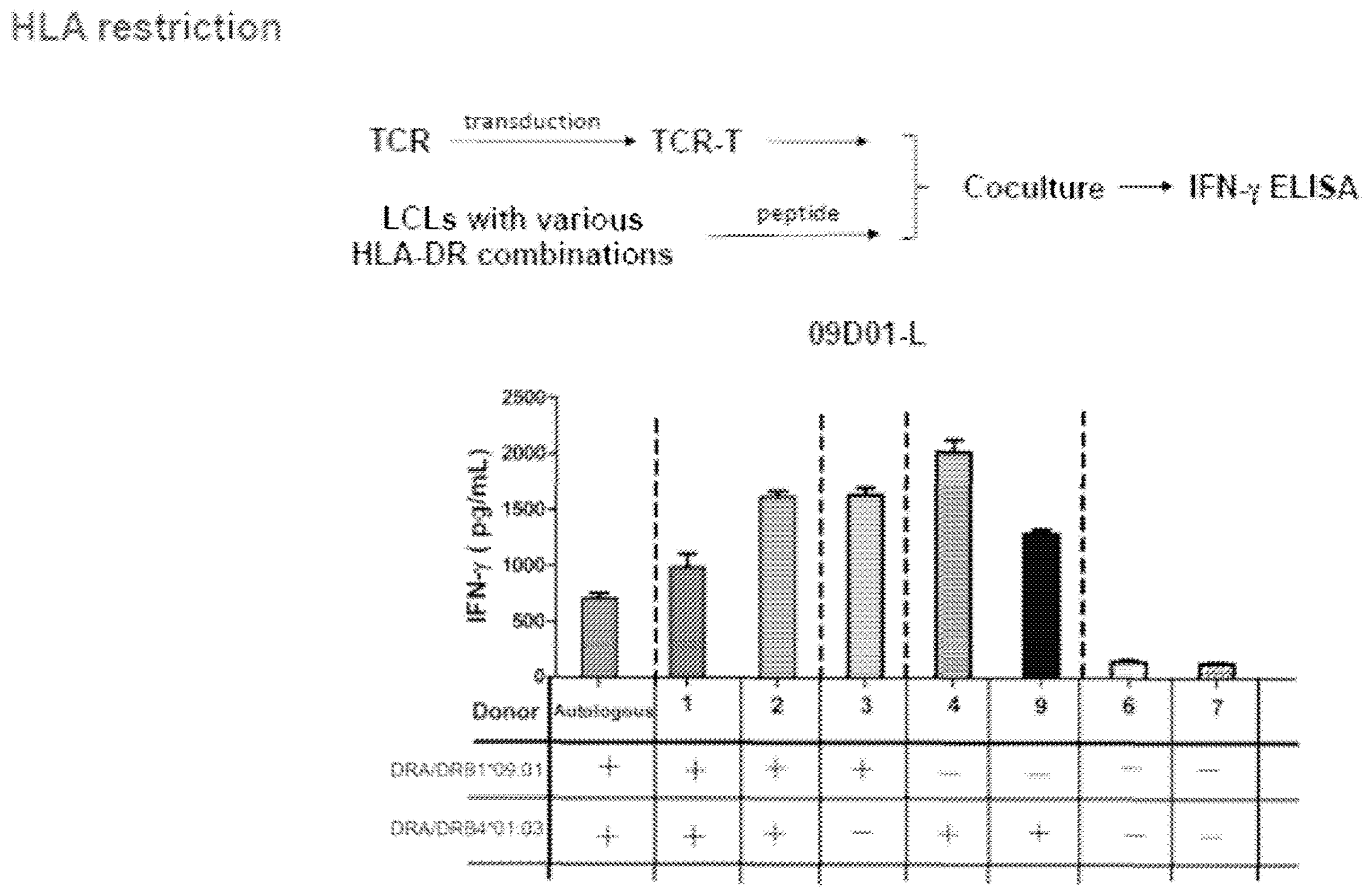
Figure 34G:
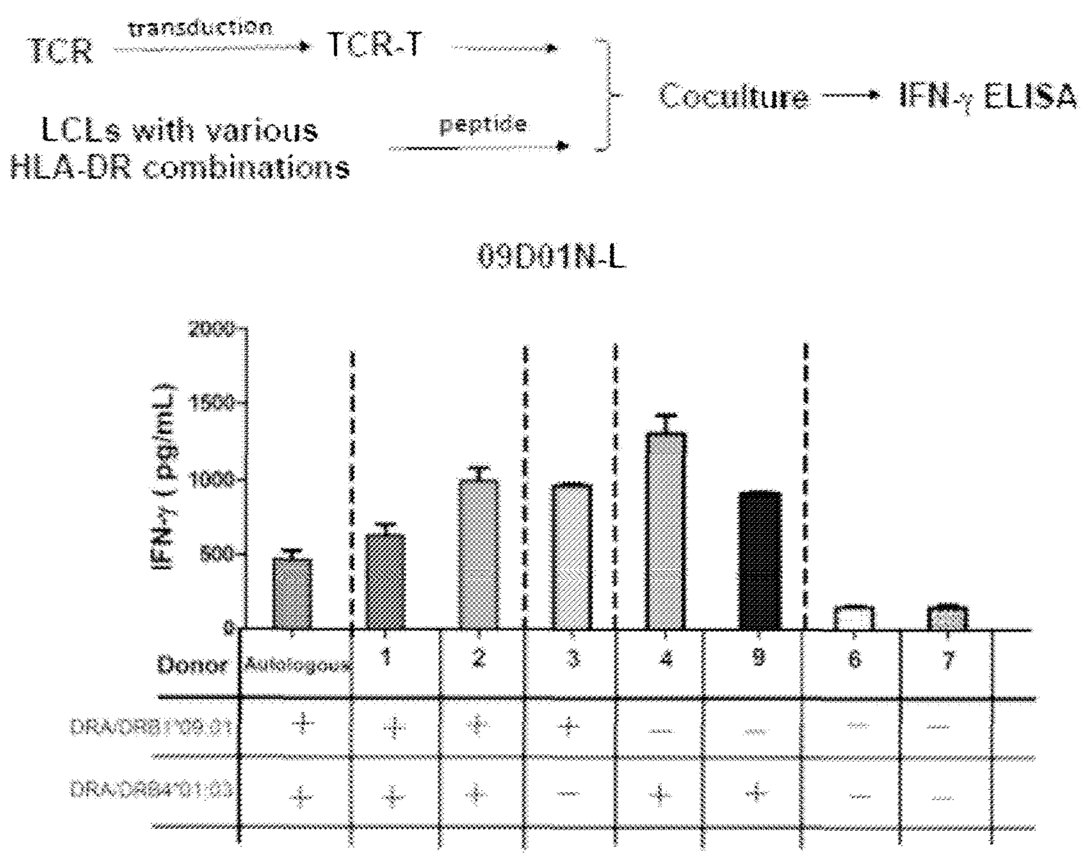
Figure 35A:
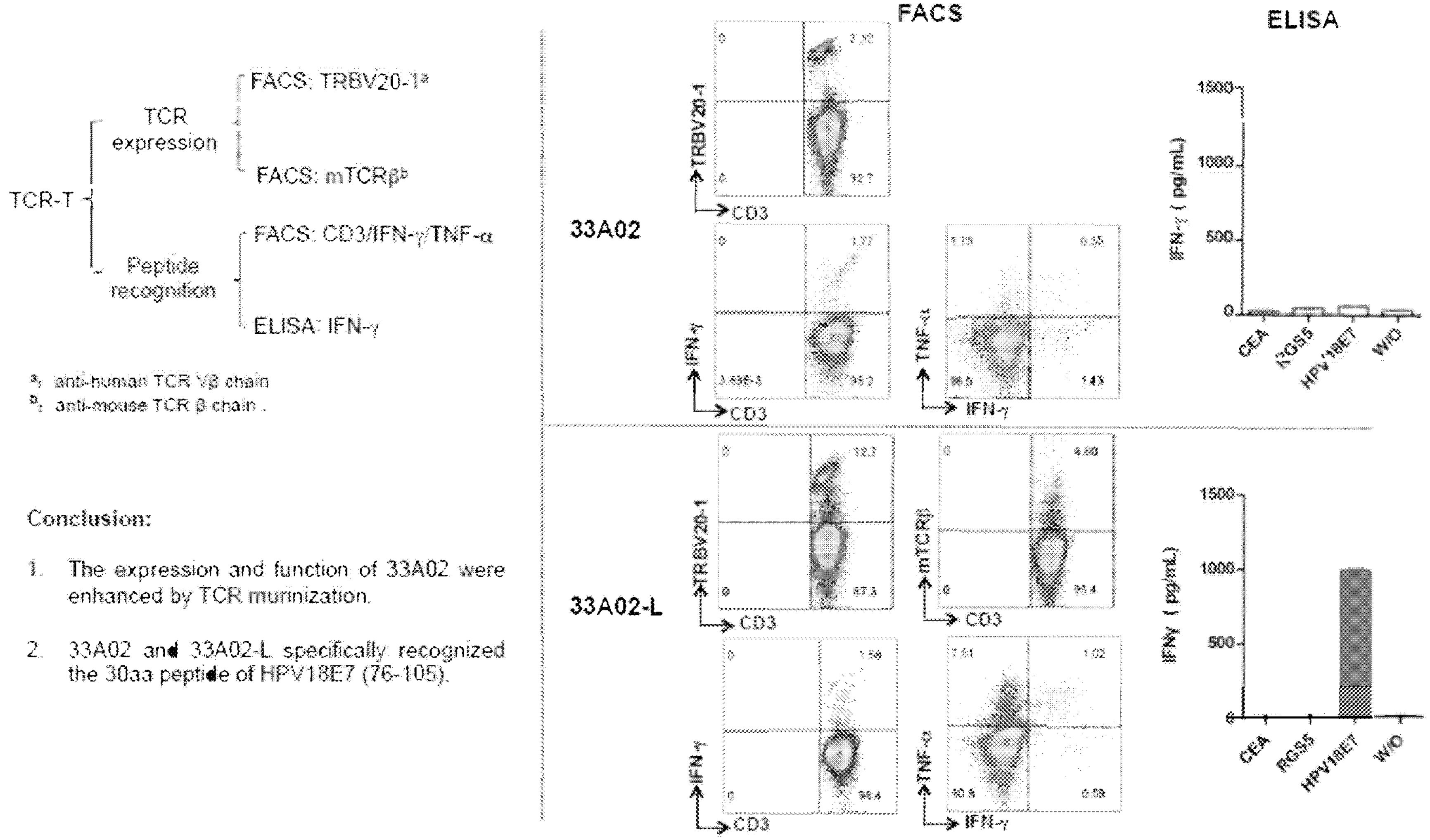
FIGS. 35A-35G show validation results of 33A02 and related TCR constructs. The sequences in FIGS. 35C and 35D are, from top to bottom: SEQ ID NO 86, and aa1-15, aa5-19, aa9-23, aa13-27, aa16-30, and aa5-19 of SEQ ID NO 86.
Figure 35B:
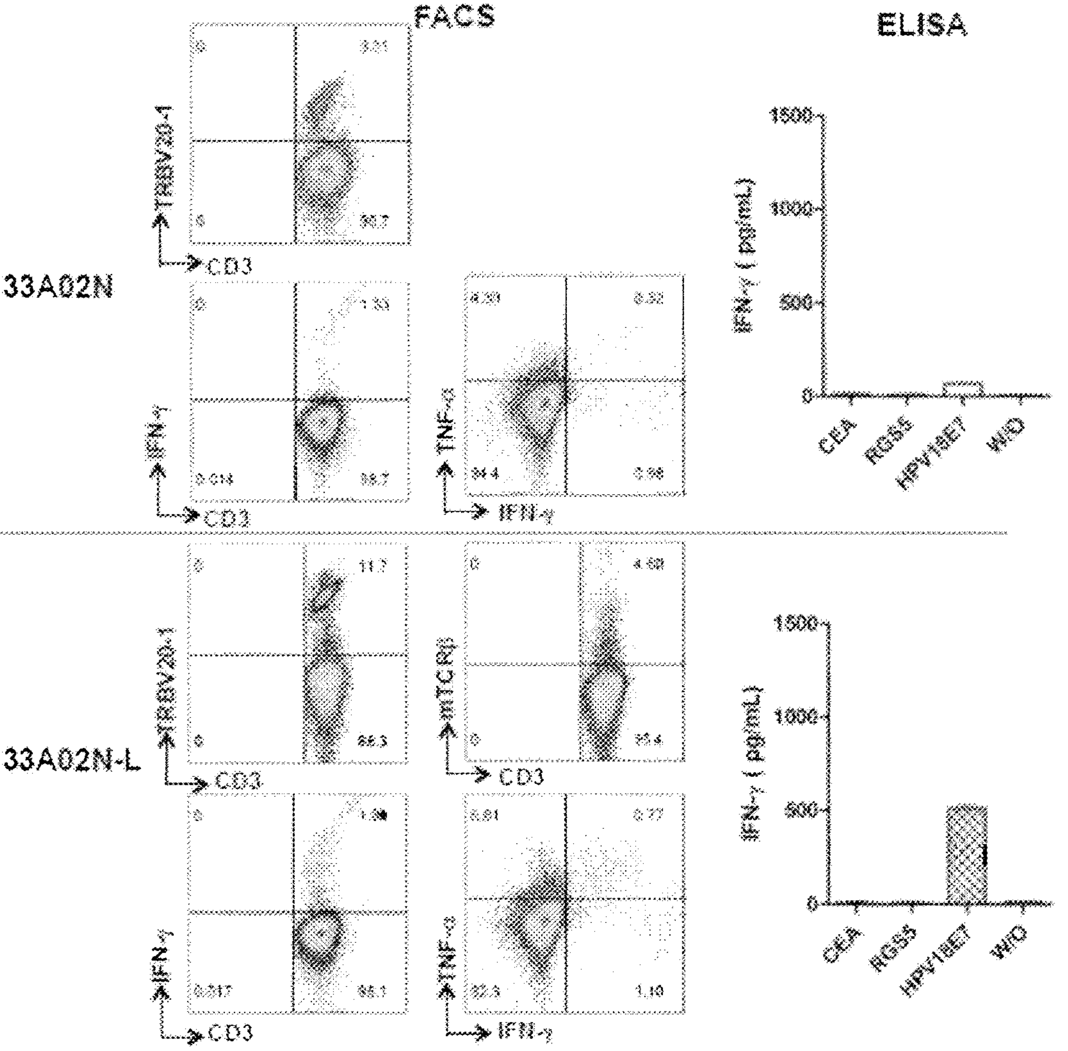
Figure 35C:
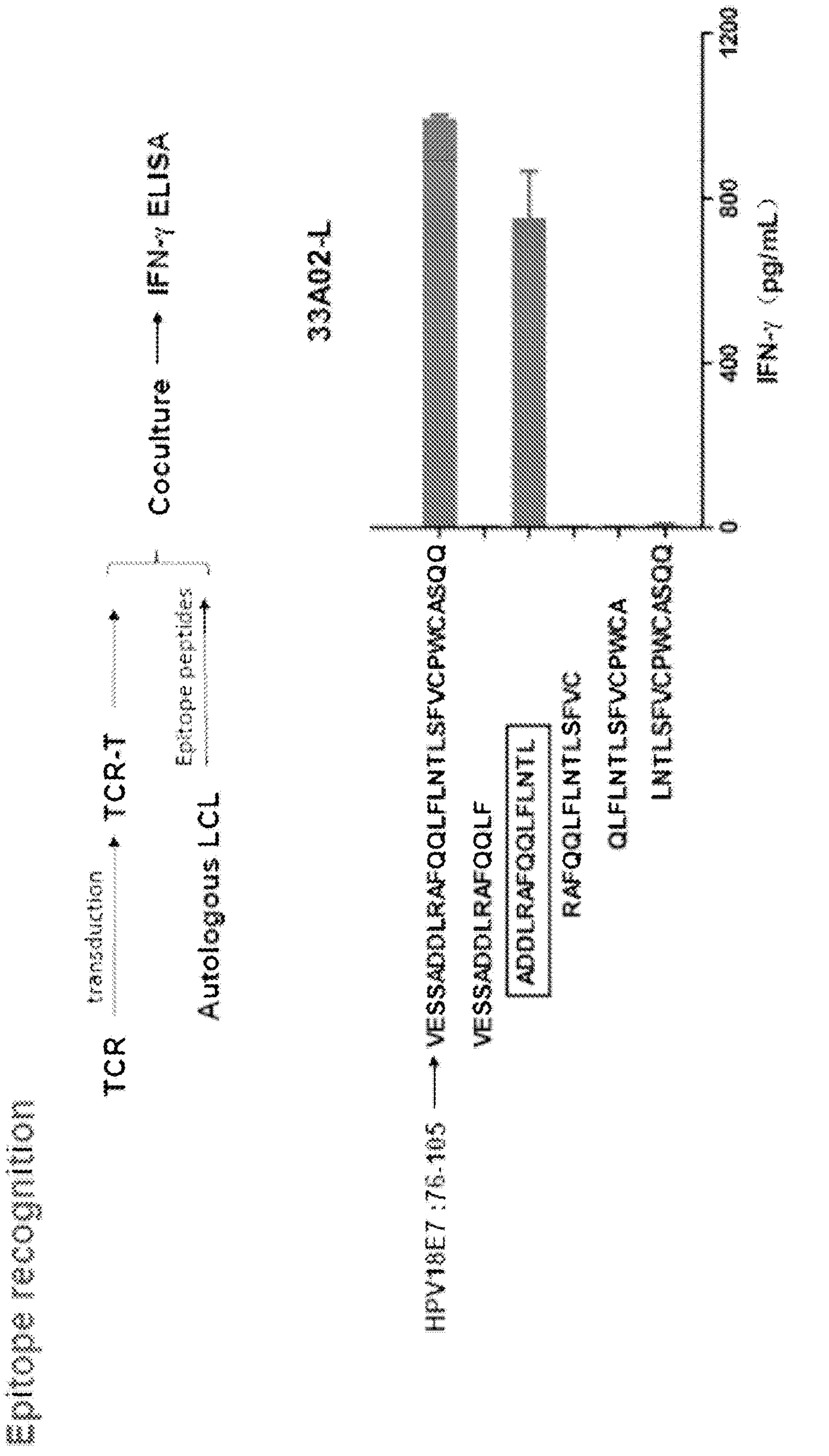
Figure 35D:
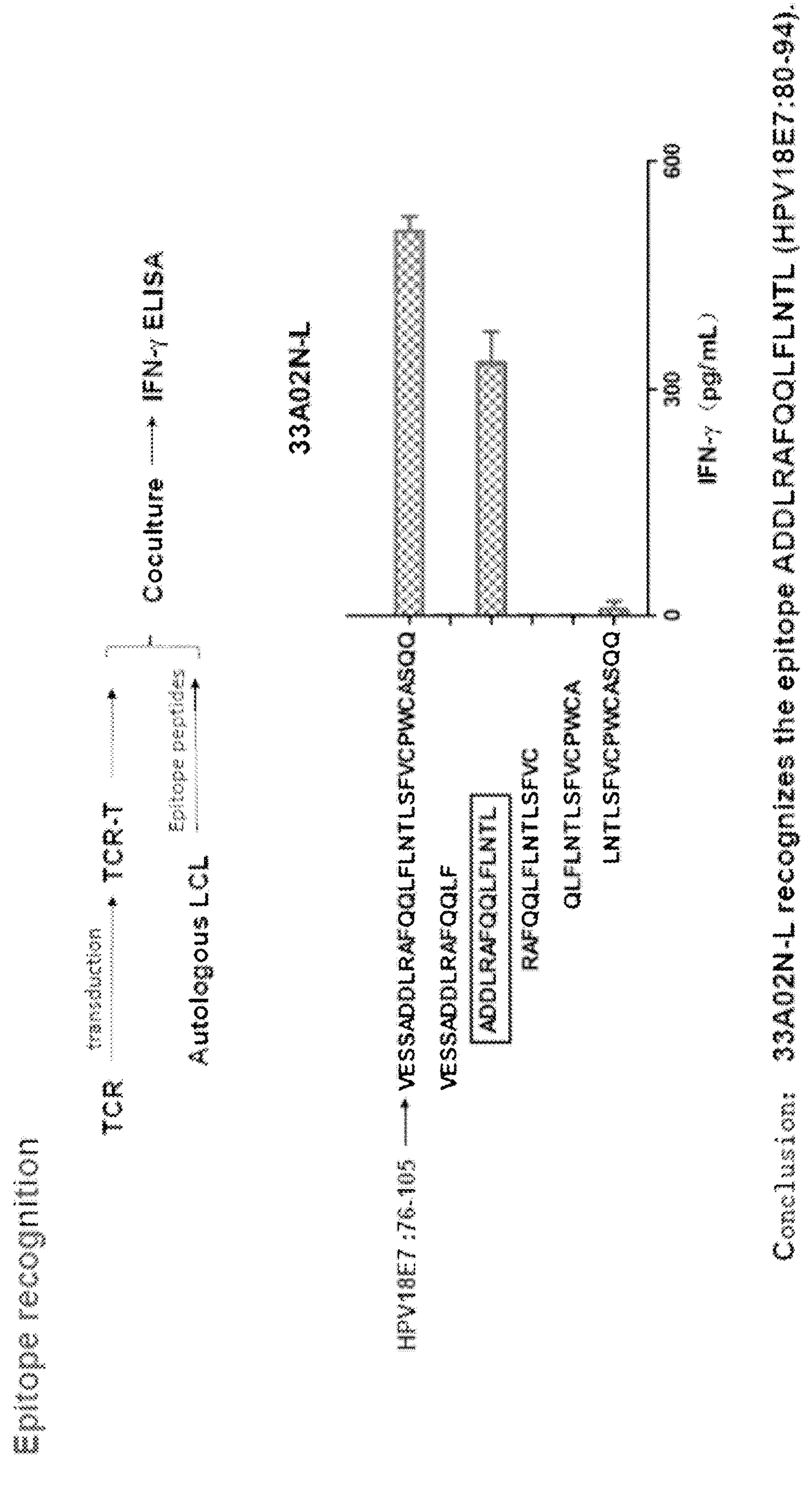
Figure 35E:
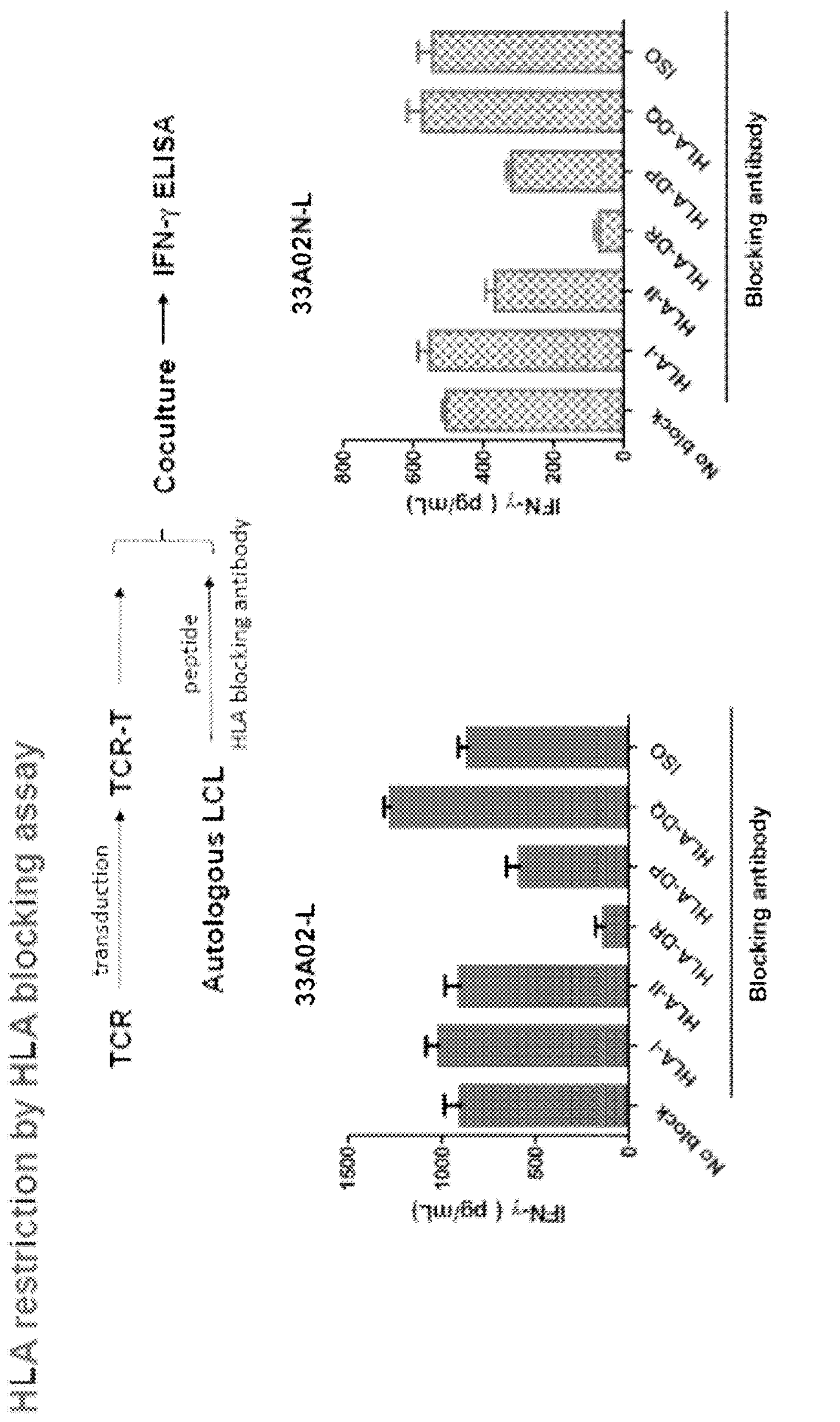
Figure 35F:
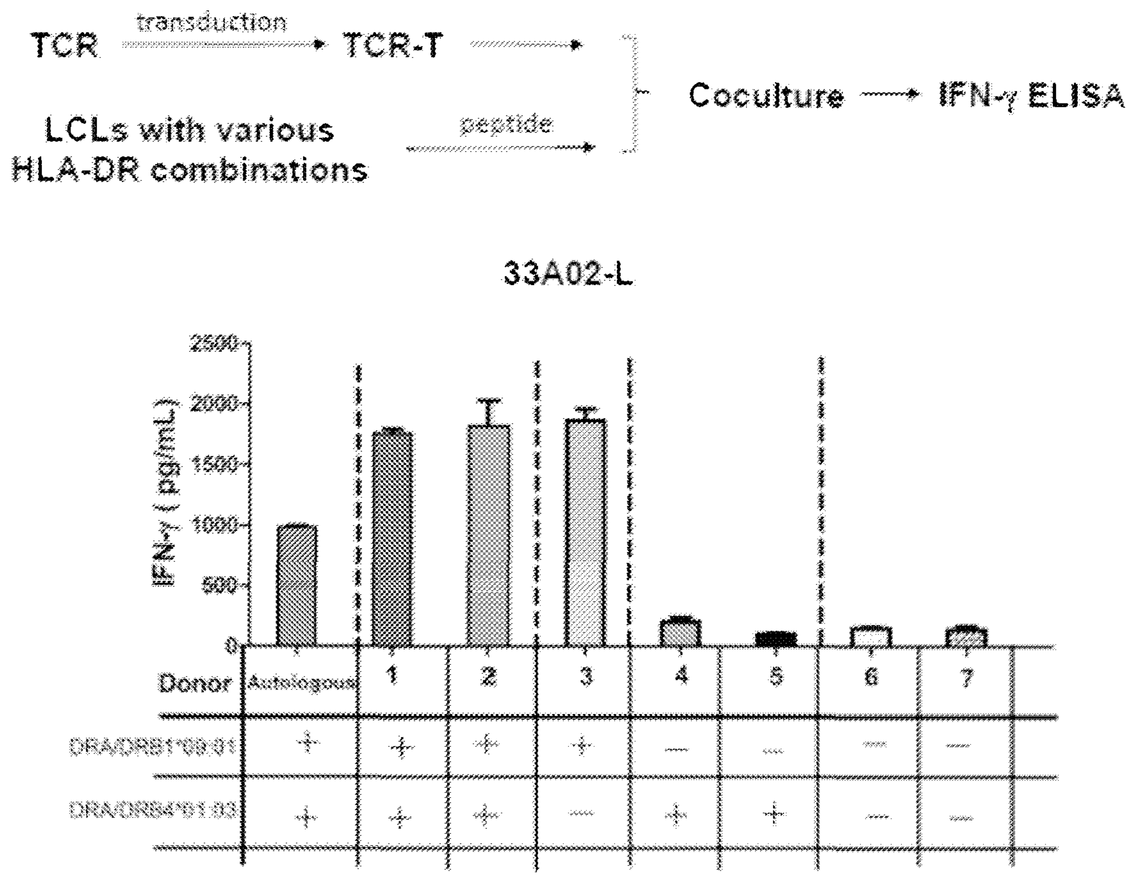
Figure 35G:
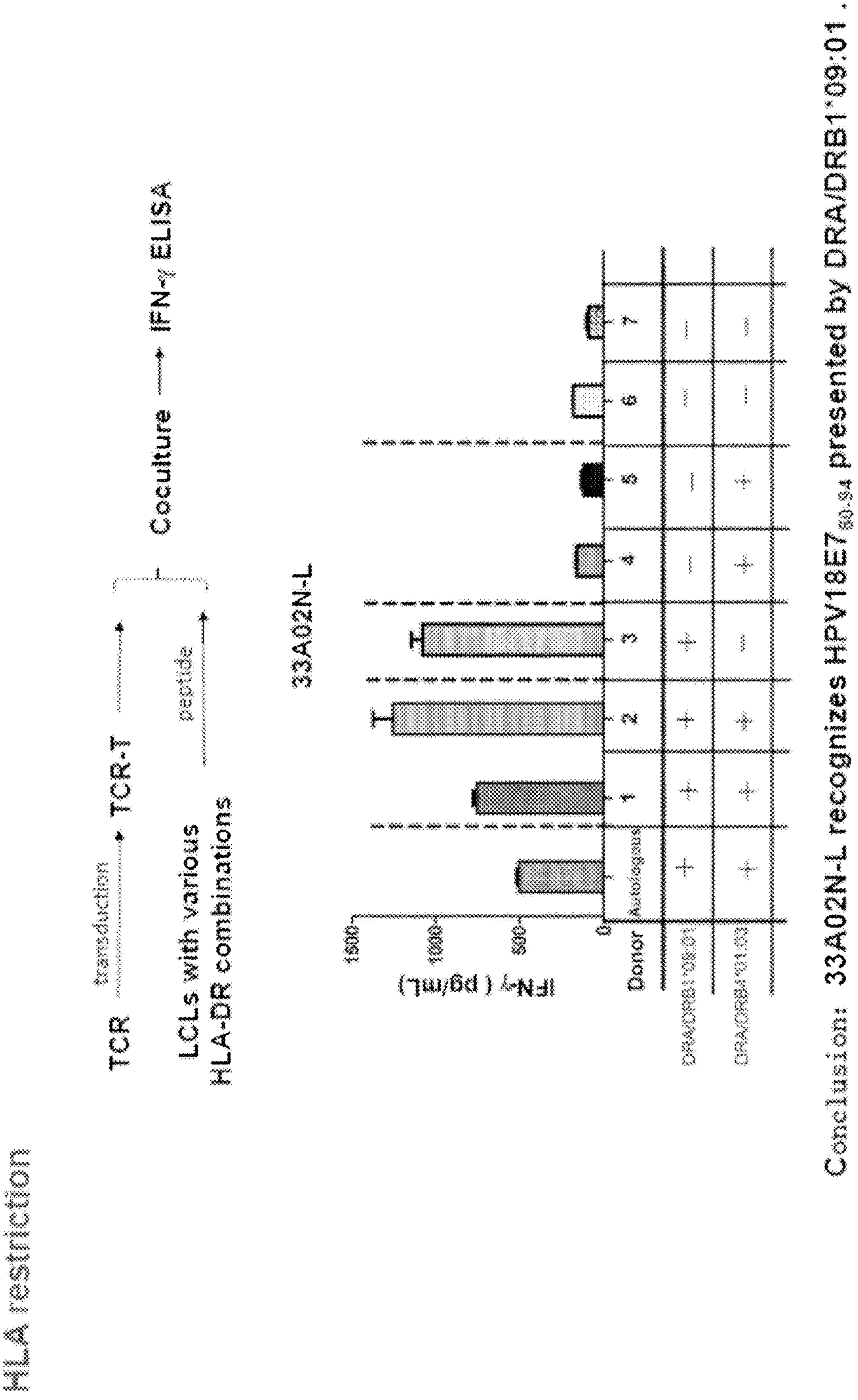

Human (i.e., wildtype) TCR and murinized TCR constructs corresponding to the were prepared (FIG. 24). The murinized TCR constructs have murine constant domains (mCα and mCβ1). 3 TCR variants having an N-terminal 19-amino acid leader sequence (SEQ ID NO: 101) were discovered and their murinized versions were prepared. FIGS. 25A-25B show the 26 TCR constructs that were prepared and validated. Multiple TCRs recognizing the same epitopes such as amino acids 16-30 of RGS5 and amino acids 84-102 of HPV18-E7 were discovered. Validation assay results for the TCR constructs are shown in FIGS. 26A-35G.

TCR Expression Assay

TCR expression was assessed using a FACS assay that detected stained TCR VP chain. Briefly, TCR transferred T cells were collected and washed by adding 10 mL PBS (containing 2% Fetal Bovine serum), centrifuged at 350 g for 5 minutes, and the supernatant was aspirated completely. Cell pellets were resuspended and adjusted to about $2\times10^6$ cells/mL by adding PBS (containing 2% Fetal Bovine serum). 100 μL/sample cell suspension was collected and used for TCR VP chain surface staining and detected by FACS.

LCL Stimulation Assay

The LCL stimulation assay was carried out as follows. First, LCLs were loaded with peptides: LCLs were collected in 15 mL tube, washed by adding 10 mL PBS, centrifuged at 350 g for 5 minutes, and the supernatant was aspirated completely. Cell pellets were resuspended in culture medium (RPMI1640 containing 10% FBS), and adjusted to $1\times10^6$ cells/mL. Tumor antigen peptide was added to LCLs to a final concentration of 5 μg/mL, and incubated for 8-24 hours in incubator. TCR-T cells were then stimulated with peptide-loaded LCLs as follows: Peptide-loaded LCLs were collected and washed by adding 10 mL PBS, centrifuged at 350 g for 5 minutes, and the supernatant was aspirated completely. The LCLs were resuspended and adjusted to $1\times10^6$ cells/mL or $1\times10^5$ cells/mL by adding AIM-V medium (containing 10% Fetal Bovine serum). TCR-transduced T cells were collected, washed by adding 10 mL PBS, centrifuge at 350 g for 5 minutes, and the supernatant was aspirated completely. TCR transduced T cells were then resuspended, and adjusted to $2\times10^6$ cells/mL or $5\times10^5$ cells/mL by adding AIM-V medium (containing 10% Fetal Bovine serum). 100 μL/well of LCL ($1\times10^6$ cells/mL) and 100 μL/well TCR-transduced T cells ($2\times10^6$ cells/mL) were mixed into a 96 wells plate. Brefeldin A (final concentration of 3 μg/mL) was added to the wells, and incubated for 4 hours. After 4 hours, cells were collected and used for intracellular IFN-γ and TNF-α staining and detected by FACS. For ELISA detection of IFN-γ, 100 μL/well of LCL ($1\times10^5$ cells/mL) and 100 μL/well TCR-transduced T cells ($5\times10^5$ cells/mL) were mixed into a 96 wells plate, and incubated for 24 hours in an incubator. After 24 hours, 175 μL supernatant was collected per well in the 96 well plate, and used in ELISA detection of IFN-γ using an IFN-γ ELISA HRP Kit.

HLA Blocking Assay

HLA blocking assay was carried out as follows. Peptide loaded LCLs were collected after LCLs stimulation, washed by adding 10 mL PBS, centrifuged at 350 g for 5 minutes, and the supernatant was aspirated completely. Cell pellets were resuspended, adjusted to $1\times10^5$ cells/mL by adding AIM-V medium (containing 10% Fetal Bovine serum). 100 μL/well cell suspension was added to 96 wells plate, and HLA blocking antibody was added (final concentration of 50 μg/mL) to appropriate wells, and incubated for 2 hours in an incubator. TCR transferred T cells were collected, washed by adding 10 mL of PBS, centrifuged at 350 g for 5 minutes, and the supernatant was aspirated completely. Cell pellets were collected and adjusted to $5\times10^5$ cells/mL by adding AIM-V medium (containing 10% Fetal Bovine serum). 100 μL/well TCR transduced cell suspension was added to the corresponding well, mixed with the LCLs and incubated for 24 hours in an incubator. After 24 hours, 175 μL supernatant was collected per well of the 96 well plate, and subjected to ELISA detection of IFN-γ using an IFN-γ ELISA HRP Kit.

HLA Restriction Assay

LCLs from different donors (Table 4) with various HLA-II genotypes were loaded with peptides to stimulate TCR-T in the HLA restriction assay. The rest of steps were the same as LCL stimulation assay.

TABLE 4

Donors with different HLA genotypes.

| | Donor | 1 | 2 | 3 | 4 | 5 | 6 | 7 | 8 | 9 | 10 |
|---|---|---|---|---|---|---|---|---|---|---|---|
| HLA-DR | DRA/DRB1*09:01 | + | + | + | − | − | − | − | + | − | − |
| | DRA/DRB4*01:03 | + | + | − | + | + | − | − | + | + | + |
| HLA-DP | HLA-DPA1*02:02/DPB1*05:01 | + | + | + | − | − | + | − | − | − | + |
| | HLA-DPA1*01:03/DPB1*02:01 | − | − | − | − | + | − | + | + | + | − |
| | HLA-DPA1*01:03/DPB1*05:01 | − | − | + | + | − | − | − | − | − | − |
| | HLA-DPA1*02:02/DPB1*02:01 | − | − | − | − | − | − | + | + | − | − |
| HLA-DQ | DQA1*03:02/DQB1*03:03 | + | + | + | − | − | − | − | + | − | − |

Human IFN-γ ELISA

On Day 1, a high protein binding ELISA plate was coated with antibody 1-D1K (IFN-γ ELISA HRP Kit), diluted to 2 μg/mL in PBS, pH 7.4, by adding 50 μL/well, and incubated overnight at 4° C. On Day 2, the plate was washed twice with PBS (200 μL/well). The plate was blocked by adding 200 μL/well culture medium, and incubated for 1 hour at room temperature (RT). Human IFN-γ standard (IFN-γ ELISA HRP Kit) was prepared in 2 mL PBS with 1% BSA to a concentration of 0.5 μg/mL, and left at RT for 15 minutes and then the tube was vortexed. 50 μL/well of samples or standards was diluted in culture medium and incubated for 2 hours at RT. The samples and standard probes were tested in duplicates. The plate was washed five times with PBS containing 0.05% Tween 20. 50 μL/well of antibody 7-B6-1-biotin (IFN-γ ELISA HRP Kit) was added at 1 μg/mL in PBS, incubated for 1 hour at RT, and washed. 50 μL/well of Streptavidin-HRP (IFN-γ ELISA HRP Kit) diluted 1:1000 in PBS was added, incubated for 1 hour at RT, and washed. 100 μL/well of TMB substrate solution was added, incubated at RT at dark place for 15-30 minutes till solution in wells turn visible blue. 50 μL/well of stop solution was added to stop enzymatic reaction. The solution color changed from blue to yellow. The optical density was measured in an ELISA reader at 450 nm.

Figure 36:
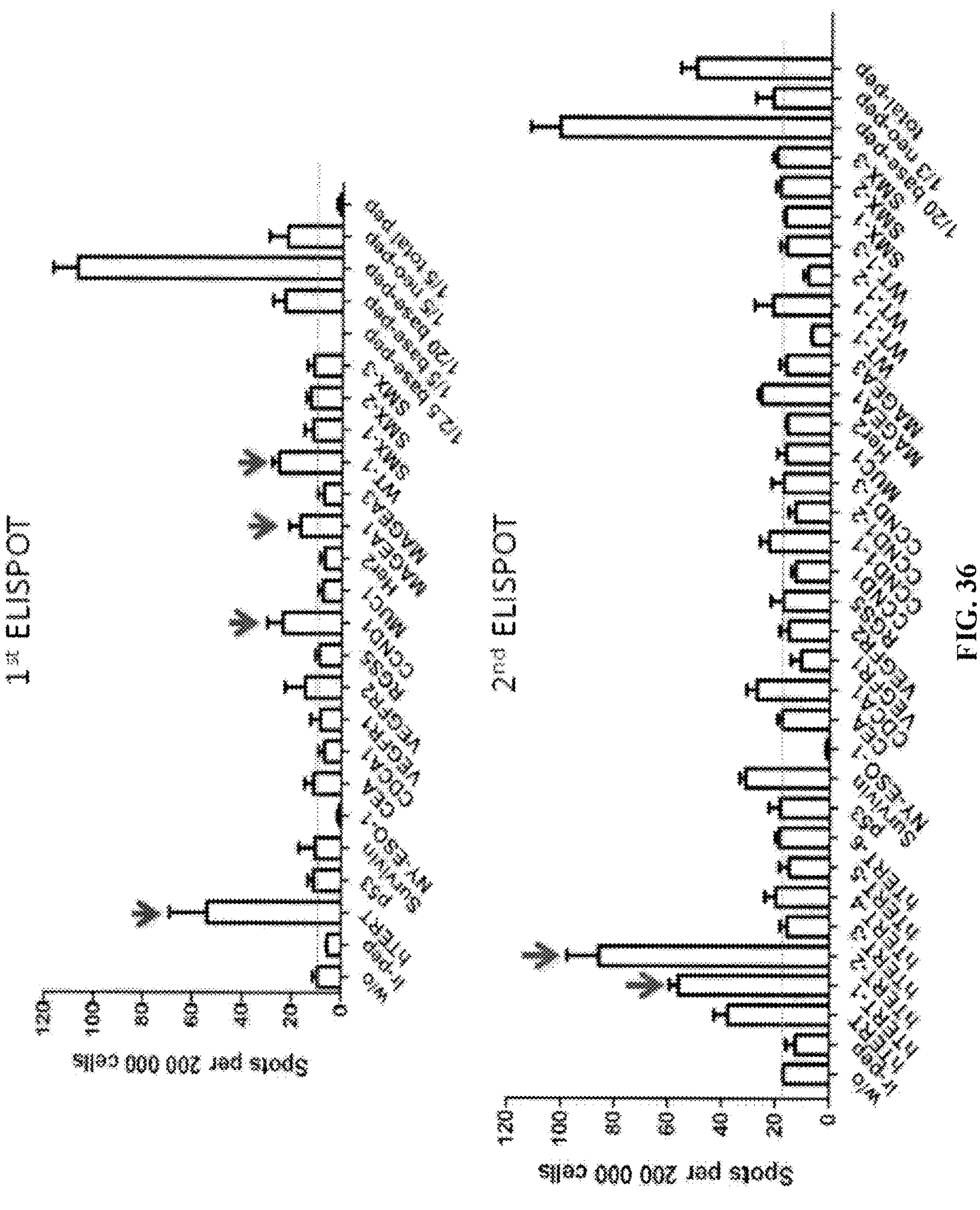
FIG. 36 shows specific immune response by the patient's PBMCs against the tumor antigen peptide pools, and each tumor antigen peptide in the pool after MASCT treatments as determined by ELISPOT assays. Percentages indicate reduced peptide concentration. For example, 1/20 base-pep indicates a pool of general tumor antigen peptides at 20 times dilution.

Example 5: Two-Round Tumor Specific T Cell Amplification from a Patient Treated with MASCT Patient SMZ was diagnosed with metastatic lung cancer, and received 5 cycles of improved MASCT treatment (see, PCT/CN2018/081338 and PCT/CN2019/080535) with activated T cells prepared using DCs loaded with a pool of general tumor antigen peptides (hTERT, p53, Survivin, NY-ESO-1, CEA, CDCA1, VEGFR1, VEGFR2, RGS5, CCND1, MUC1, Her2, MAGEA1, MAGEA3, WT-1) and neoantigen peptides (SMX-1, SMX-2 and SMX-3). The top panel of FIG. 36 shows antigen-specific T cell response by the patient's PBMC sample after the $5^{th}$ cycle of improved MASCT in an ELISPOT assay. Four tumor antigens, hTERT, CCND1, MAGE-A1 and WT-1, in particular, induced strong immune response. The patient was subsequently treated with an additional cycle (cycle 6) of improved MASCT. The bottom panel of FIG. 36 shows antigen-specific T cell response by the patient's PBMC sample after the $6^{th}$ cycle of improved MASCT in an ELISPOT assay. In the ELISPOT assay, single peptides from each of the tumor antigen peptide sub-pools corresponding to antigens hTERT, CCND1, MAGE-A1, and WT-1, were used to detect antigen-specific immune responses and to identify immune-dominant tumor antigen peptides. Peptides hTERT-1 and hTERT-2 showed particularly strong immune response.

PBMC samples from Patient SMZ were obtained to prepare tumor specific T cells using a two-round protocol.

Round 1

Figure 37:
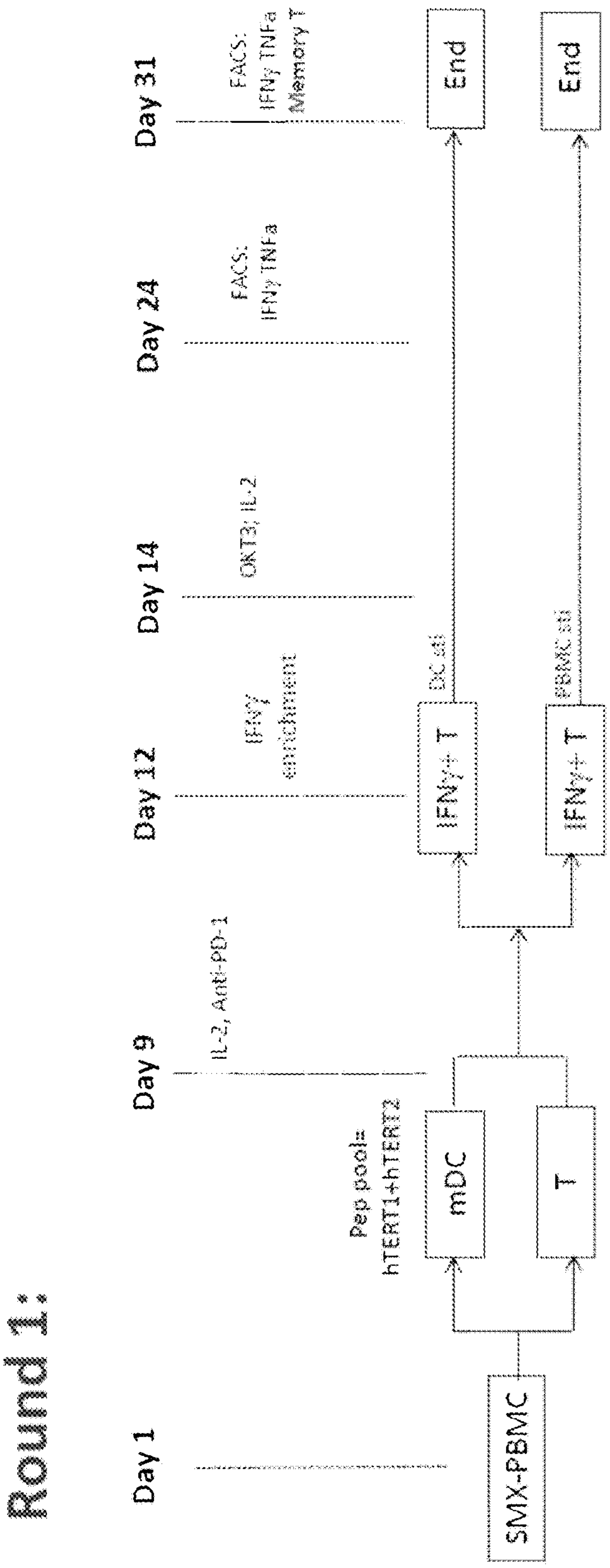
FIG. 37 shows Round 1 protocol of an exemplary two-round method for preparing tumor antigen-specific T cells using PBMCs from Patient SMZ.

FIG. 37 provides an overview of the protocol for Round 1 of tumor-specific T cells preparation used in this example. Briefly, on Day 1, peripheral blood mononuclear cells (PBMCs) from the patient were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed with a peptide pool comprising two tumor antigen peptides derived from hTERT (i.e., hTERT1 and hTERT2, 1 μg/mL/peptide), and then cultured in a DC maturation medium to differentiate into mature DCs. On Day 8, PBMCs were stimulated with the peptide pool. On Day 9, an IFNγ secretion assay-cell enrichment and detection kit (Miltenyi Biotec) was used to isolate a population of IFNγ$^{+}$ T cells from the stimulated PBMCs. On Day 9, the IFNγ$^{+}$ T cells were co-cultured with antigen-loaded mature DCs in a medium containing IL-2 and an anti-PD-1 antibody. On Day 11, the co-culture was stimulated with PBMCs pulsed with the peptide pool or each individual peptide. On Day 12, an IFNγ secretion assay-cell enrichment and detection kit (Miltenyi Biotec) was used to isolate a population of IFNγ$^{+}$ T cells. Meanwhile, the antigen-loaded mature DCs ("DC sti") or PBMCs ("PBMC sti") were prepared and co-cultured with the IFNγ$^{+}$ T cells. On Day 14, an anti-CD3 antibody (OKT3) and IL-2 (at least about 2000 IU/mL) were added to the co-culture, which was continued to be cultured to Day 31 to obtain tumor antigen-specific T cells.

Figure 38A:
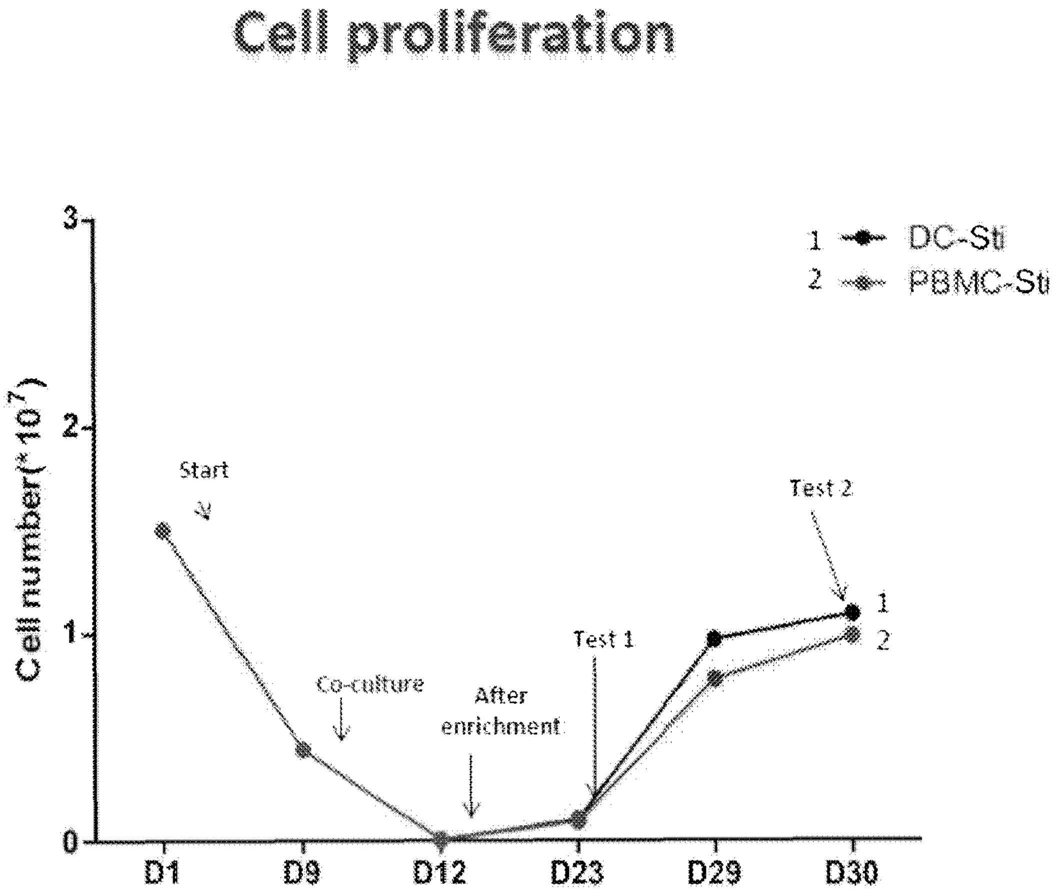
FIG. 38A shows cell proliferation at various time points in Round 1.

Cell proliferation was assessed using cell samples from Day 1 (PBMCs), Day 9 (before IFNγ enrichment), Day 12 (after IFNγ enrichment), and Days 23, 29 and 30 (co-culture of IFNγ$^{+}$ T cells with antigen-loaded DCs or PBMCs) by methods described in Example 2. As shown in FIG. 38A, protocols with antigen-loaded DCs or PBMCs yielded similar T cell proliferation results.

Figure 38B:
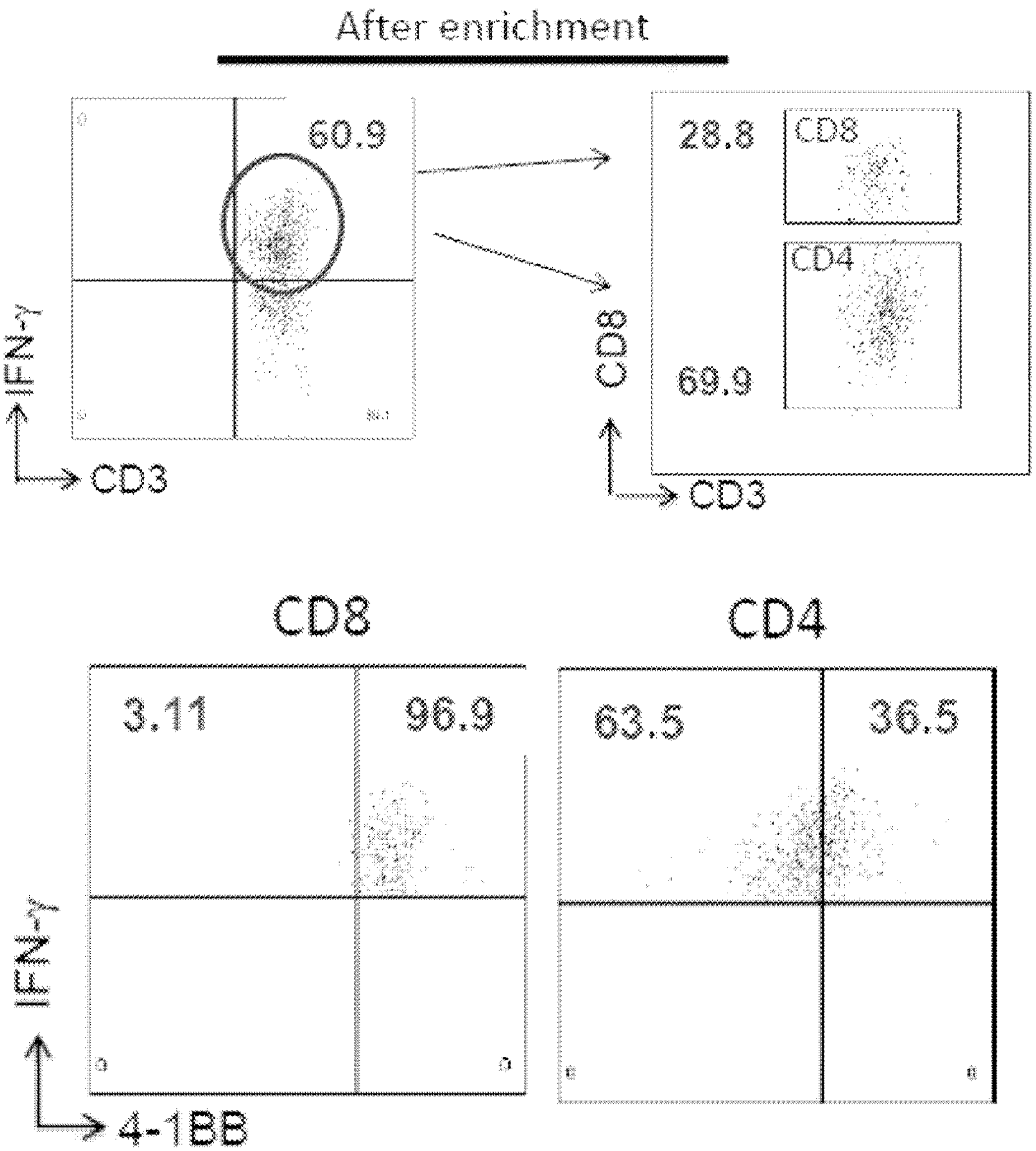
FIG. 38B shows percentages of $IFN\gamma^+CD3^+$ tumor antigen-specific T cell populations after the enrichment step.
Figure 39A:
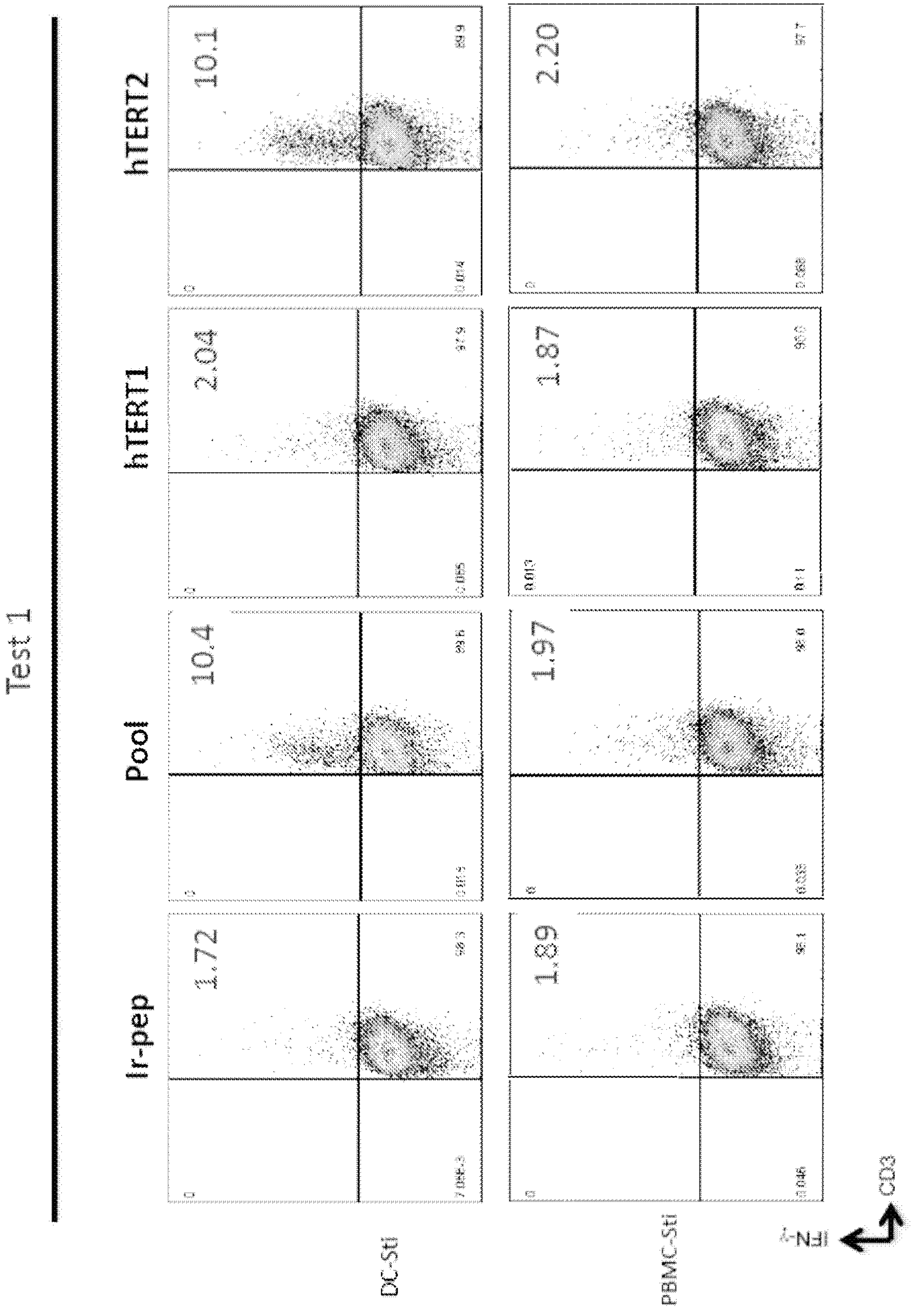
FIGS. 39A-39E shows percentages of tumor antigen-specific T cell populations in various co-culture samples of Round 1.
Figure 39B:
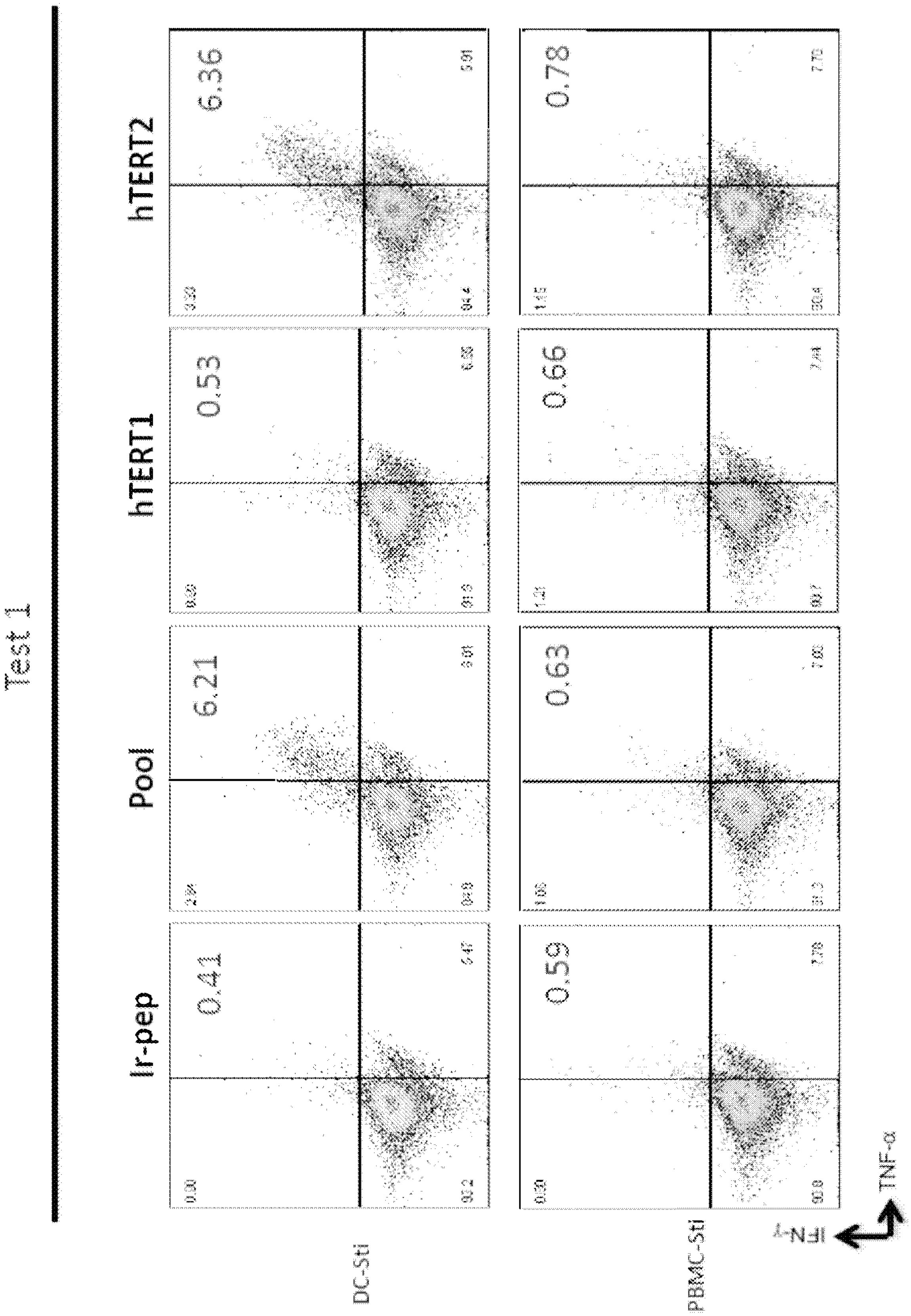
Figure 39C:
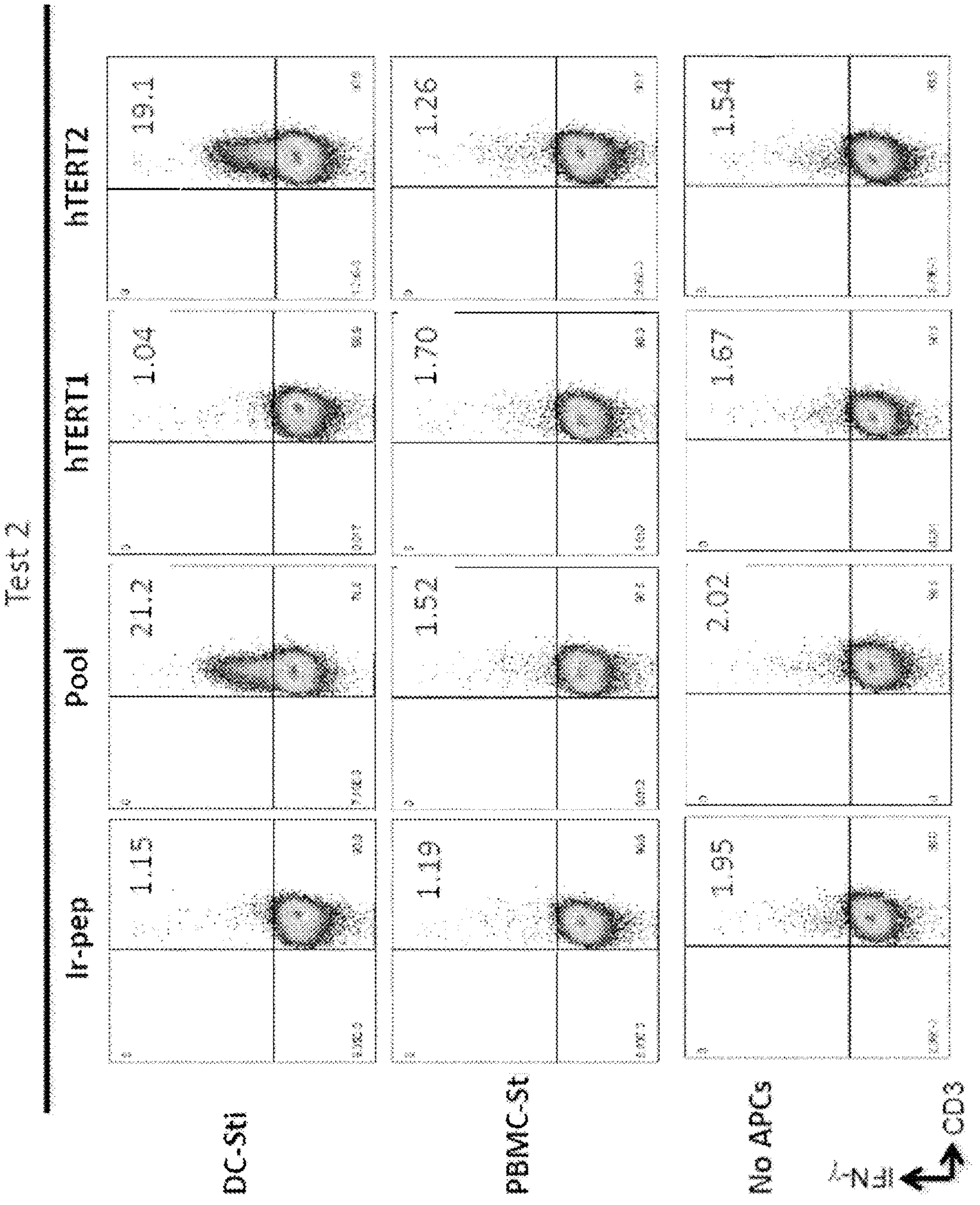
Figure 39D:
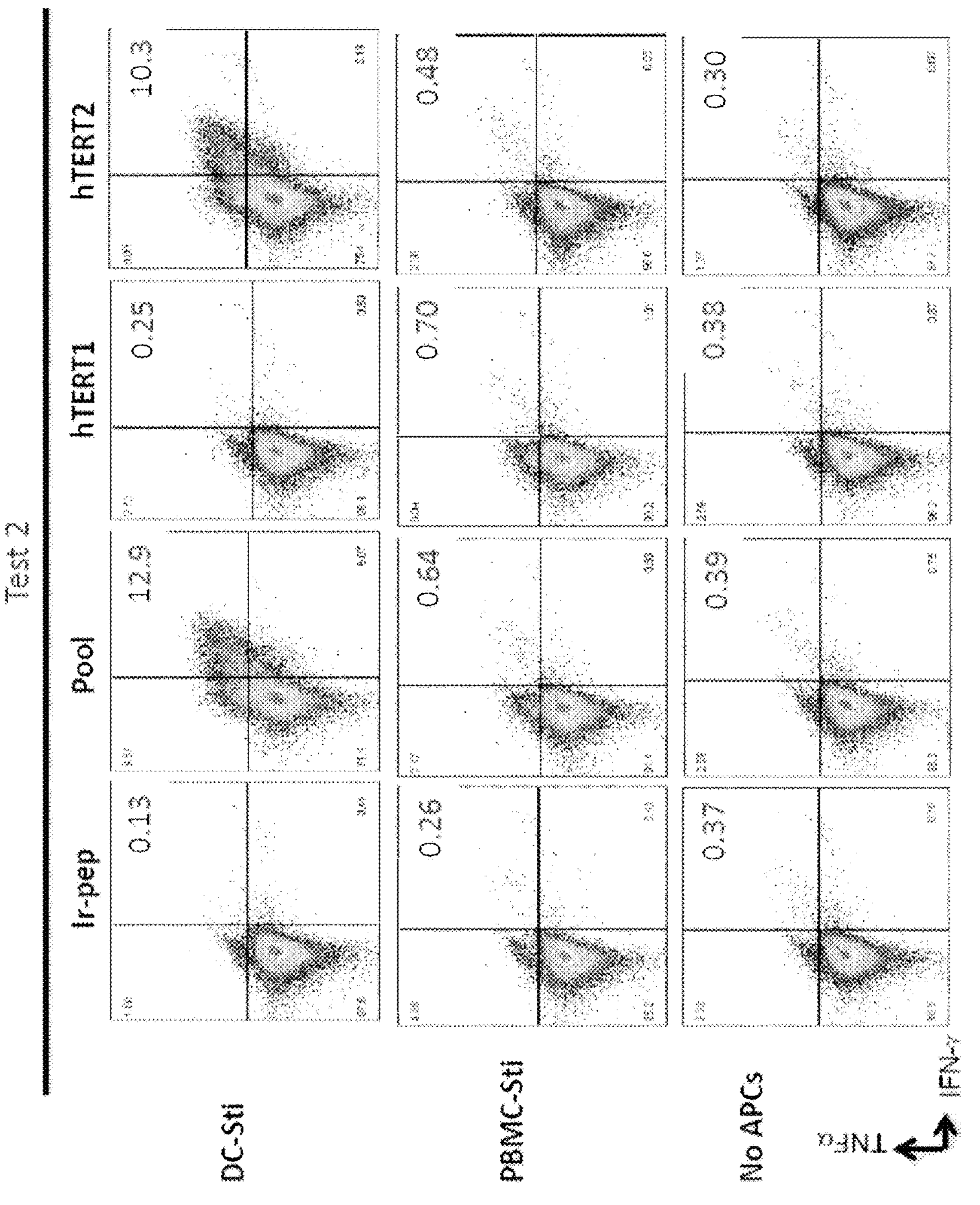
Figure 39E:
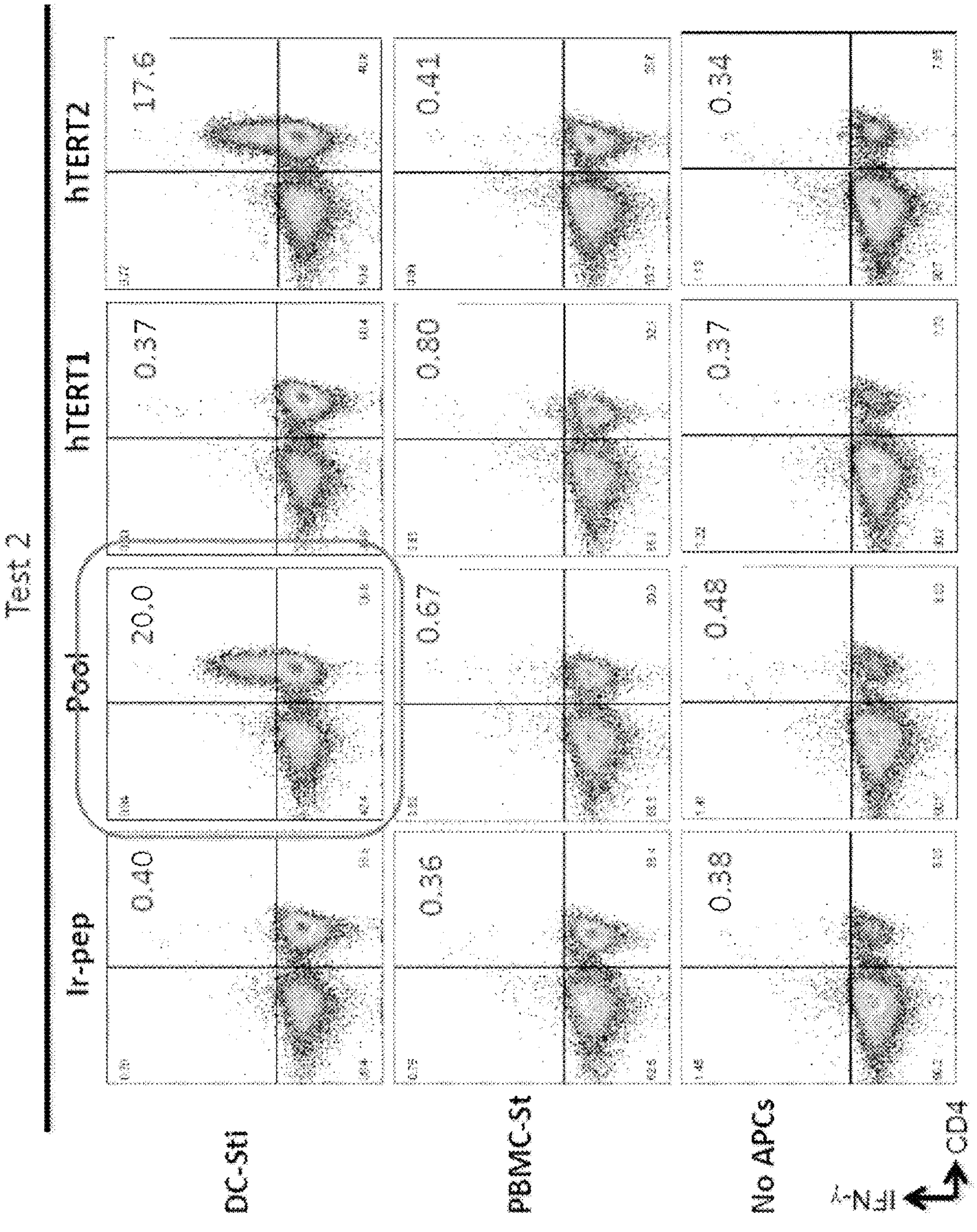
Figure 39F:
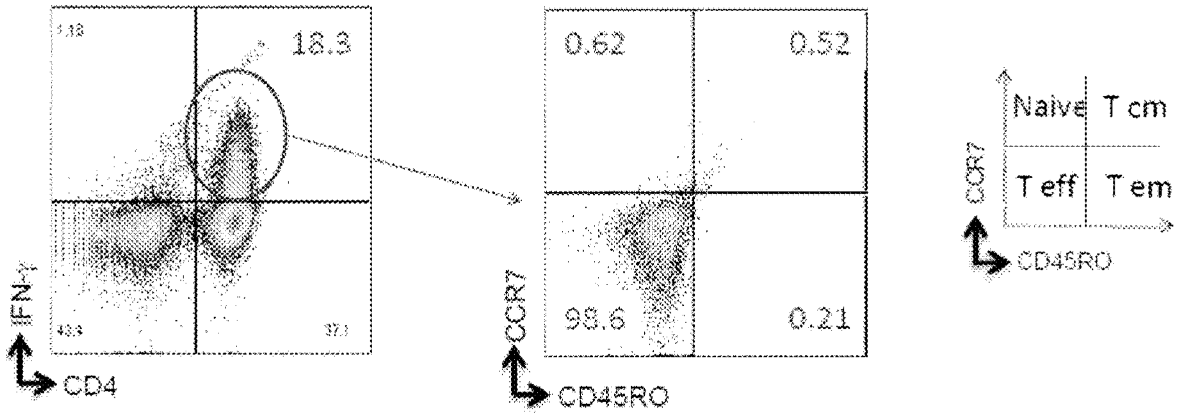
FIG. 39F shows effector T cell populations in $IFN\gamma^+CD4^+$ tumor antigen-specific T cells obtained at the end of Round 1.

The IFNγ production levels by tumor antigen-specific T cells in various co-culture samples were determined by methods described in Example 2. FIG. 38B shows percentages of various T cell populations after the enrichment step. FIGS. 39A-39E compare the percentages of various tumor-specific T cell populations in the cell samples on Days 23 and 30 as determined by assessing IFNγ$^{+}$CD3+, IFNγ$^{+}$CD4+ and IFNγ$^{+}$TNFα$^{+}$ cells in response to stimulation by the tumor antigen peptide pool or individual antigen peptides. Co-culture with antigen-loaded DCs yielded the highest percentages of tumor-specific T cells. As shown in FIG. 39F, 98.6% of the IFNγ$^{+}$CD4$^{+}$ cells in the sample on Day 30 are CCR7$^{-}$ CD45RO$^{-}$ effector T cells.

Round 2

Figure 40:
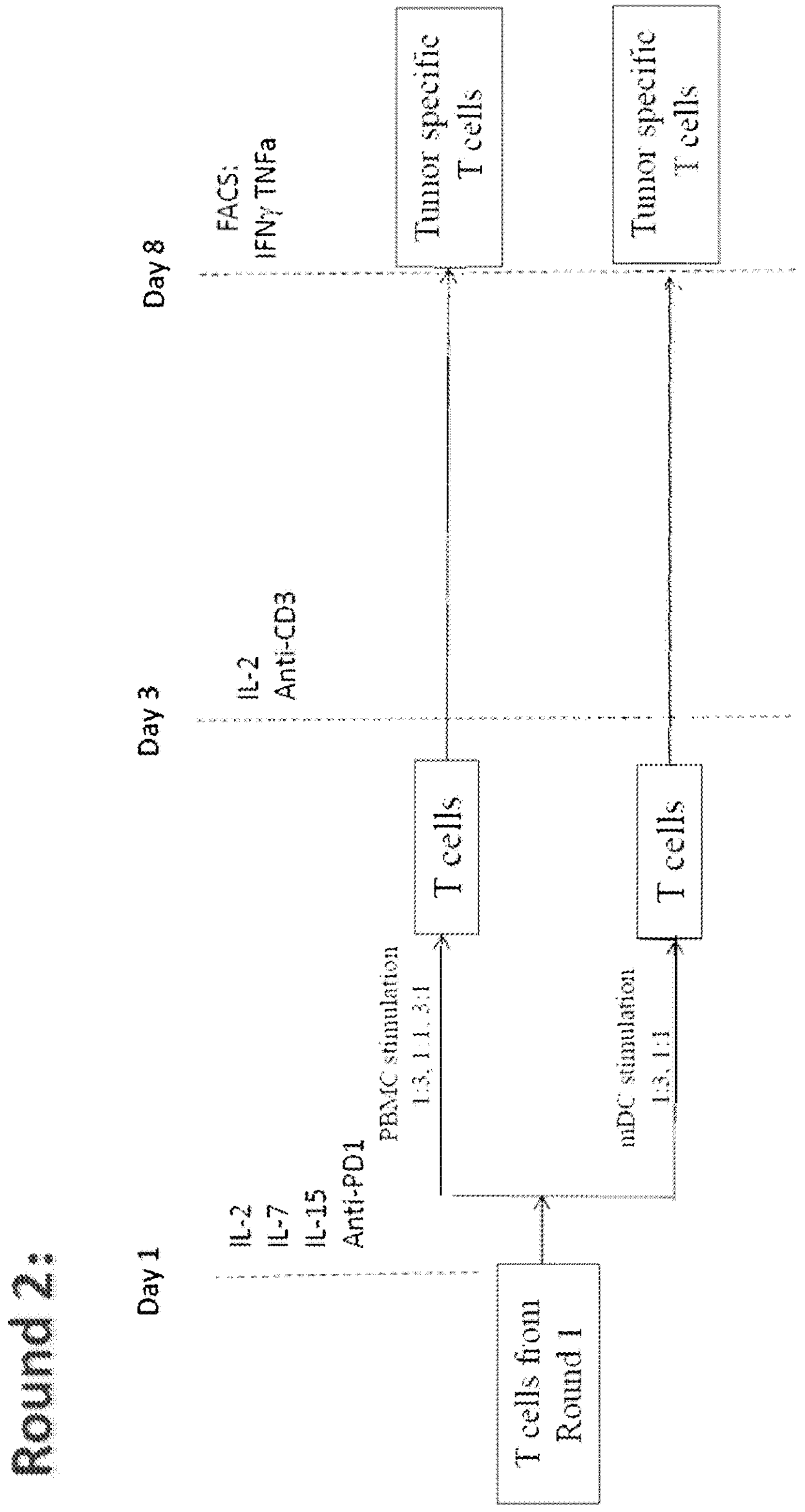
FIG. 40 shows Round 2 protocol of an exemplary two-round method for preparing tumor antigen-specific T cells using PBMCs from Patient SMZ.

FIG. 40 provides an overview of the protocol for Round 2 of tumor-specific T cells preparation used in this example. Briefly, on Day 1, tumor-specific T cells from Round 1 were cultured in a medium comprising a cytokine cocktail (IL-2, IL-7, and IL-15) and an anti-PD-1 antibody. PBMCs or mature DCs loaded with the hTERT-2 peptide were prepared. The tumor-specific T cells and the antigen-loaded DCs or PBMCs were co-cultured at a ratio between T cells and PBMCs of 1:3, 1:1 or 3:1 or at a ratio between T cells and DCs of 3:1 and 1:1. On Day 3, an anti-CD3 antibody (OKT3) and IL-2 were added to the co-culture, which was continued to be cultured to Day 8 to obtain tumor antigen-specific T cells.

Figure 41A:
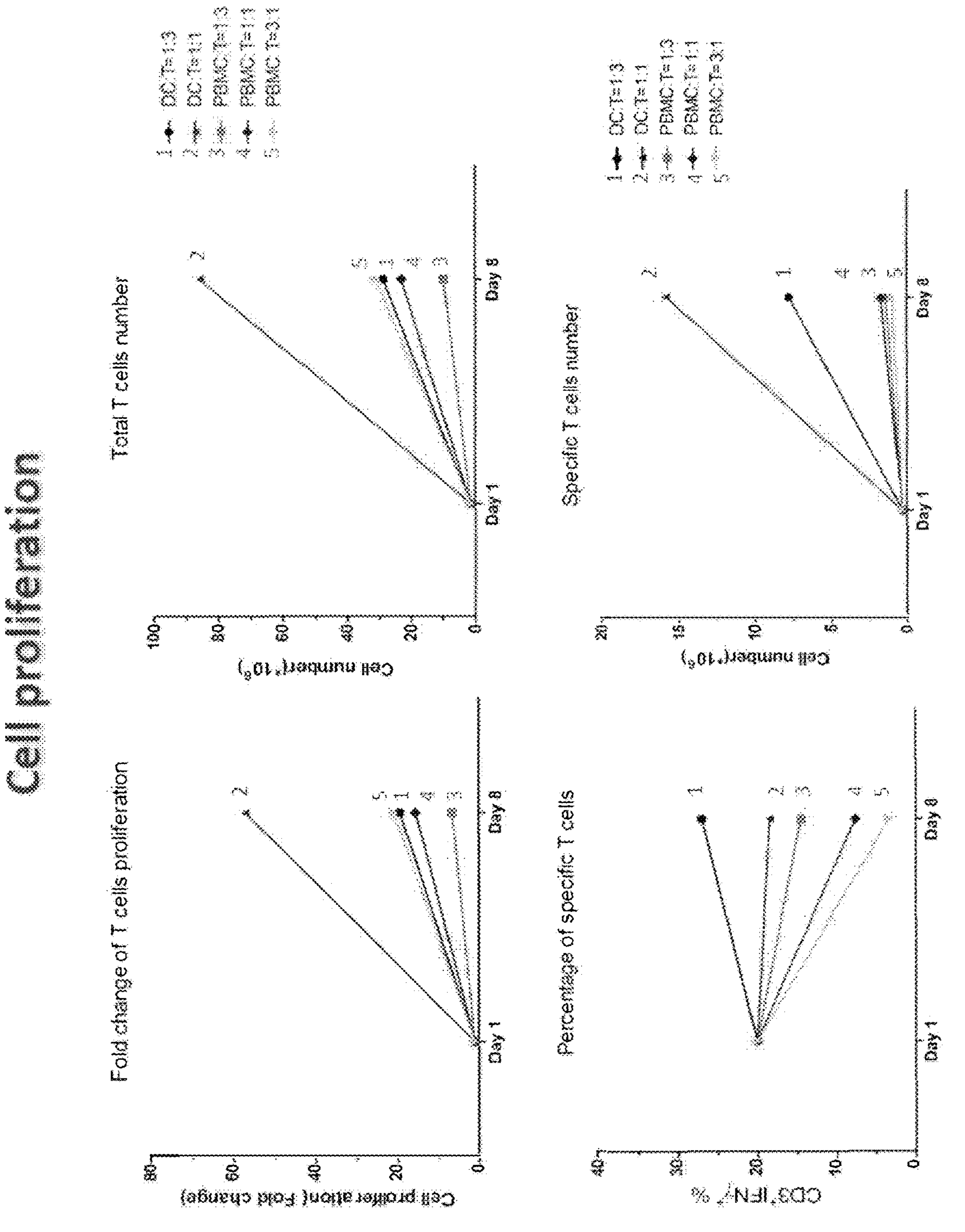
FIG. 41A shows number of T cells and tumor-specific T cells at various time points in Round 2.

Cell proliferation was assessed using cell samples from Day 1 (round 1 tumor-specific T cells), and Day 8 (co-culture of IFNγ$^+$ T cells with antigen-loaded DCs or PBMCs) by methods described in Example 2. The IFNγ production levels by tumor antigen-specific T cells in various co-culture samples were determined by methods described in Example 2. As shown in FIG. 41A, co-culture with antigen-loaded DCs yielded the highest number of T cells and highest percentage of tumor-specific T cells on Day 8.

Figure 41B:
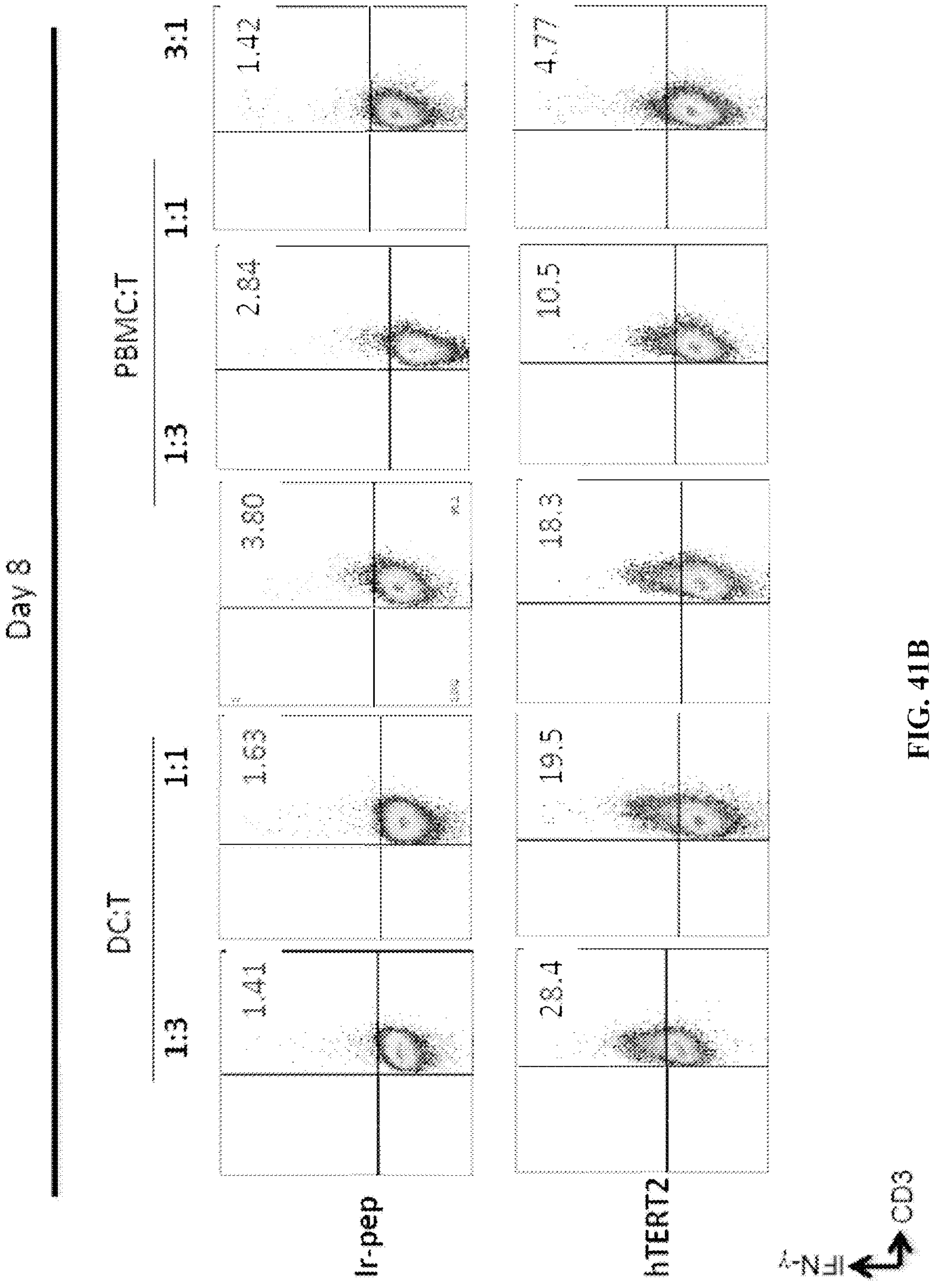
FIGS. 41B-41C show percentages of tumor antigen-specific T cell populations in various co-culture samples of Round 2.
Figure 41C:
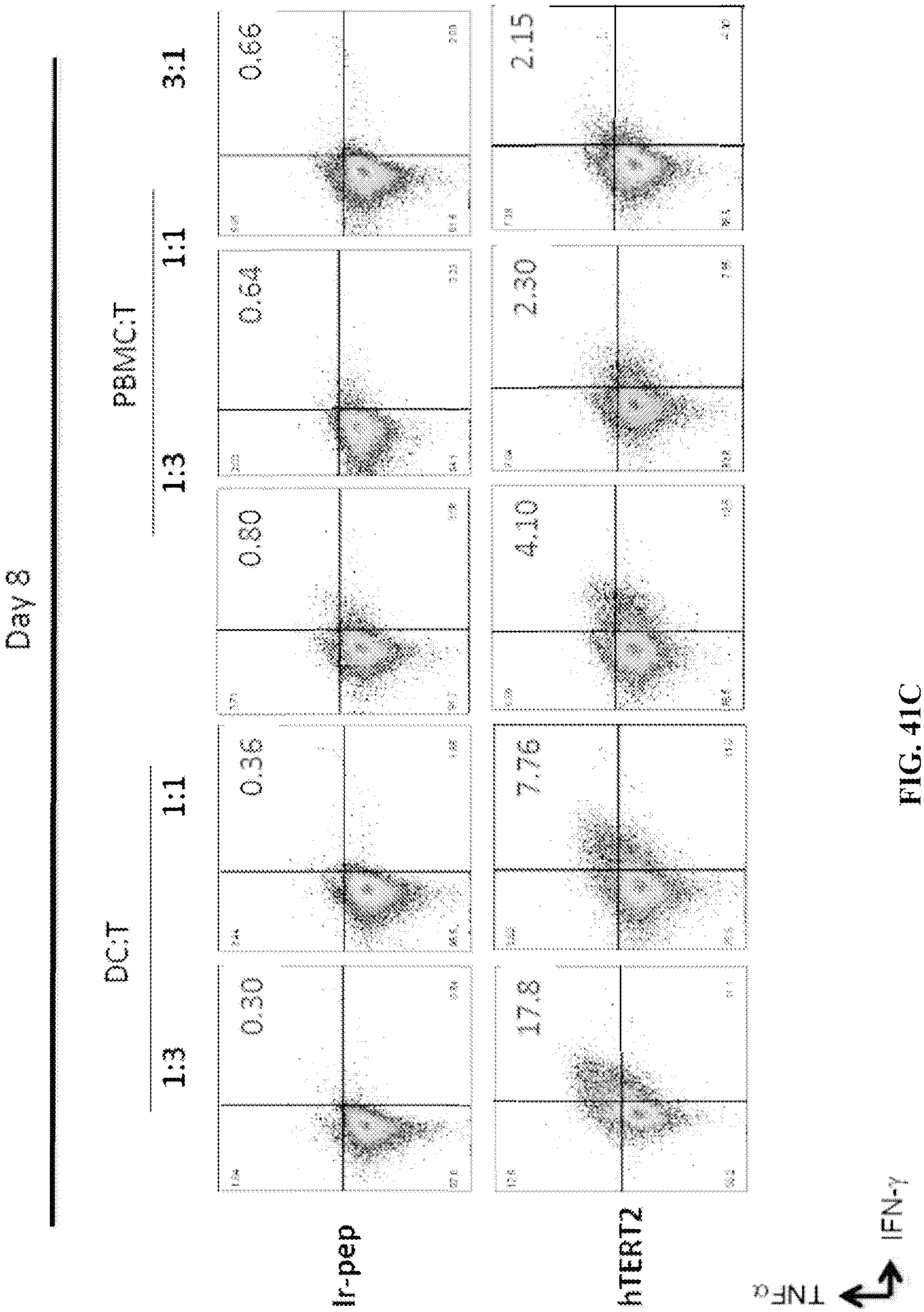

FIGS. 41B-41C compare the percentages of various tumor-specific T cell populations in the cell samples on Day 8 as determined by assessing IFNγ$^+$CD3+ and IFNγ$^+$ TNFα$^+$ cells in response to stimulation by the hTERT2 antigen peptide. Co-culture with antigen-loaded DCs with a ratio between DCs to T cells of 3:1 yielded the highest percentages of tumor-specific T cells.

Figure 42:
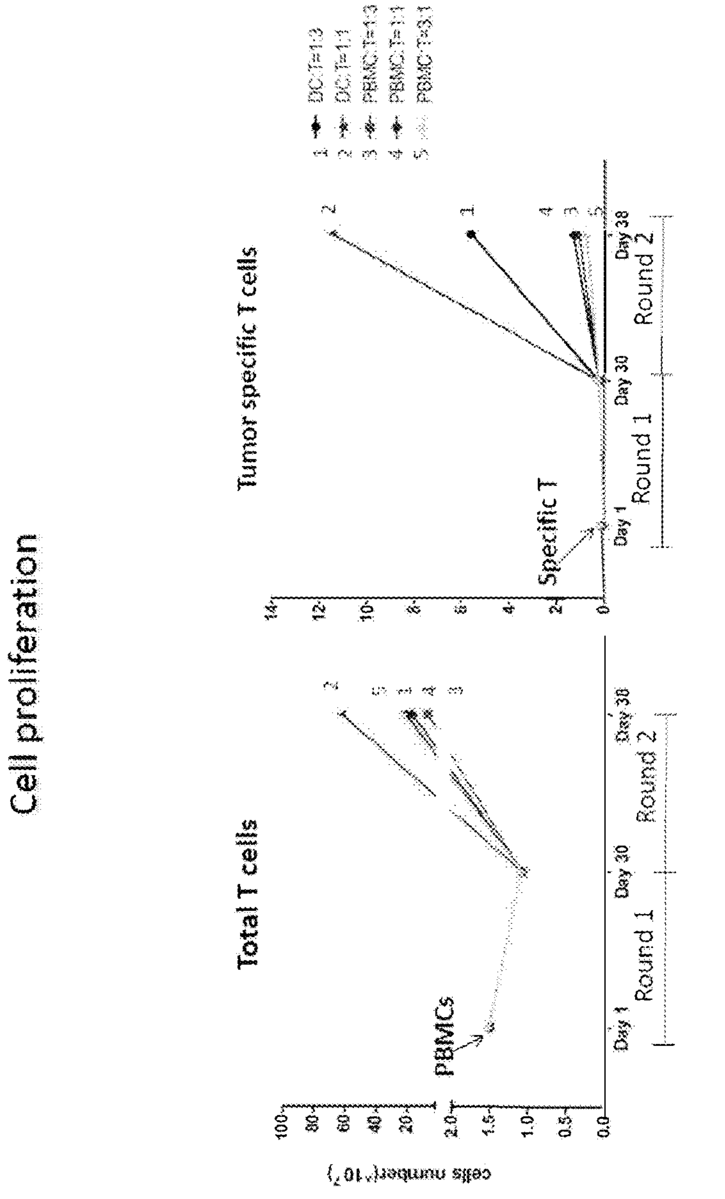
FIG. 42 show number of T cells and tumor antigen-specific T cells at various time points of Round 1 and Round 2.

FIG. 42 shows the number of T cells and tumor-specific T cells on Day 1 and Day 30 of Round 1, and on Day 38, i.e., Day 8 of Round 2. The two-round protocols are effective in amplifying tumor-specific T cells. Stimulation by antigen-loaded DCs in Round 2 yielded the higher number of T cells and higher percentage tumor-specific T cells than stimulation by antigen-loaded PBMCs. The tumor-specific T cells obtained at the end of Round 1 are effector T cells.

Table 5, below, provides the CDR sequences of exemplary TCRs.

TABLE 5

CDR sequences of Exemplary TCRs.

| TCR ID | TCR chain | CDR1 | SEQ ID NO | CDR2 | SEQ ID NO | CDR3 | SEQ ID NO |
|---|---|---|---|---|---|---|---|
| P09E06 | Alpha | TISGNE | 254 | GLKNN | 255 | CIVRAWYNNNDMRF | 28 |
| | Beta | SGHAT | 256 | QFQNNGV | 257 | CASRDTEAFF | 31 |
| 09D01 | Alpha | NSASQS | 258 | VYSSGN | 259 | CVVNMRDSSYKLIF | 34 |
| | Beta | DFQATT | 260 | SNEGSKA | 261 | CSAHERITDTQYF | 37 |
| 09H05 | Alpha | NSASQS | 262 | VYSSGN | 263 | CVVNMKDSSYKLIF | 40 |
| | Beta | DFQATT | 264 | SNEGSKA | 265 | CSALEGTSGKETQYF | 43 |
| 09E01 | Alpha | TTLSN | 266 | LVKSGEV | 267 | CAGPGNQFYF | 46 |
| | Beta | MNHEY | 268 | SVGAGI | 269 | CASSSWDRDQPQHF | 49 |
| 09B03 | Alpha | YSGSPE | 270 | HISR | 271 | CALSALPYNQGGKLIF | 52 |
| | Beta | GTSNPN | 272 | SVGIG | 273 | CAWARSRELFF | 55 |
| P09B08 | Alpha | NSAFQY | 274 | TYSSGN | 275 | CAFYAGNNRKLIW | 58 |
| | Beta | LNHD | 276 | SQIVND | 277 | CASSIDPATSHEQFF | 61 |
| 10F04 | Alpha | NSAFQY | 278 | TYSSGN | 279 | CAMSPRSGYALNF | 70 |
| | Beta | LNHDA | 280 | SQIVND | 281 | CASSMDAALGEKLFF | 73 |
| 09B12 | Alpha | ATGYPS | 282 | ATKADDK | 283 | CALRSGGSNYKLTF | 76 |
| | Beta | SGDLS | 284 | YYNGE | 285 | CASSVEWGTYEQYF | 79 |
| 33A02 | Alpha | YGATPY | 286 | YFSGDTLV | 287 | CAVYQGAQKLVF | 87 |
| | Beta | DFQATT | 288 | SNEGSKA | 289 | CSAPWLAGLYNEQFF | 90 |
| 33D05 | Alpha | SSYSPS | 290 | YTSAATLV | 291 | CVVSAIGYSSASKIIF | 93 |
| | Beta | SEHNR | 292 | FQNEAQ | 293 | CASSLVAGGPAETQYF | 96 |

What is claimed is:

1. A method of treating a cervical cancer comprising RGS5 in an individual, comprising intravenously administering to the individual an effective amount of a pharmaceutical composition comprising an engineered immune cell comprising a tumor-specific T-cell receptor (TCR) and a pharmaceutically acceptable carrier, wherein the TCR binds to an epitope of RGS5 comprising the amino acid sequence of SEQ ID NO: 82 or SEQ ID NO: 83, wherein the engineered immune cell is from the same individual, and wherein the TCR is selected from the group consisting of the following TCRs:

(a) a TCR comprising a TCRα chain comprising a CDR1 comprising the amino acid sequence of SEQ ID NO: 254, a CDR2 comprising the amino acid sequence of SEQ ID NO: 255, and a CDR3 comprising the amino acid sequence of SEQ ID NO: 28; and a TCRβ chain comprising a CDR1 comprising the amino acid sequence of SEQ ID NO: 256, a CDR2 comprising the amino acid sequence of SEQ ID NO: 257, and a CDR3 comprising the amino acid sequence of SEQ ID NO: 31;

(b) a TCR comprising a TCRα chain comprising a CDR1 comprising the amino acid sequence of SEQ ID NO: 258, a CDR2 comprising the amino acid sequence of SEQ ID NO: 259, and a CDR3 comprising the amino acid sequence of SEQ ID NO: 34; and a TCRβ chain comprising a CDR1 comprising the amino acid sequence of SEQ ID NO: 260, a CDR2 comprising the amino acid sequence of SEQ ID NO: 261, and a CDR3 comprising the amino acid sequence of SEQ ID NO: 37;

(c) a TCR comprising a TCRα chain comprising a CDR1 comprising the amino acid sequence of SEQ ID NO: 262, a CDR2 comprising the amino acid sequence of SEQ ID NO: 263, and a CDR3 comprising the amino acid sequence of SEQ ID NO: 40; and a TCRβ chain comprising a CDR1 comprising the amino acid sequence of SEQ ID NO: 264, a CDR2 comprising the amino acid sequence of SEQ ID NO: 265, and a CDR3 comprising the amino acid sequence of SEQ ID NO: 43;

(d) a TCR comprising a TCRα chain comprising a CDR1 comprising the amino acid sequence of SEQ ID NO: 266, a CDR2 comprising the amino acid sequence of SEQ ID NO: 267, and a CDR3 comprising the amino acid sequence of SEQ ID NO: 46; and a TCRβ chain comprising a CDR1 comprising the amino acid sequence of SEQ ID NO: 268, a CDR2 comprising the amino acid sequence of SEQ ID NO: 269, and a CDR3 comprising the amino acid sequence of SEQ ID NO: 49; and (e) a TCR comprising a TCRα chain comprising a CDR1 comprising the amino acid sequence of SEQ ID NO: 270, a CDR2 comprising the amino acid sequence of SEQ ID NO: 271, and a CDR3 comprising the amino acid sequence of SEQ ID NO: 52; and a TCRβ chain comprising a CDR1 comprising the amino acid sequence of SEQ ID NO: 272, a CDR2 comprising the amino acid sequence of SEQ ID NO: 273, and a CDR3 comprising the amino acid sequence of SEQ ID NO: 55.

2. The method of claim 1, wherein the TCR comprises the TCRα chain comprising the CDR1 comprising the amino acid sequence of SEQ ID NO: 254, the CDR2 comprising the amino acid sequence of SEQ ID NO: 255, and the CDR3 comprising the amino acid sequence of SEQ ID NO: 28; and the TCRβ chain comprising the CDR1 comprising the amino acid sequence of SEQ ID NO: 256, the CDR2 comprising the amino acid sequence of SEQ ID NO: 257, and the CDR3 comprising the amino acid sequence of SEQ ID NO: 31.

3. The method of claim 2, wherein the TCRα chain comprises a variable region comprising the amino acid sequence of SEQ ID NO: 214, and the TCRβ chain comprises a variable region comprising the amino acid sequence of SEQ ID NO: 212.

4. The method of claim 2, wherein the TCRα chain comprises an amino acid sequence having at least about 80% identity to the amino acid sequence of SEQ ID NO: 29, and the TCRβ chain comprises an amino acid sequence having at least about 80% identity to the amino acid sequence of SEQ ID NO: 32.

5. The method of claim 2, wherein the TCRα chain comprises the amino acid sequence of SEQ ID NO: 29, and the TCRβ chain comprises the amino acid sequence of SEQ ID NO: 32.

6. The method of claim 1, wherein the TCR comprises the TCRα chain comprising the CDR1 comprising the amino acid sequence of SEQ ID NO: 258, the CDR2 comprising the amino acid sequence of SEQ ID NO: 259, and the CDR3 comprising the amino acid sequence of SEQ ID NO: 34; and the TCRβ chain comprising the CDR1 comprising the amino acid sequence of SEQ ID NO: 260, the CDR2 comprising the amino acid sequence of SEQ ID NO: 261, and the CDR3 comprising the amino acid sequence of SEQ ID NO: 37.

7. The method of claim 6, wherein the TCRα chain comprises a variable region comprising the amino acid sequence of SEQ ID NO: 242, and the TCRβ chain comprises a variable region comprising the amino acid sequence of SEQ ID NO: 240.

8. The method of claim 6, wherein the TCRα chain comprises an amino acid sequence having at least about 80% identity to the amino acid sequence of SEQ ID NO: 35, and the TCRβ chain comprises an amino acid sequence having at least about 80% identity to the amino acid sequence of SEQ ID NO: 38.

9. The method of claim 6, wherein the TCRα chain comprises the amino acid sequence of SEQ ID NO: 35, and the TCRβ chain comprises the amino acid sequence of SEQ ID NO: 38.

10. The method of claim 1, wherein the TCR comprises the TCRα chain comprising the CDR1 comprising the amino acid sequence of SEQ ID NO: 262, the CDR2 comprising the amino acid sequence of SEQ ID NO: 263, and the CDR3 comprising the amino acid sequence of SEQ ID NO: 40; and the TCRβ chain comprising the CDR1 comprising the amino acid sequence of SEQ ID NO: 264 the CDR2 comprising the amino acid sequence of SEQ ID NO: 265, and the CDR3 comprising the amino acid sequence of SEQ ID NO: 43.

11. The method of claim 10, wherein the TCRα chain comprises a variable region comprising the amino acid sequence of SEQ ID NO: 238, and the TCRβ chain comprises a variable region comprising the amino acid sequence of SEQ ID NO: 236.

12. The method of claim 10, wherein the TCRα chain comprises an amino acid sequence having at least about 80% identity to the amino acid sequence of SEQ ID NO: 41, and the TCRβ chain comprises an amino acid sequence having at least about 80% identity to the amino acid sequence of SEQ ID NO: 44.

13. The method of claim 10, wherein the TCRα chain comprises the amino acid sequence of SEQ ID NO: 41, and the TCRβ chain comprises the amino acid sequence of SEQ ID NO: 44.

14. The method of claim 1, wherein the TCR comprises the TCRα chain comprising the CDR1 comprising the amino acid sequence of SEQ ID NO: 266, the CDR2 comprising the amino acid sequence of SEQ ID NO: 267, and the CDR3 comprising the amino acid sequence of SEQ ID NO: 46; and the TCRβ chain comprising the CDR1 comprising the amino acid sequence of SEQ ID NO: 268, the CDR2 comprising the amino acid sequence of SEQ ID NO: 269, and the CDR3 comprising the amino acid sequence of SEQ ID NO: 49.

15. The method of claim 14, wherein the TCRα chain comprises a variable region comprising the amino acid sequence of SEQ ID NO: 222, and the TCRβ chain comprises a variable region comprising the amino acid sequence of SEQ ID NO: 220.

16. The method of claim 14, wherein the TCRα chain comprises an amino acid sequence having at least about 80% identity to the amino acid sequence of SEQ ID NO: 47, and the TCRβ chain comprises an amino acid sequence having at least about 80% identity to the amino acid sequence of SEQ ID NO: 50.

17. The method of claim 1, wherein the TCR comprises the TCRα chain comprising the CDR1 comprising the amino acid sequence of SEQ ID NO: 270, the CDR2 comprising the amino acid sequence of SEQ ID NO: 271, and the CDR3 comprising the amino acid sequence of SEQ ID NO: 52; and the TCRβ chain comprising the CDR1 comprising the amino acid sequence of SEQ ID NO: 272, the CDR2 comprising the amino acid sequence of SEQ ID NO: 273, and the CDR3 comprising the amino acid sequence of SEQ ID NO: 55.

18. The method of claim 17, wherein the TCRα chain comprises a variable region comprising the amino acid sequence of SEQ ID NO: 210, and the TCRβ chain comprises a variable region comprising the amino acid sequence of SEQ ID NO: 208.

19. The method of claim 17, wherein the TCRα chain comprises an amino acid sequence having at least about 80% identity to the amino acid sequence of SEQ ID NO: 53, and the TCRβ chain comprises an amino acid sequence having at least about 80% identity to the amino acid sequence of SEQ ID NO: 56.

20. The method of claim 1, wherein the engineered immune cell is selected from the group consisting of a peripheral blood mononuclear cell (PBMC), a T cell, a cytotoxic T cell, a helper T cell, a natural killer T cell, and a regulatory T cell.

* * * * *